US012741926B2

(12) United States Patent
Jong et al.

(10) Patent No.: US 12,741,926 B2
(45) Date of Patent: Sep. 22, 2026

(54) LIPOXYGENASE INHIBITORS

(71) Applicant: SRI International, Menlo Park, CA (US)

(72) Inventors: Ling Jong, Menlo Park, CA (US); Nathan Collins, Menlo Park, CA (US); Raymond Ng, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 828 days.

(21) Appl. No.: 17/788,275

(22) PCT Filed: Dec. 18, 2020

(86) PCT No.: PCT/US2020/066191
§ 371 (c)(1),
(2) Date: Jun. 22, 2022

(87) PCT Pub. No.: WO2021/133689
PCT Pub. Date: Jul. 1, 2021

(65) Prior Publication Data

US 2023/0117592 A1 Apr. 20, 2023

Related U.S. Application Data

(60) Provisional application No. 62/953,023, filed on Dec. 23, 2019.

(51) Int. Cl.

| | |
|---|---|
| ***C07C 217/86*** | (2006.01) |
| ***C07C 211/53*** | (2006.01) |
| ***C07C 211/54*** | (2006.01) |
| ***C07C 211/56*** | (2006.01) |
| ***C07C 217/92*** | (2006.01) |
| ***C07D 209/14*** | (2006.01) |
| ***C07D 213/74*** | (2006.01) |
| ***C07D 215/38*** | (2006.01) |
| ***C07D 249/08*** | (2006.01) |
| ***C07D 295/13*** | (2006.01) |
| ***C07D 305/08*** | (2006.01) |
| ***C07D 309/04*** | (2006.01) |
| ***C07D 401/12*** | (2006.01) |
| ***C07D 403/06*** | (2006.01) |
| ***C07D 403/12*** | (2006.01) |
| ***C07D 405/06*** | (2006.01) |
| ***C07D 405/12*** | (2006.01) |
| ***C07D 405/14*** | (2006.01) |
| ***C07D 409/12*** | (2006.01) |
| ***C07D 413/12*** | (2006.01) |

(52) U.S. Cl.
CPC .......... *C07C 217/86* (2013.01); *C07C 211/53* (2013.01); *C07C 211/54* (2013.01); *C07C 211/56* (2013.01); *C07C 217/92* (2013.01); *C07D 209/14* (2013.01); *C07D 213/74* (2013.01); *C07D 215/38* (2013.01); *C07D 249/08* (2013.01); *C07D 295/13* (2013.01); *C07D 305/08* (2013.01); *C07D 309/04* (2013.01); *C07D 401/12* (2013.01); *C07D 403/06* (2013.01); *C07D 403/12* (2013.01); *C07D 405/06* (2013.01); *C07D 405/12* (2013.01); *C07D 405/14* (2013.01); *C07D 409/12* (2013.01); *C07D 413/12* (2013.01)

(58) Field of Classification Search
CPC .................................................... C07C 217/86
See application file for complete search history.

(56) References Cited

U.S. PATENT DOCUMENTS

| | | | |
|---|---|---|---|
| 3,743,663 | A | 7/1973 | Baschang et al. |
| 3,743,667 | A | 7/1973 | Wagner et al. |
| 4,731,258 | A | 3/1988 | Liberman |
| 4,731,358 | A | 3/1988 | Huth et al. |
| 4,822,811 | A | 4/1989 | Summers |
| 4,906,662 | A | 3/1990 | Hashimoto et al. |
| 5,420,289 | A | 5/1995 | Musser et al. |
| 6,399,631 | B1 | 6/2002 | Elliott et al. |
| 6,800,655 | B2 | 10/2004 | Jong et al. |
| 7,462,628 | B2 | 12/2008 | Ishihara et al. |
| 8,207,214 | B2 | 6/2012 | Alisi et al. |
| 10,646,471 | B2 | 5/2020 | Jong |
| 10,961,277 | B2 | 3/2021 | Lutz et al. |
| 11,382,893 | B2 | 7/2022 | Maccecchini |
| 11,447,486 | B2 | 9/2022 | Kim et al. |
| 2004/0067999 | A1 | 4/2004 | Block et al. |

(Continued)

FOREIGN PATENT DOCUMENTS

| | | | |
|---|---|---|---|
| CN | 10425025 | A | 12/2014 |
| CN | 106879256 | A | 6/2017 |

(Continued)

OTHER PUBLICATIONS

Ackermann et al., "The double-edged role of 12/15-lipoxygenase during inflammation and immunity", Biochimica et Biophysica Acta, 1862:371-381 (2017).

(Continued)

*Primary Examiner* — David K O'Dell

(74) *Attorney, Agent, or Firm* — Dicke, Billig & Czaja, PLLC

(57) ABSTRACT

Various embodiments of the present disclosure are directed to compounds having Formula I, Formula II, Formula IIA, Formula III, Formula IIIA, Formula IIIB, and/or pharmaceutically acceptable salts thereof. The compounds can be suitable for inhibiting lipoxygenases and/or treating associated diseases. In some embodiments, subject compounds are used to prepare a composition that is effective in treating neurodegenerative diseases.

10 Claims, No Drawings

(56) References Cited

U.S. PATENT DOCUMENTS

| | | | |
|---|---|---|---|
| 2008/0280899 | A1 | 11/2008 | Bilodeau et al. |
| 2010/0069355 | A1 | 3/2010 | Jong et al. |
| 2010/0240726 | A1 | 9/2010 | Gazit et al. |
| 2011/0013263 | A1 | 1/2011 | Miteva et al. |
| 2013/0041238 | A1 | 2/2013 | Joseph et al. |
| 2013/0345214 | A1 | 12/2013 | Jong |
| 2017/0001955 | A1 | 1/2017 | Maloney et al. |
| 2018/0092919 | A1 | 4/2018 | Shiba et al. |
| 2018/0222861 | A1 | 8/2018 | Tang et al. |
| 2018/0265777 | A1 | 9/2018 | Ambrosek et al. |

FOREIGN PATENT DOCUMENTS

| | | | |
|---|---|---|---|
| EP | 0234708 | A1 | 9/1987 |
| EP | 1382598 | A1 | 1/2004 |
| EP | 2720727 | A1 | 4/2014 |
| JP | S 59-044386 | A | 3/1984 |
| JP | S 59-089678 | A | 5/1984 |
| JP | H 10-511663 | A | 11/1998 |
| JP | 2014510753 | A | 5/2014 |
| KR | 2016-0020616 | A | 2/2016 |
| WO | 198903818 | A1 | 5/1989 |
| WO | 1998/050033 | A | 11/1998 |
| WO | 1999032433 | A1 | 7/1999 |
| WO | 2001/007409 | A1 | 2/2001 |
| WO | 2001/096299 | A2 | 12/2001 |
| WO | 2002/051806 | A1 | 4/2002 |
| WO | 2006/083458 | A2 | 8/2006 |
| WO | 2006/105196 | A2 | 10/2006 |
| WO | 2010008864 | A2 | 1/2010 |
| WO | 2010029300 | A1 | 3/2010 |
| WO | 2010/118339 | A2 | 10/2010 |
| WO | 2010/129622 | A1 | 11/2010 |
| WO | 2012/135133 | A1 | 10/2012 |
| WO | 2012/177807 | A1 | 12/2012 |

OTHER PUBLICATIONS

Banwell et al., "Exploitation of Cyclopropane Ring-Cleavage Reactions for the Rapid Assembly of Tetracyclic Framework Related to Gibberellins", Organic Letters, 8(23):5341-5344 abstract, compound 5 (2006).
Cannon, Chapter 19 in "Burger's Medicinal Chemistry and Drug Discovery", Fifth Ed, Principles and Practice, Wiley-Interscience, vol. 1(19):783-802, (1995).
Chao et al., "Computer-Aided Rational Drug Design: A Novel Agent (SR13668) Designed to Mimic the Unique Anticancer Mechanisms of Dietary Indole-3-Carbinol to Block Akt Signaling", J. Med. Chem., 50:3412-3415 (Jan. 11, 2007).
Chu et al., "5-lipoxygenase as an endogenous modulator of amyloid beta formation in vivo", Ann Neurol., 69(1):34-46 (Jan. 2011).
Crowell et al., "Targeting the AKT protein kinase for cancer chemoprevention", Mol. Cancer. Ther., 6(8), 23 pgs (Aug. 2007).
European Office Action (Art 94(3)) for related EP Patent Appl No. 12763995.3 (5 pg) (May 23, 2018).
Foster, "Deuterium isotope effects in studies of drug metabolism", Trends Pharmacol. Sci., 5(12):524-527 (1984). (Abstract).
International Search Report and Written Opinion for related PCT Application PCT/US2021/024103 mailed Jul. 26, 2021.
Kuhn et al., "Mammalian lipoxygenases and their biological relevance", Biochimica et Biophysica Acta, 1851(4):308-330 (Apr. 2015).
Listi, et al., "Role of Cyclooxygenase-2 and 5-Lipoxygenase Polymorphisms in Alzheimer's Disease in a Population from Northern Italy: Implication for Pharmacogenomics", J. Alzheimers. Dis., 19(2):551-557 (Jan. 7, 2010).
Manev et al., "Cyclooxygenases and 5-lipoxygenase in Alzheimer's disease", Prog. Neuropsychopharmacol Biol. Psychiatry, 35(2):315-319 (Mar. 30, 2011). (Abstract).
Manev et al., "5-Lipoxygenase in the Central Nervous System: Therapeutic Implications", Curr. Med. Chem—Anti—Inflammatory & Anti-Allergy Agents, 1(2):115-121 (2002).
Mashima et al., "The role of lipoxygenases in pathophysiology; new insights and future perspectives", Redox Biology, 6:297-310 (2015).
PUBCHEM-SID 315864309 Deposit Date Aug. 2, 2016 pp. 1-5.
Pufahl et al., "Development of a fluorescence-based enzyme assay of human 5-lipoxygenase", Anal. Biochem., 364 (2):204-212 (May 15, 2007) (Abstract).
Remington, The Science and Practice of Pharmacy, R. Hendrickson, ed., 21st edition, Lippincott, Williams & Wilkins, Philadelphia, Pa., (2005), at p. 732, Table 38-5.
Waslidge et al., "A Colorimetric Method for the Determination of Lipoxygenase Activity Suitable for Use in a High Throughput Assay Format", Anal. Biochem., 231(2):354-358 (Nov. 1995) (Abstract).
Wisastra et al., "Inflammation, Cancer and Oxidative Lipoxygenase Activity are Intimately Linked", Cancers, 6:1500-1521 (2014).
International Search Report and Written Opinion for related PCT Application PCT/US2020/066191 mailed Jun. 29. 2021.
Berge et al., "Pharmaceutical Salts," J. Pharma Sci., 66(1):1-19 (Jan. 1977).
Pubchem-SID: 104787593 Deposit Date Feb. 22, 2011 pp. 1-6.
Pubchem-SID: 399039609 Deposit Date Dec. 7, 2019 pp. 1-5.
Kenyon, et al. "Novel Human Lipoxygenase Inhibitors Discovered Using Virtual Screening with Homology Models" Journal of Medicinal Chemistry, vol. 49, No. 4, Jan. 31, 2006, pp. 1356-1363.
Extended European Search Report for related EP Appl No. 20904761.2, pp. 11, Dec. 14, 2023.
Bedford et al., "Intramolecular Direct Arylation in the Synthesis of Fluorinated Carbazoles", Tetrahedron, 64(26):6038-6050 (Mar. 4, 2008).
Gritsenko et al., "Synthesis of 3,5-Disubstituted 10, 11-Dihydro-5H-Dibenz [b,f] Azepines", Pharmaceutical Chemistry Journal, 32(9):500-503 (Sep. 1, 1998).
Gu et al., "Facile One-Pot Synthesis of Novel 6-Monosubstituted 5,11-Dihydroindolo [3,2-b] carbazoles and Preparation of Different Derivatives", Synlett, 2006(10):1535-1538 (Jun. 12, 2006).
Ishii et al., "Polymerisation of Indole. Part 3. Two Indolylquinolines, an Indole Tetramer, and the Dihydro Derivative of the Indole Dimer", Journal of the Chemical Society Perkin Transactions 1, 1988(8):2387-2396 (Aug. 1, 1988).
Li et al., "Direct Access to Substituted Benzo [b] Carbazoles through Cascade Annulation of 2-Vinylbenzaldehyde with Indoles", Chemical Communications, 55(23):3339-3342 (Feb. 14, 2019).
PUBCHEM-CID: 21901897, "2,3,8,8a-Tetrahydropyrrolo[2,3-b]indole" Compound Summary (Dec. 5, 2007).
Mascio et al., "Singlet Molecular Oxygen Reactions with Nucleic Acids, and Proteins", Chemical Reviews, 119(3):A-AR (Feb. 5, 2019).
Roy et al., "Hexahydropyrrolo[2,3-b]indole alkaloids of biological relevance: proposed biosynthesis and synthetic approaches", Arkivoc, Part i:437-471 (Oct. 22, 2020).
Shagako et al., "Synthesis in the Phenothiazine Series. XX. 2-Alkylaminoacylamino- and 2-alkylaminoalkylamino-Substituted Phenothiazine and 10-Methyl-Phenothiazine", Chemistry of Heterocyclic Compounds, 3(2):213-215 (Jul. 1, 1967).
Chinese First Office Action from CN202080097156.X, mailed Mar. 27, 2024.
Extended European Search Report from EP21774060.4, mailed Apr. 4, 2024.
International Search Report from PCT/US2023/082278, mailed Apr. 17, 2024.
Pawar Py, et al., "Synthesis and in vitro screening of some 1,3,4-oxadiazole derivatives as lipoxygenase inhibitors", Biosciences Biotechnology Research Asia, vol. 4, No. 2, Jan. 1, 2007 (Jan. 1, 2007), pp. 609-614, XP009139856.
Asselin, et al., "Cycloalkanoindles. 2. 1-Alkyl-1,2,3,4-Tetrahydrocarbaxole-1-ethanamines and Related Compounds, Potential Antidepressants", Journal of Medicinal Chemistry, 1976, 19(6), p. 792-797.
Kleks, et al., "Orthoscuticellines A-E, P-Carboline Alkaloids from the Bryozoan Orthoscuticella ventricosa Collected in Australia", Journal of Natural Products, 2020, 83, 422-428.
Pouilhes, et al., "6',7'-Dihydrokeramamine C and Analogues: synthesis and Biological Evaluation", Tetrahedron Letters, 42, 2001, 8297-8299.

(56) References Cited

OTHER PUBLICATIONS

Database Registry Online, Retrieved from STN Registry, May 17, 2019, pp. 1-55.

LIPOXYGENASE INHIBITORS

BACKGROUND

Lipoxygenases (LOXs) and their catalyzed products, such as inflammatory leukotrienes (LTs) and hydroxyeicosatetraenoic acids (HETEs) have been implicated in the pathogenesis of a variety of human diseases, including inflammatory disease, cancer and neurodegenerative diseases. Lipoxygenase inhibitors are known to be useful for the treatment of all kinds of LOXs-related inflammatory diseases, including neurodegenerative diseases, such as Alzheimer's disease.

SUMMARY

The present invention is directed to overcoming the above-mentioned challenges and others related to compounds, such as compounds that are LOX inhibitors.

Various embodiments of the present disclosure are directed to a compound having Formula I:

Formula I

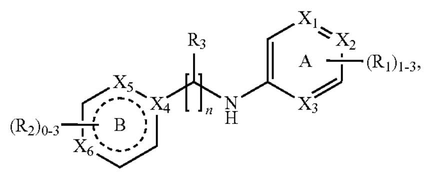

wherein: n is 0-2, such that when n=0, there is a direct bond between B and the NH group and with no $R_3$, and when n=1 or 2, the carbons in these bonds are optionally substituted with one $R_3$ group; A is a 6 membered heteroaryl or a 6 membered aryl, wherein the 6 membered heteroaryl or 6 membered aryl is further independently substituted with one to three $R_1$ groups; B is a 5-6-membered heterocycle, a 5-6 membered aryl, or a 5-6 membered cyclohexyl, wherein the 5-6 membered heterocycle, 5-6 membered aryl, or 5-6 membered cyclohexyl is unsubstituted or independently substituted with up to three $R_2$ groups; $X_1$, $X_2$, $X_3$, $X_4$, $X_5$, and $X_6$ are each independently C, N, or O; each $R_1$ independently comprising: halo, $C_{1-4}$ alkyl, $—NR_xR_y$, $—O(CH_2)_2R_x$, $—O(CH_2)_2NR_xR_y$, $—NHC(O)—C_{2-4}$ alkyl, $—(CH_2)_3NR_xR_y$, $—NH(CH_2)_2R_xR_y$, $—NHCH_2CR_xR_yR_z$, a 5-6 membered aryl, a 5-10 membered heterocycle, a 5-10 membered heteroaryl, or a 5-10 membered heterocyclic aryl, wherein the one to three $R_1$ groups are optionally further substituted with $R_a$ and/or $R_b$, wherein two $R_1$ groups optionally come together to form a 5-6 membered heteroaryl, [5-6 membered heterocycle, 5-6 membered cycloalkyl, 5-6 membered aryl], wherein the 5-6 membered heteroaryl, [5-6 membered heterocycle, 5-6 membered cycloalkyl, 5-6 membered aryl] is optionally further substituted with one to three $R_a$ groups; each $R_2$ independently comprising: halo, $C_{1-2}$ methoxy, or $—C(O)OR_x$; wherein two $R_2$ groups on adjacent atoms optionally come together to from a 5-6 membered aryl, wherein the 5-6 membered aryl is optionally further substituted with one to three $R_a$ groups; $R_3$ comprising: $C_{1-3}$ haloalkyl, or oxo; $R_x$, $R_y$, and $R_z$ each independently comprising: H, halo, $C_{1-2}$ alkyl, $C_{1-2}$ alcohol, $C_{1-2}$ alkoxy, $C_{1-2}$ haloalky, or $—NR_aR_b$, wherein any two of $R_x$, $R_y$, or $R_z$ optionally come together to form a 4-6 membered heterocycle, 5-6 membered aryl, wherein $R_x$, $R_y$, and $R_z$ are each optionally further substituted with $R_a$ and $R_b$; $R_a$ and $R_b$ each independently comprising: H, halo, cyano, oxo, $C_{1-3}$ alkyl, $—C(O)OR'$, $C_{1-3}$ haloalkyl, 5-6 membered aryl, 5-6 membered heteroaryl, or 4-6 membered heterocycle, wherein $R_a$ and $R_b$ are each optionally further substituted with R'; and R' is $C_{1-3}$ alkyl, $C_{1-3}$ haloalkyl, or $C_{5-6}$ membered heteroaryl; and a pharmaceutically acceptable salt thereof.

In some embodiments, each $R_1$ is independently selected from:

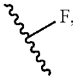 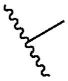, 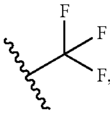 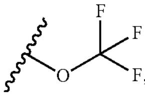

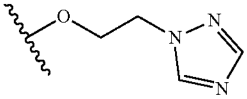, 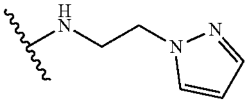,

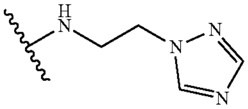, 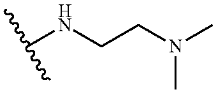,

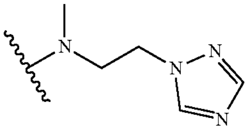, 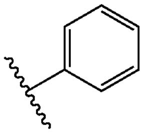, 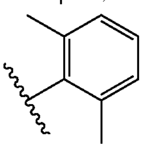,

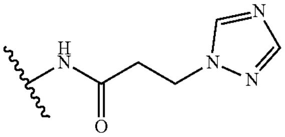, 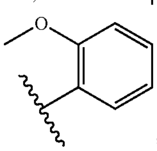,

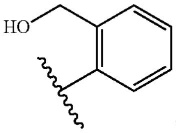, 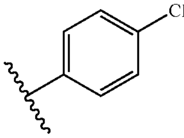

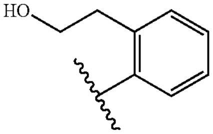, 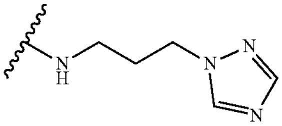,

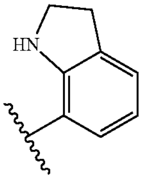, 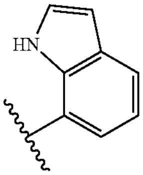, 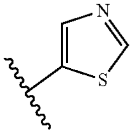,

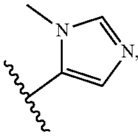 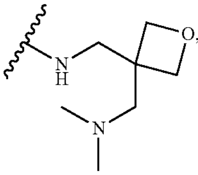 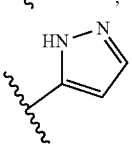,

-continued
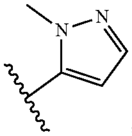, 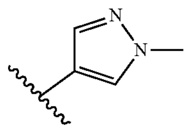, 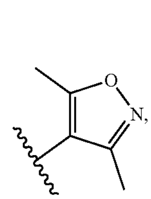
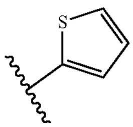, 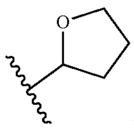,
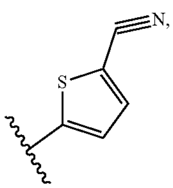
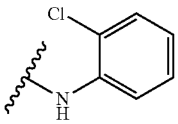, 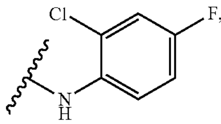
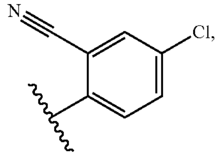 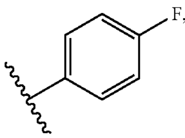
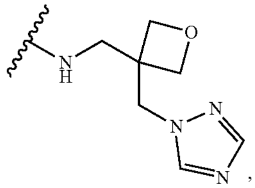
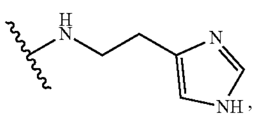
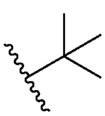, 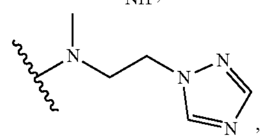, 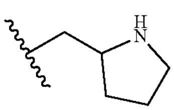,
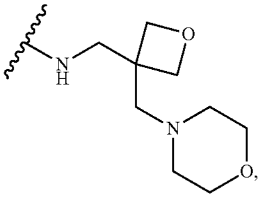
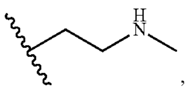,
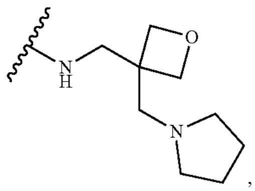, 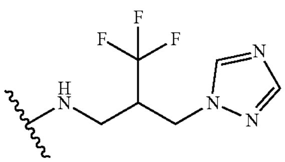,
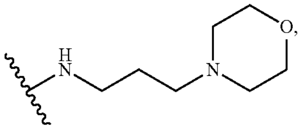 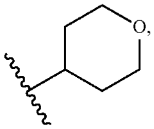
-continued
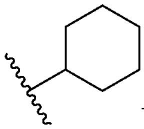 -$NH_2$, 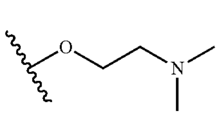,
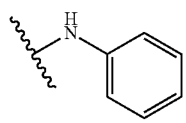, 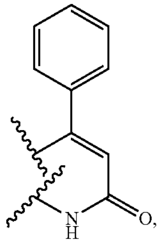, 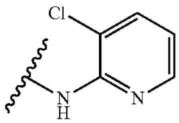,
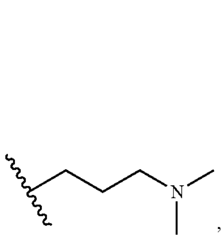, 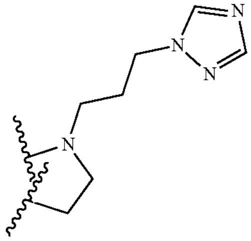,
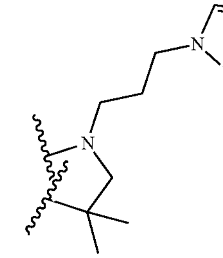, 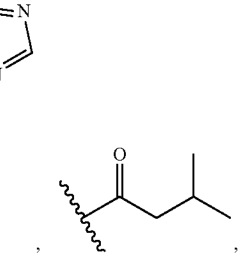,
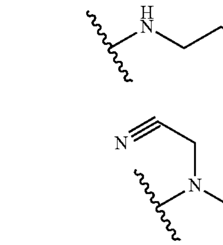
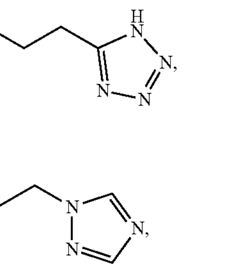
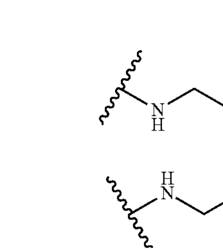 and
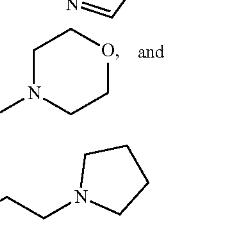.
In some embodiments, wherein each $R_2$ is independently selected from:
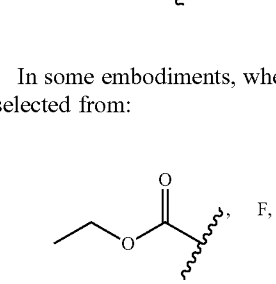 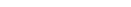, F, Cl, and 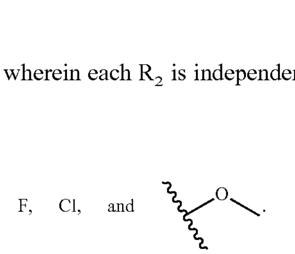 .
In some embodiments, the compound (of Formula I) is selected from:
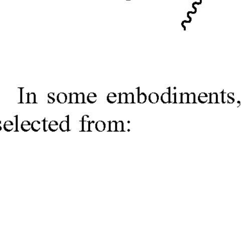 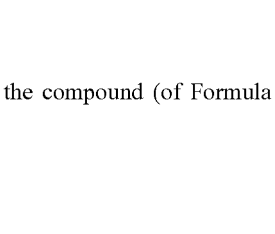

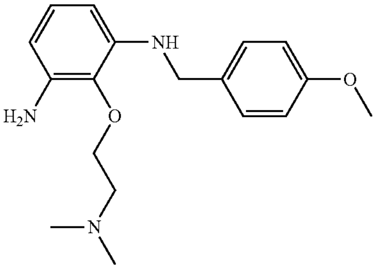
,
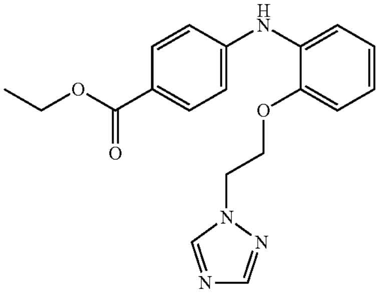
,
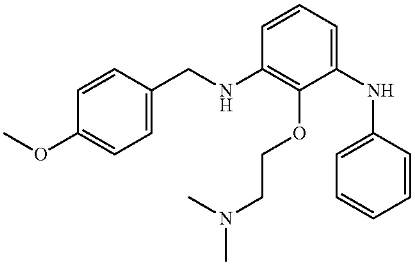
,
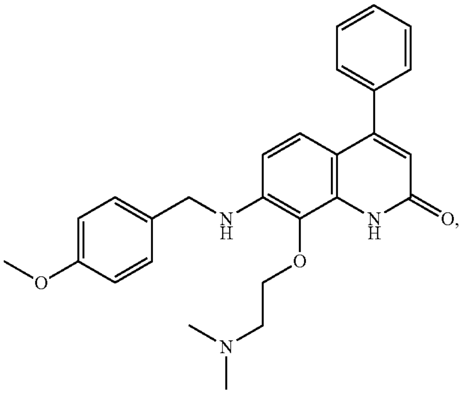
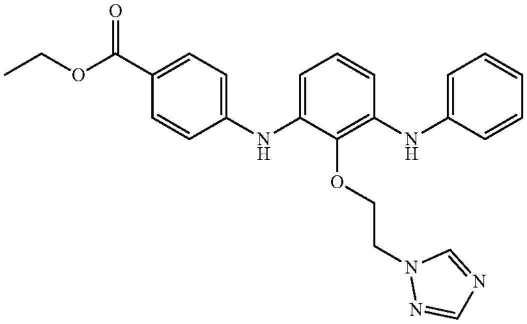
,
-continued
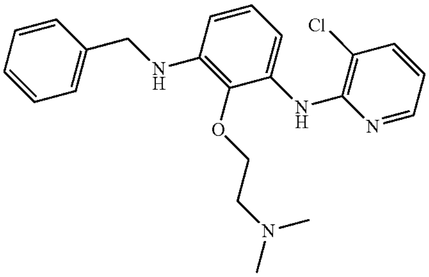
,
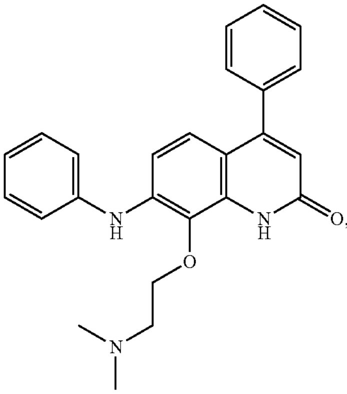
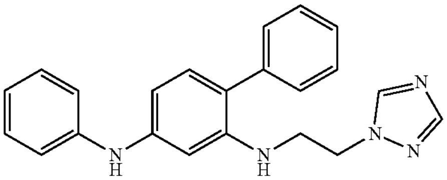
,
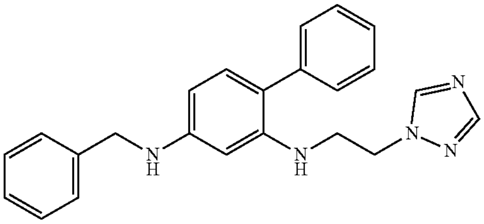
,
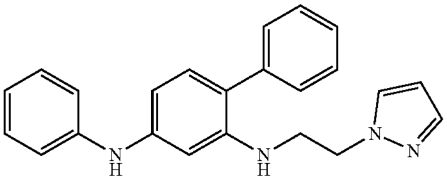
,
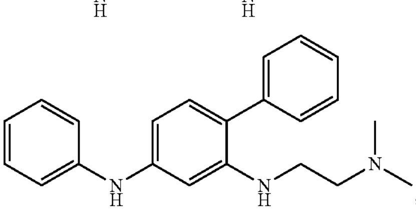
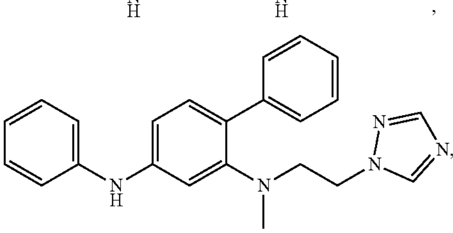

-continued
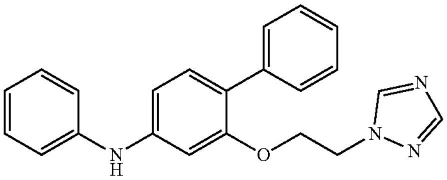
,
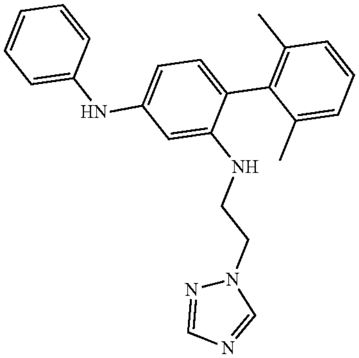
,
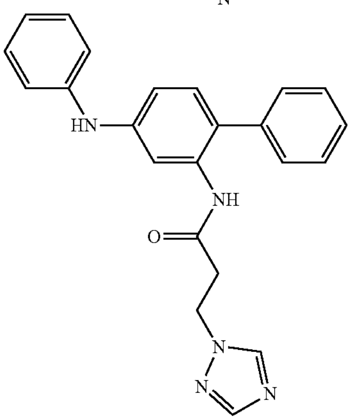
,
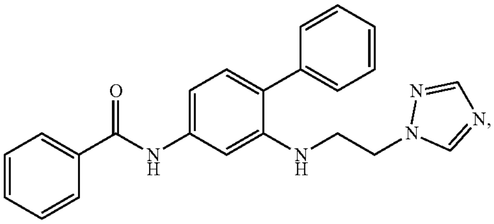
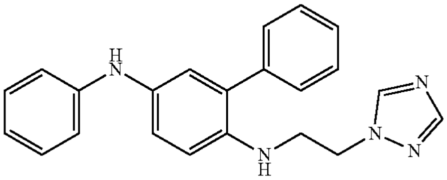
,
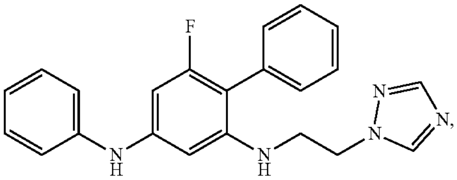
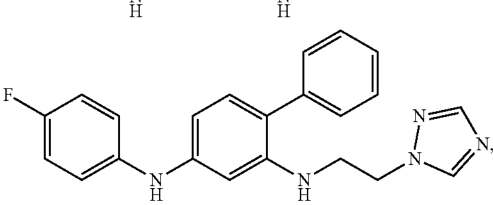
-continued
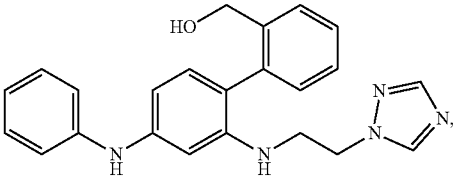
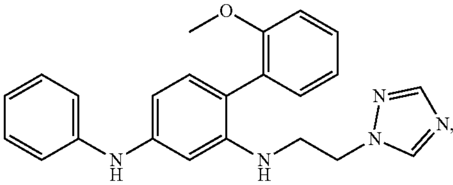
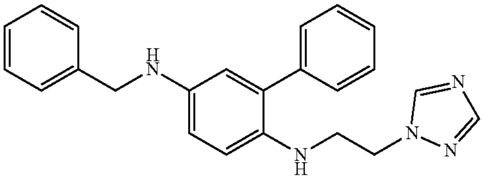
,
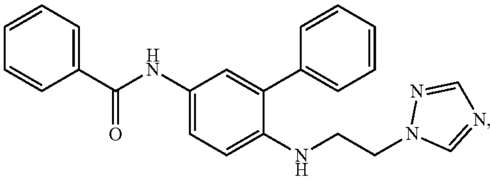
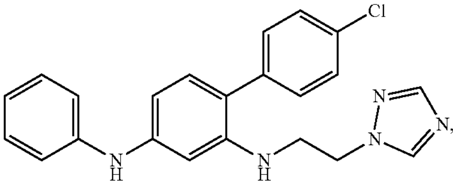
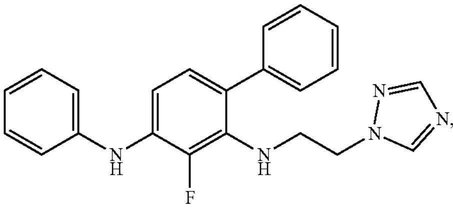
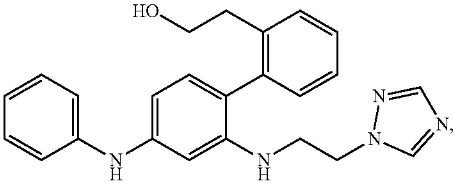
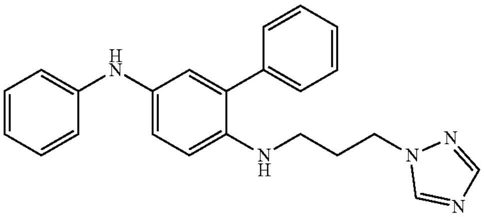
, -continued
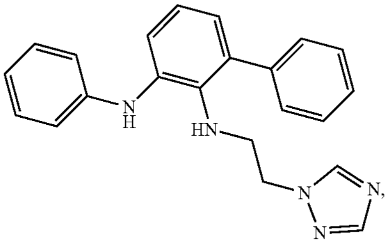
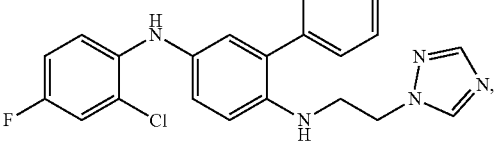
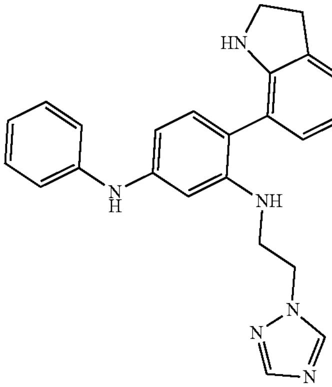
,
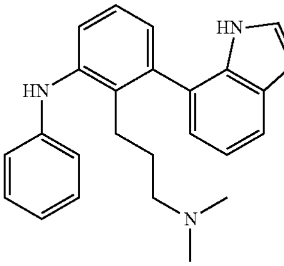
,
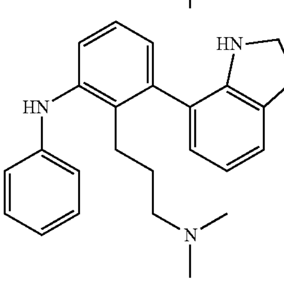
,
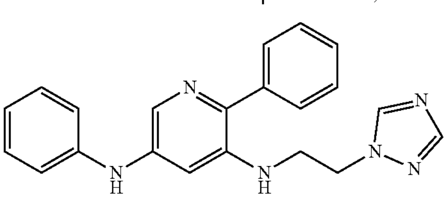
,
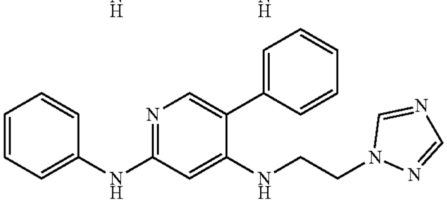
,
-continued
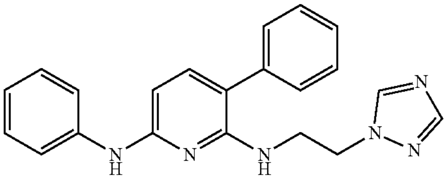
,
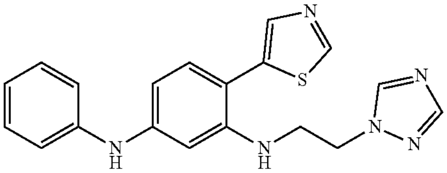
,
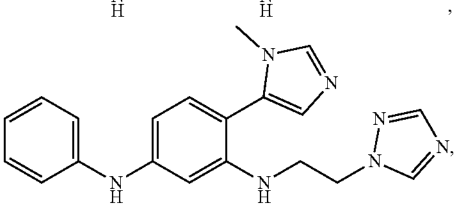
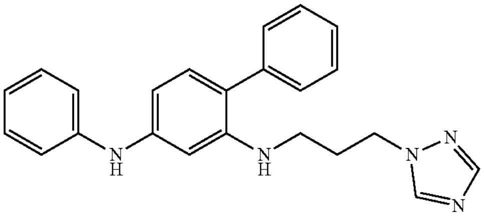
,
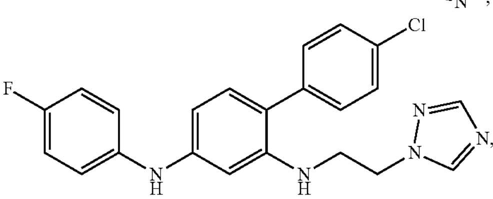
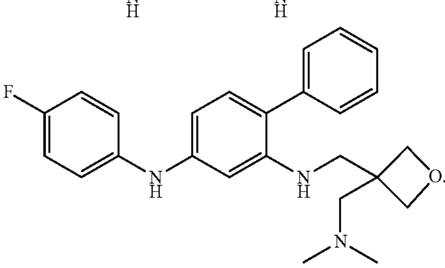
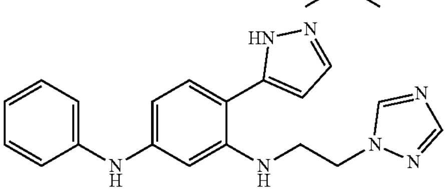
,
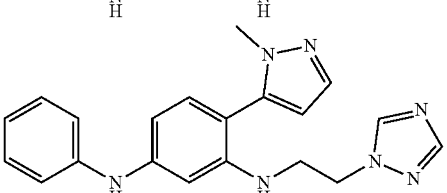
,
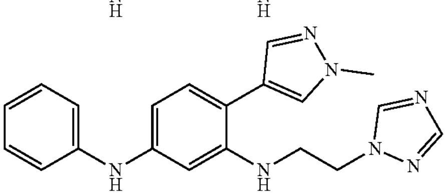
, -continued
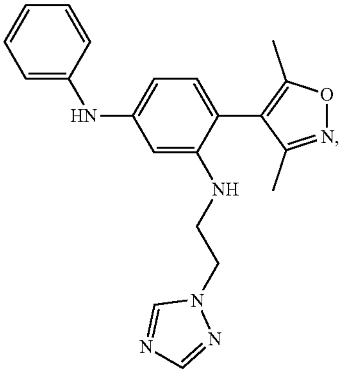
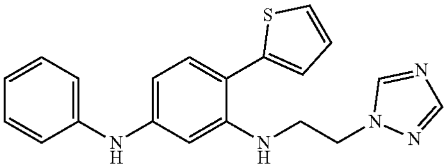
,
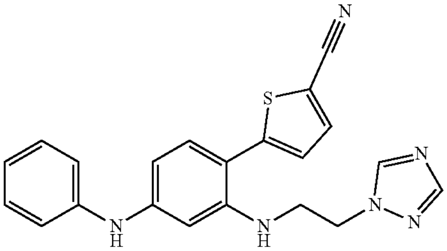
,
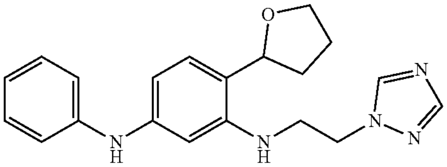
,
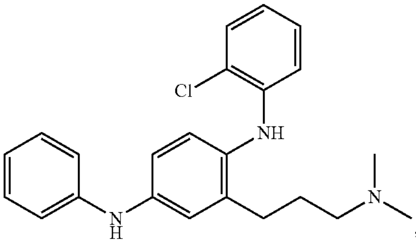
,
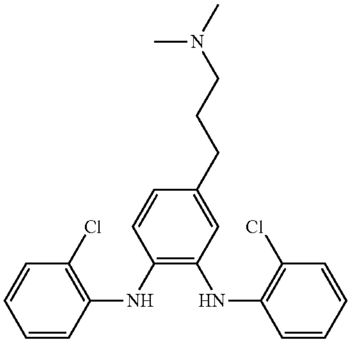
,
-continued
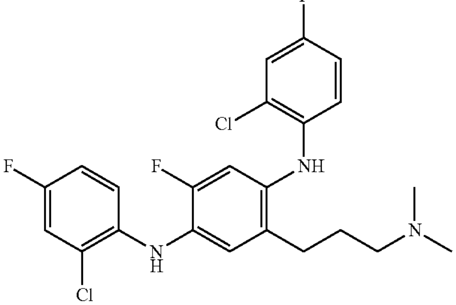
,
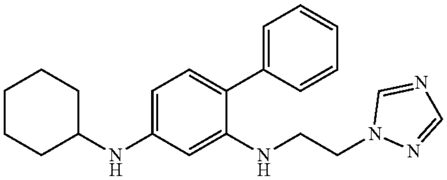
,
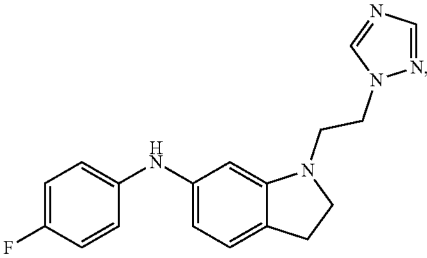
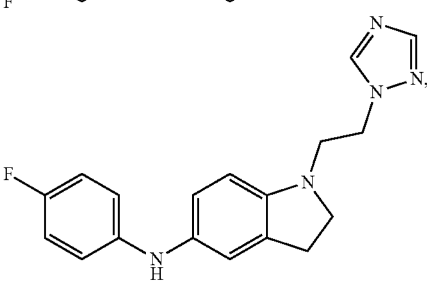
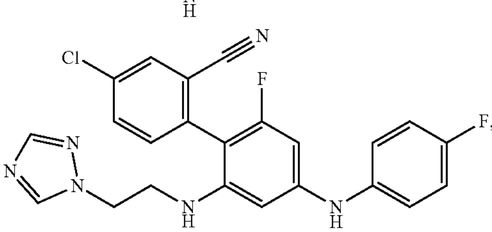
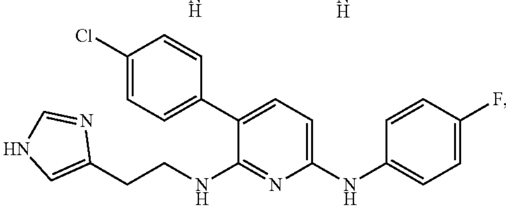
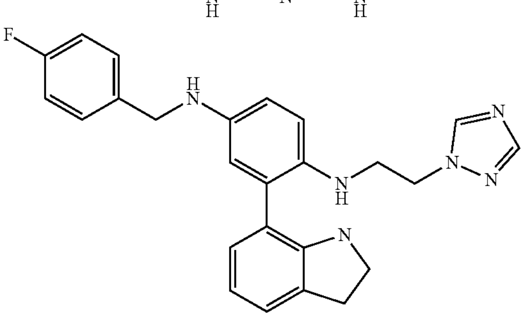
, -continued
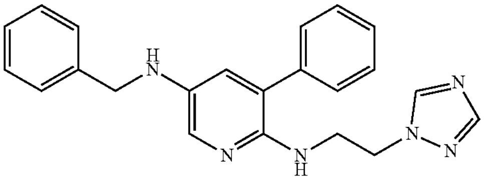
,
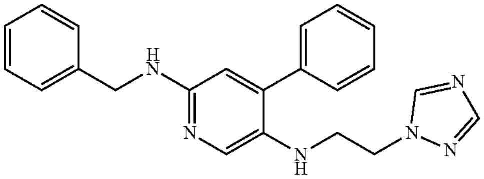
,
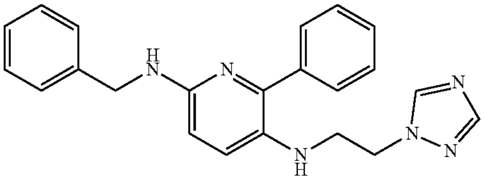
,
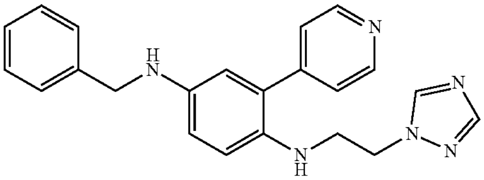
,
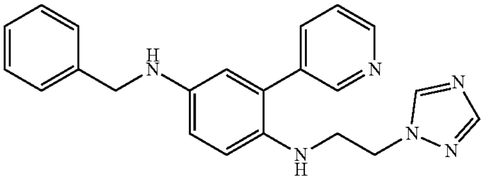
,
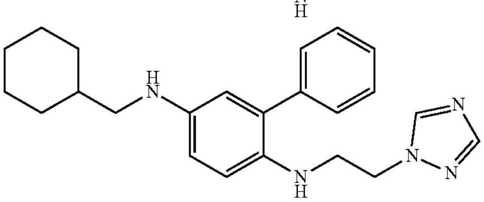
,
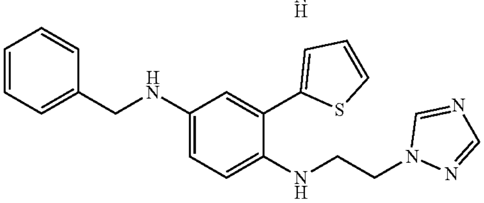
,
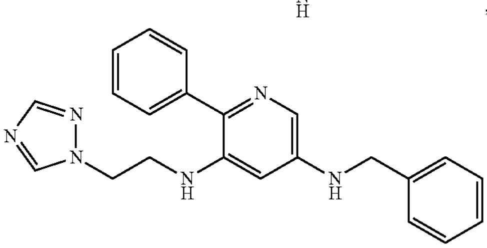
,
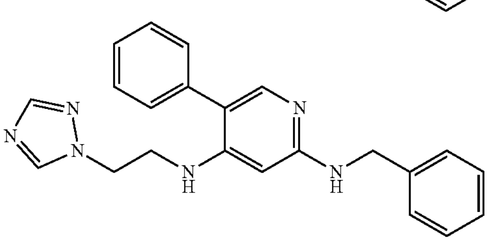
,
-continued
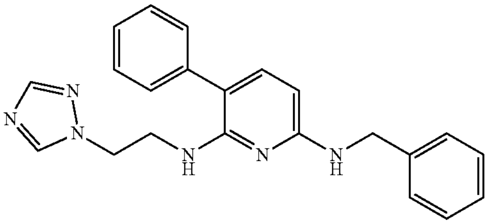
,
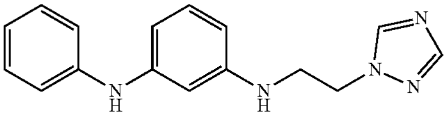
,
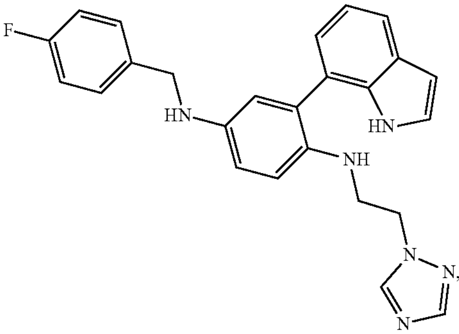
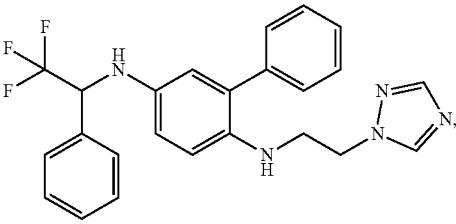
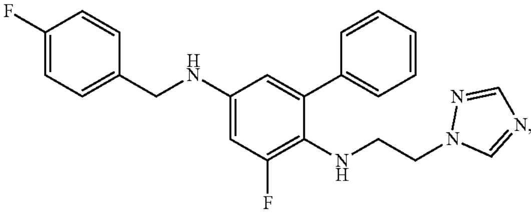
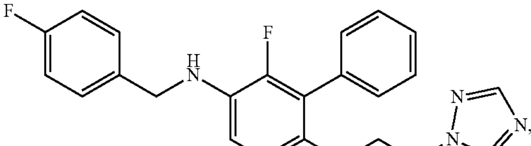
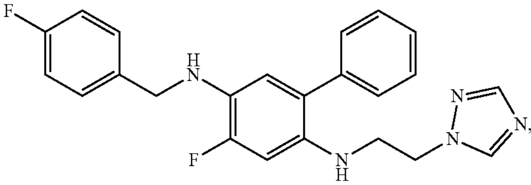

-continued
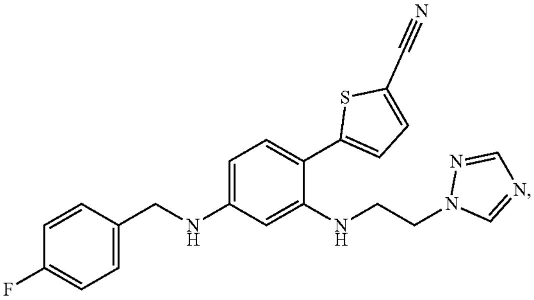
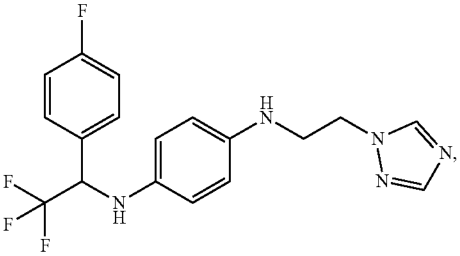
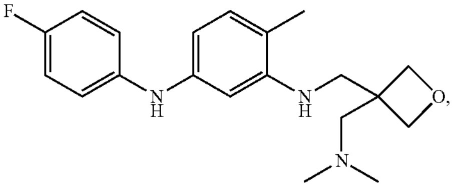
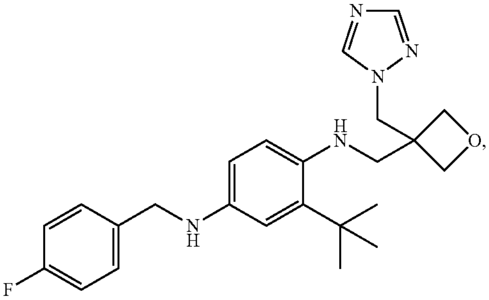
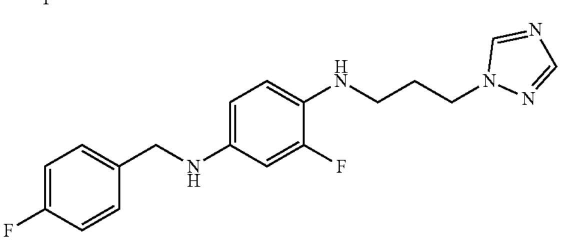
,
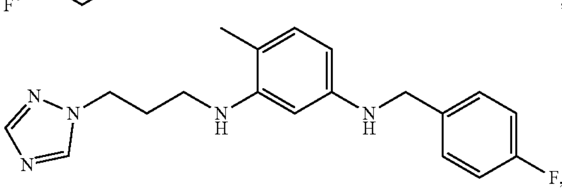
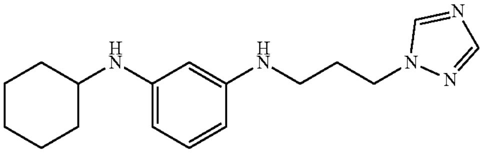
,
-continued
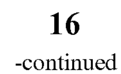
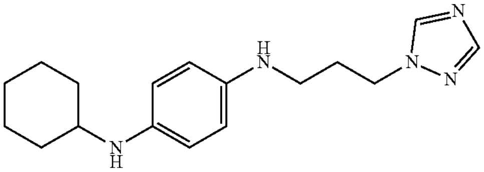
,
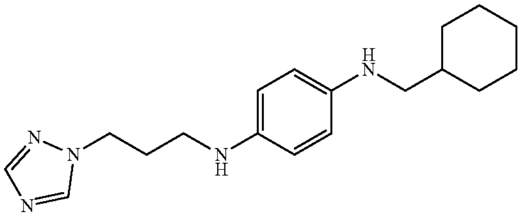
,
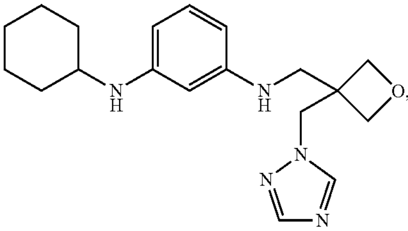
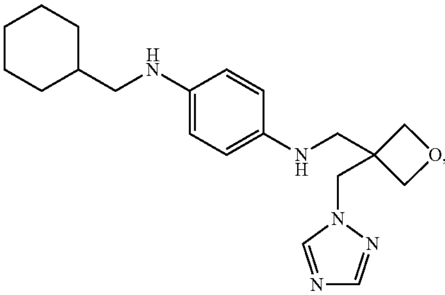
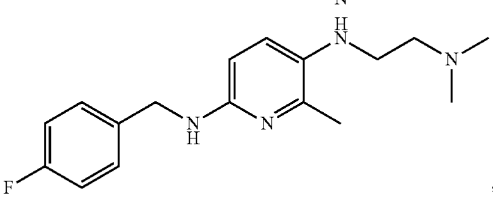
,
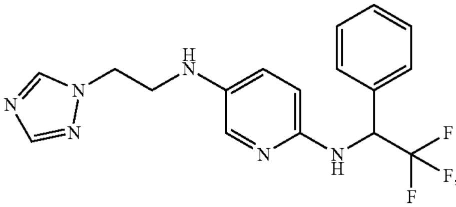
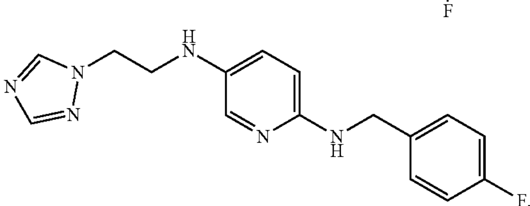
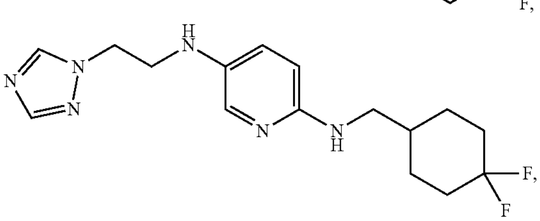

-continued
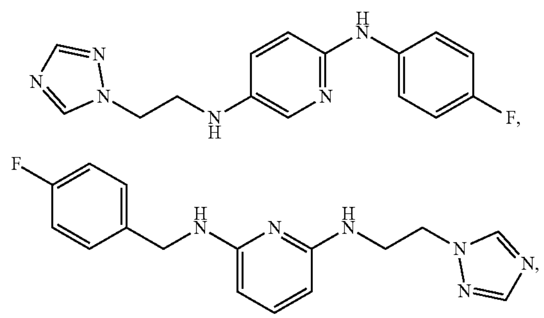
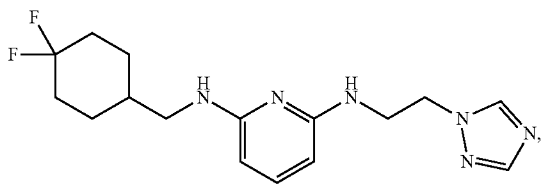
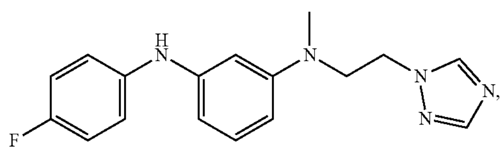
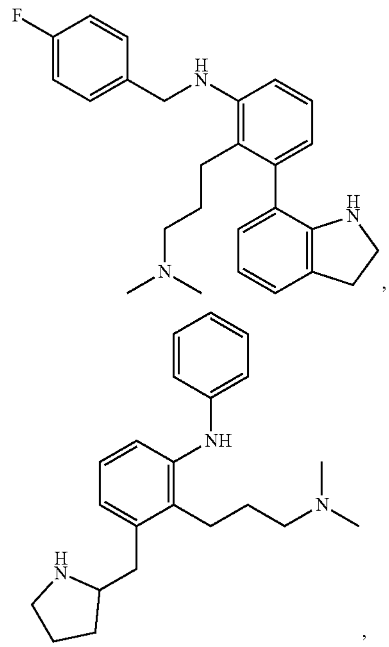
,
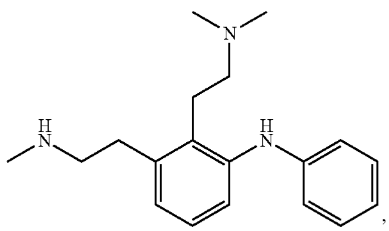
,
-continued
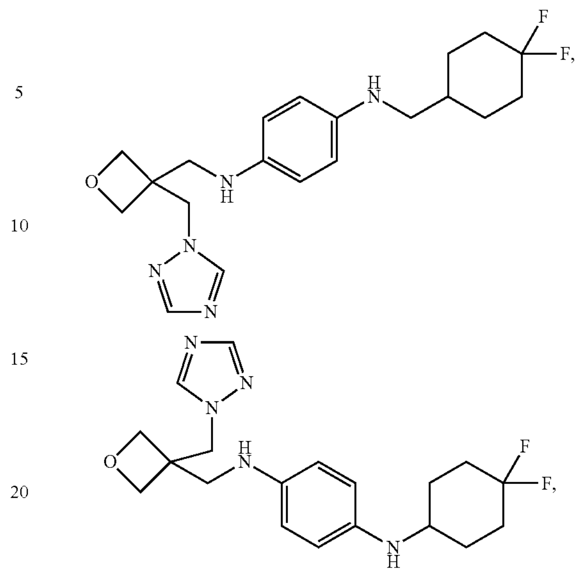
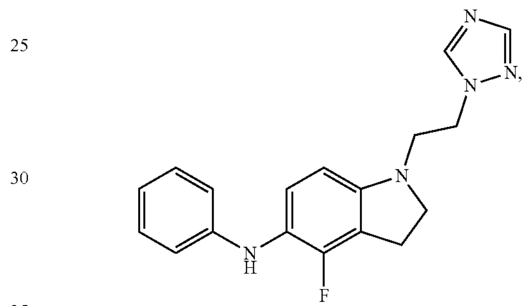
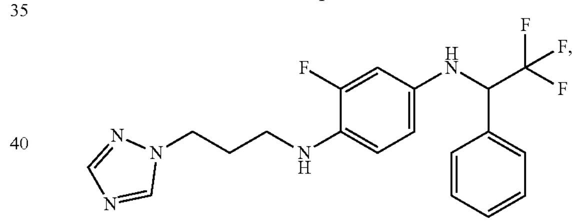
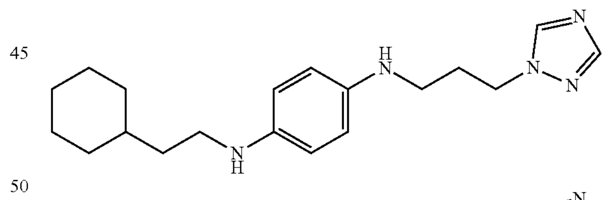
,
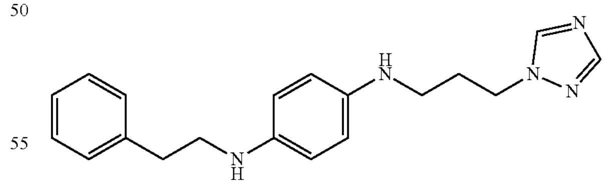
,
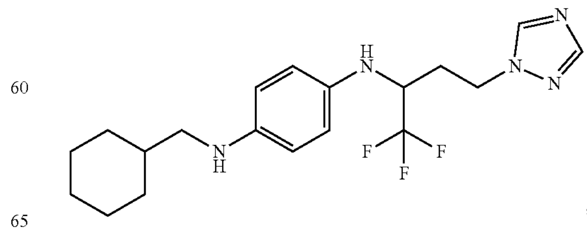
, -continued
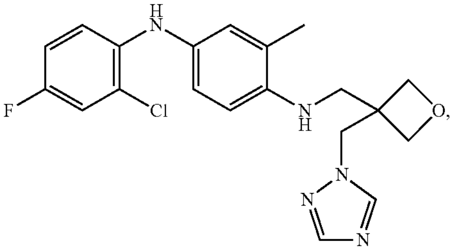
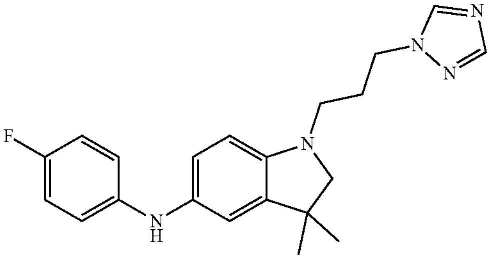
,
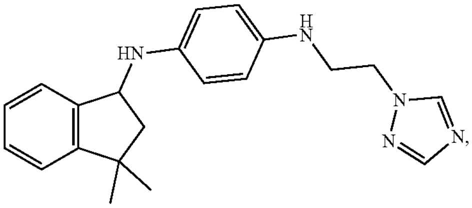
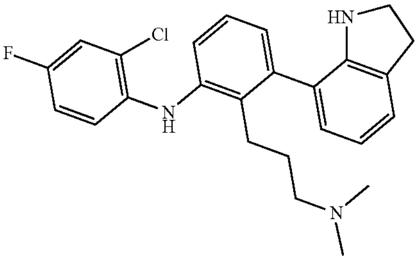
,
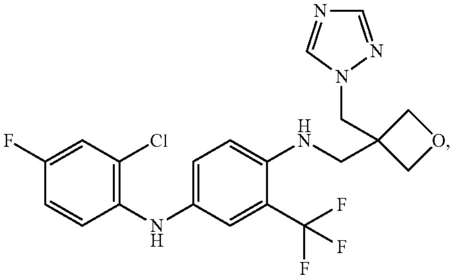
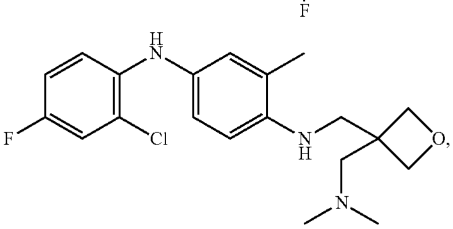
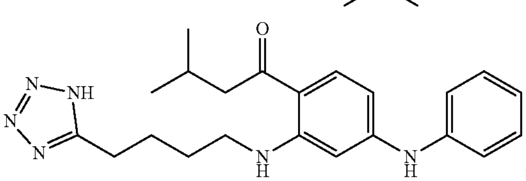
,
-continued
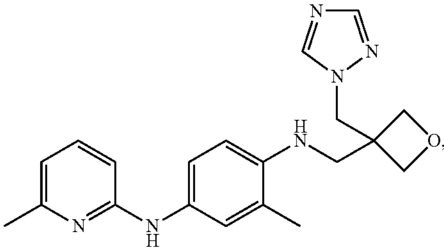
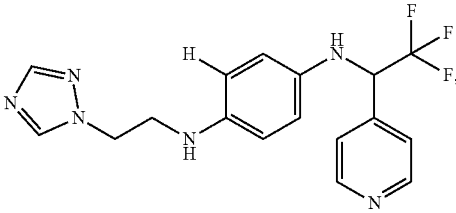
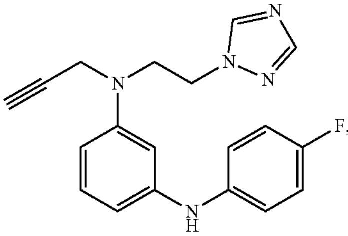
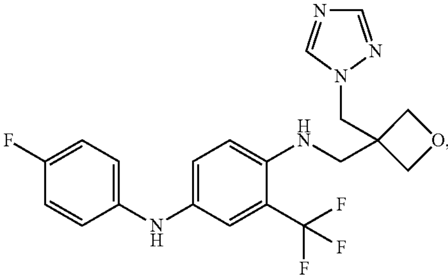
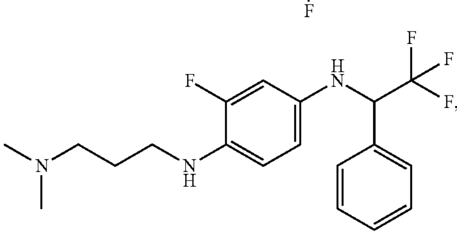
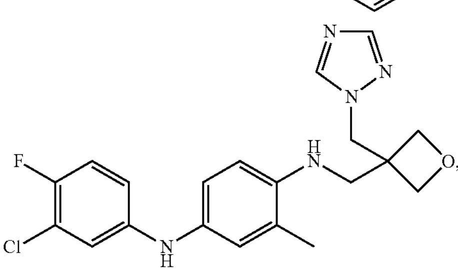
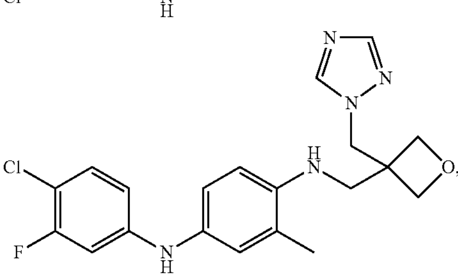

-continued
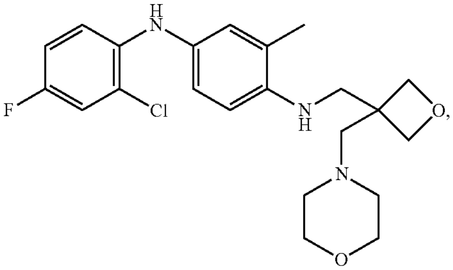
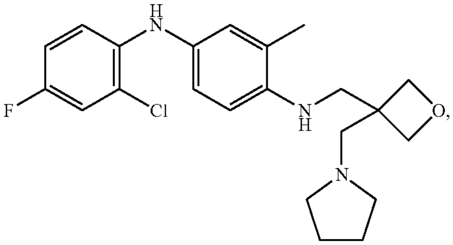
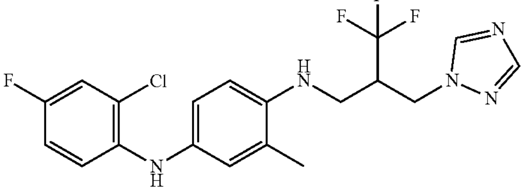
,
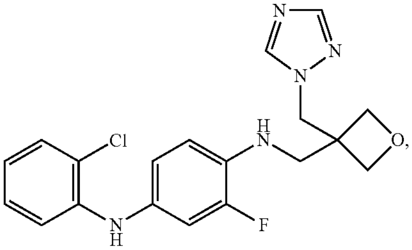
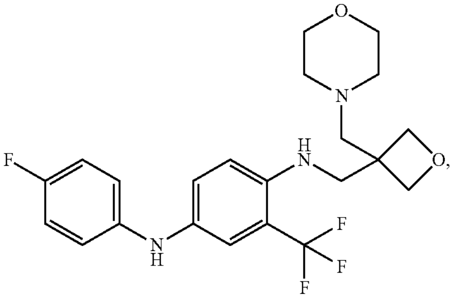
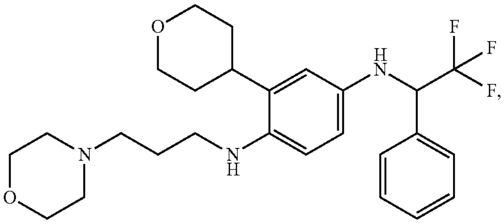
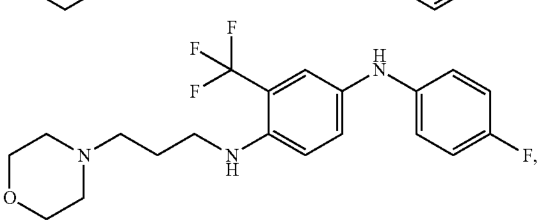
-continued
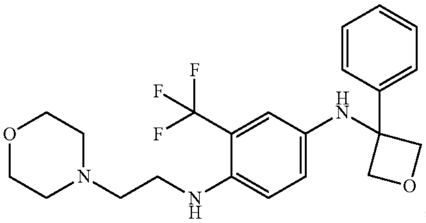
,
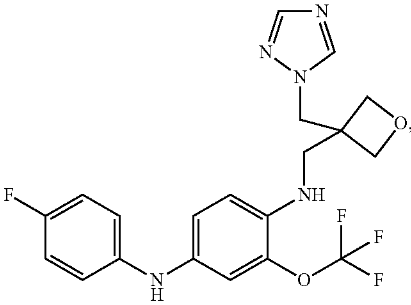
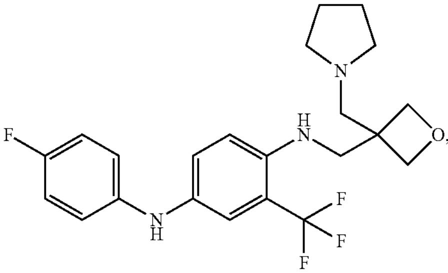
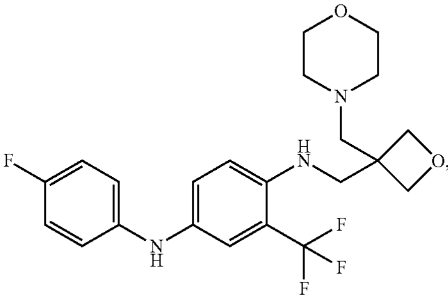
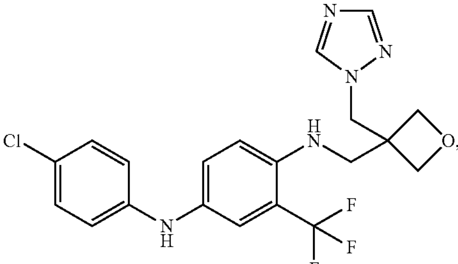
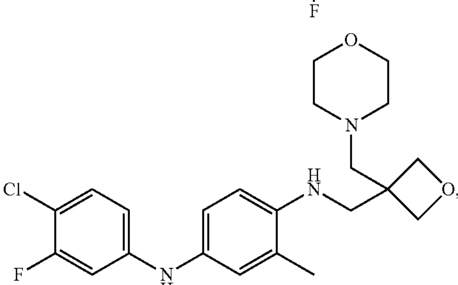

-continued

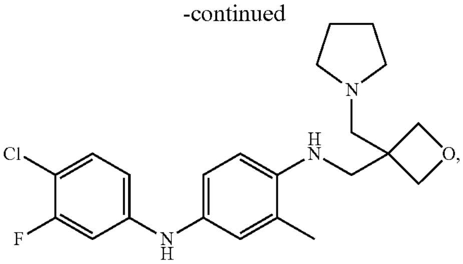

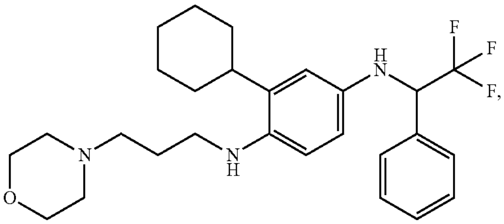

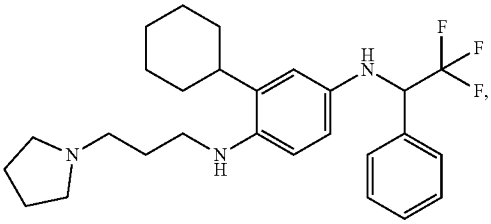

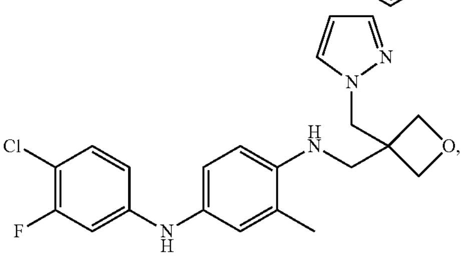

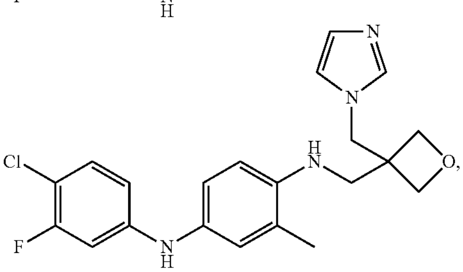

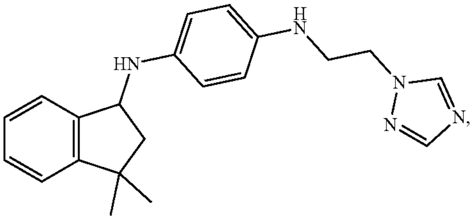

and pharmaceutically acceptable salts thereof.

Various embodiments of the present disclosure are directed to a compound having Formula II:

Formula II

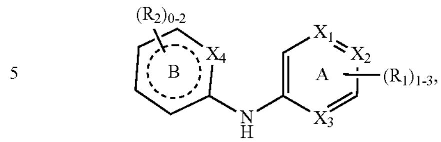

wherein A is a 6 membered heteroaryl or a 6 membered aryl, wherein the 6 membered heteroaryl or 6 membered aryl is independently substituted with one to three $R_1$ groups; B is a 6 membered heterocycle, a 6 membered aryl, or a 6 membered cyclohexyl, wherein the 6 membered heterocycle, 6 membered aryl, or 6 membered cyclohexyl is either unsubstituted or independently substituted with up to two $R_2$ groups; each $X_1$, $X_2$, $X_3$, and $X_4$ independently comprising: C, N, or O; each $R_1$ independently comprising: halo, $C_{1-4}$ alkyl, $—NR_xR_y$, $—O(CH_2)_2R_xR_y$, $—O(CH_2)_2NR_xR_y$, $—NHC(O)\text{-alkyl}_{(2-4)}$, $—(CH_2)_3NR_xR_y$, $—NH(CH_2)_2R_xR_y$, $—NHCH_2CR_xR_yR_z$, a 5-6 membered aryl, a 5-10 membered heterocycle, a 5-10 membered heteroaryl, or a 5-10 membered heterocyclic aryl, wherein two $R_1$ groups optionally come together to form a 5-6 membered heteroaryl, [5-6 membered heterocycle, 5-6 membered cycloalkyl, 5-6 membered aryl], wherein the 5-6 membered heteroaryl, [5-6 membered heterocycle, 5-6 membered cycloalkyl, 5-6 membered aryl] is optionally further substituted with one to three $R_a$ groups, wherein each of the one to three $R_1$ groups are optionally independently further substituted with $R_a$ or $R_b$; each $R_2$ independently comprising: halo, $C_{1-2}$ methoxy, or $—C(O)OR_x$; each $R_x$, $R_y$, and $R_z$ independently comprising: H, halo, $C_{1-2}$ alkyl, $C_{1-2}$ alcohol, $C_{1-2}$ alkoxy, $C_{1-2}$ haloalkyl, or $—NR_aR_b$, wherein two of $R_x$, $R_y$, or $R_z$ optionally come together to form a 4-6 membered heterocycle, 5-6 membered aryl, wherein each of the $R_x$, $R_y$, and $R_z$ are optionally further substituted with $R_a$ and $R_b$; $R_a$ and $R_b$ each independently comprising: H, halo, cyano, oxo, $C_{1-3}$ alkyl, $—C(O)OR'$, $C_{1-3}$ haloalkyl, a 5-6 membered aryl, a 5-6 membered heteroaryl, or a 4-6 membered heterocycle, wherein $R_a$ and $R_b$ are optionally and independently further substituted with R'; and R' is $C_{1-3}$ alkyl, $C_{1-3}$ haloalkyl, or a 5-6 membered heteroaryl; or a pharmaceutically acceptable salt thereof.

In some embodiments, each $R_1$ is independently selected from:

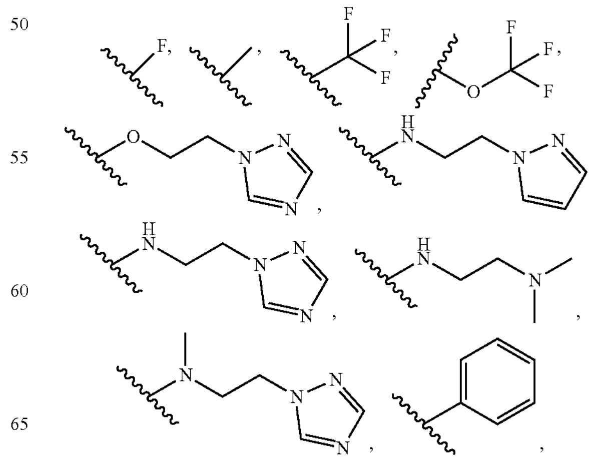

-continued
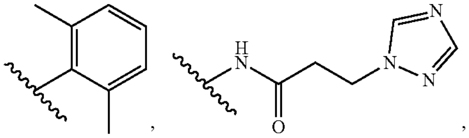
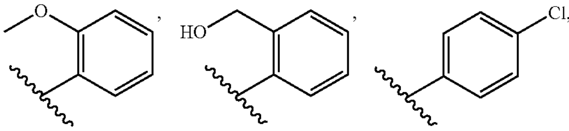
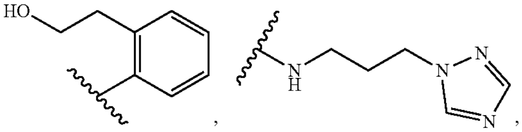
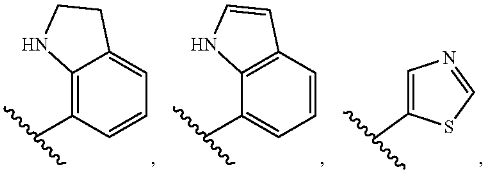
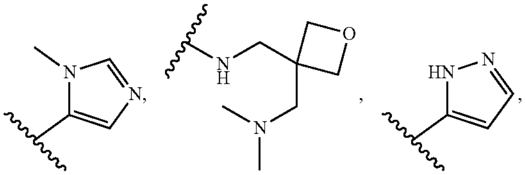
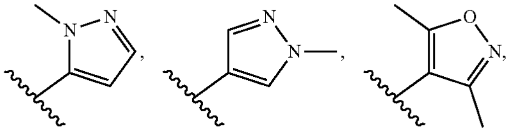
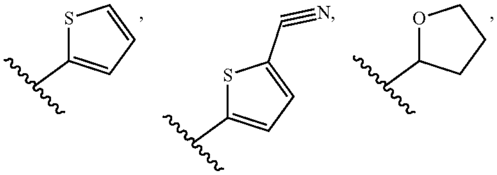
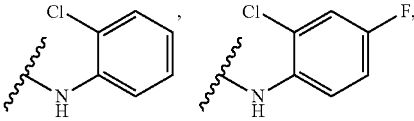
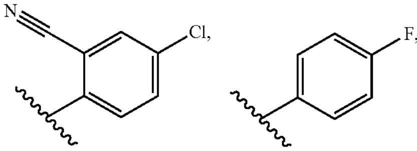
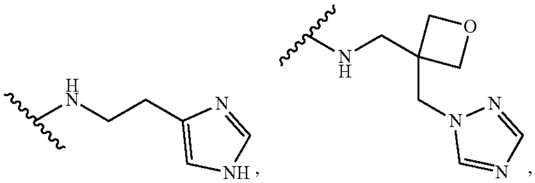
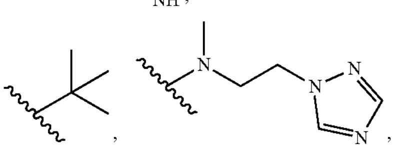
-continued
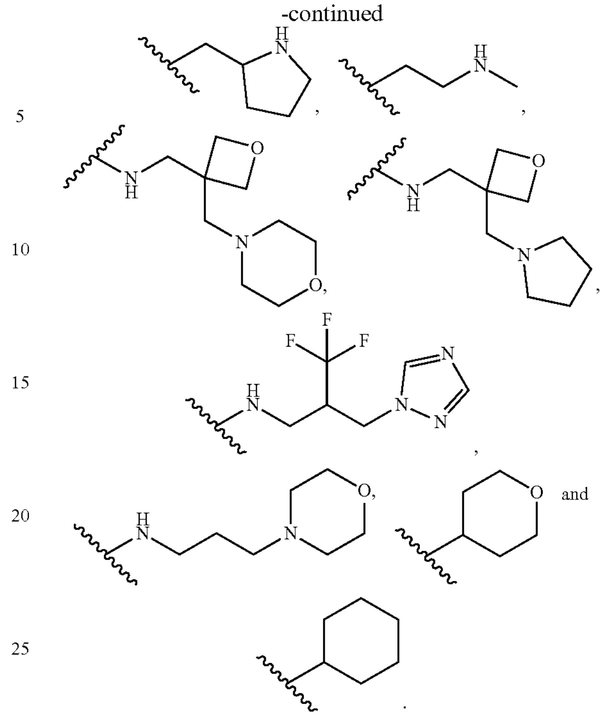
In some embodiments, each $R_2$ is independently selected from:
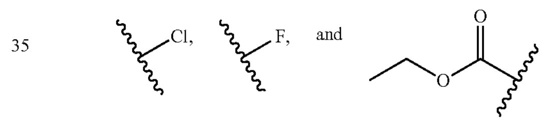
In some embodiments, the compound (of Formula II) is selected from:
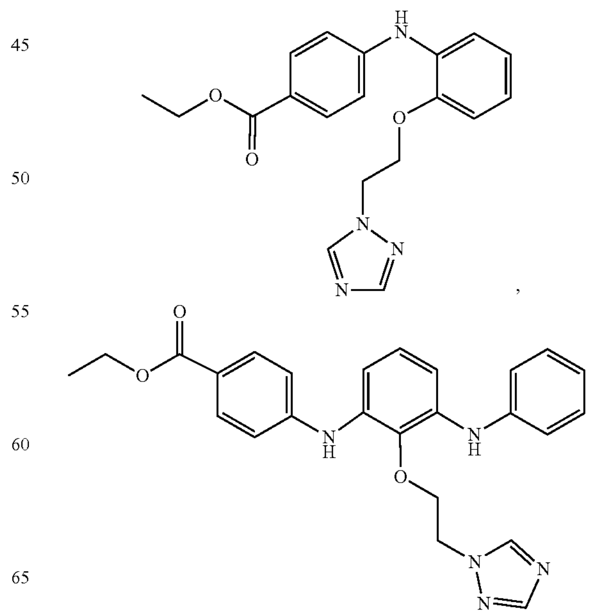

-continued
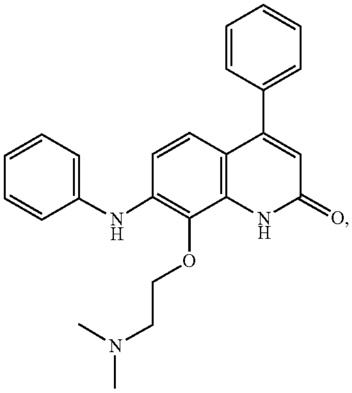
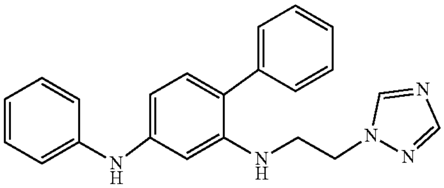
,
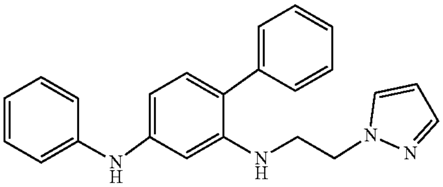
,
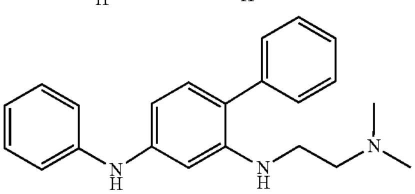
,
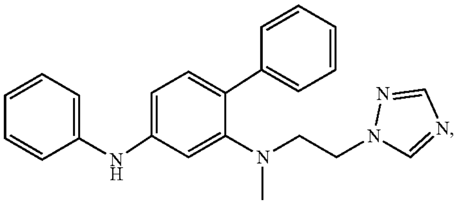
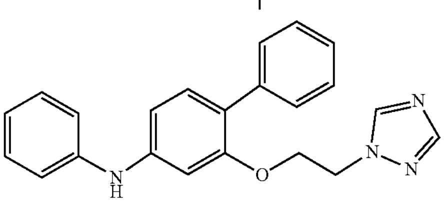
,
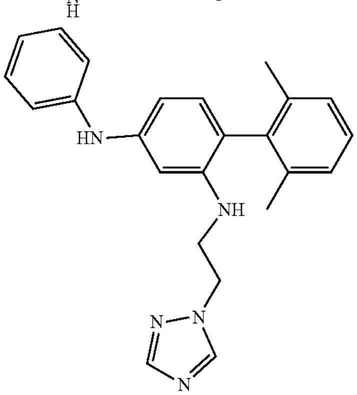
,
-continued
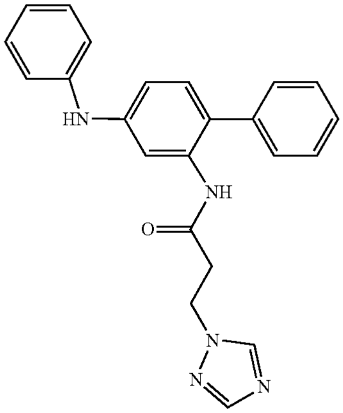
,
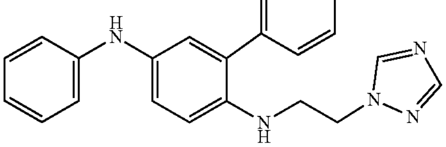
,
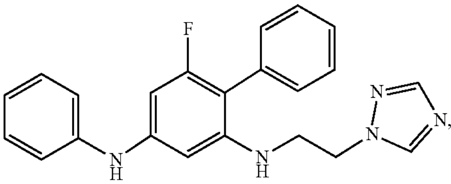
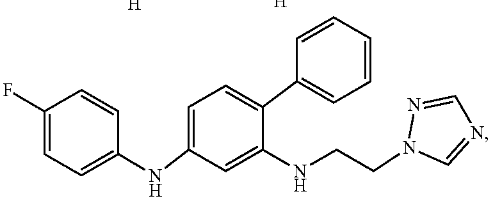
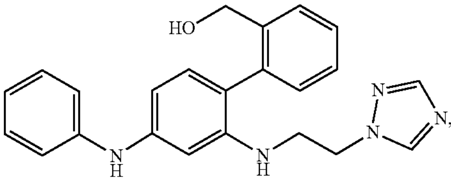
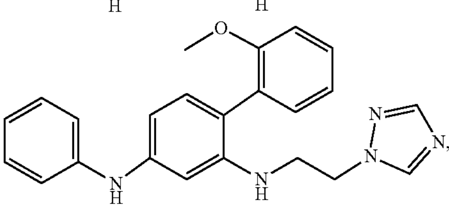
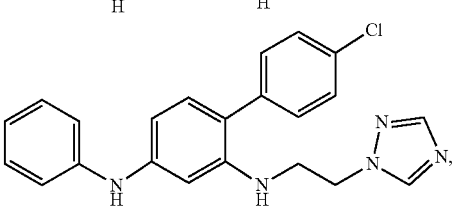
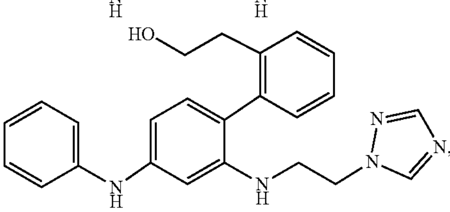

-continued
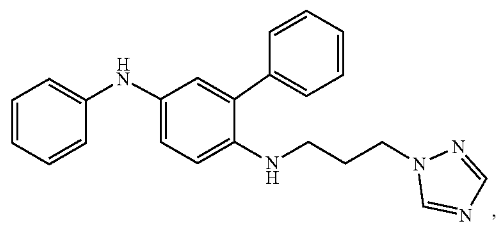
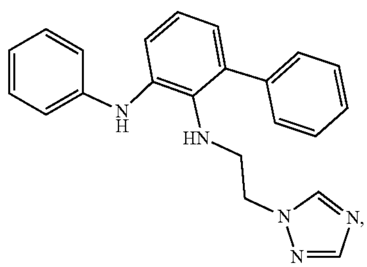
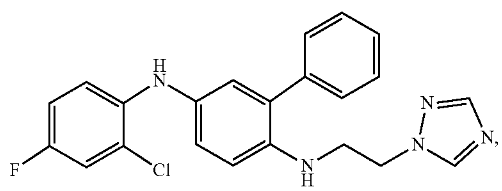
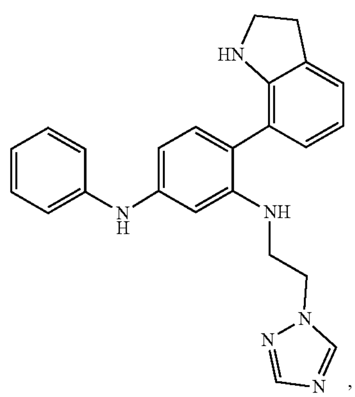
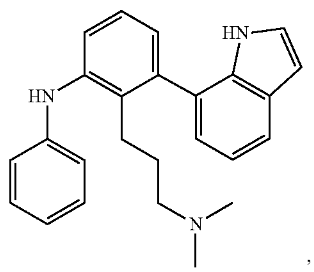
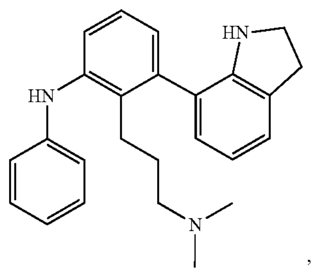
-continued
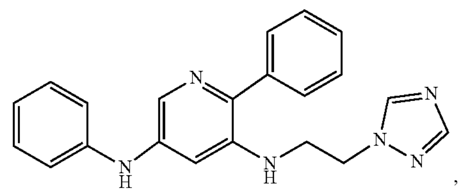
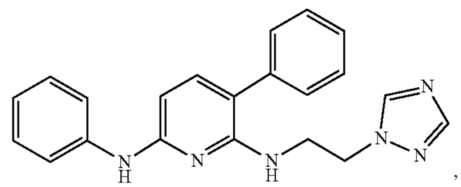
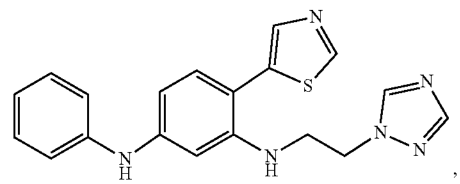
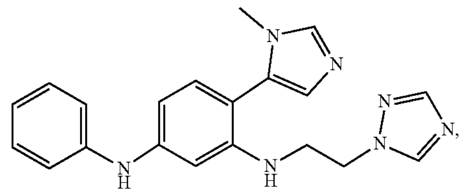
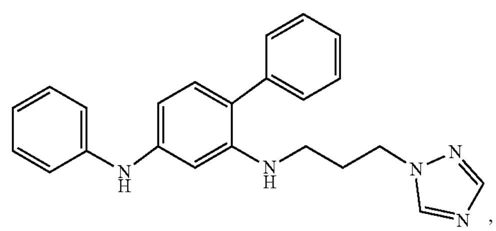
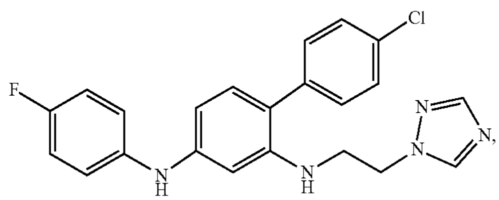
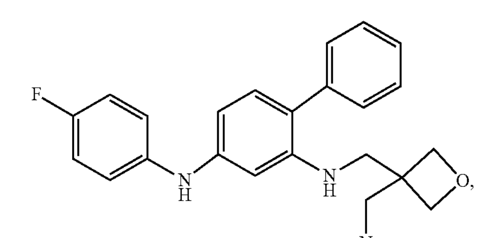
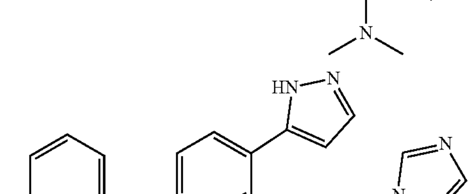

-continued
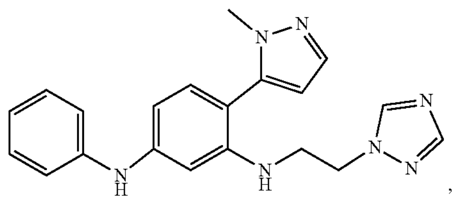
,
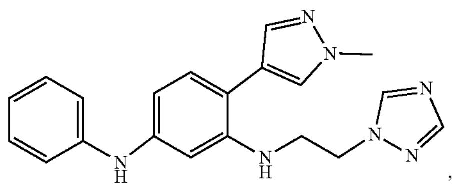
,
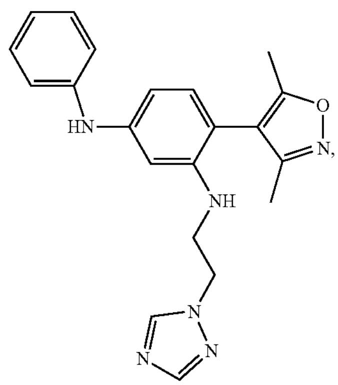
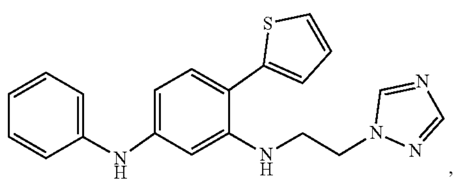
,
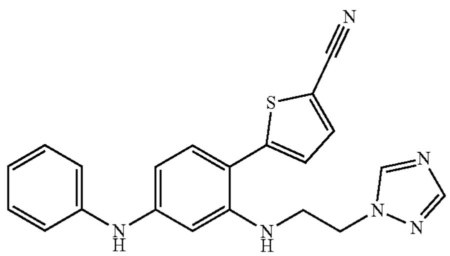
,
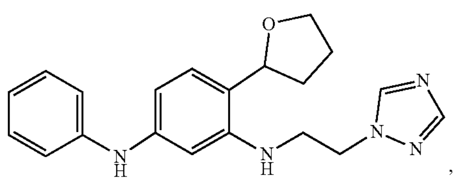
,
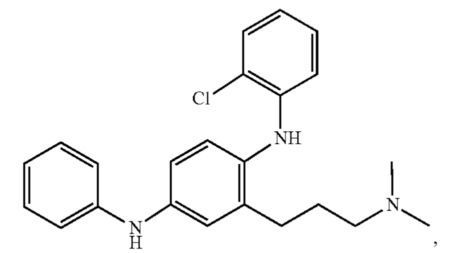
,
-continued
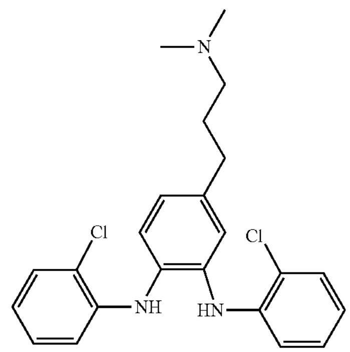
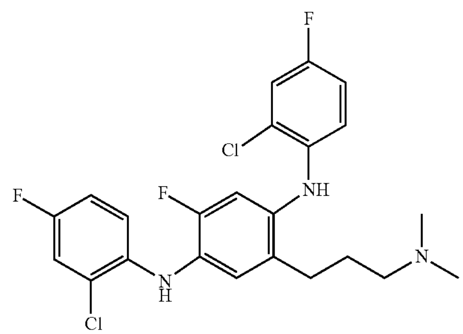
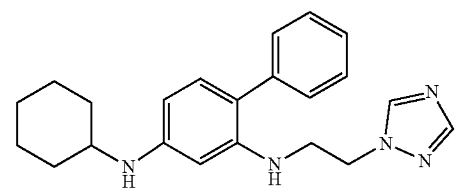
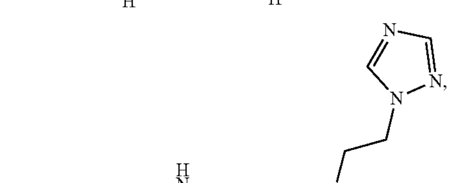
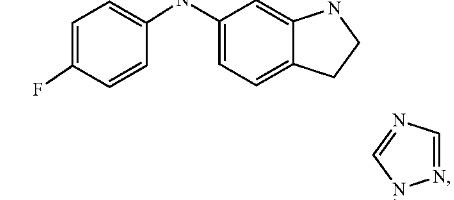
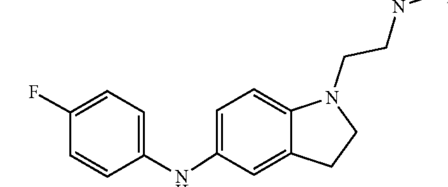
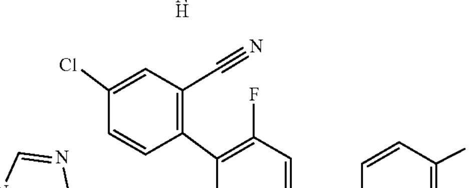
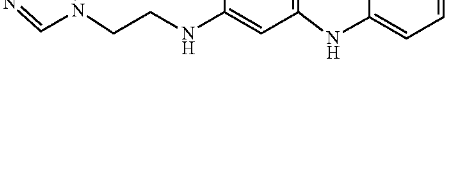

-continued
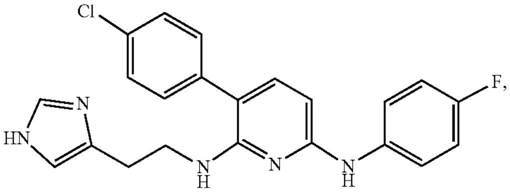
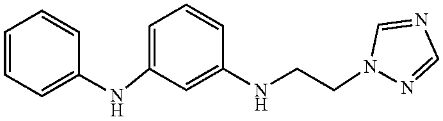
,
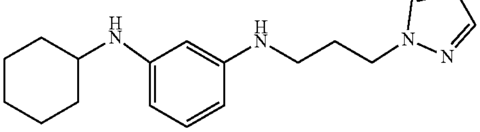
,
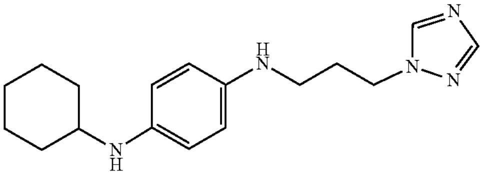
,
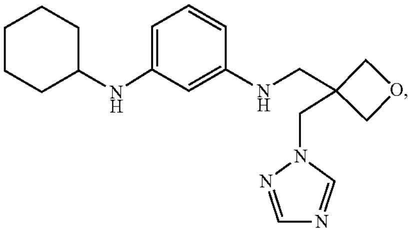
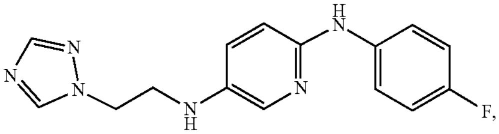
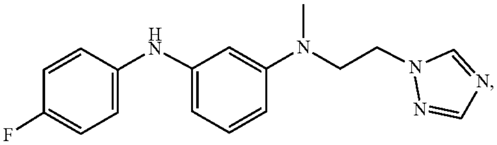
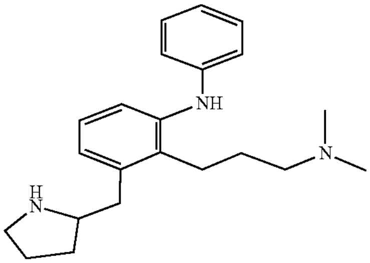
,
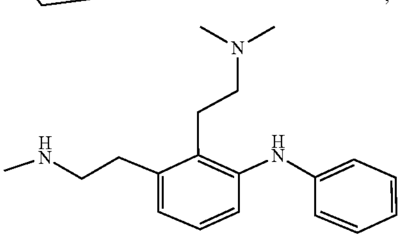
-continued
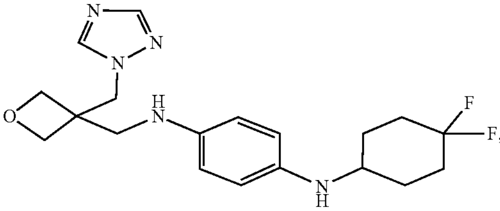
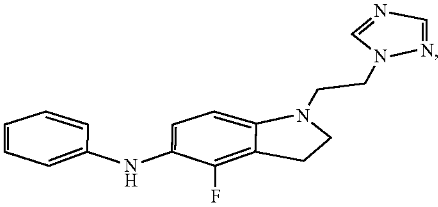
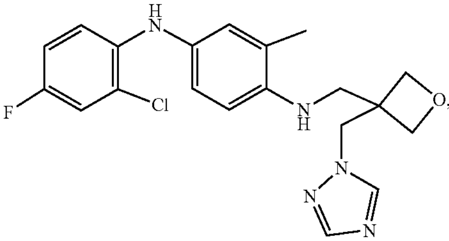
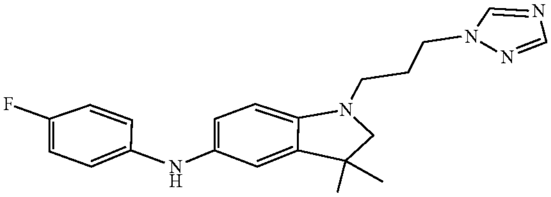
,
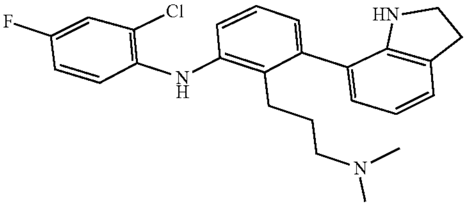
,
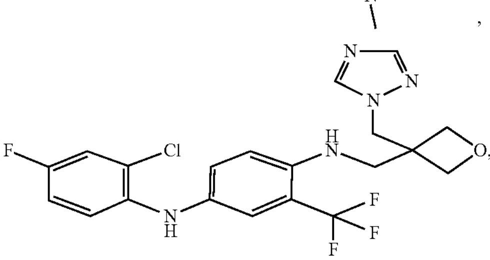
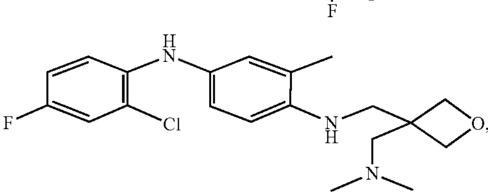
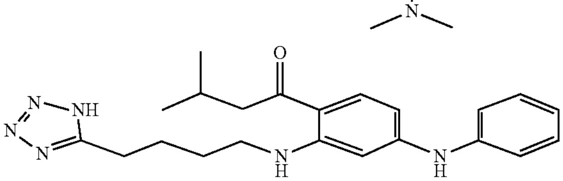
, -continued

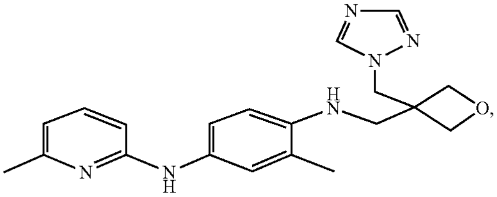

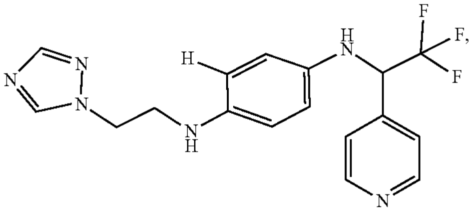

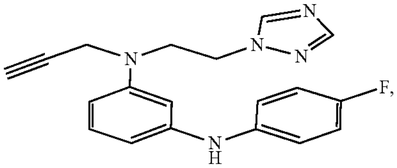

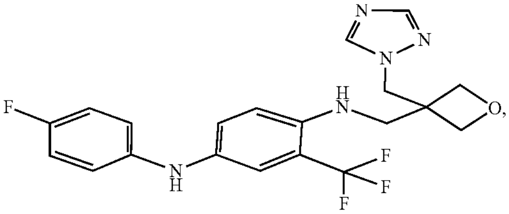

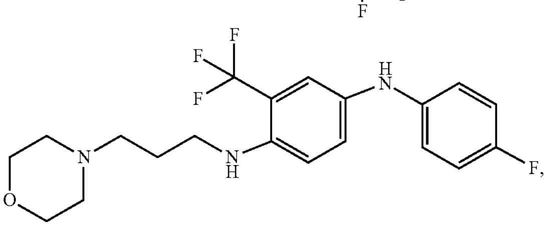

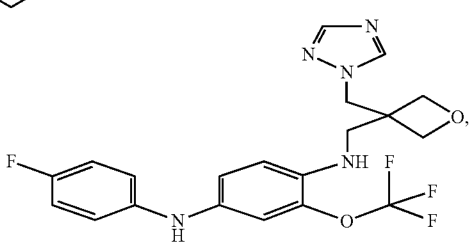

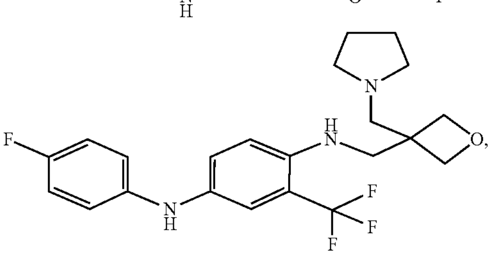

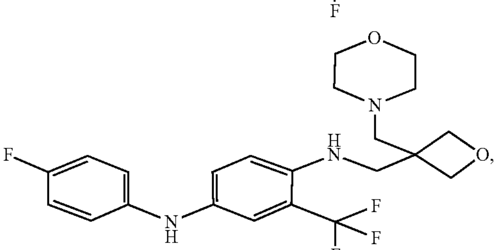

-continued

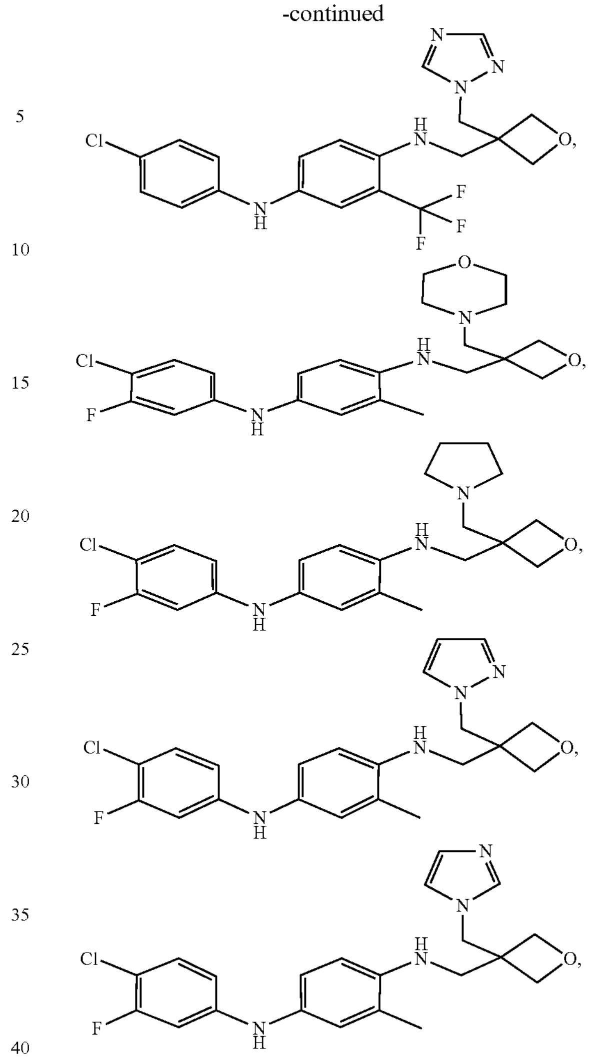

and pharmaceutically acceptable salts thereof.

Various embodiments are directed to a compound having Formula IIA:

Formula IIA

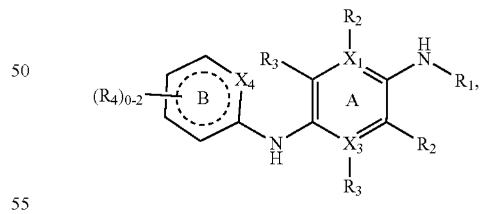

wherein: B is cyclohexyl, a 6-membered heterocycle, a 6-membered aryl, or a 6-membered heteroaryl; $X_1$ $X_3$, and $X_4$ are each independently C, N, or O; $R_1$ is $—C_{1-3}$ alkyl-$R_x$, $—(CH_2)_2NR_xR_y$, $—CH_2C(R_xR_y)R_a$, $—CH_2C(R_xR_y)NR_aR_b$, or a 5-6 membered aryl, wherein $R_1$ is optionally further substituted with $R_a$ or $R_b$; $R_2$ is H, halo, $C_{1-3}$ alkyl, $C_{1-3}$ haloalkyl, or $C_{1-3}$ haloalkoxy, wherein $R_1$ and $R_2$ optionally come together to form a 5-6 membered heterocycle, wherein the 5-6 membered heterocycle is optionally further substituted with $R_a$ or $R_b$, or both $R_a$ and $R_b$; $R_4$ is halo, or $C_{1-3}$ alkyl; $R_x$ and $R_y$ are each independently a $C_{5-6}$ membered heterocycle, $R_a$ and $R_b$ are each independently $C_{1-3}$ alkyl or $C_{1-3}$ haloalkyl, wherein $R_a$ and $R_b$ are optionally further substituted with a R' group; R' group is a 5 membered heteroaryl or a 5-6 membered heterocycle; and pharmaceutically acceptable salts thereof.

In some embodiments, $R_1$ is selected from:

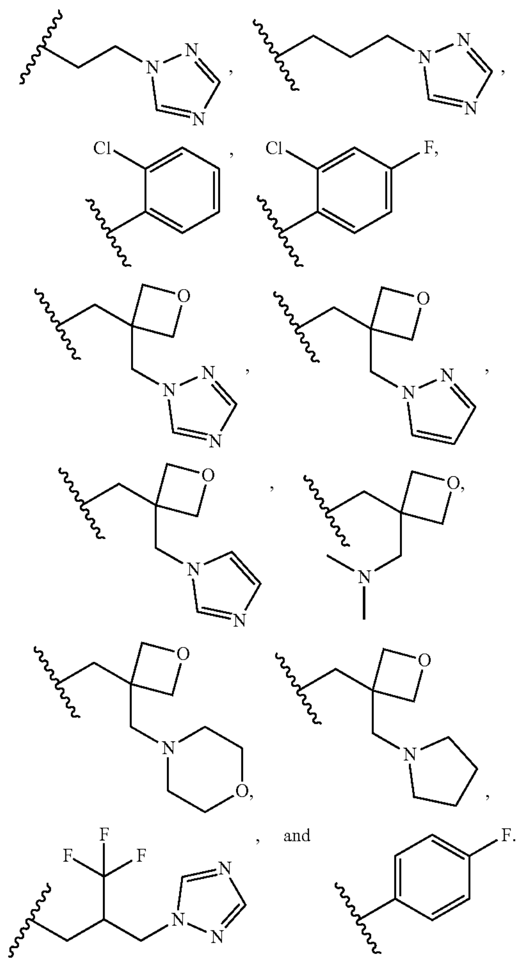

and

In some embodiments, each $R_2$ is independently selected from:

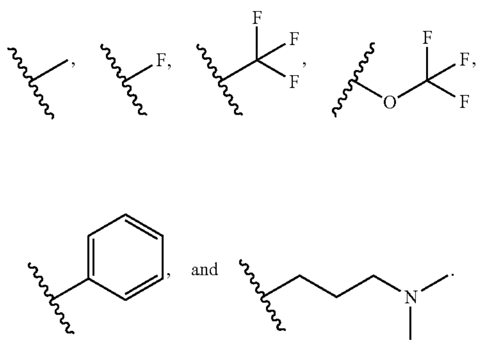

and

In some embodiments, wherein the compound (of Formula IIA) is selected from:

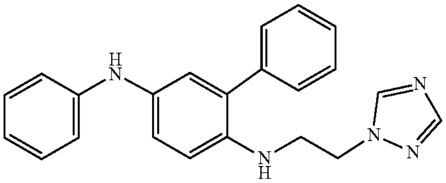

,

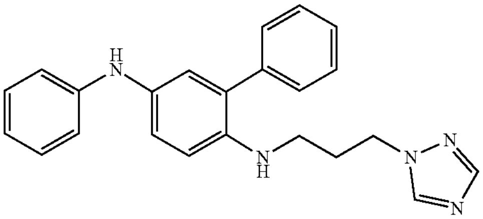

,

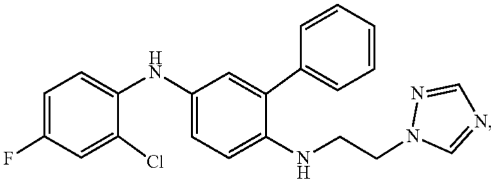

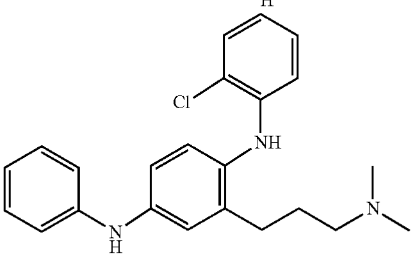

,

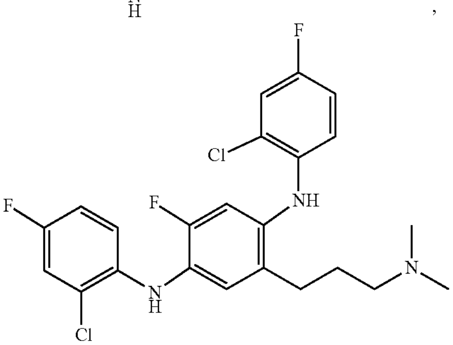

,

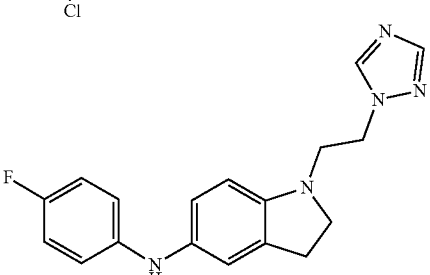

,

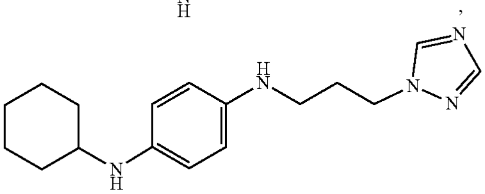

,

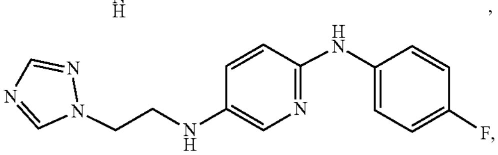

-continued
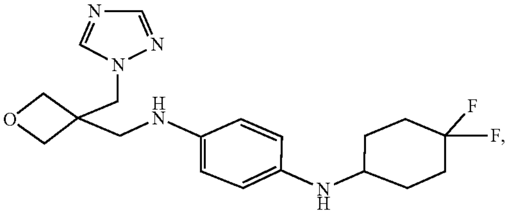
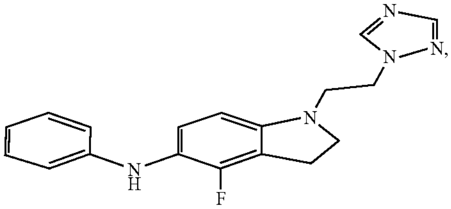
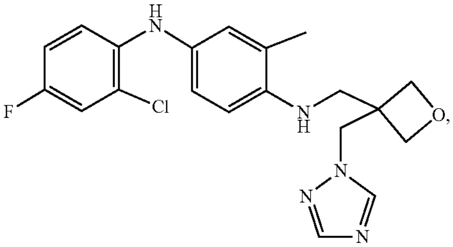
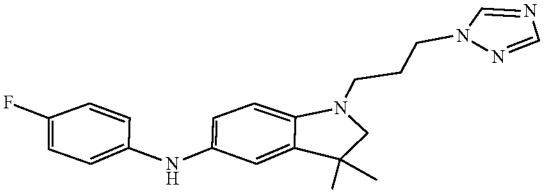
,
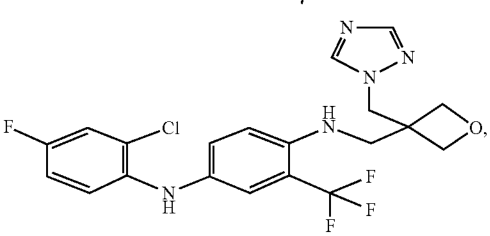
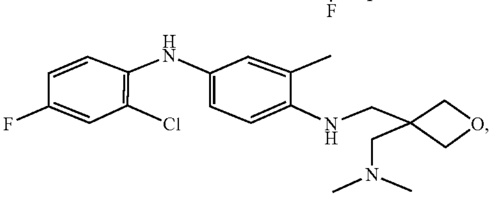
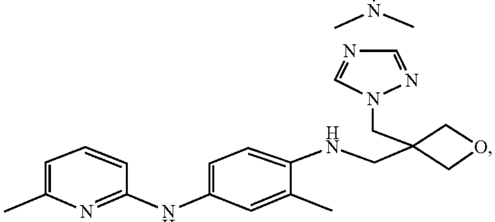
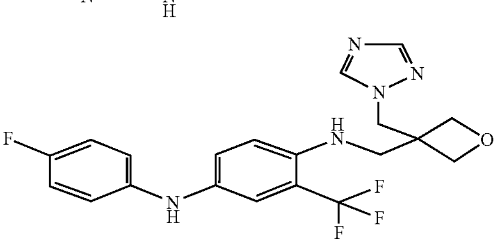
-continued
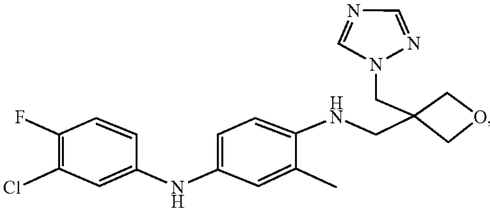
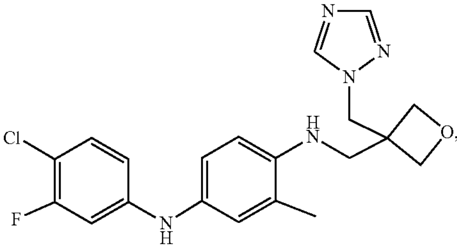
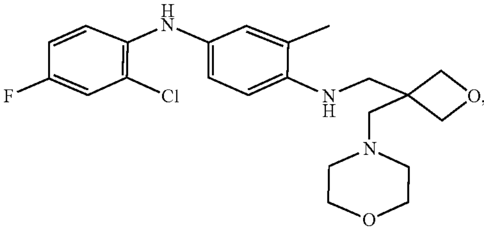
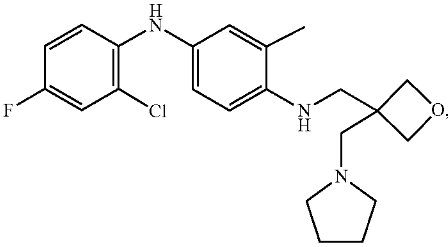
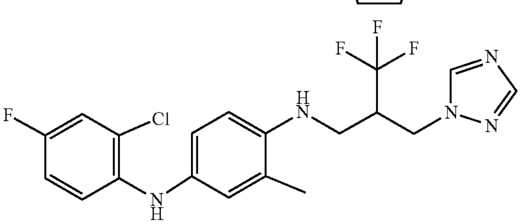
,
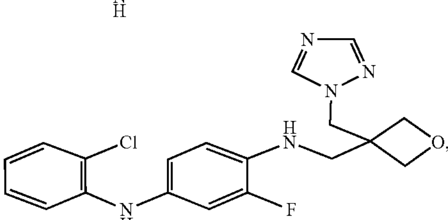
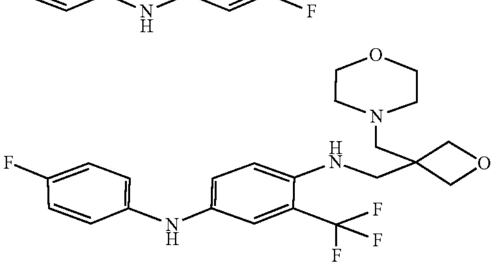

-continued

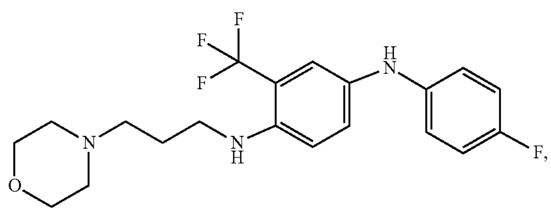

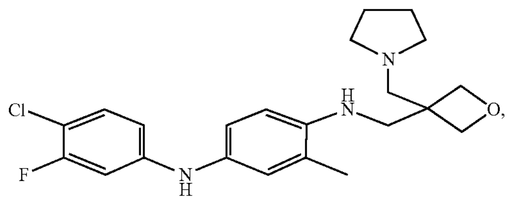

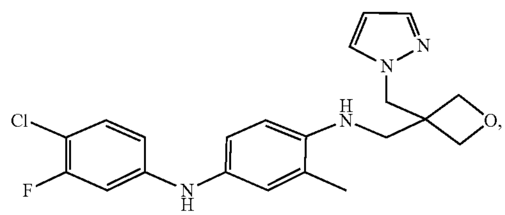

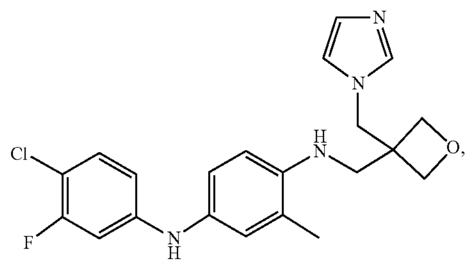

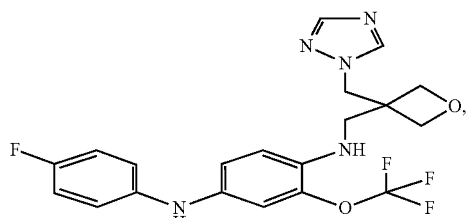

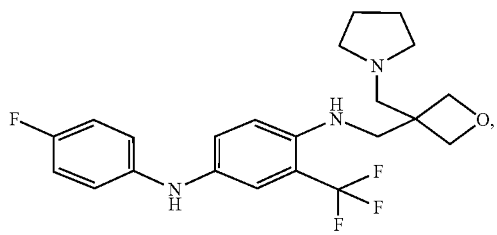

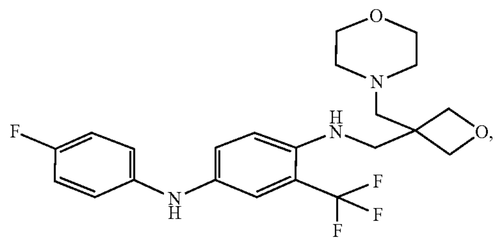

-continued

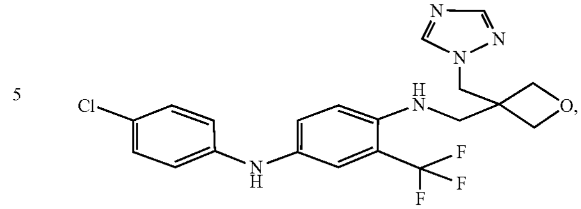

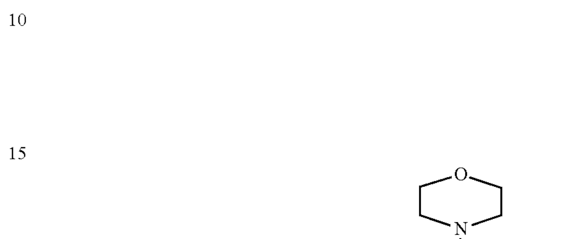

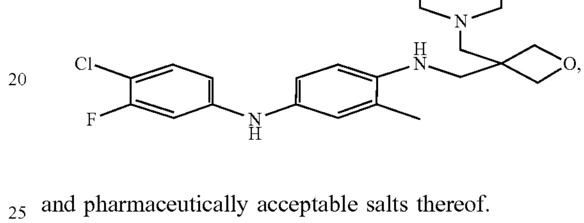

and pharmaceutically acceptable salts thereof.

Various embodiments are directed to a compound having Formula IIB:

Formula IIB

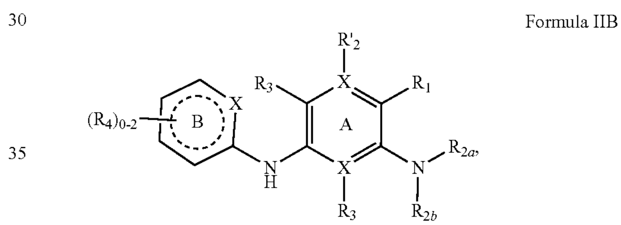

wherein: B is cyclohexyl, a 6 membered heterocycle, a 6 membered aryl, or a 6 membered heteroaryl; each X is independently C, N, or O; $R_1$ is H, $C_{1-3}$ alkyl, a 5-6 membered heterocycle, a 5-6 membered aryl, a 5-6 membered heteroaryl, a 5-10 membered cycloheteroaryl, a 5-10 membered heteroaryl, or —C(O)$R_x$; $R_{2a}$ and $R_{2b}$ are each independently: H, $C_{1-3}$ alkyl, a 5-6 membered aryl, —$NR_x(CH_2)_2R_y$, —$NR_x(CH_2)_3R_y$, —$NR_xC(O)(CH_2)_2R_y$, —$NH(CH_2)_2NR_xR_y$, —$O(CH_2)_2R_x$, —$NH(CH_2)CR_xR_yCH_2R_a$, —$NH(CH_2)CR_xR_yCH_2NR_aR_b$, —$(CH_2)_3NR_xR_y$, a 5-10 membered cycloheteroaryl, or —$NR_xR_y$; $R'_2$ is H or a halo; each $R_3$ is H, halo, $C_{1-3}$ alkyl, —$O(CH_2)_2NR_xR_y$, —$NR_x(CH_2)_2R_y$, —$NR_xR_y$, or —$(CH_2)_3NR_xR_y$; $R_4$ is halo; further wherein $R_1$ with either $R_{2a}$ or $R_{2b}$ optionally come together to form a 5-6 membered heterocycle, the 5-6 membered heterocycle is optionally further substituted with $R_a$ and/or $R_b$, and wherein $R_1$, $R_{2a}$, $R_{2b}$, $R'_2$, and $R_3$ are each optionally and independently substituted with one or more $R_a$; $R_x$ and $R_y$ are independently H, $C_{1-4}$ alkyl, 5-6 membered aryl, 5-6 membered heteroaryl, —$NR_aR_b$, wherein $R_x$ and $R_y$ each optionally come together to form 4-5 membered heterocycle, and wherein $R_x$ or $R_y$ optionally and independently are further substituted with $R_a$ and/or $R_b$; $R_a$ and $R_b$ are each independently H, halo, oxo, cyano, $C_{1-3}$ alkyl, $C_{1-3}$ alcohol, $C_{1-3}$ alkoxy, phenyl, —$(CH_2)_2R'$, 5-6 membered heteroaryl, or 5-6 membered heterocycle; R' is a 5 membered heteroaryl; and pharmaceutically acceptable salts thereof.

In some embodiments, $R_1$ is selected from:
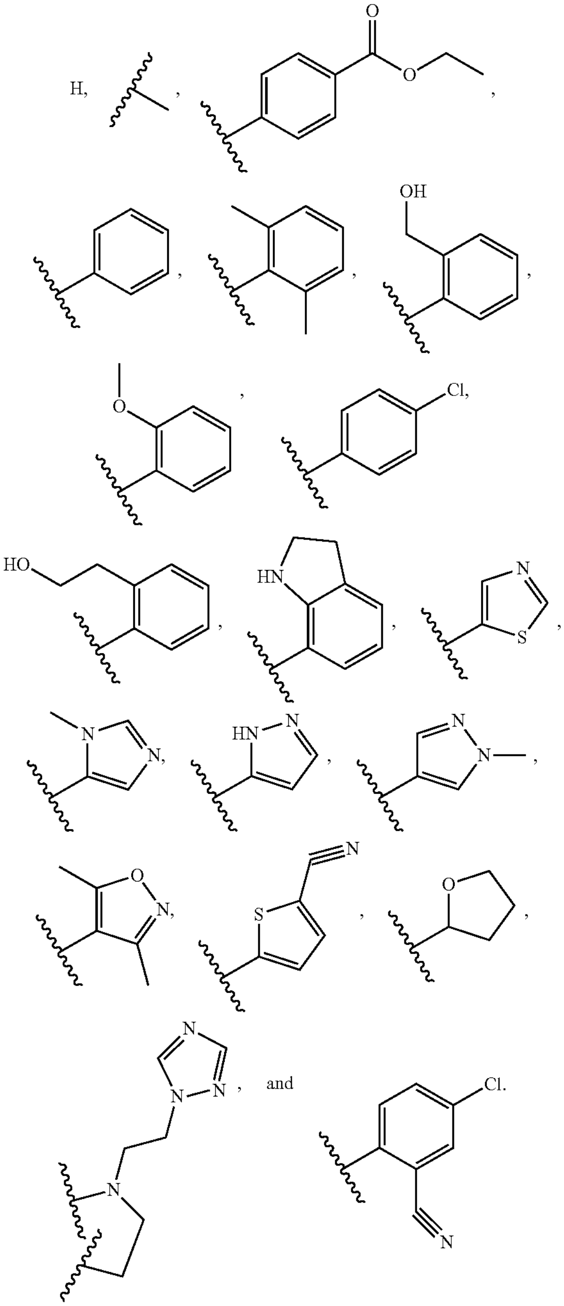
In some embodiments, $R_{2a}$ and $R_{2b}$ are each independently selected from:
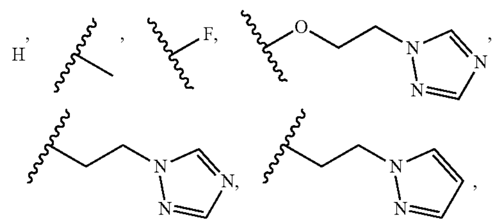
-continued
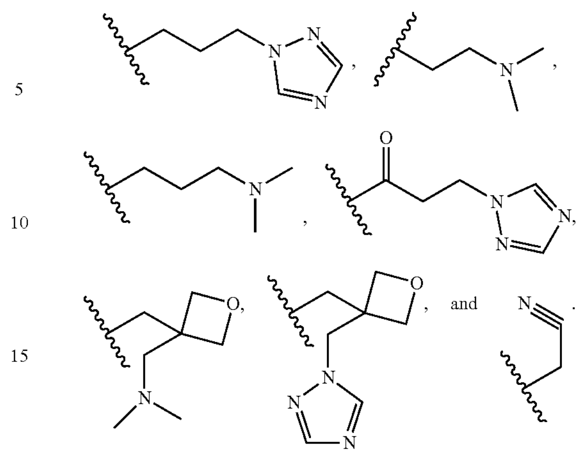
In some embodiments, each $R_3$ is independently H
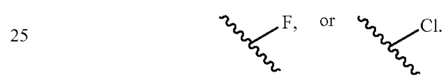
In some embodiments, the compound (of Formula IIB) is selected from:
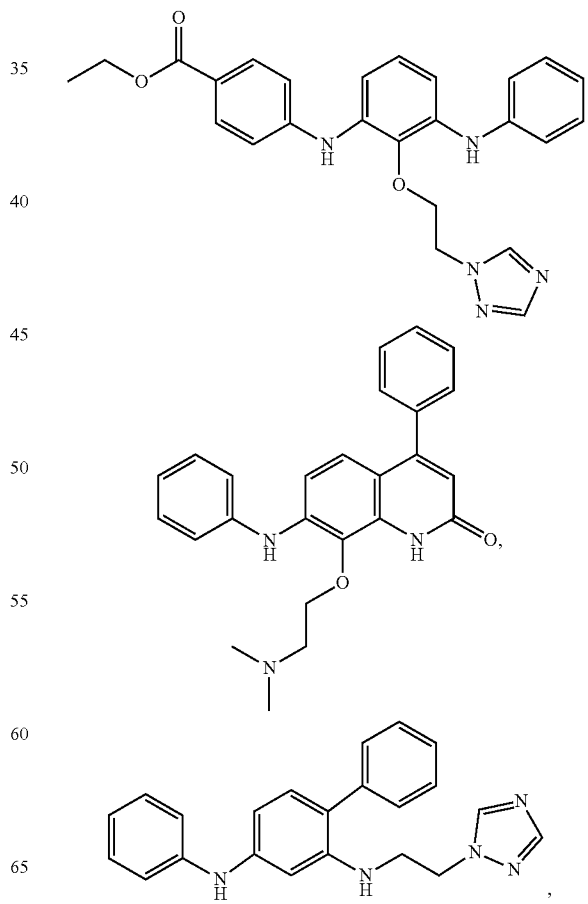

-continued
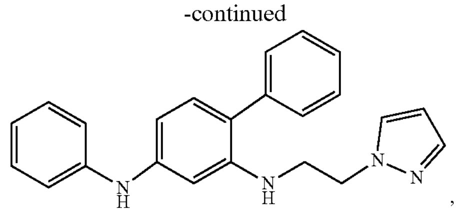
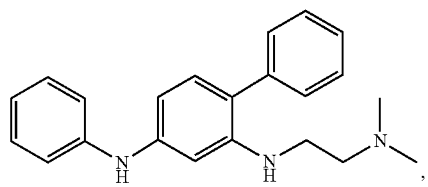
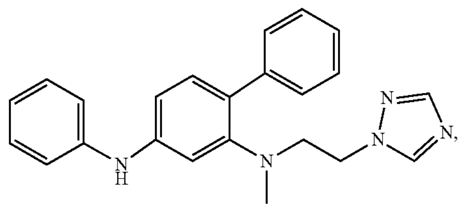
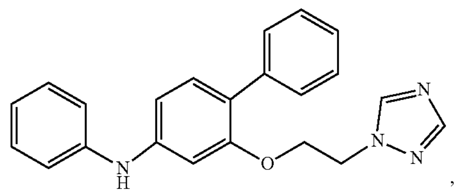
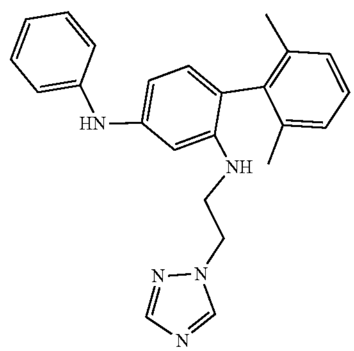
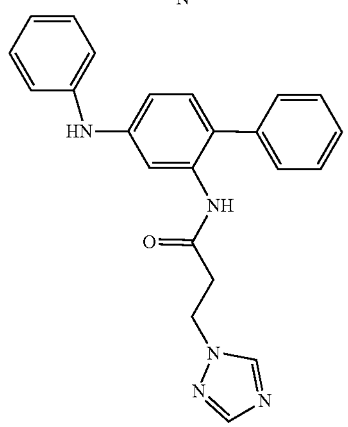
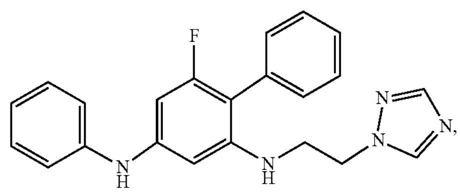
-continued
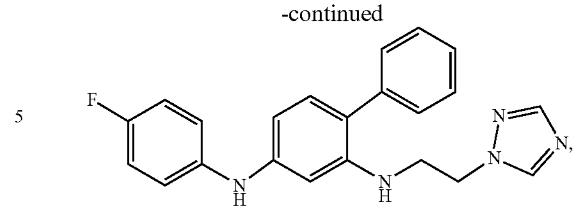
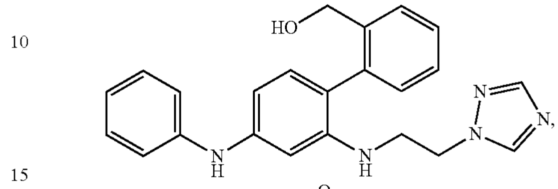
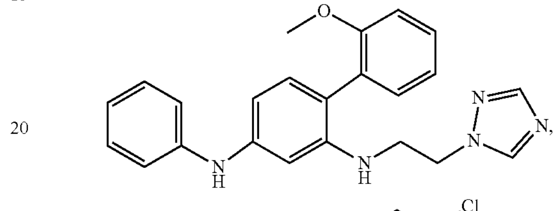
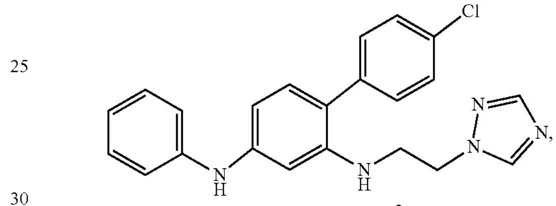
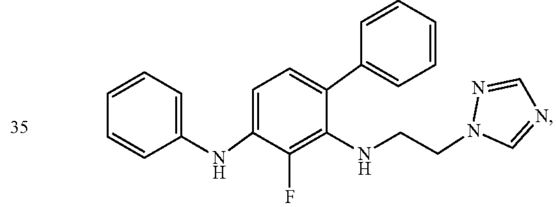
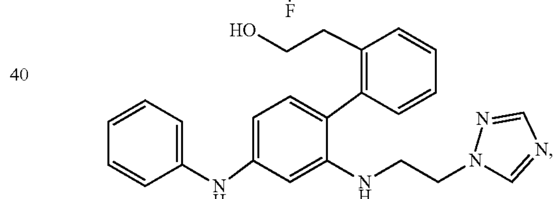
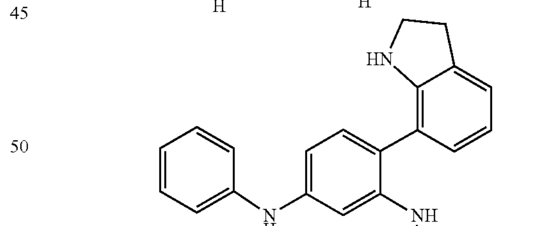
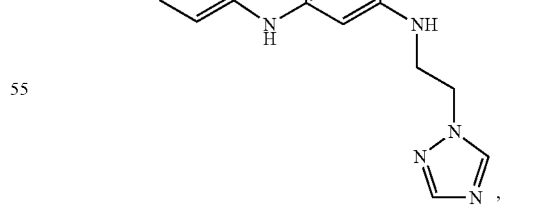
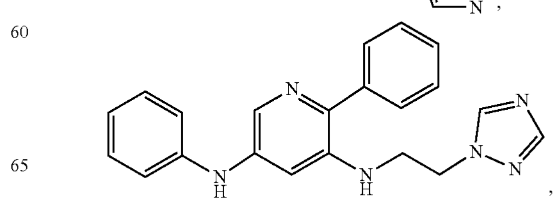

-continued
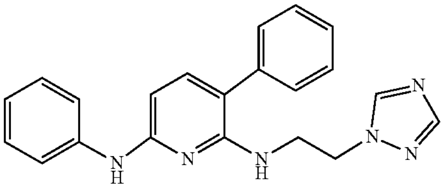
,
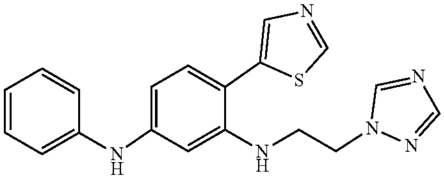
,
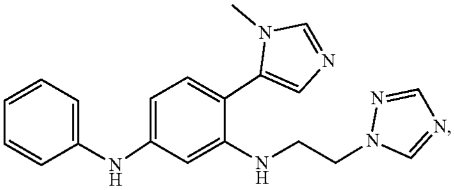
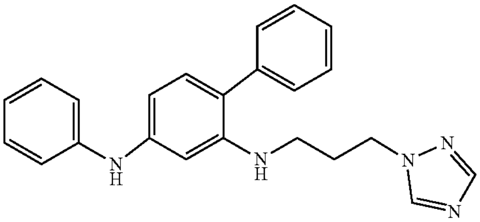
,
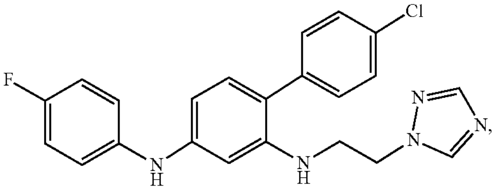
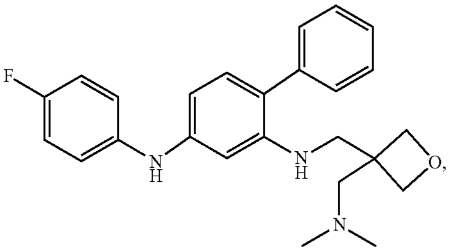
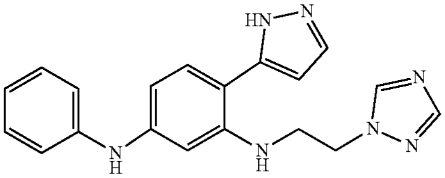
,
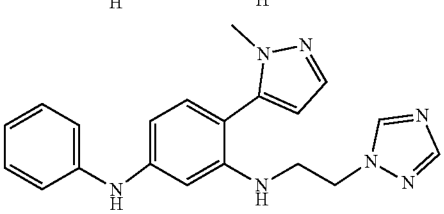
,
-continued
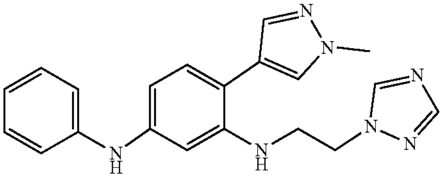
,
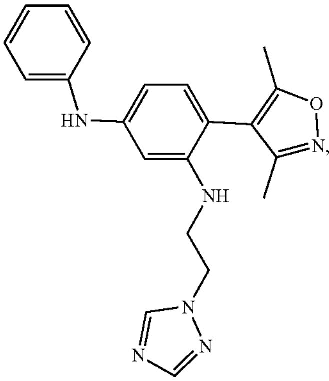
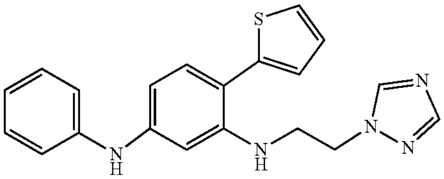
,
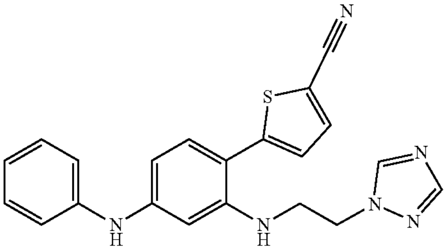
,
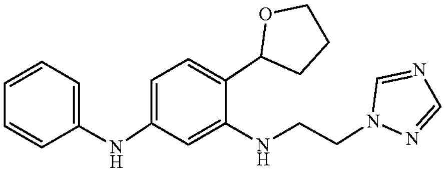
,
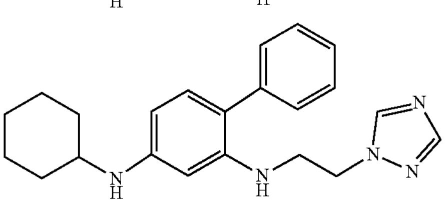
,
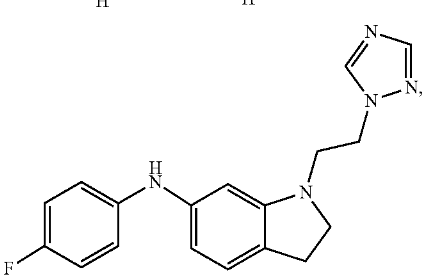

-continued

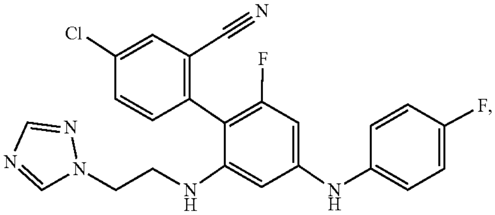

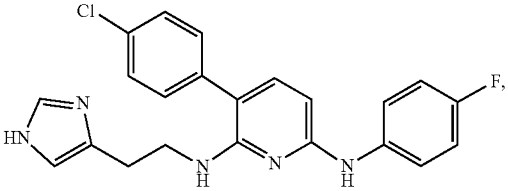

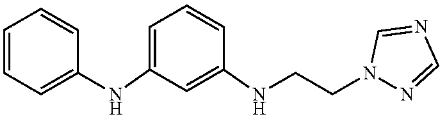

,

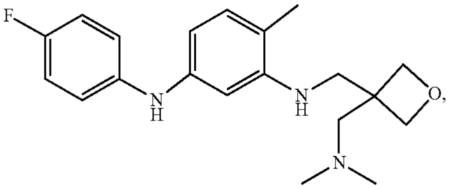

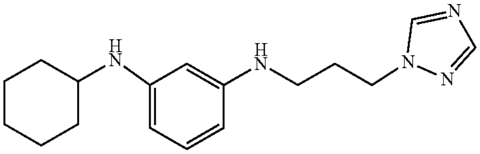

,

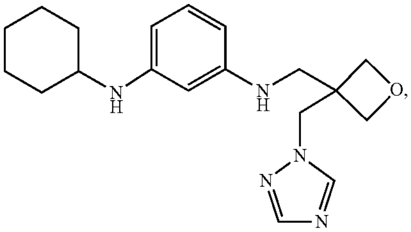

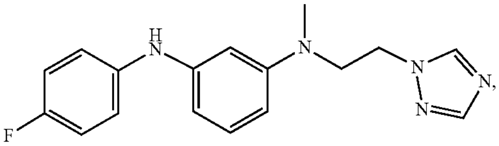

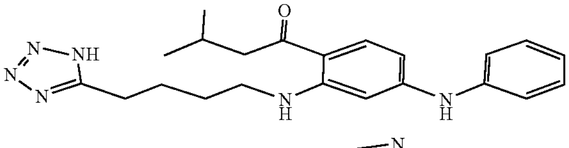

,

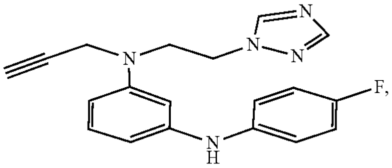

and pharmaceutically acceptable salts thereof.

Various embodiments are directed to a compound having Formula III:

Formula III

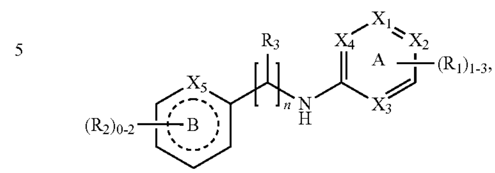

Wherein n is 1-2; B is a cyclohexyl, a 6-membered heterocycle, a 6-membered aryl, or a 6-membered heteroaryl; $X_1$, $X_2$, $X_3$, $X_4$, and $X_5$ are each independently C, N, or O; $R_1$ is halo, $C_{1-4}$ alkyl, $—NR_xR_y$, $—O(CH_2)_2NR_xR_y$, a 6 membered cyclohexyl, a 6 membered heterocycle, a 6 membered aryl, a 6 membered heteroaryl, or a 5-10 membered cycloalkyl, wherein when there are two $R_1$ groups, the two $R_1$ groups optionally come together to form a 6 membered heteroaryl; wherein each (one or more) $R_1$ is optionally and independently further substituted with one or more $R_a$; each $R_2$ is halo or $C_{1-3}$ alkoxy; each $R_3$ is independently H, oxo, a $C_{1-3}$ haloalkyl, or a hydroxyalkyl, wherein when one or more $R_3$ is hydroxyalkyl, the one or more of $R_3$ optionally comes together with a C of the Formula III to form a 4 membered heterocycle; $R_x$ and $R_y$ are each independently H, $C_{1-3}$ alkyl, a 6 membered aryl, or a 6 membered heteroaryl, wherein $R_x$ and $R_y$ are each optionally and independently further substituted with one or more $R_a$; $R_a$ is halo, oxo, cyano, $C_{1-3}$ haloalkyl, —NR'R', a 5-6 membered aryl, a 5-6 membered heteroaryl, or a 5-6 membered heterocycle, and wherein the one or more $R_a$ optionally come together to form a 4-5 membered heterocycle; R' is $C_{1-3}$ alkyl; and pharmaceutically acceptable salts thereof.

In some embodiments, each $R_1$ is independently selected from:

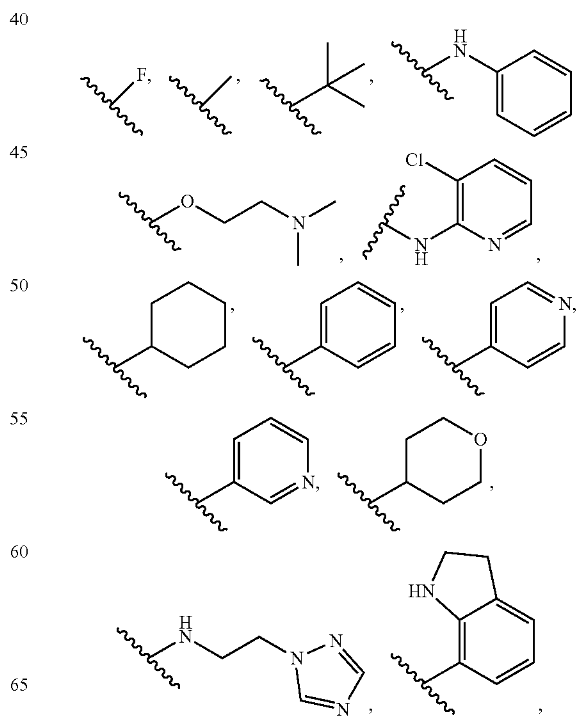

-continued
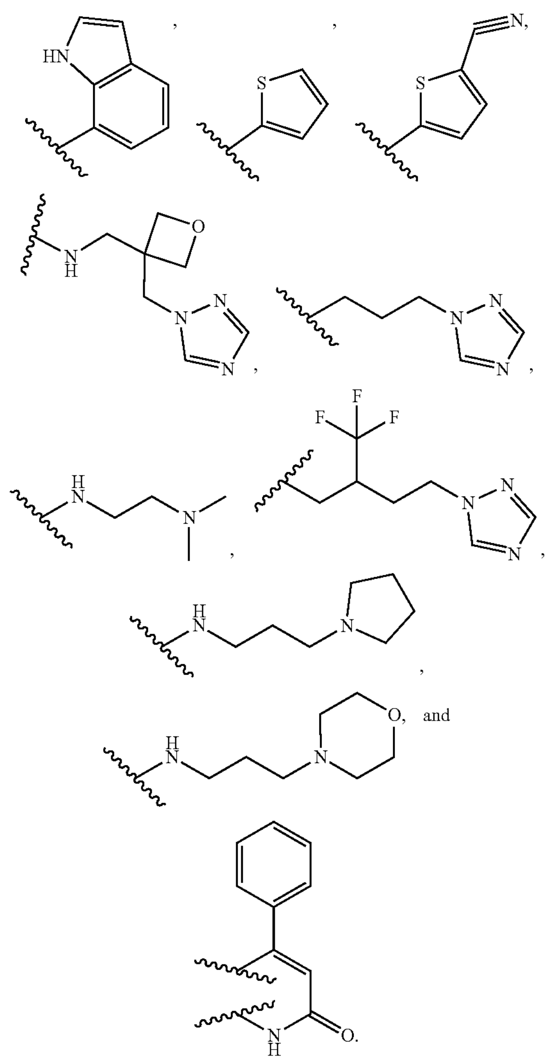
, , , , , , and
In some embodiments, each $R_2$ is independently: H,
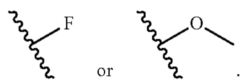
or .
In some embodiments, $R_3$ is: H, oxo, or
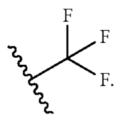 [SMILES: *C(F)(F)F]
In some embodiments, the compound (of Formula III) is selected from:
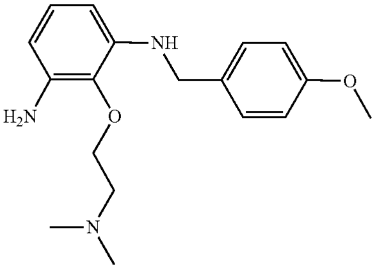
,
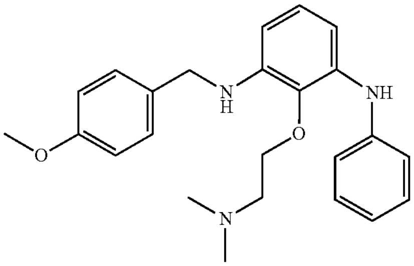
,
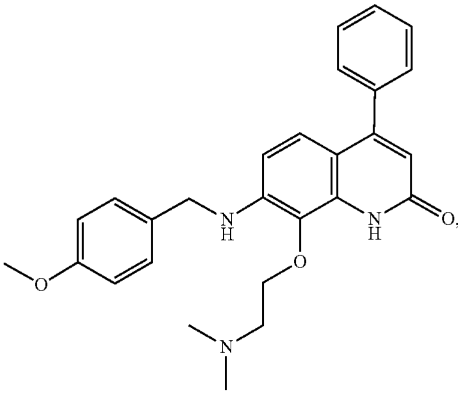
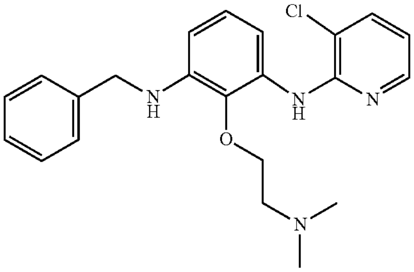
,
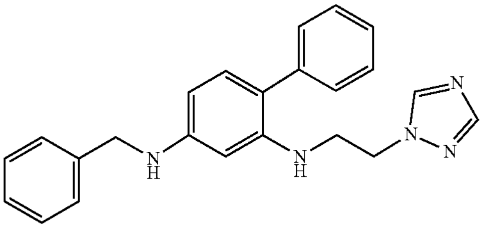
,
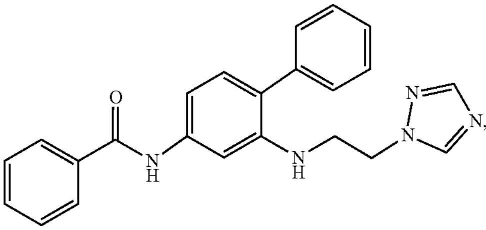

-continued
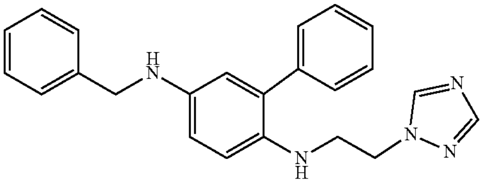
,
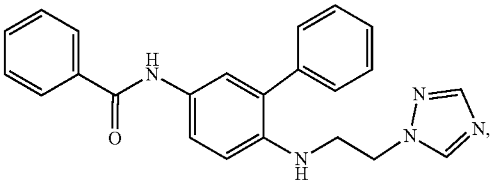
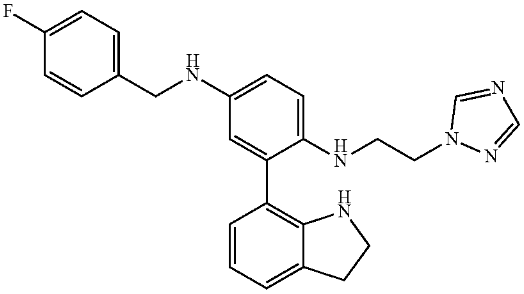
,
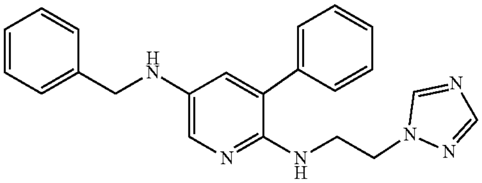
,
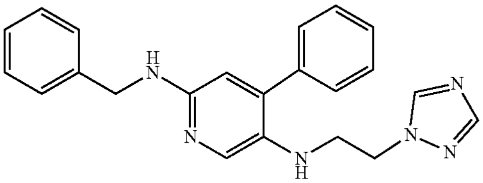
,
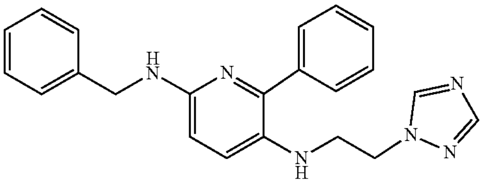
,
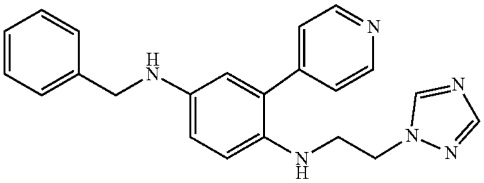
,
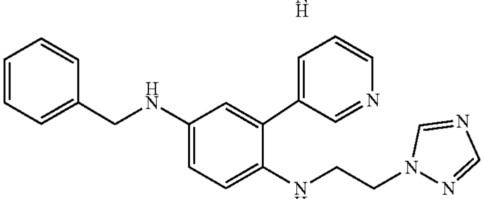
,
-continued
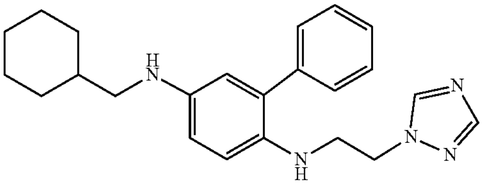
,
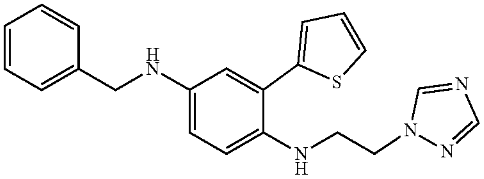
,
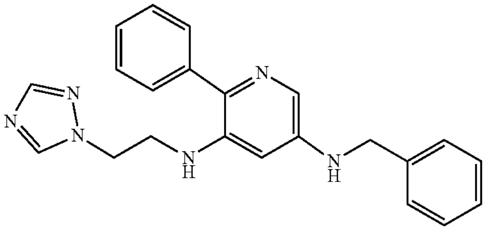
,
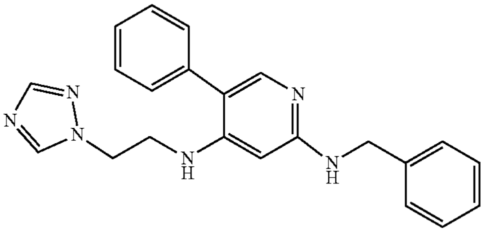
,
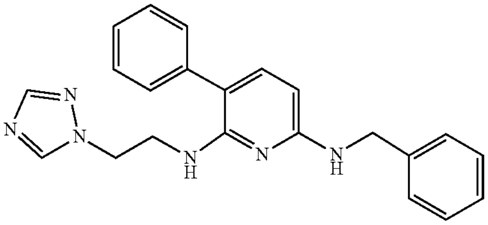
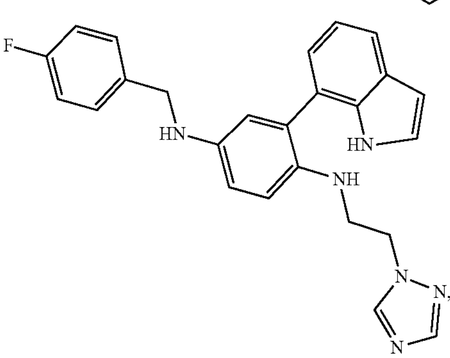
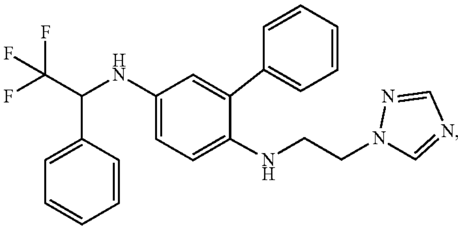

-continued
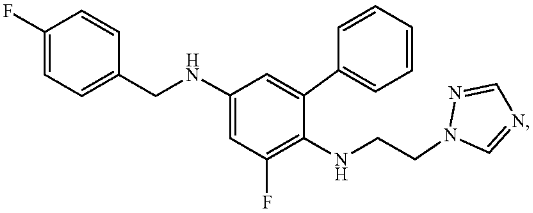
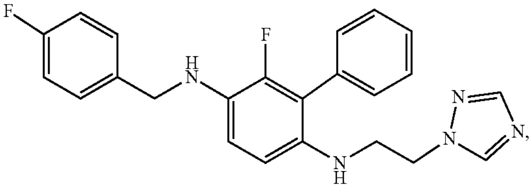
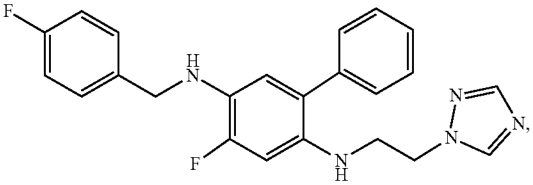
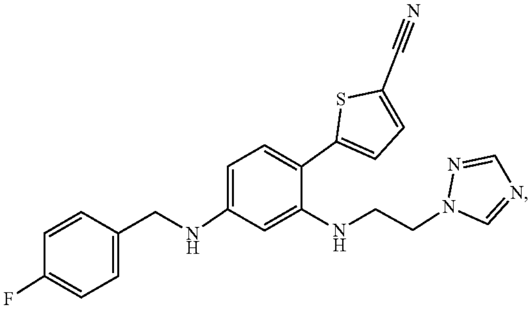
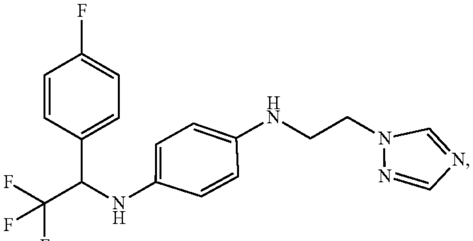
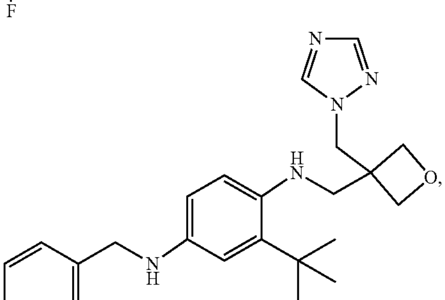
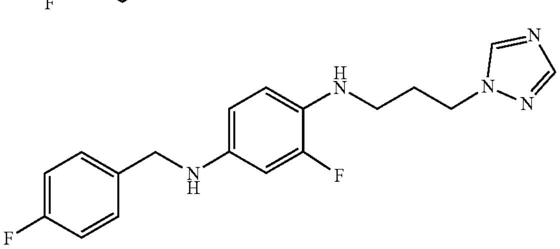
,
-continued
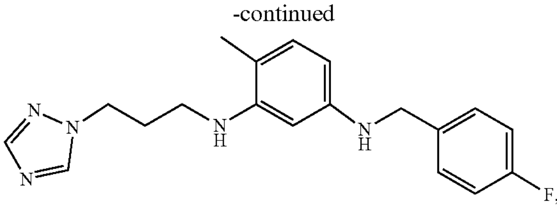
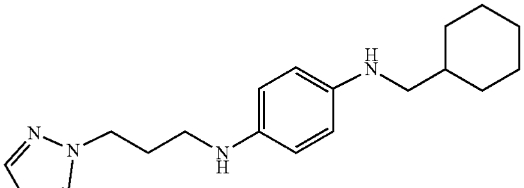
,
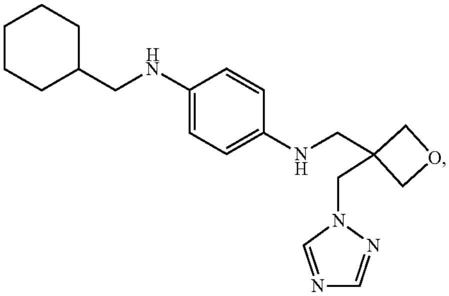
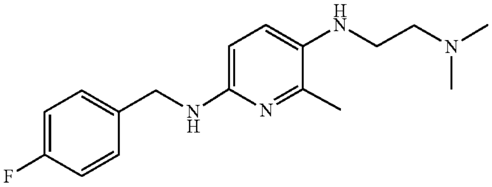
,
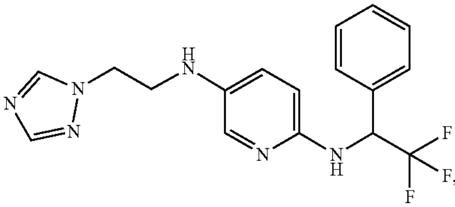
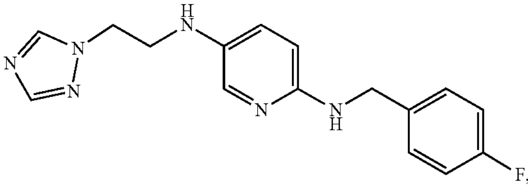
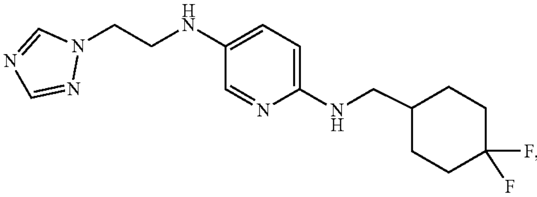
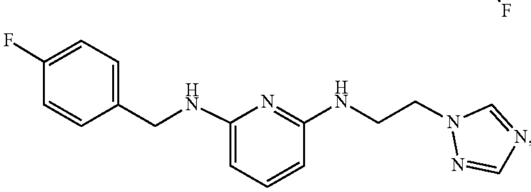

-continued

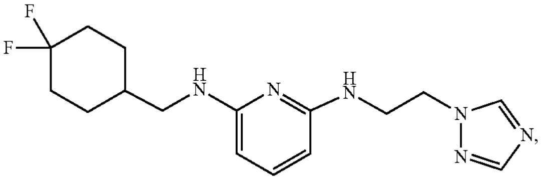

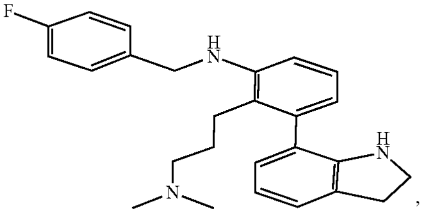

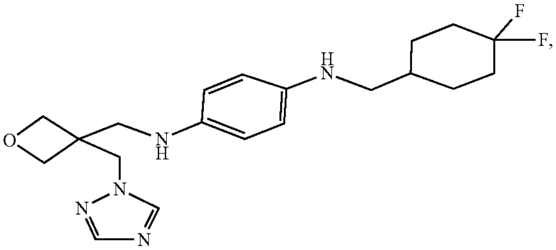

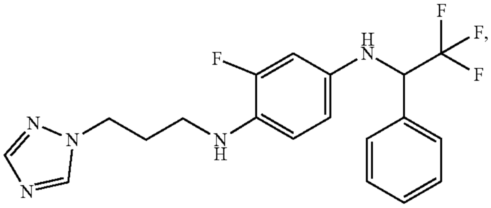

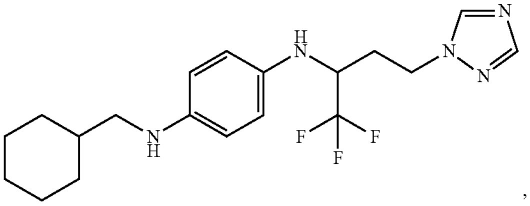

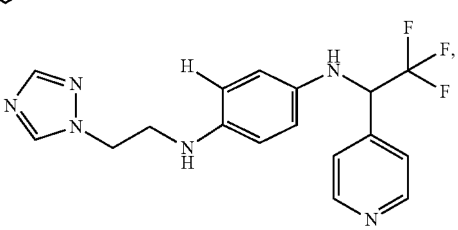

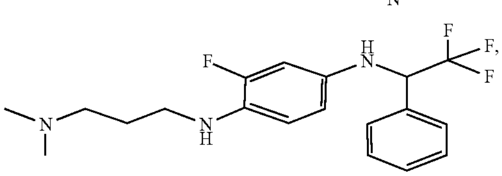

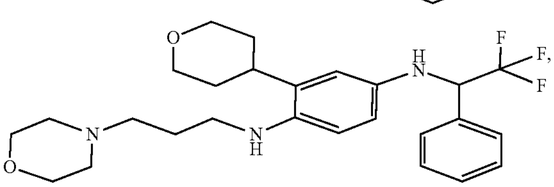

-continued

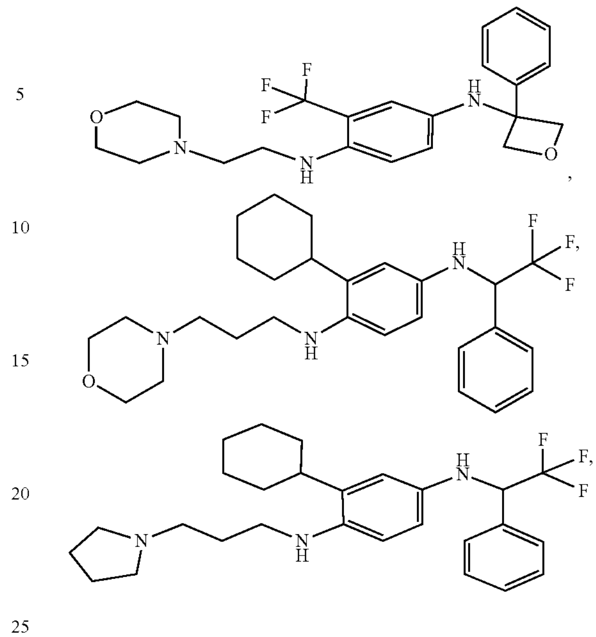

and pharmaceutically acceptable salts thereof.

Various embodiments are directed to a compound having Formula IIIA:

Formula IIIA

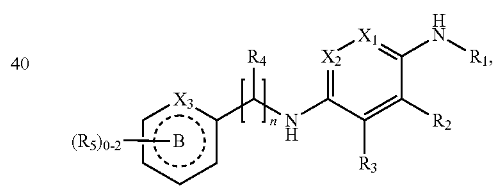

Wherein n is 1-2; B is a cyclohexyl, a 6-membered heterocycle, a 6-membered aryl, or a 6-membered heteroaryl; $X_1$, $X_2$, and $X_3$ are each independently C, N, or O; $R_1$ is $C_{1-3}$ alkyl, $R_2$ is H, halo, $C_{1-3}$ haloalkyl, $C_{1-4}$ alkyl, 5-6 membered aryl, 5-6 membered cycloalkyl, 5-6 membered heterocycle, 5-10 membered heteroaryl, 5-10 membered cycloaryl; $R_3$ is H or halo; each $R_4$ is independently H, oxo, a $C_{1-3}$ haloalkyl, or a hydroxyalkyl, wherein when one or more of $R_4$ is hydroxyalkyl, the one or more $R_4$ optionally comes together with a C of the Formula IIIA to form a 4 membered heterocycle; $R_5$ is halo, or a 4-5 membered heterocycle; $R_1$, $R_2$, $R_4$, and $R_5$ are each optionally and independently be substituted with up to two $R_a$ or $R_b$; $R_a$ and $R_b$ are each independently $C_{1-3}$ alkyl, $C_{1-3}$ haloalkyl, 5-6 membered heterocycle, 5-6 membered heteroaryl, —N/—NR'R', wherein an $R_a$ and $R_b$ optionally come together to form a 4-5 membered heterocycle, wherein $R_a$ and $R_b$ are optionally and independently further substituted with one or more R' groups; R' is halo or $C_{1-3}$ alkyl; and pharmaceutically acceptable salts thereof.

In some embodiments, $R_1$ is selected from:
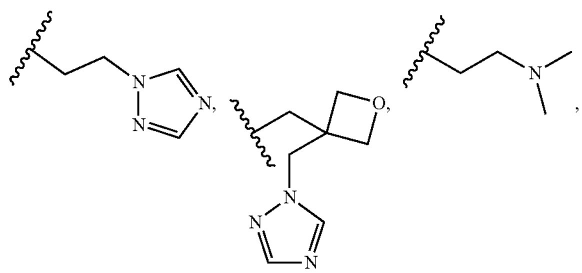
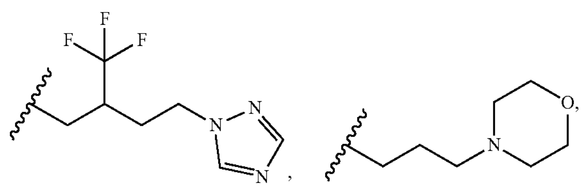
and
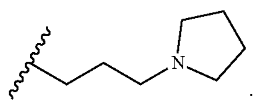
In some embodiments, $R_2$ is selected from:
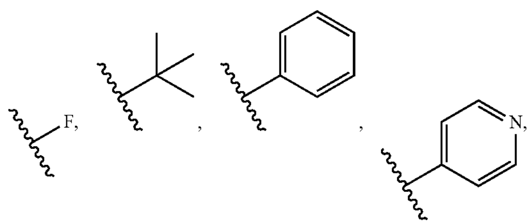
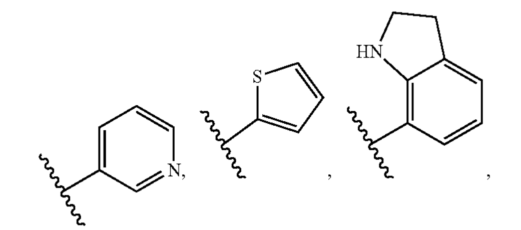
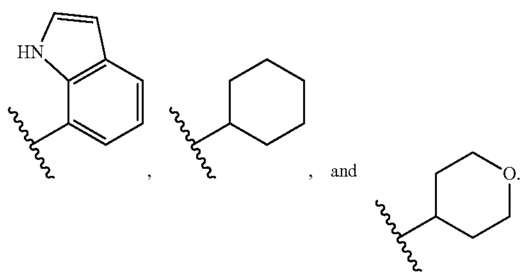
In some embodiments, $R_3$ is H or F.
In some embodiments, $R_4$ is H,
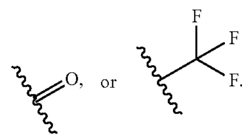
In some embodiments, $R_5$ is
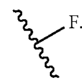
In some embodiments, the compound (of Formula IIIA) is selected from:
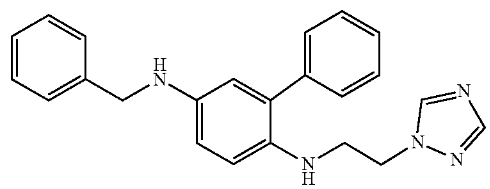
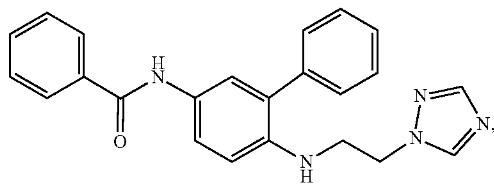
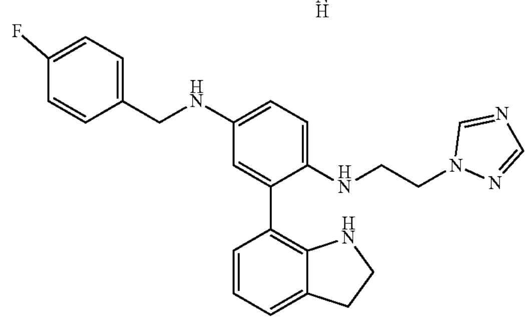
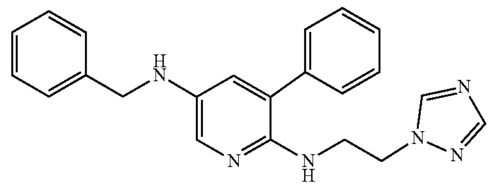
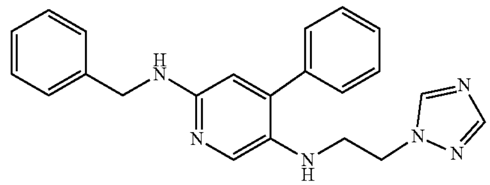
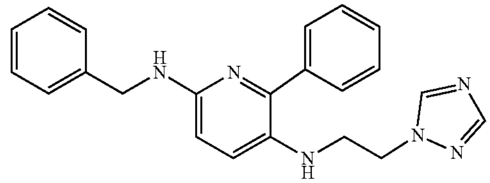

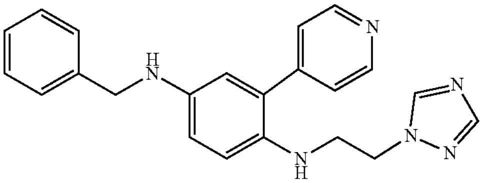
,
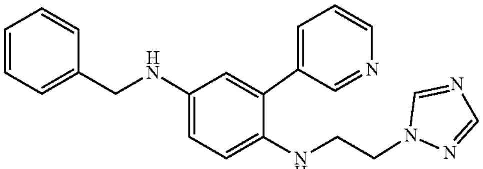
,
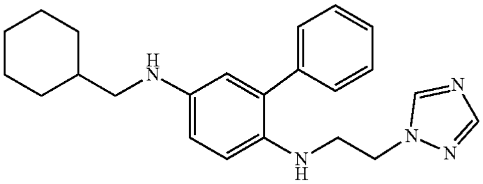
,
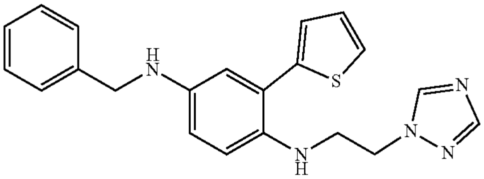
,
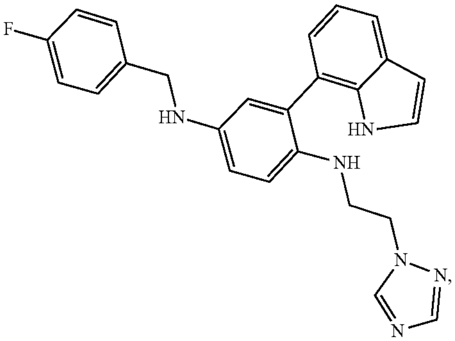
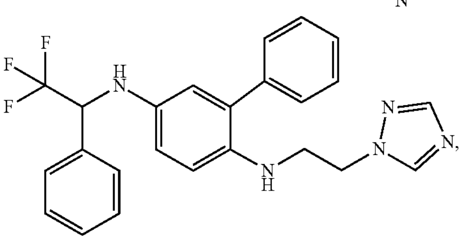
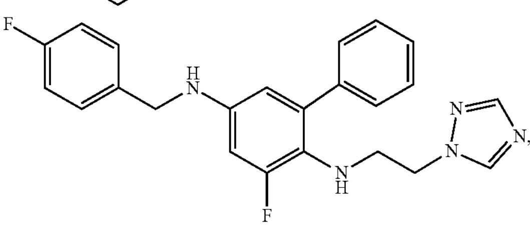
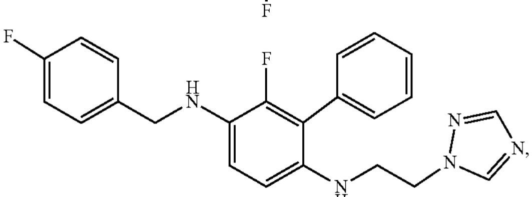
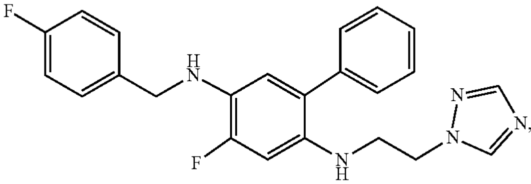
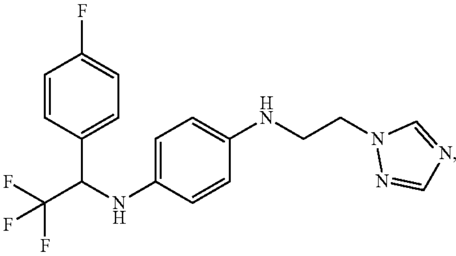
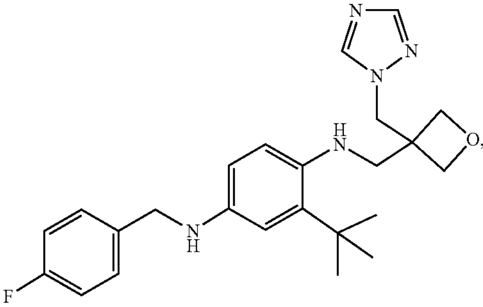
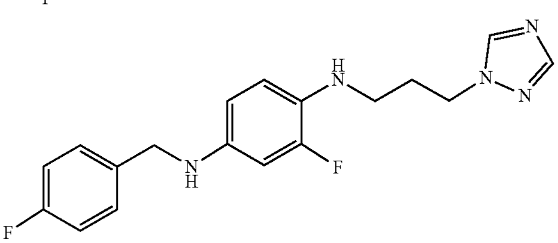
,
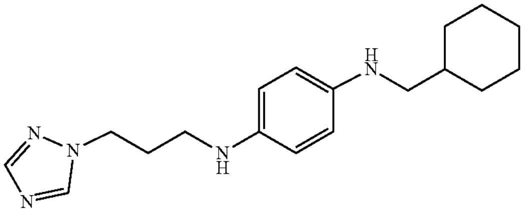
,
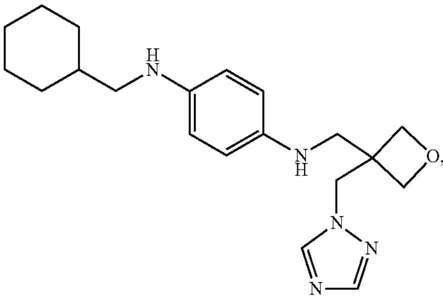
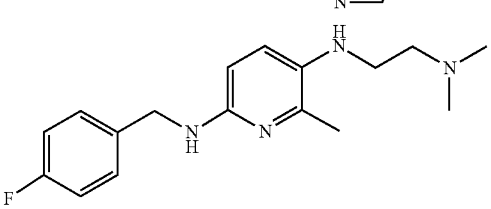
, -continued

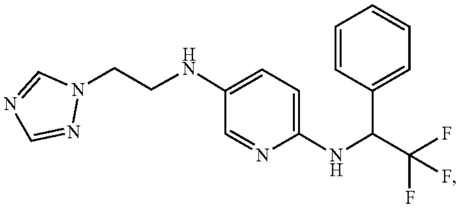

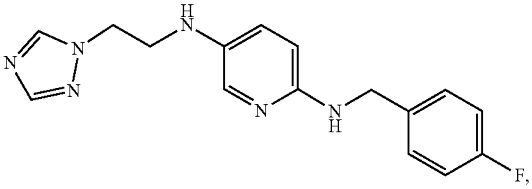

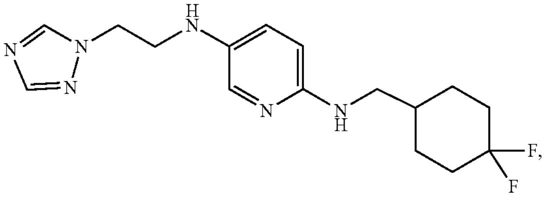

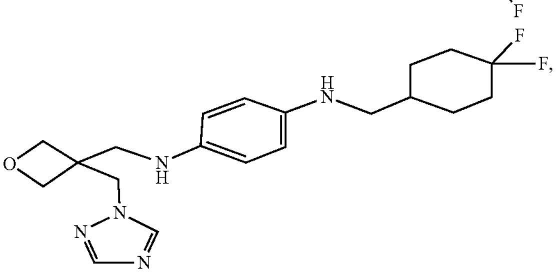

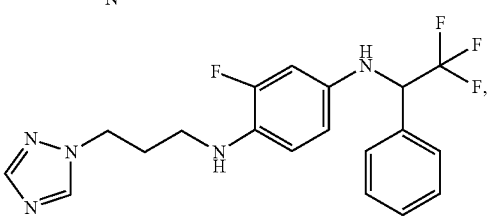

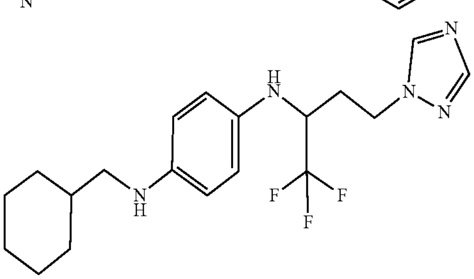

,

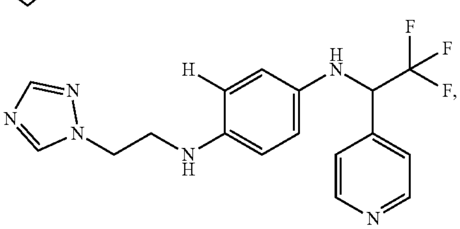

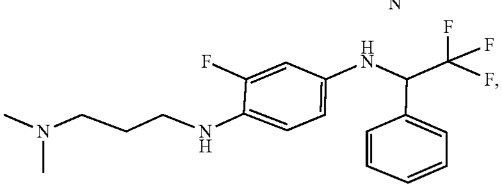

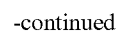

-continued

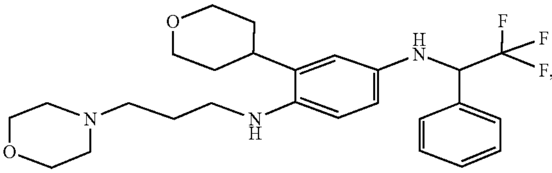

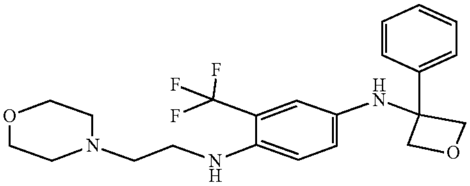

,

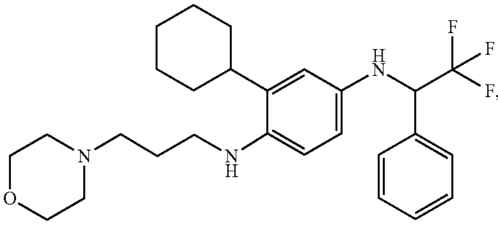

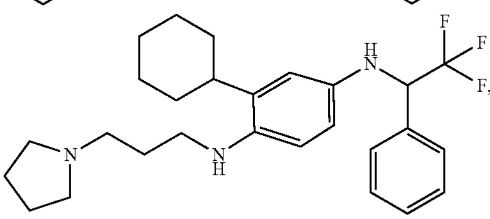

and pharmaceutically acceptable salts thereof.

Various embodiments are directed to a compound having Formula RIB:

Formula IIIB

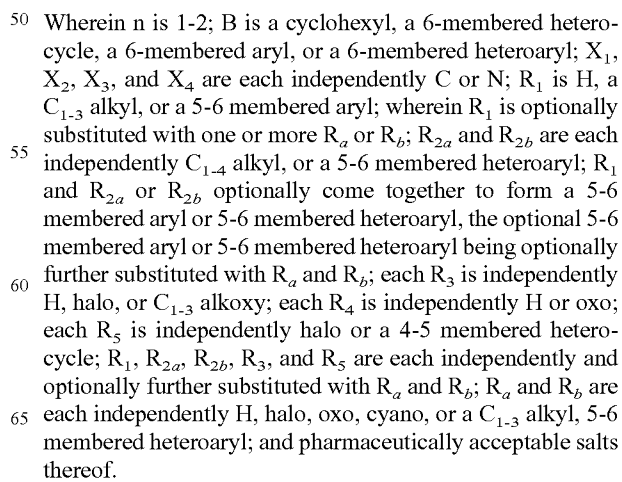

Wherein n is 1-2; B is a cyclohexyl, a 6-membered heterocycle, a 6-membered aryl, or a 6-membered heteroaryl; $X_1$, $X_2$, $X_3$, and $X_4$ are each independently C or N; $R_1$ is H, a $C_{1-3}$ alkyl, or a 5-6 membered aryl; wherein $R_1$ is optionally substituted with one or more $R_a$ or $R_b$; $R_{2a}$ and $R_{2b}$ are each independently $C_{1-4}$ alkyl, or a 5-6 membered heteroaryl; $R_1$ and $R_{2a}$ or $R_{2b}$ optionally come together to form a 5-6 membered aryl or 5-6 membered heteroaryl, the optional 5-6 membered aryl or 5-6 membered heteroaryl being optionally further substituted with $R_a$ and $R_b$; each $R_3$ is independently H, halo, or $C_{1-3}$ alkoxy; each $R_4$ is independently H or oxo; each $R_5$ is independently halo or a 4-5 membered heterocycle; $R_1$, $R_{2a}$, $R_{2b}$, $R_3$, and $R_5$ are each independently and optionally further substituted with $R_a$ and $R_b$; $R_a$ and $R_b$ are each independently H, halo, oxo, cyano, or a $C_{1-3}$ alkyl, 5-6 membered heteroaryl; and pharmaceutically acceptable salts thereof.

In some embodiments, $R_1$ is:
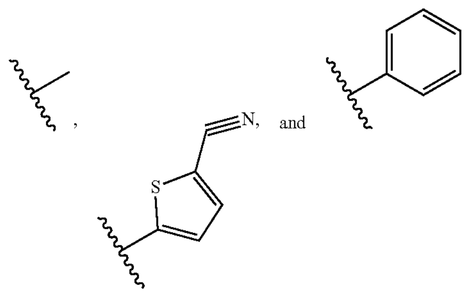
In some embodiments, $R_{2a}$ and $R_{2b}$ are each independently: H,
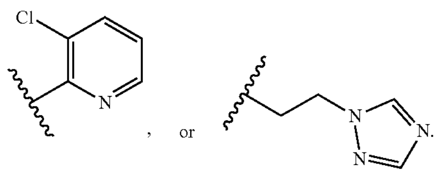 [SMILES: *c1ncccc1Cl ; *CCn1cncn1]
In some embodiments, each $R_3$ is independently H or
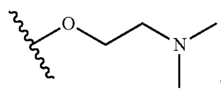 [SMILES: *OCCN(C)C]
In some embodiments, $R_4$ is: H or oxo.
In some embodiments, each $R_5$ is independently:
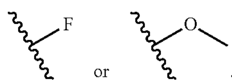
In some embodiments, the compound (of Formula IIIB) is selected from:
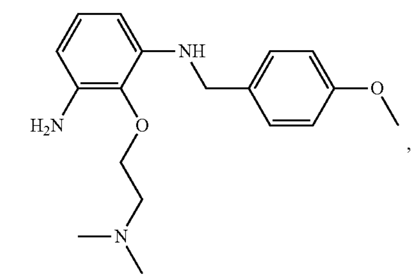
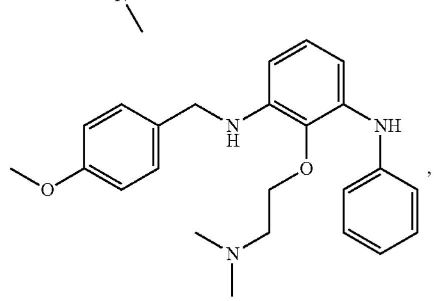
-continued
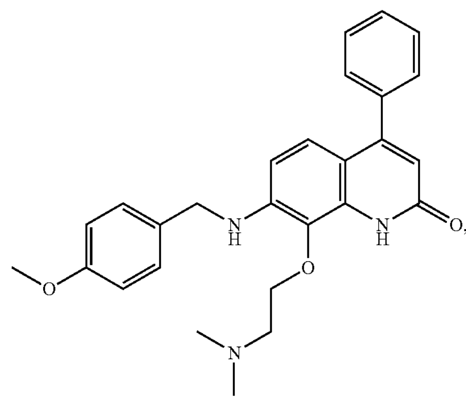
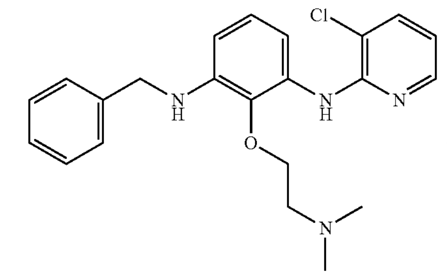
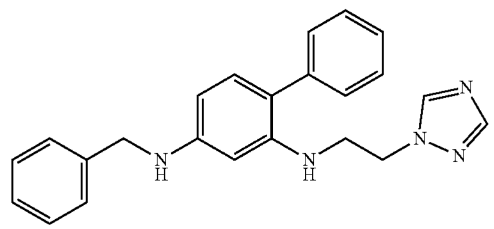
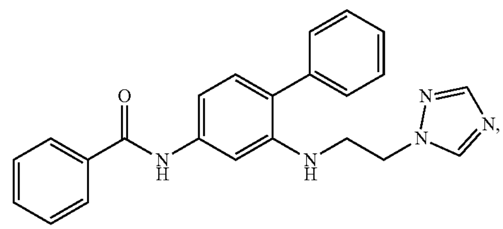
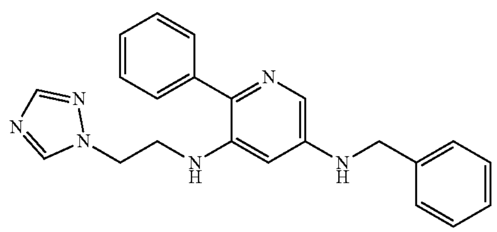
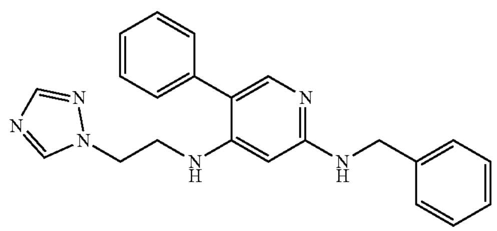

-continued

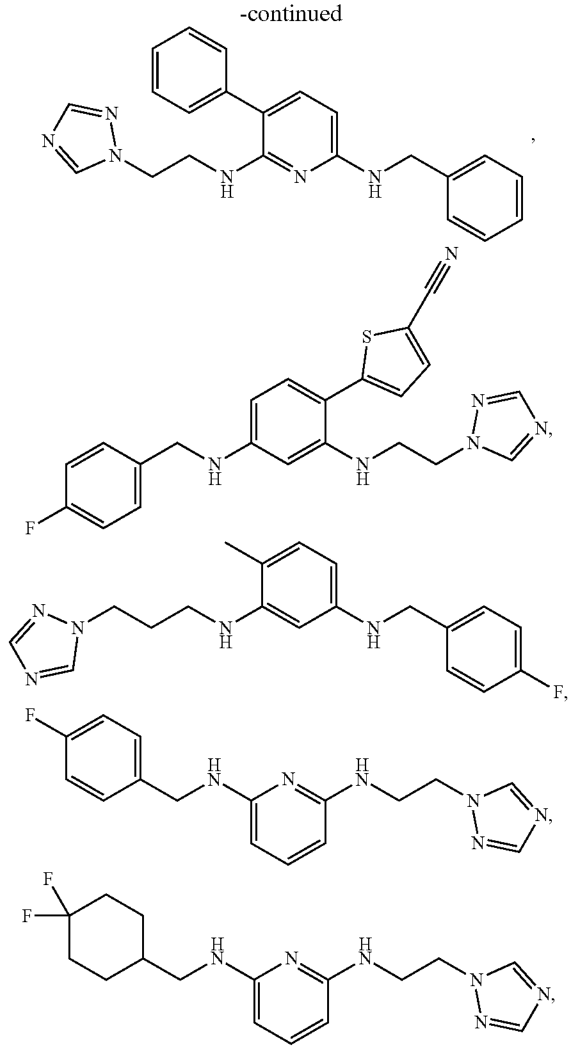

and pharmaceutically acceptable salts and/or hydrates thereof.

Various embodiments are directed to methods of lipoxygenase in cells determined to be in need thereof comprising contacting the cells with, or administering to the cells, a compound having structure disclosed in any of the above claims, such as in claim 1. In some embodiments, the cells are human cells that are either in vivo or isolated in vitro. In some embodiments, the cells are in situ as part of a person determined to be in need of lipoxygenase inhibition or suffering from a disease associated with pathogenic lipoxygenase activity, wherein the disease is selected from an acute or chronic inflammatory disease or a neurodegenerative disease.

In some embodiments, the disease is: (i) an acute or chronic inflammatory disease that is asthma, rheumatoid arthritis, inflammatory bowel disease, psoriasis, hereditary ichthyosis, dermatitis, nephritis, atherosclerosis, or cardiovascular disease, or (ii) a neurodegenerative disease that is age-related neurodegeneration, amyloid beta-associated disease, Alzheimer's Disease, ischemia-related disorder, creutzfeldt-jakob disease/prion peptide toxicity, ALS, dementia or Parkinson Disease.

In some embodiments, the method further comprises (i) measuring a lipoxygenase activity in a sample of the person; (ii) determining a level of a lipoxygenase metabolite in a sample of the person; or (iii) determining the person has the disease.

Various embodiments are directed to a pharmaceutical composition comprising a compound of claim 1 for inhibiting lipoxygenase activity, or a pharmaceutically acceptable salt thereof, and a pharmaceutically acceptable carrier.

Various embodiments are directed to a pharmaceutical composition comprising a compound of claim 4 for inhibiting lipoxygenase activity, or a pharmaceutically acceptable salt thereof, and a pharmaceutically acceptable carrier.

Various embodiments are directed to composition comprising a compound of Formula I, supra, and a second anti-neurodegenerative disease drug.

Various embodiments are directed to methods of identifying lipoxygenase inhibitor comprising the steps of screening for lipoxygenase inhibitory activity of a compound of Formula I.

Embodiments in accordance with the present disclosure include all combinations of the recited particular embodiments. Further embodiments and the full scope of applicability of the invention will become apparent from the detailed description provided hereinafter. However, it should be understood that the detailed description and specific embodiments, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

DETAILED DESCRIPTION

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

As used herein and in the claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

The prefix "Cx-y" indicates that the following group has from x (e.g., 1) to y (e.g. 6) carbon atoms, one or more of which, in certain groups (e.g., heteroalkyl, heteroaryl, heteroarylalkyl, etc.), may be replaced with one or more heteroatoms or heteroatomic groups. For example, "$C_{1-6}$ alkyl" indicates that the alkyl group has from 1 to 6 carbon atoms. Likewise, the term "x-y membered" rings, wherein x and y are numerical ranges, such as "3-12 membered heterocyclyl", refers to a ring containing x-y atoms (e.g., 3-12), of which up to half may be heteroatoms, such as N, O, S, P, and the remaining atoms are carbon. Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—CH—CH), propargyl (—$CH_2C\equiv CH$), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH2. Amino groups may also be substituted as described herein, such as with alkyl, carbonyl or other amino groups. The term "alkylamino" refers to an amino group substituted with one or two alkyl substituents (e.g., dimethylamino or propylamino).

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like.

"Arylalkyl" (also "aralkyl") refers to any combination aryl group and an alkyl group. Arylalkyl groups include, but are not limited to, those groups derived from benzyl, tolyl, dimethylphenyl, 2-phenylethan-1-yl, 2-naphthylmethyl, and the like. An arylalkyl group comprises from 6 to 30 carbon atoms, for example the alkyl group can comprise from 1 to 10 carbon atoms and the aryl group can comprise from 5 to 20 carbon atoms.

"Cycloaryl" refers to a combination an aryl group and a cyclic ring. Some representative example of a cycloaryl comprise 2,3-dihydro-1H-indene, 1,2,3,4-tetrahydronaphthalene, 3a,5,6,7-tetrahydro-4H-indene, and the like.

"Heterocyclo-aryl" refers to a combination of an aryl group and a heterocylic group. Some representative examples of a heterocyclo-aryl comprise 1,2,3,4-tetrahydroisoquinoline, isochromane, 1,3-dihydroisobenzofuran, isoindoline, and the like.

"Cycloalkyl" refers to a cyclic alkyl and alkenyl groups. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcycloproyl (cyclopropylmethyl), ethylcyclopropyl, cyclohexenyl and the like. Another example includes $C_{5-7}$ cycloakenyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —CH2Cl, —CH2F, —CH2Br, —CFClBr, —CH2CH2Cl, —CH2CH2F, —CF3, —CH2CF3, —CH2CCl3, and the like, as well as alkyl groups such as perfluoroalkyl in which all hydrogen atoms are replaced by fluorine atoms.

"Hydroxyalkyl" refers to an alkyl wherein one or more hydrogen atoms are each replaced by a hydroxyl group. Examples include, but are not limited to, —CH2OH, —CH2CH2OH, —C(CH3)2OH, and the like.

"Halo 3-6 membered heterocyclyl" refers to a heterocyclyl group substituted at a carbon atom with at least one halogen atom, and may include multiple halogen atoms, such as 3,3-difluoroazetidinyl.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —P(O)2-, —S(O)—, —S(O)2-, and the like, where R is H, alkyl, aryl, cycloalkyl, heteroalkyl, heteroaryl or cycloheteroalkyl. Heteroalkyl groups include, but are not limited to, —OCH3, —CH2OCH3, —SCH3, —CH2SCH3, —NRCH3, —CH2NRCH3, —CH2OH and the like, where R is hydrogen, alkyl, aryl, arylalkyl, heteroalkyl, or heteroaryl, each of which may be optionally substituted. A heteroalkyl group comprises from 1 to 10 carbon and up to three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-14 members, 5-10 members, or 5-6 members.

"Heterocycle," "heterocyclic," and "heterocyclyl" refer to a saturated or partially unsaturated non-aromatic ring or a partially non-aromatic multiple-ring system with at least one heteroatom or heteroatomic group, as defined above. Heterocycles include, but are not limited to, groups derived from azetidine, aziridine, imidazolidine, morpholine, thiomorpholine, tetrahydro-2H-thiopyran, 1-iminotetrahydro-2H-thiopyran 1-oxide, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like. Heterocyclyl groups also include partially unsaturated ring systems containing one or more double bonds, including fused ring systems with one aromatic ring and one non-aromatic ring, but not fully aromatic ring systems. Examples include dihydroquinolines, e.g., 3,4-dihydroquinoline, dihydroisoquinolines, e.g., 1,2-dihydroisoquinoline, dihydroimidazole, tetrahydroimidazole, etc., indoline, isoindoline, isoindolones (e.g., isoindolin-1-one), isatin, dihydrophthalazine, quinolinone, spiro[cyclopropane-1,1'-isoindolin]-3'-one, and the like. Heterocycle groups may have 3-12 members, or 3-10 members, or 3-7 members, or 5-6 members.

"Hydroxyl" and "hydroxy" are used interchangeably and refer to —OH. "Oxo" refers to =O, or oxide where N-oxide or S-oxide exist. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g., $CH_3CH_2NHC(O)—$) C1-6 alkoxycarbonyl (e.g., CH3O—C(O)—), 5-7 membered heterocyclyl-C1-6 alkyl (e.g. piperazinyl-CH2-), C1-6 alkylsulfonyl-5-7 membered heterocyclyl (e.g., CH3S(O)2-morpholinyl-), 5-7 membered heterocyclyl C1-6 alkoxy (e.g., pyrrolidinyl-O—), 5-7 membered heterocyclyloxy, (4-7 membered heterocyclyl)-4-7 membered heterocyclyl (e.g. oxetanyl-pyrrolidinyl-), C3-6 cycloalkylaminocarbonyl (e.g., cyclopropyl-NH—C(O)—), 5-7 membered heterocyclyl-C2-6 alkynyl (e.g., N-piperazinyl-CH2C≡CCH2-), and C6-10 arylaminocarbonyl (e.g. phenyl-NH—C(O)—).

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

As used herein and in the claims, "hydrogen" and "H", "oxygen" and "O", "carbon" and "C", and "nitrogen" and "N" are interchangeably used, and each respectively refer to a hydrogen atom, an oxygen atom, a carbon atom, and/or a nitrogen atom. As used herein and in the claims, the rings of various compounds are sometimes interchangeably referred to as "ring A" or "A" and "ring B" or "B", both of which respectively refer to the specifically referenced ring. Similarly, as used herein and in the claims, the various groups of the compounds are sometimes interchangeably referred with or without "atom" or "group" at the end, such as "$R_1$" and $R_1$ group", both of which respectively refer to the specifically referenced atom or chemical group.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

"Treating" and "treatment" of a disease include the following:

(1) preventing or reducing the risk of developing the disease, i.e., causing the clinical symptoms of the disease not to develop in a subject that may be exposed to or predisposed to the disease but does not yet experience or display symptoms of the disease, (2) inhibiting the disease, i.e., arresting or reducing the development of the disease or its clinical symptoms, and/or (3) relieving the disease, i.e., causing regression of the disease or its clinical symptoms.

"Effective amount" refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated. The effective amount can include a range of amounts.

The compounds of the invention include solvates, hydrates, tautomers, stereoisomers and salt forms thereof.

The pharmaceutical compositions of compounds of the disclosed formulas may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. In one aspect, the compounds described herein may be administered orally. Oral administration may be via, for example, capsule or enteric coated tablets.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

In certain embodiments, a compound of the present disclosure is a compound of Formula I:

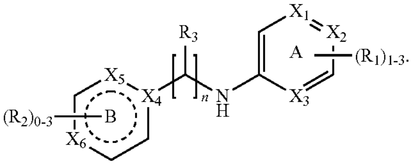

Wherein n is either 0, 1, or 2. When n is 0, this indicates that there is a direct bond between B and the NH group attached to ring A (as shown) and $R_3$ is absent. When n is 1 or 2, a $R_3$ group may be substituted with either of the CH atoms.

For example, the 1 or 2 CH groups can each independently be unsubstituted or substituted with an $R_3$ group.

In some embodiments, ring A is a 6 membered heteroaryl. In some embodiments, ring A is a 6 membered aryl. In some embodiments, ring A is a 6 membered heteroaryl that is substituted with one, two, or three $R_1$ groups, where the $R_1$ groups can either be the same or different. In some embodiments, ring A is a 6 membered aryl that is substituted with one, two, or three $R_1$ groups, where the $R_1$ groups can either be the same or different. In some embodiments where ring A is a heteroaryl, $X_1$, $X_2$, and $X_3$ are independently C, N, or O.

In some embodiments, ring B can be a 5-6 membered heterocycle, a 5-6 membered aryl, or a 5-6 membered cyclohexyl. In some embodiments, ring B can be a 5-6-membered heterocycle that is independently substituted with up to three $R_2$ groups. In some embodiments, ring B can be a 5-6 membered aryl that is independently substituted with up to three $R_2$ groups. In some embodiments, ring B can be a 5-6 membered cyclohexyl that is independently substituted with up to three $R_2$ groups. In some embodiments, where ring B is a 5-6 membered aryl, $X_4$, $X_5$, and $X_6$ are all carbons. In some embodiments, where ring B is a 5-6-membered heterocycle or a 5-6 membered heteroaryl, each $X_4$, $X_5$, and $X_6$ can independently be C, N, or O.

In some embodiments, $R_1$ can be halo, $C_{1-4}$ alkyl, $—NR_xR_y$, $—O(CH_2)_2R_x$, $—O(CH_2)_2NR_xR_y$, —NHC(O)—$C_{2-4}$ alkyl, $—(CH_2)_3NR_xR_y$, $—NH(CH_2)_2R_xR_y$, $—NHCH_2CR_xR_yR_z$, 5-6 membered aryl, 5-10 membered heterocycle, 5-10 membered heteroaryl, or 5-10 membered heterocyclic aryl. As used herein, a hetrocyclic aryl refers to two rings, such as a heterocyclic ring fused to an aryl. In some embodiments, $R_1$ can be further independently substituted with 1, 2, or 3 $R_a$ or $R_b$ groups. In some embodiments, two $R_1$ groups can come together to form a 5-6 membered heteroaryl, a 5-6 membered heterocycle, a 5-6 membered cycloalkyl, or a 5-6 membered aryl. In some embodiments, when two $R_1$ groups come together to form a 5-6 membered heteroaryl, a 5-6 membered heterocycle, a 5-6 membered cycloalkyl, or a 5-6 membered aryl, the resulting 5-6 membered heteroaryl, 5-6 membered heterocycle, 5-6 membered cycloalkyl, or 5-6 membered aryl can further be substituted with one, two, or three $R_a$ groups.

In some embodiments, $R_1$ is:

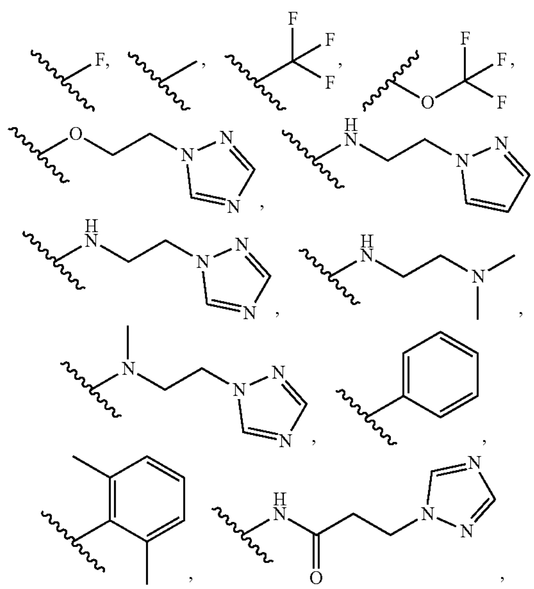

-continued

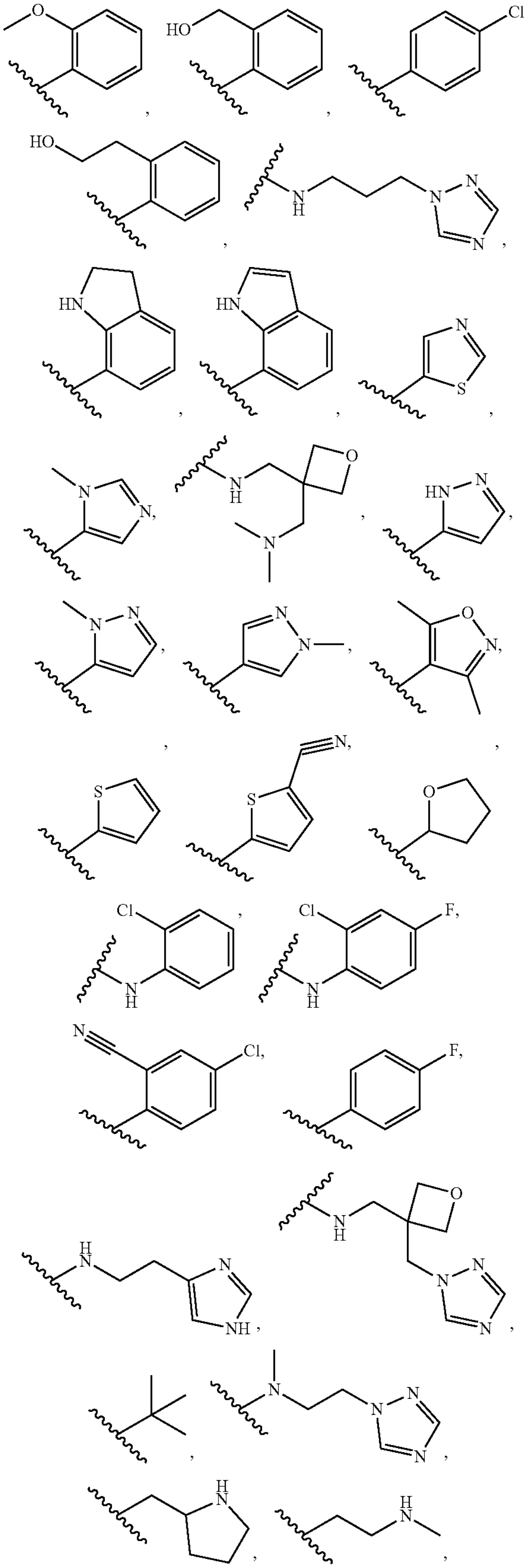

-continued

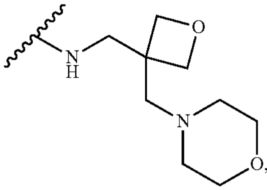

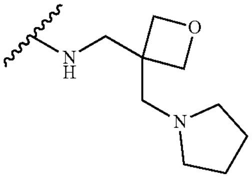,

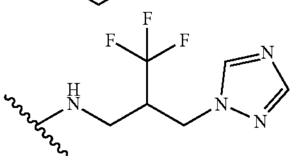,

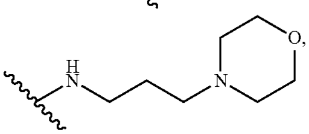

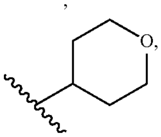

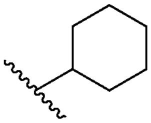

$-NH_2$,

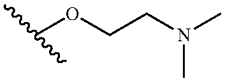,

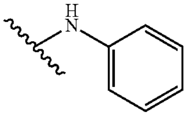,

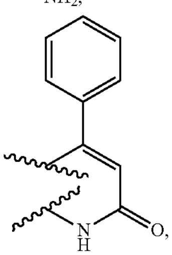,

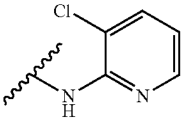,

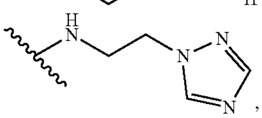,

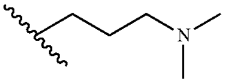,

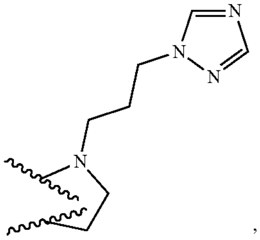,

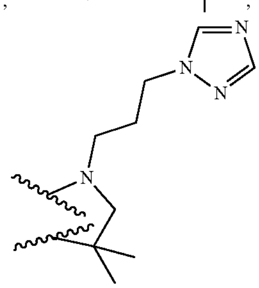,

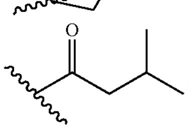,

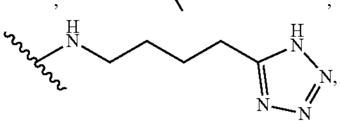

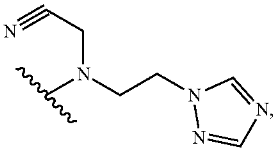

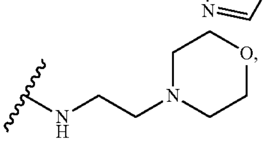 or

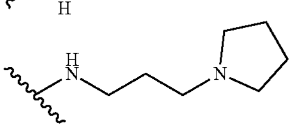,

In some embodiments, each $R_2$ can independently be a halogen atom, a $C_{1-2}$ methoxy, or —C(O)OR$_x$. In some embodiments, two $R_2$ groups on adjacent atoms can come together to from a 5-6 membered aryl ring. In some embodiments, two $R_2$ groups on adjacent atoms can come together to from a 5-6 membered aryl ring. The 5-6 membered aryl ring can be independently substituted with one, two, or three $R_a$ groups or can be unsubstituted.

In some embodiments, $R_2$ is

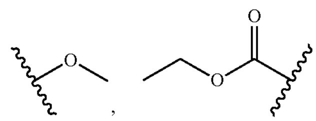

F, Cl or H.

In some embodiments, $R_3$ is either a $C_{1-3}$ haloalkyl or an oxo.

In some embodiments, $R_x$, $R_y$, and $R_z$ can each independently be a hydrogen, a halogen atom, $C_{1-2}$ alkyl, $C_{1-2}$ alcohol, $C_{1-2}$ alkoxy, $C_{1-2}$ haloalky, or —NR$_a$R$_b$. In some embodiments, $R_x$, $R_y$, and $R_z$ can each independently be a cyano group, an oxygen or oxo, a $C_{1-3}$ alkyl, a —C(O)OR', a $C_{1-3}$ haloalkyl, a 5-6 membered aryl, a 5-6 membered heteroaryl, or a 4-6 membered heterocycle. In some embodiments, any two of $R_x$, $R_y$, and $R_z$ can come together to form a 4-6 membered heterocycle or a 5-6 membered aryl. In some embodiments, $R_x$, $R_y$, and $R_z$ can be further substituted with $R_a$ and/or $R_b$.

In some embodiments, $R_a$ and $R_b$ are each independently a hydrogen atom, a halogen atom, a cyano group, an oxygen atom, a $C_{1-3}$ alkyl, a —C(O)OR', a $C_{1-3}$ haloalkyl, a 5-6 membered aryl, a 5-6 membered heteroaryl, or a 4-6 membered heterocycle. In some embodiments, $R_a$ and/or $R_b$ can further independently be substituted with an R' group.

In some embodiments, R' can be a $C_{1-3}$ alkyl, a $C_{1-3}$ haloalkyl, or a 5-6 membered heteroaryl.

In some embodiments, the compounds disclosed are pharmaceutically acceptable salts or pharmaceutically acceptable hydrates of Formula I.

In some embodiments, the compound having a structure of Formula I is selected from:

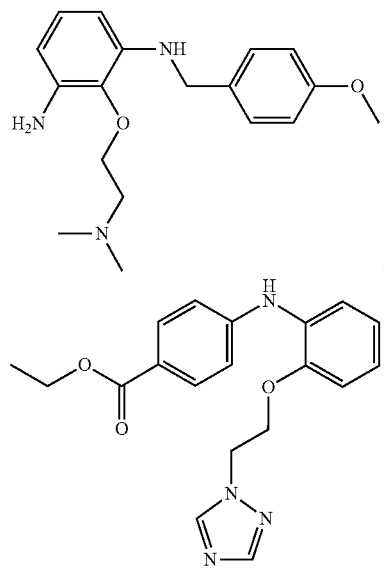

-continued
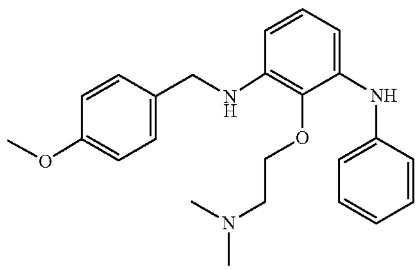
,
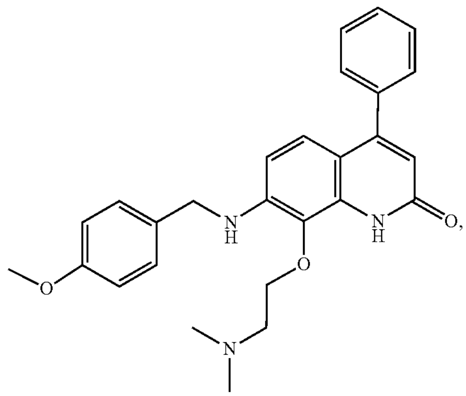
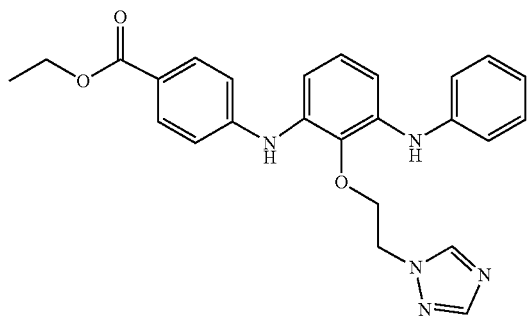
,
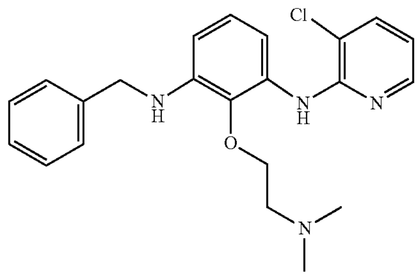
,
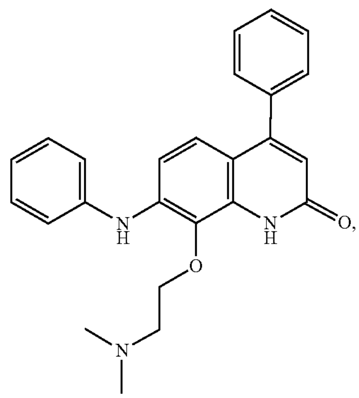
-continued
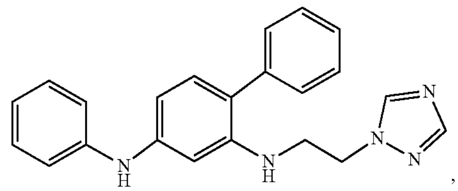
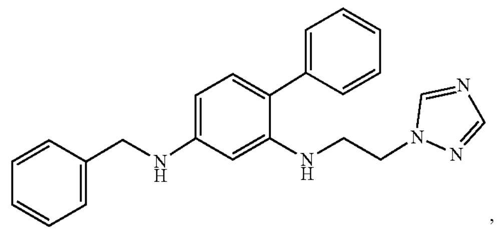
,
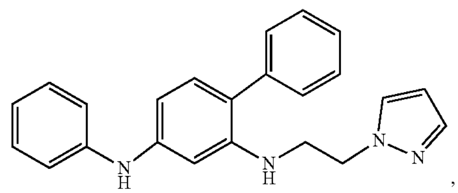
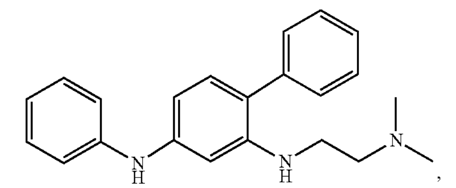
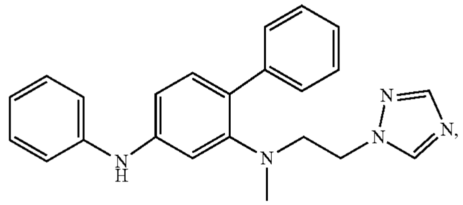
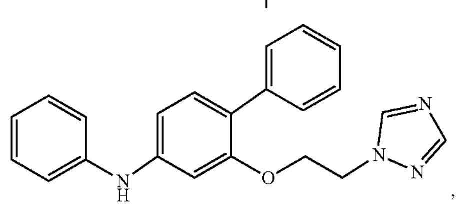
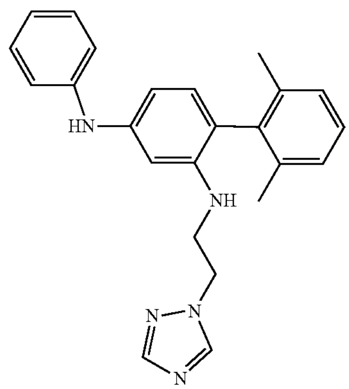
, -continued
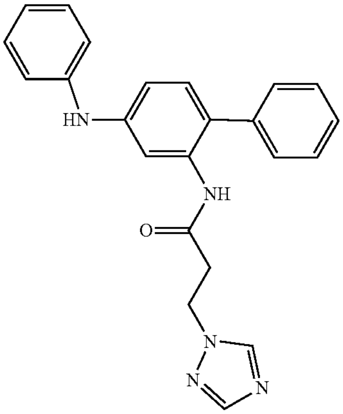
,
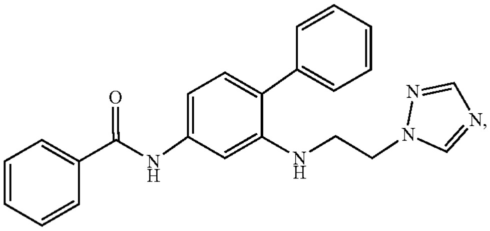
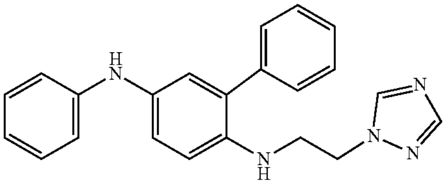
,
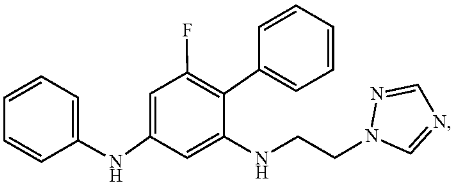
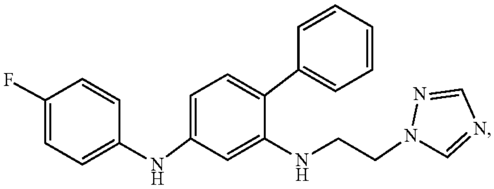
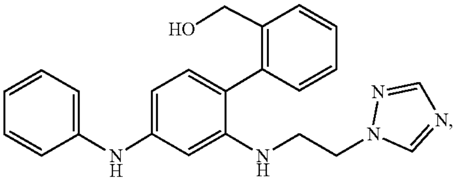
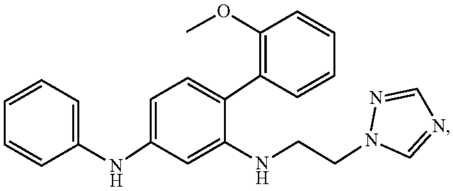
-continued
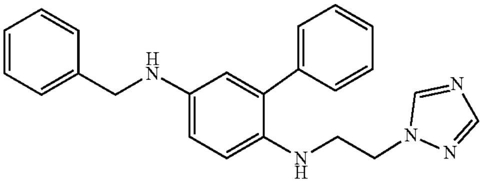
,
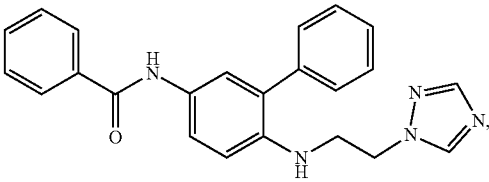
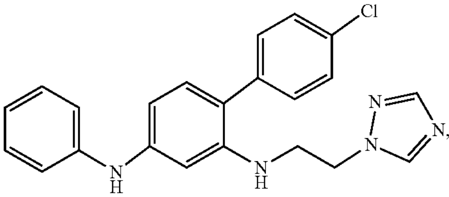
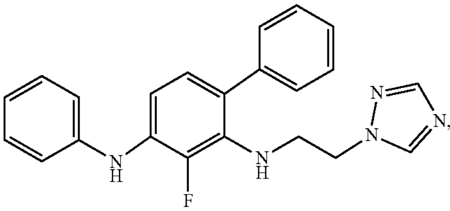
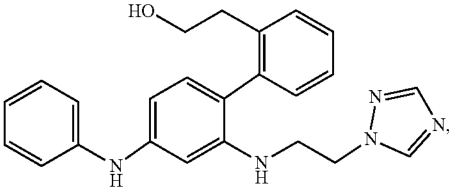
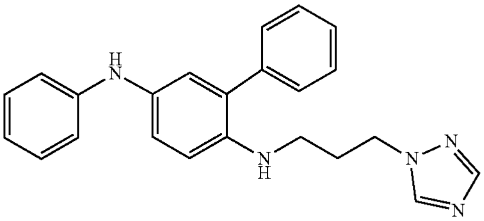
,
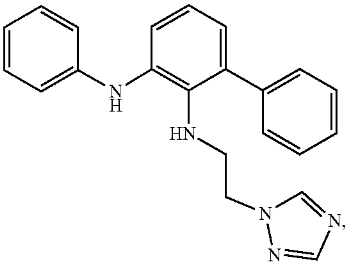
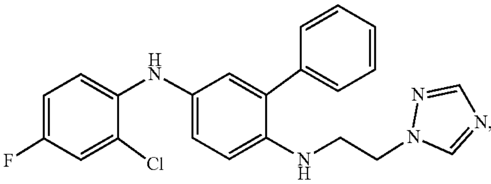

-continued
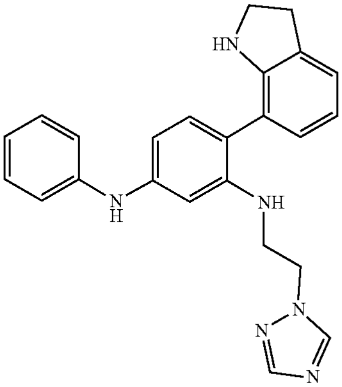
,
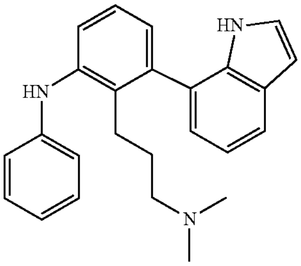
,
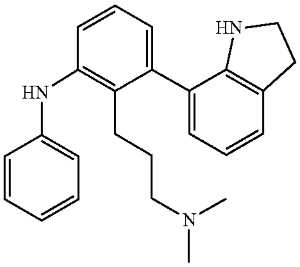
,
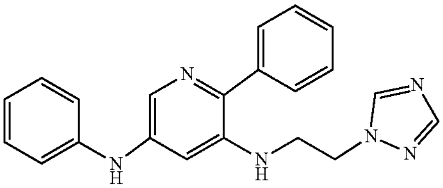
,
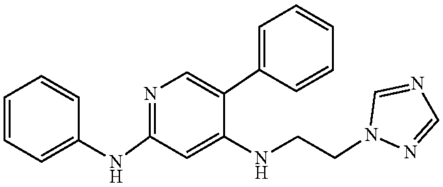
,
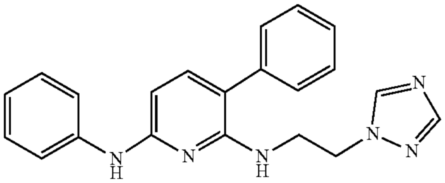
,
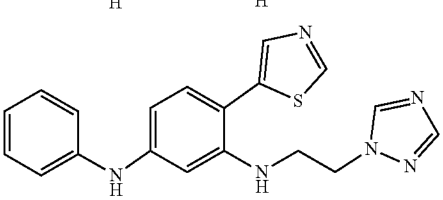
,
-continued
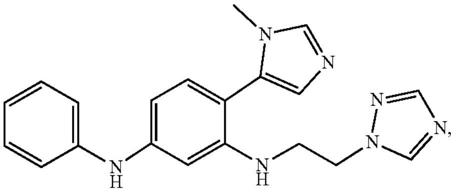
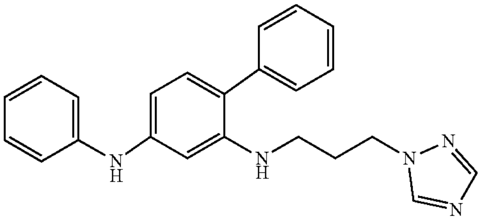
,
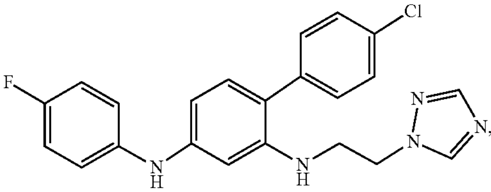
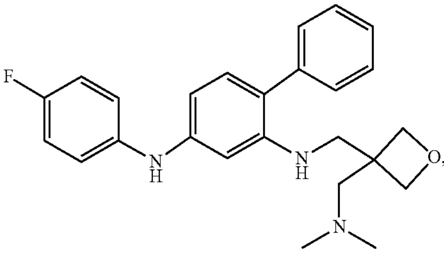
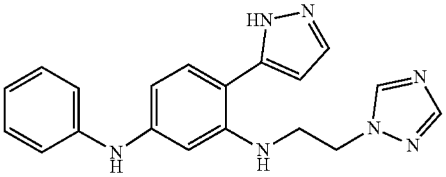
,
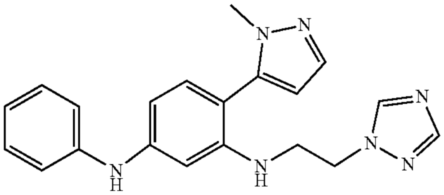
,
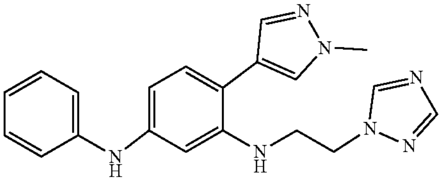
, -continued
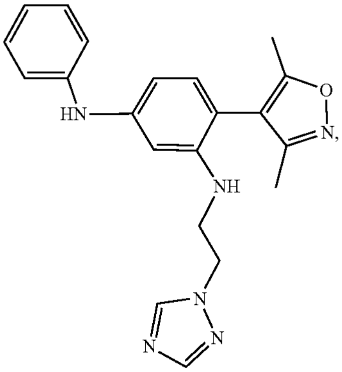
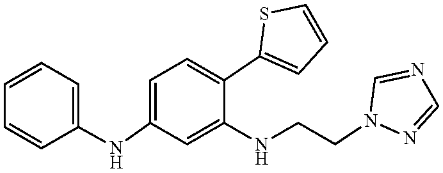
,
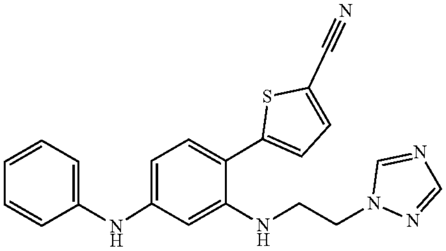
,
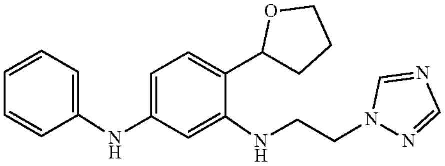
,
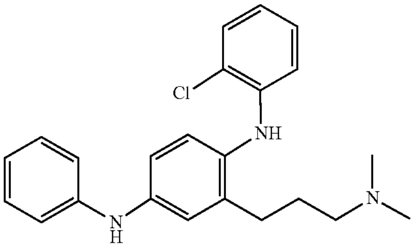
,
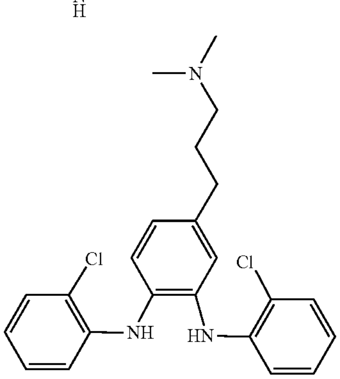
,
-continued
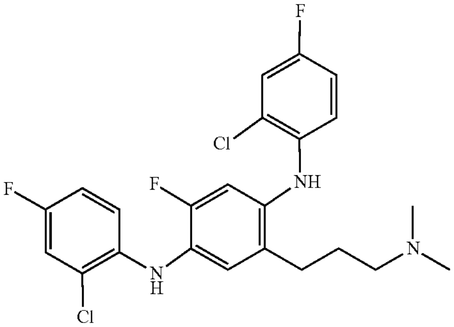
,
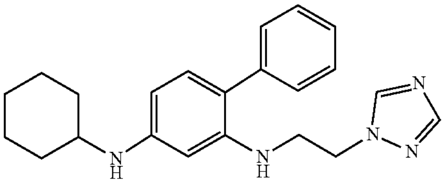
,
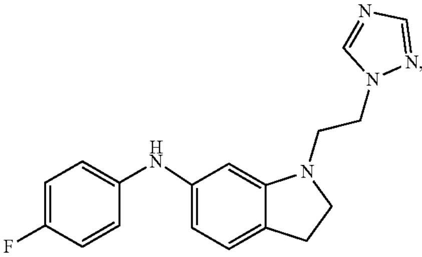
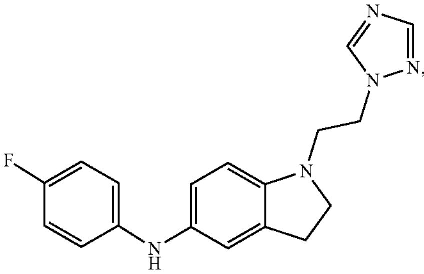
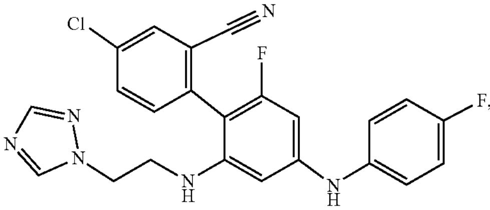
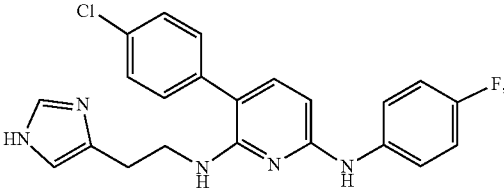

-continued
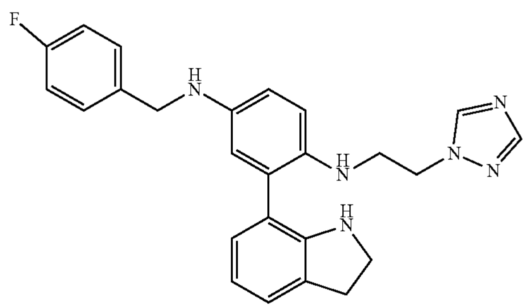
,
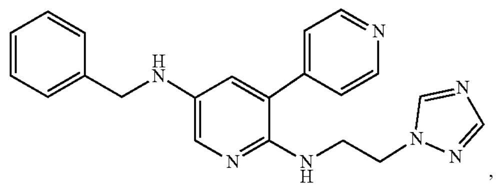
,
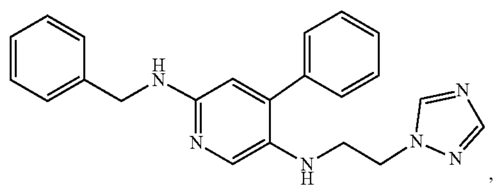
,
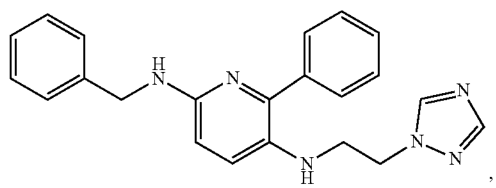
,
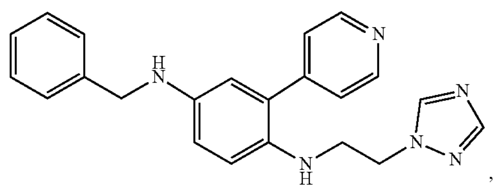
,
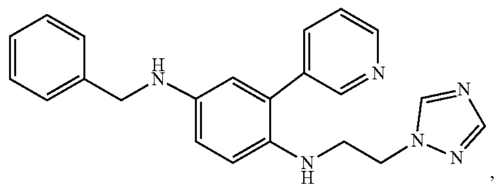
,
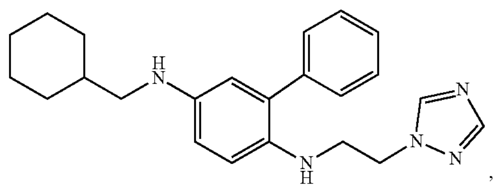
,
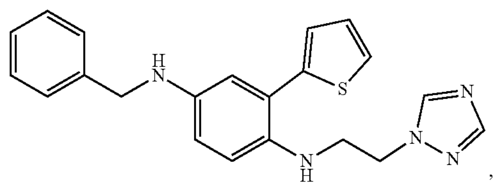
,
-continued
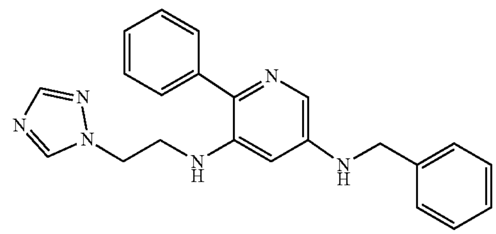
,
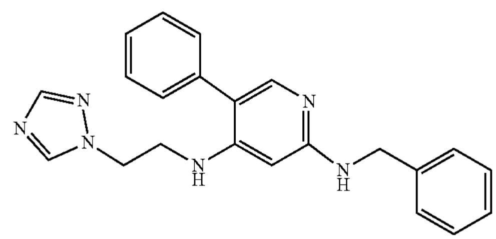
,
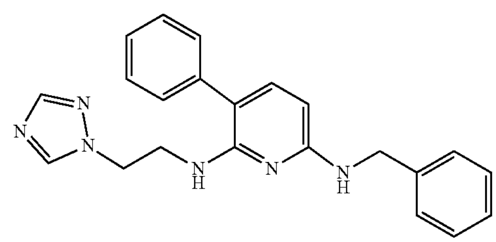
,
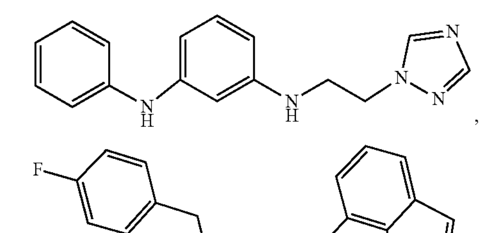
,
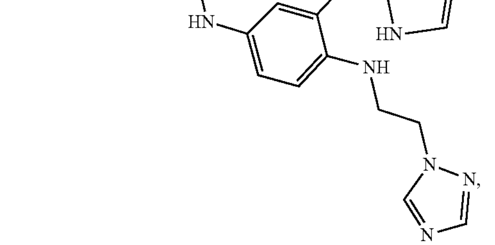
,
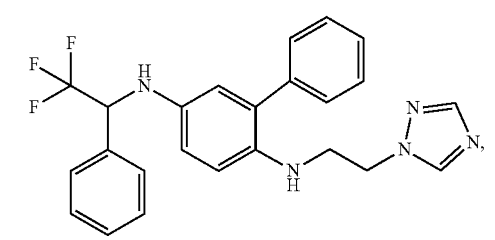
,
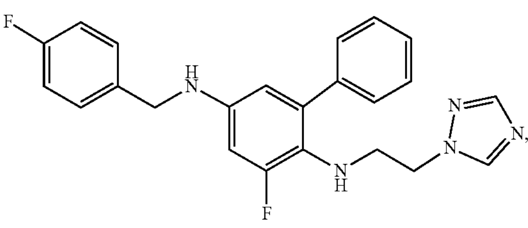
, -continued
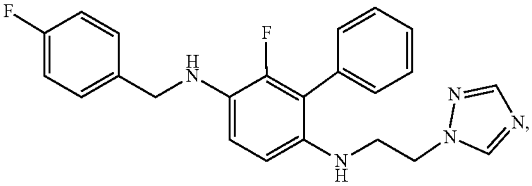
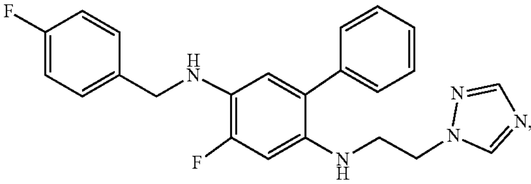
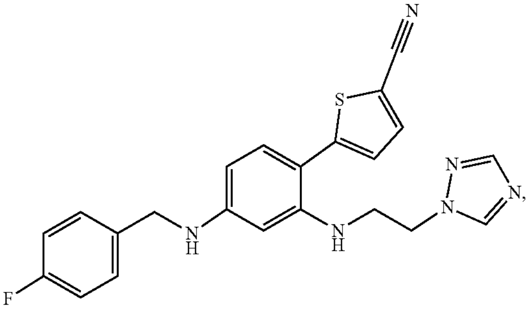
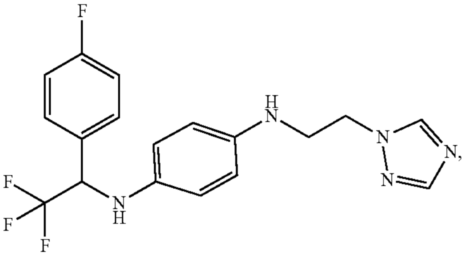
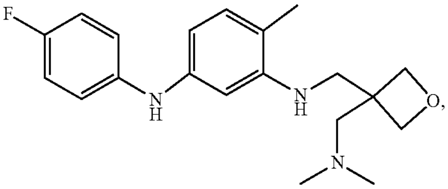
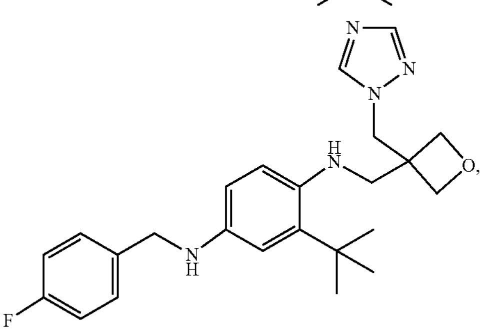
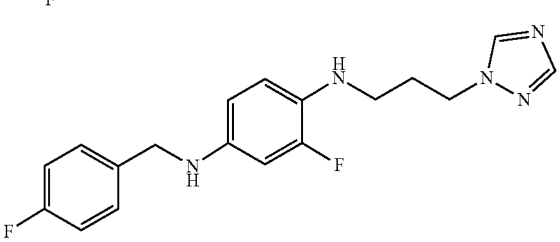
,
-continued
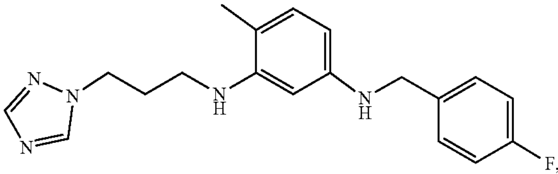
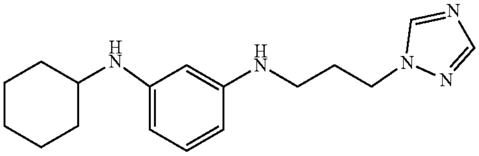
,
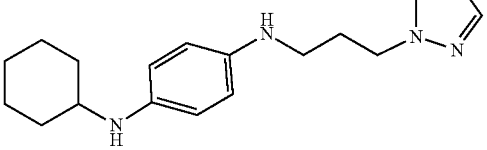
,
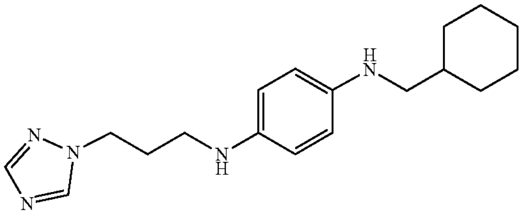
,
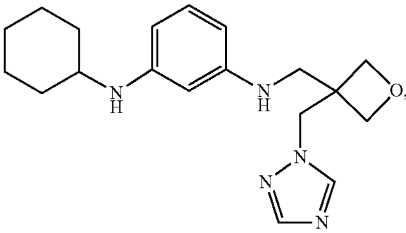
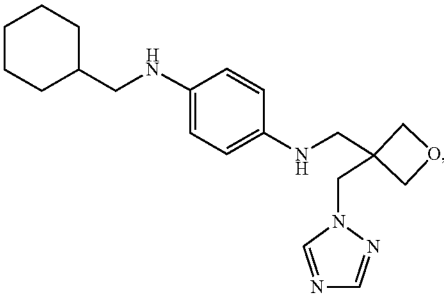
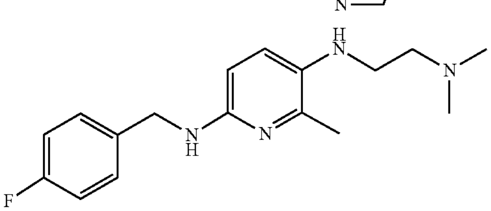
,
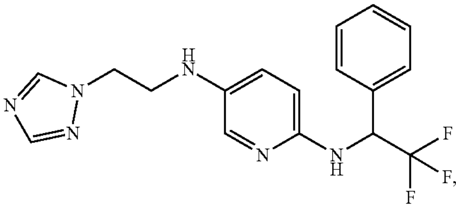

-continued
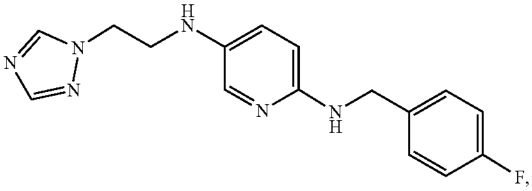
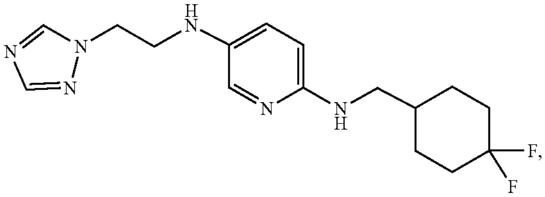
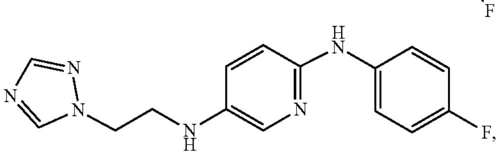
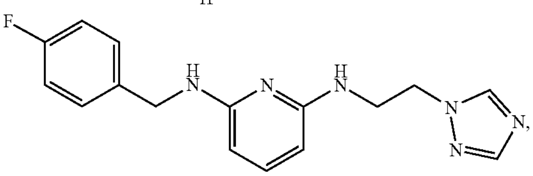
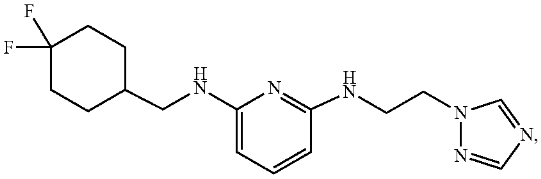
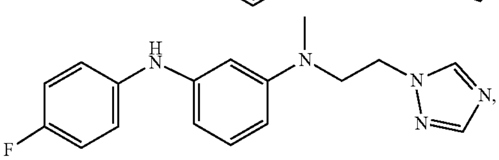
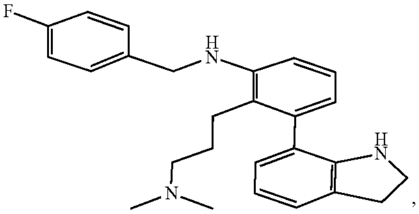
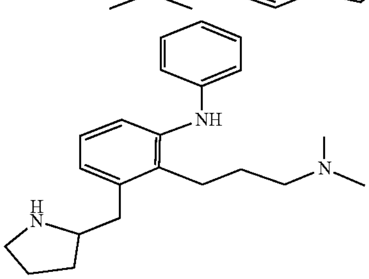
,
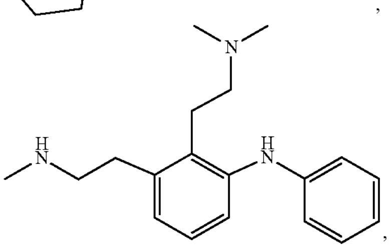
-continued
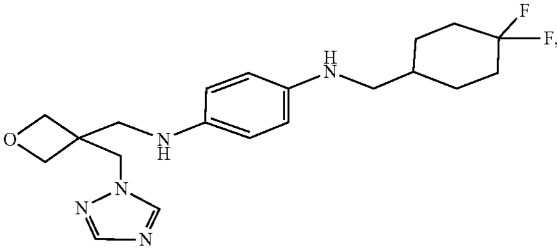
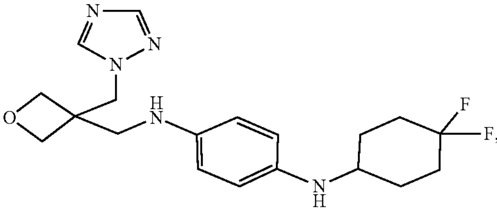
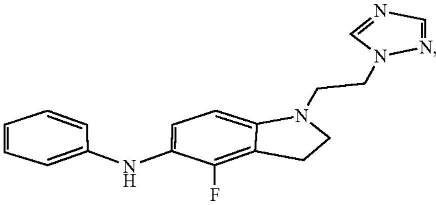
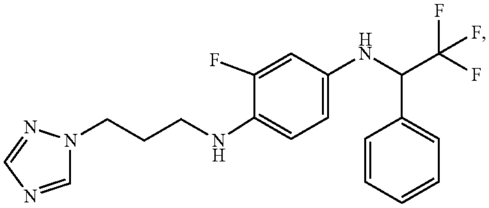
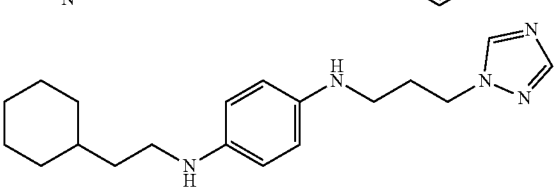
,
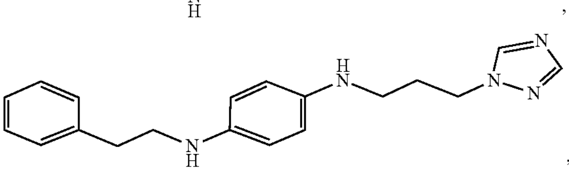
,
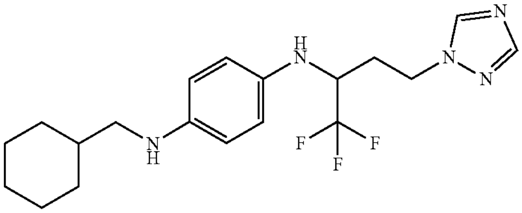
,
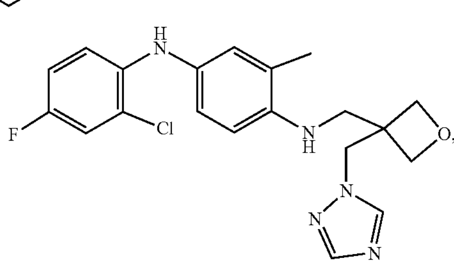

-continued
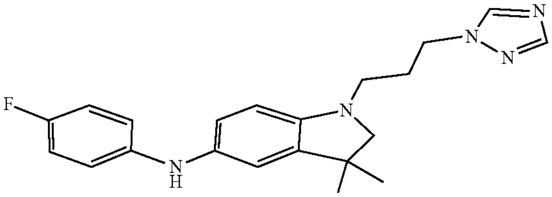
,
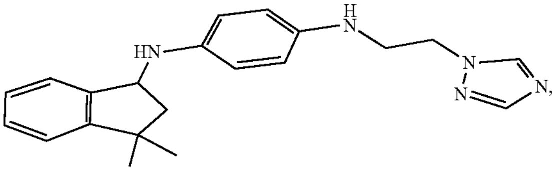
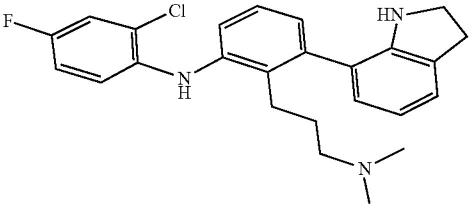
,
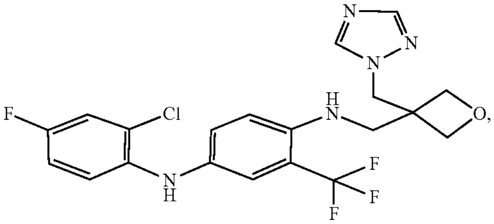
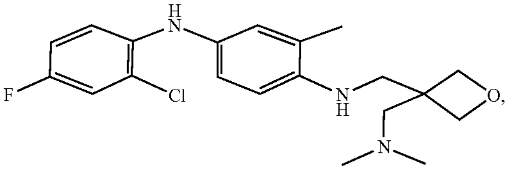
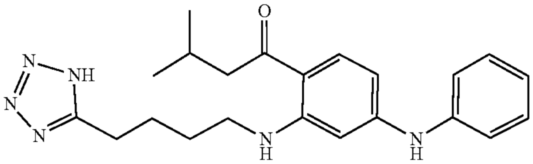
,
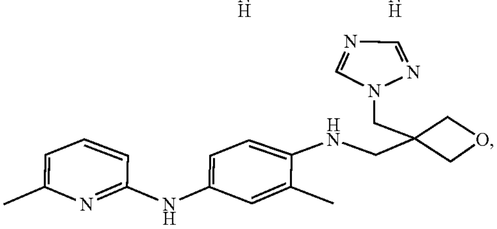
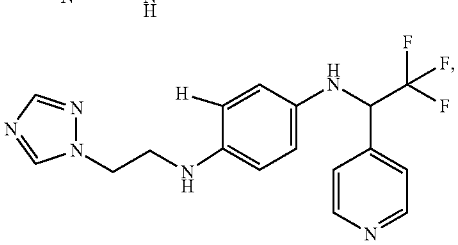
-continued
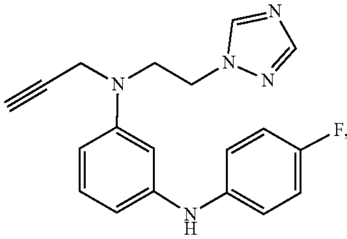
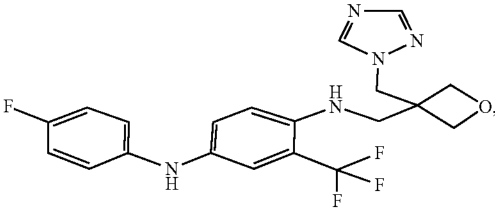
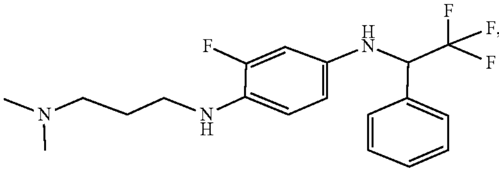
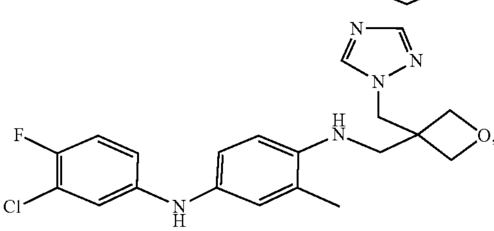
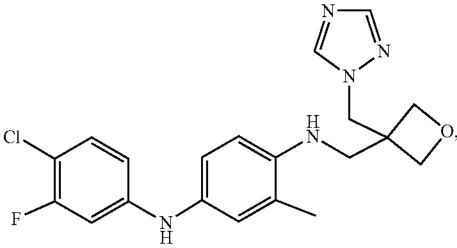
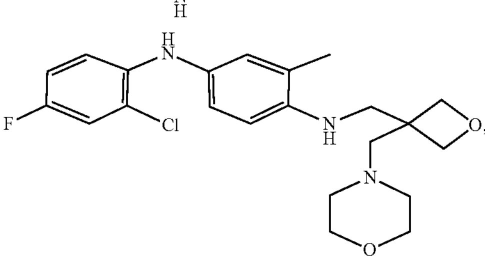
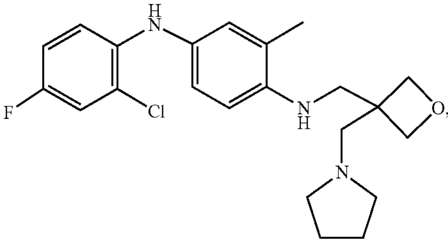

-continued
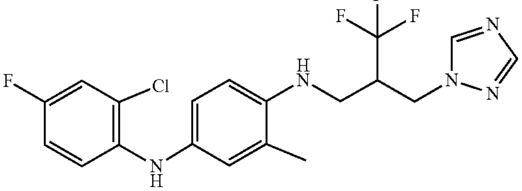
,
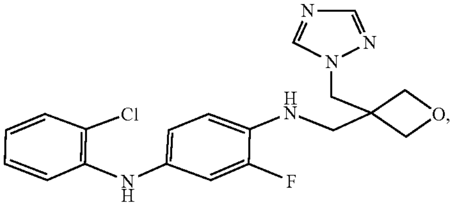
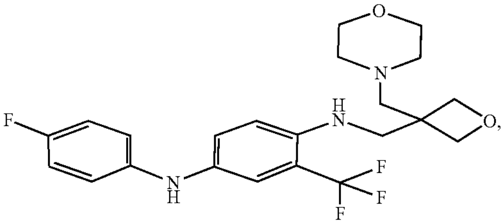
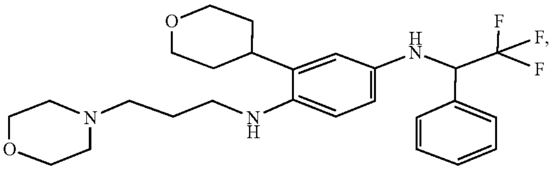
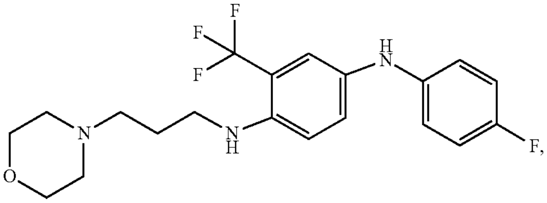
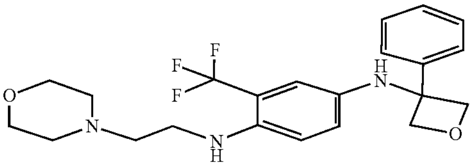
,
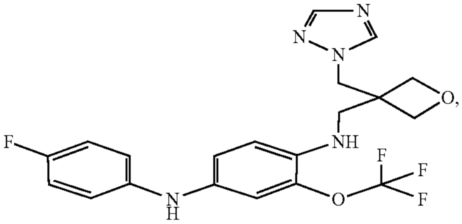
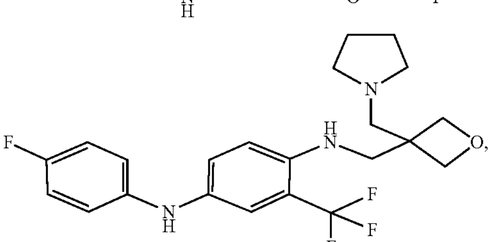
-continued
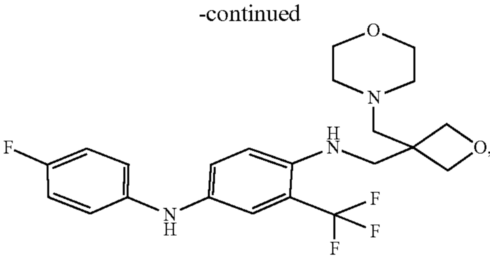
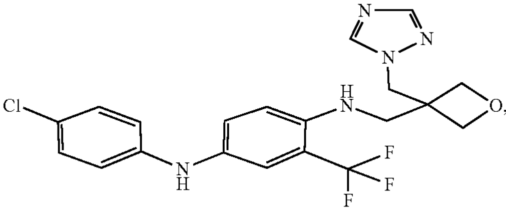
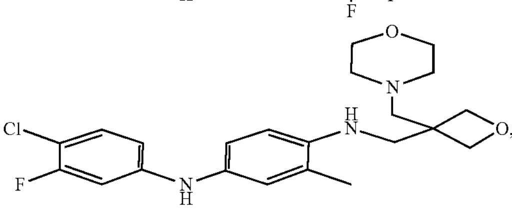
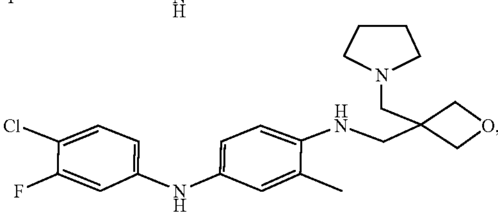
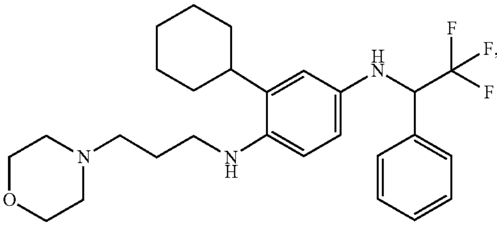
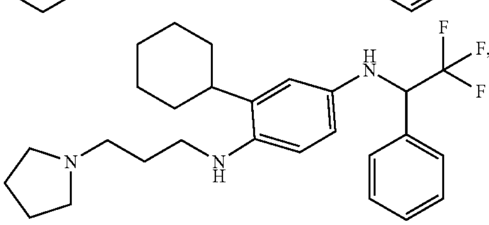
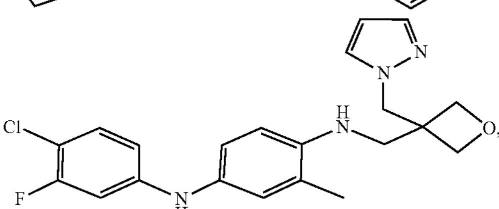
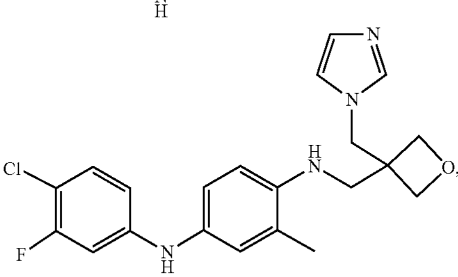

-continued

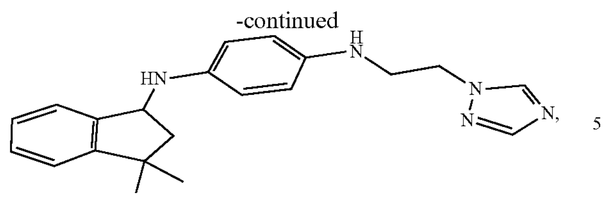

and pharmaceutically acceptable salts or hydrates thereof.

In some embodiments, the compounds disclosed have a structure corresponding to Formula II:

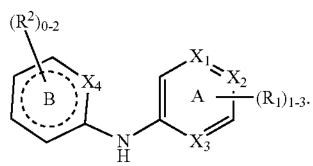

In some embodiments of Formula II, ring A is either a 6 membered heteroaryl or a 6 membered aryl. In some embodiments of Formula II, ring A is either a 6 membered heteroaryl or a 6 membered aryl ring, where ring A is independently substituted with one, two, or three $R_1$ groups. In some embodiments of Formula II, ring A is either an unsubstituted 6 membered heteroaryl or an unsubstituted 6 membered aryl. In embodiments of ring A, where ring A is a 6 membered heteroaryl, $X_1$, $X_2$, and $X_3$ are independently C, N, or O.

In some embodiments of Formula II, ring B is either a 6 membered heterocycle, a 6 membered aryl, or a 6 membered cyclohexyl ring. In some embodiments of Formula II, ring B is either a 6 membered heterocycle, a 6 membered aryl, or a 6 membered cyclohexyl ring, where ring B is unsubstituted. In some embodiments of Formula II, ring B is either a 6 membered heterocycle, a 6 membered aryl, or a 6 membered cyclohexyl ring, where ring B is independently substituted with up to two $R_2$ groups. Further, in embodiments of ring B where ring B is a 6 membered heterocycle, $X_4$ can a C, a N, or an O.

In some embodiments of Formula II, $R_1$ can be a halogen atom, a $C_{1-4}$ alkyl, a $—NR_xR_y$, a $—O(CH_2)_2R_xR_y$, a $—O(CH_2)_2NR_xR_y$, a $—NHC(O)\text{-alkyl}_{(2-4)}$, a $—(CH_2)_3NR_xR_y$, a $—NH(CH_2)_2R_xR_y$, a $—NHCH_2CR_xR_yR_z$, a 5-6 membered aryl, a 5-10 membered heterocycle, a 5-10 membered heteroaryl, or a 5-10 membered heterocyclic aryl. In some embodiments, two $R_1$ groups can come together to form a 5-6 membered heteroaryl, 5-6 membered heterocycle, 5-6 membered cycloalkyl, 5-6 membered aryl. In some embodiments, two $R_1$ groups can come together to form a 5-6 membered heteroaryl, 5-6 membered heterocycle, 5-6 membered cycloalkyl, 5-6 membered aryl, wherein the 5-6 membered heteroaryl, 5-6 membered heterocycle, 5-6 membered cycloalkyl, or 5-6 membered aryl can be further substituted with one to three $R_a$ groups. In some embodiments, each of the one to three $R_1$ groups can independently be further substituted with one to three $R_a$ groups and/or one to three $R_b$ groups.

In some embodiments of Formula II, $R_1$ is:

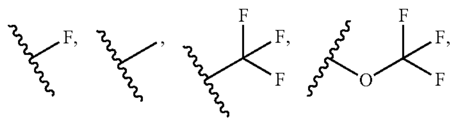

-continued

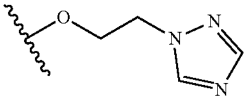, 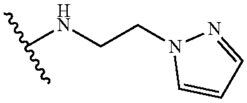,

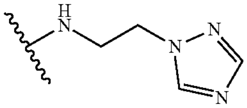, 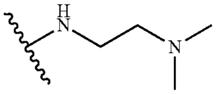,

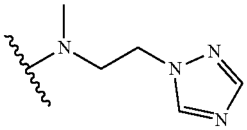, 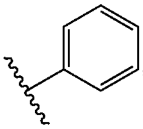, 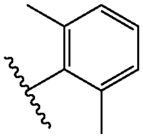,

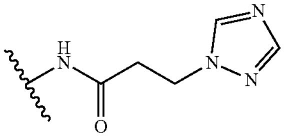, 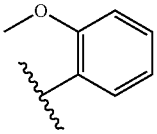,

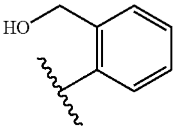, 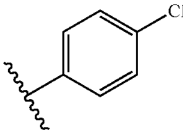

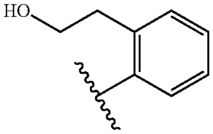, 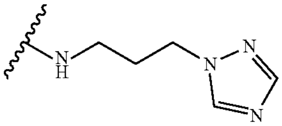,

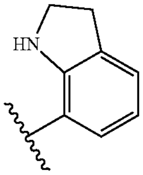, 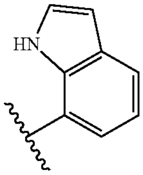, 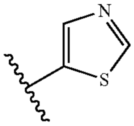,

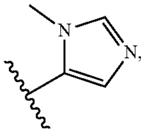 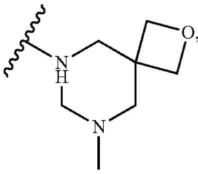 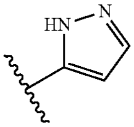,

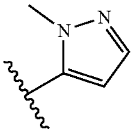, 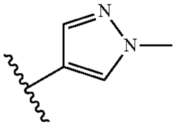, 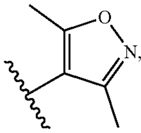

, ,

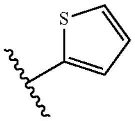 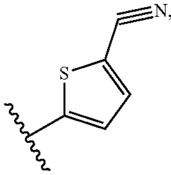 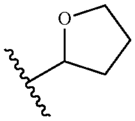

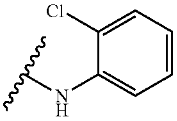, 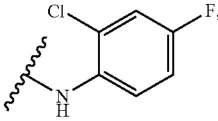

-continued

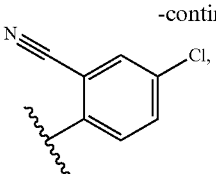, 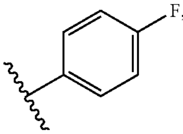,

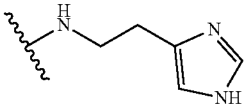, 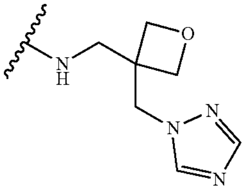,

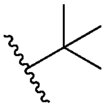, 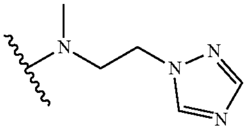, 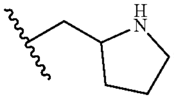,

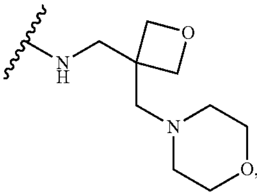

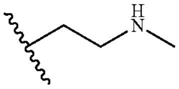,

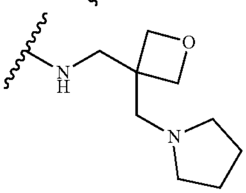, 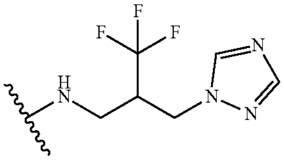,

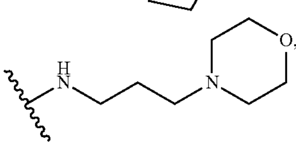, 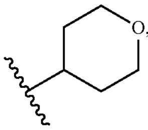, or

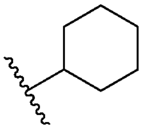.

In some embodiments of Formula II, each $R_2$ can independently be a halogen atom, a $C_{1-2}$ methoxy, or —C(O)$OR_x$.

In some embodiments of Formula II, each $R_2$ is independently

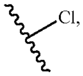, 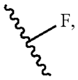, or 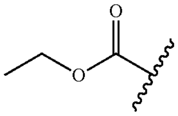.

In some embodiments of Formula II, $R_1$ and/or $R_2$, can contain one or more $R_x$, $R_y$, and/or $R_z$ groups, where each $R_x$, $R_y$, and $R_z$ group can each independently be a hydrogen atom, a halogen atom, $C_{1-2}$ alkyl, $C_{1-2}$ alcohol, $C_{1-2}$ alkoxy, $C_{1-2}$ haloalkyl, or —$NR_aR_b$. In some embodiments of Formula II, where two $R_x$, $R_y$, or $R_z$ are present, any two of the $R_x$, $R_y$, or $R_z$ can come together to form a 4-6 membered heterocycle or 5-6 membered aryl ring. In some embodiments of Formula II, each of $R_x$, $R_y$, and $R_z$ can further be substituted with a $R_a$ group or a $R_a$ and a $R_b$ group.

In some embodiments of Formula II, $R_a$ and $R_b$ can each independently be a hydrogen atom, a halogen atom, a cyano group, an oxygen atom, an $C_{1-3}$ alkyl, a —C(O)OR', a $C_{1-3}$ haloalkyl, a 5-6 membered aryl, a 5-6 membered heteroaryl, or a 4-6 membered heterocycle. In some embodiments of Formula II, where $R_a$ and/or $R_b$ are each independently an $C_{1-3}$ alkyl, a —C(O)OR', a $C_{1-3}$ haloalkyl, a 5-6 membered aryl, a 5-6 membered heteroaryl, or a 4-6 membered heterocycle, $R_a$ and/or $R_b$ can further be substituted with an R' group. In some embodiments of Formula II, R' can be a $C_{1-3}$ alkyl, a $C_{1-3}$ haloalkyl, or a 5-6 membered heteroaryl ring. In some embodiments, the disclosed compounds are either pharmaceutically acceptable salts or hydrates of Formula II.

In some embodiments, example compounds of Formula II have the following structures:

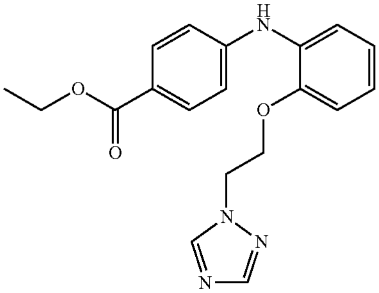,

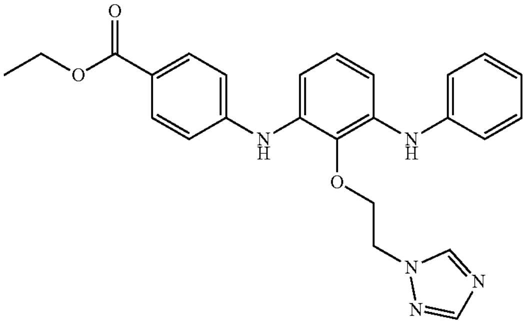,

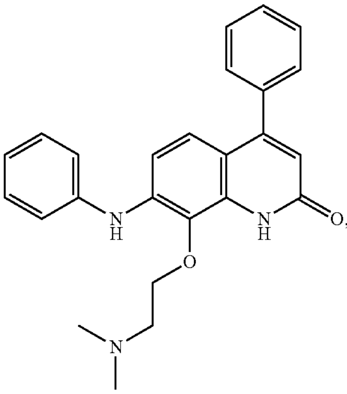,

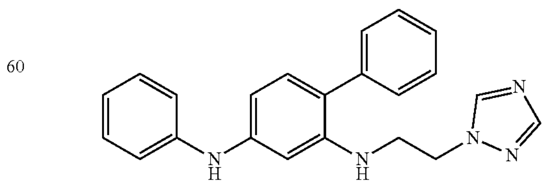,

-continued
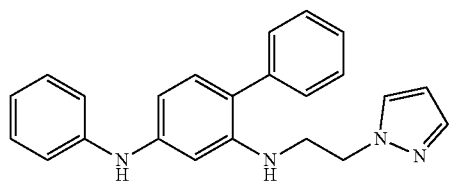
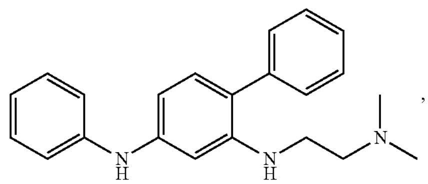
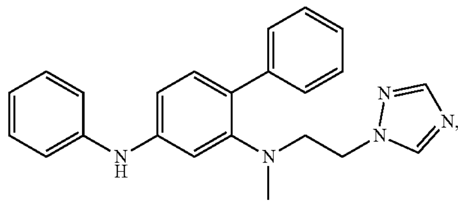
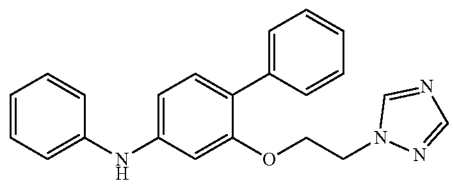
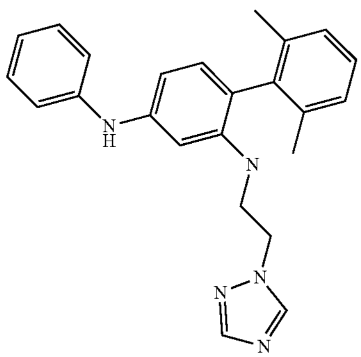
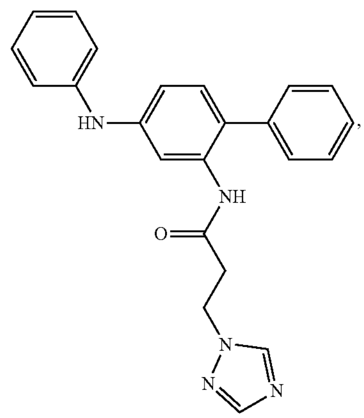
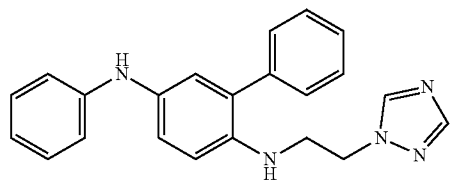
-continued
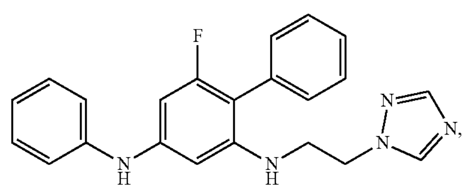
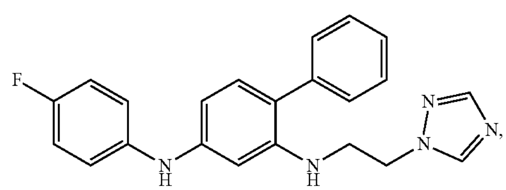
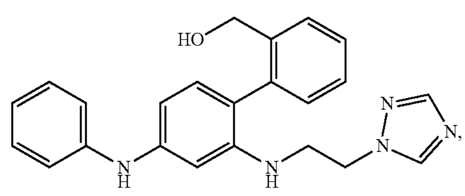
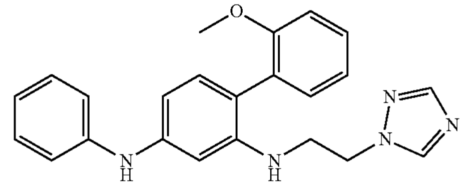
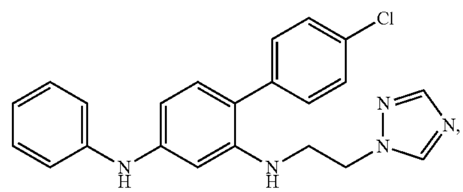
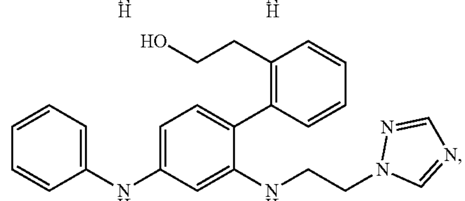
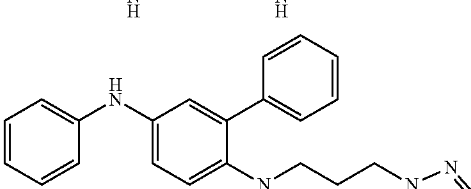
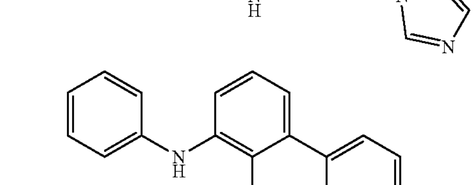
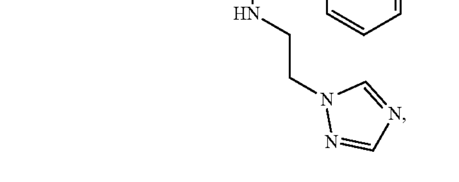
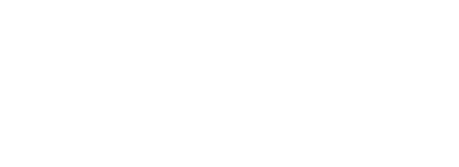

-continued
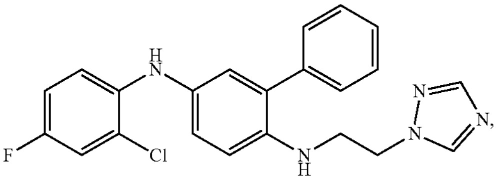
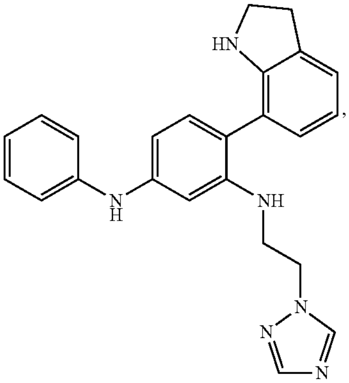
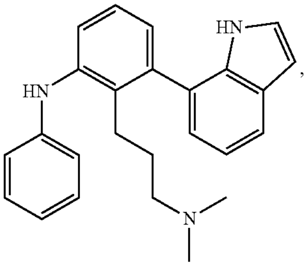
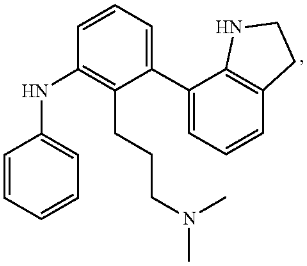
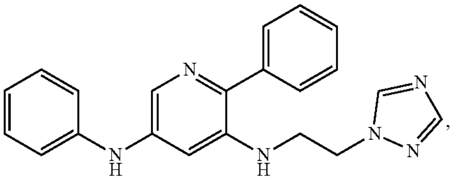
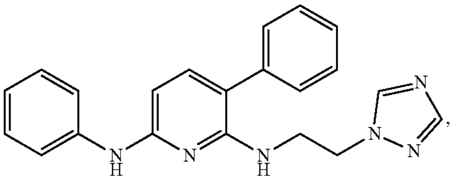
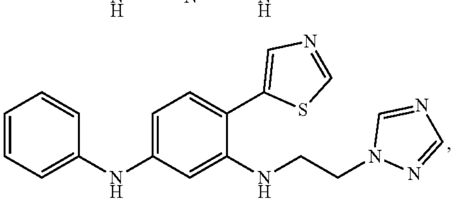
-continued
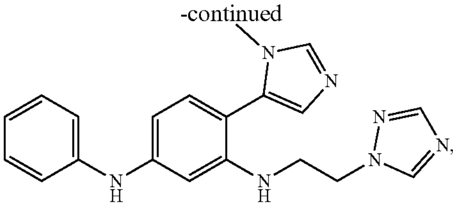
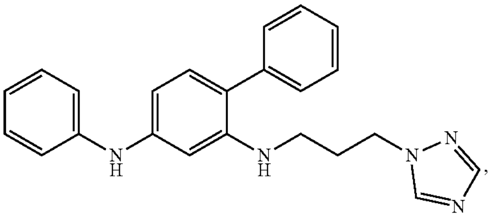
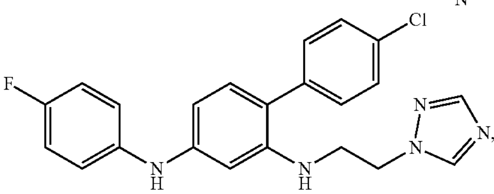
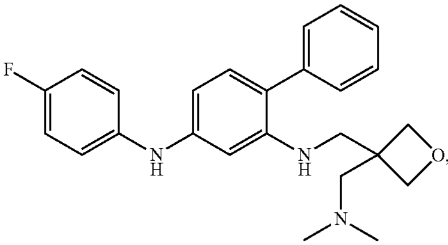
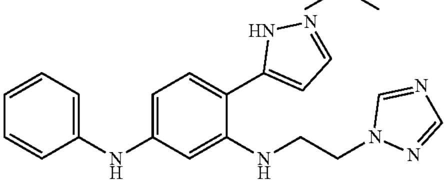
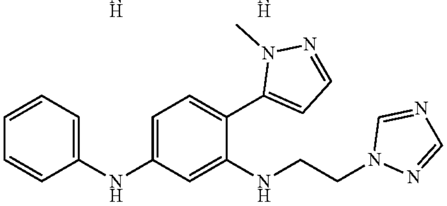
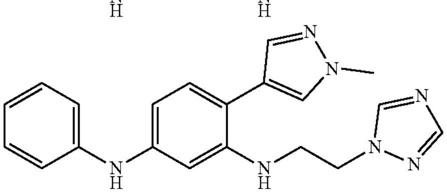
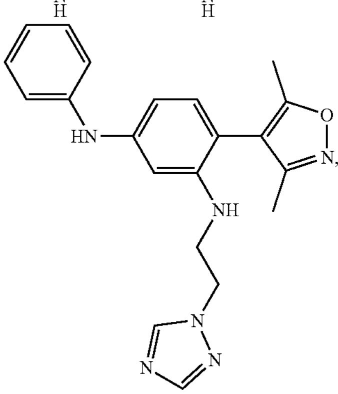

-continued
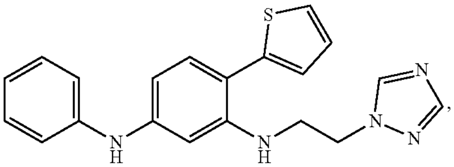
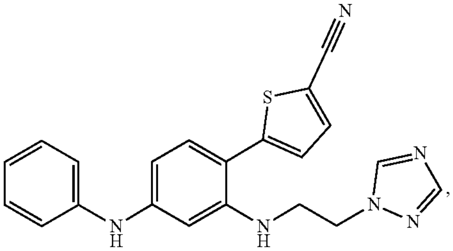
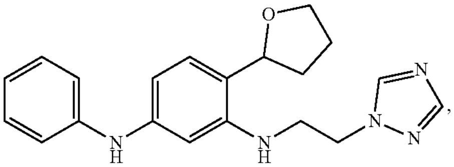
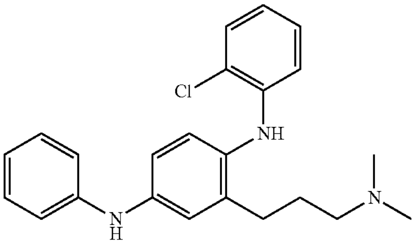
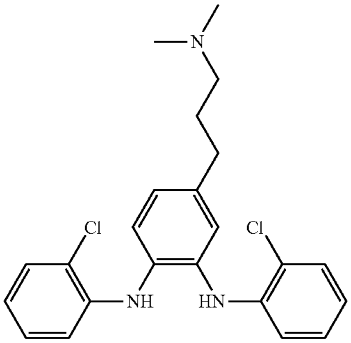
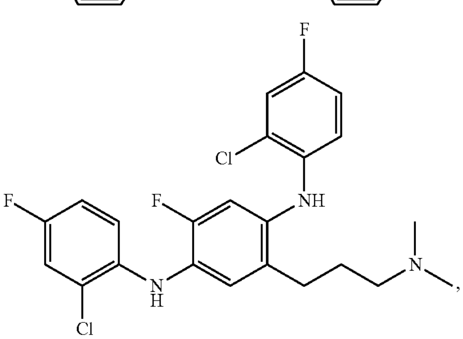
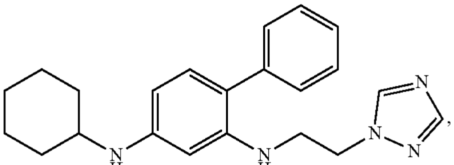
-continued
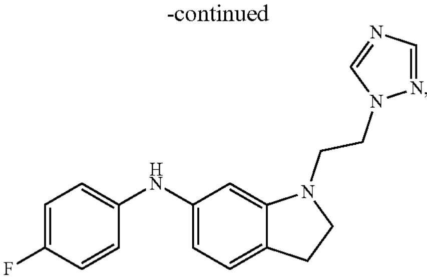
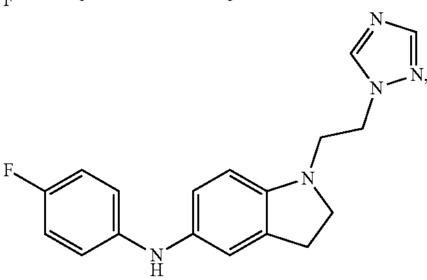
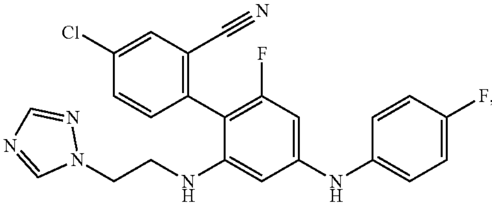
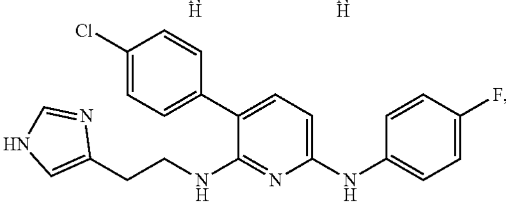
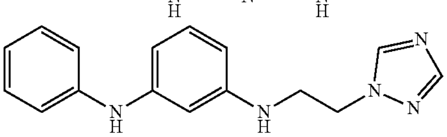
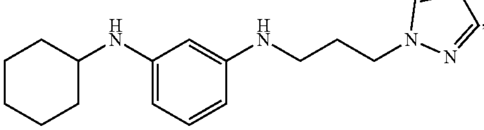
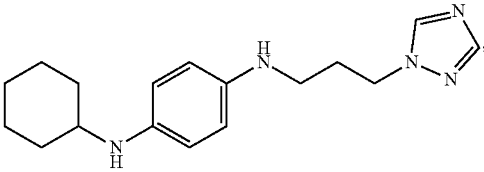
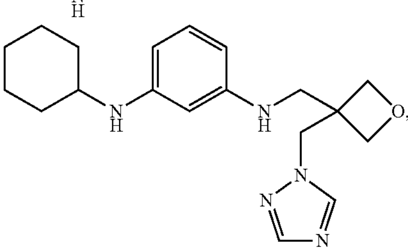
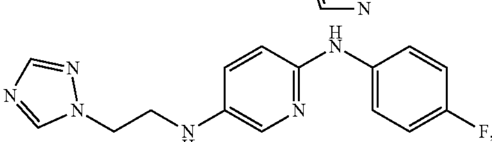

-continued
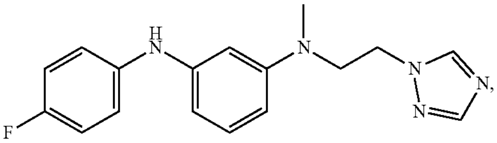
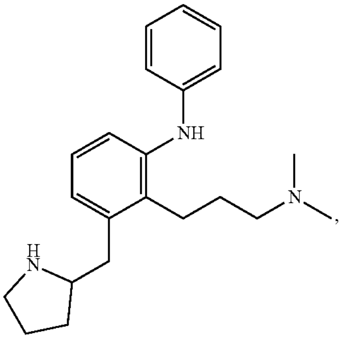
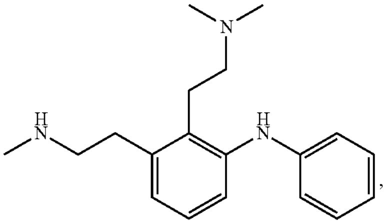
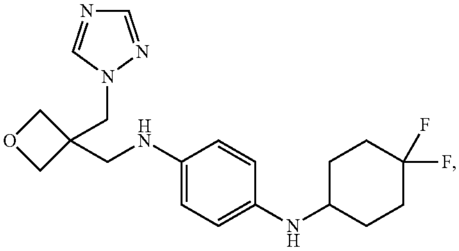
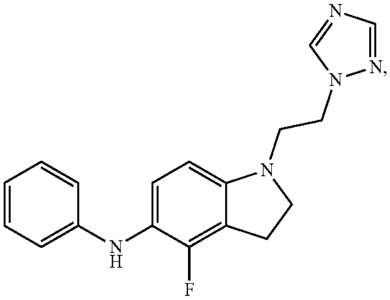
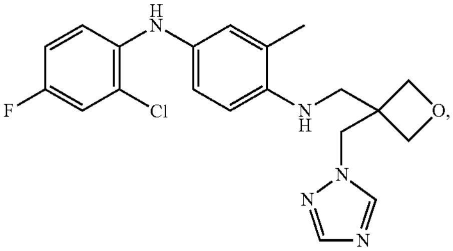
-continued
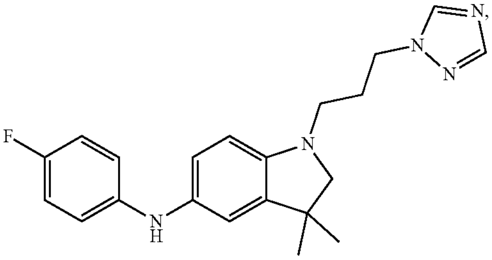
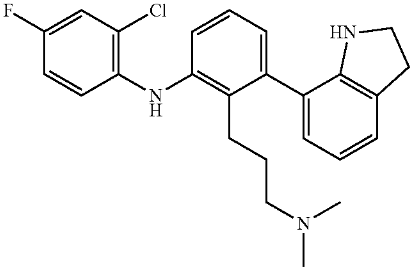
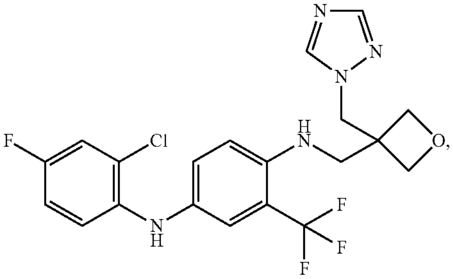
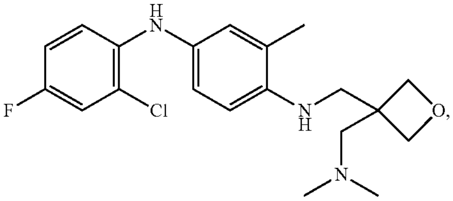
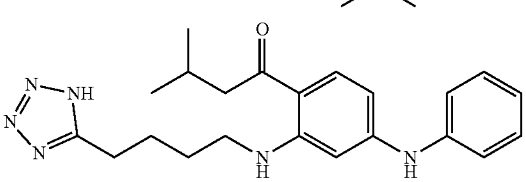
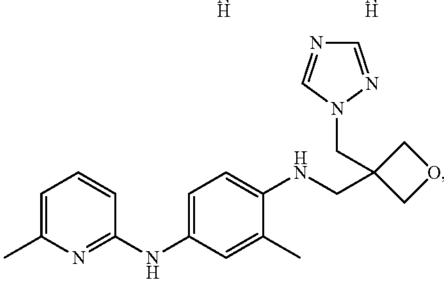
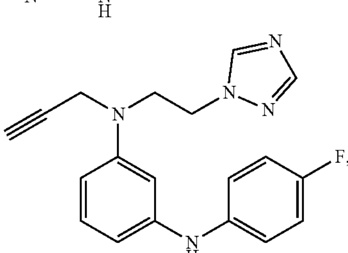

-continued

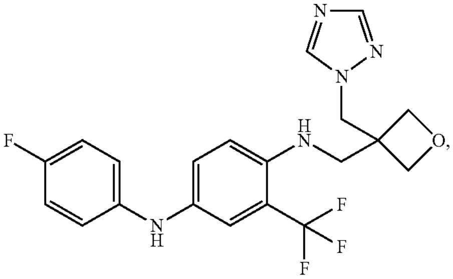

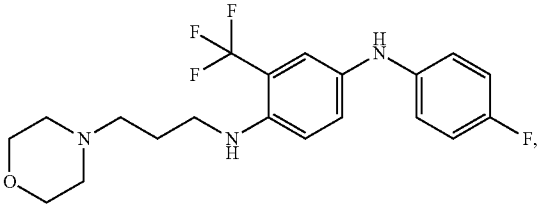

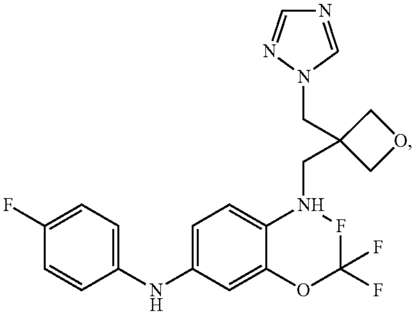

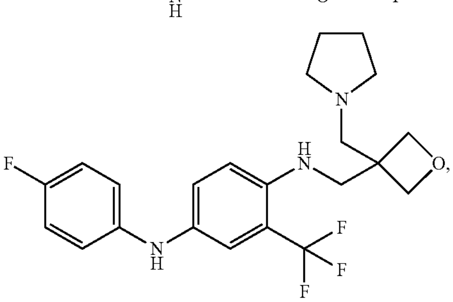

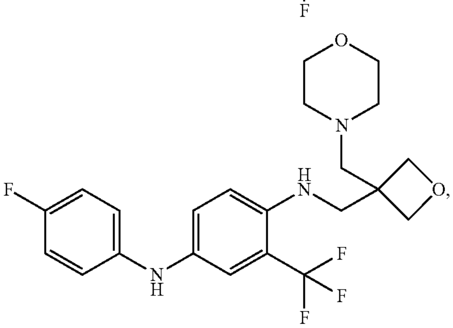

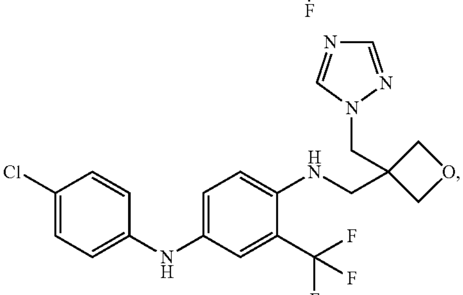

-continued

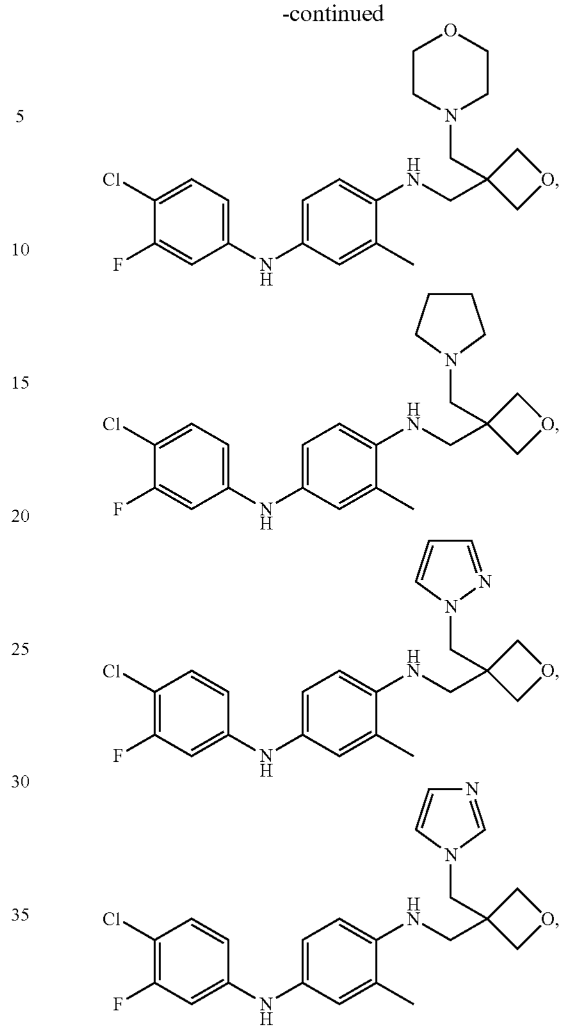

and pharmaceutically acceptable salts or hydrates thereof.

In some embodiments, the compounds disclosed have a structure corresponding to Formula IIA:

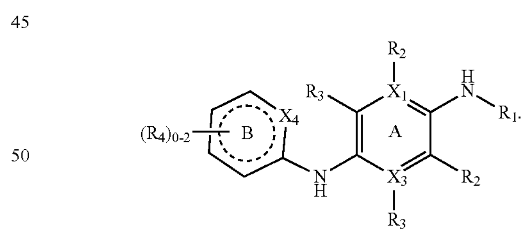

Wherein in some embodiments, ring B can be a cyclohexyl, a 6-membered heterocycle, a 6-membered aryl, or a 6-membered heteroaryl. In some embodiments of Formula IIA, where ring B is a cyclohexyl, a 6-membered heterocycle, or a 6-membered heteroaryl, $X_4$ can either be a C, N, or an O. In some embodiments of Formula IIA, where ring B is a cyclohexyl, a 6-membered heterocycle, or a 6-membered heteroaryl, ring B can be independently substituted with up to two $R_4$ groups.

In some embodiments, the $X_1$ and $X_3$ of ring A can independently be a C, N, or an O.

In some embodiments, $R_1$ can be a $—C_{1-3}$ alkyl-$R_x$, a $—(CH_2)_2NR_xR_y$, a $—CH_2C(R_xR_y)R_a$, a $—CH_2C(R_xR_y)$ $NR_aR_b$, or a 5-6 membered aryl ring. In some embodiments, where $R_1$ is substituted, $R_1$ can be substituted with a $R_a$ and/or $R_b$ group. In some embodiments, $R_2$ can be a hydrogen atom, a halogen atom, $C_{1-3}$ alkyl, $C_{1-3}$ haloalkyl, or $C_{1-3}$ haloalkoxy. In some embodiments, $R_x$ and $R_y$ can each independently be a $C_{5-6}$ membered heterocycle ring. In some embodiments, a $R_1$ and a $R_2$ can come together to form a 5-6 membered heterocycle. In some embodiments, when the respective $R_1$ and the respective $R_2$ come together to form a 5-6 membered heterocycle ring, and/or the 5-6 membered heterocycle ring can further be substituted with $R_a$ and/or $R_b$ group(s). In some embodiments, $R_3$ is a hydrogen atom or a halogen atom. In some embodiments, $R_4$ can be a halogen atom, or a $C_{1-3}$ alkyl group. In some embodiments, $R_1$, $R_2$, $R_3$, and/or $R_4$ can be further independently substituted with one or more $R_a$ and/or $R_b$ group. In some embodiments, $R_a$ and $R_b$ can each independently be a $C_{1-3}$ alkyl or a $C_{1-3}$ haloalkyl group. In some embodiments, $R_a$ and $R_b$ can be a $C_{1-3}$ alkyl and a $C_{1-3}$ haloalkyl group that is further substituted with a R' group. In some embodiments, R' can be a 5 membered heteroaryl or a 5-6 membered heterocycle ring. In some embodiments, the disclosed compounds are either pharmaceutically acceptable salts or hydrates of Formula IIA.

In some embodiments of Formula IIA, $R_1$ is selected from:

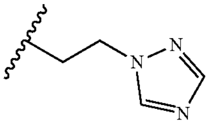
,
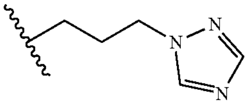
,
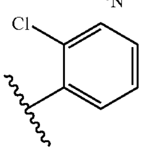
,
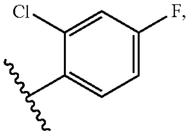
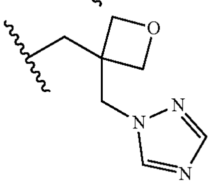
,
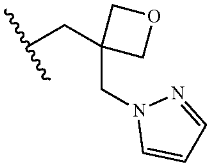
,
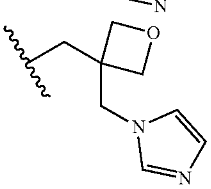
,
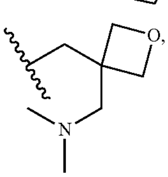
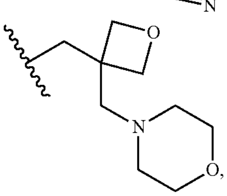
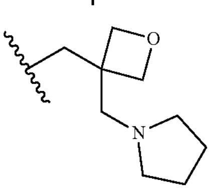
, and
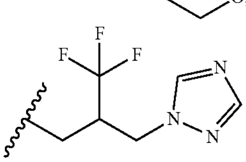
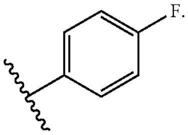

In some embodiments of Formula IIA, $R_2$ is selected from:

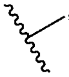
,
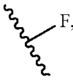
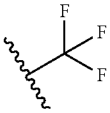
,
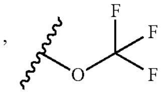
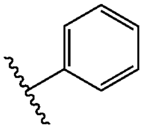
, and
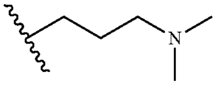
.

In some embodiments, the compounds of Formula IIA have the following structure:

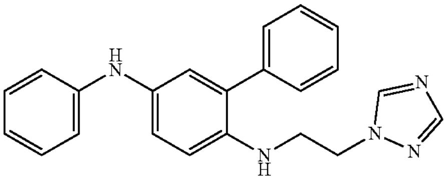
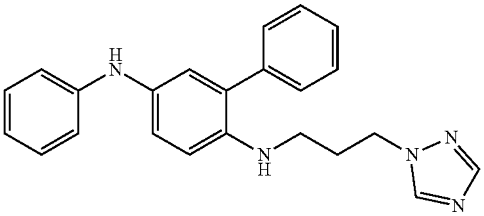
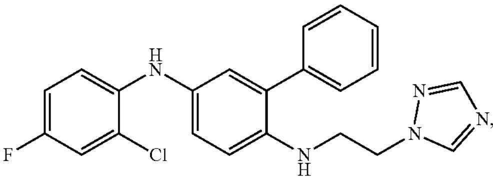
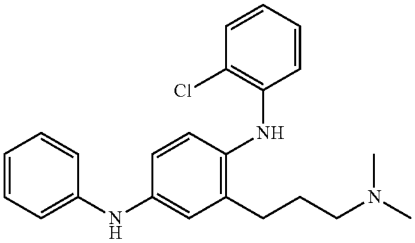
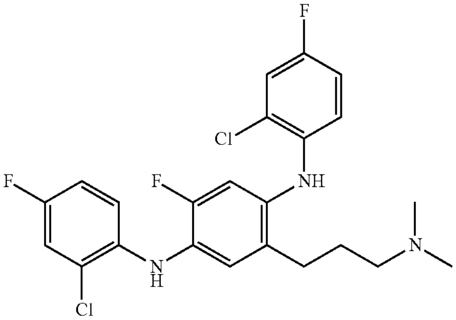

-continued
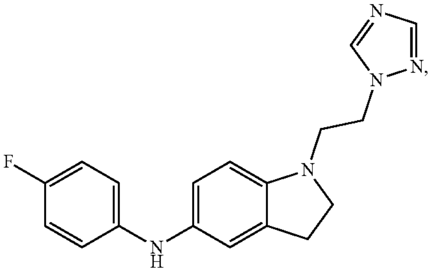
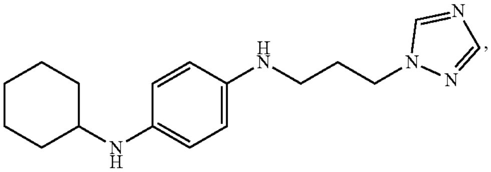
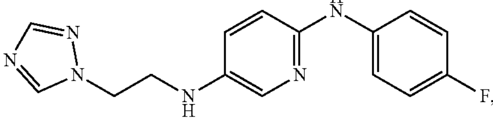
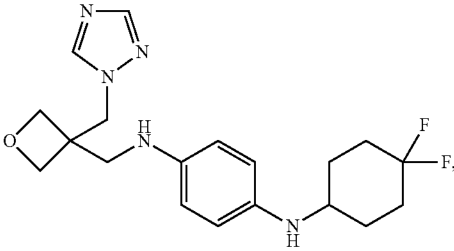
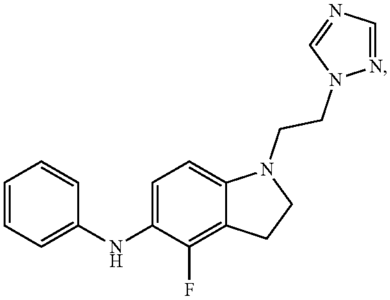
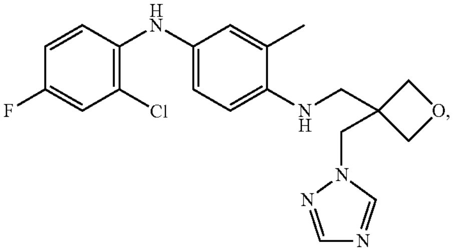
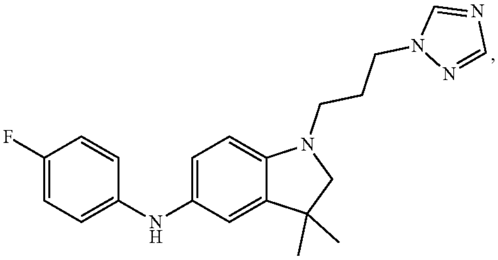
-continued
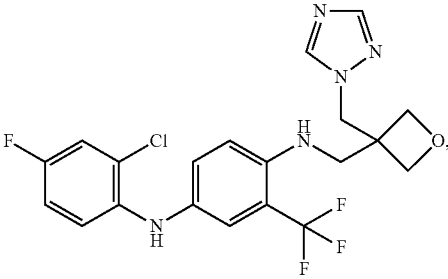
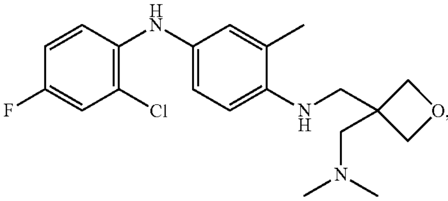
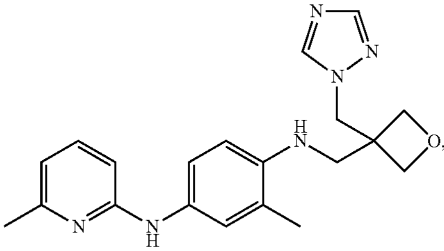
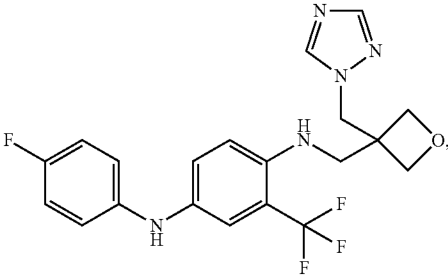
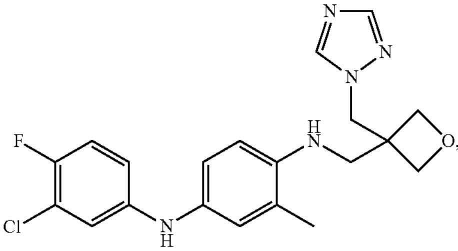
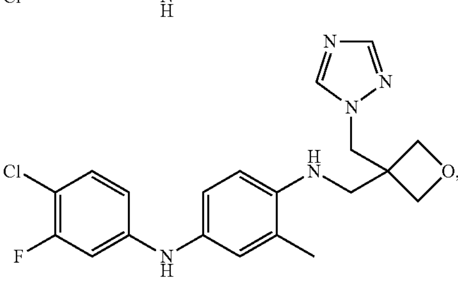

-continued
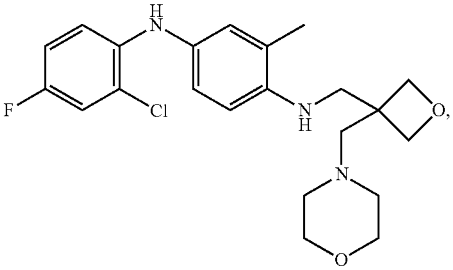
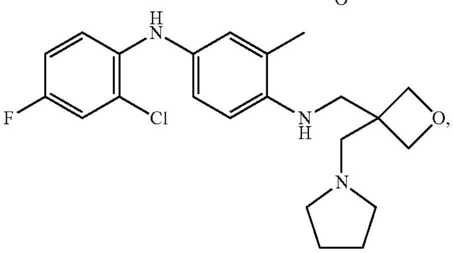
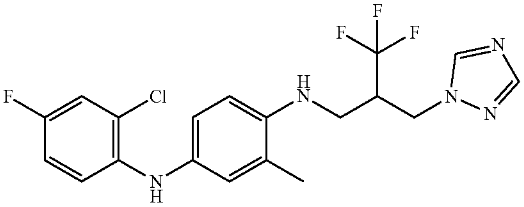
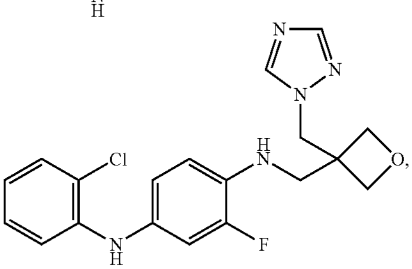
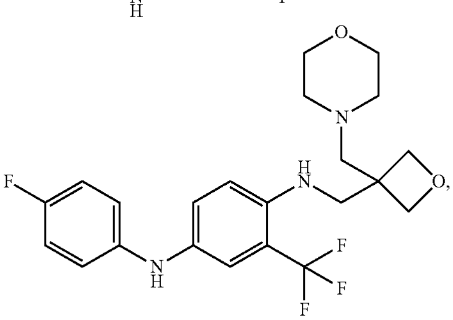
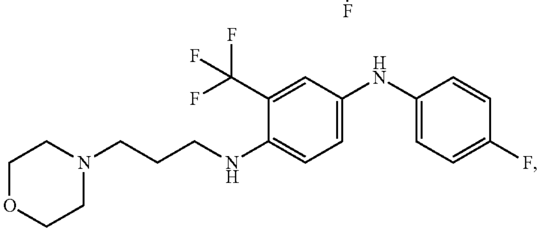
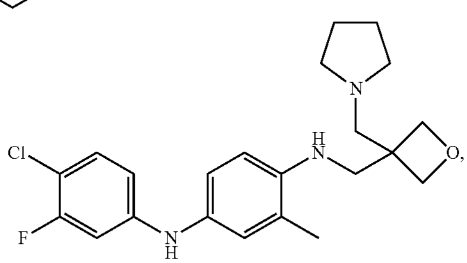
-continued
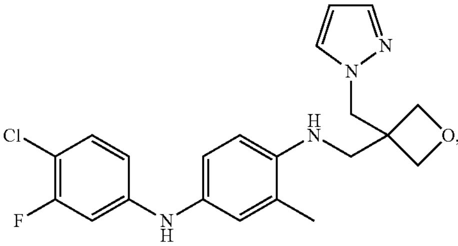
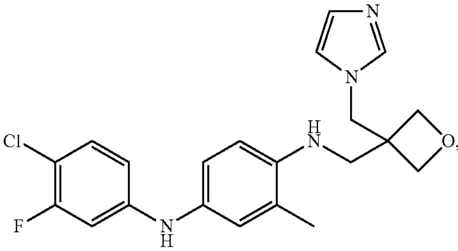
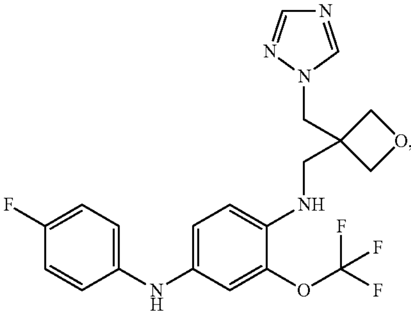
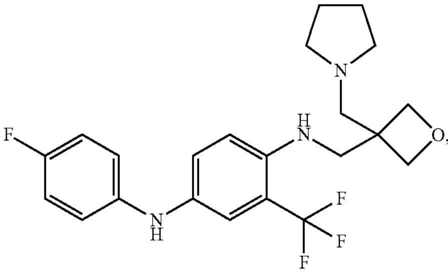
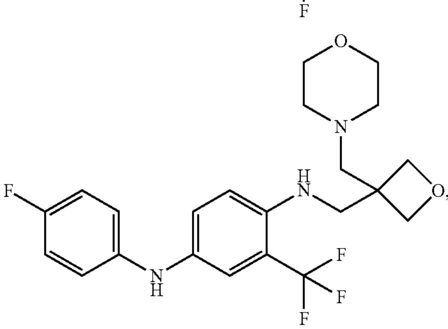
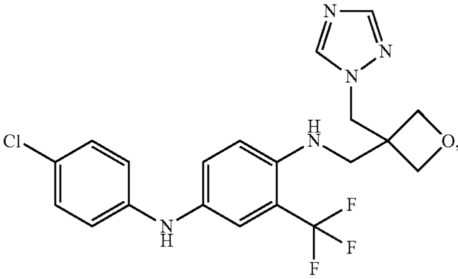

-continued

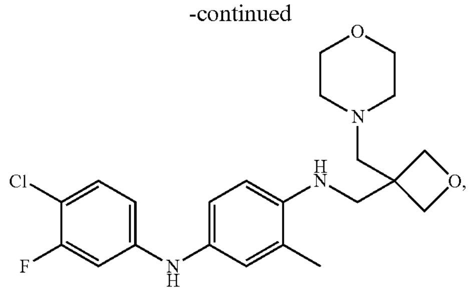

and pharmaceutically acceptable salts or hydrates thereof.

In some embodiments, the compounds disclosed have a structure corresponding to Formula IIB:

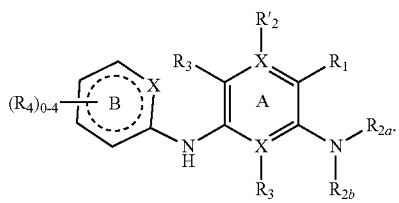

Wherein in some embodiments, ring B is either a cyclohexyl, a 6 membered heterocycle, a 6 membered aryl, or a 6 membered heteroaryl. In some embodiments, ring B is either a cyclohexyl, a 6 membered heterocycle, a 6 membered aryl, or a 6 membered heteroaryl, where the cyclohexyl, the 6 membered heterocycle, the 6 membered aryl, or the 6 membered heteroaryl can be further independently submitted with up to two $R_4$ groups.

In some embodiments, when ring B is a 6 membered heterocycle or a 6 membered heteroaryl, X is either a N or an O.

In some embodiments, each X of ring A and/or ring B can be independently either C, N, or O. In some embodiments, ring A can be independently substituted with $R_1$, $R'_2$, and/or one or two $R_3$.

In some embodiments, $R_1$ can be a hydrogen atom, a $C_{1-3}$ alkyl, a 5-6 membered heterocycle, a 5-6 membered aryl, a 5-6 membered heteroaryl, a 5-10 membered cycloheteroaryl, a 5-10 membered heteroaryl, or $—C(O)R_x$.

In some embodiments, $R_{2a}$ and $R_{2b}$ can each independently be a hydrogen atom, a $C_{1-3}$ alkyl, a 5-6 membered aryl, $—NR_x(CH_2)_2R_y$, $—NR_x(CH_2)_3R_y$, $—NR_xC(O)(CH_2)_2R_y$, $—NH(CH_2)_2NR_xR_y$, $—O(CH_2)_2R_x$, $—NH(CH_2)CR_xR_yCH_2R_a$, $—NH(CH_2)CR_xR_yCH_2NR_aR_b$, $—(CH_2)_3NR_xR_y$, 5-10 membered cycloheteroaryl, or $—NR_xR_y$.

In some embodiments, $R'_2$ can be a hydrogen atom or a halogen atom.

In some embodiments, each $R_3$ can independently be a hydrogen atom, a halogen atom, $C_{1-3}$ alkyl, $—O(CH_2)_2NR_xR_y$, $—NR_x(CH_2)_2R_y$, $—NR_xR_y$, or $—(CH_2)_3NR_xR_y$.

In some embodiments, $R_4$ is a halogen atom.

In some embodiments, $R_1$ with either $R_{2a}$ or $R_{2b}$ can come together to form a 5-6 membered heterocycle.

In some embodiments, $R_1$ with either $R_{2a}$ or $R_{2b}$ can come together to form a 5-6 membered heterocycle that can further be substituted with one or more $R_a$ and/or $R_b$ groups.

In some embodiments, $R_1$, $R'_2$, $R_{2a}$, $R_{2b}$ and/or $R_3$ can each be further independently substituted with one or more $R_a$ group(s).

In some embodiments, $R_x$ and $R_y$ can each independently be a hydrogen atom, $C_{1-4}$ alkyl, 5-6 membered aryl, 5-6 membered heteroaryl, or $—NR_aR_b$. In some embodiments, $R_x$ and $R_y$ can come together to form 4-5 membered heterocycle and/or wherein the 4-5 membered heterocycle formed by $R_x$ and $R_y$ can be substituted with $R_a$ or $R_b$.

In some embodiments, $R_a$ and $R_b$ can independently be a hydrogen atom, a halogen atom, an oxygen atom, a cyano group, $C_{1-3}$ alkyl, $C_{1-3}$ alcohol, $C_{1-3}$ alkoxy, phenyl, $—(CH_2)_2R'$, 5-6 membered heteroaryl, or 5-6 membered heterocycle.

In some embodiments, R' is a 5 membered heteroaryl.

In some embodiments, the disclosed compounds are either pharmaceutically acceptable salts or hydrates of Formula IIB.

In some embodiments of Formula IIB, $R_1$ is:

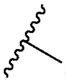, 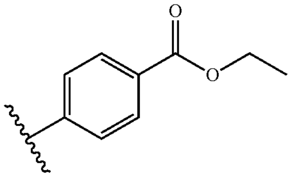, 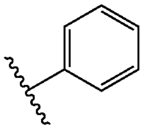,

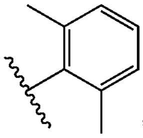, 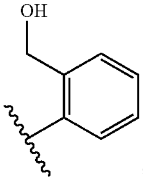, 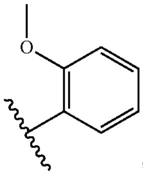,

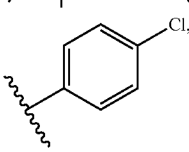 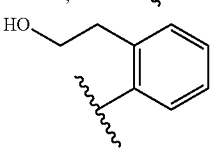,

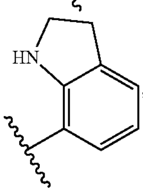, 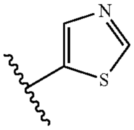, 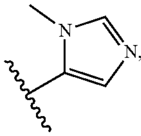

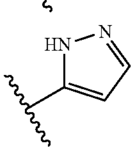, 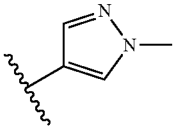, 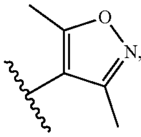

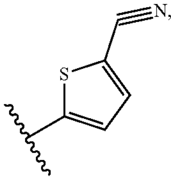 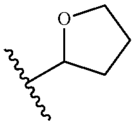, 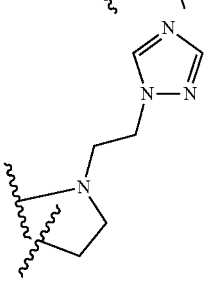, or

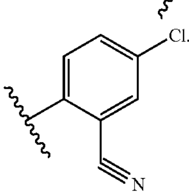

In some embodiments of Formula IIB, $R_{2a}$ and $R_{2b}$ are each independently selected from:

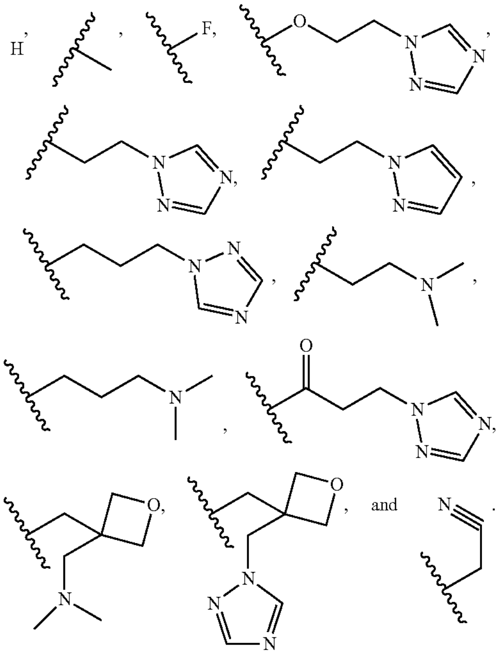
In some embodiments of Formula IIB, $R_3$ is H,
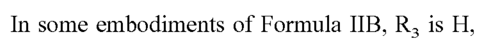
In some embodiments of Formula IIB, compounds have the following structure:
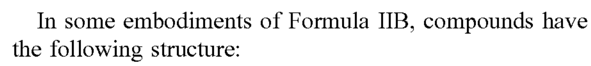
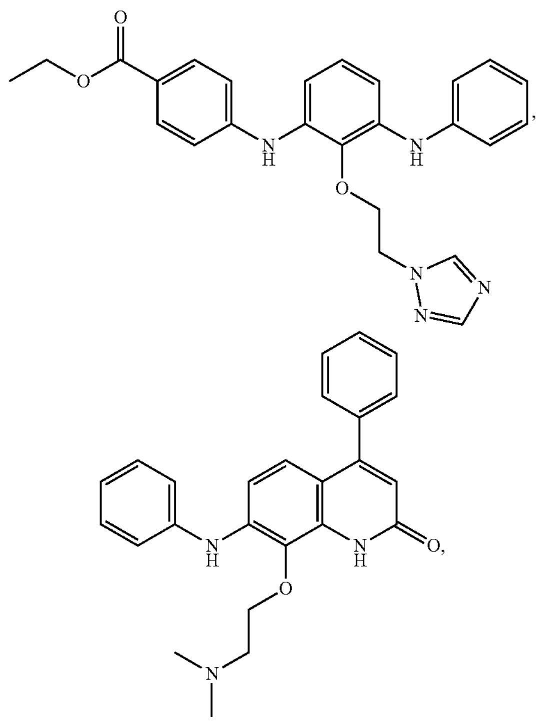
-continued
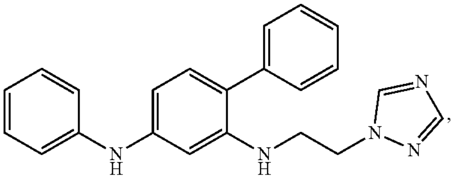
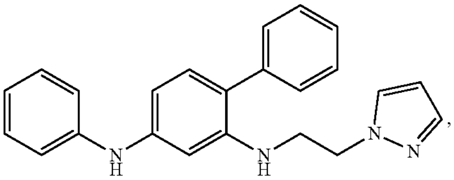
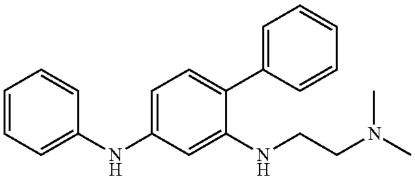
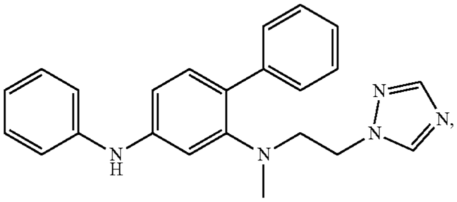
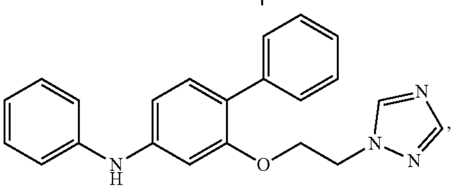
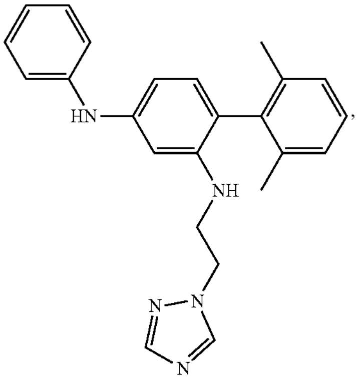
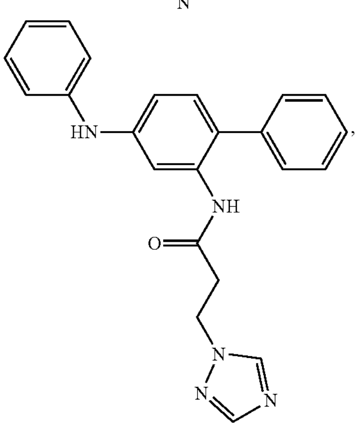

-continued
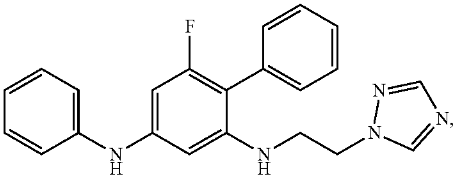
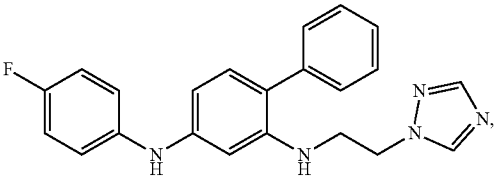
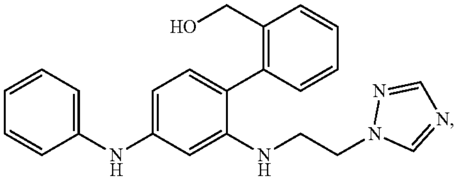
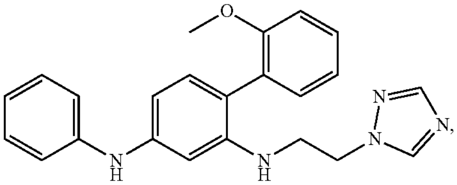
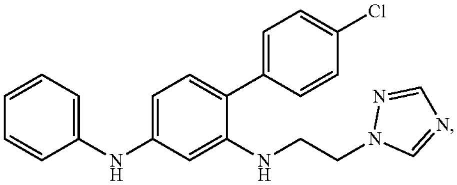
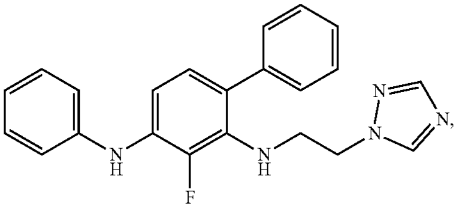
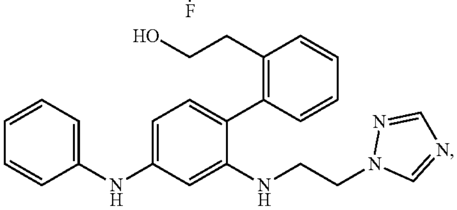
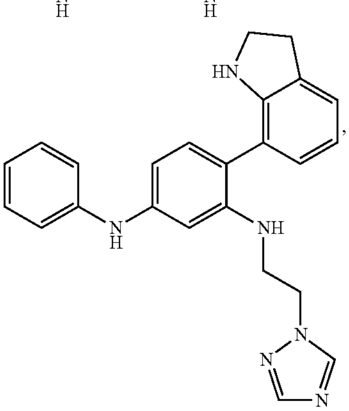
-continued
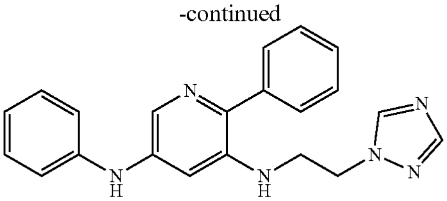
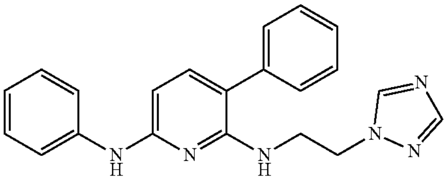
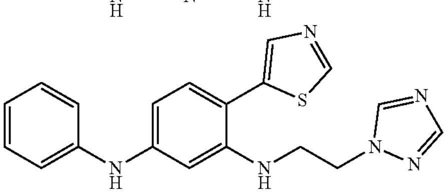
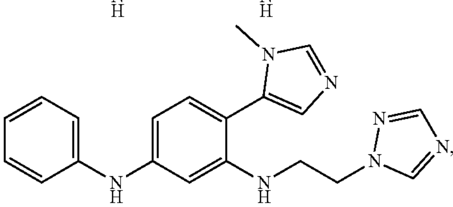
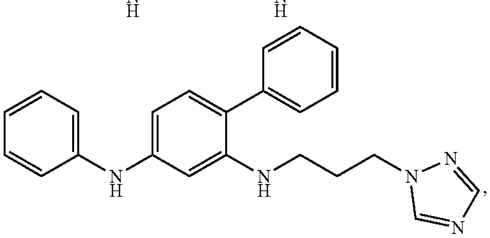
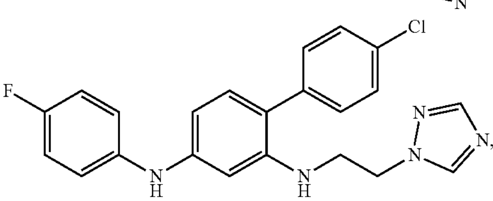
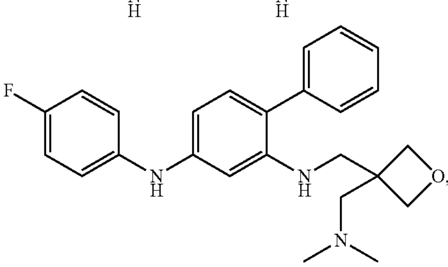
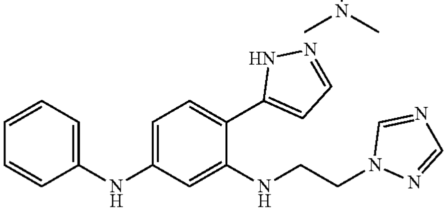
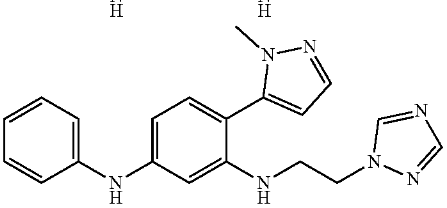

-continued
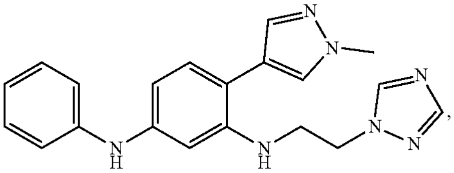
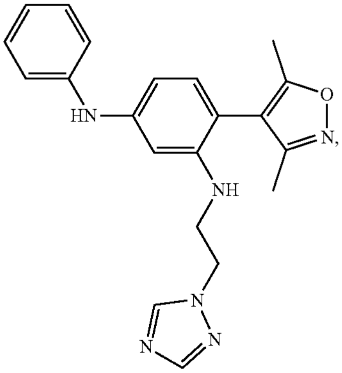
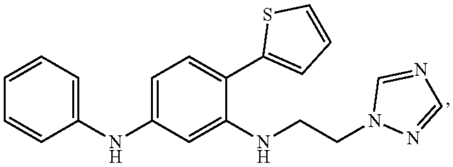
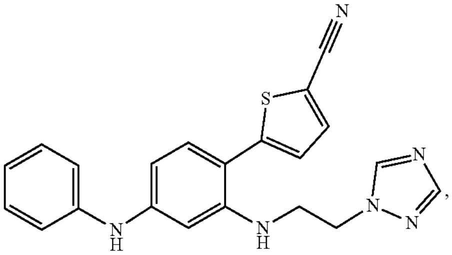
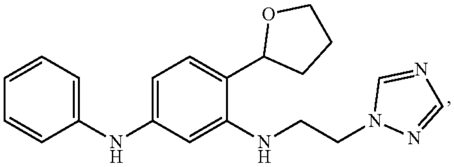
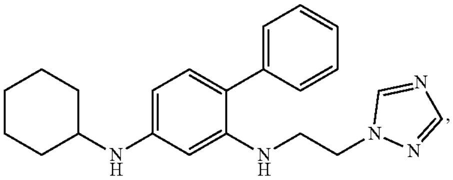
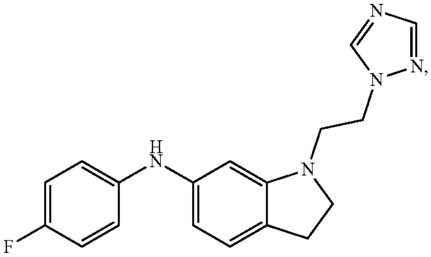
-continued
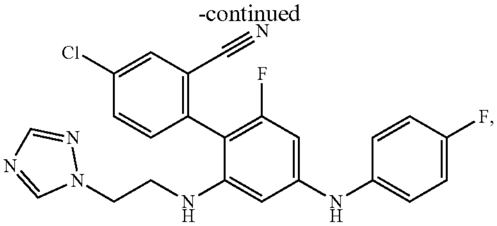
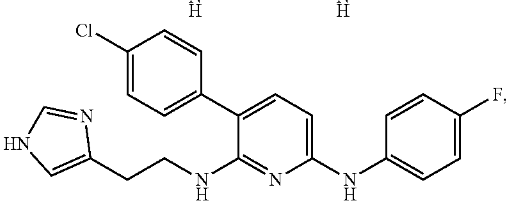
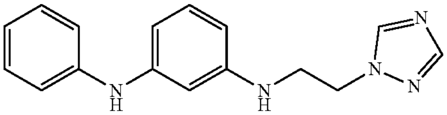
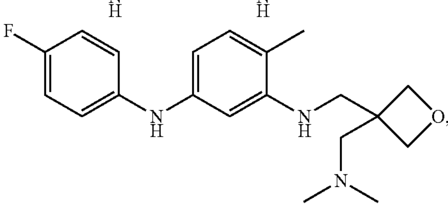
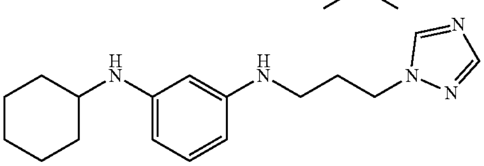
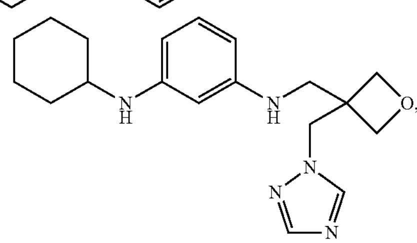
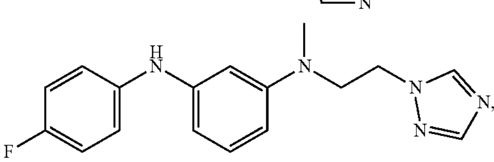
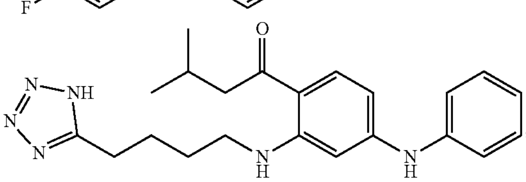
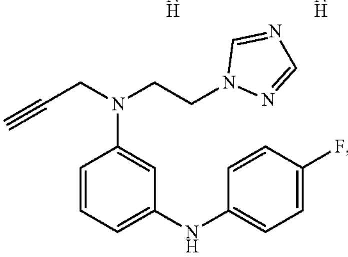
and pharmaceutically acceptable salts or hydrates thereof.
In some embodiments, the compounds disclosed have a structure corresponding to Formula III:

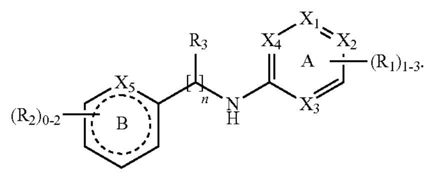

In some embodiments, n is 1-2.

In some embodiments, $X_1$, $X_2$, $X_3$, and $X_4$ of ring A can each independently be C, N, or O.

In some embodiments, ring A can independently be substituted with one, two, or three $R_1$ groups.

In some embodiment, ring B can either be a cyclohexyl, a 6-membered heterocycle, a 6-membered aryl, or a 6-membered heteroaryl.

In some embodiments, where ring B is a 6-membered heterocycle or a 6-membered heteroaryl, $X_5$ can be a N or an O. In some embodiments, $X_5$ can be C.

In some embodiments, $R_1$ can be a halogen atom, a $C_{1-4}$ alkyl, a $—NR_xR_y$, a $—O(CH_2)_2NR_xR_y$, a 6 membered cyclohexyl, a 6 membered heterocycle, a 6 membered aryl, a 6 membered heteroaryl, or a 5-10 membered cycloalkyl.

In some embodiments, where two $R_1$ groups are present, the two $R_1$ groups can come together to form a 6 membered heteroaryl. In some embodiments where two $R_1$ are present, the two $R_1$ groups can come together to form a 6 membered heteroaryl, either of the two $R_1$ groups can be further substituted with one or more $R_a$ groups.

In some embodiments, each $R_2$ is either a halogen atom or a $C_{1-3}$ alkoxy group.

In some embodiments, $R_3$ is or each $R_3$ is independently a hydrogen atom, an oxygen atom, a $C_{1-3}$ haloalkyl group, or a hydroxyalkyl group. In some embodiments, when one or more $R_3$ is hydroxyalkyl, the one or more of $R_3$ optionally comes together with a C of Formula III to form a 4 membered heterocycle.

In some embodiments, $R_x$ and $R_y$ can each independently be a hydrogen atom, a $C_{1-3}$ alkyl, a 6 membered aryl, or a 6 membered heteroaryl. In some embodiments, where $R_x$ or $R_y$ are either a $C_{1-3}$ alkyl, a 6 membered aryl, or a 6 membered heteroaryl, $R_x$ and/or $R_y$ can be further substituted with one or more $R_a$.

In some embodiments, $R_a$ is a halogen atom, an oxygen atom, a cyano, a $C_{1-3}$ haloalkyl, a —NR'R', a 5-6 membered aryl, a 5-6 membered heteroaryl, or a 5-6 membered heterocycle. In some embodiments, one or more $R_a$ can come together to form a 4-5 membered heterocycle.

In some embodiments, R' is a $C_{1-3}$ alkyl. In some embodiments, the disclosed compounds are either pharmaceutically acceptable salts or hydrates of Formula III.

In some embodiments, Formula III is:

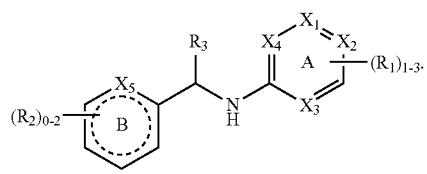

In some embodiments of Formula III, $R_1$ is:

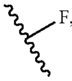, 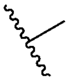, 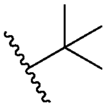, 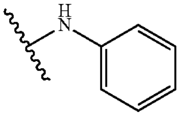,

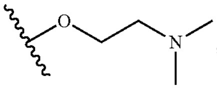, 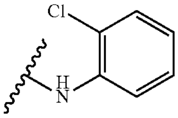,

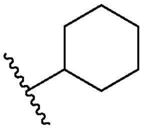, 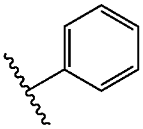, 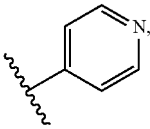,

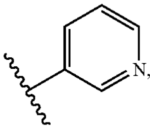, 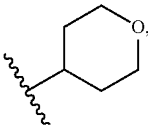, 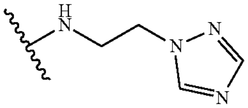,

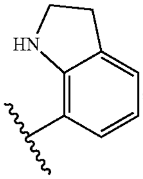, 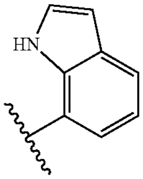, 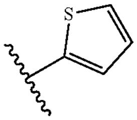,

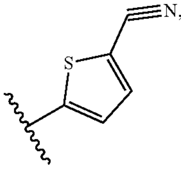, 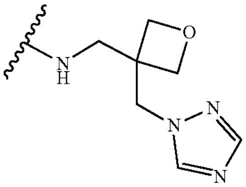,

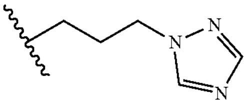, 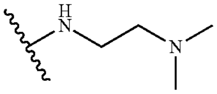,

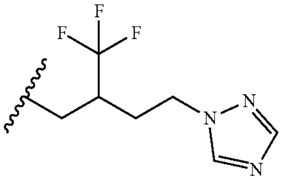,

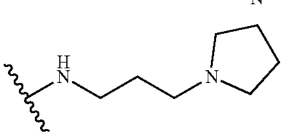,

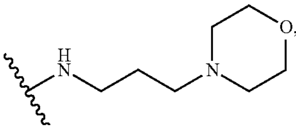, or

-continued
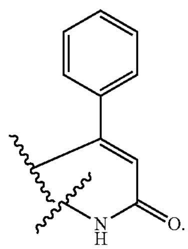 [SMILES: *NC(=O)/C=C(\*)c1ccccc1]
In some embodiments of Formula III, $R_2$ is: H
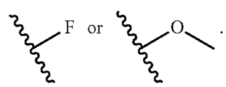
In some embodiments of Formula III, $R_3$ is: H, oxo, or
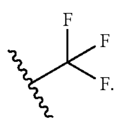 [SMILES: *C(F)(F)F]
In some embodiments of Formula III, compounds have the following structure:
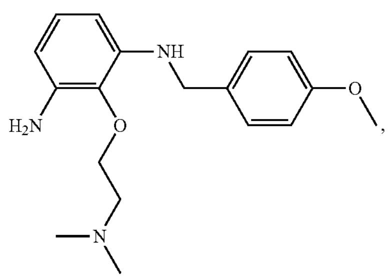
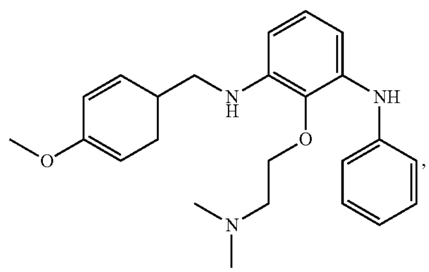
-continued
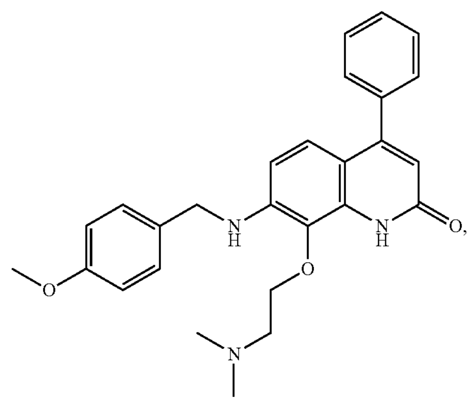
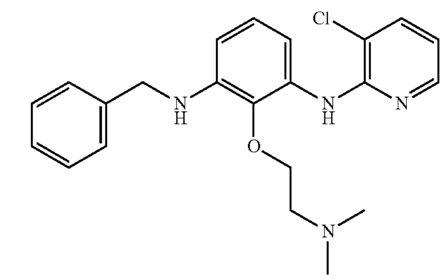
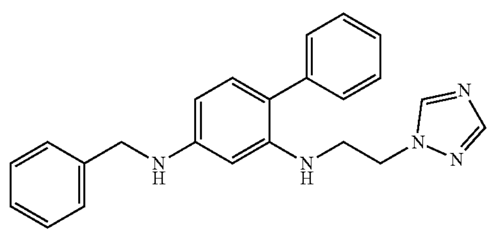
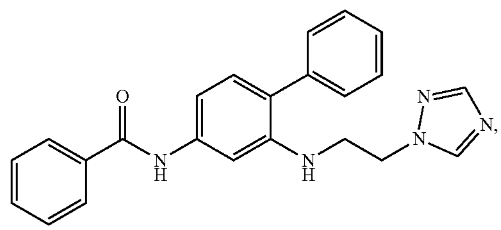
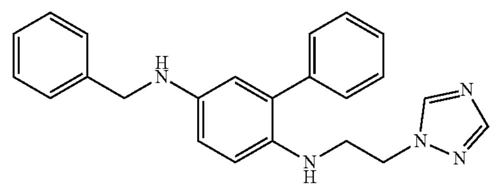
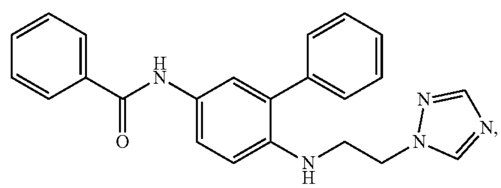

-continued
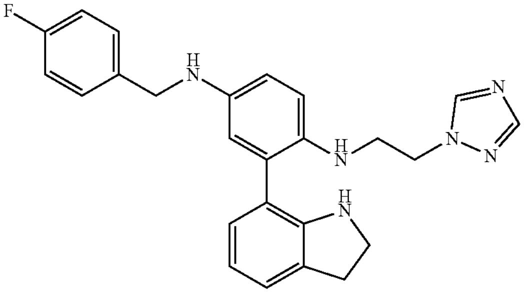
,
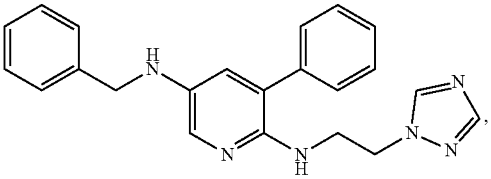
,
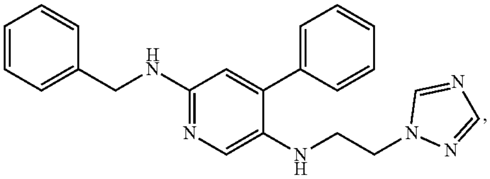
,
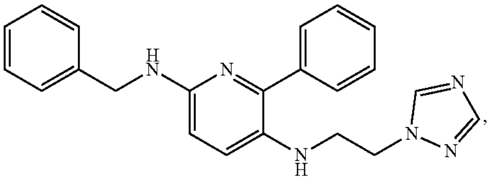
,
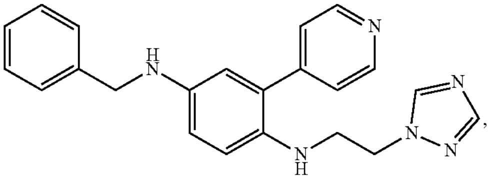
,
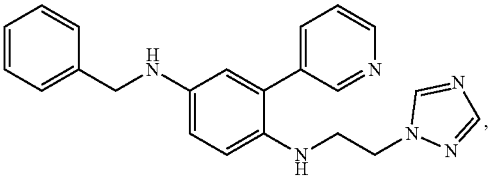
,
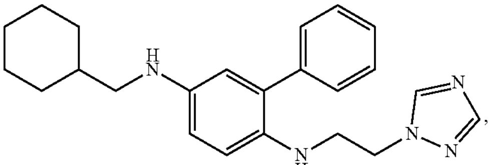
,
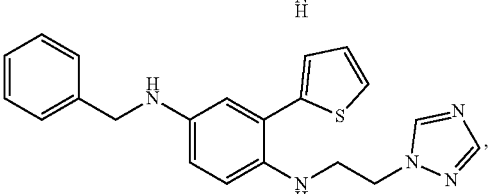
,
-continued
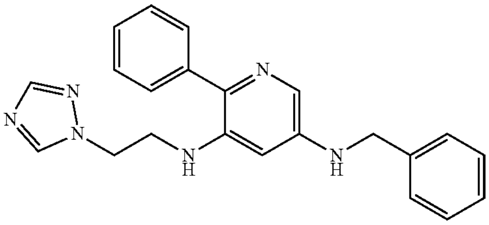
,
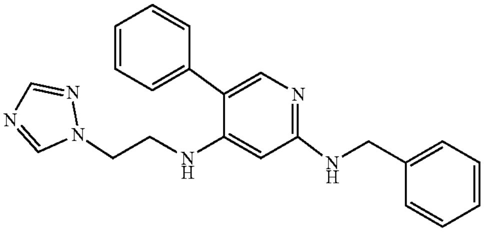
,
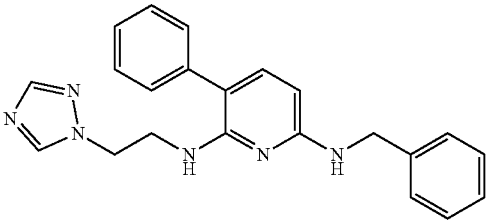
,
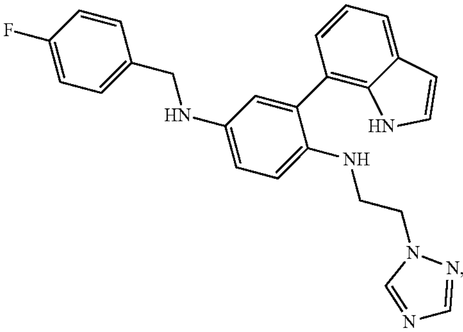
,
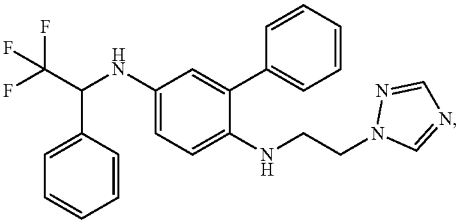
,
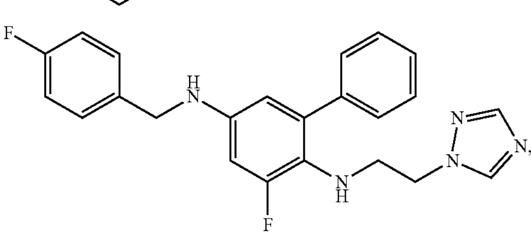
,
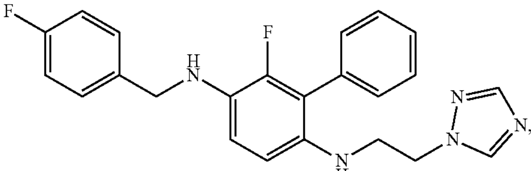
, -continued
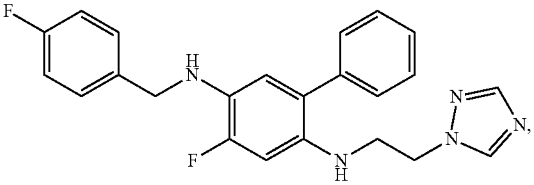
,
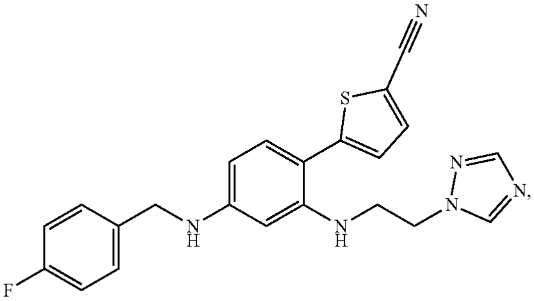
,
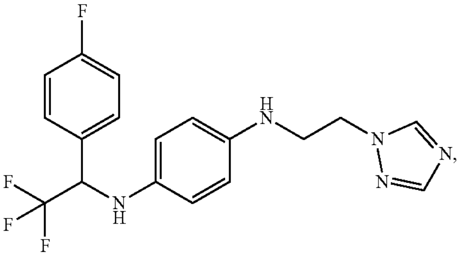
,
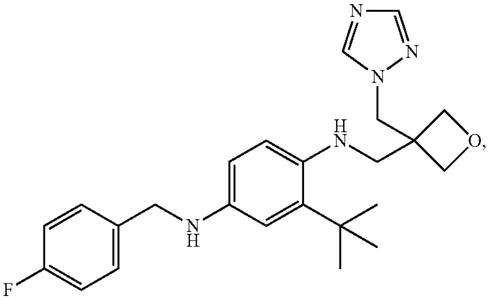
,
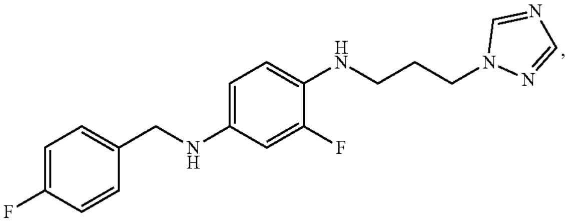
,
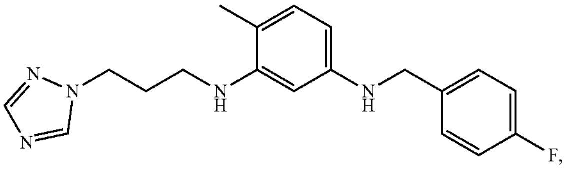
,
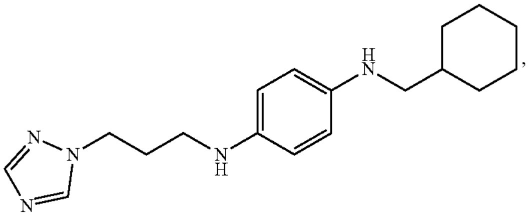
,
-continued
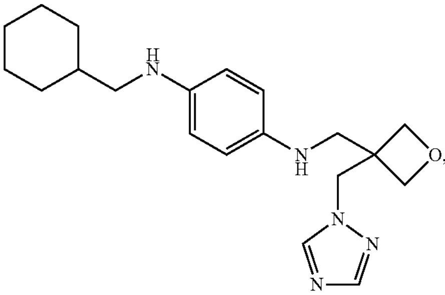
,
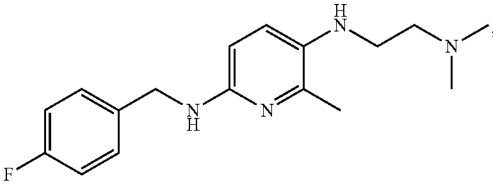
,
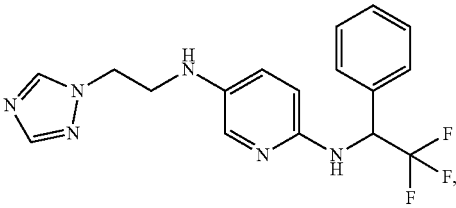
,
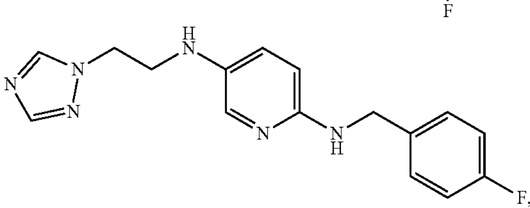
,
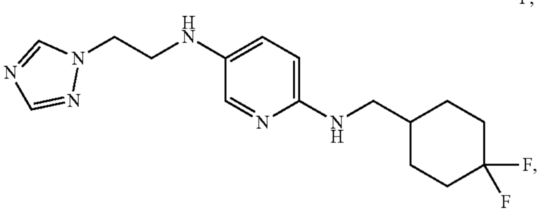
,
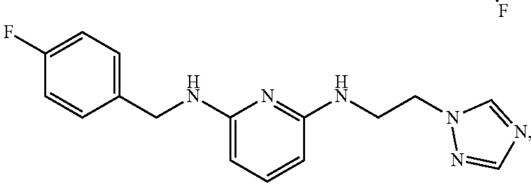
,
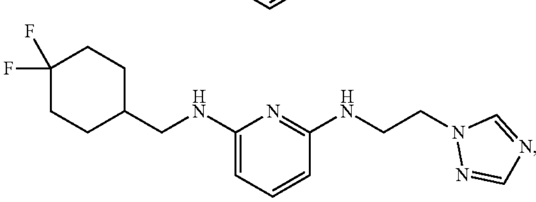
,
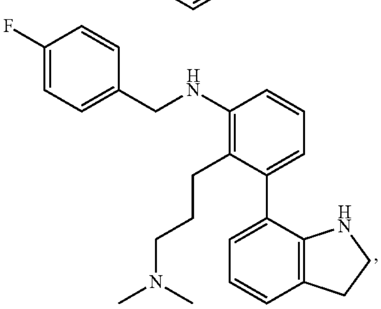
, -continued

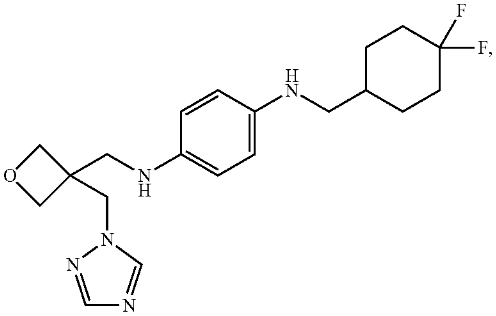

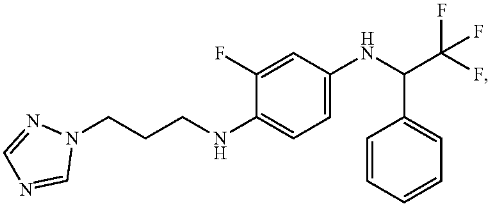

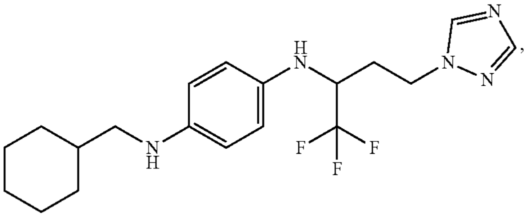

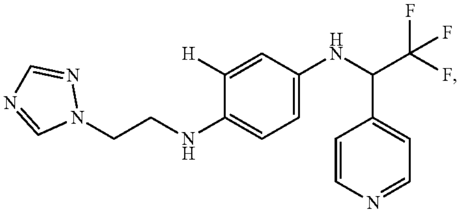

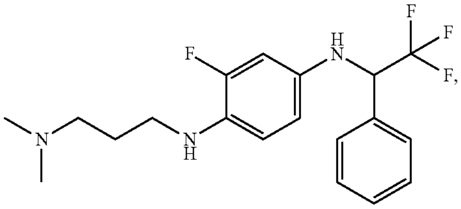

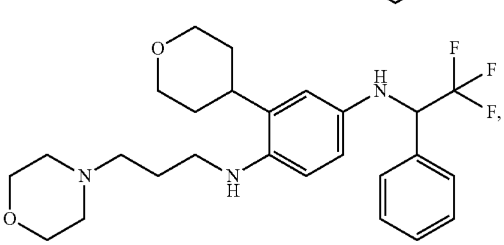

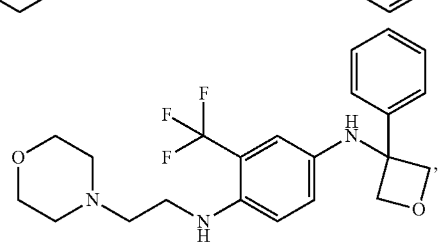

-continued

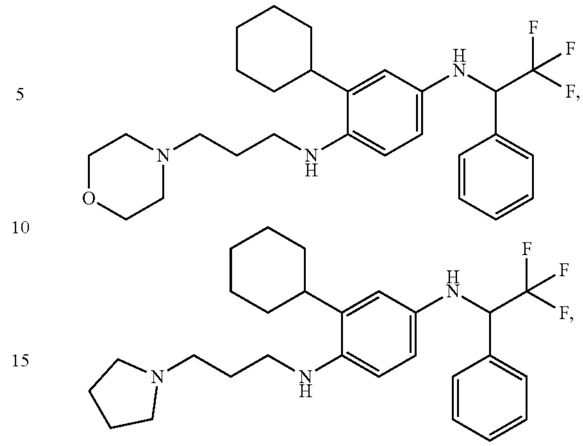

and pharmaceutically acceptable salts or hydrates thereof.

In certain embodiments, a compound of the present disclosure is a compound of Formula IIIA:

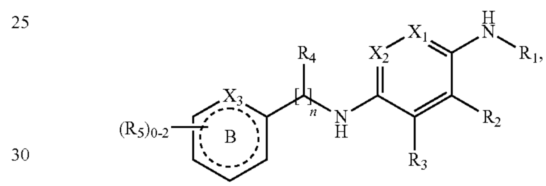

In some embodiments, n is 1-2.

In some embodiments, ring B is either cyclohexyl, 6-membered heterocycle, 6-membered aryl, or 6-membered heteroaryl.

In some embodiments, $X_1$, $X_2$, and $X_3$ can each independently be C, N or O.

In some embodiments, $R_1$ is $C_{1-3}$ alkyl. In some embodiments, $R_1$ is $C_{1-3}$ alkyl that is further substituted with one or more $R_a$ or $R_b$.

In some embodiments, $R_2$ can be a hydrogen atom, a halogen atom, $C_{1-3}$ haloalkyl, $C_{1-4}$ alkyl, 5-6 membered aryl, 5-6 membered cycloalkyl, 5-6 membered heterocycle, 5-10 membered heteroaryl, or 5-10 membered cycloaryl. In some embodiments, $R_3$ is a hydrogen atom or a halogen atom. In some embodiments, $R_4$ can be or each $R_4$ can independently be a hydrogen atom, an oxygen atom, a $C_{1-3}$ haloalkyl group, or a hydroxyalkyl group. In some embodiments, when one or more of $R_4$ is hydroxyalkyl, the one or more $R_4$ optionally comes together with a C of Formula IIIA to form a 4 membered heterocycle. In some embodiments, $R_5$ can be a halogen atom or a 4-5 membered heterocycle. In some embodiments, $R_1$, $R_2$, $R_4$, and/or $R_5$ can be substituted with up to two $R_a$ and/or $R_b$ groups, where the $R_a$ and/or $R_b$ groups are $C_{1-3}$ alkyl, $C_{1-3}$ haloalkyl, 5-6 membered heterocycle, 5-6 membered heteroaryl, —NR'R'. In some embodiments, where $R_1$, $R_2$, $R_4$, and/or $R_5$ is be substituted with a $R_a$ and/or $R_b$ groups, the $R_a$ and $R_b$ can come together to form a 4-5 membered heterocycle. In some embodiments, the $R_a$ and $R_b$ can further each independently be substituted with one or more R' groups, where if there is more than one R' group, the R' groups can either be the same or different. In some embodiments, R' can be a halogen atom or a $C_{1-3}$ alkyl group. In some embodiments, the disclosed compounds are either pharmaceutically acceptable salts or hydrates of Formula IIIA.

In some embodiments of Formula IIIA, $R_1$ is:
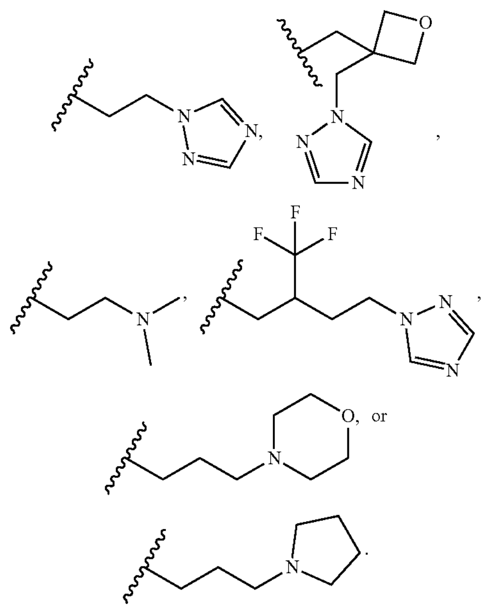
In some embodiments of Formula IIIA, $R_2$ is:
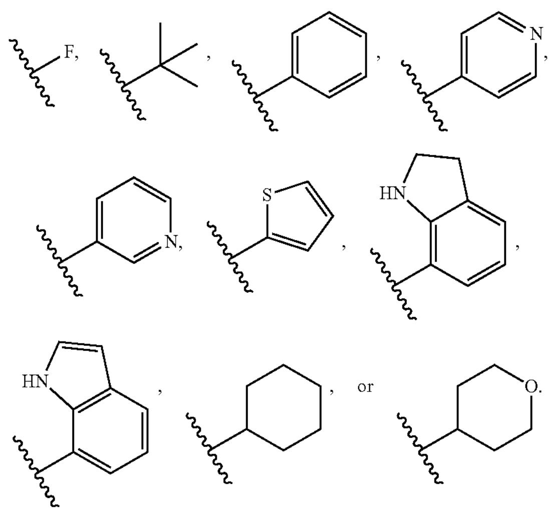
In some embodiments of Formula IIIA, $R_3$ and $R_5$ are independently a H or a F atom. In some embodiments, $R_5$ is an F atom. In some embodiments of Formula IIIA, $R_4$ is H,
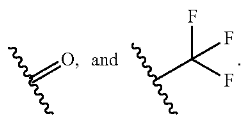
In some embodiments, Formula IIIA is:
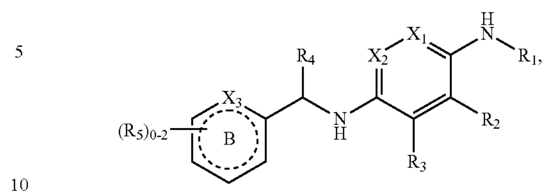
In some embodiments of Formula IIIA, the compounds have the following structures:
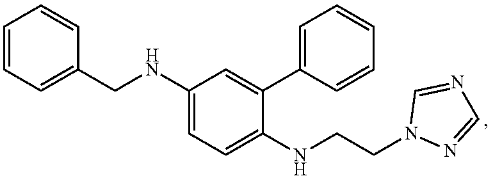
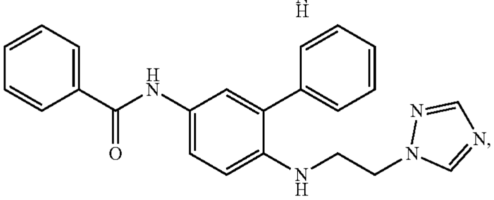
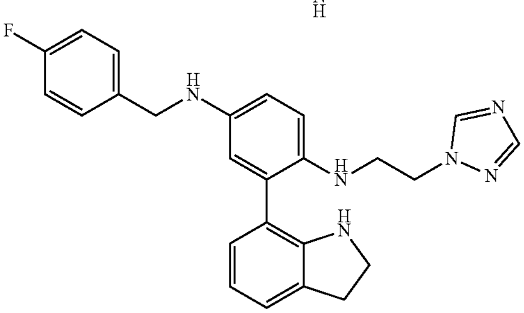
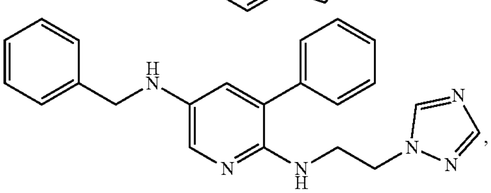
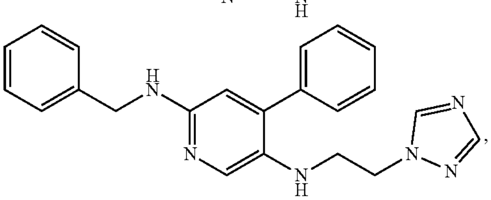
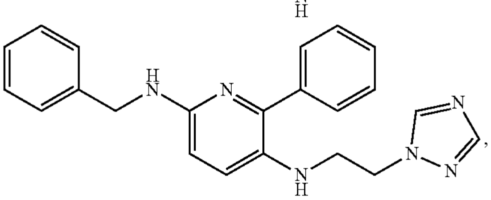
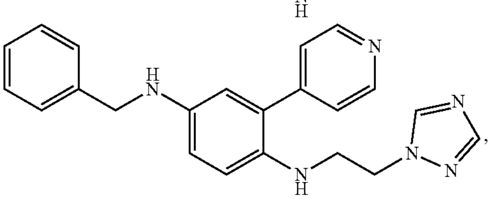

-continued
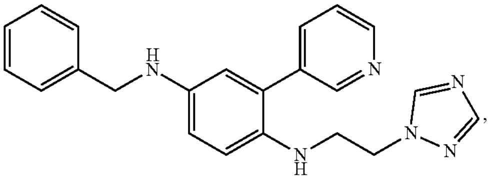
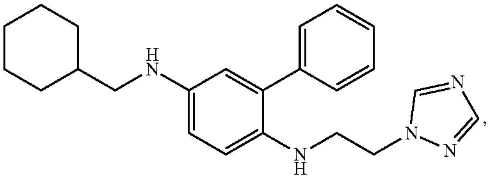
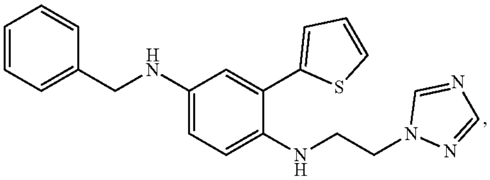
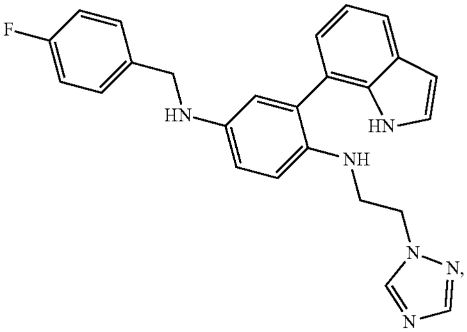
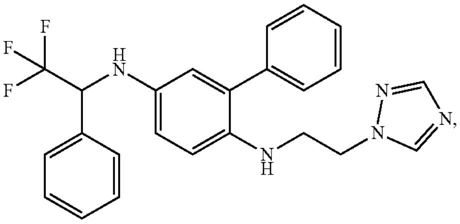
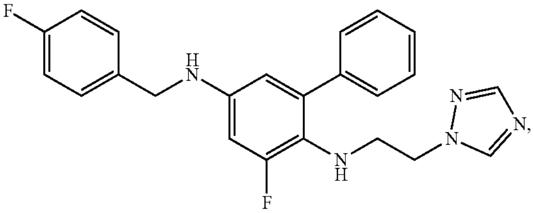
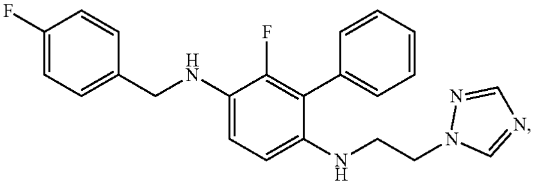
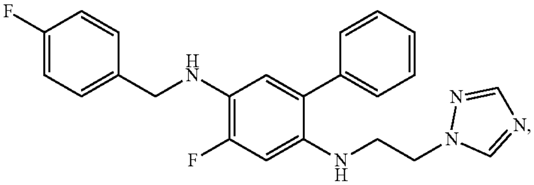
-continued
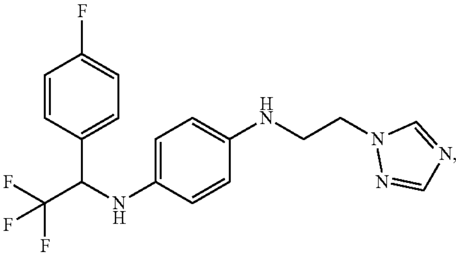
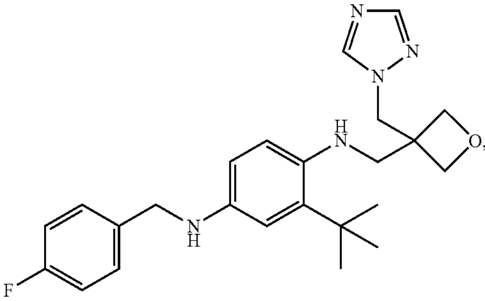
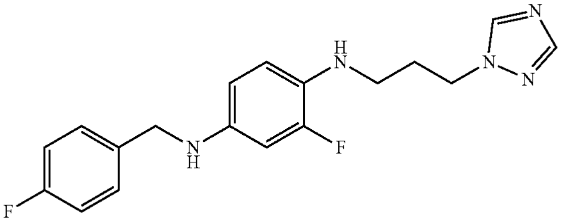
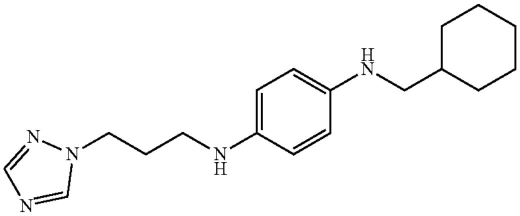
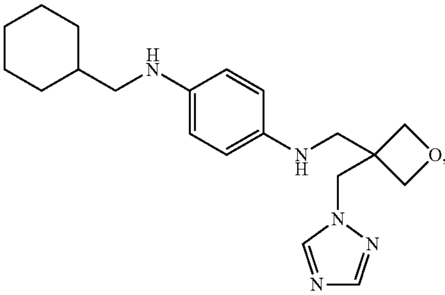
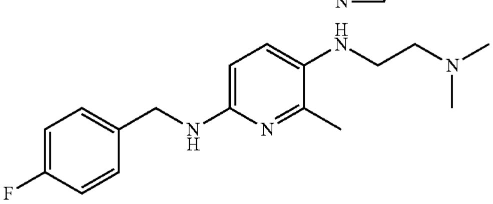
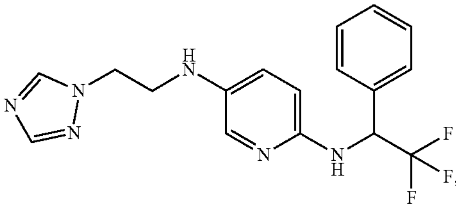

-continued

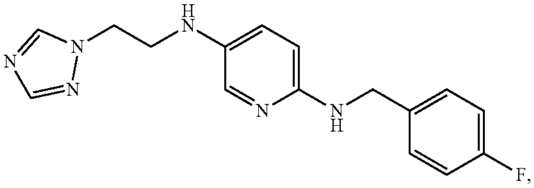

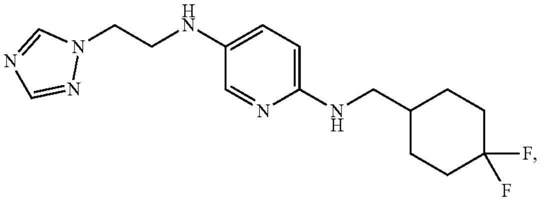

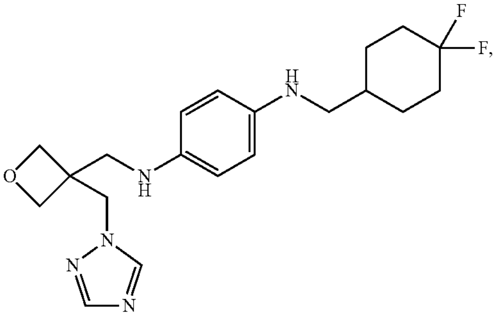

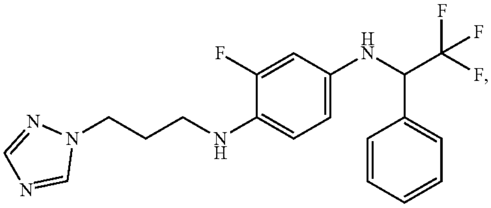

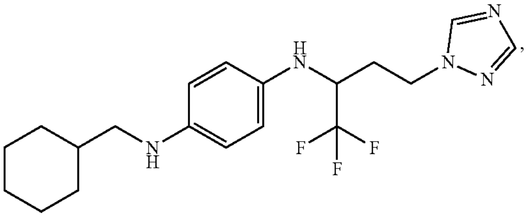

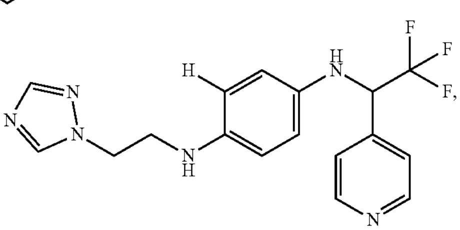

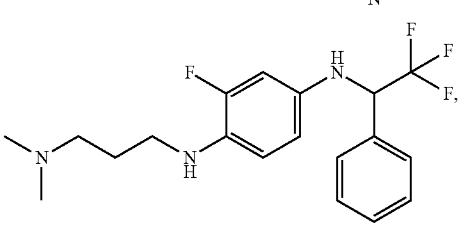

-continued

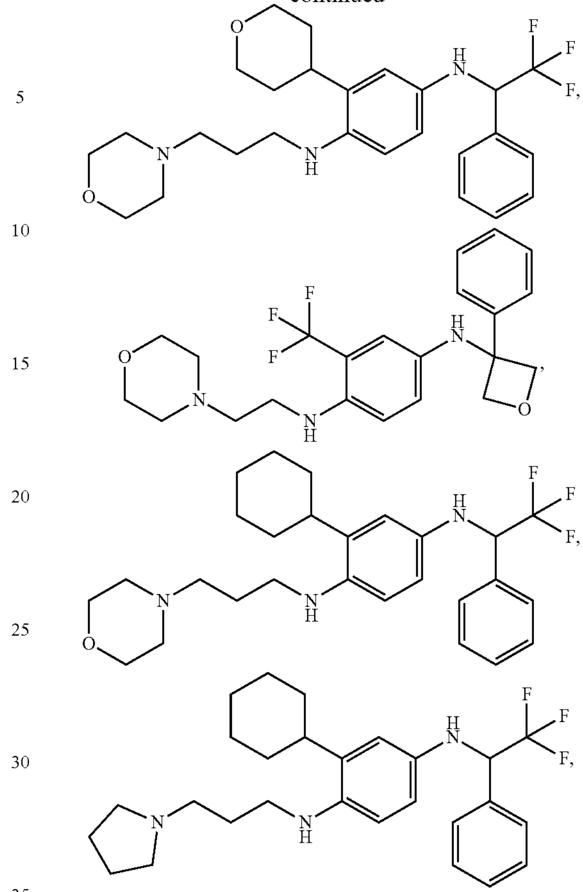

and pharmaceutically acceptable salts or hydrates thereof.

In certain embodiments, a compound of the present disclosure is a compound of Formula IIIB:

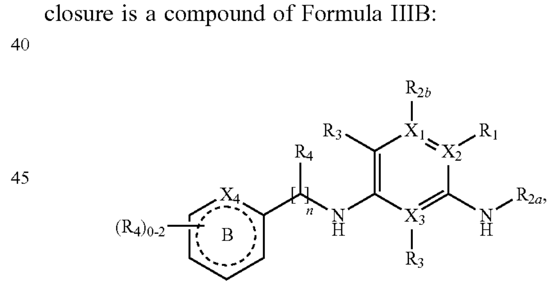

In some embodiments, n is 1-2.

In some embodiments, ring B can be cyclohexyl, 6-membered heterocycle, 6-membered aryl, or 6-membered heteroaryl. In some embodiments, ring B can be cyclohexyl, 6-membered heterocycle, 6-membered aryl, or 6-membered heteroaryl, where ring B can be further substituted with up to two $R_5$ groups.

In some embodiment, $X_1$, $X_2$, $X_3$ and $X_4$ can each independently be either a C or an N.

In some embodiments, $R_1$ is a hydrogen atom, a $C_{1-3}$ alkyl, or a 5-6 membered aryl. In some embodiments, $R_1$ is a hydrogen atom, a $C_{1-3}$ alkyl, or a 5-6 membered aryl and where when $R_1$ is a $C_{1-3}$ alkyl, or a 5-6 membered aryl, $R_1$ can be substituted with one or more $R_a$ and/or $R_b$.

In some embodiments, $R_{2a}$ and $R_{2b}$ can each independently be a $C_{1-4}$ alkyl or a 5-6 membered heteroaryl. In some embodiments, $R_1$ and $R_{2a}$, or $R_{2b}$ can optionally come together to form a 5-6 membered aryl or 5-6 membered heteroaryl, the optional 5-6 membered aryl or 5-6 membered heteroaryl being optionally further substituted with $R_a$ and $R_b$.

In some embodiments, $R_3$ is a hydrogen atom, a halogen atom, or a $C_{1-3}$ alkoxy.

In some embodiments, $R_4$ is or each $R_4$ is independently a hydrogen atom or an oxygen atom. In some embodiments, $R_5$ is a halogen atom or a 4-5 membered heterocycle. In some embodiments, $R_1$, $R_{2a}$, $R_{2b}$, $R_3$ and $R_5$ can each independently be substituted with up to two $R_a$ or $R_b$, where $R_a$ and $R_b$ can be a halogen atom, an oxygen atom, a cyano, a $C_{1-3}$ alkyl, or a 5-6 membered heteroaryl. In some embodiments, the disclosed compounds are either pharmaceutically acceptable salts or hydrates of Formula IIIB.

In some embodiments of Formula IIIB, $R_1$ is H,

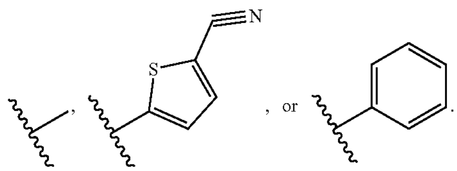

In some embodiments of Formula IIIB, $R_{2a}$ and $R_{2b}$ are each independently H,

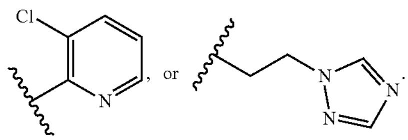 [SMILES: *c1ncccc1Cl ; *CCn1cncn1]

In some embodiments of Formula IIIB, each $R_3$ is H or

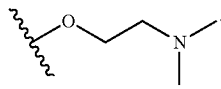 [SMILES: *OCCN(C)C]

In some embodiments of Formula IIIB, $R_4$ is a hydrogen or an oxygen atom. In some embodiments of Formula IIIB, $R_5$ is H,

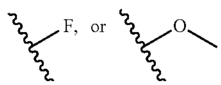

In some embodiments of Formula IIIB, $R_5$ is

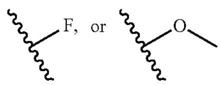

In some embodiments, Formula IIIB is:

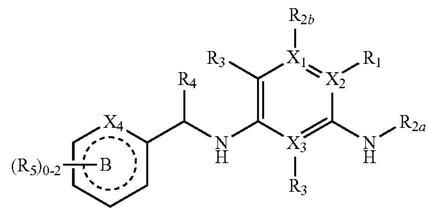

In some embodiments of Formula IIIB, the compounds have the following structures:

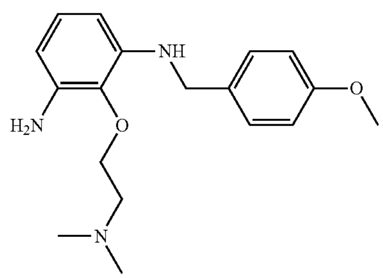

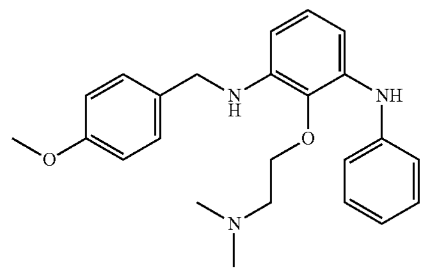

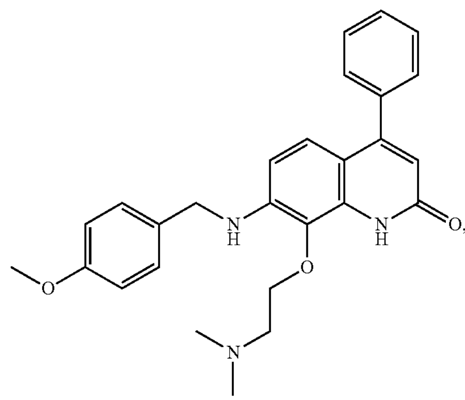

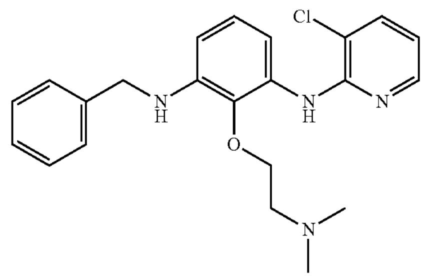

-continued

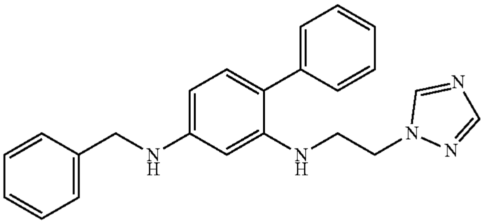

,

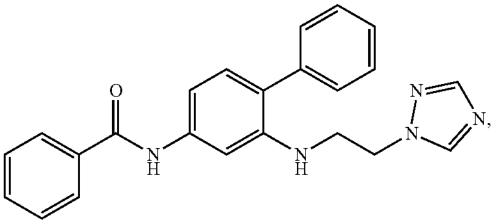

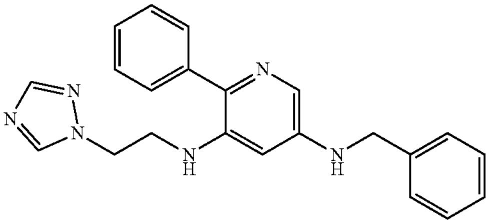

,

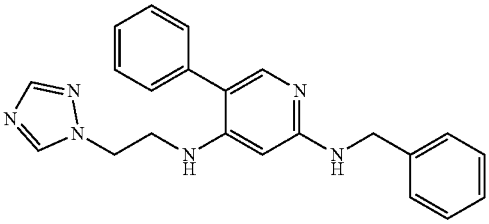

,

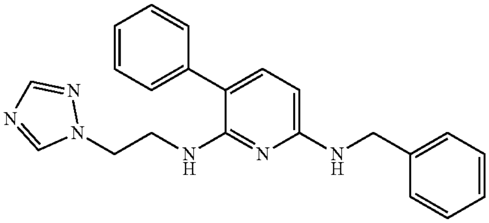

,

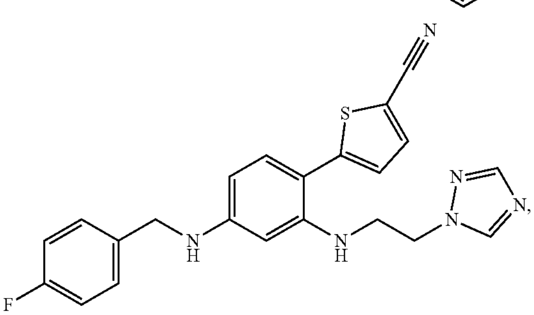

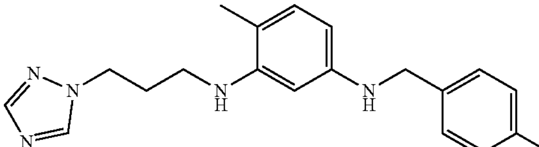

-continued

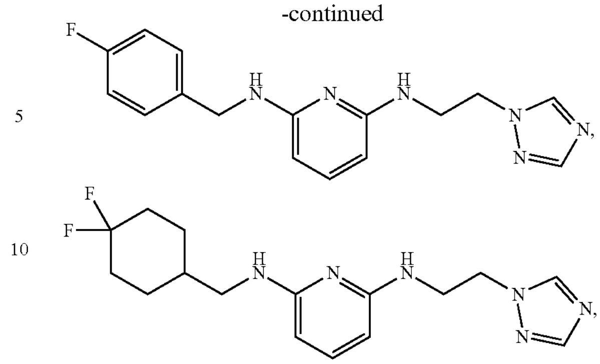

and pharmaceutically acceptable salts and/or hydrates thereof.

Some embodiments are methods of inhibiting a lipoxygenase in cells determined to be in need thereof, comprising contacting the cells with (or administering to the cells) a compound having structure disclosed in any of the compounds above, where the cells are human cells that are either in vivo or isolated in vitro. In some embodiments, the cells are in situ as part of a person determined to be in need of lipoxygenase inhibition or suffering from a disease associated with pathogenic lipoxygenase activity, wherein the disease is selected from an acute or chronic inflammatory disease or a neurodegenerative disease. Some of the methods further comprising: (i) measuring a lipoxygenase activity in a sample of the person; (ii) determining a level of a lipoxygenase metabolite in a sample of the person; or (iii) determining the person has the disease. In some of the methods, the disease is: (i) an acute or chronic inflammatory disease that is asthma, rheumatoid arthritis, inflammatory bowel disease, psoriasis, hereditary ichthyosis, dermatitis, nephritis, atherosclerosis, or cardiovascular disease, or (ii) a neurodegenerative disease that is age-related neurodegeneration, amyloid beta-associated disease, Alzheimer's Disease, ischemia-related disorder, creutzfeldt-jakob disease/prion peptide toxicity, ALS, dementia or Parkinson Disease.

Further conceived are pharmaceutical compositions comprising a compound disclosed above for inhibiting lipoxygenase activity, or a pharmaceutically acceptable salt thereof, and a pharmaceutically acceptable carrier. Further conceived of are pharmaceutical compositions comprising compounds disclosed above for inhibiting lipoxygenase activity, or a pharmaceutically acceptable salt thereof, and a pharmaceutically acceptable carrier. Further conceived are compositions comprising a compound of Formula I, supra, and a second anti-neurodegenerative disease drug. Further conceived of are methods for identifying a lipoxygenase inhibitor, comprising the step of screening for lipoxygenase inhibitory activity of one or more of the above compounds.

As described herein in more detail, subject compounds can be used in pharmaceutically acceptable alternative forms, such as pharmaceutically acceptable salts, prodrugs (e.g. sulfamates, phosphates, esters, ethers, amides, etc.), and the like. Unless otherwise specified, all references herein to compounds according to Formula (I) are intended to include such alternative forms. Pharmaceutically acceptable and pharmaceutically active combinations of such forms, such as salts of prodrugs, are possible and within the scope of the disclosure as well. Some examples of salts and prodrugs are provided herein.

In some embodiments, subject compounds are used to prepare a composition that is effective in treating neurodegenerative diseases (also referred to herein as "neurodegenerative conditions"). Examples of neurodegenerative diseases include neuroinflammation-associated neurodegeneration, Alzheimer's Disease, ischemia-related disorder, creutzfeldt-jakob disease/prion peptide toxicity, ALS, dementia, and Parkinson Disease. In some embodiments, treatment of a neurodegenerative disease involves administering a formulation containing a subject compound. As described in more detail herein, the composition may comprise one or more active agents and one or more pharmaceutically acceptable additives. Furthermore, the compositions may be formulated into any suitable dosage form.

In some embodiments, the subject compositions contain a compound according to Formula (I) as the sole active agent; such formulations may include pharmaceutically inactive components such as carriers and the like.

In some embodiments, subject compounds are administered in combination with one or more additional anti-neurodegenerative disease drug(s). The additional drug may be present along with a subject compound in a single formulation, and therefore administered at the same time. Alternatively, the additional drug may be in a separate formulation, and may be administered according to a regimen that is separate from the regimen for administration of the formulation containing a subject compounds. In such embodiments the two regimens may be related; for example the second formulation is administered along with, or immediately before, or immediately after administration of the first formulation. Examples of additional anti-neurodegenerative disease drugs include acetylcholinesterase inhibitors (e.g., tacrine, rivastigmine, galantamine, donepezil, etc.), N-methyl-D-aspartate (NMDA) receptor antagonists (e.g., memantine), hyperzine A, latrepirdine, hypothalamic proline-rich peptide 1 (PRP-1), and the like.

Subject compounds may be administered as a free base, or in the form of a salt, ester, amide, prodrug, active metabolite, analog, or the like, provided that the salt, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 5th Ed. (New York: Wiley-Interscience, 2001), and Green, *Protective Groups in Organic Synthesis,* 3rd Ed. (New York: Wiley-Interscience, 1999).

A pharmaceutically acceptable salt may be prepared from any pharmaceutically acceptable organic acid or base, any pharmaceutically acceptable inorganic acid or base, or combinations thereof.

Suitable organic acids for preparing acid addition salts include, e.g., $C_1$-$C_6$ alkyl and $C_6$-$C_{12}$ aryl carboxylic acids, di-carboxylic acids, and tri-carboxylic acids such as acetic acid, propionic acid, succinic acid, maleic acid, fumaric acid, tartaric acid, glycolic acid, citric acid, pyruvic acid, oxalic acid, malic acid, malonic acid, benzoic acid, cinnamic acid, mandelic acid, salicylic acid, phthalic acid, and terephthalic acid, and aryl and alkyl sulfonic acids such as methanesulfonic acid, ethanesulfonic acid, and p-toluenesulfonic acid, and the like. Suitable inorganic acids for preparing acid addition salts include, e.g., hydrochloric acid, hydrobromic acid, hydroiodic acid, sulfuric acid, nitric acid, and phosphoric acid, and the like. An acid addition salt may be reconverted to the free base by treatment with a suitable base.

Suitable organic bases for preparing basic addition salts include, e.g., primary, secondary and tertiary amines, such as trimethylamine, triethylamine, tripropylamine, N,N-dibenzylethylenediamine, 2-dimethylaminoethanol, ethanolamine, ethylenediamine, glucamine, glucosamine, histidine, and polyamine resins, cyclic amines such as caffeine, N-ethylmorpholine, N-ethylpiperidine, and purine, and salts of amines such as betaine, choline, and procaine, and the like. Suitable inorganic bases for preparing basic addition salts include, e.g., salts derived from sodium, potassium, ammonium, calcium, ferric, ferrous, aluminum, lithium, magnesium, or zinc such as sodium hydroxide, potassium hydroxide, calcium carbonate, sodium carbonate, and potassium carbonate, and the like. A basic addition salt may be reconverted to the free acid by treatment with a suitable acid.

Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system. For example, a compound according to Formula I may be in the form of a pharmaceutically acceptable prodrug such as the sulfamate prodrug.

Other derivatives and analogs of the active agents may be prepared using standard techniques known to those skilled in the art of synthetic organic chemistry, or may be deduced by reference to the pertinent literature.

Any of the compounds of the disclosure may be the active agent in a subject formulation. Formulations containing the compounds of the disclosure may include 1, 2, 3 or more of the subject compounds, and may also include one or more additional active agents such as analgesics and other antibiotics. By "any of the compounds of the disclosure" is meant any compound selected from a subject compound per se (i.e. as a free base) and salts, prodrugs, etc. thereof.

The amount of active agent in the formulation typically ranges from about 0.05 wt % to about 95 wt % based on the total weight of the formulation. For example, the amount of active agent may range from about 0.05 wt % to about 50 wt %, or from about 0.1 wt % to about 25 wt %. Alternatively, the amount of active agent in the formulation may be measured so as to achieve a desired dose.

Formulations containing a subject compound may be presented in unit dose form or in multi-dose containers with an optional preservative to increase shelf life.

The compositions of the disclosure may be administered to the patient by any appropriate method. In general, both systemic and localized methods of administration are acceptable. It will be obvious to those skilled in the art that the selection of a method of administration will be influenced by a number of factors, such as the condition being treated, frequency of administration, dosage level, and the wants and needs of the patient. For example, certain methods may be better suited for rapid delivery of high doses of active agent, while other methods may be better suited for slow, steady delivery of active agent. Examples of methods of administration that are suitable for delivery of the compounds of the disclosure include parental and transmembrane absorption (including delivery via the digestive and respiratory tracts). Formulations suitable for delivery via these methods are well known in the art.

For example, formulations containing the compounds of the disclosure may be administered parenterally, such as via intravenous, subcutaneous, intraperitoneal, or intramuscular injection, using bolus injection and/or continuous infusion. Generally, parenteral administration employs liquid formulations.

The compositions may also be administered via the digestive tract, including orally and rectally. Examples of formulations that are appropriate for administration via the digestive tract include tablets, capsules, pastilles, chewing gum, aqueous solutions, and suppositories.

The formulations may also be administered via transmucosal administration. Transmucosal delivery includes delivery via the oral (including buccal and sublingual), nasal, vaginal, and rectal mucosal membranes. Formulations suitable for transmucosal deliver are well known in the art and include tablets, chewing gums, mouthwashes, lozenges, suppositories, gels, creams, liquids, and pastes.

The formulations may also be administered transdermally. Transdermal delivery may be accomplished using, for example, topically applied creams, liquids, pastes, gels and the like as well as what is often referred to as transdermal "patches."

The formulations may also be administered via the respiratory tract. Pulmonary delivery may be accomplished via oral or nasal inhalation, using aerosols, dry powders, liquid formulations, or the like. Aerosol inhalers and imitation cigarettes are examples of pulmonary dosage forms.

Liquid formulations include solutions, suspensions, and emulsions. For example, solutions may be aqueous solutions of the active agent and may include one or more of propylene glycol, polyethylene glycol, and the like. Aqueous suspensions can be made by dispersing the finely divided active agent in water with viscous material, such as natural or synthetic gums, resins, methylcellulose, sodium carboxymethylcellulose, or other well known suspending agents. Also included are formulations of solid form which are intended to be converted, shortly before use, to liquid form.

Tablets and lozenges may comprise, for example, a flavored base such as compressed lactose, sucrose and acacia or tragacanth and an effective amount of an active agent. Pastilles generally comprise the active agent in an inert base such as gelatin and glycerine or sucrose and acacia.

The subject compounds may inhibit one or more lipoxygenases, e.g. by at least 50%, or by at least 75%, or by at least 85%, or by at least 95%, or by at least 98%. In some embodiments, the compounds are selective inhibitors, and are inhibitors of a subsection of the LOX family of enzymes. In some embodiments, the subject compounds may inhibit 5-LOX, 12-LOX, or 15-LOX. In some embodiments, the subject compounds may inhibit various combinations of 5-LOX, 12-LOX, and 15-LOX, such as inhibiting 5-LOX and 12-LOX, inhibiting 5-LOX and 15-LOX, inhibiting 12-LOX and 15-LOX, and/or inhibiting 5-LOX, 12-LOX, and 15-LOX.

Subject compounds are useful in therapies for treating diseases associated with pathogenic lipoxygenase activity, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, neuroinflammation-associated disease, Alzheimer's Disease, ischemia-related disorder, creutzfeldt-jakob disease/prion peptide toxicity, ALS, dementia and Parkinson Disease.

For example, the methods may involve administering a subject compound to a patient in need thereof (e.g. a patient suffering from a neurodegenerative disease such as Alzheimer's Disease, or a patient at risk for such conditions, or a patient exhibiting symptoms of such conditions, etc.). In some embodiments, subject compounds are used in a method for reducing or eliminating the severity of symptoms associated with a subject disease. For example, the method may involve contacting nervous system cells or cells located in a nervous system, or contacting tissue associated with a nervous system, and such contacting results in one or more of the following: the inhibition of further neurodegeneration; the inhibition of abnormal cell growth and development; the inhibition of growth of non-cell objects in a nervous system; the reduction of neuroinflammation; the reduction in severity of symptoms associated with a neurodegenerative disease, and the like.

In some embodiments, subject compounds are used to prepare a composition that is effective in treating a subject disease. As described in more detail herein, the composition may comprise one or more active agents and one or more pharmaceutically acceptable additives. Furthermore, the compositions may be formulated into any suitable dosage form.

In some embodiments, treatment of a subject disease involves administering a formulation containing a subject compound. As described in more detail herein, such formulations may include any of a number of additives and/or additional active agents, and such formulations may be prepared in any of a variety of dosage forms. In some embodiments, treatment of a subject disease using a compound involves determining that the person has a subject disease associated with pathogenic lipoxygenase activity. Such determination may be made by any means appropriate for the particular condition, including blood tests and imaging tests.

In some embodiments, the methods involve measuring a lipoxygenase activity (such as 5-LOX, 12-LOX, or 15-LOX, and/or various combinations thereof) in a patient prior to treatment with a subject compound, after treatment with a subject compound, or both prior to and after treatment. In some embodiments, the methods involve measuring a level of a lipoxygenase metabolite in a patient. An example metabolite is 5-HETE. In these methods, measuring enzyme activity or measuring metabolite levels may be carried out using any appropriate sample from the person, such as a body fluid (e.g., blood, urine, etc.).

Various embodiments are implemented in accordance with the underlying Provisional Application (Ser. No. 62/953,023), entitled "Lipoxygenase Inhibitors," filed Dec. 23, 2019, to which benefit is claimed and which is fully incorporated herein by reference for their general and specific teachings. For instance, embodiments herein and/or in the provisional application can be combined in varying degrees (including wholly). Reference can also be made to the experimental teachings and underlying references provided in the underlying Provisional Application. Embodiments discussed in the Provisional Application are not intended, in any way, to be limiting to the overall technical disclosure, or to any part of the claimed disclosure unless specifically noted.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXPERIMENTAL EMBODIMENTS

The compounds disclosed herein were found to inhibit Akt and ERK activation by inhibiting 12-LOX mediated metabolism of arachidonic acid.

5-LOX FI assay Fluorescent Assay

The enzyme assay (100 μL) contained 50 mM Tris, pH 7.5, 0.1 mM EDTA, 0.3 mM $CaCl_2$, 20 μM AA, 100 μM ATP, 1 μM DHR123, and recombinant 5-LOX cell lysate (0.5 μL/100 μL). Inhibitors (dissolved in DMSO) were plated at 1 μL into 96-well assay microplates followed by a 40 μL addition of a solution containing 5-LOX enzyme. Enzyme was pre-incubated with compounds for 15 mins. The assay was initiated by the addition of a 40 μL substrate solution containing AA and ATP, and 20 μL addition of a solution containing DHR123. Enzymatic reaction proceeded for 30 min with kinetic reading at 500 nm excitation & 536 nm emission in SpectraMax Paradigm (MolecularDevice). Percent inhibition was calculated for each compound dose for $IC_{50}$ curve fitting using 4 Parameter Logistic Model or Sigmoidal Dose-Response Model.

12-LOX/15-LOX Fluorescent Assay

The enzyme assay (100 ul) contained 50 mM Tris, pH 7.5, 0.05% Tween-20, 20 μM AA/LA, 1 μM DHR123, and 100 nM recombinant 12-LOX enzyme/50 nM recombinant 15-LOX enzyme. Inhibitors (dissolved in DMSO) were plated at 1 μL into 96-well assay microplates followed by a 40 μL addition of a solution containing 12-LOX/15-LOX enzyme. Enzyme was pre-incubated with compounds for 15 mins. The assay was initiated by the addition of a 40 μL substrate solution containing AA/LA, and 20 μL addition of a solution containing DHR123. Enzymatic reaction proceeded for 30 min with kinetic reading at 500 nm excitation & 536 nm emission in SpectraMax Paradigm (MolecularDevice). Percent inhibition was calculated for each compound dose for $IC_{50}$ curve fitting using 4 Parameter Logistic Model or Sigmoidal Dose-Response Model.

Inhibitory activity against a panel of lipoxygenases was demonstrated in cell-based assays, e.g. for 5-LOX, a fluorescence-based enzyme assay of human 5-LOX (Anal. Biochem., 364:204.) was used, and for 12-LOX, a colorimetric method to determine platelet 12-LOX activity (Anal. biochem., 231:354) was used. Table 1 provides results for exemplary compounds on 5-LOX, 12-LOX, and 15-LOX.

TABLE 1

IC50 (μM) values for in vitro lipoxygenase inhibition

| Structure | Name | SPII-SRI Compound Code | 5-LOX | 12-LOX | 15-LOX |
|---|---|---|---|---|---|
| 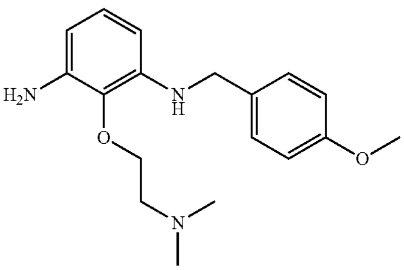 [SMILES: COc1ccc(CNc2cccc(N)c2OCCN(C)C)cc1] | 2-(2-(dimethylamino)ethoxy)-N$^1$-(4-methoxybenzyl)benzene-1,3-diamine | SS20308-0025-01 | 7.31 | 1.29 | 45.93 |
| 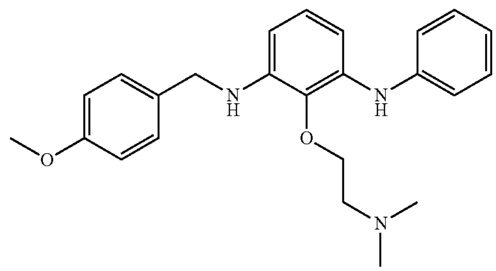 [SMILES: COc1ccc(CNc2cccc(Nc3ccccc3)c2OCCN(C)C)cc1] | 2-(2-(dimethylamino)ethoxy)-N$^1$-(4-methoxybenzyl)-N$^3$-phenylbenzene-1,3-diamine | SS20308-0052-01 | 1.32 | 0.62 | 1.56 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 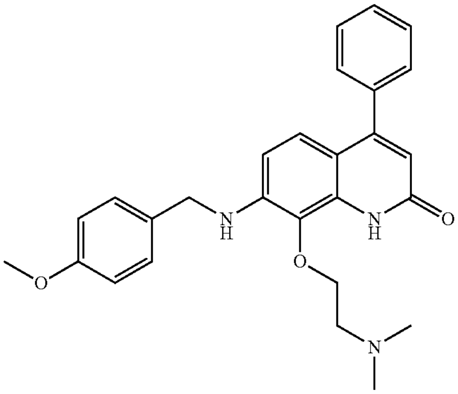 [SMILES: COc1ccc(CNc2ccc3c(-c4ccccc4)cc(=O)[nH]c3c2OCCN(C)C)cc1] | 8-(2-(dimethylamino) ethoxy)-7-((4-methoxybenzyl) amino)-4-phenylquinolin-2(1H)-one | SS20308-0053-01 | 3.36 | 5.2 | 1.33 |
| 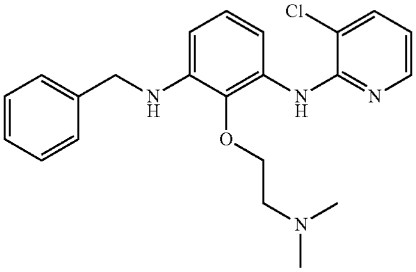 [SMILES: CN(C)CCOc1c(NCc2ccccc2)cccc1Nc1ncccc1Cl] | $N^1$-benzyl-$N^3$-(3-chloropyridin-2-yl)-2-(2-(dimethylamino) ethoxy)benzene-1,3-diamine | SS20308-0071-01 | 5.73 | 4.9 | 11.52 |
| 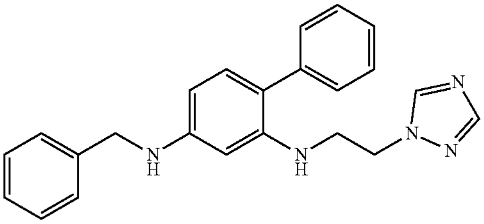 [SMILES: c1ccc(CNc2ccc(-c3ccccc3)c(NCCn3cncn3)c2)cc1] | $N^2$-(2-(1H-1,2,4-triazol-1-yl)ethyl)-$N^4$-benzyl-[1,1'-biphenyl]-2,4-diamine | SS20308-0096-01 | 0.55 | 0.24 | 1.00 |
| 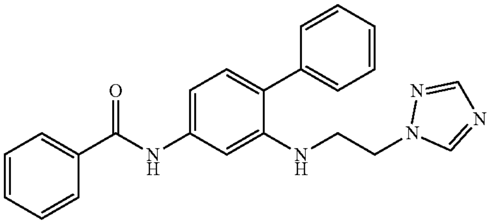 [SMILES: O=C(Nc1ccc(-c2ccccc2)c(NCCn2cncn2)c1)c1ccccc1] | N-(2-((2-(1H-1,2,4-triazol-1-yl)ethyl)amino)-[1,1'-biphenyl]-4-yl)benzamide | SS20308-0135-01 | 25.75 | 20.76 | 52.99 |
| 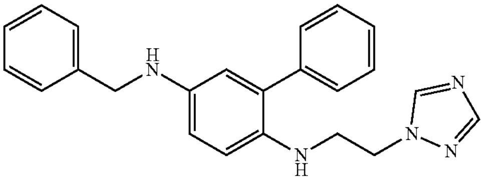 | $N^2$-(2-(1H-1,2,4-triazol-1-yl)ethyl)-$N^5$-benzyl-[1,1'-biphenyl]-2,5-diamine | SS20308-0145-01 | 0.03; 0.05; 0.05 | 0.02; 0.02; 0.02 | 0.06; 0.14; 0.12 |
| 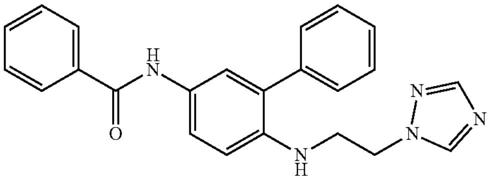 [SMILES: O=C(Nc1ccc(NCCn2cncn2)c(-c2ccccc2)c1)c1ccccc1] | N-(6-((2-(1H-1,2,4-triazol-1-yl)ethyl)amino)-[1,1'-biphenyl]-3-yl)benzamide | SS20308-0146-01 | 3.77 | 4.02 | 7.81 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 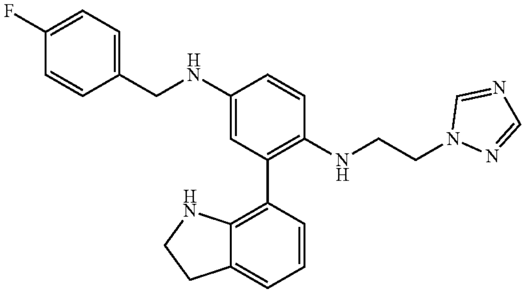 [SMILES: Fc1ccc(CNc2ccc(NCCn3cncn3)c(-c3cccc4c3NCC4)c2)cc1] | $N^1$-(2-(1H-1,2,4-triazol-1-yl)ethyl)-$N^4$-(4-fluorobenzyl)-2-(indolin-7-yl)benzene-1,4-diamine | SS20308-0211-01 | 0.08; 0.07 | 0.04; 0.03 | 0.22; 0.17 |
| 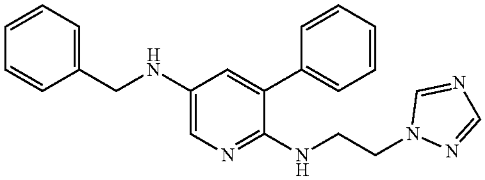 [SMILES: c1ccc(CNc2cnc(NCCn3cncn3)c(-c3ccccc3)c2)cc1] | $N^2$-(2-(1H-1,2,4-triazol-1-yl)ethyl)-$N^5$-benzyl-3-phenylpyridine-2,5-diamine | SS20308-0212-01 | 2.93 | 1.61 | 3.29 |
| 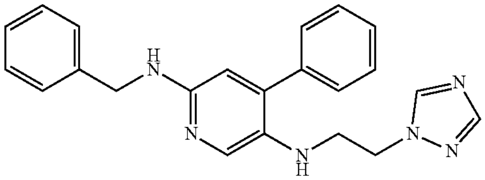 [SMILES: c1ccc(CNc2cc(-c3ccccc3)c(NCCn3cncn3)cn2)cc1] | $N^5$-(2-(1H-1,2,4-triazol-1-yl)ethyl)-$N^2$-benzyl-4-phenylpyridine-2,5-diamine | SS20308-0213-01 | 0.61 | 0.08 | 0.6 |
| 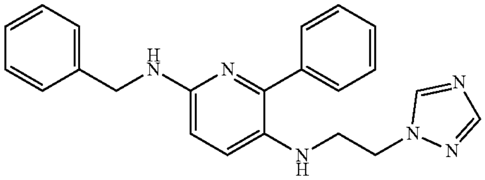 [SMILES: c1ccc(CNc2ccc(NCCn3cncn3)c(-c3ccccc3)n2)cc1] | $N^5$-(2-(1H-1,2,4-triazol-1-yl)ethyl)-$N^2$-benzyl-6-phenylpyridine-2,5-diamine | SS20308-0214-01 | 0.16 | 0.05 | 0.28 |
| 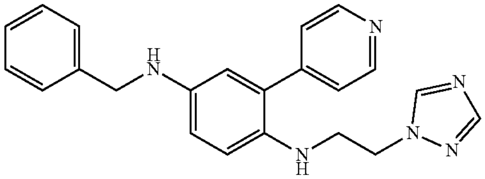 [SMILES: c1ccc(CNc2ccc(NCCn3cncn3)c(-c3ccncc3)c2)cc1] | $N^1$-(2-(1H-1,2,4-triazol-1-yl)ethyl)-$N^4$-benzyl-2-(pyridin-4-yl)benzene-1,4-diamine | SS20308-0215-01 | 0.07; 0.09 | 0.04; 0.03 | 0.17; 0.15 |
| 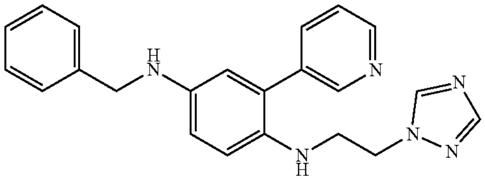 [SMILES: c1ccc(CNc2ccc(NCCn3cncn3)c(-c3cccnc3)c2)cc1] | $N^1$-(2-(1H-1,2,4-triazol-1-yl)ethyl)-$N^4$-benzyl-2-(pyridin-3-yl)benzene-1,4-diamine | SS20308-0216-01 | 0.04 | 0.03 | 0.07 |
| 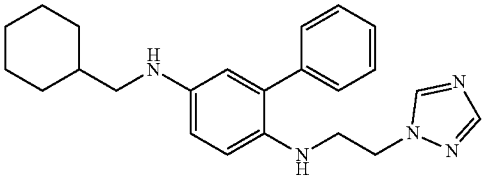 [SMILES: c1ccc(-c2cc(NCC3CCCCC3)ccc2NCCn2cncn2)cc1] | $N^2$-(2-(1H-1,2,4-triazol-1-yl)ethyl)-$N^5$-(cyclohexylmethyl)-[1,1'-biphenyl]-2,5-diamine | SS20308-0217-01 | 0.02; 0.06 | 0.02; 0.04 | 0.06; 0.12 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 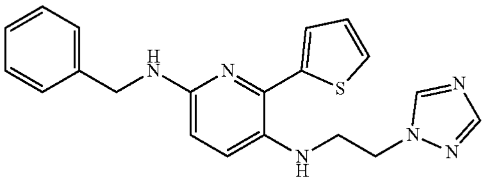 [SMILES: c1ccc(CNc2ccc(NCCn3cncn3)c(-c3cccs3)n2)cc1] | $N^5$-(2-(1H-1,2,4-triazol-1-yl)ethyl)-$N^2$-benzyl-6-(thiophen-2-yl)pyridine-2,5-diamine | SS20308-0218-01 | 0.02 | 0.01 | 0.03 |
| 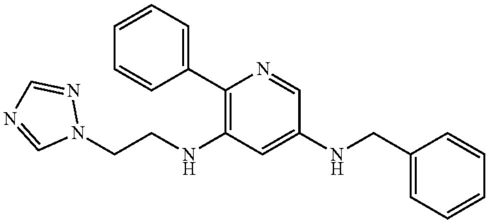 [SMILES: c1ccc(CNc2cnc(-c3ccccc3)c(NCCn3cncn3)c2)cc1] | $N^3$-(2-(1H-1,2,4-triazol-1-yl)ethyl)-$N^5$-benzyl-2-phenylpyridine-3,5-diamine | SS20308-0219-01 | 4.78 | 2.68 | 22.26 |
| 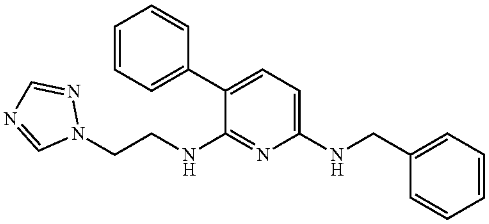 [SMILES: c1ccc(CNc2ccc(-c3ccccc3)c(NCCn3cncn3)n2)cc1] | $N^2$-(2-(1H-1,2,4-triazol-1-yl)ethyl)-$N^6$-benzyl-3-phenylpyridine-2,6-diamine | SS20308-0221-01 | 0.66 | 0.11 | 1.29 |
| 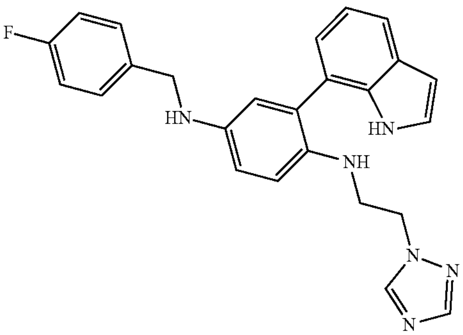 [SMILES: Fc1ccc(CNc2ccc(NCCn3cncn3)c(-c3cccc4cc[nH]c34)c2)cc1] | $N^1$-(2-(1H-1,2,4-triazol-1-yl)ethyl)-$N^4$-(4-fluorobenzyl)-2-(1H-indol-7-yl)benzene-1,4-diamine | SS20308-0225-01 | 0.05 | 0.03 | 0.16 |
| 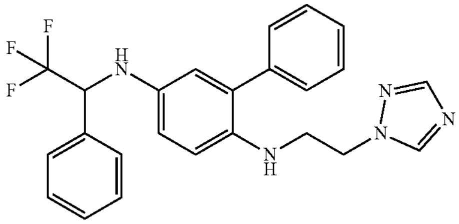 [SMILES: FC(F)(F)C(Nc1ccc(NCCn2cncn2)c(-c2ccccc2)c1)c1ccccc1] | $N^2$-(2-(1H-1,2,4-triazol-1-yl)ethyl)-$N^5$-(2,2,2-trifluoro-1-phenylethyl)-[1,1'-biphenyl]-2,5-diamine | SS20308-0226-01 | 0.14 | 0.06 | 0.17 |
| 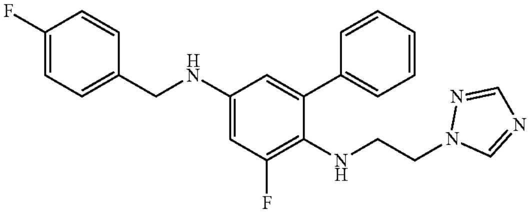 [SMILES: Fc1ccc(CNc2cc(F)c(NCCn3cncn3)c(-c3ccccc3)c2)cc1] | $N^2$-(2-(1H-1,2,4-triazol-1-yl)ethyl)-3-fluoro-$N^5$-(4-fluorobenzyl)-[1,1'-biphenyl]-2,5-diamine | SS20308-0227-01 | 0.39 | 0.03 | 4.39 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 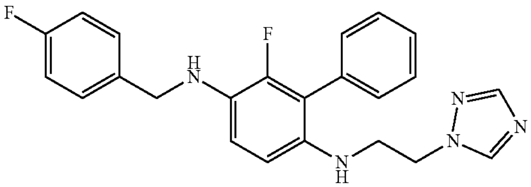 [SMILES: Fc1ccc(CNc2ccc(NCCn3cncn3)c(-c3ccccc3)c2F)cc1] | $N^2$-(2-(1H-1,2,4-triazol-1-yl)ethyl)-6-fluoro-$N^5$-(4-fluorobenzyl)-[1,1'-biphenyl]-2,5-diamine | SS20308-0228-01 | 0.16 | 0.02 | 0.1 |
| 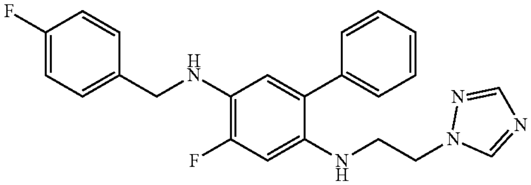 [SMILES: Fc1ccc(CNc2cc(-c3ccccc3)c(NCCn3cncn3)cc2F)cc1] | N2-(2-(1H-1,2,4-triazol-1-yl)ethyl)-4-fluoro-N5-(4-fluorobenzyl)-[1,1'-biphenyl]-2,5-diamine | SS20308-0229-01 | 0.08; 0.26 | 0.02 | 0.01 |
| 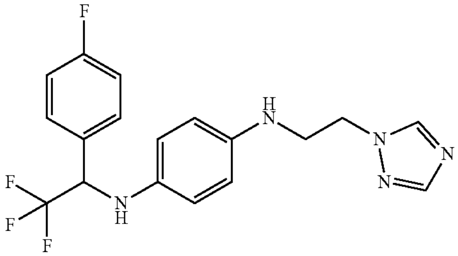 [SMILES: Fc1ccc(C(Nc2ccc(NCCn3cncn3)cc2)C(F)(F)F)cc1] | $N^1$-(2-(1H-1,2,4-triazol-1-yl)ethyl)-$N^4$-(2,2,2-trifluoro-1-(4-fluorophenyl)ethyl) benzene-1,4-diamine | SS20308-0232-01 | 0.69 | 0.14 | 0.74 |
| 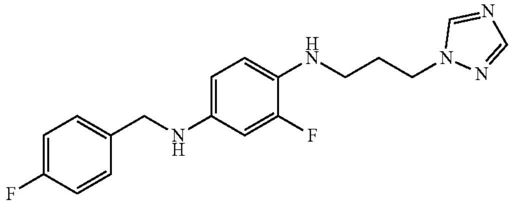 [SMILES: Fc1ccc(CNc2ccc(NCCCn3cncn3)c(F)c2)cc1] | $N^1$-(3-(1H-1,2,4-triazol-1-yl)propyl)-2-fluoro-$N^4$-(4-fluorobenzyl) benzene-1,4-diamine | SS20308-0236-01 | 0.1; 0.18 | 0.04; 0.03 | 0.19; 0.2 |
| 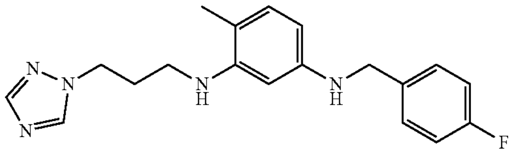 [SMILES: Cc1ccc(NCc2ccc(F)cc2)cc1NCCCn1cncn1] | $N^3$-(2-(1H-1,2,4-triazol-1-yl)ethyl)-$N^1$-(4-fluorobenzyl)-4-methylbenzene-1,3-diamine | SS20308-0237-01 | 0.28 | 0.18 | 0.74 |
| 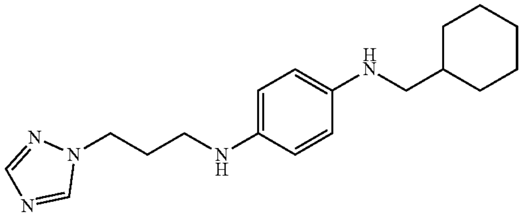 [SMILES: c1ncn(CCCNc2ccc(NCC3CCCCC3)cc2)n1] | $N^1$-(3-(1H-1,2,4-triazol-1-yl)propyl)-$N^4$-(cyclohexylmethyl) benzene-1,4-diamine | SS20308-0240-01 | 0.02; 0.03 | 0.01 | 0.08 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 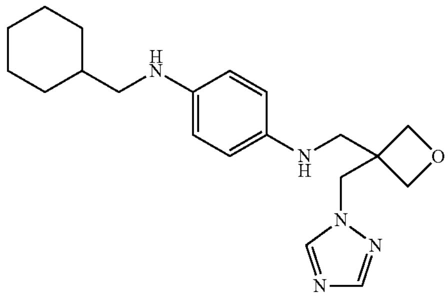 [SMILES: c1ncn(CC2(CNc3ccc(NCC4CCCCC4)cc3)COC2)n1] | $N^1$-((3-((1H-1,2,4-triazol-1-yl)methyl)oxetan-3-yl)methyl)-$N^4$-(cyclohexylmethyl) benzene-1,4-diamine | SS20308-0242-01 | 0.09 | 0.05 | 0.31 |
| 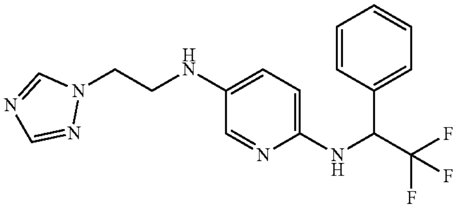 [SMILES: FC(F)(F)C(Nc1ccc(NCCn2cncn2)cn1)c1ccccc1] | $N^5$-(2-(1H-1,2,4-triazol-1-yl)ethyl)-$N^2$-(2,2,2-trifluoro-1-phenylethyl) pyridine-2,5-diamine | SS20308-0245-01 | 1.19 | 0.51 | 2.69 |
| 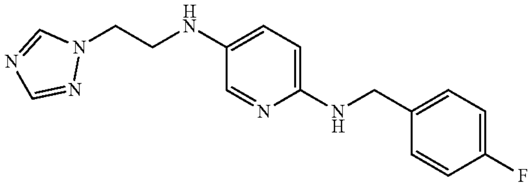 [SMILES: Fc1ccc(CNc2ccc(NCCn3cncn3)cn2)cc1] | $N^5$-(2-(1H-1,2,4-triazol-1-yl)ethyl)-$N^2$-(4-fluorobenzyl) pyridine-2,5-diamine | SS20308-0246-01 | 0.51 | 0.08 | 3.73 |
| 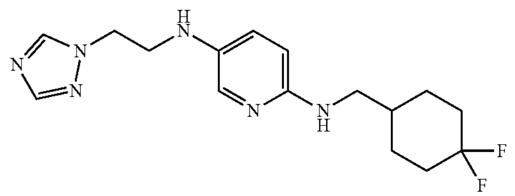 [SMILES: FC1(F)CCC(CNc2ccc(NCCn3cncn3)cn2)CC1] | $N^5$-(2-(1H-1,2,4-triazol-1-yl)ethyl)-$N^2$-((4,4-difluorocyclohexyl) methyl)pyridine-2,5-diamine | SS20308-0247-01 | 0.63 | 0.13 | 3.41 |
| 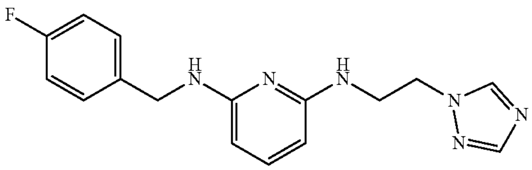 [SMILES: Fc1ccc(CNc2cccc(NCCn3cncn3)n2)cc1] | $N^2$-(2-(1H-1,2,4-triazol-1-yl)ethyl)-$N^6$-(4-fluorobenzyl)pyridine-2,6-diamine | SS20308-0249-01 | 1.59 | 0.37 | 14.02 |
| 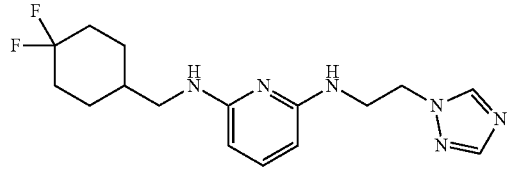 [SMILES: FC1(F)CCC(CNc2cccc(NCCn3cncn3)n2)CC1] | $N^2$-(2-(1H-1,2,4-triazol-1-yl)ethyl)-$N^6$-((4,4-difluorocyclohexyl) methyl)pyridine-2,6-diamine | SS20308-0250-01 | 1.26 | 0.32 | 4.34 |

TABLE 1-continued

| Structure | Name | SPII-SRI Compound Code | 5-LOX | 12-LOX | 15-LOX |
|---|---|---|---|---|---|
| IC50 (µM) values for in vitro lipoxygenase inhibition | | | | | |
| 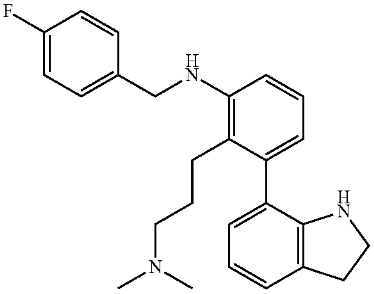 [SMILES: CN(C)CCCc1c(NCc2ccc(F)cc2)cccc1-c1cccc2c1NCC2] | 2-(3-(dimethylamino)propyl)-N-(4-fluorobenzyl)-3-(indolin-7-yl)aniline | SS20308-0253-01 | 0.31 | 0.29 | 0.92 |
| 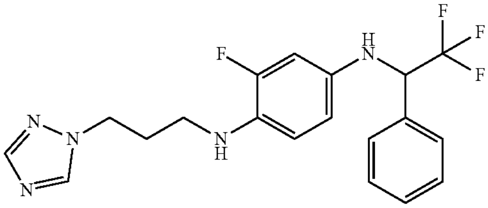 [SMILES: Fc1cc(NC(c2ccccc2)C(F)(F)F)ccc1NCCCn1cncn1] | 4-(3-(1H-1,2,4-triazol-1-yl)propyl)-3-fluoro-N-(2,2,2-trifluoro-1-phenylethyl)aniline | SS20308-0265-01 | | | |
| 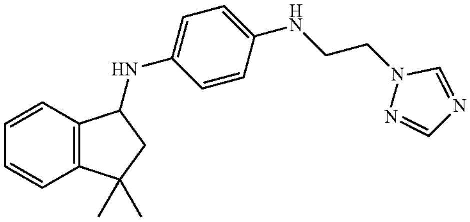 [SMILES: CC1(C)CC(Nc2ccc(NCCn3cncn3)cc2)c2ccccc21] | $N^1$-(2-(1H-1,2,4-triazol-1-yl)ethyl)-$N^4$-(3,3-dimethyl-2,3-dihydro-1H-inden-1-yl)benzene-1,4-diamine | SS20308-0275-01 | 0.26; 0.1 | 0.05; 0.04 | 0.44; 0.2 |
| 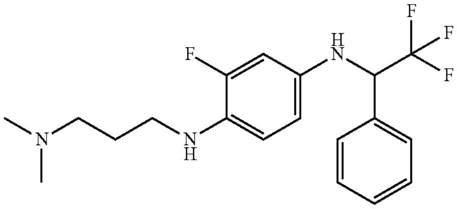 [SMILES: CN(C)CCCNc1ccc(NC(c2ccccc2)C(F)(F)F)cc1F] | $N^1$-(3-(dimethylamino)propyl)-2-fluoro-$N^4$-(2,2,2-trifluoro-1-phenylethyl)benzene-1,4-diamine | SS20308-0302-01 | 0.25 | 0.21 | 0.78 |
| 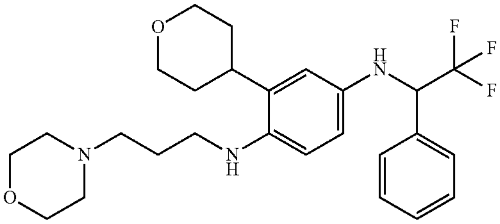 [SMILES: FC(F)(F)C(Nc1ccc(NCCCN2CCOCC2)c(C2CCOCC2)c1)c1ccccc1] | $N^1$-(3-morpholinopropyl)-2-(tetrahydro-2H-pyran-4-yl)-$N^4$-(2,2,2-trifluoro-1-phenylethyl)benzene-1,4-diamine | SS20308-0315-01 | 0.07 | 0.06 | 0.15 |
| 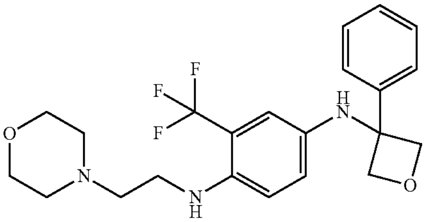 [SMILES: FC(F)(F)c1cc(NC2(c3ccccc3)COC2)ccc1NCCN1CCOCC1] | $N^1$-(2-morpholinoethyl)-$N^4$-(3-phenyloxetan-3-yl)-2-(trifluoromethyl)benzene-1,4-diamine | SS20308-0317-01 | 0.57 | 0.32 | 0.73 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 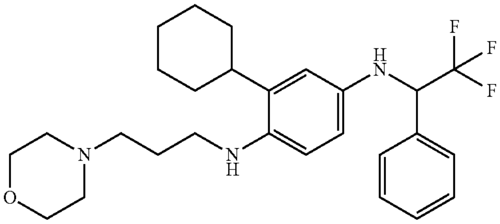 | 2-cyclohexyl-$N^1$-(3-morpholinopropyl)-$N^4$-(2,2,2-trifluoro-1-phenylethyl) benzene-1,4-diamine | SS20308-0325-01 | 0.04 | 0.03 | 0.07 |
| 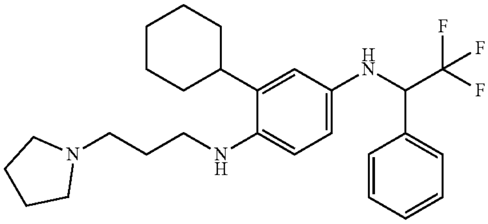 [SMILES: FC(F)(F)C(Nc1ccc(NCCCN2CCCC2)c(C2CCCCC2)c1)c1ccccc1] | 2-cyclohexyl-$N^1$-(3-(pyrrolidin-1-yl)propyl)-$N^4$-(2,2,2-trifluoro-1-phenylethyl) benzene-1,4-diamine | SS20308-0326-01 | | | |
| 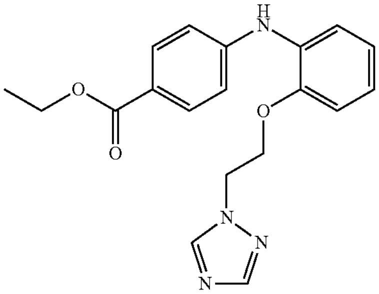 [SMILES: CCOC(=O)c1ccc(Nc2ccccc2OCCn2cncn2)cc1] | ethyl 4-((2-(2-(1H-1,2,4-triazol-1-yl)ethoxy)phenyl) amino)benzoate | SS20308-0033-01 | 50.31 | 23.9 | 17.02 |
| 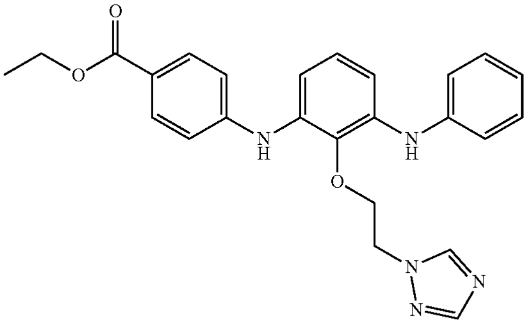 [SMILES: CCOC(=O)c1ccc(Nc2cccc(Nc3ccccc3)c2OCCn2cncn2)cc1] | ethyl 4-((2-(2-(dimethylamino) ethoxy)-3-(phenylamino) phenyl) amino)benzoate | SS20308-0055-01 | 3.33 | 1.64 | 1.46 |
| 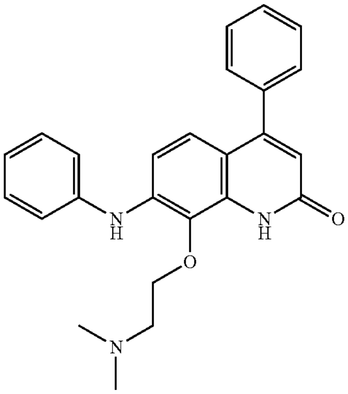 [SMILES: CN(C)CCOc1c(Nc2ccccc2)ccc2c(-c3ccccc3)cc(=O)[nH]c12] | 8-(2-(dimethylamino) ethoxy)-4-phenyl-7-(phenylamino) quinolin-2(1H)-one | SS20308-0072-01 | 7.23 | 3.37 | 2.53 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 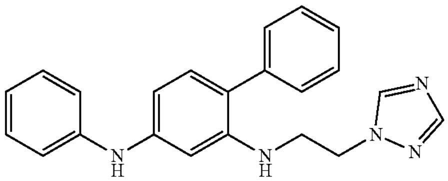 [SMILES: c1ccc(Nc2ccc(-c3ccccc3)c(NCCn3cncn3)c2)cc1] | $N^2$-(2-(1H-1,2,4-triazol-1-yl)ethyl)-$N^4$-phenyl-[1,1'-biphenyl]-2,4-diamine | SS20308-0095-01 | 0.35 | 0.18 | 0.43 |
| 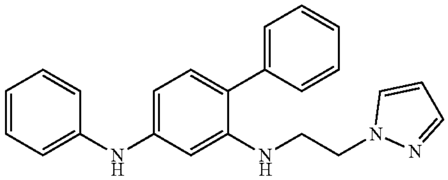 [SMILES: c1ccc(Nc2ccc(-c3ccccc3)c(NCCn3cccn3)c2)cc1] | $N^2$-(2-(1H-pyrazol-1-yl)ethyl)-$N^4$-phenyl-[1,1'-biphenyl]-2,4-diamine | SS20308-0129-01 | 0.25 | 0.19 | 0.44 |
| 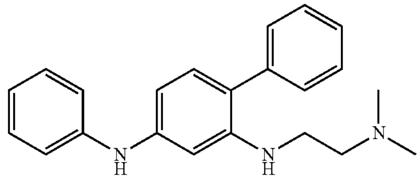 [SMILES: CN(C)CCNc1cc(Nc2ccccc2)ccc1-c1ccccc1] | $N^2$-(2-(dimethylamino)ethyl)-$N^4$-phenyl-[1,1'-biphenyl]-2,4-diamine | SS20308-0130-01 | 0.24 | 0.25 | 1.12 |
| 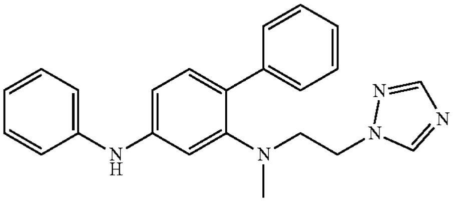 [SMILES: CN(CCn1cncn1)c1cc(Nc2ccccc2)ccc1-c1ccccc1] | $N^2$-(2-(1H-1,2,4-triazol-1-yl)ethyl)-$N^2$-methyl-$N^4$-phenyl-[1,1'-biphenyl]-2,4-diamine | SS20308-0131-01 | 0.25 | 0.19 | 0.26 |
| 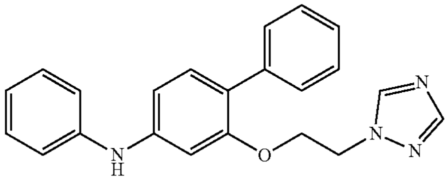 [SMILES: c1ccc(Nc2ccc(-c3ccccc3)c(OCCn3cncn3)c2)cc1] | 2-(2-(1H-1,2,4-triazol-1-yl)ethoxy)-N-phenyl-[1,1'-biphenyl]-4-amine | SS20308-0132-01 | 0.6 | 0.49 | 10.41 |
| 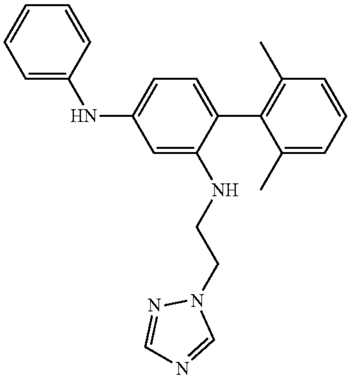 [SMILES: Cc1cccc(C)c1-c1ccc(Nc2ccccc2)cc1NCCn1cncn1] | $N^2$-(2-(1H-1,2,4-triazol-1-yl)ethyl)-2',6'-dimethyl-$N^4$-phenyl-[1,1'-biphenyl]-2,4-diamine | SS20308-0133-01 | 0.22 | 0.14 | 0.41 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 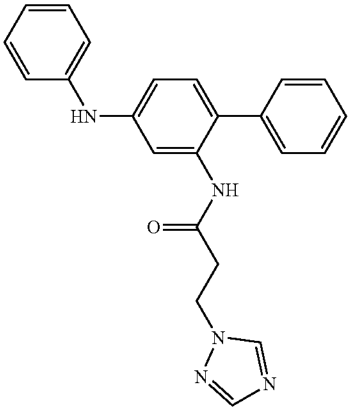 [SMILES: O=C(CCn1cncn1)Nc1cc(Nc2ccccc2)ccc1-c1ccccc1] | N-(4-(phenylamino)-[1,1'-biphenyl]-2-yl)-3-(1H-1,2,4-triazol-1-yl)propanamide | SS20308-0134-01 | 2.32 | 1.49 | 3.48 |
| 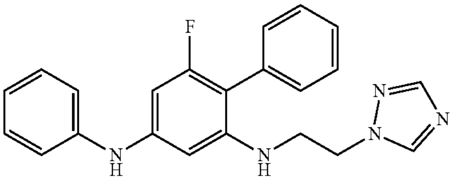 [SMILES: Fc1cc(Nc2ccccc2)cc(NCCn2cncn2)c1-c1ccccc1] | $N^2$-(2-(1H-1,2,4-triazol-1-yl)ethyl)-6-fluoro-$N^4$-phenyl-[1,1'-biphenyl]-2,4-diamine | SS20308-0141-01 | | | |
| 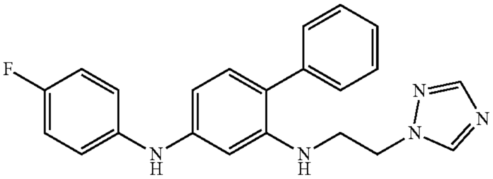 [SMILES: Fc1ccc(Nc2ccc(-c3ccccc3)c(NCCn3cncn3)c2)cc1] | $N^2$-(2-(1H-1,2,4-triazol-1-yl)ethyl)-$N^4$-(4-fluorophenyl)-[1,1'-biphenyl]-2,4-diamine | SS20308-0142-01 | 0.18; 0.34 | 0.09; 0.17 | 0.12; 0.33 |
| 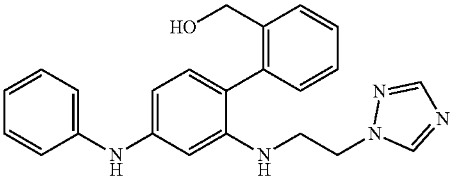 [SMILES: OCc1ccccc1-c1ccc(Nc2ccccc2)cc1NCCn1cncn1] | (2'-((2-(1H-1,2,4-triazol-1-yl)ethyl)amino)-4'-(phenylamino)-[1,1'-biphenyl]-2-yl)methanol | SS20308-0143-01 | 0.94 | 0.33 | 1.87 |
| 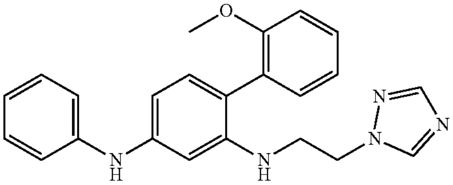 [SMILES: COc1ccccc1-c1ccc(Nc2ccccc2)cc1NCCn1cncn1] | $N^2$-(2-(1H-1,2,4-triazol-1-yl)ethyl)-2'-methoxy-$N^4$-phenyl-[1,1'-biphenyl]-2,4-diamine | SS20308-0144-01 | 0.4 | 0.18 | 0.63 |
| 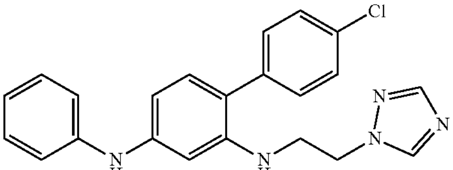 | $N^2$-(2-(1H-1,2,4-triazol-1-yl)ethyl)-4'-chloro-$N^4$-phenyl-[1,1'-biphenyl]-2,4-diamine | SS20308-0147-01 | 0.17 | 0.14 | 0.16 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 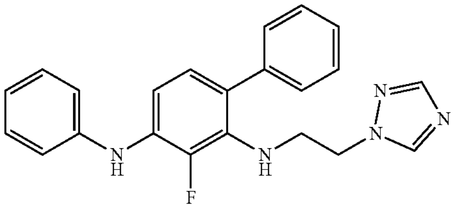 [SMILES: Fc1c(Nc2ccccc2)ccc(-c2ccccc2)c1NCCn1cncn1] | $N^2$-(2-(1H-1,2,4-triazol-1-yl)ethyl)-3-fluoro-$N^4$-phenyl-[1,1'-biphenyl]-2,4-diamine | SS20308-0148-01 | 3.77; 0.76 | 4.02; 0.29 | 7.81; 5.98 |
| 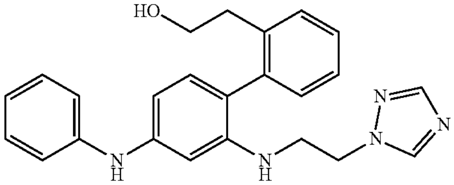 [SMILES: OCCc1ccccc1-c1ccc(Nc2ccccc2)cc1NCCn1cncn1] | 2-(2'-((2-(1H-1,2,4-triazol-1-yl)ethyl)amino)-4'-(phenylamino)-[1,1'-biphenyl]-2-yl)ethan-1-ol | SS20308-0149-01 | 0.63 | 0.3 | 1.27 |
| 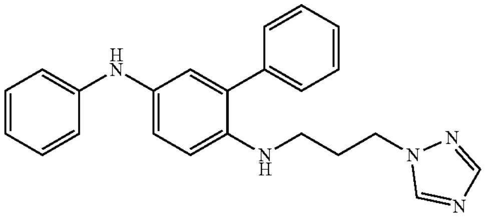 [SMILES: c1ccc(Nc2ccc(NCCCn3cncn3)c(-c3ccccc3)c2)cc1] | $N^2$-(3-(1H-1,2,4-triazol-1-yl)propyl)-$N^4$-phenyl-[1,1'-biphenyl]-2,4-diamine | SS20308-0151-01 | 0.07; 0.04 | 0.02; 0.02 | 0.1; 0.08 |
| 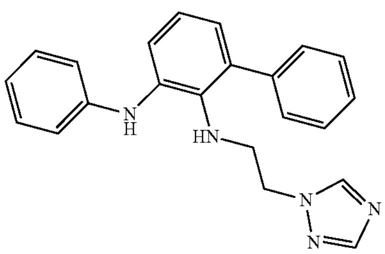 [SMILES: c1ccc(Nc2cccc(-c3ccccc3)c2NCCn2cncn2)cc1] | $N^2$-(2-(1H-1,2,4-triazol-1-yl)ethyl)-$N^3$-phenyl-[1,1'-biphenyl]-2,3-diamine | SS20308-0153-01 | 0.71 | 0.2 | 0.48 |
| 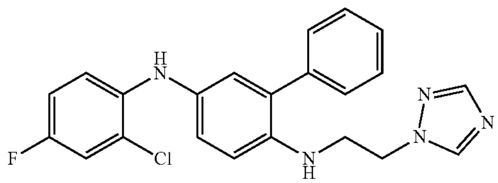 [SMILES: Fc1ccc(Nc2ccc(NCCn3cncn3)c(-c3ccccc3)c2)c(Cl)c1] | 6-(3-(1H-1,2,4-triazol-1-yl)propyl)-N-(2-chloro-4-fluorophenyl)-[1,1'-biphenyl]-3-amine | SS20308-0165-01 | 0.03; 0.23 | 0.08; 0.06 | 0.05; 0.12 |
| 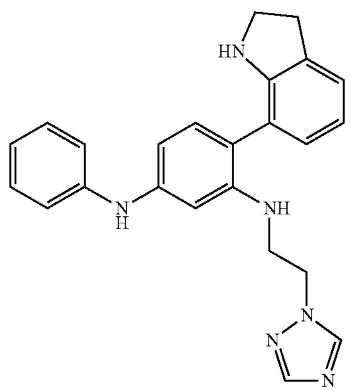 [SMILES: c1ccc(Nc2ccc(-c3cccc4c3NCC4)c(NCCn3cncn3)c2)cc1] | $N^3$-(2-(1H-1,2,4-triazol-1-yl)ethyl)-4-(indolin-7-yl)-$N^1$-phenylbenzene-1,3-diamine | SS20308-0166-01 | 0.14 | 0.07 | 0.31 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 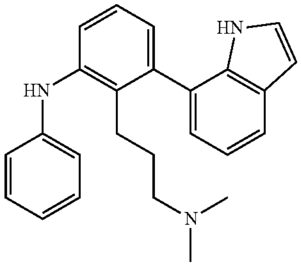 [SMILES: CN(C)CCCc1c(Nc2ccccc2)cccc1-c1cccc2cc[nH]c12] | 2-(3-(dimethylamino)propyl)-3-(1H-indol-7-yl)-N-phenylaniline | SS20308-0171-01 | | | |
| 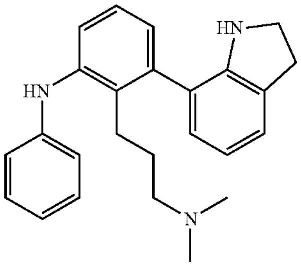 [SMILES: CN(C)CCCc1c(Nc2ccccc2)cccc1-c1cccc2c1NCC2] | 2-(3-(dimethylamino)propyl)-3-(indolin-7-yl)-N-phenylaniline | SS20308-0172-01 | 0.23 | 0.36 | 0.75 |
| 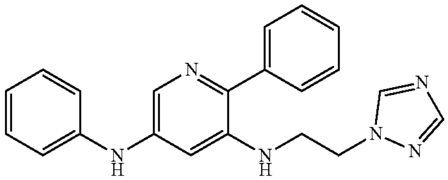 [SMILES: c1ccc(Nc2cnc(-c3ccccc3)c(NCCn3cncn3)c2)cc1] | $N^3$-(2-(1H-1,2,4-triazol-1-yl)ethyl)-$N^5$,2-diphenylpyridine-3,5-diamine | SS20308-0173-01 | 2.22 | 1.09 | 14.17 |
| 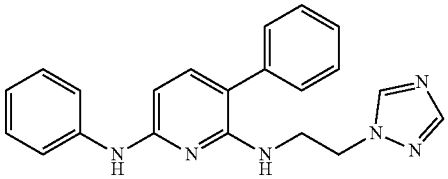 [SMILES: c1ccc(Nc2ccc(-c3ccccc3)c(NCCn3cncn3)n2)cc1] | $N^2$-(2-(1H-1,2,4-triazol-1-yl)ethyl)-$N^6$,3-diphenylpyridine-2,6-diamine | SS20308-0175-01 | 0.32 | 0.26 | 0.81 |
| 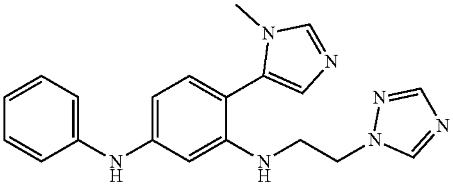 [SMILES: Cn1cncc1-c1ccc(Nc2ccccc2)cc1NCCn1cncn1] | $N^3$-(2-(1H-1,2,4-triazol-1-yl)ethyl)-4-(1-methyl-1H-imidazol-5-yl)-$N^1$-phenylbenzene-1,3-diamine | SS20308-0177-01 | 1.45 | 0.72 | 3.82 |
| 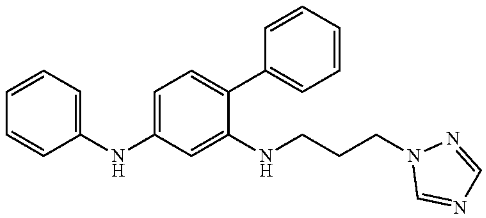 [SMILES: c1ccc(Nc2ccc(-c3ccccc3)c(NCCCn3cncn3)c2)cc1] | $N^2$-(3-(1H-1,2,4-triazol-1-yl)propyl)-$N^4$-phenyl-[1,1'-biphenyl]-2,4-diamine | SS20308-0178-01 | 0.15; 0.21; 0.09; 0.21 | 0.09; 0.11; 0.07; 0.14 | 0.25; 0.19; 0.12; 0.23 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 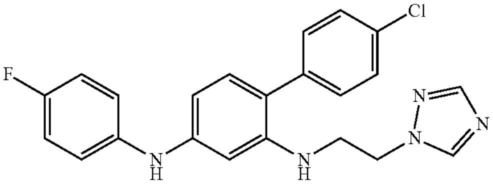 [SMILES: Fc1ccc(Nc2ccc(-c3ccc(Cl)cc3)c(NCCn3cncn3)c2)cc1] | $N^2$-(2-(1H-1,2,4-triazol-1-yl)ethyl)-4'-chloro-$N^4$-(4-fluorophenyl)-[1,1'-biphenyl]-2,4-diamine | SS20308-0181-01 | 0.16 | 0.16 | 0.21 |
| 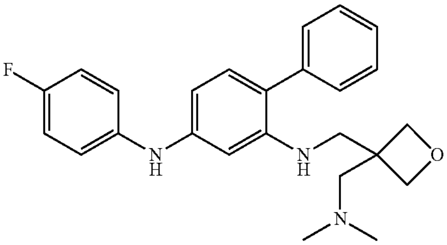 [SMILES: CN(C)CC1(CNc2cc(Nc3ccc(F)cc3)ccc2-c2ccccc2)COC1] | $N^2$-((3-((dimethylamino)methyl)oxetan-3-yl)methyl)-$N^4$-(4-fluorophenyl)-[1,1'-biphenyl]-2,4-diamine | SS20308-0184-01 | 0.16 | 0.18 | 0.24 |
| 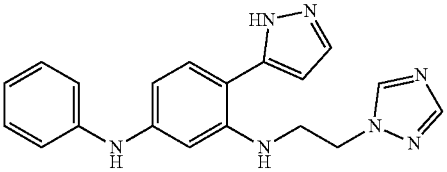 [SMILES: c1ccc(Nc2ccc(-c3ccn[nH]3)c(NCCn3cncn3)c2)cc1] | $N^3$-(2-(1H-1,2,4-triazol-1-yl)ethyl)-$N^1$-phenyl-4-(1H-pyrazol-5-yl)benzene-1,3-diamine | SS20308-0189-01 | 0.17; 0.28 | 0.08; 0.15 | 0.36; 0.38 |
| 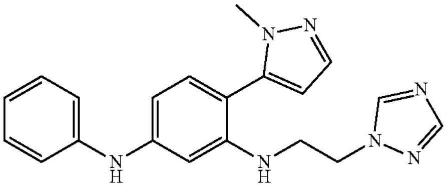 [SMILES: Cn1nccc1-c1ccc(Nc2ccccc2)cc1NCCn1cncn1] | $N^3$-(2-(1H-1,2,4-triazol-1-yl)ethyl)-4-(1-methyl-1H-pyrazol-5-yl)-$N^1$-phenylbenzene-1,3-diamine | SS20308-0190-01 | 1.35 | 0.93 | 5.58 |
| 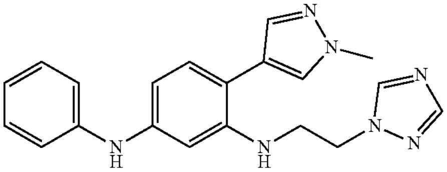 [SMILES: Cn1cc(-c2ccc(Nc3ccccc3)cc2NCCn2cncn2)cn1] | $N^3$-(2-(1H-1,2,4-triazol-1-yl)ethyl)-4-(1-methyl-1H-pyrazol-4-yl)-$N^1$-phenylbenzene-1,3-diamine | SS20308-0191-01 | 4.18 | 1.96 | 4.08 |
| 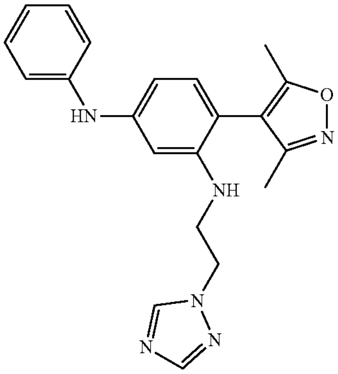 [SMILES: Cc1noc(C)c1-c1ccc(Nc2ccccc2)cc1NCCn1cncn1] | $N^3$-(2-(1H-1,2,4-triazol-1-yl)ethyl)-4-(3,5-dimethylisoxazol-4-$N^1$-phenylbenzene-1,3-diamine | SS20308-0192-01 | 0.83 | 0.59 | 3.76 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 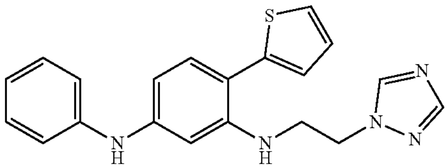 [SMILES: c1ccc(Nc2ccc(-c3cccs3)c(NCCn3cncn3)c2)cc1] | $N^3$-(2-(1H-1,2,4-triazol-1-yl)ethyl)-$N^1$-phenyl-4-(thiophen-2-yl)benzene-1,3-diamine | SS20308-0193-01 | 0.28 | 0.14 | 0.41 |
| 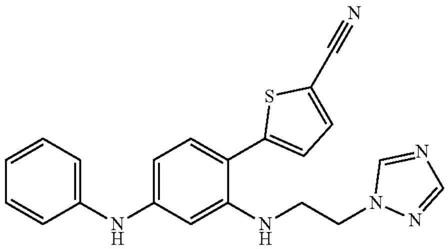 [SMILES: N#Cc1ccc(-c2ccc(Nc3ccccc3)cc2NCCn2cncn2)s1] | 5-(2-((2-(1H-1,2,4-triazol-1-yl)ethyl)amino)-4-(phenylamino) phenyl)thiophene-2-carbonitrile | SS20308-0194-01 | 0.19 | 0.13 | 0.17 |
| 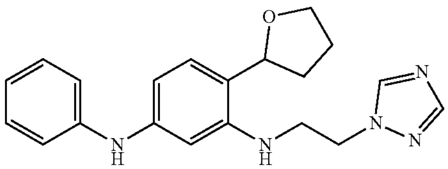 [SMILES: c1ccc(Nc2ccc(C3CCCO3)c(NCCn3cncn3)c2)cc1] | $N^3$-(2-(1H-1,2,4-triazol-1-yl)ethyl)-$N^1$-phenyl-4-(tetrahydrofuran-2-yl)benzene-1,3-diamine | SS20308-0195-01 | 0.76 | 0.36 | 1.1 |
| 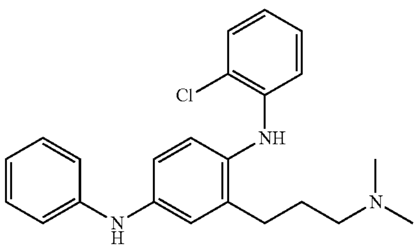 [SMILES: CN(C)CCCc1cc(Nc2ccccc2)ccc1Nc1ccccc1Cl] | $N^1$-(2-chlorophenyl)-2-(3-(dimethylamino) propyl)-$N^4$-phenylbenzene-1,4-diamine | SS20308-0197-01 | 0.16; 0.36 | 0.12; 0.13 | 0.09; 0.17 |
| 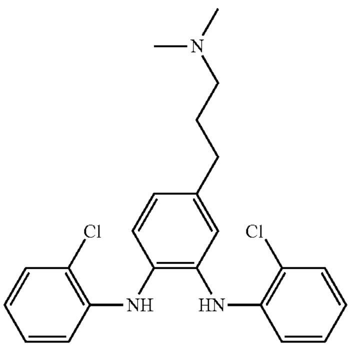 [SMILES: CN(C)CCCc1ccc(Nc2ccccc2Cl)c(Nc2ccccc2Cl)c1] | $N^1$,$N^2$-bis(2-chlorophenyl)-4-(3-(dimethylamino) propyl)benzene-1,2-diamine | SS20308-0198-01 | 0.25 | 0.32 | 0.71 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 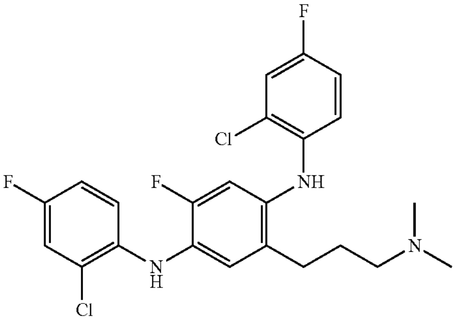 [SMILES: CN(C)CCCc1cc(Nc2ccc(F)cc2Cl)c(F)cc1Nc1ccc(F)cc1Cl] | 4-(2-chloro-4-fluorobenzyl)-N-(2-chloro-4-fluorophenyl)-5-(3-(dimethylamino) propyl)-2-fluoroaniline | SS20308-0199-01 | 0.68 | 0.51 | 0.43 |
| 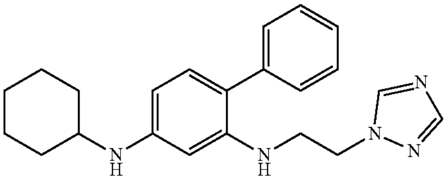 [SMILES: c1ccc(-c2ccc(NC3CCCCC3)cc2NCCn2cncn2)cc1] | $N^2$-(2-(1H-1,2,4-triazol-1-yl)ethyl)-$N^4$-cyclohexyl-[1,1'-biphenyl]-2,4-diamine | SS20308-0200-01 | 0.4 | 0.17 | 0.54 |
| 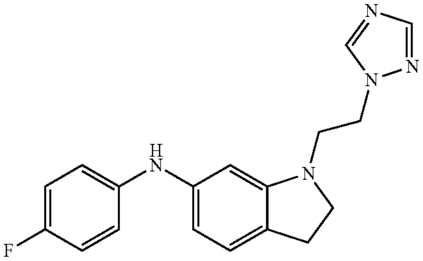 [SMILES: Fc1ccc(Nc2ccc3c(c2)N(CCn2cncn2)CC3)cc1] | 1-(2-(1H-1,2,4-triazol-1-yl)ethyl)-N-(4-fluorophenyl) indolin-6-amine | SS20308-0201-01 | 0.19 | 0.05 | 0.37 |
| 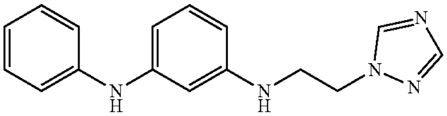 [SMILES: c1ccc(Nc2cccc(NCCn3cncn3)c2)cc1] | $N^1$-(2-(1H-1,2,4-triazol-1-yl)ethyl)-$N^3$-phenylbenzene-1,3-diamine | SS20308-0223-01 | 0.49 | 0.11 | 0.46 |
| 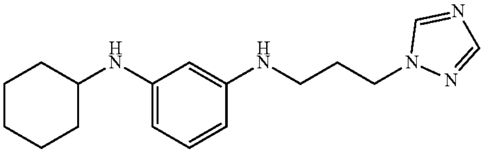 [SMILES: c1cc(NCCCn2cncn2)cc(NC2CCCCC2)c1] | $N^1$-(3-(1H-1,2,4-triazol-1-yl)propyl)-$N^3$-cyclohexyl-benzene-1,3-diamine | SS20308-0238-01 | 0.4 | 0.17 | 3.48 |
| 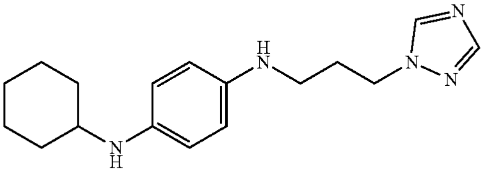 [SMILES: c1ncn(CCCNc2ccc(NC3CCCCC3)cc2)n1] | $N^1$-(3-(1H-1,2,4-triazol-1-yl)propyl)-$N^4$-cyclohexyl-benzene-1,4-diamine | SS20308-0239-01 | 0.04; 0.07 | 0.03 | 0.15 |
| 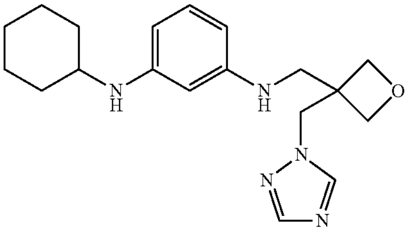 [SMILES: c1cc(NCC2(Cn3cncn3)COC2)cc(NC2CCCCC2)c1] | $N^1$-((3-((1H-1,2,4-triazol-1-yl)methyl)oxetan-3-yl)methyl)-$N^3$-cyclohexylbenzene-1,3-diamine | SS20308-0241-01 | 1.09 | 0.36 | 7.07 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 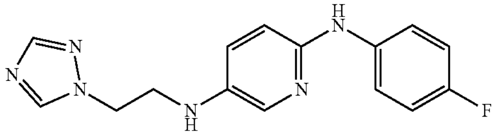 [SMILES: Fc1ccc(Nc2ccc(NCCn3cncn3)cn2)cc1] | $N^5$-(2-(1H-1,2,4-triazol-1-yl)ethyl)-$N^2$-(4-fluorophenyl) pyridine-2,5-diamine | SS20308-0248-01 | 0.63 | 0.1 | 1.17 |
| 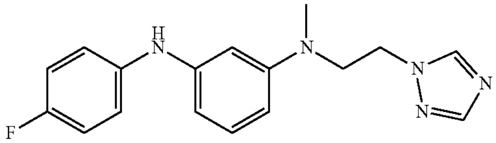 [SMILES: CN(CCn1cncn1)c1cccc(Nc2ccc(F)cc2)c1] | $N^1$-(2-(1H-1,2,4-triazol-1-yl)ethyl)-$N^3$-(4-fluorophenyl)-N1-methylbenzene-1,3-diamine | SS20308-0252-01 | 1.09 | 0.26 | 2.49 |
| 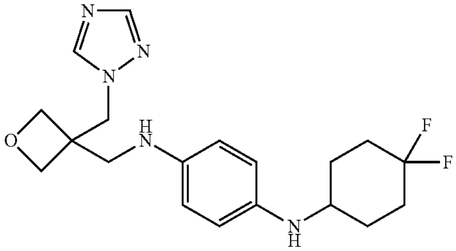 [SMILES: FC1(F)CCC(Nc2ccc(NCC3(Cn4cncn4)COC3)cc2)CC1] | N-((3-((1H-1,2,4-triazol-1-yl)methyl)oxetan-3-yl)methyl)-4-((4,4-difluorocyclohexyl) methyl)aniline | SS20308-0263-01 | 0.22; 0.12 | 0.06; 0.03 | 0.38; 0.6 |
| 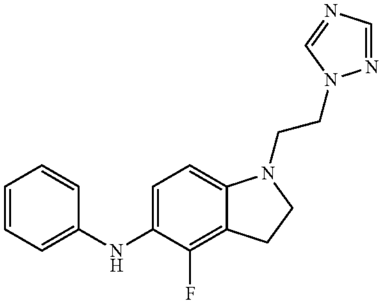 [SMILES: Fc1c(Nc2ccccc2)ccc2c1CCN2CCn1cncn1] | 1-(2-(1H-1,2,4-triazol-1-yl)ethyl)-4-fluoro-N-phenylindolin-5-amine | SS20308-0264-01 | 0.27 | 0.05 | 0.19 |
| 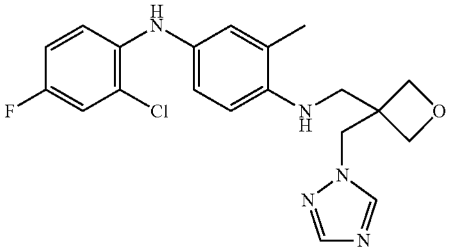 [SMILES: Cc1cc(Nc2ccc(F)cc2Cl)ccc1NCC1(Cn2cncn2)COC1] | $N^1$-((3-((1H-1,2,4-triazol-1-yl)methyl)oxetan-3-yl)methyl)-$N^4$-(2-chloro-4-fluorophenyl)-2-methylbenzene-1,4-diamine | SS20308-0272-01 | 0.22; 0.28; 0.11; 0.26 | 0.03; 0.08; 0.06; 0.06 | 0.15; 0.25; 0.29; 0.23 |
| 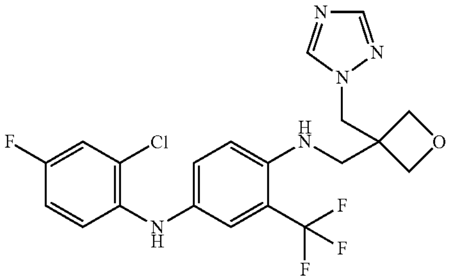 [SMILES: Fc1ccc(Nc2ccc(NCC3(Cn4cncn4)COC3)c(C(F)(F)F)c2)c(Cl)c1] | $N^1$-((3-((1H-1,2,4-triazol-1-yl)methyl)oxetan-3-yl)methyl)-$N^4$-(2-chloro-4-fluorophenyl)-2-(trifluoromethyl) benzene-1,4-diamine | SS20308-0279-01 | 0.64 | 0.28 | 0.7 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 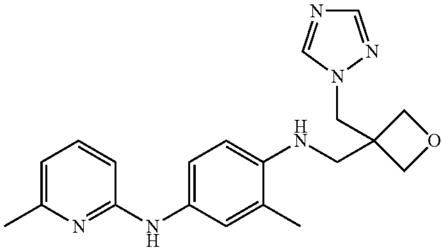 [SMILES: Cc1cccc(Nc2ccc(NCC3(Cn4cncn4)COC3)c(C)c2)n1] | $N^1$-((3-((1H-1,2,4-triazol-1-yl)methyl)oxetan-3-yl)methyl)-2-methyl-$N^4$-(6-methylpyridin-2-yl)benzene-1,4-diamine | SS20308-0289-01 | 0.25; 0.61 | 0.07; 0.15 | 1.13; 1.49 |
| 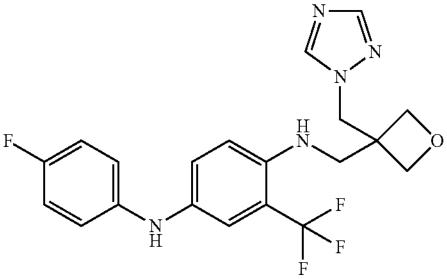 [SMILES: Fc1ccc(Nc2ccc(NCC3(Cn4cncn4)COC3)c(C(F)(F)F)c2)cc1] | $N^1$-((3-((1H-1,2,4-triazol-1-yl)methyl)oxetan-3-yl)methyl)-$N^4$-(4-fluorophenyl)-2-(trifluoromethyl) benzene-1,4-diamine | SS20308-0296-01 | 0.08 | 0.06 | 0.08 |
| 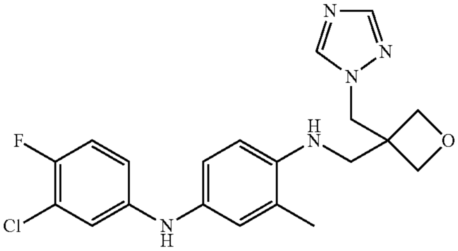 [SMILES: Cc1cc(Nc2ccc(F)c(Cl)c2)ccc1NCC1(Cn2cncn2)COC1] | $N^1$-((3-((1H-1,2,4-triazol-1-yl)methyl)oxetan-3-yl)methyl)-$N^4$-(3-chloro-4-fluorophenyl)-2-methylbenzene-1,4-diamine | SS20308-0307-01 | 0.05; 0.06 | 0.02; 0.06 | 0.13; 0.2 |
| 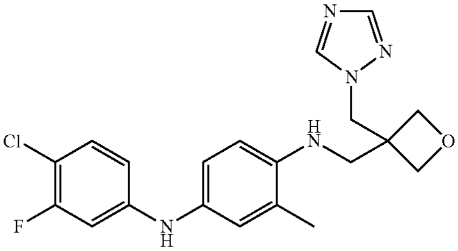 [SMILES: Cc1cc(Nc2ccc(Cl)c(F)c2)ccc1NCC1(Cn2cncn2)COC1] | $N^1$-((3-((1H-1,2,4-triazol-1-yl)methyl)oxetan-3-yl)methyl)-$N^4$-(4-chloro-3-fluorophenyl)-2-methylbenzene-1,4-diamine | SS20308-0308-01 | 0.04; 0.03; 0.05; 0.09 | 0.02; 0.02; 0.05; 0.06 | 0.16; 0.13; 0.11; 0.39 |
| 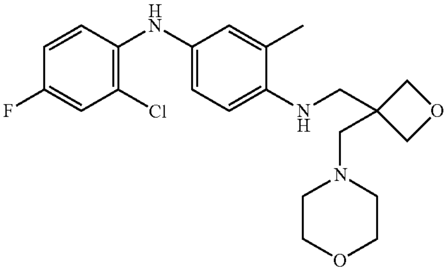 [SMILES: Cc1cc(Nc2ccc(F)cc2Cl)ccc1NCC1(CN2CCOCC2)COC1] | $N^4$-(2-chloro-4-fluorophenyl)-2-methyl-$N^1$-((3-(morpholinomethyl) oxetan-3-yl)methyl)benzene-1,4-diamine | SS20308-0309-01 | 0.09; 0.12 | 0.04; 0.08 | 0.41; 0.37 |

TABLE 1-continued

| IC50 (μM) values for in vitro lipoxygenase inhibition | | | | | |
|---|---|---|---|---|---|
| Structure | Name | SPII-SRI Compound Code | 5-LOX | 12-LOX | 15-LOX |
| 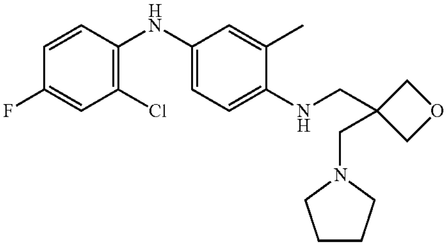 [SMILES: Cc1cc(Nc2ccc(F)cc2Cl)ccc1NCC1(CN2CCCC2)COC1] | $N^4$-(2-chloro-4-fluorophenyl)-2-methyl-$N^1$-((3-(pyrrolidin-1-ylmethyl)oxetan-3-yl)methyl)benzene-1,4-diamine | SS20308-0310-01 | 0.11; 0.14; 0.1; 0.19; 0.29 | 0.08; 0.05; 0.05; 0.7; 0.14 | 0.32; 0.42; 0.19; 0.22; 0.42 |
| 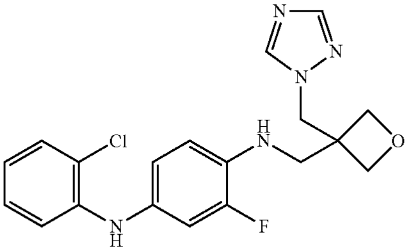 [SMILES: Fc1cc(Nc2ccccc2Cl)ccc1NCC1(Cn2cncn2)COC1] | $N^1$-((3-((1H-1,2,4-triazol-1-yl)methyl)oxetan-3-yl)methyl)-$N^4$-(2-chlorophenyl)-2-fluorobenzene-1,4-diamine | SS20308-0313-01 | 0.35 | 0.11 | 0.5 |
| 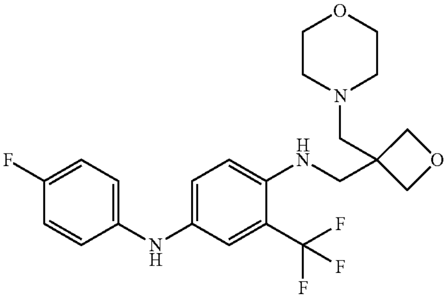 [SMILES: Fc1ccc(Nc2ccc(NCC3(CN4CCOCC4)COC3)c(C(F)(F)F)c2)cc1] | $N^4$-(4-fluorophenyl)-$N^1$-((3-(morpholinomethyl) oxetan-3-yl)methyl)-2-(trifluoromethyl) benzene-1,4-diamine | SS20308-0314-01 | 0.06 | 0.04 | 0.10 |
| 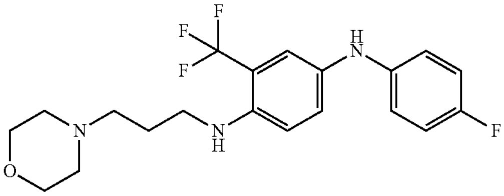 [SMILES: Fc1ccc(Nc2ccc(NCCCN3CCOCC3)c(C(F)(F)F)c2)cc1] | $N^4$-(4-fluorophenyl)-$N^1$-(3-morpholinopropyl)-2-(trifluoromethyl) benzene-1,4-diamine | SS20308-0316-01 | 0.07 | 0.03 | 0.06 |
| 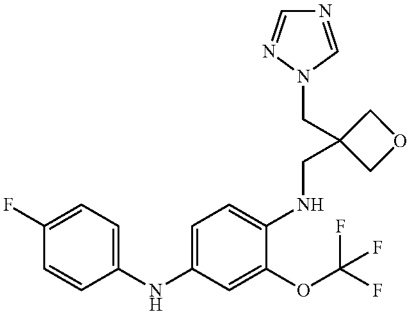 [SMILES: Fc1ccc(Nc2ccc(NCC3(Cn4cncn4)COC3)c(OC(F)(F)F)c2)cc1] | $N^1$-((3-((1H-1,2,4-triazol-1-yl)methyl)oxetan-3-yl)methyl)-$N^4$-(4-fluorophenyl)-2-(trifluoromethoxy) benzene-1,4-diamine | SS20308-0319-01 | 0.15 | 0.05 | 0.13 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 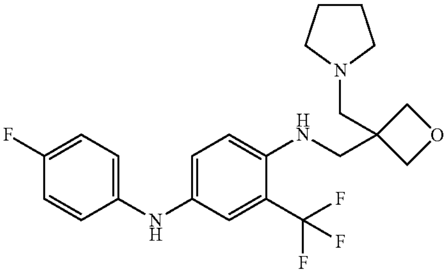 [SMILES: Fc1ccc(Nc2ccc(NCC3(CN4CCCC4)COC3)c(C(F)(F)F)c2)cc1] | $N^4$-(4-fluorophenyl)-$N^1$-((3-(pyrrolidin-1-ylmethyl)oxetan-3-yl)methyl)-2-(trifluoromethyl) benzene-1,4-diamine | SS20308-0320-01 | 0.06 | 0.08 | 0.08 |
| 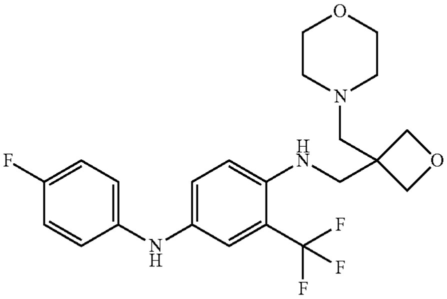 [SMILES: Fc1ccc(Nc2ccc(NCC3(CN4CCOCC4)COC3)c(C(F)(F)F)c2)cc1] | $N^4$-(4-fluorophenyl)-$N^1$-((3-(morpholinomethyl) oxetan-3-yl)methyl)-2-(trifluoromethyl) benzene-1,4-diamine | SS20308-0321-01 | 0.08 | 0.06 | 0.09 |
| 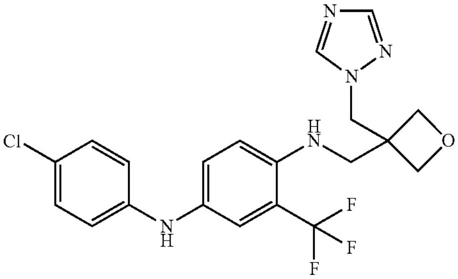 [SMILES: FC(F)(F)c1cc(Nc2ccc(Cl)cc2)ccc1NCC1(Cn2cncn2)COC1] | $N^1$-((3-((1H-1,2,4-triazol-1-yl)methyl)oxetan-3-yl)methyl)-$N^4$-(4-chlorophenyl)-2-(trifluoromethyl) benzene-1,4-diamine | SS20308-0322-01 | 0.05 | 0.05 | 0.08 |
| 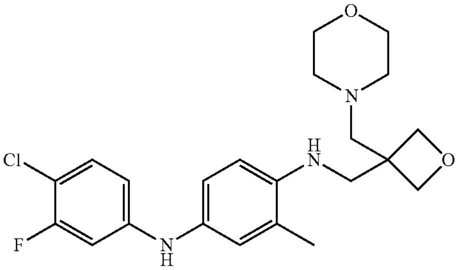 [SMILES: Cc1cc(Nc2ccc(Cl)c(F)c2)ccc1NCC1(CN2CCOCC2)COC1] | $N^4$-(4-chloro-3-fluorophenyl)-2-methyl-$N^1$-((3-(morpholinomethyl) oxetan-3-yl)methyl)benzene-1,4-diamine | SS20308-0323-01 | 0.05 | 0.02 | 0.07 |
| 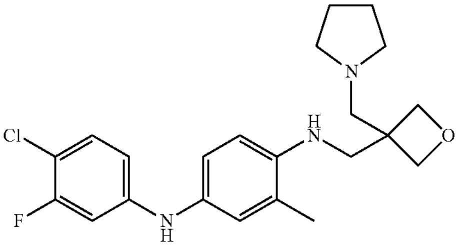 [SMILES: Cc1cc(Nc2ccc(Cl)c(F)c2)ccc1NCC1(CN2CCCC2)COC1] | $N^4$-(4-chloro-3-fluorophenyl)-2-methyl-$N^1$-((3-(pyrrolidin-1-ylmethyl)oxetan-3-yl)methyl)benzene-1,4-diamine | SS20308-0324-01 | 0.15; 0.44 | 0.03; 0.03 | 0.16; 0.08 |

TABLE 1-continued

IC50 (μM) values for in vitro lipoxygenase inhibition

| Structure | Name | SPII-SRI Compound Code | 5-LOX | 12-LOX | 15-LOX |
|---|---|---|---|---|---|
| 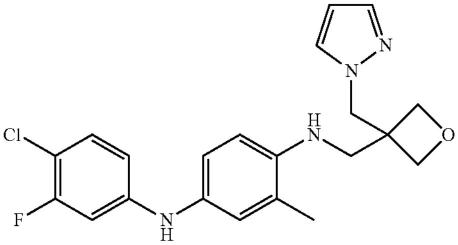 [SMILES: Cc1cc(Nc2ccc(Cl)c(F)c2)ccc1NCC1(Cn2cccn2)COC1] | $N^1$-((3-((1H-pyrazol-1-yl)methyl)oxetan-3-yl)methyl)-$N^4$-(4-chloro-3-fluorophenyl)-2-methylbenzene-1,4-diamine | SS20308-0327-01 | 0.07 | 0.04 | 0.14 |
| 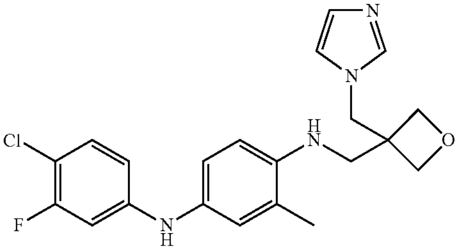 [SMILES: Cc1cc(Nc2ccc(Cl)c(F)c2)ccc1NCC1(Cn2ccnc2)COC1] | $N^1$-((3-(1H-imidazol-1-yl)methyl)oxetan-3-yl)methyl)-$N^4$-(4-chloro-3-fluorophenyl)-2-methylbenzene-1,4-diamine | SS20308-0328-01 | 0.04 | 0.03 | 0.07 |

General Information Examples: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in 6 values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

Example 1

SS20308-0025-01

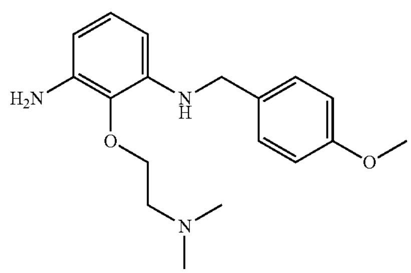

Chemical Formula: $C_{18}H_{25}N_3O_2$
Molecular Weight: 315.41

Example Route for Example 1

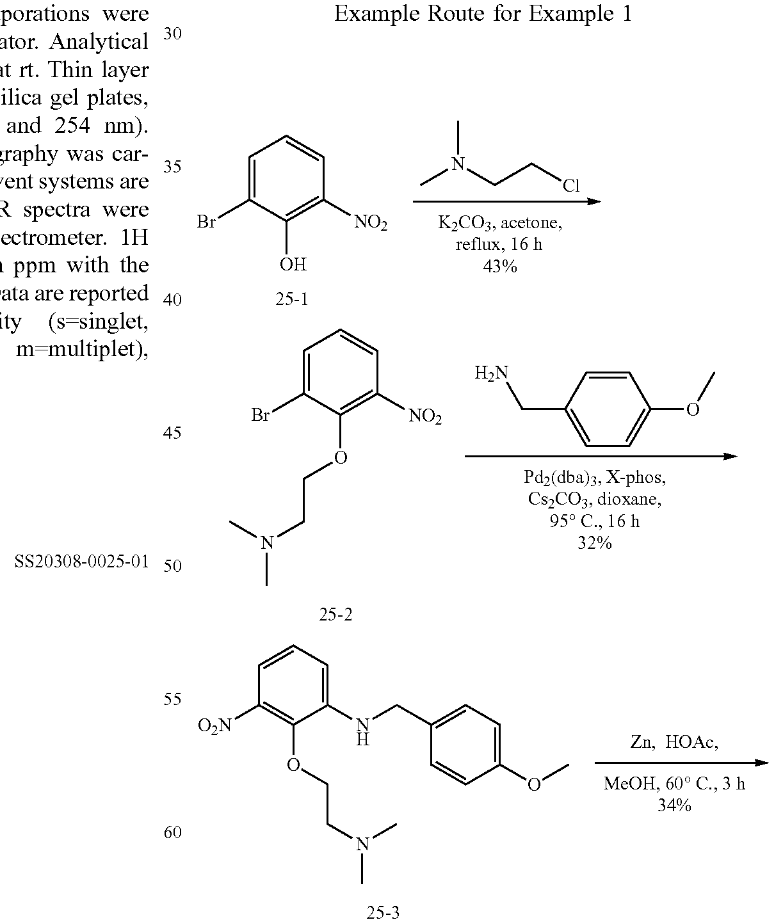

25-1

25-2

25-3

-continued

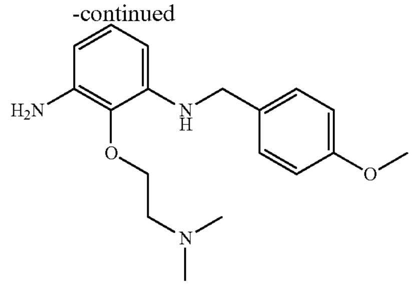

SS20308-0025-01

The Synthesis of 2-(2-bromo-6-nitrophenoxy)-N,N-dimethylethanamine (25-1)

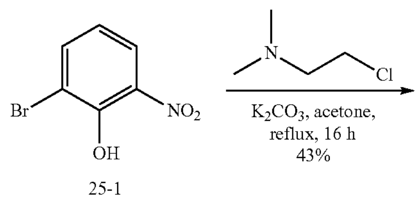

25-1

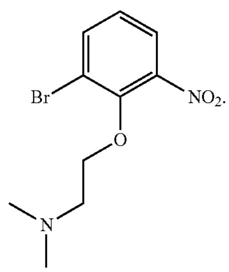

25-2

A mixture of 25-1 (4.0 g, 18.4 mmol), 2-chloro-N,N-dimethylethanamine hydrochloride (5.3 g, 36.8 mmol) and $K_2CO_3$ (7.6 g, 55.2 mmol) in acetone (50 mL) was heated to reflux for 16 h. The mixture was diluted with EtOAc (150 mL). The organic layer was successively washed with water (100 mL), saturated bicarbonate solution (100 mL), and brine (100 mL). The organic layer was then dried with $MgSO_4$ and concentrated under reduced pressure. The crude product was purified by column chromatography on silica gel (petroleum ether/EtOAc=1/4) to give 25-2 (2.3 g, 43% yield) as an oil. MS Calcd.: 288.0; MS Found: 289.1 $[M+H]^+$.

The Synthesis of 2-(2-(dimethylamino)ethoxy)-N-(4-methoxybenzyl)-3-nitroaniline (25-3)

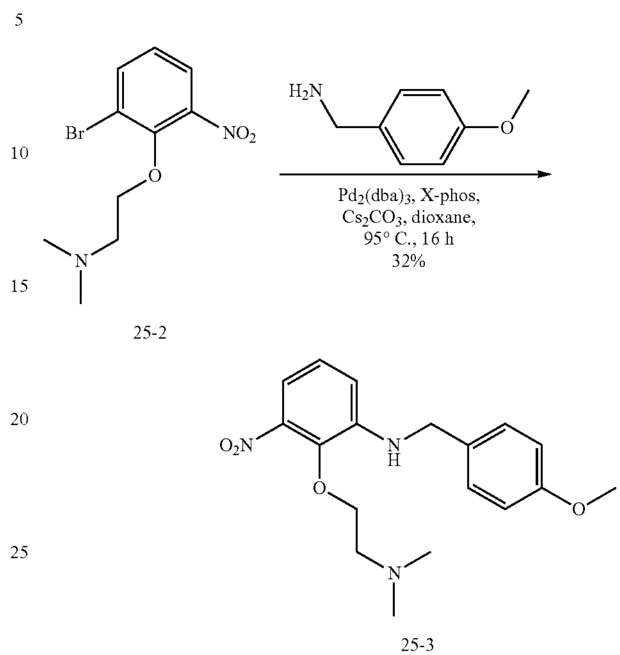

25-2

25-3

A mixture of 25-2 (600 mg, 2.1 mmol), (4-methoxyphenyl)methanamine (288 mg, 2.1 mmol), $Pd_2(dba)_3$ (183 mg, 0.2 mmol), X-phos (173 mg, 0.3 mmol) and $Cs_2CO_3$ (1.4 g, 4.2 mmol) in dioxane (20 mL) was stirred at 95° C. for 16 h under nitrogen. The reaction mixture was cooled to room temperature, and then the mixture was filtered and washed with EtOAc (50 mL). The organic phase was successively washed with water (50 mL) and brine (50 mL). The ethyl acetate layer was dried with $MgSO_4$ and concentrated under reduced pressure. The crude product was purified by column chromatography on silica gel (petroleum ether/EtOAc=1/5) to give 25-3 (230 mg, about 32% yield) as a solid. MS Calcd.: 345.2; MS Found: 346.3 $[M+H]^+$.

The Synthesis of 2-(2-(dimethylamino)ethoxy)-N1-(4-methoxybenzyl)benzene-1,3-diamine (SS20308-0025-01)

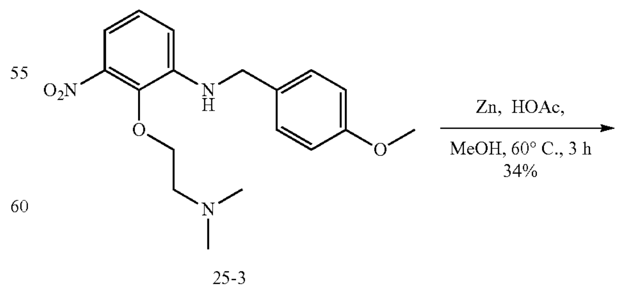

25-3

-continued

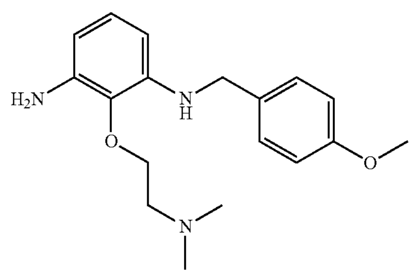

SS20308-0025-01

A mixture of 25-3 (200 mg, 0.6 mmol), Zn powder (195 mg, 3.0 mmol) in HOAc (0.1 mL) and MeOH (10 mL) was stirred at 60° C. for 3 h. The reaction mixture was cooled to room temperature, and then the mixture was filtered and washed with MeOH (20 mL). The organic phase was concentrated under reduced pressure. The crude product was purified by Prep-HPLC to give SS20308-0025-01 (62 mg, about 34% yield) as a solid.

$^1$H NMR (400 MHz, $CDCl_3$) δ 7.30 (d, J=8.4 Hz, 2H), 6.87 (d, J=8.8 Hz, 2H), 6.77 (dd, J=8.0, 8.0 Hz, 1H), 6.12 (dd, J=8.0, 1.2 Hz, 1H), 6.08 (d, J=8.4 Hz, 1H), 4.24 (s, 2H), 3.93 (t, J=5.0 Hz, 2H), 3.80 (s, 3H), 2.55 (t, J=5.0 Hz, 2H), 2.17 (s, 6H).

Example 2

SS23008-0052-01

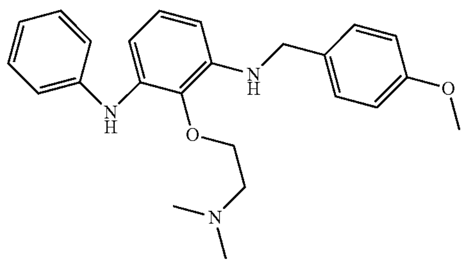

Chemical Formula: $C_{24}H_{29}N_3O_2$
Molecular Weight: 391.51

Example Route for Example 2

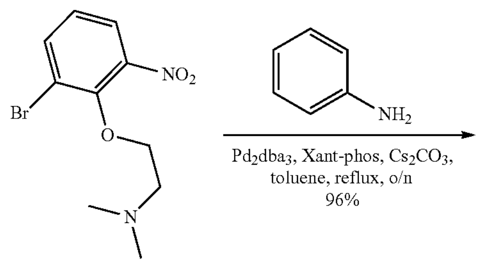

52-1

-continued

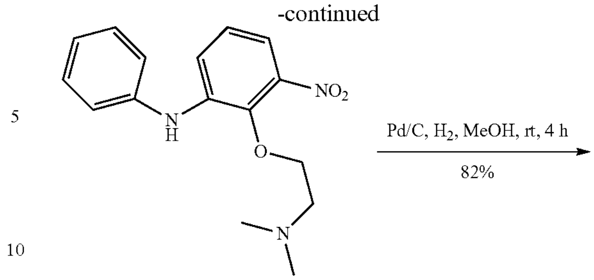

52-2

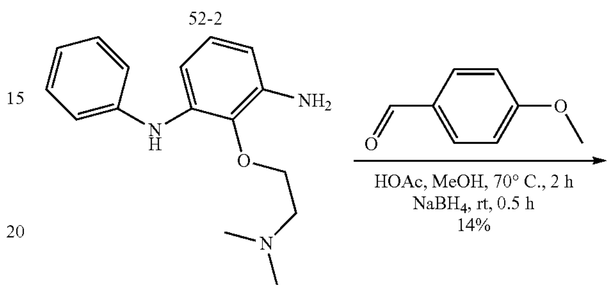

52-3

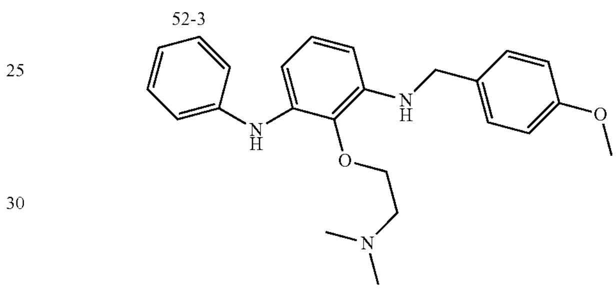

SS23008-0052-01

The Synthesis of 2-(2-(dimethylamino)ethoxy)-3-nitro-N-phenylaniline (52-2)

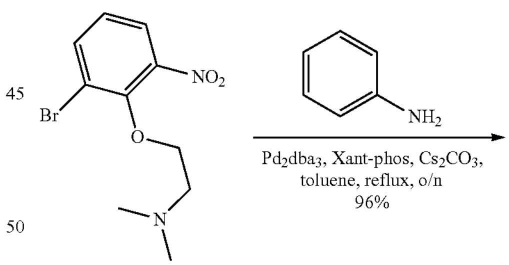

52-1

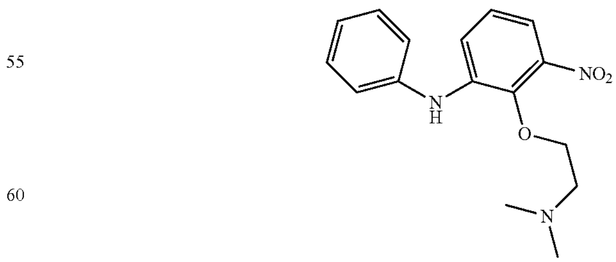

52-2

A mixture of 52-1 (500 mg, 1.73 mmol), aniline (322 mg, 3.46 mmol), $Pd_2dba_3$ (79 mg, 0.09 mmol), Xant-Phos (98 mg, 0.17 mmol) and $Cs_2CO_3$ (845 mg, 2.56 mmol) in toluene (25 mL) was heated to reflux under nitrogen atmosphere overnight. After being cooled to room temperature, the mixture was filtered. The filtrate was concentrated and the residue was purified by column chromatography (petroleum ether/EtOAc=8/1) to give 52-2 (500 mg, 96% yield) as a solid. MS Calcd.: 301.1; MS Found: 302.4 $[M+H]^+$.

The Synthesis of 2-(2-(dimethylamino)ethoxy)-$N^1$-phenylbenzene-1,3-diamine (52-3)

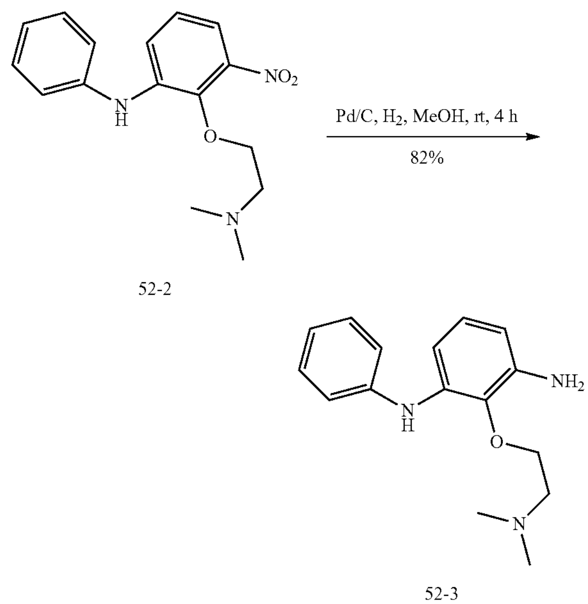

52-2

52-3

To a solution of 52-2 (500 mg, 1.66 mmol) in MeOH (20 mL) was Pd/C (10%, 50 mg). The mixture was stirred under nitrogen atmosphere at room temperature for 4 h. Then the reaction mixture was filtered. The filtrate was concentrated to give 52-3 (370 mg, about 82% yield) as an oil. MS Calcd.: 271.2; MS Found: 272.4 $[M+H]^+$.

The Synthesis of 2-(2-(dimethylamino)ethoxy)-$N^1$-(4-methoxybenzyl)-$N^3$-phenylbenzene-1,3-diamine (SS20308-0052-01)

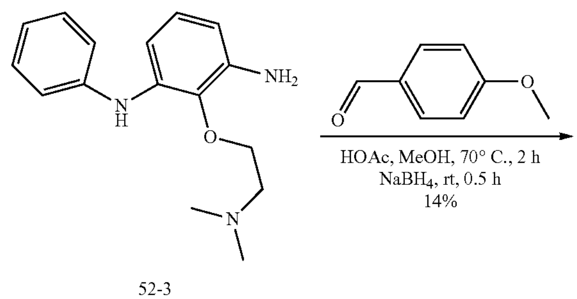

52-3

-continued

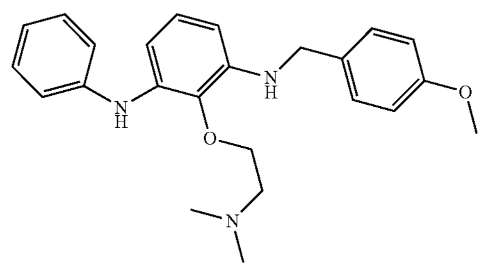

SS23008-0052-01

A mixture of 52-3 (290 mg, 1.07 mmol) and p-methoxybenzaldehyde (146 mg, 1.07 mmol) in HOAc (1 mL) and MeOH (20 mL) was stirred at 70° C. for 2 h. After cooled to room temperature, $NaBH_4$ (40 mg, 1.07 mmol) was added and the mixture was stirred at room temperature for 0.5 h. Then the mixture was poured into water and basified with 1N NaOH till pH reached 9. The mixture was then extracted with EtOAc (3×30 mL). The combined organic layers were washed with water and brine, dried over $Na_2SO_4$ and concentrated. The residue was purified by Prep-HPLC to give SS2308-0052-01 (60 mg, about 14% yield) as a solid. MS Calcd.: 391.2; MS Found: 392.2 $[M+H]^+$.

$^1H$ NMR (400 MHz, DMSO-$d_6$) δ 8.01 (s, 1H), 7.26 (d, J=8.8 Hz, 2H), 7.16 (dd, J=8.4, 7.2 Hz, 2H), 6.98 (d, J=7.6 Hz, 2H), 6.87 (d, J=8.8 Hz, 2H), 6.74 (dd, J=7.6, 7.2 Hz, 1H), 6.69 (t, J=8.4 Hz, 1H), 6.45 (dd, J=8.0, 0.8 Hz, 1H), 6.12-6.05 (m, 2H), 4.21 (d, J=6.0 Hz, 2H), 3.87 (t, J=4.8 Hz, 2H), 3.70 (s, 3H), 2.14 (s, 6H).

Example 3

SS20308-0053-01

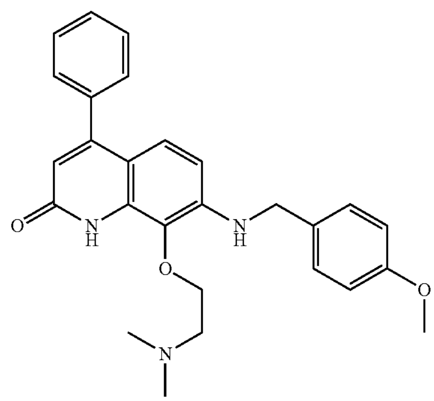

Chemical Formula: $C_{27}H_{29}N_3O_3$
Molecular Weight: 443.54

Example Route for Example 3

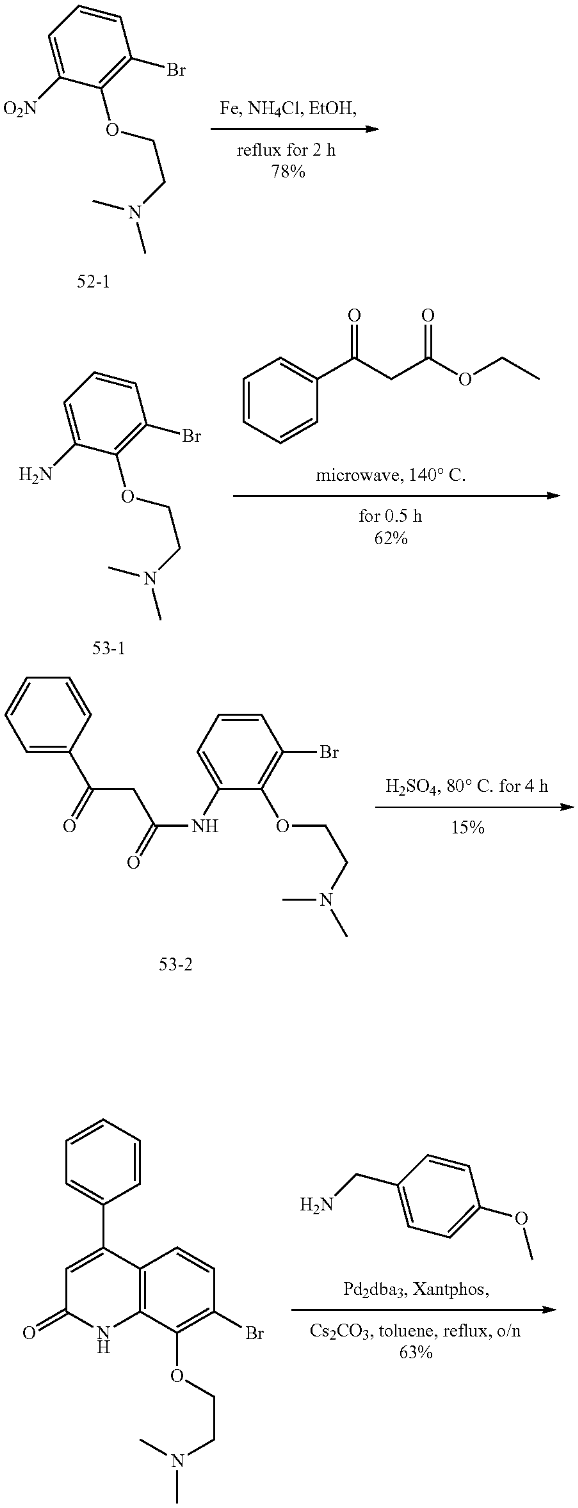

52-1

53-1

53-2

53-3

-continued

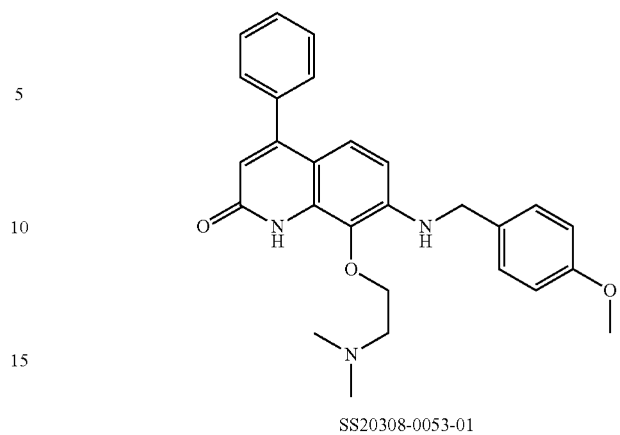

SS20308-0053-01

The Synthesis of 3-bromo-2-(2-(dimethylamino) ethoxy)aniline (53-1)

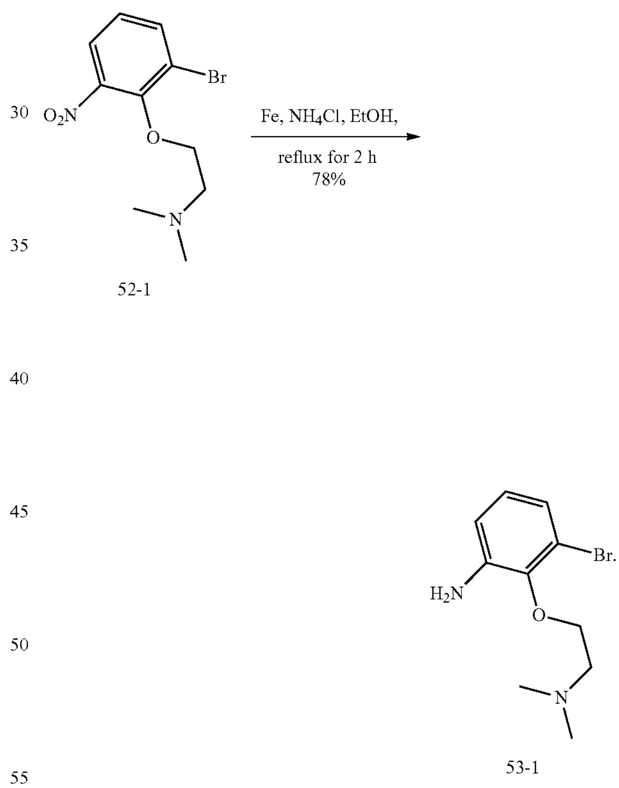

52-1

53-1

A mixture of 52-1 (1.0 g, 3.46 mmol), iron powder (1.9 g, 34.59 mmol) and $NH_4Cl$ (93 mg, 1.74 mmol) in ethanol (16 mL) and water (4 mL) was stirred at 85° C. for 2 h. Then the reaction mixture was filtered through celite. The filtrate was basified with NaOH solution until the pH value reached 10.0-11.0 and extracted with DCM (20 mL×3). The combined organic layers were washed with brine (10 mL×2), dried over sodium sulfate, and concentrated to give 53-1 (0.7 g, about 78% yield) as a solid. MS Calcd.: 258.0; MS Found: 259.2 $[M+H]^+$.

The Synthesis of N-(3-bromo-2-(2-(dimethylamino)ethoxy)phenyl)-3-oxo-3-phenylpropanamide (53-2)

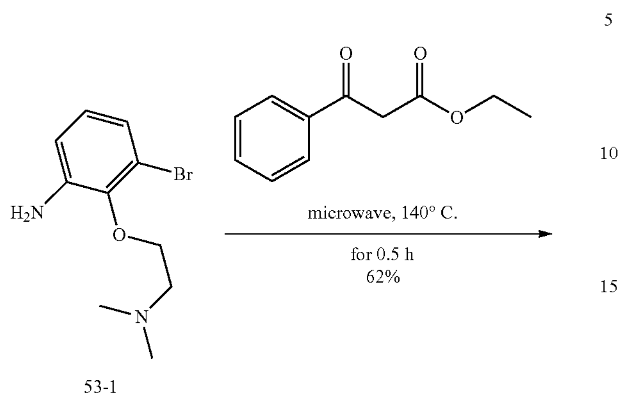

53-1

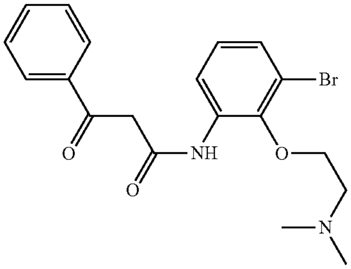

53-2

A mixture of 53-1 (410 mg, 1.58 mmol) and ethyl benzoylacetate (760 mg, 3.95 mmol) was stirred and heated to 140° C. for 0.5 h under microwave irradiation and nitrogen atmosphere. The reaction mixture was purified by silica gel column chromatography (petroleum ether/EtOAc=10/1, 5/1, 3/1, 1/1, $CH_2Cl_2$/MeOH=20/1) to give 53-2 (400 mg, about 62% yield) as a solid. MS Calcd.: 404.1; MS Found: 405.3 $[M+H]^+$.

The Synthesis of 7-bromo-8-(2-(dimethylamino)ethoxy)-4-phenylquinolin-2(1H)-one (53-3)

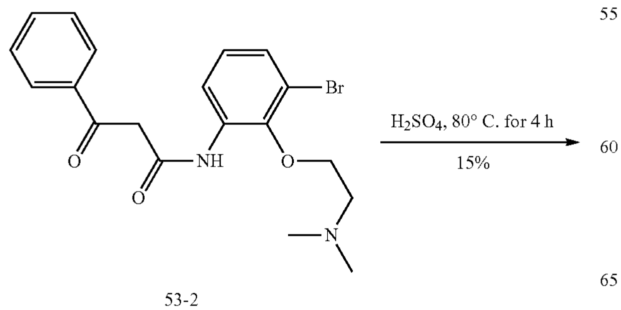

53-2

-continued

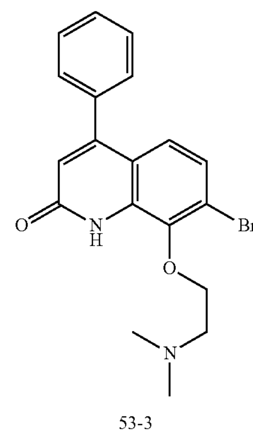

53-3

A mixture of 53-2 (500 mg, 1.23 mmol) in $H_2SO_4$ (5 mL) was stirred and heated to 80° C. for 4 h. The reaction mixture was cooled down to room temperature and poured into ice, basified with NaOH (40%) solution until the pH value reached 9.0-10.0 and extracted with EtOAc (20 mL×3). The combined organic layers were washed with brine (10 mL×2), dried over sodium sulfate, and concentrated to dryness. The residue was purified by Prep-TLC ($CH_2Cl_2$/MeOH=20/1) to give 53-3 (70 mg, about 15% yield) as an oil. MS Calcd.: 386.1; MS Found: 387.2 $[M+H]^+$.

The Synthesis of 8-(2-(dimethylamino)ethoxy)-7-(4-methoxybenzylamino)-4-phenylquinolin-2(1H)-one (SS20308-0053-01)

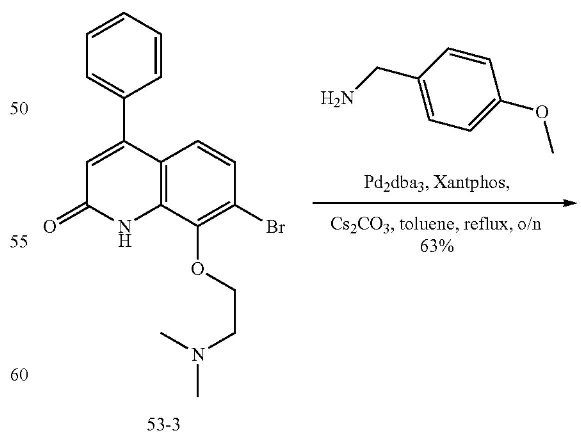

53-3

-continued

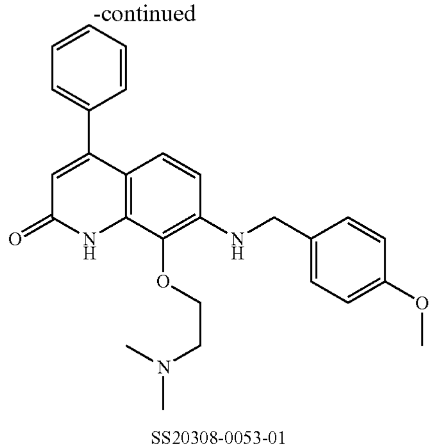

SS20308-0053-01

A solution of 53-3 (85 mg, 0.22 mmol), (4-methoxyphenyl)methanamine (151 mg, 1.1 mmol), Xantphos (13 mg, 0.022 mmol), $Pd_2(dba)_3$ (10 mg, 0.011 mmol), and anhydrous cesium carbonate (108 mg, 0.33 mmol) were suspended in toluene (4 mL). The reaction mixture was heated overnight at reflux under nitrogen atmosphere and then filtered, rinsing with EtOAc. The filtrate was concentrated and purified by Prep-TLC ($CH_2Cl_2$/MeOH=20/1) to give SS20308-0053-01 (61 mg, about 63% yield) as a solid. MS Calcd.: 443.2; MS Found: 444.3 $[M+H]^+$.

$^1H$ NMR (400 MHz, DMSO-$d_6$) δ 12.58 (brs, 1H), 7.51-7.44 (m, 3H), 7.41-7.36 (m, 2H), 7.26 (d, J=8.8 Hz, 2H), 6.88-6.83 (m, 3H), 6.77 (t, J=6.2 Hz, 1H), 6.44 (d, J=9.2 Hz, 1H), 5.97 (d, J=1.6 Hz, 1H), 4.34 (d, J=6.4 Hz, 2H), 4.01-4.09 (m, 2H), 3.70 (s, 3H), 2.66 (t, J=4.2 Hz, 2H), 2.35 (s, 6H).

Example 4

SS20308-0071-01

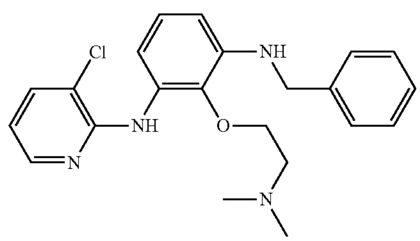

Chemical Formula: $C_{22}H_{25}ClN_4O$
Molecular Weight: 396.91

Example Route for Example 4

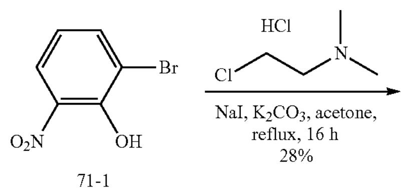

71-1

-continued

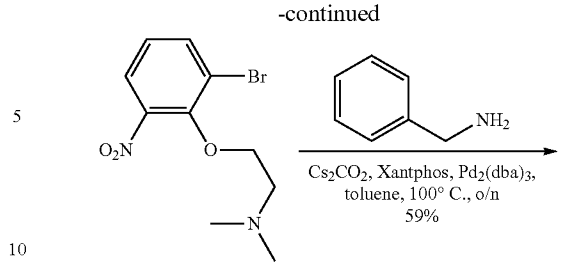

71-2

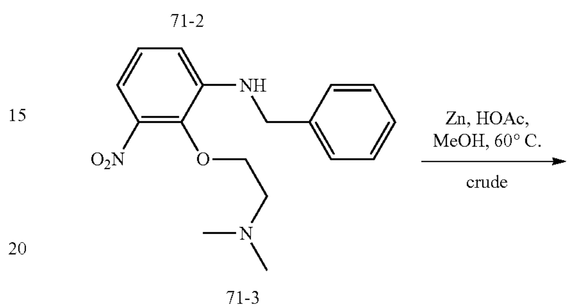

71-3

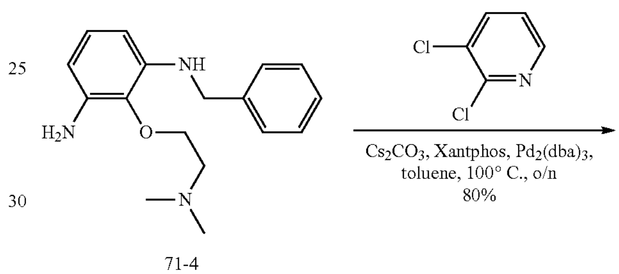

71-4

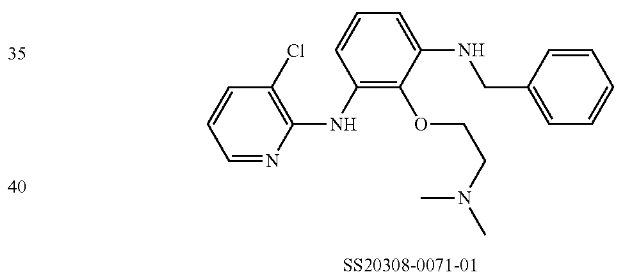

SS20308-0071-01

The Synthesis of 2-(2-bromo-6-nitrophenoxy)-N,N-dimethylethanamine (71-1)

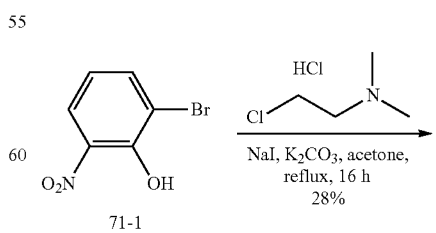

71-1

-continued

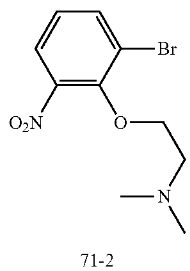

71-2

The mixture of 71-1 (3.0 g, 13.6 mmol), 2-chloro-N,N-dimethylethanamine hydrochloride (2.2 g, 15.0 mmol), $K_2CO_3$ (3.8 g, 27.3 mmol) and NaI (1.0 g, 6.8 mmol) in acetone (25 mL) was stirred at 60° C. for 16 h. The reaction mixture was cooled to room temperature and filtered through celite. The filtrate was diluted with water (50 mL) and then extracted with EtOAc (30 mL×5). The organic layer was washed with brine and concentrated to dryness to give 71-2 (1.1 g, about 28% yield) as an oil. MS Calcd.: 288.0; MS Found: 289.1 [M+H]$^+$.

The Synthesis of N-benzyl-2-(2-(dimethylamino) ethoxy)-3-nitroaniline (71-3)

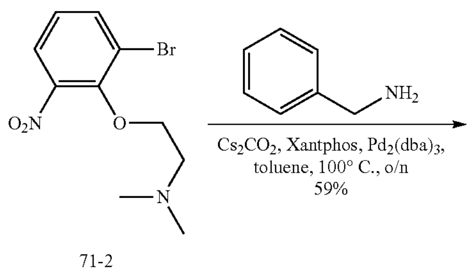

71-2

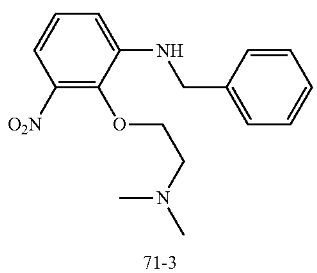

71-3

To a solution of 71-2 (300 mg, 1.0 mmol) in toluene (3 mL) was added benzylamine (111 mg, 1.0 mmol), $Cs_2CO_3$ (696 mg, 2.0 mmol), Xantphos (62 mg, 0.1 mmol) and $Pd_2(dba)_3$ (98 mg, 0.1 mmol), then the reaction mixture was stirred at 100° C. under nitrogen atmosphere overnight. The reaction mixture was cooled to room temperature and filtered through celite then diluted with EtOAc (20 mL). The organic layer was washed with brine and concentrated to dryness. The residue was purified by column chromatography (EtOAc/petroleum ether=1/1~1/0) to give 71-3 (200 mg, about 59% yield) as an oil. MS Calcd.: 315.2; MS Found: 316.3 [M+H]$^+$.

The Synthesis of N[1]-benzyl-2-(2-(dimethylamino) ethoxy)benzene-1,3-diamine (71-4)

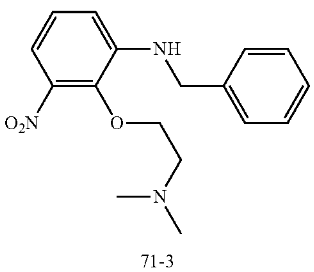

Zn, HOAc,
MeOH, 60° C.
crude 71-3

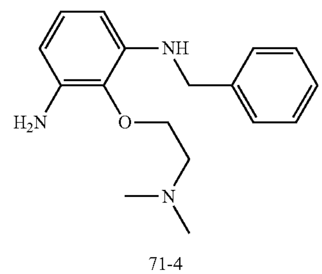

71-4

To a solution of 71-3 (200 mg, 0.63 mmol) in MeOH (6 mL) was added Zn powder (166 mg, 2.5 mmol), and HOAc (152 mg, 2.5 mmol), then the reaction mixture was stirred at 60° C. for 4 h. The mixture was diluted with water and extracted with EtOAc (150 mL). The organic layer was washed with brine and concentrated to dryness to give 71-4 (200 mg, crude) as an oil. MS Calcd.: 285.2; MS Found: 286.2 [M+H]$^+$.

The Synthesis of N[1]-benzyl-N[3]-(3-chloropyridin-2-yl)-2-(2-(dimethylamino)ethoxy)benzene-1,3-diamine (SS20308-0071-01)

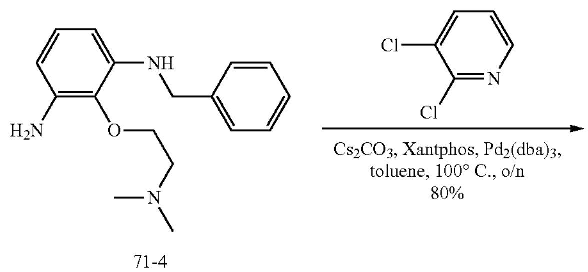

71-4

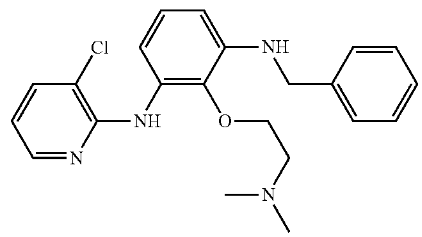

SS20308-0071-01

To a solution of 71-4 (380 mg, 1.33 mmol) in toluene (15 mL) was added 2,3-dichloropyridine (237 mg, 1.60 mmol), $Cs_2CO_3$ (868 mg, 2.66 mmol), Xantphos (77 mg, 0.1 mmol)

and $Pd_2(dba)_3$ (61 mg, 0.13 mmol), then the reaction mixture was stirred at 100° C. under nitrogen atmosphere overnight. The reaction mixture was cooled to room temperature, diluted with water and extracted with EtOAc (10 mL×3). The organic layer was washed with brine and concentrated to dryness. The residue was purified by Prep-TLC (EtOAc) to give SS20308-0071-01 (420 mg, about 80% yield) as an oil. MS Calcd.: 396.2; MS Found: 397.3 $[M+H]^+$.

$^1H$ NMR (400 MHz, $CDCl_3$) δ 8.08 (dd, J=4.8, 1.6 Hz, 1H), 7.69-7.67 (m, 2H), 7.49 (dd, J=7.6, 1.6 Hz, 1H), 7.34-7.32 (m, 2H), 7.28-7.24 (m, 2H), 7.20-7.19 (m, 1H), 6.90 (dd, J=8.4, 8.0 Hz, 1H), 6.61 (dd, J=8.0, 6.4 Hz, 1H), 6.26 (dd, J=8.0, 1.2 Hz, 1H), 5.93 (t, J=5.2 Hz, 1H), 4.28 (d, J=5.6 Hz, 2H), 3.94 (d, J=4.4 Hz, 2H), 2.56 (br, 2H), 2.09 (s, 6H).

Example 5

SS20308-0096-01

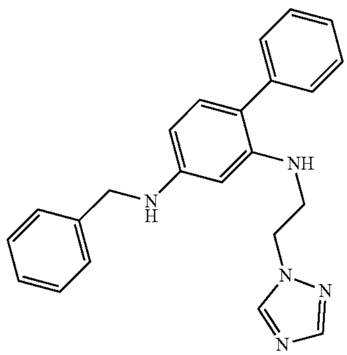

Chemical Formula: $C_{23}H_{23}N_5$
Molecular Weight: 369.46

Example Route for Example 5

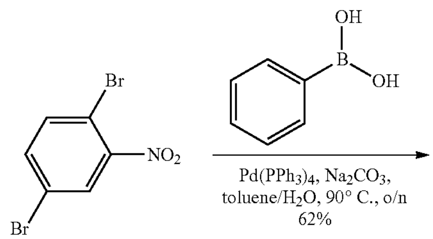

95-1

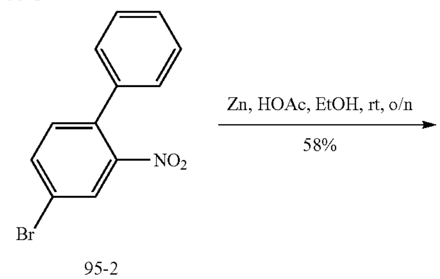

95-2

-continued

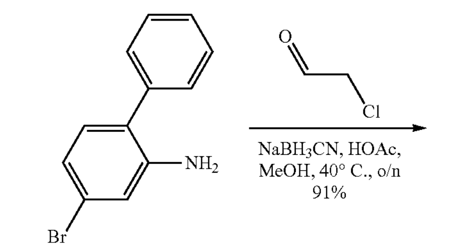

95-3

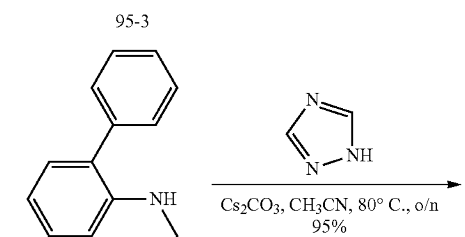

95-4

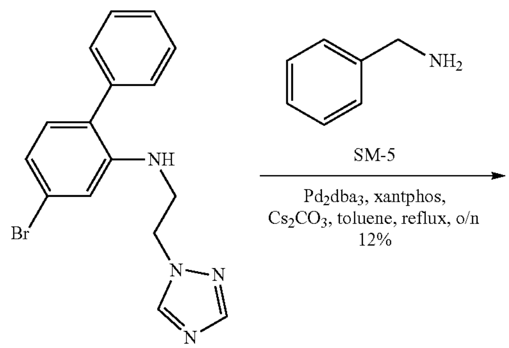

95-5

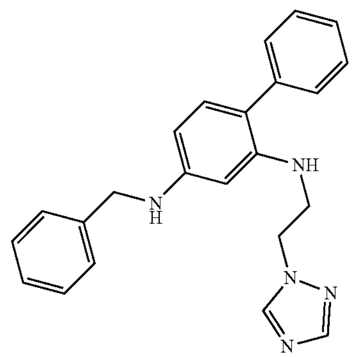

SS20308-0096-01

The Synthesis of 4-bromo-2-nitrobiphenyl (95-2)

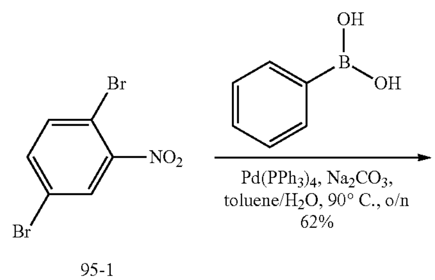

95-1

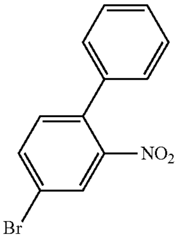

95-2

The mixture of 95-1 (6.00 g, 21.36 mmol), phenylboronic acid (2.60 g, 21.36 mmol), $Pd(PPh_3)_4$ (1.23 g, 1.07 mmol) and $Na_2CO_3$ (7.90 g, 74.76 mmol) in toluene/$H_2O$ (60 mL, 5/1) was stirred at 90° C. overnight under $N_2$ atmosphere. After cooled to room temperature, the reaction mixture was poured into water and extracted with EtOAc (60 mL×3). The organic layers were washed with brine, dried over $Na_2SO_4$ and concentrated. The residue was purified column chromatography (petroleum ether) to give 95-2 (3.70 g, about 62% yield) as an oil.

$^1$H NMR (400 MHz, $CDCl_3$) δ 8.00 (d, J=2.0 Hz, 1H), 7.75 (dd, J=8.4 Hz, 2.0 Hz, 1H), 7.45-7.40 (m, 3H), 7.33 (d, J=8.4 Hz, 1H), 7.31-7.27 (m, 2H).

The Synthesis of 4-bromobiphenyl-2-amine (95-3)

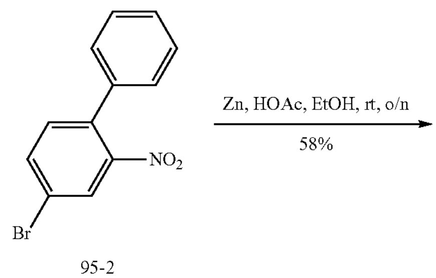

95-2

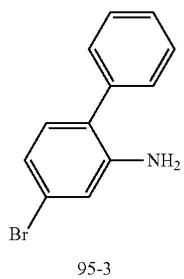

95-3

The mixture of 95-2 (3.70 g, 13.30 mmol), Zn powder (8.70 g, 133.00 mmol) and HOAc (3.5 mL) in EtOH (35 mL) was stirred at room temperature overnight. Then the reaction mixture was concentrated and poured into water. The mixture was basified with 40% NaOH till pH reached 10. The resulting mixture was filtered through celite and washed with MeOH. The filtrate was extracted with EtOAc (50 mL×3). The organic layers were washed with brine, dried over $Na_2SO_4$ and concentrated. The residue was purified column chromatography (petroleum ether/EtOAc=20/1) to give 95-3 (1.90 g, about 58% yield) as an oil. MS Calcd.: 247.0; MS Found: 248.1 $[M+H]^+$.

The Synthesis of 4-bromo-N-(2-chloroethyl)biphenyl-2-amine (95-4)

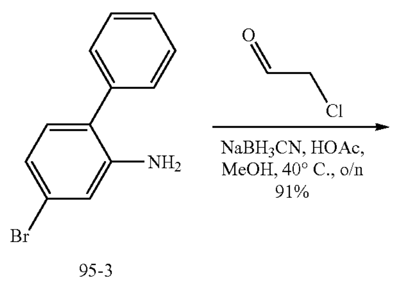

95-3

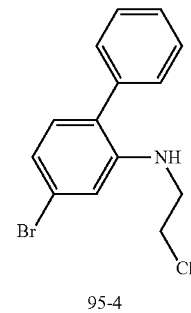

95-4

To a solution of 95-3 (1.75 g, 7.05 mmol) in MeOH (20 mL) was added 2-chloroacetaldehyde (2.77 g, 14.11 mmol, 40%), AcOH (846 mg, 14.11 mmol), and $NaBH_3CN$ (887 mg, 14.11 mmol), then the reaction mixture was stirred at 40° C. overnight. Then the reaction mixture was poured into water and basified with 1N NaOH till pH reached 10. The mixture was extracted with EtOAc (50 mL×3). The organic layers were washed with brine, dried over $Na_2SO_4$ and concentrated. The residue was purified column chromatography (petroleum ether/EtOAc=20/1) to give 95-4 (2.00 g, about 91% yield) as an oil. MS Calcd.: 309.0; MS Found: 309.8 $[M+H]^+$.

The Synthesis of N-(2-(1H-1,2,4-triazol-1-yl)ethyl)-4-bromobiphenyl-2-amine (95-5)

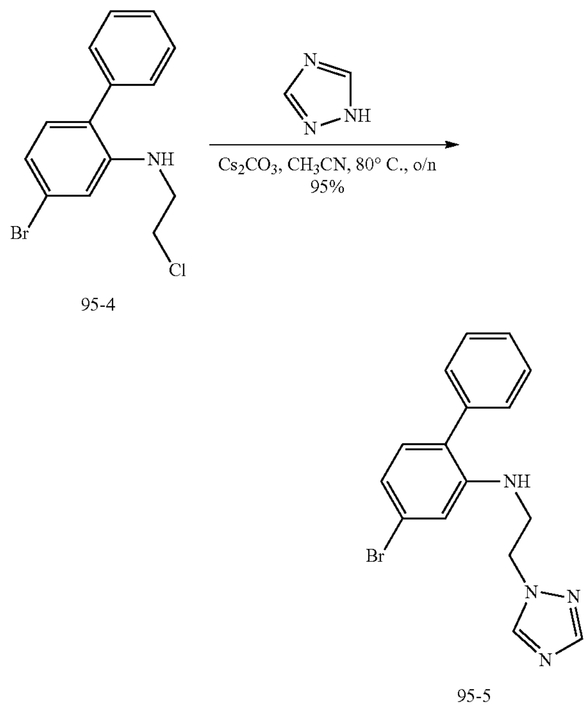

95-4

95-5

A mixture of 95-4 (2.00 g, 6.44 mmol), 1H-1,2,4-triazole (677 mg, 9.66 mmol) and $Cs_2CO_3$ (4.20 g, 12.88 mmol) in $CH_3CN$ (40 mL) was stirred at 80° C. overnight. The reaction mixture was then cooled to room temperature and filtered through celite and concentrated. The residue was purified by column chromatography (petroleum ether/EtOAc=2/1) to give 95-5 (2.10 g, about 95% yield) as an oil. MS Calcd.: 342.1; MS Found: 342.8 $[M+H]^+$.

The Synthesis of $N^2$-(2-(1H-1,2,4-triazol-1-yl)ethyl)-$N^4$-benzylbiphenyl-2,4-diamine (SS20308-0096-01)

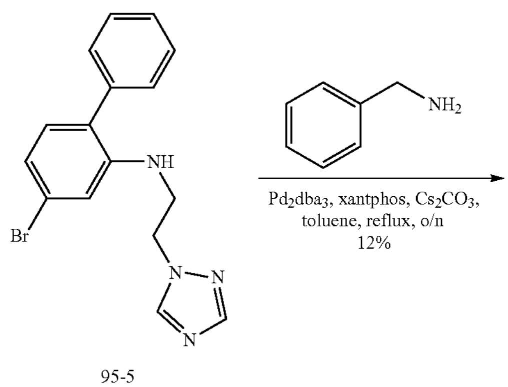

95-5

-continued

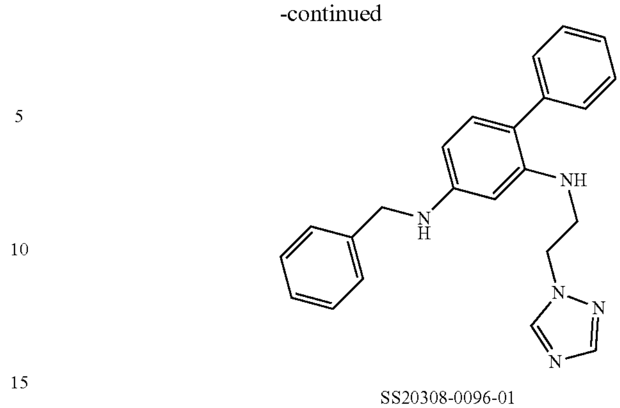

SS20308-0096-01

The mixture of 95-5 (200 mg, 0.58 mmol), benzylamine (75 mg, 0.70 mmol), $Pd_2dba_3$ (53 mg, 0.06 mmol), Xantphos (67 mg, 0.12 mmol) and $Cs_2CO_3$ (378 mg, 1.16 mmol) in toluene (20 mL) was stirred at 110° C. overnight under $N_2$ atmosphere. The reaction mixture was then cooled to room temperature and filtered through celite and concentrated. The residue was purified by Prep-HPLC to give SS20308-0096-01 (25 mg, about 12% yield) as a solid. MS Calcd.: 369.2; MS Found: 370.1 $[M+H]^+$.

$^1H$ NMR (400 MHz, $CDCl_3$) δ 7.88 (s, 1H), 7.86 (s, 1H), 7.44-7.40 (m, 2H), 7.40-7.33 (m, 4H), 7.31-7.26 (m, 2H), 7.23-7.19 (m, 2H), 6.93 (d, J=8.0 Hz, 1H), 6.15 (dd, J=8.0 Hz, 2.0 Hz, 1H), 5.92 (d, J=2.0 Hz, 1H), 4.39 (s, 2H), 4.19 (t, J=6.0 Hz, 2H), 4.14 (s, 1H), 4.09 (t, J=6.0 Hz, 1H), 3.55-3.48 (m, 2H).

Example 6

SS20308-0135

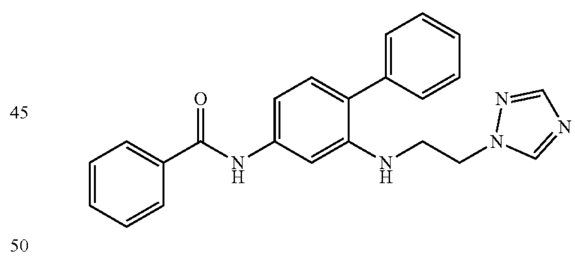

Example Route for Example 6

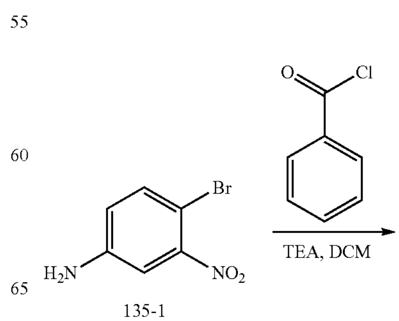

135-1

-continued

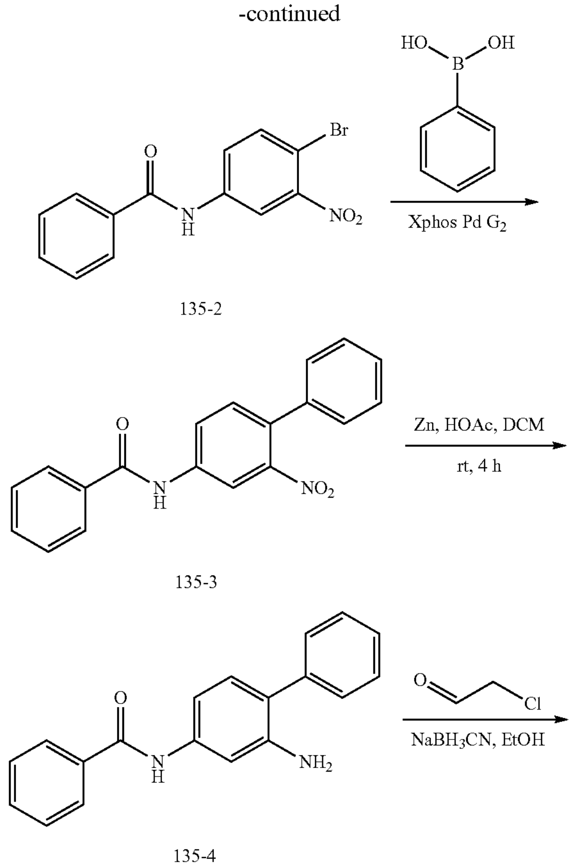

135-2

135-3

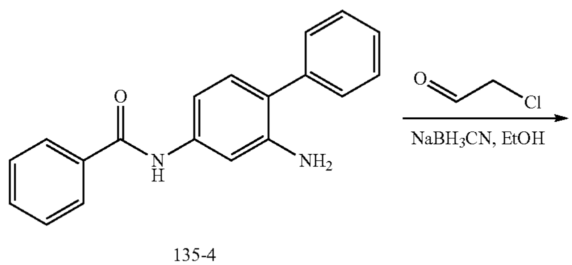

135-4

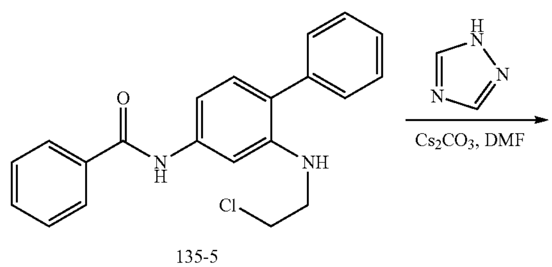

135-5

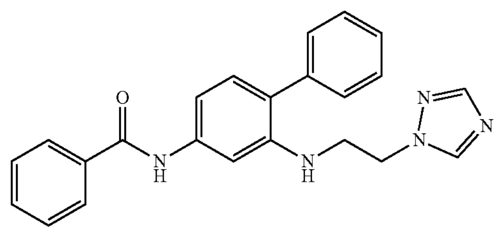

SS2030
8-0135

The Synthesis of N-(4-bromo-3-nitrophenyl)benzamide (135-2)

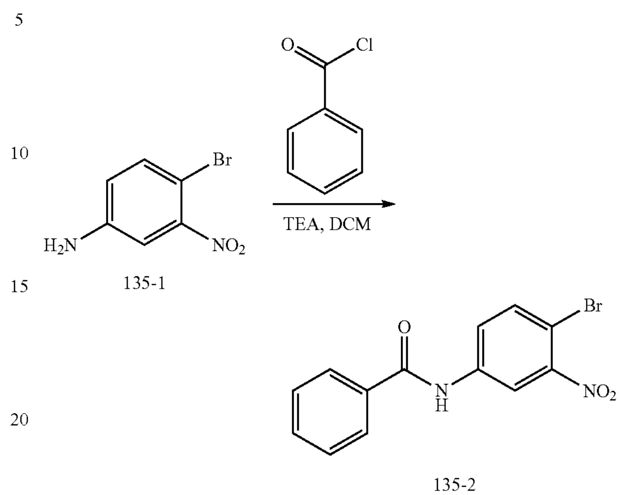

135-1

135-2

To a solution of 135-1 (432 mg, 2 mmol) in DCM (50 mL) was added benzoyl chloride (420 mg, 3 mmol). The mixture was stirred at rt for 2 h, the solution was washed by $H_2O$ (40 mL) and brine (40 mL). The organic layer was dried with $MgSO_4$, filtered and concentrated under reduced pressure. The crude product was purified by column chromatography on silica gel (Hexanes/EtOAc=5/1 to 1/1) to give 135-2 (350 mg, about 54% yield) as a solid. MS Calcd.: 320.0; MS Found: 321.2 $[M+H]^+$ The Synthesis of N-(2-nitro-[1,1'-biphenyl]-4-yl) benzamide (135-3)

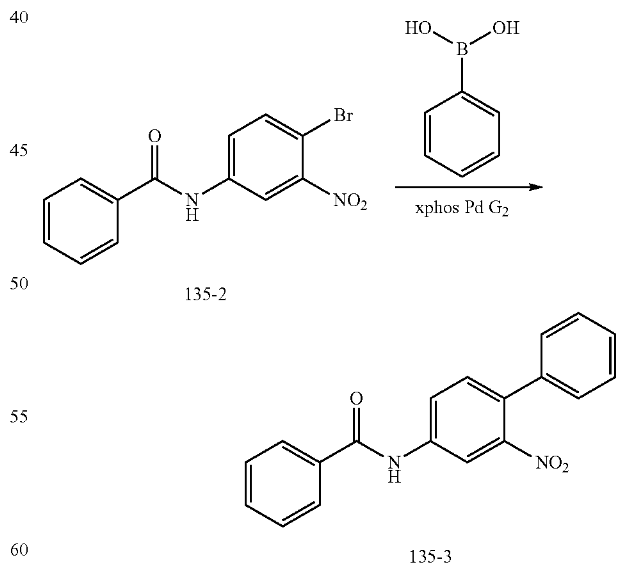

135-2

135-3

To a mixture of 135-2 (320 mg, 1 mmol) and phenylboronic acid (146 mg, 1.2 mmol) in toluene/$H_2O$ (30 mL/3 mL) was added $Cs_2CO_3$ (652 mg, 2 mmol) and xphos Pd $G_2$ (20 mg). The mixture was heated to reflux for 6 h. The mixture was diluted with EtOAc (50 mL), the organic layer was washed with water (50 mL) and brine (50 mL). The organic layer was dried by $MgSO_4$, filtered and concentrated under reduced pressure. The crude product was purified by column chromatography on silica gel (petroleum ether/EtOAc=3/1) to give 135-3 (230 mg, about 72% yield) as an oil. MS Calcd.: 318.1; MS Found: 319.2 $[M+H]^+$ The Synthesis of N-(2-amino-[1,1'-biphenyl]-4-yl) benzamide (135-4)

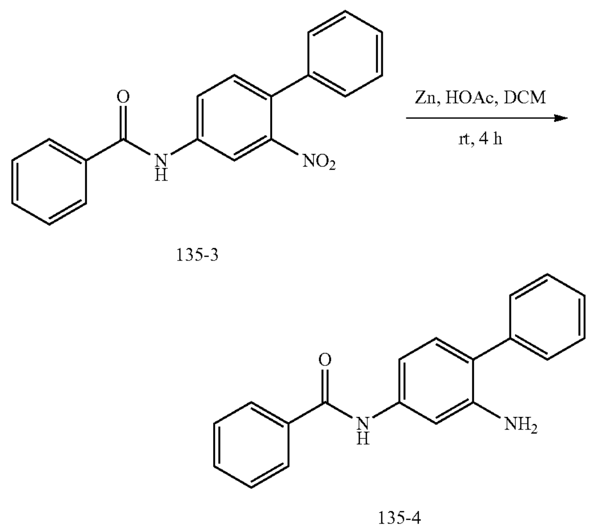

135-3

135-4

To a mixture of 135-3 (230 mg, 0.72 mmol) in DCM (50 mL) was added HOAc (5 mL) and Zn powder (150 mg) at room temperature. The mixture was stirred at rt for 4 h, filtered and the organic layer was concentrated under reduced pressure. The crude product was purified by column chromatography on silica gel (hexanes/EtOAc=1/1) to give 135-4 (140 mg, about 68% yield) as an oil. MS Calcd.: 288.1; MS Found: 288.2 $[M+H]^+$ The Synthesis of N-(2-((2-chloroethyl)amino)-[1,1'-biphenyl]-4-yl)benzamide (135-5)

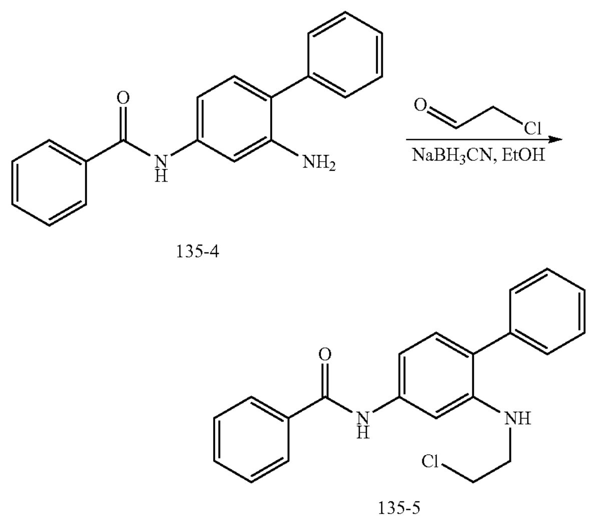

135-4

135-5

To a mixture of 135-4 (144 mg, 0.5 mmol) in EtOH (30 mL) was added 2-chloroacetaldehyde (1 mL) and HOAc (1 mL) at room temperature, $NaBH_3CN$ (0.3 g) was added. The mixture was stirred at rt for 6 h, filtered and the filtrate was concentrated and purified by column chromatography on silica gel (hexanes/EtOAc=2/1) to give 135-5 (85 mg, about 48% yield) as an oil. MS Calcd.: 350.1; MS Found: 350.2 $[M+H]^+$ The Synthesis of N-(2-((2-(1H-1,2,4-triazol-1-yl) ethyl)amino)-[1,1'-biphenyl]-4-yl)benzamide (SS20308-0135)

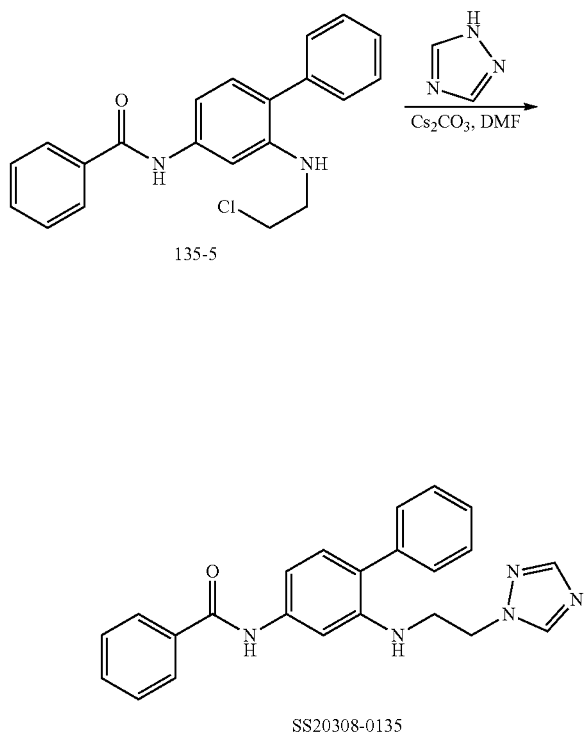

135-5

SS20308-0135

To a mixture of 135-5 (85 mg, 0.24 mmol) in DMF (15 mL) was added 1H-1,2,4-triazole (69 mg, 1 mmol) and $Cs_2CO_3$ (326 g, 1 mmol) at room temperature. The mixture was stirred at 80° C. for 8 h. filtered and the solid was washed with DCM (50 mL). The organic layer was dried with $MgSO_4$, filtered and concentrated under reduced pressure. The crude product was purified by column chromatography on silica gel (DCM/MeOH=15/1) to give SS20308-0135 (25 mg, about 27% yield) as a solid. MS Calcd.: 383.5; MS Found: 384.2 $[M+H]^+$ $^1H$ NMR (400 MHz, DMSO-$d_6$) δ 3.50 (br d, J=5.77 Hz, 2H), 4.42 (t, J=6.02 Hz, 2H), 4.80 (s, 1H), 6.97 (d, J=8.53 Hz, 1H), 7.23-7.28 (m, 4H), 7.34 (s, 1H), 7.41 (d, J=7.53 Hz, 2H), 7.53-7.63 (m, 3H), 7.96-8.00 (m, 3H), 8.48 (s, 1H), 10.12 (s, 1H).

Example 7

SS20308-0145-01

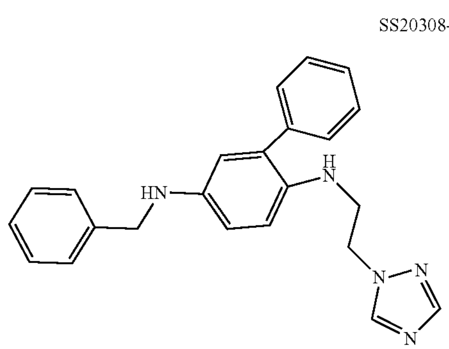

Example Route for Example 7

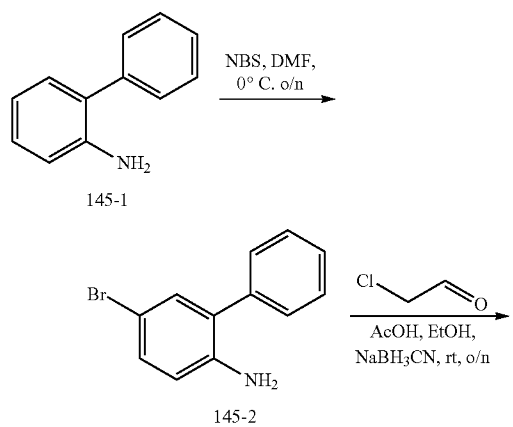

145-1

145-2

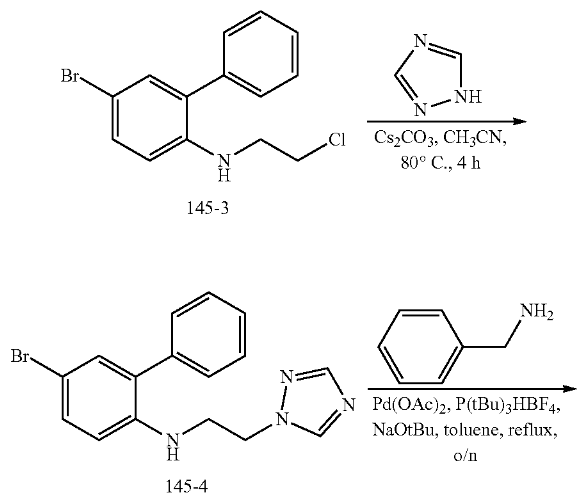

145-3

145-4

-continued

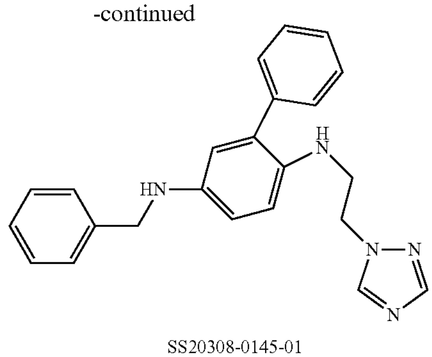

SS20308-0145-01

The Synthesis of 5-bromobiphenyl-2-amine (145-2)"

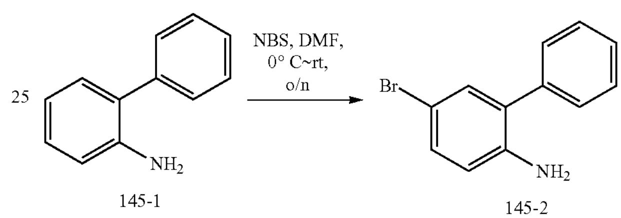

145-1

145-2

The mixture of 145-1 (6.40 g, 37.82 mmol) and NBS (6.70 g, 37.82 mmol) in DMF (10 mL) was stirred at 0° C. overnight. Then mixture was poured into water and extracted with ethyl acetate (30 mL×3) and the organic layers were washed with brine, dried over $MgSO_4$ and concentrated. The residue was purified by column chromatography (petroleum ether/EtOAc=20/1) to give 145-2 (5.7 g, about 57.6% yield) as an oil. MS Calcd.: 247.0; MS Found: 248.2 $[M+H]^+$.

The Synthesis of 5-bromo-N-(2-chloroethyl)biphenyl-2-amine (145-3)

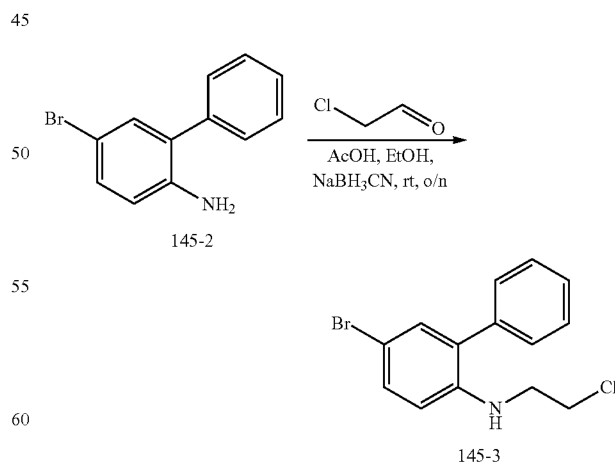

145-2

145-3

The mixture of 145-2 (5.70 g, 22.97 mmol), 2-chloroacetaldehyde (2.1 g, 27.56 mmol) and $NaBH_3CN$ (1.44 g, 22.97 mmol) in EtOH/AcOH (60 mL, 5/1) was stirred at rt overnight. The resulting mixture was extracted with EtOAc (30 mL×3) and the organic layers were washed with brine, dried over $MgSO_4$ and concentrated. The residue was purified by column chromatography (petroleum ether/EtOAc=10/1) to give 145-3 (6.0 g, about 84% yield) as a solid. MS Calcd.: 309.0; MS Found: 310.0 $[M+H]^+$.

The Synthesis of N-(2-(1H-1,2,4-triazol-1-yl)ethyl)-5-bromobiphenyl-2-amine (145-4)

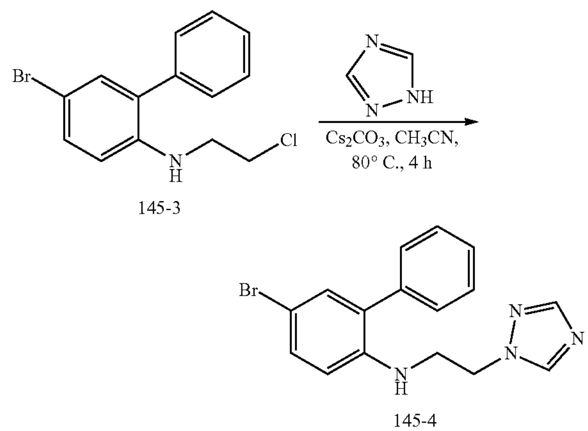

145-3

145-4

The mixture of 145-3 (5.00 g, 16.10 mmol), 1H-1,2,4-triazole (1.33 g, 19.32 mmol) and $Cs_2CO_3$ (15.73 g, 48.30 mmol) in $CH_3CN$ (15 mL) was stirred at 80° C. for 4 h. Then the mixture was poured into water and extracted with $CH_2Cl_2$ (3×30 mL). The combined organic layers were washed with brine, dried over $Na_2SO_4$ and concentrated. The residue was purified by column chromatography (petroleum ether/EtOAc=1/2) to give 145-4 (3.8 g, about 70% yield) as a solid. MS Calcd.: 342.1; MS Found: 343.9 $[M+H]^+$.

The Synthesis of $N^2$-(2-(1H-1,2,4-triazol-1-yl)ethyl)-$N^5$-benzylbiphenyl-2,5-diamine (SS20308-0145-01)

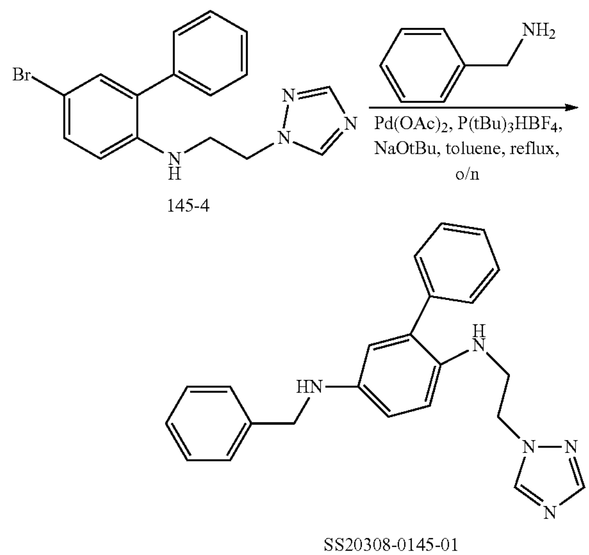

145-4

SS20308-0145-01

The mixture of 145-4 (450 mg, 1.31 mmol), benzylamine (420 mg, 3.93 mmol), $Pd(OAc)_2$ (29 mg, 0.13 mmol), $P(tBu)_3HBF_4$ (76 mg, 0.26 mmol) and NaOtBu (378 mg, 3.93 mmol) in toluene (5 mL) was stirred at 110° C. overnight under $N_2$ atmosphere. Then the reaction mixture was filtered and concentrated. The residue was purified by Prep-TLC (petroleum ether/EtOAc=1/2) to give SS20308-0145-01 (100 mg, about 21% yield) as an oil. MS Calcd.: 369.2; MS Found: 370.3 $[M+H]^+$ $^1H$ NMR (400 MHz, $CDCl_3$) δ 7.93 (s, 1H), 7.89 (s, 1H), 7.39-7.43 (m, 5H), 7.32-7.37 (m, 3H), 7.29-7.31 (m, 1H), 7.25-7.28 (m, 1H), 6.64 (d, J=2 Hz, 2H), 6.56-6.7 (m, 1H), 4.30 (t, J=5.6 Hz, 4H), 3.66 (brs, 1H), 3.55 (t, J=5.2 Hz 2H).

Example 8

SS20308-0146-01

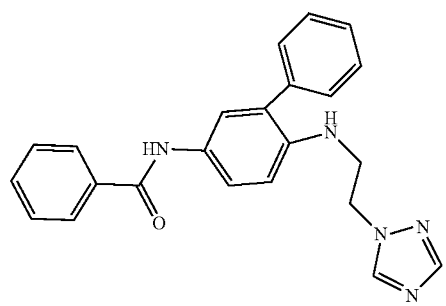

Example Route for Example 8

The Synthesis of 5-bromobiphenyl-2-amine (146-2)

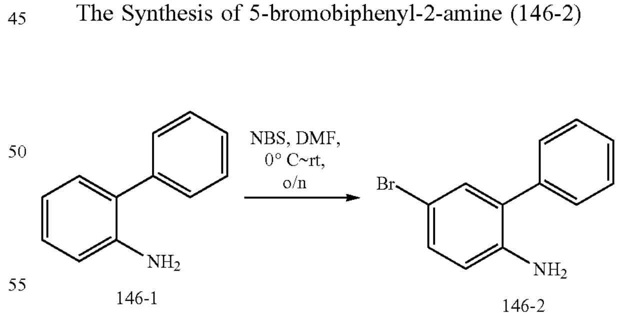

146-1

146-2

The mixture of 146-1 (6.40 g, 37.82 mmol) and NBS (6.70 g, 37.82 mmol) in DMF (10 mL) was stirred at 0° C. overnight. Then mixture was poured into water and extracted with ethyl acetate (30 mL×3) and the organic layers were washed with brine, dried over $MgSO_4$ and concentrated. The residue was purified by column chromatography (petroleum ether/EtOAc=20/1) to give 146-2 (5.7 g, about 57.6% yield) as an oil. MS Calcd.: 247.0; MS Found: 248.2 $[M+H]^+$.

The Synthesis of 5-bromo-N-(2-chloroethyl)biphenyl-2-amine (146-3)

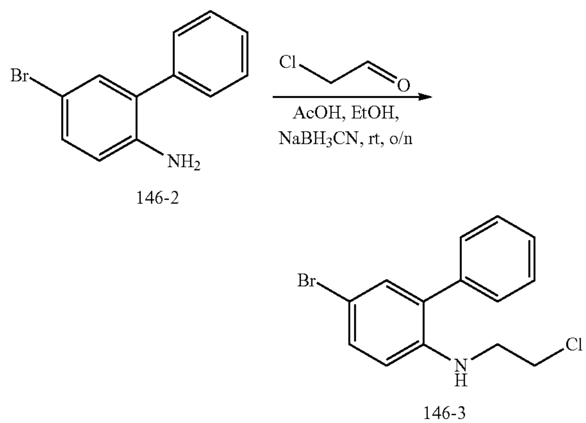

146-2

146-3

The mixture of 146-2 (5.70 g, 22.97 mmol), 2-chloroacetaldehyde (2.1 g, 27.56 mmol) and $NaBH_3CN$ (1.44 g, 22.97 mmol) in EtOH/AcOH (60 mL, 5/1) was stirred at rt overnight. The resulting mixture was extracted with ethyl acetate (30 mL×3) and the organic layers were washed with brine, dried over $MgSO_4$ and concentrated. The residue was purified by column chromatography (petroleum ether/EtOAc=10/1) to give 146-3 (6.0 g, about 84% yield) as a solid. MS Calcd.: 309.0; MS Found: 310.0 $[M+H]^+$.

The Synthesis of N-(2-(1H-1,2,4-triazol-1-yl)ethyl)-5-bromobiphenyl-2-amine (146-4)

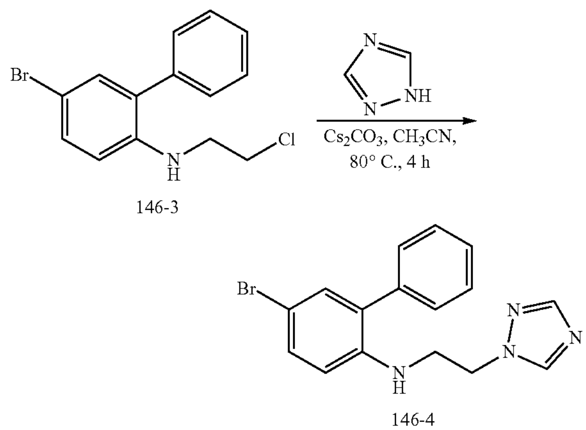

146-3

146-4

The mixture of 146-3 (5.00 g, 16.10 mmol), 1H-1,2,4-triazole (1.33 g, 19.32 mmol) and $Cs_2CO_3$ (15.73 g, 48.30 mmol) in $CH_3CN$ (15 mL) was stirred at 80° C. for 4 h. Then the mixture was poured into water and extracted with $CH_2Cl_2$ (3×30 mL). The combined organic layers were washed with brine, dried over $Na_2SO_4$ and concentrated. The residue was purified by column chromatography (petroleum ether/EtOAc=1/2) to give 146-4 (3.8 g, about 70% yield) as a solid. MS Calcd.: 342.1; MS Found: 343.9 $[M+H]^+$.

The Synthesis of N-(6-(2-(1H-1,2,4-triazol-1-yl)ethylamino)biphenyl-3-yl)benzamide (SS20308-0146-01)

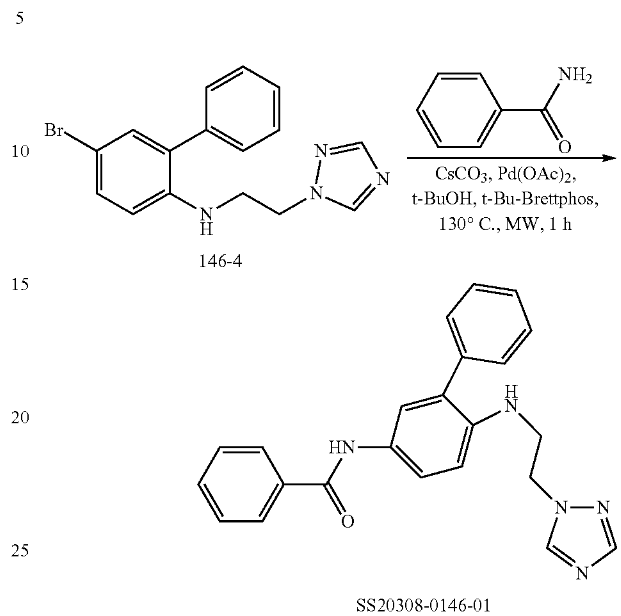

146-4

SS20308-0146-01

The mixture of 146-4 (350 mg, 1.02 mmol), benzamide (372 mg, 3.06 mmol), $Pd(OAc)_2$ (22 mg, 0.10 mmol), t-Bu-Bretphos (97 mg, 0.20 mmol) and $Cs_2CO_3$ (997 mg, 3.06 mmol) in t-BuOH (5 mL) was stirred at 130° C. with MW for 1 h under N2 atmosphere. Then the reaction mixture was filtered and concentrated. The residue was purified by Prep-TLC (petroleum ether/EtOAc=1/2) to give SS20308-0146-01 (50 mg, about 13% yield) as an oil. M.S Calcd.: 384.2; MS Found: 384.2 $[M+H]^+$ 1

$^1H$ NMR (400 MHz, DMSO-$d_6$) δ 9.99 (s, 1H), 8.46 (s, 1H), 7.96 (s, 1H), 7.91-7.93 (m, 2H), 7.43-7.59 (m, 7H), 7.37 (d, J=7.2 Hz, 1H), 7.28 (d, J=6.8 Hz, 2H), 6.72 (d, J=8.8 Hz, 1H), 4.66 (t, J=6.4 Hz, 1H) 4.36 (t, J=6.0 Hz, 2H), 3.49 (q, J=6.0 Hz, 2H).

Example 9

SS20308-0211-01

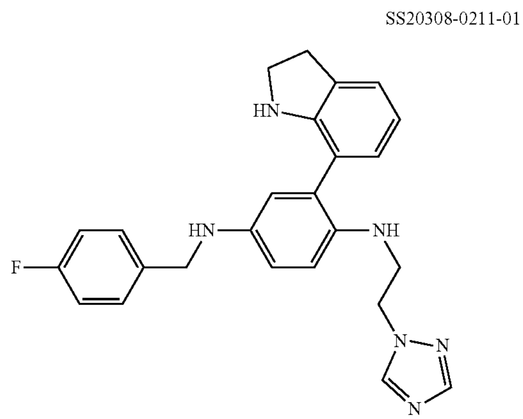 [SMILES: Fc1ccc(CNc2ccc(NCCn3cncn3)c(-c3cccc4c3NCC4)c2)cc1]

Example Route for Example 9 (SS20308-0211-01& SS20308-0225-01)

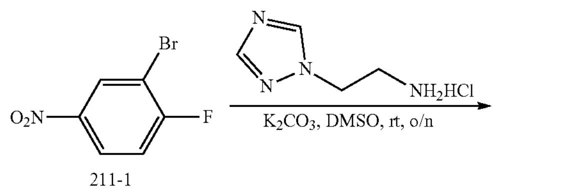

211-1

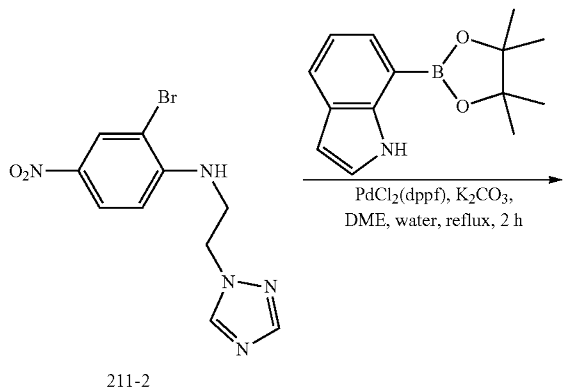

211-2

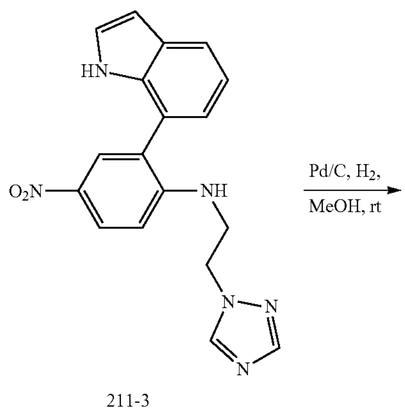

211-3

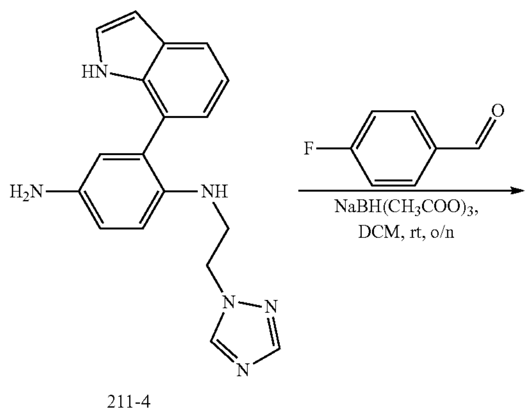

211-4

-continued

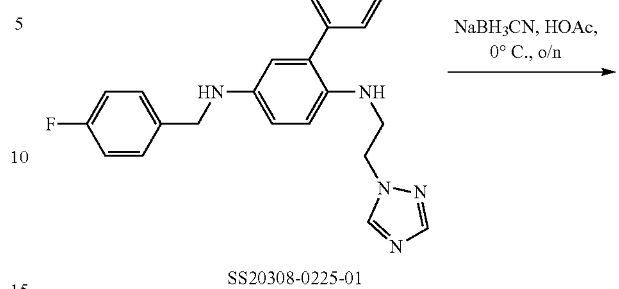

SS20308-0225-01

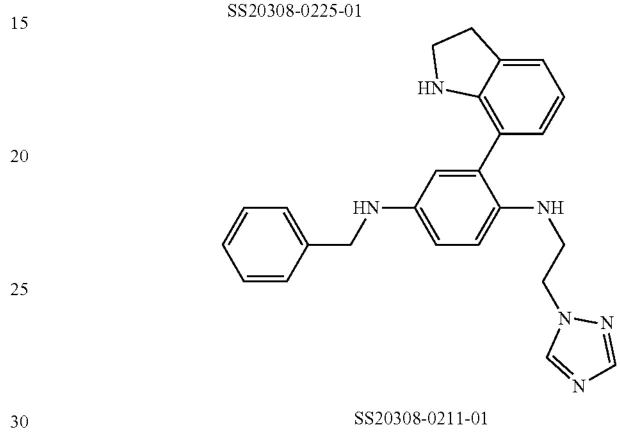

SS20308-0211-01

The Synthesis of N-(2-(1H-1,2,4-triazol-1-yl)ethyl)-2-bromo-4-nitroaniline (211-2)

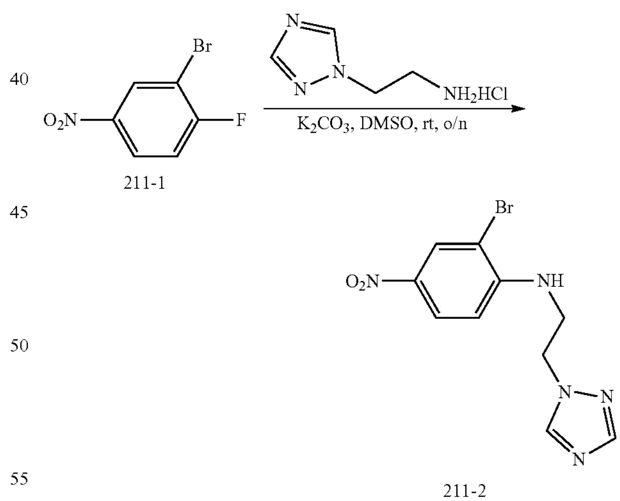

211-1

211-2

The mixture of 211-1 (2.20 g, 10.00 mmol), 2-(1H-1,2,4-triazol-1-yl)ethanamine hydrochloride (1.78 g, 12.00 mmol) and $K_2CO_3$ (4.15 g, 30.00 mmol) in DMSO (10 mL) was stirred at rt overnight. Then mixture was poured into water and extracted with EtOAc (30 mL×3) and the organic layers were washed with brine, dried over $MgSO_4$ and concentrated. The residue was purified by column chromatography (petroleum ether/EtOAc=1/1) to give 211-2 (2.00 g, about 64% yield) as a solid. MS Calcd.: 311.0; MS Found: 312.0 $[M+H]^+$.

The Synthesis of N-(2-(1H-1,2,4-triazol-1-yl)ethyl)-2-(1H-indol-7-yl)-4-nitroaniline (211-3)

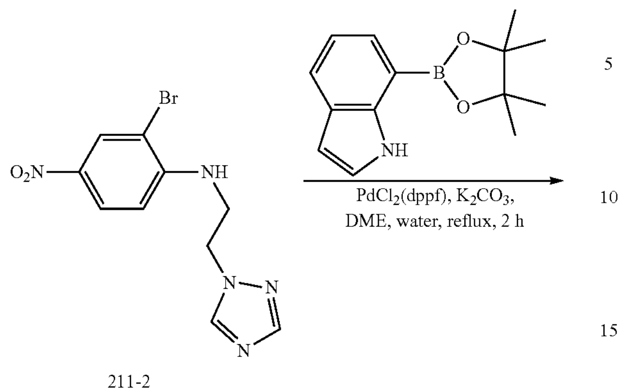

211-2

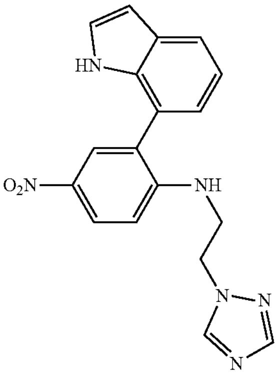

211-3

The mixture of 211-2 (2.00 g, 6.41 mmol), 7-(4,4,5,5-tetramethyl-1,3,2-dioxaborolan-2-yl)-1H-indole (2.34 g, 9.61 mmol), $Pd(dppf)Cl_2$ (469 mg, 0.64 mmol) and $K_2CO_3$ (2.66 g, 19.23 mmol) in $DME/H_2O$ (10 mL, 5/1) was stirred at 80° C. for 2 h under N2 atmosphere. The resulting mixture was extracted with ethyl acetate (30 mL×3) and the organic layers were washed with brine, dried over $MgSO_4$ and concentrated. The residue was purified by column chromatography (petroleum ether/EtOAc=1/1) to give 211-3 (1.80 g, about 81% yield) as a solid. MS Calcd.: 348.1; MS Found: 349.4 $[M+H]^+$.

The Synthesis of $N^1$-(2-(1H-1,2,4-triazol-1-yl)ethyl)-2-(1H-indol-7-yl)benzene-1,4-diamine (211-4)

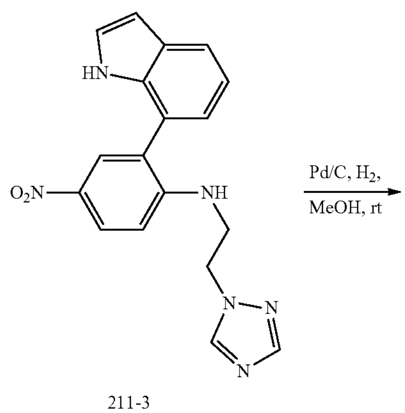

211-3

-continued

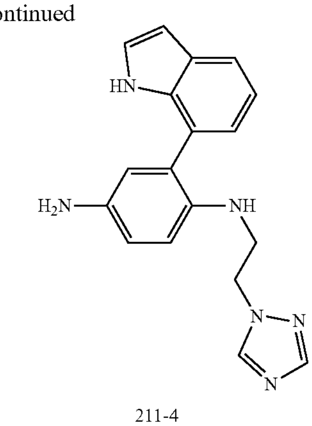

211-4

The mixture of 211-3 (1.00 g, 2.87 mmol), and 10% Pd/C (339 mg, 1.38 mmol) in MeOH (10 mL) was stirred at rt for 3 h under $H_2$ atmosphere. The reaction mixture was then cooled to room temperature and was purified by column chromatography (petroleum ether/EtOAc=1/1) to give 221-4 (0.78 g, about 86% yield) as a solid. MS Calcd.: 318.2; MS Found: 319.0 $[M+H]^+$ The Synthesis of $N^1$-(2-(1H-1,2,4-triazol-1-yl)ethyl)-$N^4$-(4-fluorobenzyl)-2-(1H-indol-7-yl)benzene-1,4-diamine (SS20308-0225-01)

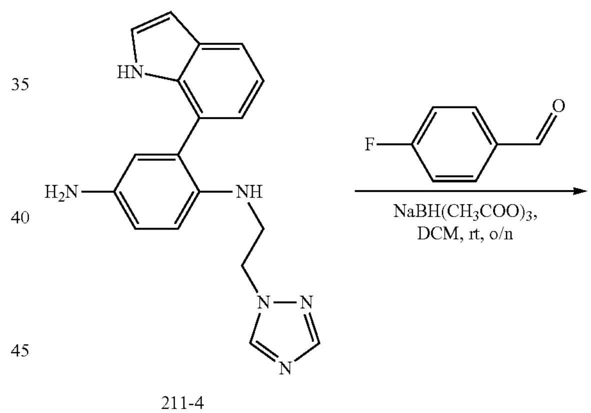

211-4

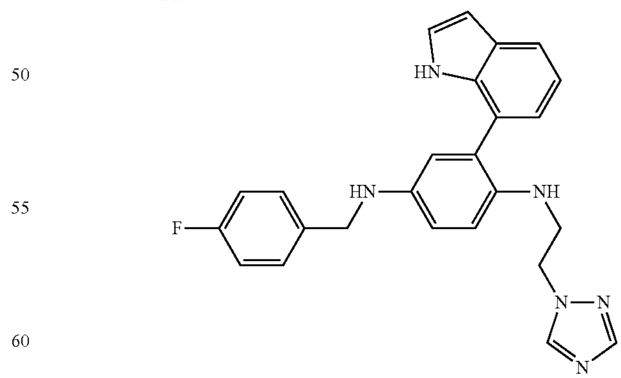

SS20308-0225-01

The mixture of 211-4 (600 mg, 1.88 mmol), 4-fluorobenzaldehyde (281 mg, 2.26 mmol), and $NaBH(CH_3COO)_3$ (479 mg, 2.26 mmol) in DCM (10 mL) was stirred at rt overnight. Then the mixture was poured into water and extracted with $CH_2Cl_2$ (3×30 mL). The combined organic layers were washed with water and brine, dried over $Na_2SO_4$ and concentrated. The residue was purified by column chromatography (petroleum ether/EtOAc=1/2) to give SS20308-0225-01 (360 mg, about 45% yield) as a solid. MS Calcd.: 426.2; MS Found: 427.0 $[M+H]^+$.

$^1H$ NMR (400 MHz, $CD_3OD-d_4$) δ 8.12 (s, 1H), 7.80 (s, 1H), 7.55 (d, J=8.0 Hz, 1H), 7.40 (q, J=5.6 Hz, 2H), 7.16 (d, J=3.2 Hz, 1H), 7.01-7.08 (m, 3H), 6.88 (d, J=6.8 Hz, 1H), 6.65-6.62 (m, 3H), 6.49 (d, J=3.2 Hz, 1H), 4.20-4.26 (m, 4H), 3.46-3.50 (m, 2H).

The Synthesis of $N^1$-(2-(1H-1,2,4-triazol-1-yl)ethyl)-$N^4$-(4-fluorobenzyl)-2-(indolin-7-yl)benzene-1,4-diamine (SS20308-0211-01)

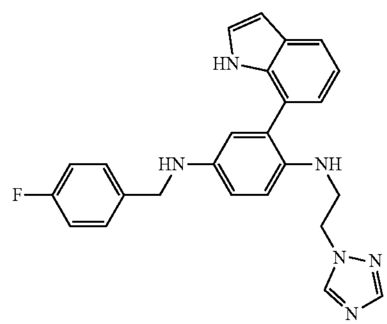

SS20308-0225-01

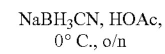

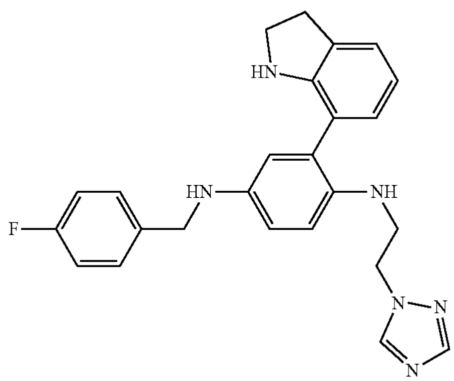

SS20308-0211-01

The mixture of SS20308-0225-01 (50 mg, 0.117 mmol), and $NaBH_3CN$ (8 mg, 0.117 mmol) in AcOH (2 mL) was stirred at 0° C. overnight. The residue was purified by Prep-HPLC to give SS20308-0211-01 (20 mg, about 40% yield) as a solid. MS Calcd.: 428.2; MS Found: 429.0 $[M+H]^+$.

$^1H$ NMR (400 MHz, DMSO-$d_6$) δ 8.43 (s, 1H), 7.94 (s, 1H), 7.36-7.40 (m, 2H), 7.11-7.15 (t, 2H), 7.01 (d, J=7.2 Hz, 1H), 6.71-6.73 (d, J=8.0 Hz, 1H), 6.56-6.62 (m, 2H), 6.49 (q, J=2.4 Hz, 1H), 6.39 (d, J=2.4 Hz, 1H), 5.63-5.66 (m, 1H), 4.69 (s, 1H), 4.28-4.30 (m, 2H), 4.17 (d, J=5.6 Hz, 2H), 4.08-4.11 (m, 1H), 3.24-3.29 (m, 4H), 2.92-2.94 (m, 2H).

Example 10

SS20308-0212-01

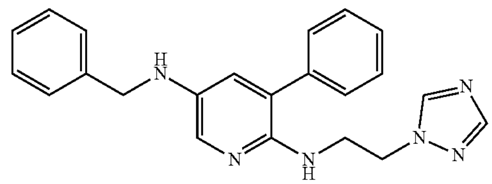

Chemical Formula: $C_{22}H_{22}N_6$
Molecular Weight: 370.45

Example Route for Example 10

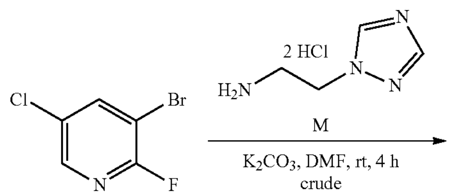

212-1

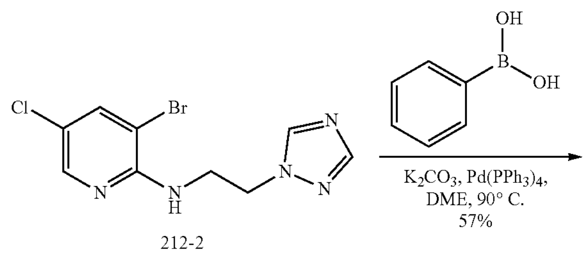

212-2

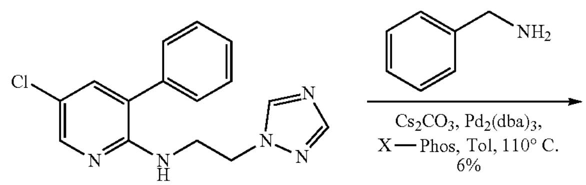

212-3

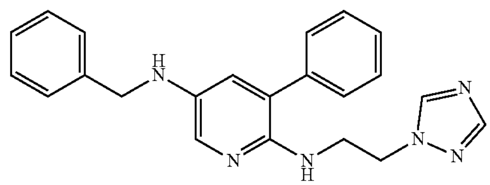

SS20308-0212-01

The Synthesis of N-(2-(1H-1,2,4-triazol-1-yl)ethyl)-3-bromo-5-chloropyridin-2-amine (212-2)

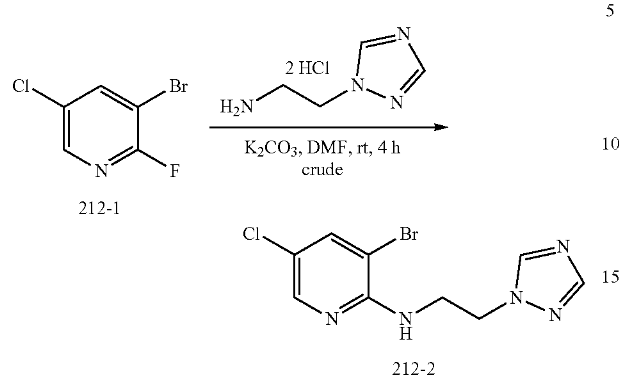

212-1

212-2

To a solution of 212-1 (500 mg, 2.38 mmol) in DMF (6 mL) was added $K_2CO_3$ (1.31 g, 9.50 mmol) and 1H-1,2,4-triazole-1-ethanamine, hydrochloride (1:2) (355 g, 2.38 mmol), the mixture was stirred at room temperature for 4 h. After the reaction was complete, the reaction mixture was poured into water (50 mL) and extracted with EtOAc (40 mL×3). The organic layer was washed brine (2×50 mL), dried over $MgSO_4$, and concentrated under vacuum to afford 212-2, which was used in the next step without further purification.

The Synthesis of N-(2-(1H-1,2,4-triazol-1-yl)ethyl)-5-chloro-3-phenylpyridin-2-amine (212-3)

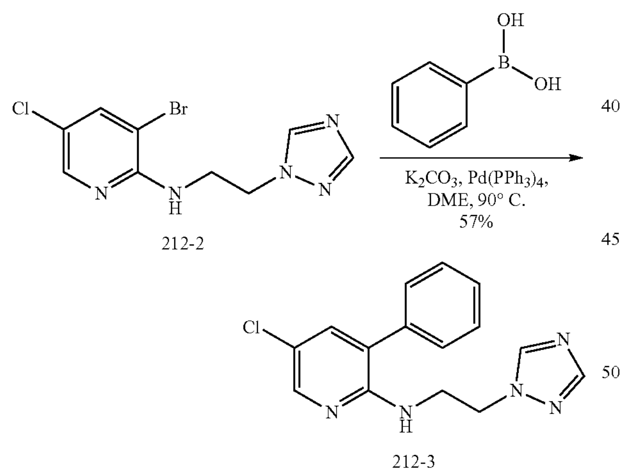

212-2

212-3

A mixture of 212-2 (300 mg, 0.99 mmol), phenylboronic acid (121 mg, 0.99 mmol), $Pd(PPh_3)_4$ (115 mg, 0.10 mmol), $K_2CO_3$ (274 mg, 1.98 mmol) in DME (20 ml) was stirred at 90° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated under vacuum, which was purified by column chromatography (petroleum ether/EtOAc=1/1) to give 212-3 (170 mg, about 57% yield) as an oil. MS Calcd.: 299.1; MS Found: 300.1 $[M+H]^+$.

The Synthesis of $N^2$-(2-(1H-1,2,4-triazol-1-yl)ethyl)-$N^5$-benzyl-3-phenylpyridine-2,5-diamine (SS20308-0212-01)

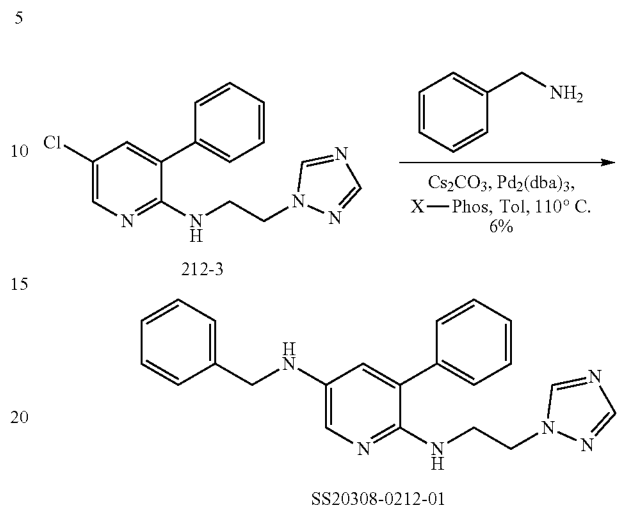

212-3

SS20308-0212-01

A mixture of 212-3 (100 mg, 0.33 mmol), phenylmethanamine (71 mg, 0.67 mmol), $Pd_2(dba)_3$ (31 mg, 0.03 mmol), X-Phos (32 mg, 0.07 mmol) and $Cs_2CO_3$ (217 mg, 0.67 mmol) in Tol (10 ml) was stirred at 110° C. under nitrogen atmosphere overnight. After the reaction was complete, the mixture was quenched with water, the insoluble material was removed by filtration, and the filtrate was extracted with EtOAc (50 mL×3). The organic layer was separated, dried over $MgSO_4$, and concentrated in vacuum. The residue was purified by Prep-HPLC to give SS20308-0212-01 (7 mg, 6% yield) as an oil. MS Calcd.: 370.2; MS Found: 371.0 $[M+H]^+$.

$^1H$ NMR (400 MHz, DMSO-$d_6$) δ 8.41 (s, 1H), 7.92 (s, 1H), 7.50 (d, J=2.8 Hz, 1H), 7.43-7.21 (m, 10H), 6.80 (d, J=2.8 Hz, 1H), 6.66 (t, J=6.4 Hz, 1H), 5.01 (t, J=6.0 Hz, 1H), 4.31 (t, J=6.0 Hz, 2H), 4.23 (d, J=6.0 Hz, 2H), 3.59-3.54 (m, 2H).

Example 11

SS20308-0213-01

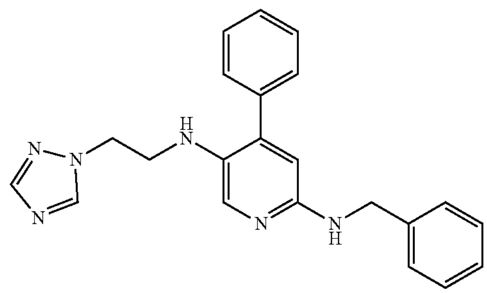

Example Route for Example 11

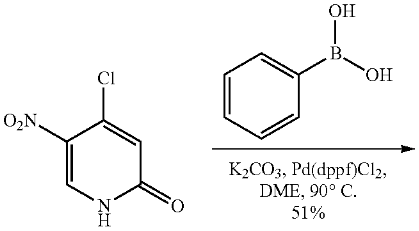

213-1

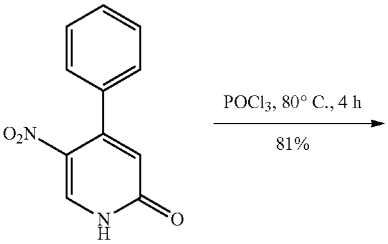

213-2

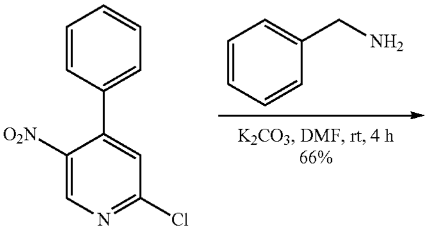

213-3

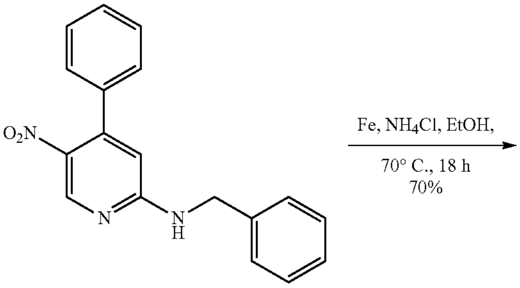

213-4

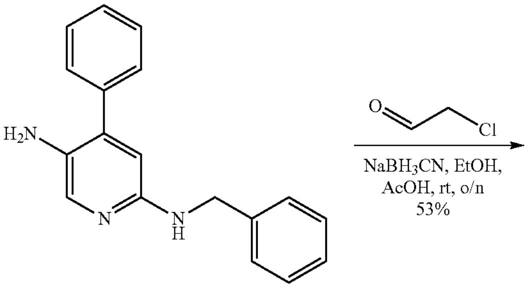

213-5

-continued

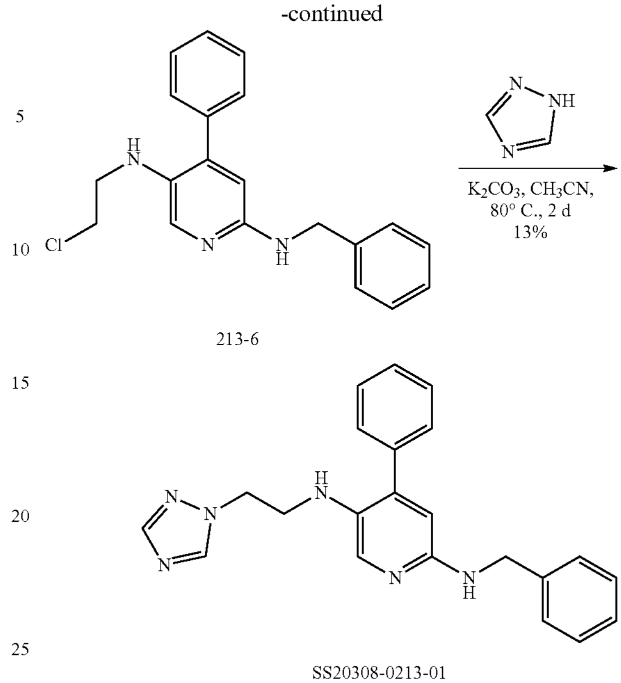

213-6

SS20308-0213-01

The Synthesis of 5-nitro-4-phenylpyridin-2(1H)-one (213-2)

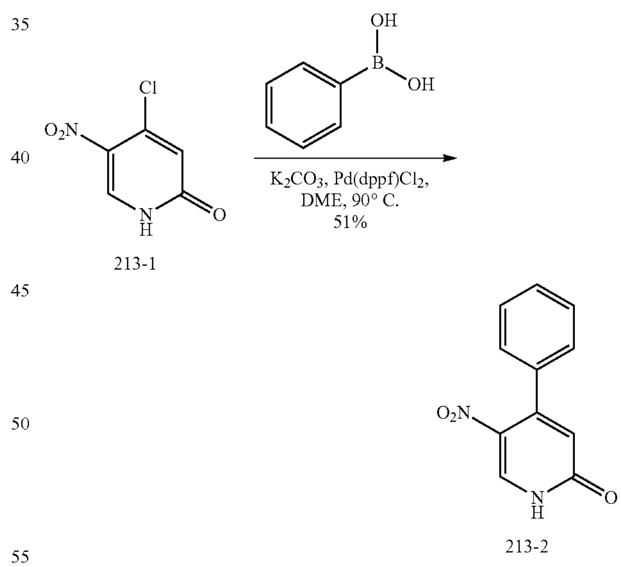

213-1

213-2

A mixture of phenylboronic acid (1.3 g, 11.0 mmol), 213-1 (2.0 g, 7.3 mmol), Pd(dppf)Cl$_2$ (534 mg, 0.73 mmol) and K$_2$CO$_3$ (3.0 g, 21.9 mmol) in DME (50 mL) and water (5 mL) was stirred at 100° C. for 18 h. After the reaction was complete, the reaction mixture was concentrated and quenched with water (100 mL), extracted with EtOAc (100 mL×3). The combined layers were dried over Na$_2$SO$_4$ and concentrated under vacuum, then purified by CC (petroleum ether/EtOAc=5/1) to give 213-2 (800 mg, about 51% yield) as a solid. MS Calcd.: 216.1; MS Found: 217.4 [M+H]$^+$.

The Synthesis of 2-chloro-5-nitro-4-phenylpyridine (213-3)

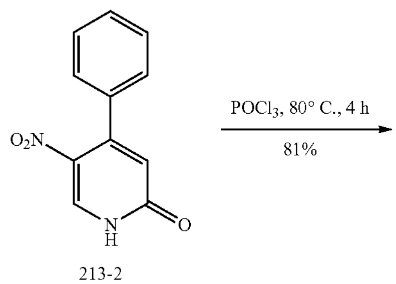

213-2

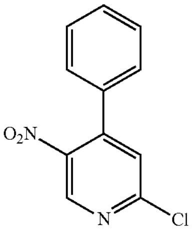

213-3

To a solution of 213-2 (800 mg, 3.7 mmol) in $POCl_3$ (10 mL) was stirred at 80° C. for 18 h. After the reaction was complete, the reaction mixture was concentrated and quenched with water (20 mL), extracted with EtOAc (20 mL×3). The combined layers were dried over $Na_2SO_4$ and concentrated under vacuum, then purified by column chromatography (petroleum ether/EtOAc=10/1) to give 213-3 (700 mg, about 81% yield) as a solid. MS Calcd.: 234.0; MS Found: 235.3 $[M+H]^+$.

The Synthesis of N-benzyl-5-nitro-4-phenylpyridin-2-amine (213-4)

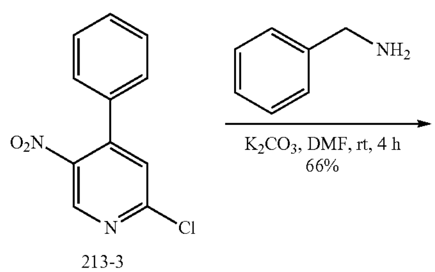

213-3

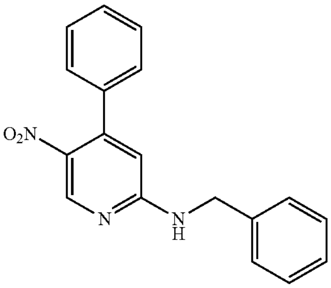

213-4

A mixture of phenylmethanamine (385 mg, 3.6 mmol), 213-3 (700 mg, 3 mmol) and $K_2CO_3$ (828 mg, 6 mmol) in DMF (10 mL) was stirred at rt for 18 h. After the reaction was complete, the reaction mixture was concentrated and quenched with water (20 mL), extracted with EtOAc (20 mL×3). The combined layers were dried over $Na_2SO_4$ and concentrated in vacuum, then purified by column chromatography (petroleum ether/EtOAc=5/1) to give 213-4 (600 mg, about 66% yield) as a solid. MS Calcd.: 305.1; MS Found: 306.4 $[M+H]^+$.

The Synthesis of $N^2$-benzyl-4-phenylpyridine-2,5-diamine (213-5)

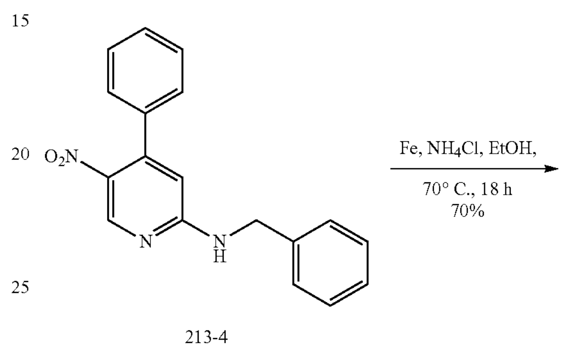

213-4

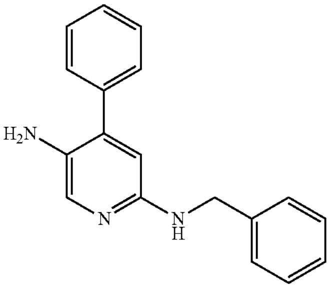

213-5

A mixture of 213-4 (800 mg, 2.6 mmol), Fe (728 mg, 13 mol) and $NH_4Cl$ (aq, 2 mL) in EtOH (20 mL) was stirred at 70° C. for 18 h. After the reaction was complete, the reaction mixture was concentrated and quenched with water (100 mL), extracted with EtOAc (100 mL×3). The combined layers were dried over $Na_2SO_4$, and concentrated under vacuum. The residue was purified by column chromatography (DCM/MeOH=20/1) to give 213-5 (500 mg, about 70% yield) as a solid. MS Calcd.: 275.1; MS Found: 276.4 $[M+H]^+$.

The Synthesis of $N^2$-benzyl-$N^5$-(2-chloroethyl)-4-phenylpyridine-2,5-diamine (213-6)

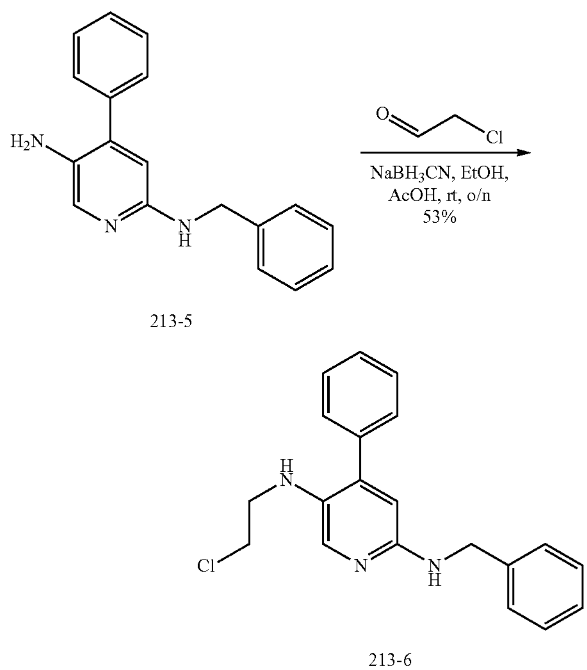

213-5

213-6

A mixture of 213-5 (250 mg, 0.91 mmol), 2-chloroacetaldehyde (213 mg, 2.73 mol), AcOH (2 drops) and $NaBH_3CN$ (118 mg, 1.82 mmol) in EtOH (10 mL) was stirred at rt overnight. After the reaction was complete, the reaction mixture was concentrated and quenched with water (20 mL), extracted with EtOAc (20 mL×3). The combined layers were dried over $Na_2SO_4$, and concentrated in vacuum. The residue was purified by column chromatography (petroleum ether/EtOAc=2/1) to give 213-6 (180 mg, about 53% yield) as a solid. MS Calcd.: 337.1; MS Found: 338.4 $[M+H]^+$.

The Synthesis of $N^5$-(2-(1H-1,2,4-triazol-1-yl)ethyl)-$N^2$-benzyl-4-phenylpyridine-2,5-diamine (SS20308-0213-01)

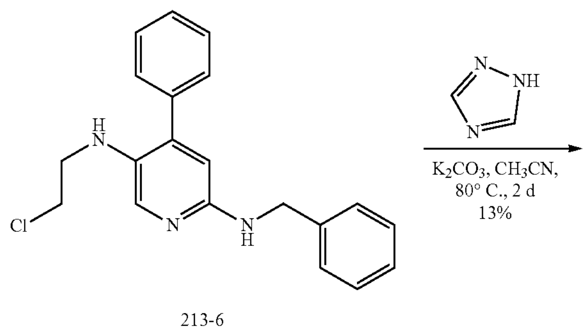

213-6

-continued

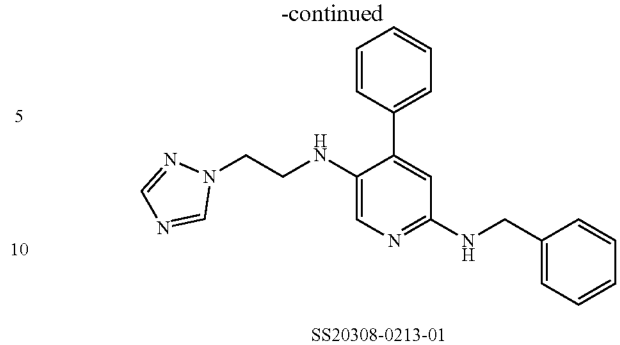

SS20308-0213-01

A mixture of 1H-1,2,4-triazole (40 mg, 0.6 mmol), 213-6 (100 mg, 0.3 mmol) and $K_2CO_3$ (120 mg, 0.9 mmol) in $CH_3CN$ (5 mL) was stirred at 80° C. for 2 d. After the reaction was complete, the reaction mixture was concentrated, quenched with water (10 mL), and extracted with EtOAc (10 mL×3). The combined layers were dried over $Na_2SO_4$ and concentrated under vacuum. The crude product was purified by Prep-HPLC to give SS20308-0213-01 (14 mg, about 13% yield) as a solid. MS Calcd.: 370.5; MS Found: 371.3 $[M+H]^+$.

$^1H$ NMR (400 MHz, DMSO-$d_6$) δ 8.43 (s, 1H), 7.93 (s, 1H), 7.54 (s, 1H), 7.45-7.38 (m, 3H), 7.36-7.27 (m, 6H), 7.22-7.18 (m, 1H), 6.46-6.44 (m, 1H), 6.31 (s, 1H), 4.42 (d, J=6.4 Hz, 2H), 4.30 (t, J=6.0 Hz, 2H), 4.06 (t, J=6.4 Hz, 1H), 3.33-3.31 (m, 2H).

Example 12

SS20308-0214-01

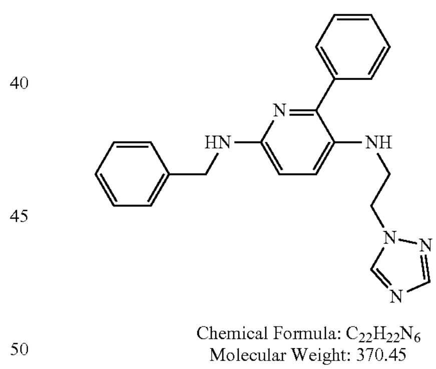

Chemical Formula: $C_{22}H_{22}N_6$
Molecular Weight: 370.45

Example Route for Example 12

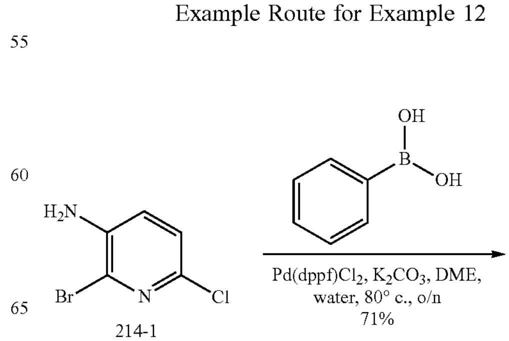

214-1

-continued

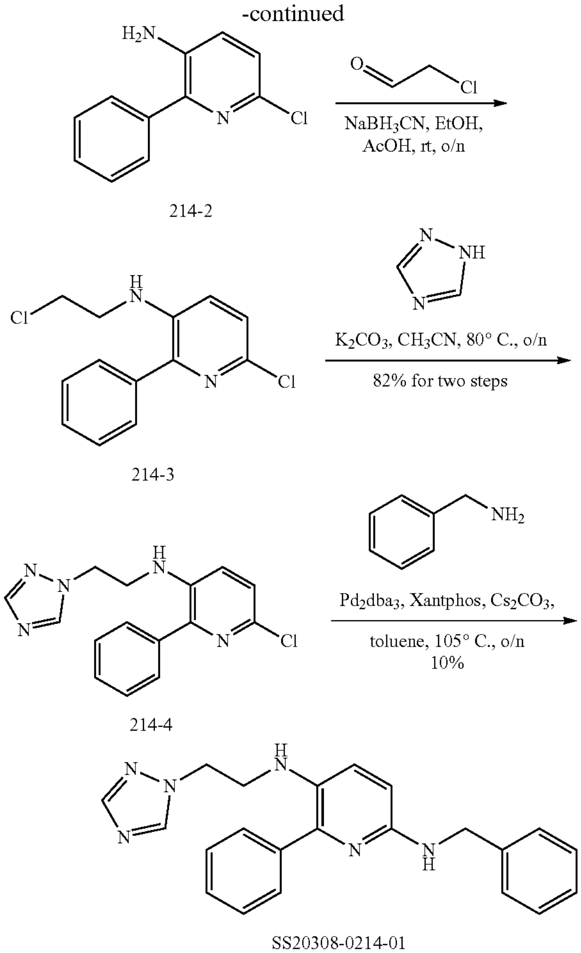

214-2

214-3

214-4

SS20308-0214-01

The Synthesis of 6-chloro-2-phenylpyridin-3-amine (214-2)

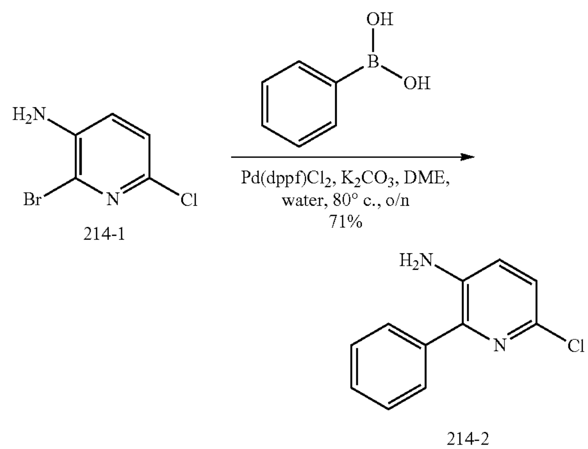

214-1

214-2

A solution of 214-1 (2.0 g, 9.64 mmol), phenylboronic acid (1.18 g, 9.64 mmol), Pd(dppf)$Cl_2$ (394 mg, 0.48 mmol), and potassium carbonate (4.0 g, 28.92 mmol) were suspended in DME (20 mL) and water (4 mL). The reaction mixture was heated to 80° C. for overnight and then filtered, and rinsed with EtOAc. The filtrate was concentrated and the residue was purified by silica gel column chromatography (petroleum ether/EtOAc=10/1, 5/1) to give compound 214-2 (1.4 g, about 71% yield) as a solid. MS Calcd.: 204.1; MS Found: 205.1 [M+H]$^+$.

The Synthesis of 6-chloro-N-(2-chloroethyl)-2-phenylpyridin-3-amine (214-3)

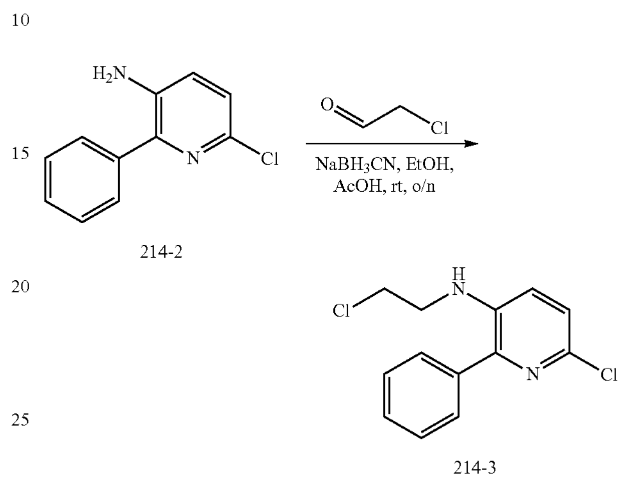

214-2

214-3

A solution of 214-2 (1.0 g, 4.89 mmol), 2-chloroacetaldehyde (3.84 g, 19.55 mmol, 40% in water), NaBH$_3$CN (461 mg, 7.34 mmol), and AcOH (2 mL) in EtOH (20 mL) was stirred at room temperature for overnight. The reaction mixture was basified with $NaHCO_3$ solution and extracted with EtOAc (20 mL×3). The combined organic layers were washed with water and brine, dried over $Na_2SO_4$ and concentrated. The residue was used in the next step without further purification. MS Calcd.: 266.0; MS Found: 267.0 [M+H]$^+$.

The Synthesis of N-(2-(1H-1,2,4-triazol-1-yl)ethyl)-6-chloro-2-phenylpyridin-3-amine (214-4)

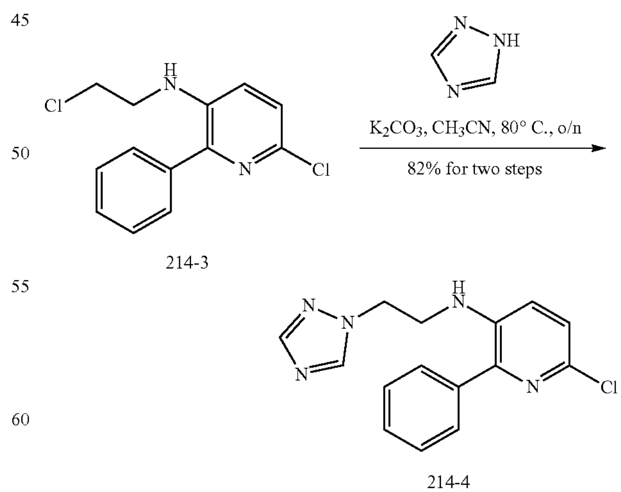

214-3

214-4

A mixture of 214-3 (1.31 g, 4.9 mmol), 1H-1,2,4-triazole (508 mg, 7.36 mmol) and $K_2CO_3$ (1.02 g, 7.36 mmol) in $CH_3CN$ (40 mL) was stirred at 80° C. for overnight. Then the reaction mixture was cooled down to room temperature and filtered. The filtrate was concentrated and purified by column chromatography (EtOAc/petroleum ether=1/1, EtOAc) to give 214-4 (1.2 g, about 82% yield for two steps) as a solid. MS Calcd.: 299.1; MS Found: 300.4 $[M+H]^+$.

The Synthesis of $N^5$-(2-(1H-1,2,4-triazol-1-yl)ethyl)-$N^2$-benzyl-6-phenylpyridine-2,5-diamine (SS20308-0214-01)

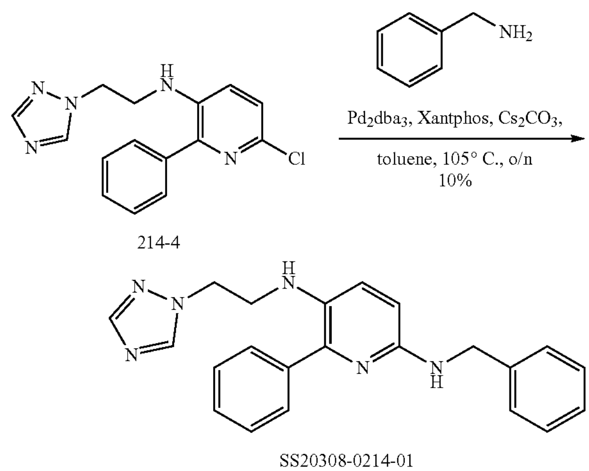

214-4

SS20308-0214-01

A solution of 214-4 (50 mg, 0.17 mmol), benzylamine (36 mg, 0.34 mmol), Xantphos (20 mg, 0.035 mmol), $Pd_2(dba)_3$ (16 mg, 0.017 mmol), and anhydrous cesium carbonate (163 mg, 0.5 mmol) were suspended in toluene (2 mL). The reaction mixture was heated to 110° C. for overnight under $N_2$ and then filtered and rinsed with EtOAc. The filtrate was concentrated and purified by Prep-HPLC to give SS20308-0214-01 (6 mg, about 10% yield) as a semisolid. MS Calcd.: 370.2; MS Found: 371.0 $[M+H]^+$.

$^1H$ NMR (400 MHz, $CD_3OD$) δ 8.32 (s, 1H), 7.92 (s, 1H), 7.43-7.35 (m, 7H), 7.34-7.29 (m, 2H), 7.26-7.20 (m, 1H), 7.11 (d, J=8.8 Hz, 1H), 6.47 (d, J=8.8 Hz, 1H), 4.44 (s, 2H), 4.33 (t, J=5.8 Hz, 2H), 3.48 (t, J=5.6 Hz, 2H).

Example 13

SS20308-0215-01

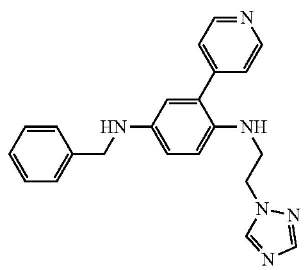

Chemical Formula: $C_{22}H_{22}N_6$
Molecular Weight: 370.45

Example Route for Example 13

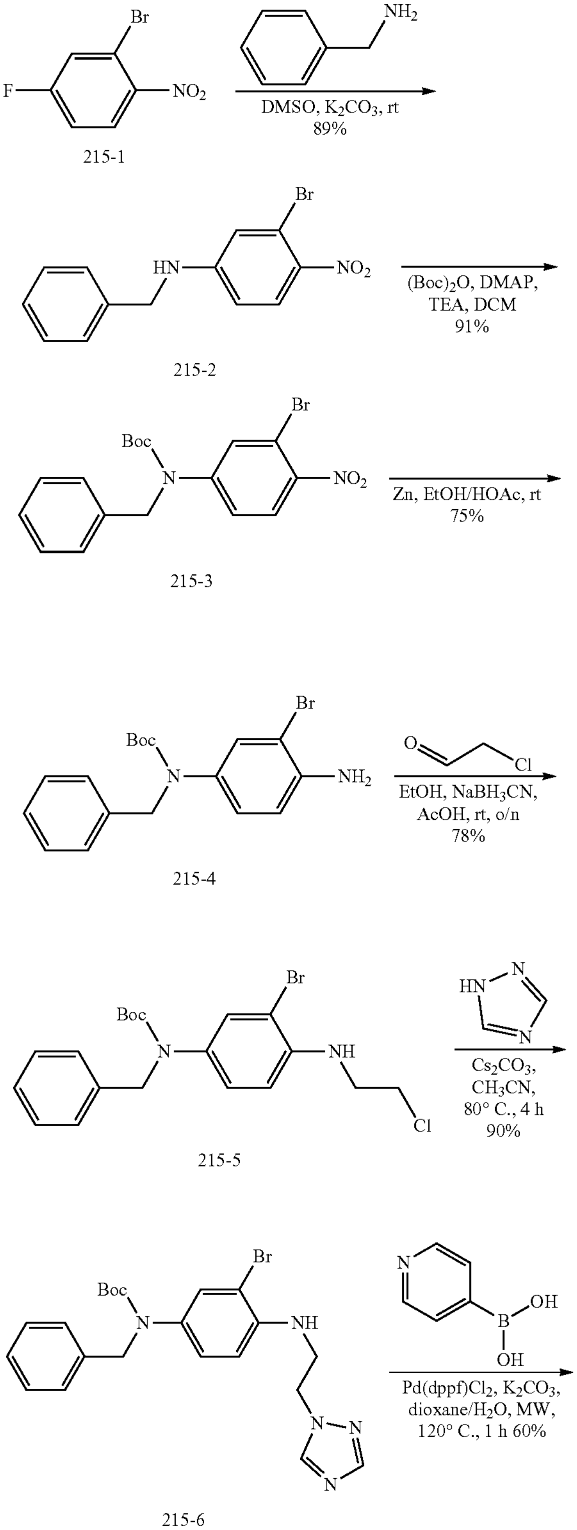

215-1

215-2

215-3

215-4

215-5

215-6

-continued

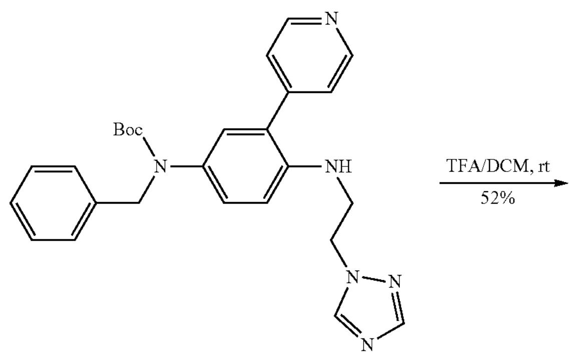

215-7

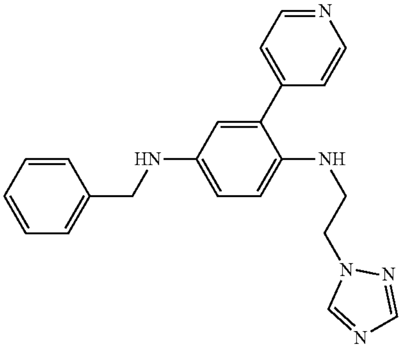

SS20308-0215-01

The Synthesis of N-benzyl-3bromo-4-nitroaniline (215-2):

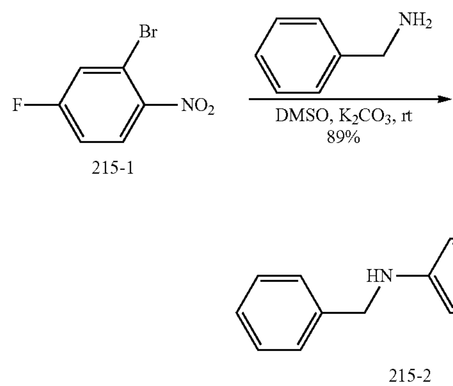

215-1

215-2

To a solution of 214-1 (5.00 g, 22.73 mmol) and phenylmethanamine (2.43 g, 22.73 mmol) in DMSO (50 mL) was added $K_2CO_3$ (6.27 g, 45.46 mmol). The reaction mixture was stirred at room temperature for overnight. The mixture was poured into water and extracted with EtOAc (50 mL×3). The combined organic layers were washed with water and brine, dried over $Na_2SO_4$ and concentrated. The crude product was purified by silica gel column chromatography (petroleum ether/EtOAc=20/1, 10/1) to give compound 0215-2 (6.2 g, about 89% yield) as a solid. MS Calcd.: 306.0; MS Found: 307.0 $[M+H]^+$.

The Synthesis of tert-butyl benzyl(3-bromo-4-nitrophenyl)carbamate (215-3)"

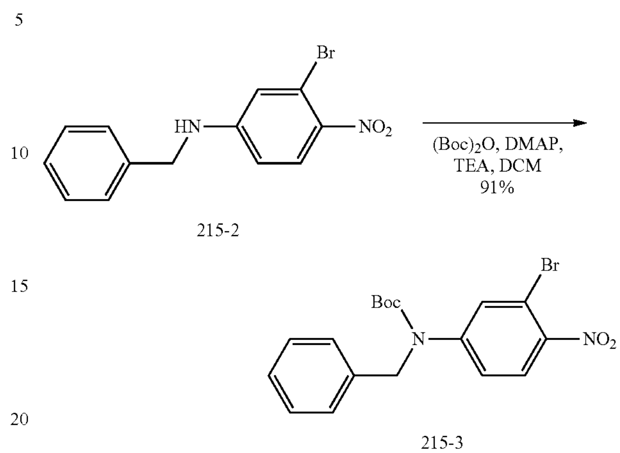

215-2

215-3

To a solution of 215-2 (5.00 g, 16.29 mmol) in DCM (50 mL) was added TEA (3.29 g, 32.57 mmol) and DMAP (1.99 g, 16.29 mmol), cooled to 0° C., then $(Boc)_2O$ (5.33 g, 24.44 mmol) was added dropwise over 10 min. The solution was then stirred at room temperature for overnight. Water was added to the solution and extracted with DCM (50 mL×3). The combined organic layers were washed with water and brine, dried over $Na_2SO_4$ and concentrated, purified by silica gel column chromatography (petroleum ether/EtOAc=30/1, 10/1) to give 215-3 (6.0 g, about 91% yield) as a solid. MS Calcd.: 406.0; MS Found: 351.0 $[M-55]^+$.

The Synthesis of tert-butyl 4-amino-3-bromophenyl(benzyl)carbamate (215-4)

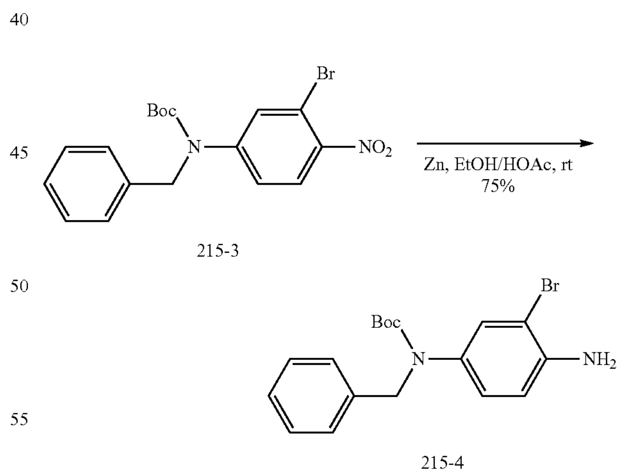

215-3

215-4

To a solution of 214-3 (6.00 g, 14.74 mmol) in EtOH (60 mL) was added AcOH (6 mL) and Zn powder (9.58 g, 147.40 mmol). The mixture was stirred at room temperature for 2 h then filtered. The filtrate was concentrated and purified by silica gel column chromatography (petroleum ether/EtOAc=10/1, 5/1) to give 215-4 (4.2 g, about 75% yield) as a solid. MS Calcd.: 376.0; MS Found: 377.0 $[M+H]^+$.

The Synthesis of tert-butyl benzyl(3-bromo-4-(2-chloroethylamino)phenyl)carbamate (215-5)

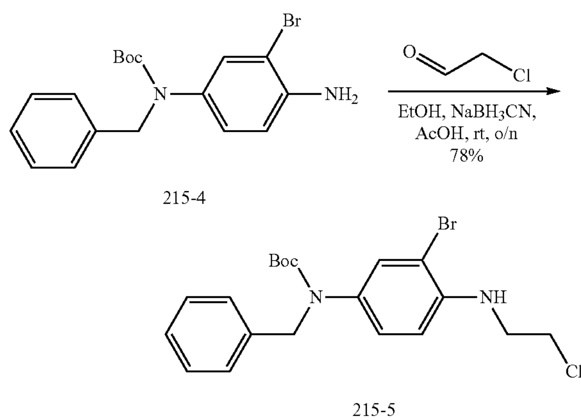

215-4

215-5

To a solution of 215-4 (4.00 g, 14.44 mmol) in EtOH (50 mL) was added 2-chloroacetaldehyde (40 wt. % aq., 5.66 g, 28.88 mmol), $NaBH_3CN$ (1.81 g, 28.88 mmol) and AcOH (5 mL). The reaction mixture was stirred at room temperature for overnight. Concentrated to remove the solvent. The residue was dissolved in EtOAc and water, extracted with EtOAc (50 mL×3). The combined organic layers were washed with water and brine, dried over $Na_2SO_4$ and concentrated, purified by silica gel column chromatography (petrol eumether/EtOAc=20/1, 10/1) to give compound 215-5 (3.6 g, about 78% yield) as a solid. MS Calcd.: 438.0; MS Found: 439.0 $[M+H]^+$.

The Synthesis of tert-butyl 4-(2-(1H-1,2,4-triazol-1-yl)ethylamino)-3-bromophenyl(benzyl)carbamate (215-6)

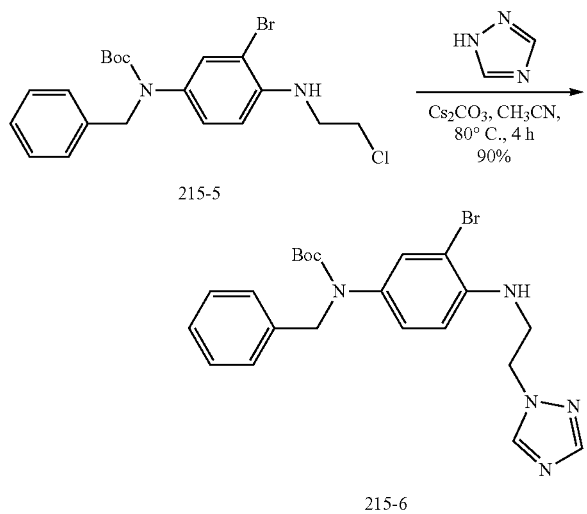

215-5

215-6

To a solution of 215-5 (3.60 g, 8.22 mmol) in $CH_3CN$ (50 mL) was added 1H-1,2,4-triazole (40 wt. % aq., 0.68 g, 9.86 mmol) and $Cs_2CO_3$ (5.36 g, 16.44 mmol). The mixture was stirred at 80° C. for 4 h. Cooled to room temperature and filtrated, the filtrate was concentrated then purified by silica gel column chromatography (petroleum ether/EtOAc=3/1 to 1/1) to give 215-6 (3.5 g, about 90% yield) as a solid.

$^1H$ NMR (400 MHz, DMSO-$d_6$) δ 8.49 (s, 1H), 7.97 (s, 1H), 7.33-7.29 (m, 2H), 7.25-7.17 (m, 4H), 6.95 (d, J=8.8 Hz, 1H), 6.61 (d, J=8.8 Hz, 1H), 5.35-5.32 (m, 1H), 4.72 (s, 2H), 4.37 (t, J=6.0 Hz, 2H), 3.51 (q, J=6 Hz, 2H), 1.37 (s, 9H).

The Synthesis of tert-butyl 4-(2-(1H-1,2,4-triazol-1-yl)ethylamino)-3-(pyridin-4-yl)phenyl(benzyl)-carbamate (215-7)

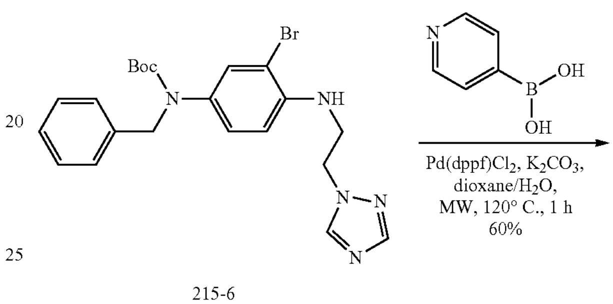

215-6

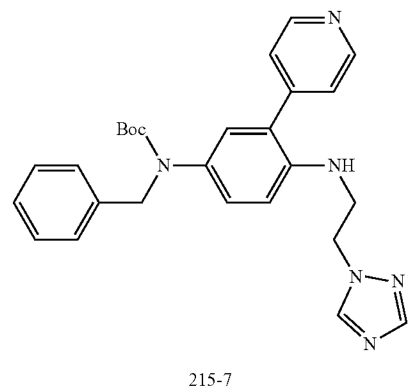

215-7

To a solution of 215-6 (200 mg, 0.42 mmol) in 1,4-dioxane/$H_2O$ (5 mL/0.5 mL) was added pyridin-4-ylboronic acid (104 mg, 0.84 mmol), $K_2CO_3$ (116 mg, 0.84 mmol) and $Pd(dppf)Cl_2$ (30 mg, 0.04 mmol). The mixture was stirred at 120° C. under microwave for 1 h. Filtered and the filtrate was concentrated then purified by silica gel column chromatography (petroleum ether/EtOAc=3/1, 1/1) to give 215-7 (120 mg, about 60% yield) as a solid. MS Calcd.: 470.0; MS Found: 471.0 $[M+H]^+$.

The Synthesis of N1-(2-(1H-1,2,4-triazol-1-yl)ethyl)-N4-benzyl-2-(pyridin-4-yl)benzene-1,4-diamine (SS20308-0215-01)

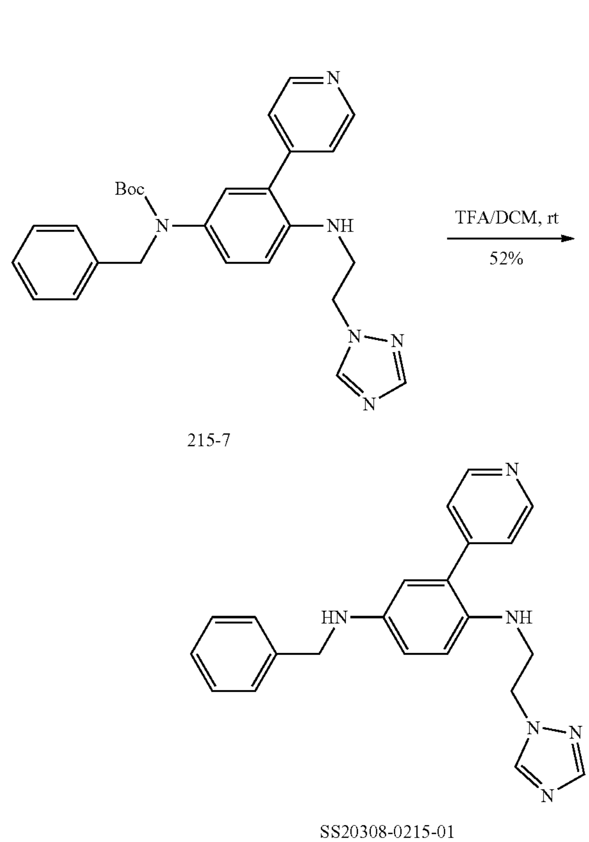

215-7

SS20308-0215-01

To a solution of 215-7 (120 mg, 0.25 mmol) in DCM (5 mL) was added TFA (1 mL). The solution was stirred at room temperature for overnight. The solution was basicified with $NaHCO_3$ solution and extracted with DCM (10 mL×3). The combined organic layers were washed with water and brine, dried over $Na_2SO_4$ and concentrated, purified by prep-HPLC to give SS20308-0215-01 (50 mg, about 52% yield) as a solid. MS Calcd.: 370.0; MS Found: 371.0 $[M+H]^+$.

$^1$H NMR (400 MHz, DMSO-$d_6$) δ 8.55-8.53 (m, 2H), 8.42 (s, 1H), 7.94 (s, 1H), 7.36-7.29 (m, 4H), 7.26-7.20 (m, 3H), 6.58-6.56 (m, 2H), 6.43 (d, J=2.4 Hz, 1H), 4.29 (t, J=6.0 Hz, 2H), 4.20 (s, 2H), 3.31 (t, J=5.6 Hz, 2H).

Example 14

SS20308-0216-01

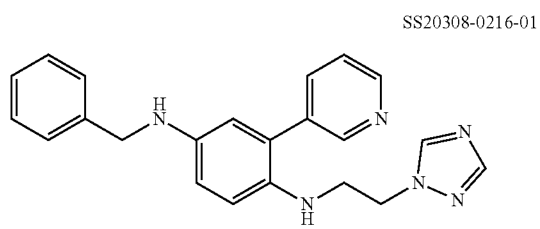 [SMILES: c1ccc(CNc2ccc(NCCn3cncn3)c(-c3cccnc3)c2)cc1]

Example Route for Example 14

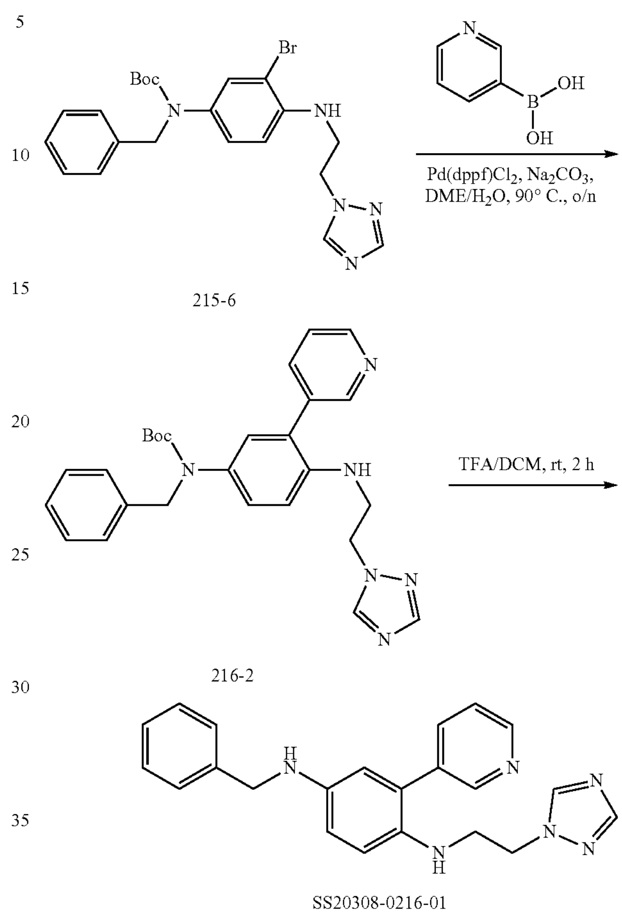

215-6

216-2

SS20308-0216-01

The Synthesis of tert-butyl 4-(2-(1H-1,2,4-triazol-1-yl)ethylamino)-3-(pyridin-3-yl)phenyl(benzyl) carbamate (SS20308-0216-2)

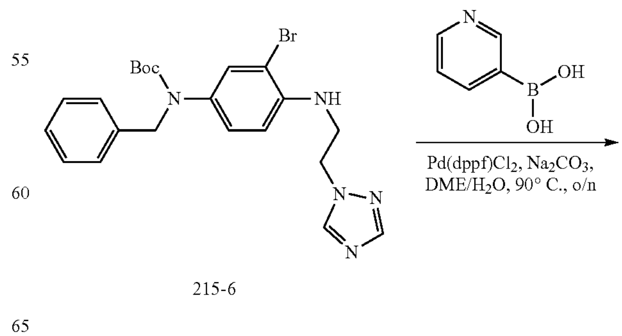

215-6

-continued

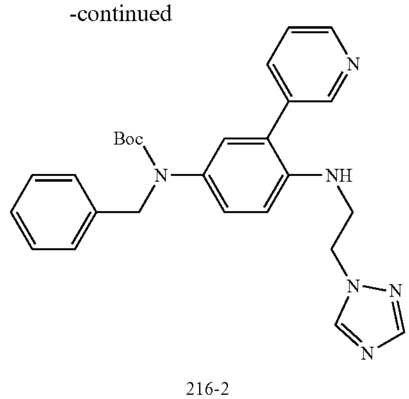

216-2

The mixture of 215-6 (300 mg, 0.64 mmol), pyridin-3-ylboronic acid (117 mg, 0.95 mmol), Pd(dppf)$Cl_2$ (47 mg, 0.064 mmol), and $Na_2CO_3$ (203 mg, 1.92 mmol) in DMF/$H_2O$ (10 mL, 5/1) was stirred at 90° C. under $N_2$ atmosphere overnight. Then mixture was poured into water and extracted with EtOAc (30 mL×3) and the organic layers were washed with brine, dried over $MgSO_4$ and concentrated. The residue was purified by Prep-TLC to give 216-2 (200 mg, about 66.8% yield) as a oil. MS Calcd.: 470.2; MS Found: 471.0 $[M+H]^+$.

The Synthesis of $N^1$-(2-(1H-1,2,4-triazol-1-yl)ethyl)-$N^4$-benzyl-2-(pyridin-3-yl)benzene-1,4-diamine (SS20308-0216-01)

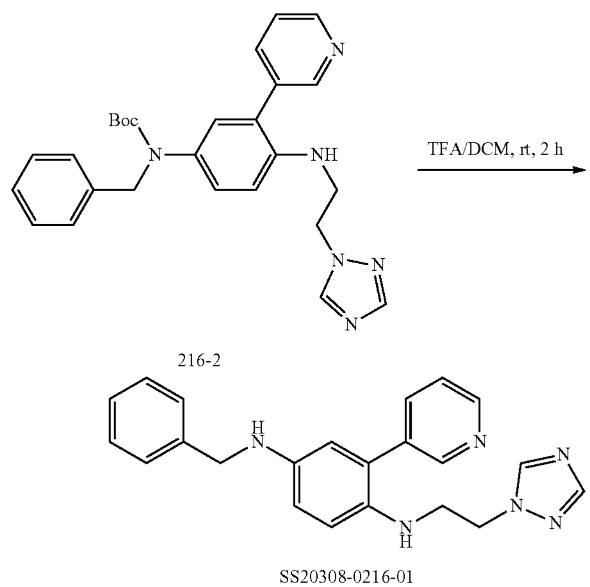

216-2

SS20308-0216-01

The mixture of 216-2 (200 mg, 0.43 mmol), and TFA (0.1 mL, 1.26 mmol) in DCM (5 mL) was stirred at rt for 2 h. Then the mixture was poured into water and extracted with $CH_2Cl_2$ (3×30 mL). The combined organic layers were washed with water and brine, dried over $Na_2SO_4$ and concentrated. The residue was purified by Prep-TLC to give SS20308-0216-01 (126 g, about 80% yield) as a solid. MS Calcd.: 370.2; MS Found: 371.0 $[M+H]^+$.

$^1$H NMR (400 MHz, DMSO-$d_6$) δ 8.50 (d, J=1.6 Hz, 1H), 8.43 (d, J=1.6 Hz, 1H), 8.41 (s, 1H), 7.92 (s, 1H), 7.62-7.65

(m, 1H), 7.29-7.41 (m, 5H), 7.21 (t, J=7.2 Hz, 1H), 6.52-6.59 (m, 2H), 6.40 (d, J=2.8 Hz, 1H), 5.67-5.70 (m, 1H), 4.20-4.29 (m, 4H), 3.28-3.30 (m, 2H).

Example 15

SS20308-0217-01

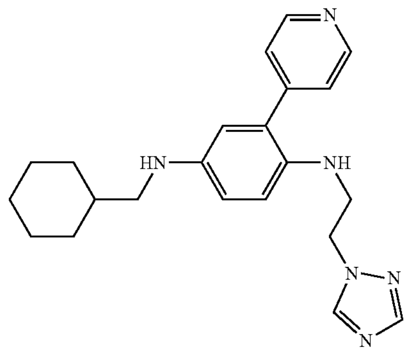

Example Route for Example 15

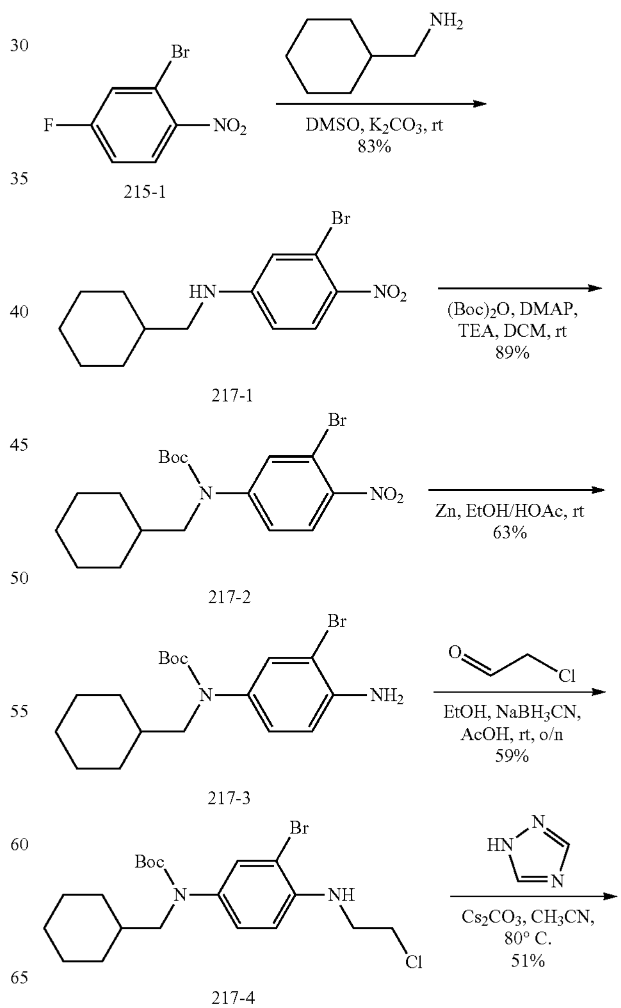

215-1

217-1

217-2

217-3

217-4

-continued

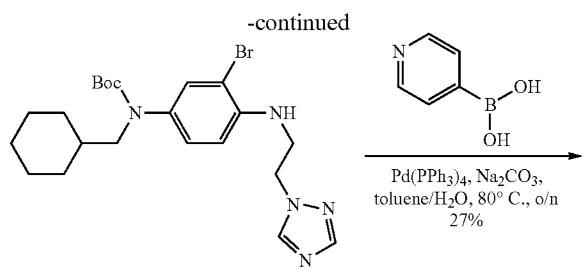

217-5

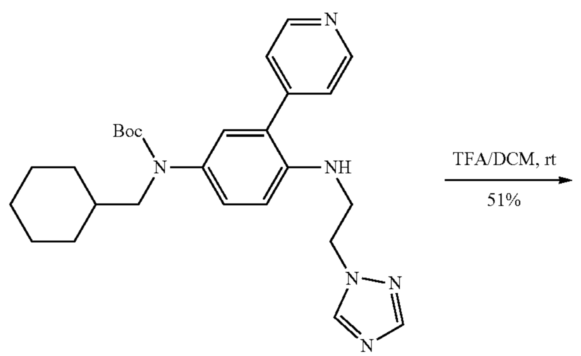

217-6

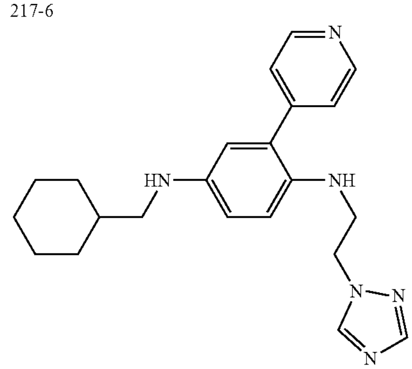

SS20308-0217-01

The Synthesis of 3-bromo-N-(cyclohexylmethyl)-4-nitroaniline (217-1)

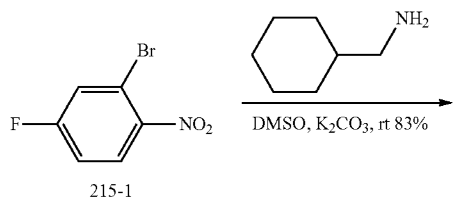

215-1

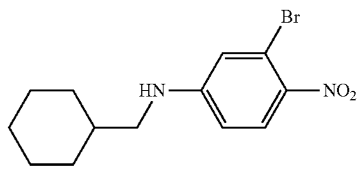

217-1

To a solution of 215-1 (3.0 g, 12.4 mmol) in DMSO (20.0 mL) was added cyclohexylmethanamine (1.7 g, 15.0 mmol) and $K_2CO_3$ (3.6 g, 27.0 mmol). Then stirred the mixture for 4 h. After the reaction was completed, the reaction mixture was quenched with water, and extracted with EtOAc (20.0 mL×3). The organic layers were washed with brine, dried over $MgSO_4$ and concentrated to give 217-1 (3.5 g, about 83% yield) as an oil. MS Calcd.: 312.0; MS Found: 313.0 $[M+H]^+$.

The Synthesis of tert-butyl 3-bromo-4-nitrophenyl(cyclohexylmethyl)carbamate (217-2)

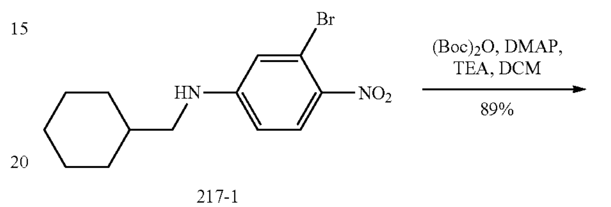

217-1

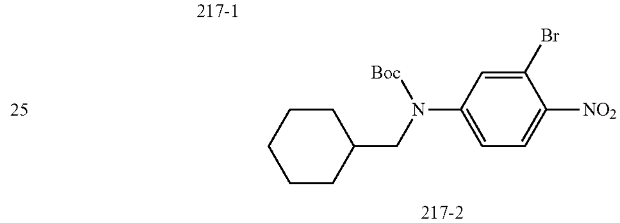

217-2

A mixture of 217-1 (3.5 g, 11.2 mmol), $(Boc)_2O$ (3.2 g, 15.0 mmol), DMAP (600.0 mg, 5.0 mmol), TEA (2.0 g, 20.0 mmol) in DCM (20.0 ml) was stirred at room temperature overnight. After the reaction was completed, the mixture was quenched with water, then extracted with EtOAc (20.0 mL×3). The organic layer was separated, dried over $MgSO_4$, and concentrated to give 217-2 (3.8 g, about 89% yield) as an oil.

The Synthesis of tert-butyl 4-amino-3-bromophenyl(cyclohexylmethyl)carbamate (217-3)

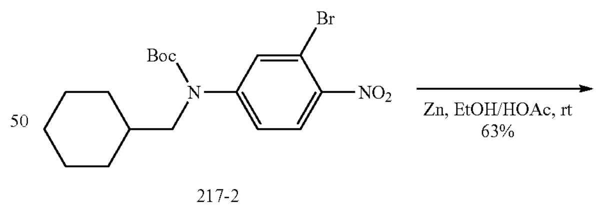

217-2

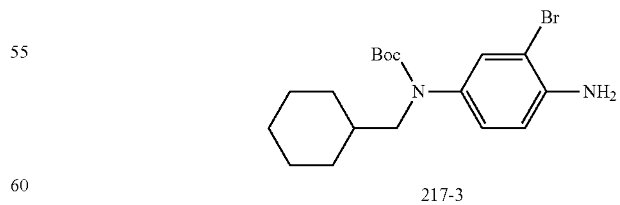

217-3

A mixture of 217-2 (3.8 g, 9.2 mmol), Zn powder (2.9 mg, 45.0 mmol) and HOAc (2.8 g, 45.0 mmol) in EtOH (20.0 ml) was stirred at room temperature overnight. After the reaction was completed, the mixture was quenched with water and $NaHCO_3$, then extracted with EtOAc (20.0 mL×3). The organic layer was separated, dried over $MgSO_4$, and concentrated. The residue was purified by column chromatography (petroleum ether/EtOAc=10/1) to give 217-3 (2.2 g, about 63% yield) as a solid. MS Calcd.: 382.0; MS Found: 328.0 $[M+H]^+$.

The Synthesis of tert-butyl 3-bromo-4-(2-chloroethylamino)phenyl(cyclohexylmethyl)carbamate (217-4)

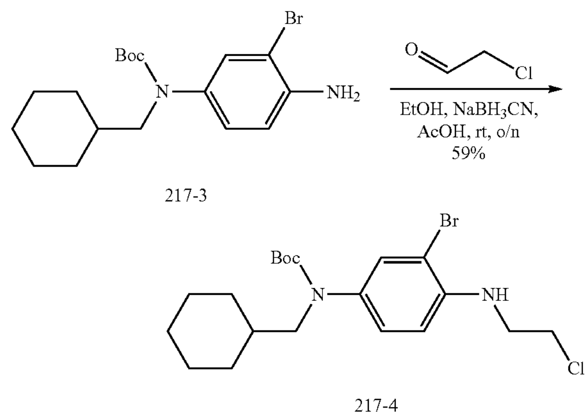

217-3

217-4

A solution of 217-3 (1.2 g, 3.0 mmol) and 2-chloroacetaldehyde (1.0 g, 4 mmol) in EtOH (10.0 mL) was added $NaBH_3CN$ (372.0 mg, 6.0 mmol), AcOH (2.0 ml). Then stirred the mixture overnight. After the reaction was completed, the reaction was purified by column chromatography to give 217-4 (770.0 mg, about 59% yield) as an oil. MS Calcd.: 444.0; MS Found: 445.0 $[M+H]^+$.

The Synthesis of tert-butyl4-(2-(1H-1,2,4-triazol-1-yl)ethylamino)-3-bromophenyl(cyclohexylmethyl) carbamate (217-5)

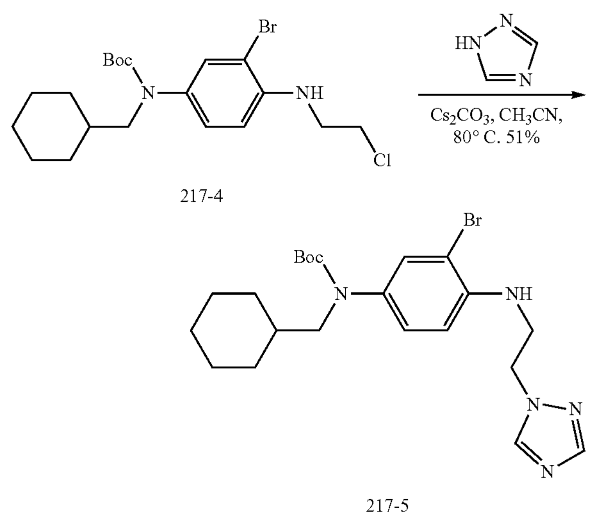

217-4

217-5

A mixture of 217-4 (770.0 mg, 1.73 mmol) and 1H-1,2,4-triazole (320 mg, 4.4 mmol) in ACN (10.0 mL) was added $Cs_2CO_3$ (1.1 g, 3.5 mmol), then stirred at 80° C. overnight.

Then the reaction mixture was quenched with $H_2O$, and extracted with EtOAc (20.0 mL×3). The organic layers were washed with water and brine, dried over $MgSO_4$ and concentrated. The residue was purified by column chromatography (petroleum ether/EtOAc=1/1) give 217-5 (420.0 mg, about 51% yield) as an oil. MS Calcd.: 477.0; MS Found: 478.0 $[M+H]^+$.

The Synthesis of tert-butyl 4-(2-(1H-1,2,4-triazol-1-yl)ethylamino)-3-(pyridin-4-yl)phenyl(cyclohexylmethyl)carbamate (217-6)

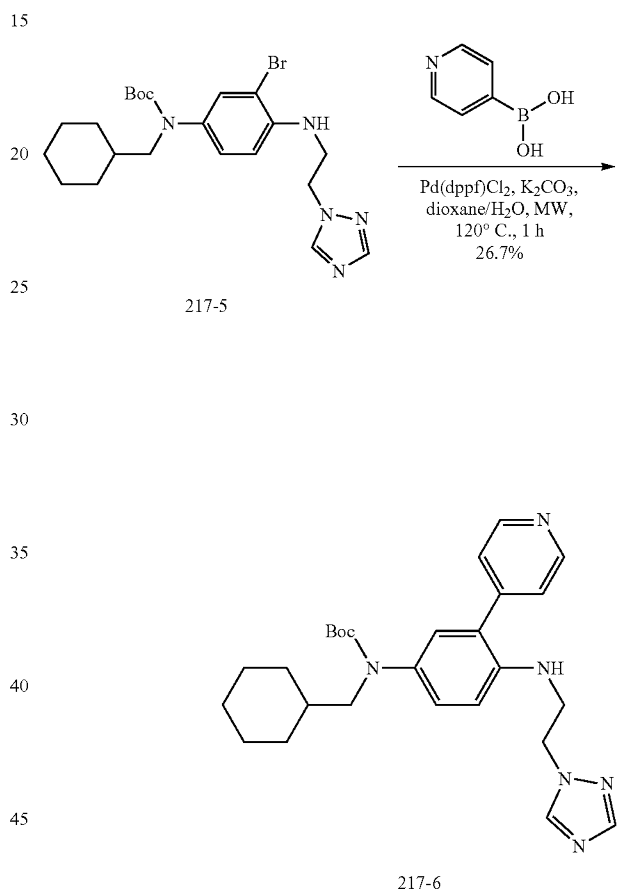

217-5

217-6

A mixture of 217-5 (300.0 mg, 0.6 mmol), pyridin-4-ylboronic acid (200.0 mg, 1.6 mmol), pd(dppf)$Cl_2$ (10.0 mg, 0.1 mmol), $K_2CO_3$ (150.0 mg, 1.1 mmol) in dioxane (3.0 mL) was stirred under MW at 120° C. for 1 h, After the reaction was completed, the mixture was quenched with water, then extracted with EtOAc (5.0 mL×3). The organic layer was separated, dried over $MgSO_4$, and concentrated, the reaction was purified by column chromatography to give 217-6 (80 mg, about 27%) as a solid. MS Calcd.: 477.0; MS Found: 478.0 $[M+H]^+$.

The Synthesis of N[1]-(2-(1H-1,2,4-triazol-1-yl)ethyl)-N[4]-(cyclohexylmethyl)-2-(pyridin-4-yl)benzene-1,4-diamine (217-01)

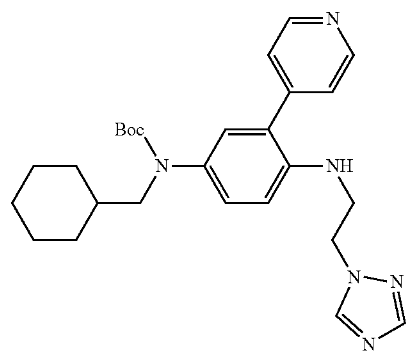

217-6

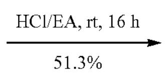

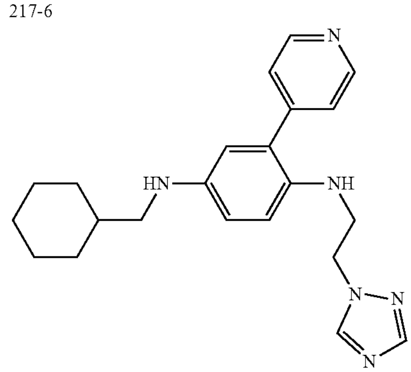

SS20308-0217-01

To a solution of 217-6 (50.0 mg, 0.1 mmol) in HCl/EA (10.0 ml of 1M). Stirred the mixture overnight. Then the reaction mixture was quenched with $H_2O$, and extracted with EtOAc (5 mL×3). The organic layers were washed with water and brine, dried over $MgSO_4$ and concentrated. The residue was purified by Prep-HPLC to give 217 (20.0 mg, about 51% yield) as an oil. MS Calcd.: 376.0; MS Found: 377.0 $[M+H]^+$.

$^1H$ NMR (400 MHz, DMSO-$d_6$+$D_2O$) δ 8.60 (s, 2H), 8.42 (s, 1H), 7.97 (s, 1H), 7.32 (s, 2H), 6.66 (s, 2H), 6.45 (s, 1H), 4.32 (s, 2H), 3.58 (s, 2H), 2.81 (s, 2H), 1.75-1.52 (m, 5H), 1.50 (s, 1H), 1.23-1.96 (m, 3H), 0.93 (s, 2H).

Example 16

SS20308-0218-01

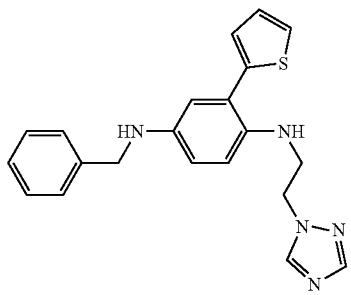

Chemical Formula: $C_{21}H_{21}N_5S$
Molecular Weight: 375.49

Example Route for Example 16

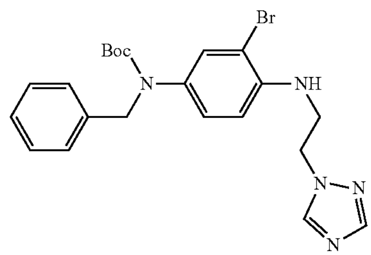

215-6

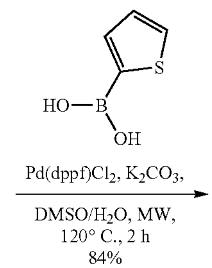

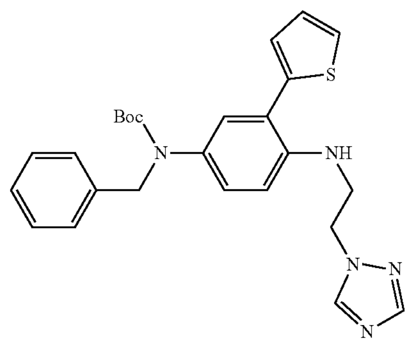

218-1

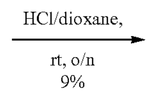

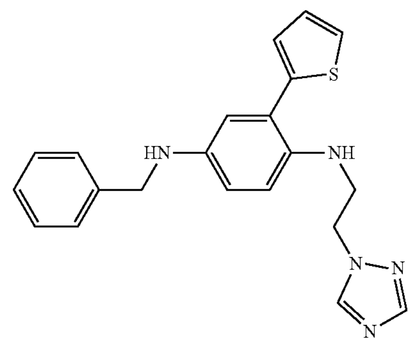

SS20308-0218-01

The Synthesis of tert-butyl 4-(2-(1H-1,2,4-triazol-1-yl)ethylamino)-3-(thiophen-2-yl)phenyl(benzyl)carbamate (218-1)

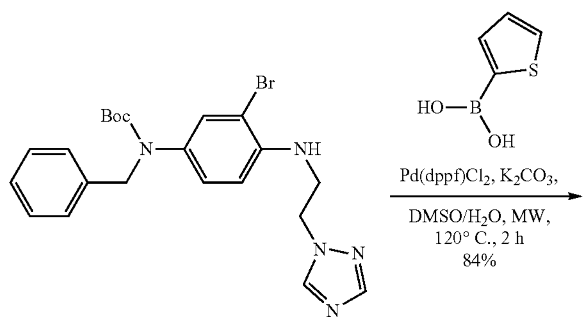

215-6

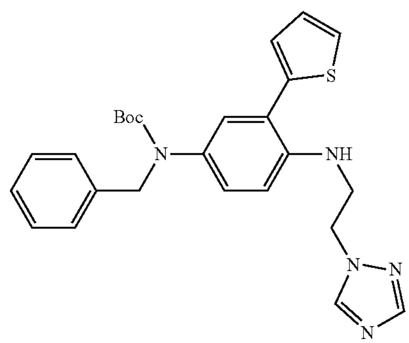

218-1

The mixture of 215-6 (500 mg, 1.06 mmol), 2-thiophene boronic acid (271 mg, 2.12 mmol), Pd(dppf)$Cl_2$ (78 mg, 0.11 mmol), and $K_2CO_3$ (293 mg, 2.12 mmol) in DMSO (5 mL) and water (0.5 mL) was stirred at 120° C. for two hours in the microwave reactor. The reaction mixture was then cooled to room temperature and filtered through celite and concentrated. Then the reaction mixture was poured into water (20 mL). The mixture was extracted with EtOAc (30 mL×3). The organic layers were washed with brine, dried over $Na_2SO_4$ and concentrated. The residue was purified via column chromatography (petroleum ether/EtOAc=1/1) to give 218-1 (450 mg, about 84% yield) as an oil. MS Calcd.: 475.2; MS Found: 476.4 $[M+H]^+$.

The Synthesis of $N^1$-(2-(1H-1,2,4-triazol-1-yl)ethyl)-$N^4$-benzyl-2-(thiophen-2-yl)benzene-1,4-diamine (SS20308-0218-01)

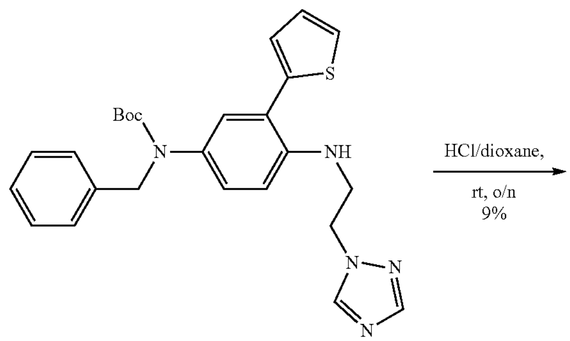

218-1

-continued

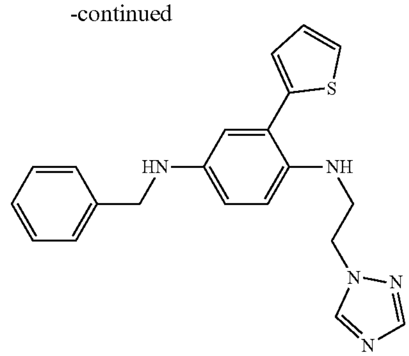

SS20308-0218-01

The mixture of 218-1 (450 mg, 0.94 mmol) and HCl (2 mL, 2 mmol, 1N in dioxane) in dioxane (5 mL) was stirred at room temperature overnight. Then the reaction mixture was poured into water and basified with 1N NaOH till pH reached 10. The mixture was extracted with EtOAc (50 mL×3). The organic layers were washed with brine, dried over $Na_2SO_4$ and concentrated. The residue was purified by column chromatography (petroleum ether/EtOAc=1/2) and Prep-HPLC to give SS20308-218-01 (31.15 mg, about 9% yield) as an oil. MS Calcd.: 375.1; MS Found: 376.0 $[M+H]^+$.

$^1$H NMR (400 MHz, DMSO-$d_6$) δ 8.45 (s, 1H), 7.94 (s, 1H), 7.50-7.49 (m, 1H), 7.36-7.28 (m, 4H), 7.22-7.18 (m, 1H), 7.09-7.04 (m, 2H), 6.58-6.56 (m, 2H), 6.51-6.49 (m, 1H), 5.74 (t, J=6.0 Hz, 1H), 4.40 (t, J=6.0 Hz, 1H), 4.35 (t, J=6.0 Hz, 2H), 4.20 (d, J=5.6 Hz, 2H), 3. (t, J=5.8 Hz, 2H)

Example 17

SS20308-0219-01

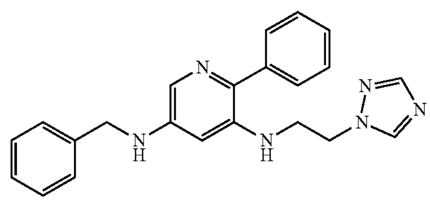

Chemical Formula: $C_{22}H_{22}N_6$
Molecular Weight: 370.45

Example Route for Example 17 (SS20308-0173-01 and 0219-01)

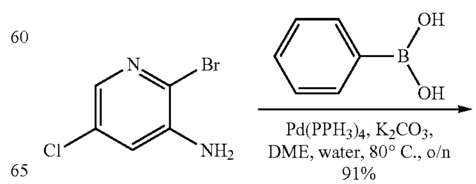

173-1

-continued

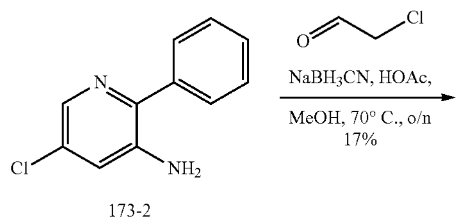

173-2

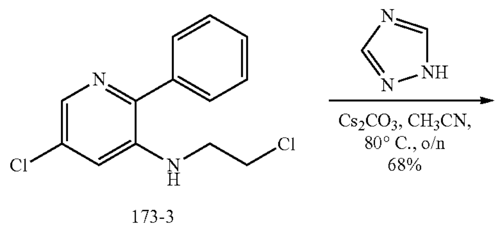

173-3

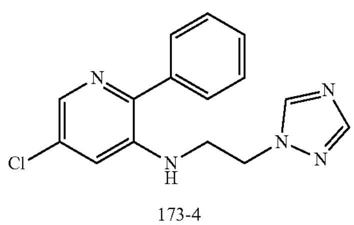

173-4

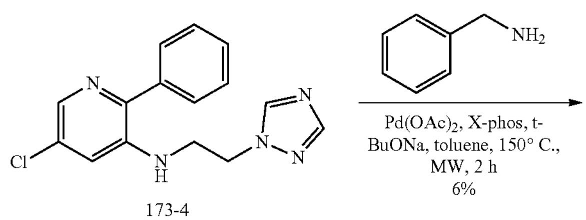

173-4

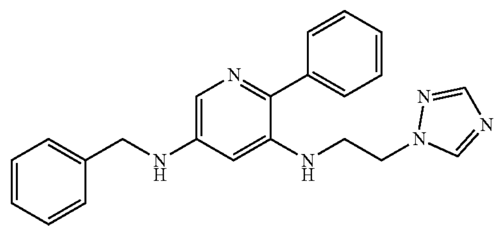

SS20308-0219-01

The Synthesis of 5-chloro-2-phenylpyridin-3-amine (173-2)

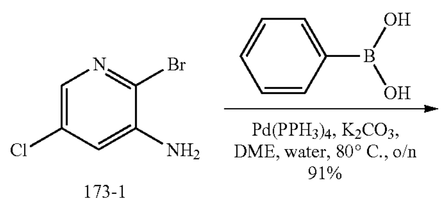

173-1

-continued

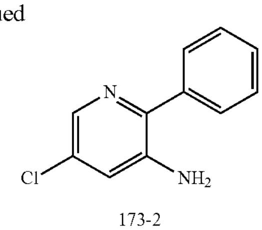

173-2

The mixture of 173-1 (500 mg, 2.42 mmol), phenyl boronic acid (590 mg, 4.84 mmol), $Pd(PPh_3)_4$ (277 mg, 0.24 mmol), $K_2CO_3$ (668 mg, 4.84 mmol) in DME (10 mL) and water (1 mL) was stirred at 80° C. overnight under N2 atmosphere. The reaction mixture was then cooled to room temperature and filtered through celite and concentrated. The residue was purified by Prep-TLC (petroleum ether/EtOAc=10/1) to give 173-2 (440 mg, about 91% yield) as an oil. MS Calcd.: 204.0; MS Found: 205.1 $[M+H]^+$.

The Synthesis of 5-chloro-N-(2-chloroethyl)-2-phenylpyridin-3-amine (173-3)

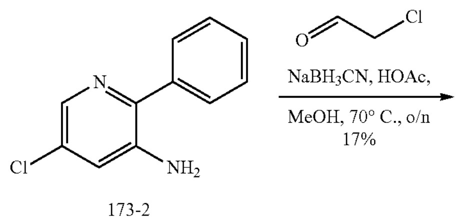

173-2

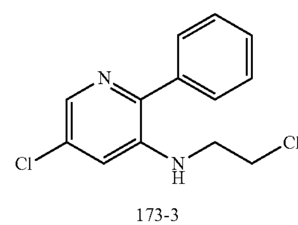

173-3

To a solution of 173-2 (450 mg, 2.20 mmol) in MeOH (10 mL) was added 2-chloroacetaldehyde (432 mg, 4.40 mmol, 40% in water), AcOH (264 mg, 4.40 mmol), and $NaBH_3CN$ (275 mg, 4.40 mmol), then the reaction mixture was stirred at room temperature overnight. Then the reaction mixture was poured into water and basified with 1N NaOH till pH reached 10. The mixture was extracted ethyl acetate (30 mL×3). The organic layers were washed with brine, dried over $Na_2SO_4$ and concentrated. The residue was purified column chromatography (petroleum ether/ethyl acetate=10/1) to give 173-3 (100 mg, about 17% yield) as a solid. MS Calcd.: 266.0; MS Found: 237.1 $[M+H]^+$.

The Synthesis of N-(2-(1H-1,2,4-triazol-1-yl)ethyl)-5-chloro-2-phenylpyridin-3-amine (173-4)

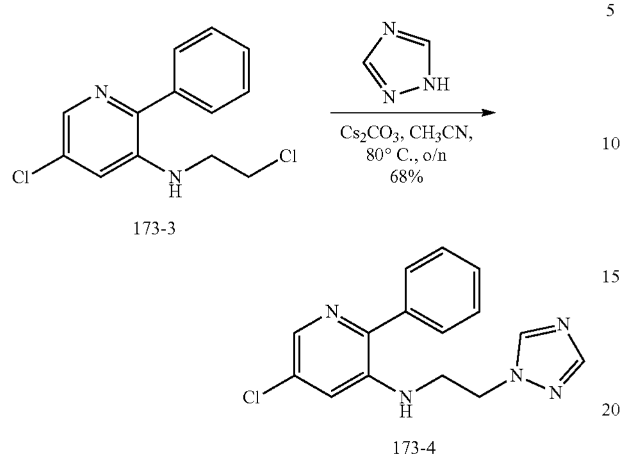

173-3

173-4

A mixture of 173-3 (100 ng, 0.37 mmol), 1H-1,2,4-triazole (52 mg, 0.74 mmol) and $Cs_2CO_3$ (240 mg, 0.74 mmol) in $CH_3CN$ (10 mL) was stirred at 80° C. overnight. The reaction mixture was then cooled to room temperature and filtered through diatomite and concentrated. The residue was purified by column chromatography (petroleum ether/ethyl acetate=1/1) to give 173-4 (77 mg, about 68% yield) as a solid. MS Calcd.: 299.1; MS Found: 300.2 $[M+H]^+$.

The Synthesis of $N^3$-(2-(1H-1,2,4-triazol-1-yl)ethyl)-$N^5$,2-diphenylpyridine-3,5-diamine (SS20308-0219-01)

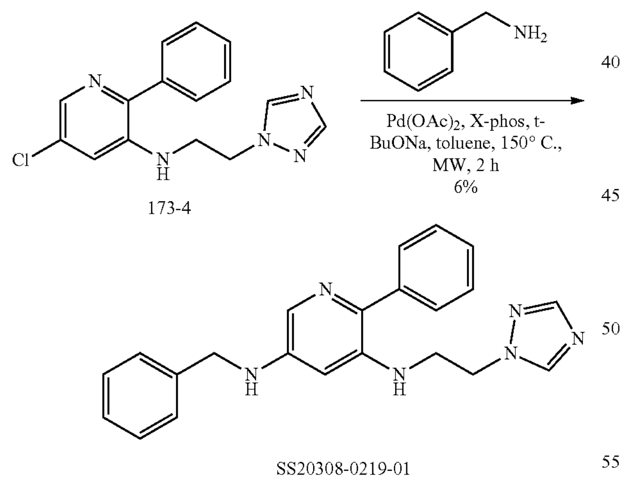

173-4

SS20308-0219-01

The mixture of 173-4 (300 mg, 1.00 mmol), phenylmethanamine (214 mg, 2.00 mmol), $Pd(OAc)_2$ (23 mg, 0.10 mmol), X-phos (95 mg, 0.20 mmol) and t-BuONa (186 mg, 2.00 mmol) in toluene (5 mL) was stirred at 150° C. two hours in microwave reactor. The reaction mixture was then cooled to room temperature and filtered through celite and concentrated. The residue was purified by Prep-TLC (petroleum ether/EtOAc=1/3) and Prep-HPLC to give SS20308-0219-01 (21 mg, about 6% yield) as a solid. MS Calcd.: 370.2; MS Found: 371.3 $[M+H]^+$.

$^1H$ NMR (400 MHz, DMSO-$d_6$) δ 8.42 (s, 1H), 7.97 (s, 1H), 7.41-7.39 (m, 9H), 7.27-7.21 (m, 2H), 6.40 (t, J=6.0 Hz, 1H), 6.25 (d, J=2.0 Hz, 1H), 4.97 (t, J=6.0 Hz, 1H), 4.32-7.28 (m, 4H), 3.40 (dd, J=12.0, 6.0 Hz, 2H).

Example 18

SS20308-0221-01

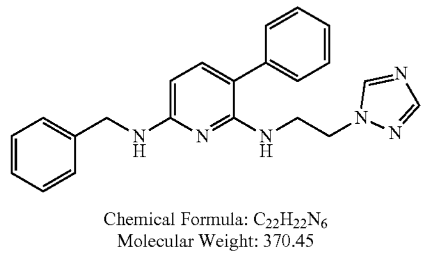

Chemical Formula: $C_{22}H_{22}N_6$
Molecular Weight: 370.45

Example Route for Example 18

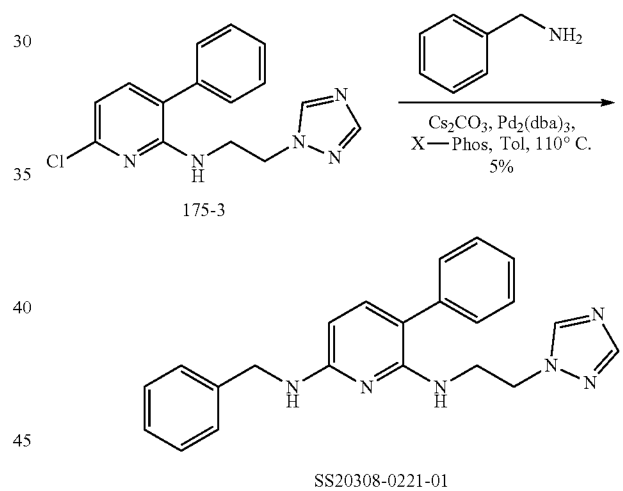

175-3

SS20308-0221-01

The Synthesis of $N^2$-(2-(1H-1,2,4-triazol-1-yl)ethyl)-$N^6$-benzyl-3-phenylpyridine-2,6-diamine (SS20308-0221-01)

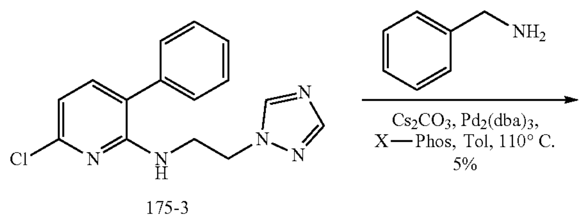

175-3

-continued

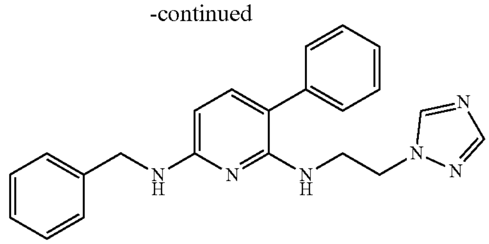

SS20308-0221-01

A mixture of 175-3 (130 mg, 0.43 mmol), phenylmethanamine (93 mg, 0.87 mmol), $Pd_2(dba)_3$ (40 mg, 0.04 mmol), $Cs_2CO_3$ (282 mg, 0.87 mmol) and X-Phos (41 mg, 0.09 mmol) in Tol (10 ml) was stirred at 110° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated under vacuum, which was purified by Prep-HPLC twice to give SS20308-0221-01 (8 mg, about 5% yield) as a solid. MS Calcd.: 370.2; MS Found: 371.3 $[M+H]^+$.

$^1H$ NMR (400 MHz, DMSO-$d_6$) δ 8.27 (s, 1H), 7.94 (s, 1H), 7.37-7.28 (m, 6H), 7.24-7.18 (m, 4H), 7.02 (d, J=8.0 Hz, 1H), 6.91 (t, J=6.0 Hz, 1H), 5.86 (d, J=8.0 Hz, 1H), 5.55 (t, J=5.6 Hz, 1H), 4.49 (d, J=6.0 Hz, 2H), 4.24 (t, J=6.0 Hz, 2H), 3.61-3.60 (m, 2H).

Example 19

SS20308-0225-01

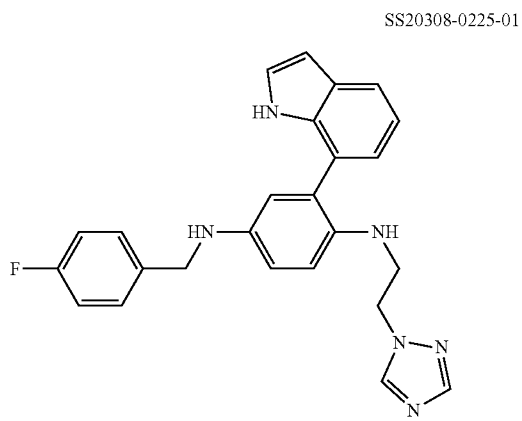 [SMILES: Fc1ccc(CNc2ccc(NCCn3cncn3)c(-c3cccc4cc[nH]c34)c2)cc1]

Example Route for Example 19

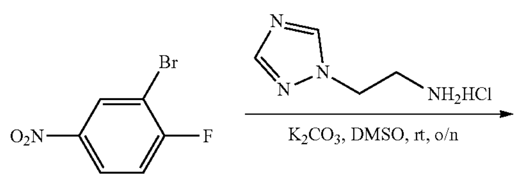

211-1

-continued

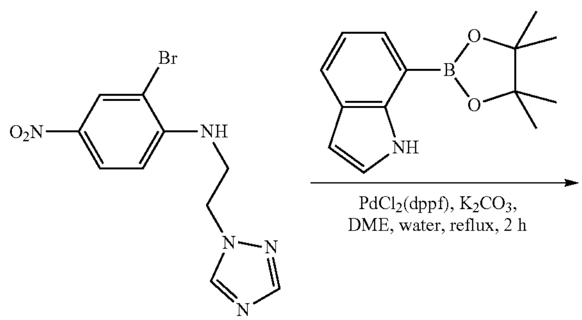

$PdCl_2(dppf)$, $K_2CO_3$,
DME, water, reflux, 2 h 211-2

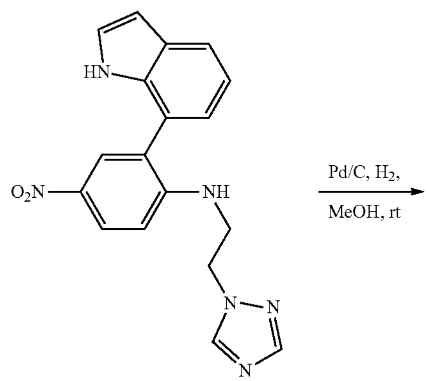

Pd/C, $H_2$,
MeOH, rt 211-3

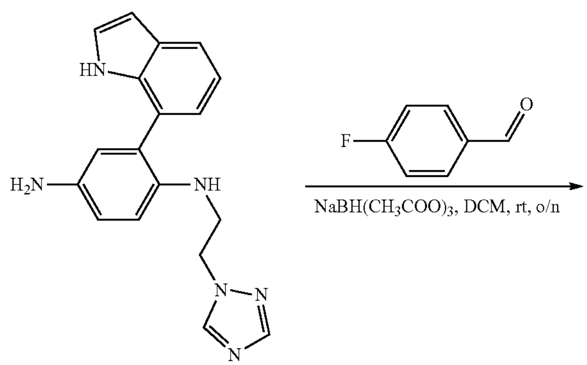

$NaBH(CH_3COO)_3$, DCM, rt, o/n 211-4

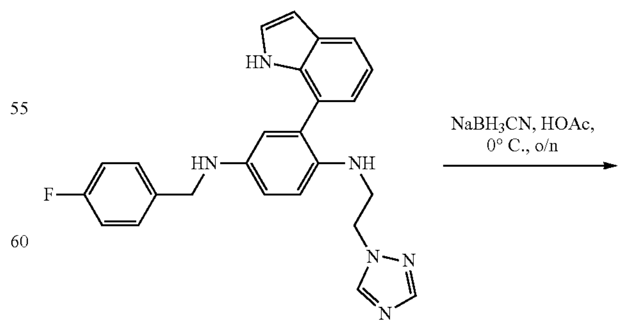

$NaBH_3CN$, HOAc,
0° C., o/n

SS20308-0225-01

-continued

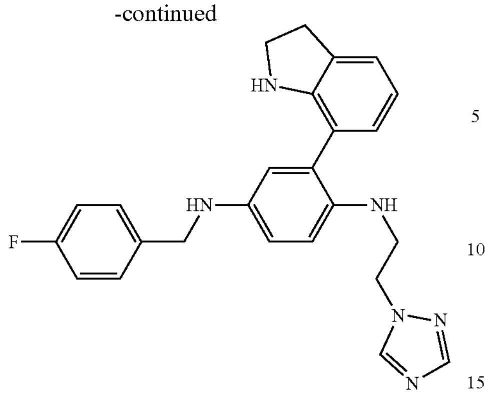

SS20308-0211-01

The Synthesis of N-(2-(1H-1,2,4-triazol-1-yl)ethyl)-2-bromo-4-nitroaniline (211-2)

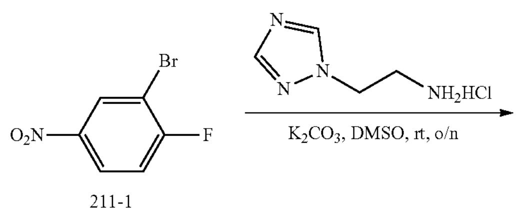

211-1

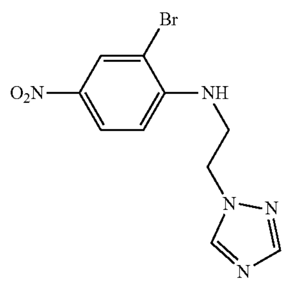

211-2

The mixture of 211-1 (2.20 g, 10.00 mmol), 2-(1H-1,2,4-triazol-1-yl)ethanamine hydrochloride (1.78 g, 12.00 mmol) and $K_2CO_3$ (4.15 g, 30.00 mmol) in DMSO (10 mL) was stirred at rt overnight. Then mixture was poured into water and extracted with ethyl acetate (30 mL×3) and the organic layers were washed with brine, dried over $MgSO_4$ and concentrated. The residue was purified by column chromatography (petroleum ether/EtOAc=1/1) to give 211-2 (2.00 g, about 64% yield) as a solid. MS Calcd.: 311.0; MS Found: 312.0 $[M+H]^+$.

The Synthesis of N-(2-(1H-1,2,4-triazol-1-yl)ethyl)-2-(1H-indol-7-yl)-4-nitroaniline (211-3)

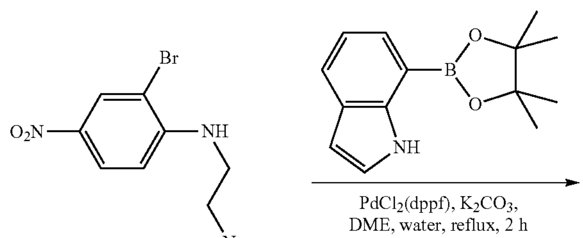

211-2

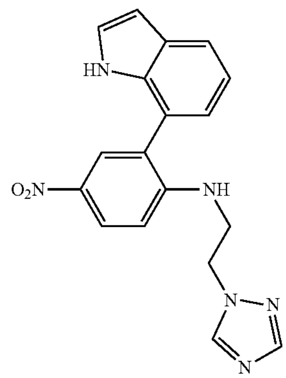

211-3

The mixture of 211-2 (2.00 g, 6.41 mmol), 7-(4,4,5,5-tetramethyl-1,3,2-dioxaborolan-2-yl)-1H-indole (2.34 g, 9.61 mmol), $Pd(dppf)Cl_2$ (469 mg, 0.64 mmol) and $K_2CO_3$ (2.66 g, 19.23 mmol) in DME/$H_2O$ (10 mL, 5/1) was stirred at 80° C. for 2 h under N2 atmosphere. The resulting mixture was extracted with ethyl acetate (30 mL×3) and the organic layers were washed with brine, dried over $MgSO_4$ and concentrated. The residue was purified by column chromatography (petroleum ether/EtOAc=1/1) to give 211-3 (1.80 g, about 81% yield) as a solid. MS Calcd.: 348.1; MS Found: 349.4 $[M+H]^+$.

The Synthesis of $N^1$-(2-(1H-1,2,4-triazol-1-yl)ethyl)-2-(1H-indol-7-yl)benzene-1,4-diamine (211-4)

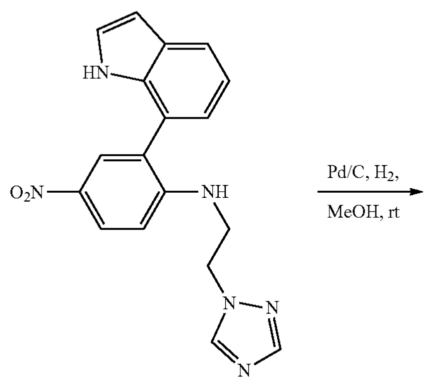

211-3

-continued

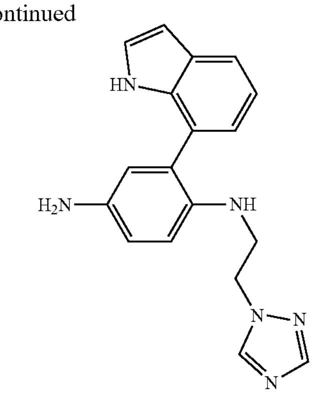

211-4

The mixture of 211-3 (1.00 g, 2.87 mmol), and 10% Pd/C (339 mg, 1.38 mmol) in MeOH (10 mL) was stirred at rt for 3 h under $H_2$ atmosphere. The reaction mixture was then cooled to room temperature and was purified by column chromatography (petroleum ether/EtOAc=1/1) to give 221-4 (0.78 g, about 86% yield) as a solid. MS Calcd.: 318.2; MS Found: 319.0 $[M+H]^+$ The Synthesis of $N^1$-(2-(1H-1,2,4-triazol-1-yl) ethyl)-$N^4$-(4-fluorobenzyl)-2-(1H-indol-7-yl)benzene-1,4-diamine (SS20308-0225-01)

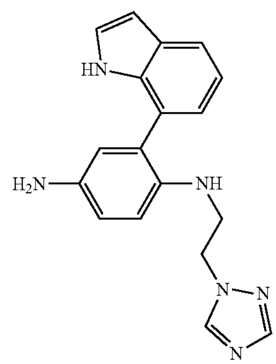

211-4

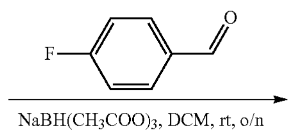

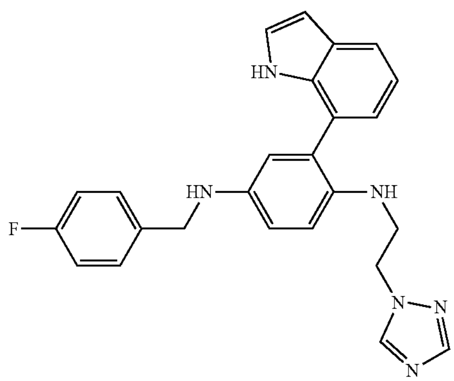

SS20308-0225-01

The mixture of 211-4 (600 mg, 1.88 mmol), 4-fluorobenzaldehyde (281 mg, 2.26 mmol), and $NaBH(CH_3COO)_3$ (479 mg, 2.26 mmol) in DCM (10 mL) was stirred at rt overnight. Then the mixture was poured into water and extracted with $CH_2Cl_2$ (3×30 mL). The combined organic layers were washed with water and brine, dried over $Na_2SO_4$ and concentrated. The residue was purified by column chromatography (petroleum ether/EtOAc=1/2) to give SS20308-0225-01 (360 mg, about 45% yield) as a solid. MS Calcd.: 426.2; MS Found: 427.0 $[M+H]^+$.

$^1H$ NMR (400 MHz, $CD_3OD-d_4$) δ 8.12 (s, 1H), 7.80 (s, 1H), 7.55 (d, J=8.0 Hz, 1H), 7.40 (q, J=5.6 Hz, 2H), 7.16 (d, J=3.2 Hz, 1H), 7.01-7.08 (m, 3H), 6.88 (d, J=6.8 Hz, 1H), 6.65-6.62 (m, 3H), 6.49 (d, J=3.2 Hz, 1H), 4.20-4.26 (m, 4H), 3.46-3.50 (m, 2H).

The Synthesis of $N^1$-(2-(1H-1,2,4-triazol-1-yl) ethyl)-$N^4$-(4-fluorobenzyl)-2-(indolin-7-yl)benzene-1,4-diamine (SS20308-0211-01)

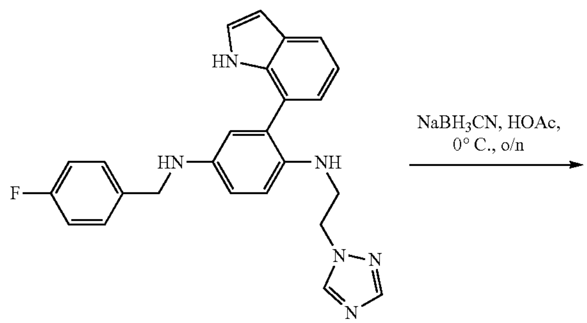

SS20308-0225-01

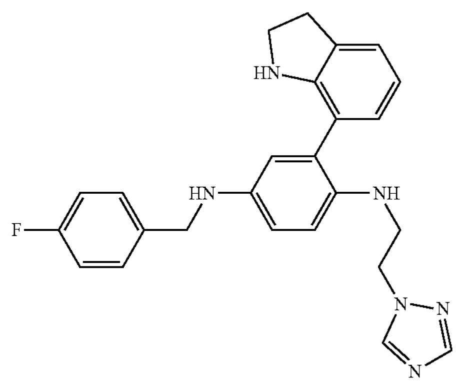

SS20308-0211-01

The mixture of SS20308-0225-01 (50 mg, 0.117 mmol), and $NaBH_3CN$ (8 mg, 0.117 mmol) in AcOH (2 mL) was stirred at 0° C. overnight. The residue was purified by Prep-HPLC to give SS20308-0211-01 (20 mg, about 40% yield) as a solid. MS Calcd.: 428.2; MS Found: 429.0 $[M+H]^+$.

$^1H$ NMR (400 MHz, DMSO-$d_6$) δ 8.43 (s, 1H), 7.94 (s, 1H), 7.36-7.40 (m, 2H), 7.11-7.15 (t, 2H), 7.01 (d, J=7.2 Hz, 1H), 6.71-6.73 (d, J=8.0 Hz, 1H), 6.56-6.62 (m, 2H), 6.49 (q, J=2.4 Hz, 1H), 6.39 (d, J=2.4 Hz, 1H), 5.63-5.66 (m, 1H), 4.69 (s, 1H), 4.28-4.30 (m, 2H), 4.17 (d, J=5.6 Hz, 2H), 4.08-4.11 (m, 1H), 3.24-3.29 (m, 4H), 2.92-2.94 (m, 2H).

Example 20

SS20308-0226-01

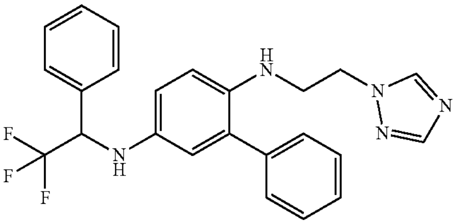

Example Route for Example 20

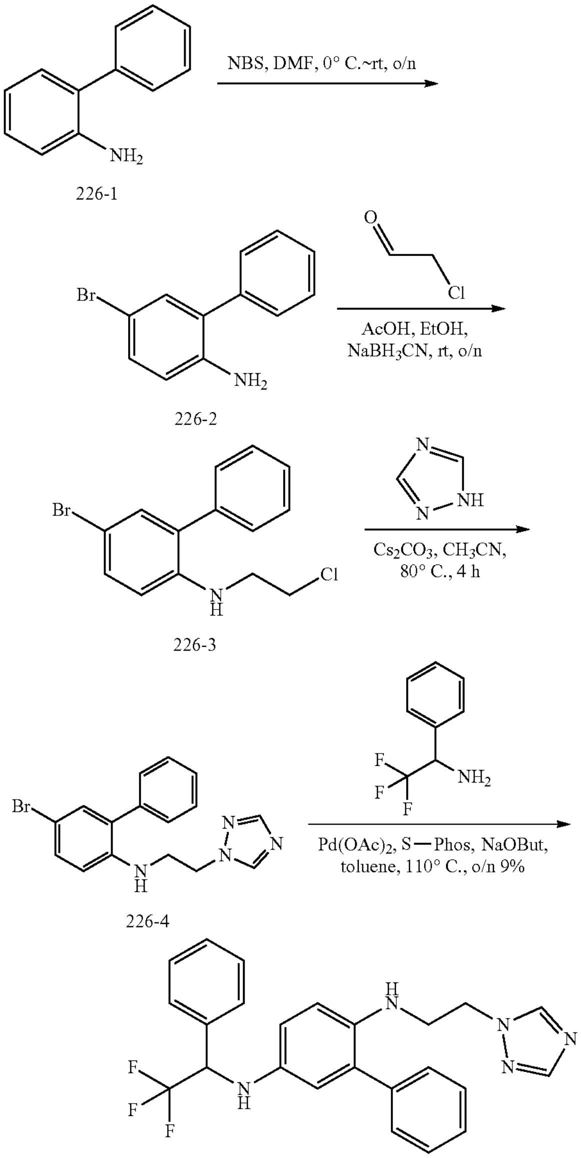

226-1

226-2

226-3

226-4

SS20308-0226-01

The Synthesis of 5-bromobiphenyl-2-amine (226-2)

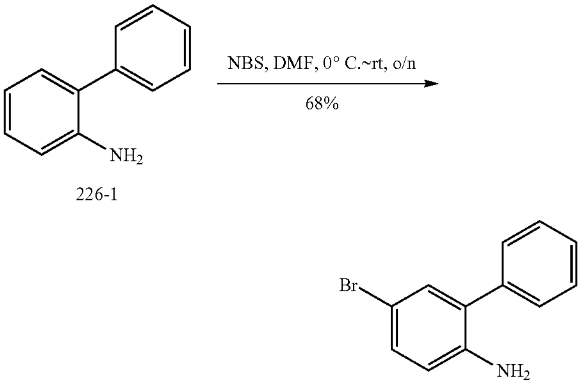

226-1

226-2

The mixture of 226-1 (5.0 g, 29.6 mmol) in DMF (30 mL) was stirred at 0° C., NBS (5.3 g, 29.6 mmol) was added, then the mixture was stirred at room temperature overnight. After being poured into water (60 mL), the mixture was extracted ethyl acetate (30 mL×4). The organic layer was washed with brine and concentrated to dryness to give 226-2 (5.0 g, about 68% yield) as an oil. MS Calcd.: 247.0; MS Found: 250.1 $[M+H]^+$.

The Synthesis of 5-bromo-N-(2-chloroethyl)biphenyl-2-amine (226-3)

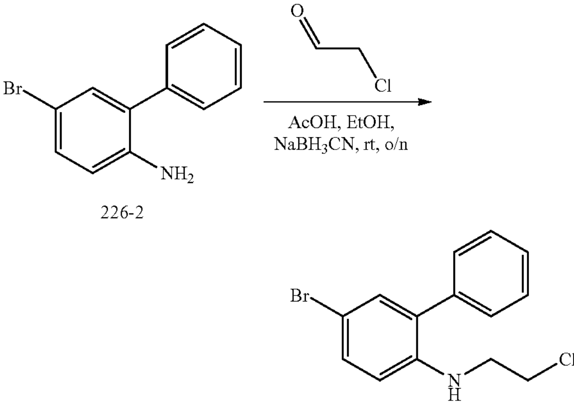

226-2

226-3

To a solution of 226-2 (2.0 g, 8.1 mmol) in EtOH (20 mL) was added 2-chloroacetaldehyde (950 mg, 12.1 mmol, 40% in water), AcOH (970 mg, 16.1 mmol), and $NaBH_3CN$ (507 mg, 8.1 mmol), then the reaction mixture was stirred at room temperature overnight. The reaction mixture was poured into cool water (50 mL), basified with saturated $Na_2CO_3$ solution until the pH value reached to 9, and then extracted ethyl acetate (150 mL). The organic layer was washed with brine and concentrated to dryness to give 226-3 (1.7 g, about 68% yield) as an oil. MS Calcd.: 309.0; MS Found: 310.0 $[M+H]^+$.

The Synthesis of N-(2-(1H-1,2,4-triazol-1-yl)ethyl)-5-bromobiphenyl-2-amine (226-4)

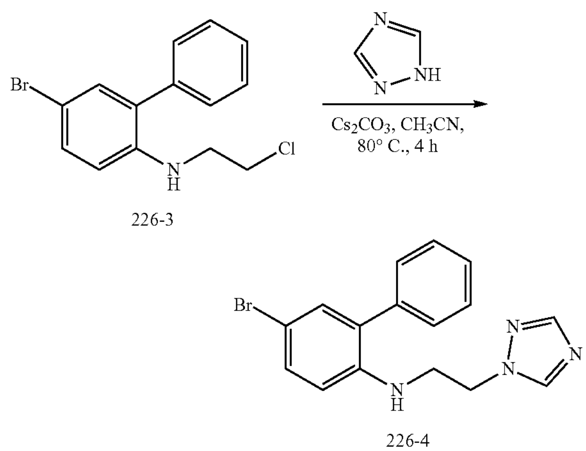

226-3

226-4

To a solution of 226-3 (1.7 g, 5.5 mmol) in $CH_3CN$ (10 mL) was added 1,2,4-triazole (756 mg, 11.0 mmol) and $Cs_2CO_3$ (3.6 g, 11.0 mmol), then the reaction mixture was stirred at 80° C. for 4 hours. The reaction mixture was cooled to room temperature and filtered through celite. The filtrate was concentrated to dryness. The residue was purified by column chromatography (ethyl acetate/petroleum ether=1/5) to give 226-4 (1.0 g, about 53% yield) as an oil. MS Calcd.: 343.2; MS Found: 345.2 $[M+H]^+$.

The Synthesis of $N^2$-(2-(1H-1,2,4-triazol-1-yl)ethyl)-$N^5$-(2,2,2-trifluoro-1-phenylethyl)biphenyl-2,5-diamine (SS20308-0226-01)

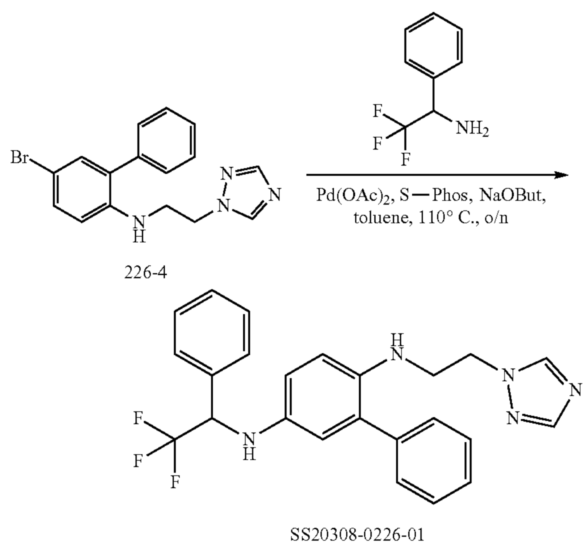

226-4

SS20308-0226-01

To a solution of 226-4 (180.0 mg, 0.5 mmol) in toluene (10.0 mL) was added 2,2,2-trifluoro-1-phenylethanamine (262.0 mg, 1.5 mmol), $Pd(OAc)_2$ (10.0 mg, 0.1 mmol), S-Phos (20.0 mg, 0.1 mmol), NaOBut (100.0 mg, 1.0 mmol). The stirred at 110° C. under nitrogen atmosphere overnight. After the reaction was completed, the reaction mixture was quenched with water, and extracted with ethyl acetate (10 mL×3). The organic layers were washed with brine, dried over $MgSO_4$ and concentrated. The residue was purified by Prep-HPLC twice to give SS20308-0226-01 (20.0 mg, about 9% yield) as a solid. MS Calcd.: 437.0; MS Found: 438.0 $[M+H]^+$.

$^1H$ NMR (400 MHz, DMSO-$d_6$) δ 8.40 (s, 1H), 7.92 (s, 1H), 7.59 (d, J=7.2 Hz, 2H), 7.29-7.40 (m, 7H), 7.18-7.20 (m, 2H), 6.72 (dd, J=8.8 Hz, 2.4 Hz, 1H), 6.63 (d, J=2.8 Hz, 1H), 6.53 (d, J=8.4 Hz, 1H), 6.07 (d, J=10.8 Hz, 1H), 5.37-5.42 (m, 1H), 4.27 (t, J=6.0 Hz, 2H), 4.11 (t, J=6.0 Hz, 1H), 3.36 (s, 2H).

Example 21

SS20308-0227-01

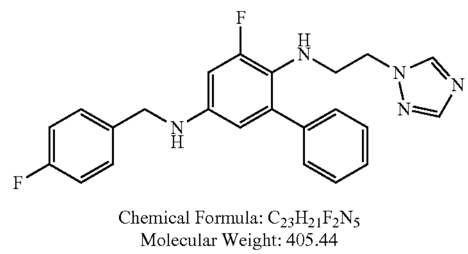

Chemical Formula: $C_{23}H_{21}F_2N_5$
Molecular Weight: 405.44

Example Route for Example 21

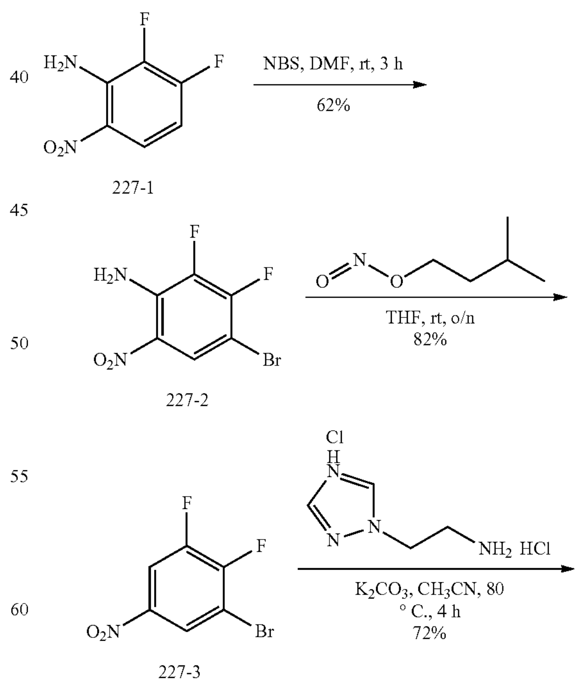

227-1

227-2

227-3

-continued

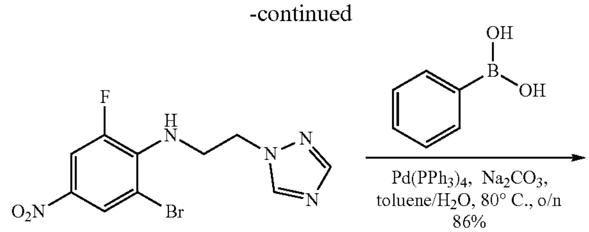

227-4

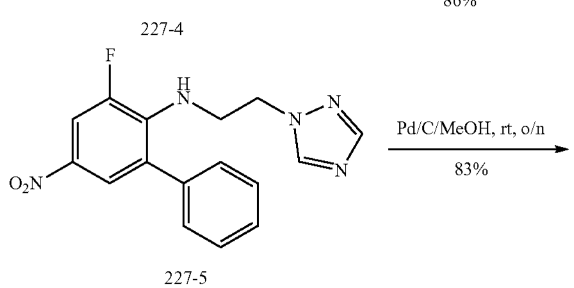

227-5

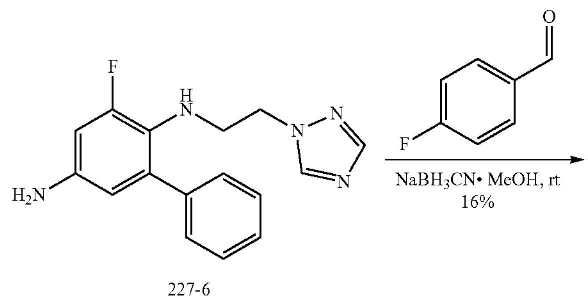

227-6

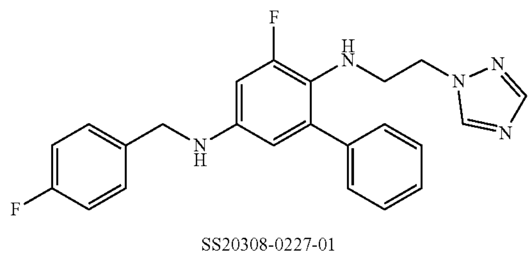

SS20308-0227-01

The Synthesis of 4-bromo-2,3-difluoro-6-nitroaniline (227-2)

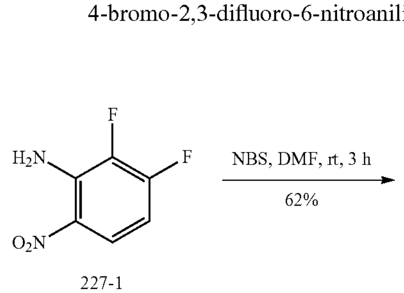

227-1

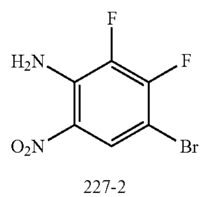

227-2

To a solution of 227-1 (200 mg, 1.15 mmol) in DMF (5 mL) was added NBS (204 mg, 1.15 mmol), the mixture was stirred at room temperature for 3 h. After the reaction was complete, the reaction was poured into water (50 mL) and extracted with EtOAc (40 mL×3). The organic layer was washed brine (2×50 mL), dried over $MgSO_4$, and concentrated in vacuum, which was purified by column chromatography (petroleum ether/EtOAc=5/1) to give 227-2 (180 mg, about 62% yield) as a solid. MS Calcd.: 251.9; MS Found: 252.9 $[M+H]^+$.

The Synthesis of 1-bromo-2,3-difluoro-5-nitrobenzene (227-3)

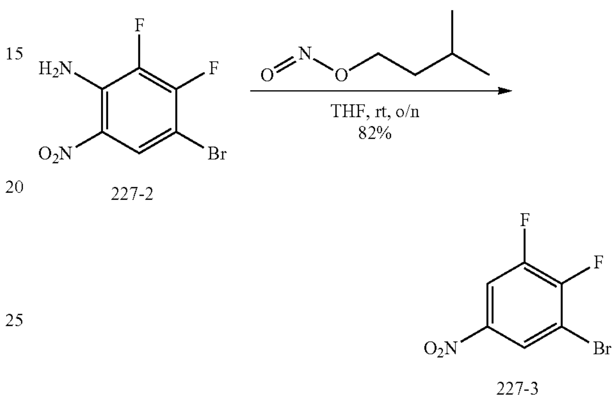

227-2

227-3

To a solution of 227-2 (3 g, 11.86 mmol) in THF (20 mL) was added isopentyl nitrite (2.78 g, 23.72 mmol), the mixture was stirred at room temperature overnight. After the reaction was complete, the reaction was poured into water (50 mL) and extracted with EtOAc (40 mL×3). The organic layer was washed brine (2×50 mL), dried over $MgSO_4$, and concentrated in vacuum, which was purified by column chromatography (petroleum ether/EtOAc=5/1) to give 227-3 (2.3 g, about 82% yield) as a solid.

The Synthesis of N-(2-(1H-1,2,4-triazol-1-yl)ethyl)-2-bromo-6-fluoro-4-nitroaniline (227-4)

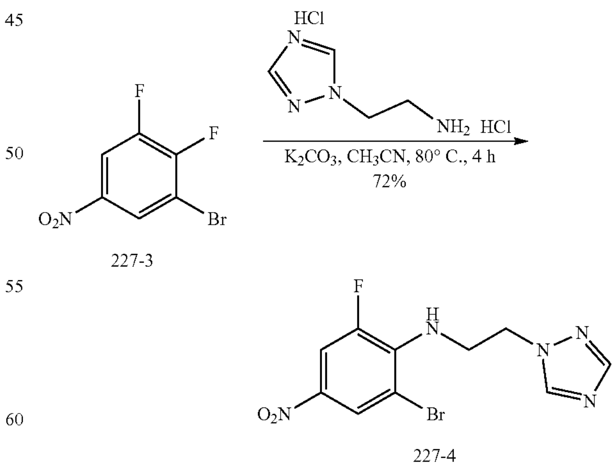

227-3

227-4

A mixture of 227-3 (2.00 g, 8.40 mmol), 2-(1H-1,2,4-triazol-1-yl)ethanamine dihydrochloride (1.56 g, 8.40 mmol) and $K_2CO_3$ (4.65 g, 33.62 mmol) in $CH_3CN$ (30 ml) was stirred at 80° C. under nitrogen atmosphere for 4 h.

After the reaction was complete, the mixture was quenched with water and extracted with EtOAc (50 mL×3). The organic layer was separated, dried over $MgSO_4$, and concentrated in vacuum, which was purified by column chromatography (petroleum ether/EtOAc=1/1) to give 227-4 (2 g, about 72% yield) as a solid. MS Calcd.: 329.0; MS Found: 330.0 $[M+H]^+$.

The Synthesis of N-(2-(1H-1,2,4-triazol-1-yl)ethyl)-3-fluoro-5-nitrobiphenyl-2-amine (227-5)

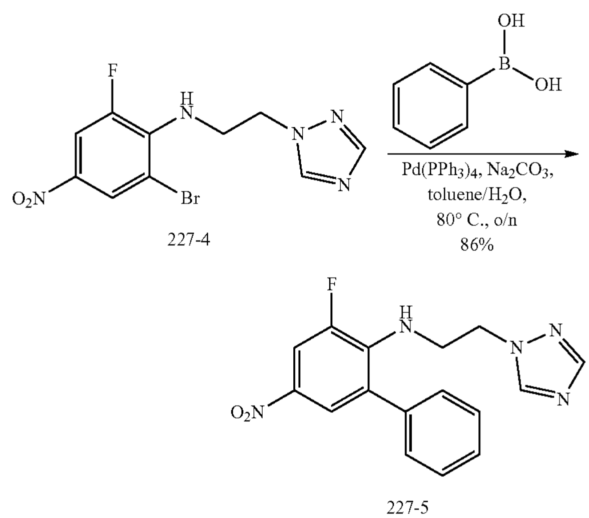

227-4

227-5

A mixture of 227-4 (1 g, 3.03 mmol), phenylboronic acid (443 mg, 3.64 mmol), $Pd(PPh_3)_4$ (700 mg, 0.61 mmol) and $Na_2CO_3$ (642 mg, 6.06 mmol) in Tol (20 ml) and water (2 ml) was stirred at 80° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated in vacuum, which was purified by column chromatography (petroleum ether/EtOAc=1/1) to give 227-5 (850 mg, about 86% yield) as a solid. MS Calcd.: 327.1; MS Found: 328.2 $[M+H]^+$.

The Synthesis of $N^2$-(2-(1H-1,2,4-triazol-1-yl)ethyl)-3-fluorobiphenyl-2,5-diamine (227-6)

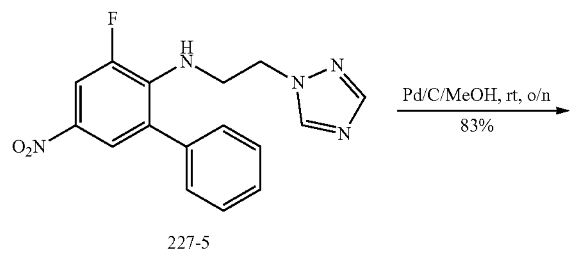

227-5

-continued

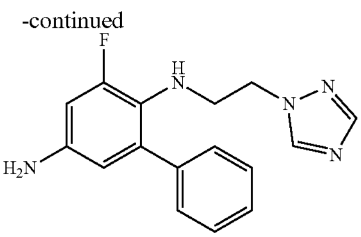

227-6

To a solution of 227-5 (200 mg, 0.61 mmol) in MeOH (20 mL) was added Pd/C (10%, 50 mg), the mixture was stirred at room temperature under $H_2$ atmosphere overnight. After the reaction was complete, the insoluble material was removed by filtration. The organic layer was concentrated in vacuum, which was purified by column chromatography (petroleum ether/EtOAc=1/2) to give 227-6 (150 mg, about 83% yield) as a solid. MS Calcd.: 297.1; MS Found: 298.2 $[M+H]^+$.

The Synthesis of $N^2$-(2-(1H-1,2,4-triazol-1-yl)ethyl)-3-fluoro-$N^5$-(4-fluorobenzyl)biphenyl-2,5-diamine (SS20308-0227-01)

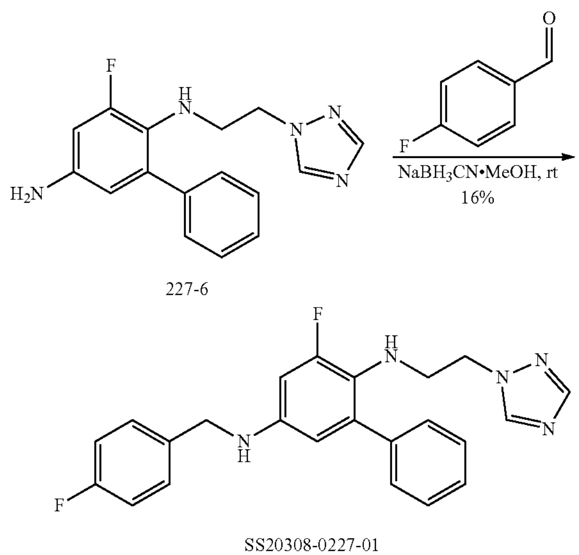

227-6

SS20308-0227-01

A mixture of 227-6 (150 mg, 0.50 mmol) and 4-fluorobenzaldehyde (75 mg, 0.61 mmol) in MeOH (10 ml) was added $NaBH_3CN$ (95 mg, 1.51 mmol), the mixture was stirred at room temperature overnight. After the reaction was complete, the mixture was quenched with water, the insoluble material was removed by filtration, and the filtrate was extracted with EtOAc (30 mL×3). The organic layer was separated, dried over $MgSO_4$, and concentrated in vacuum, which was purified by Prep-HPLC to give SS20308-0277-01 (33 mg, about 16% yield) as an oil. MS Calcd.: 405.2; MS Found: 406.0 $[M+H]^+$.

$^1H$ NMR (400 MHz, DMSO-$d_6$) δ 8.26 (s, 1H), 7.84 (s, 1H), 7.40-7.30 (m, 5H), 7.27-7.25 (m, 2H), 7.17-7.13 (m, 2H), 6.36 (dd, J=13.6 Hz, 2.4 Hz, 1H), 6.23 (d, J=2.0 Hz, 1H), 6.17 (t, J=5.6 Hz, 1H), 4.20 (d, J=6.0 Hz, 2H), 4.08 (t, J=6.0 Hz, 2H), 3.67-3.63 (m, 1H), 3.06-3.02 (m, 2H).

Example 22

SS20308-0228-01

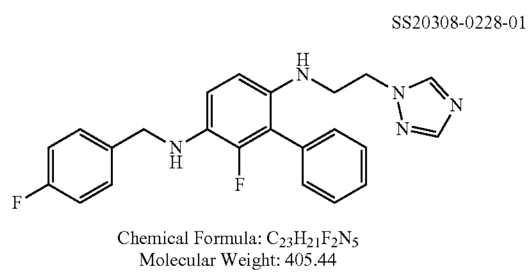 [SMILES: Fc1ccc(CNc2ccc(NCCn3cncn3)c(-c3ccccc3)c2F)cc1]

Chemical Formula: $C_{23}H_{21}F_2N_5$
Molecular Weight: 405.44

Example Route for Example 22

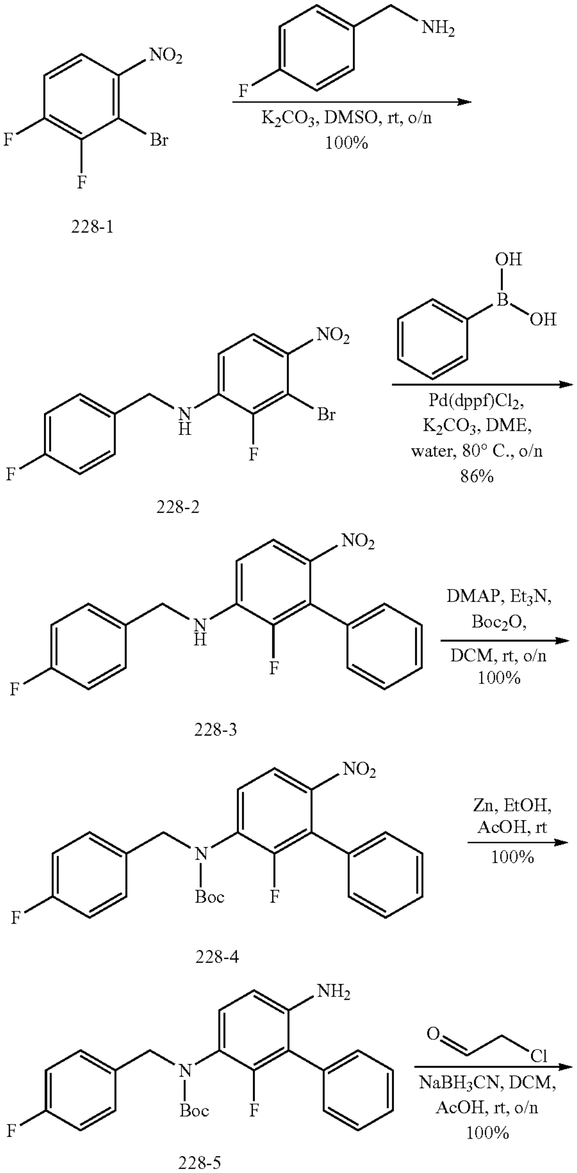

-continued

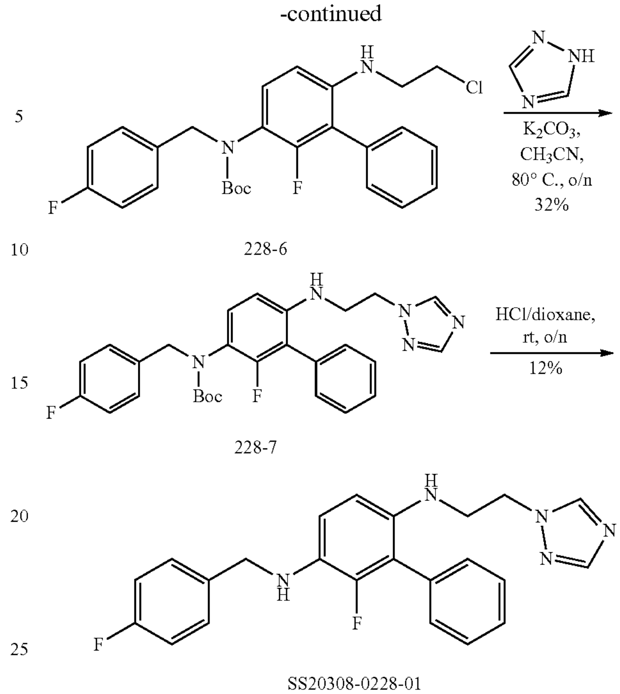

The Synthesis of 3-bromo-2-fluoro-N-(4-fluorobenzyl)-4-nitroaniline (228-2)

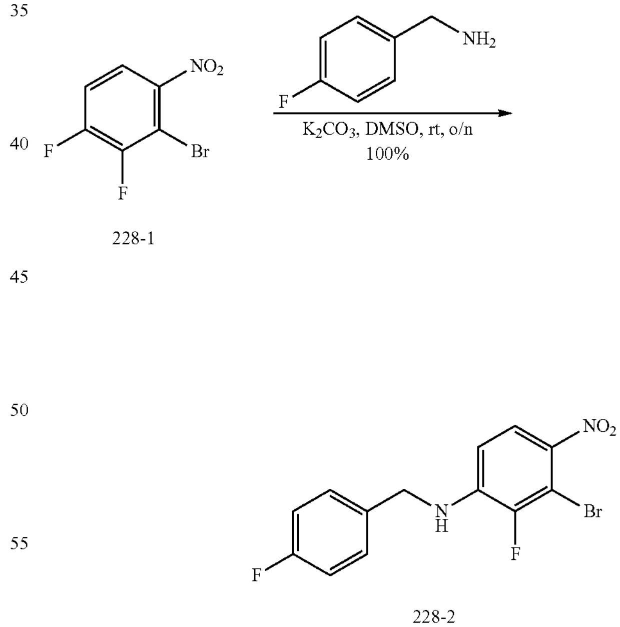

The mixture of 228-1 (2.00 g, 8.40 mmol), 4-fluorobenzylamine (2.10 g, 16.8 mmol) and $K_2CO_3$ (3.48 g, 25.2 mmol) in DMSO (40 mL) was stirred at room temperature overnight. The reaction mixture was diluted with water (160 mL). The resulting solid was collected by filtration and concentrated to give 228-2 (2.88 g, about 100% yield) as a solid. MS Calcd.: 342.0; MS Found: 343.2 $[M+H]^+$.

The Synthesis of 2-fluoro-N-(4-fluorobenzyl)-6-nitrobiphenyl-3-amine (228-3)

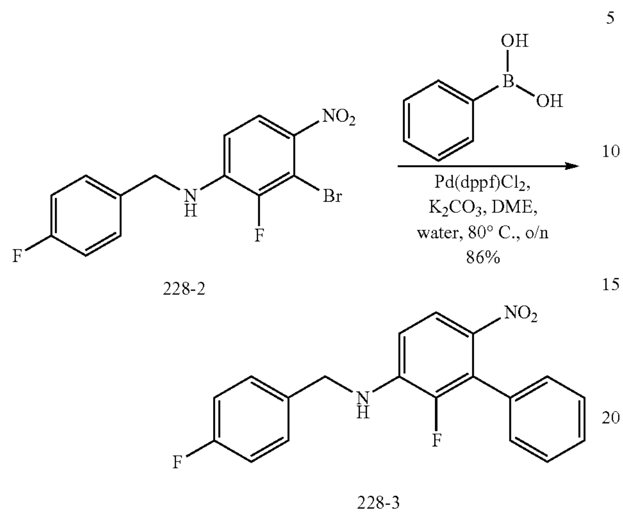

228-2

228-3

The mixture of 228-2 (2. g, 5.8 mmol), phenylboronic acid (1.42 g, 11.7 mmol), Pd(dppf)$Cl_2$ (238 mg, 0.3 mmol) and $K_2CO_3$ (2.01 g, 14.6 mmol) in DME/$H_2O$ (48 mL, 5/1) was stirred at 80° C. overnight under $N_2$ atmosphere. After cooled to room temperature, the reaction mixture was concentrated and purified by column chromatography (petroleum ether/ethyl acetate=20/1, 10/1) to give 228-3 (1.70 g, about 86% yield) as a solid. MS Calcd.: 340.1; MS Found: 341.4 $[M+H]^+$.

The Synthesis of tert-butyl 2-fluoro-6-nitrobiphenyl-3-yl(4-fluorobenzyl)carbamate (228-4)

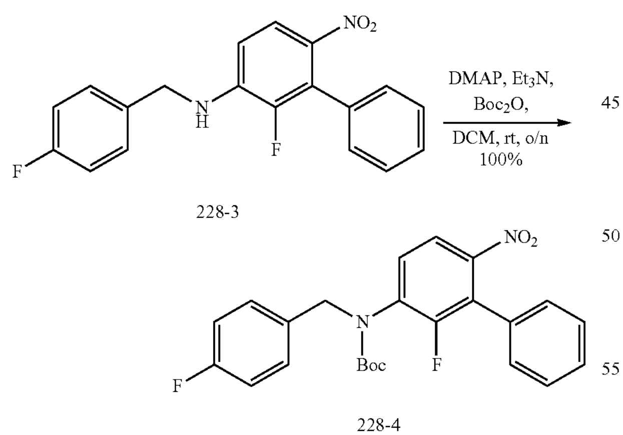

228-3

228-4

To a solution of 228-3 (1.6 g, 4.70 mmol) in DCM (20 mL) was added $(Boc)_2O$ (1.54 g, 7.05 mmol), DMAP (575 mg, 4.71 mmol) and $Et_3N$ (952 mg, 9.41 mmol). After stirring at room temperature for overnight, the reaction mixture was concentrated and purified by column chromatography (petroleum ether/ethyl acetate=100/1, 50/1, 20/1) to give 228-4 (2.07 g, about 100% yield) as an oil. MS Calcd.: 440.2; MS Found: 385.3 $[M-55]^+$.

The Synthesis of tert-butyl 6-amino-2-fluorobiphenyl-3-yl(4-fluorobenzyl)carbamate (228-5)

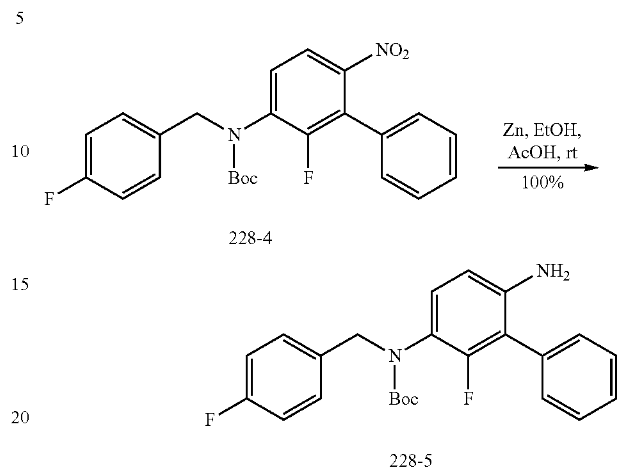

228-4

228-5

The mixture of 228-4 (2.07 g, 4.70 mmol) and Zn powder (3.07 g, 47.00 mmol in EtOH/AcOH (41 mL, 40/1) was stirred at room temperature overnight. Then the reaction mixture was filtered through celite and concentrated to give 228-5 (1.93 g, about 100% yield) as a solid. MS Calcd.: 410.2; MS Found: 355.3 $[M-55]^+$.

The Synthesis of tert-butyl 6-(2-chloroethylamino)-2-fluorobiphenyl-3-yl(4-fluorobenzyl)carbamate (228-6)

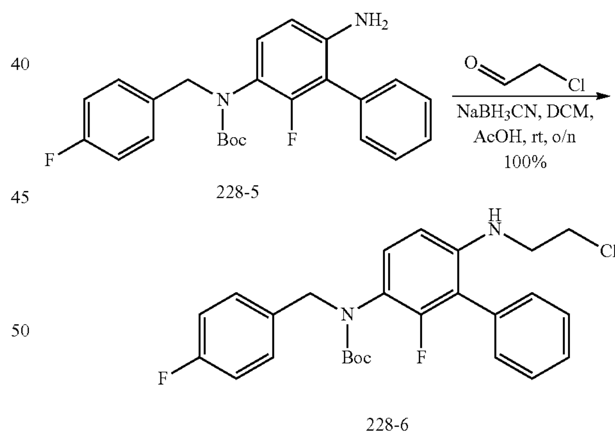

228-5

228-6

To a solution of 228-5 (500 mg, 1.22 mmol) in DCM (5 mL) was added 2-chloroacetaldehyde (957 mg, 4.88 mmol, 40% in water), $NaBH_3CN$ (115 mg, 1.83 mmol) and AcOH (0.5 mL), then the reaction mixture was stirred at room temperature overnight. Then the reaction mixture was poured into water and basicified with $NaHCO_3$ solution till pH reached 8. The mixture was extracted DCM (20 mL×3). The organic layers were washed with brine, dried over $Na_2SO_4$ and concentrated to give 228-6 (576 mg, about 100% yield) as an oil. MS Calcd.: 472.2; MS Found: 417.3 $[M-56]^+$.

The Synthesis of tert-butyl 6-(2-(1H-1,2,4-triazol-1-yl)ethylamino)-2-fluorobiphenyl-3-yl(4-fluorobenzyl)carbamate_(228-7)

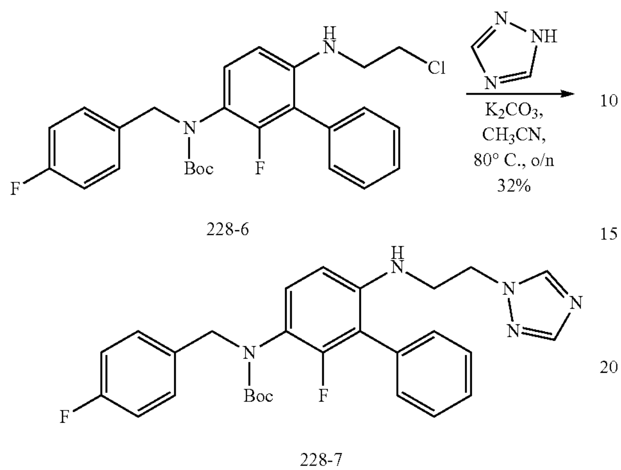

228-6

228-7

A mixture of 228-6 (576 mg, 1.22 mmol), 1H-1,2,4-triazole (126 mg, 1.83 mmol) and $Cs_2CO_3$ (595 mg, 1.83 mmol) in DMF (10 mL) was stirred at 80° C. for overnight. The reaction mixture was then cooled to room temperature and filtered through celite and concentrated. The residue was purified by column chromatography (petroleum ether/EtOAc=1/2) to give 228-7 (200 mg, about 32% yield) as an oil. MS Calcd.: 505.2; MS Found: 506.4 $[M+H]^+$.

The Synthesis of $N^2$-(2-(1H-1,2,4-triazol-1-yl)ethyl)-6-fluoro-$N^5$-(4-fluorobenzyl)biphenyl-2,5-diamine (SS20308-0228-01)

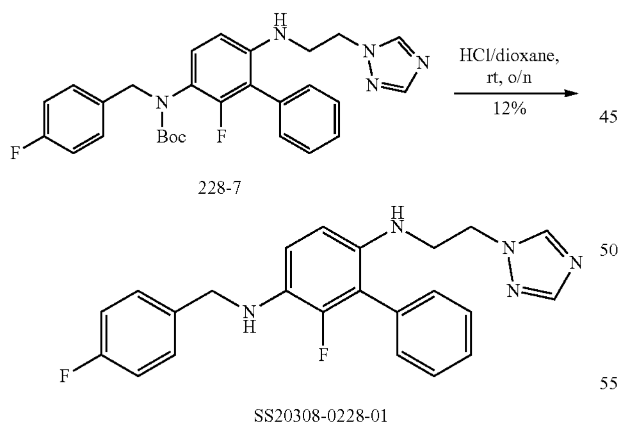

228-7

SS20308-0228-01

The 228-7 (400 mg, 1.27 mmol) was dissolved in HCl/dioxane (10 mL, 1 N) and stirred at room temperature overnight. Then the reaction mixture was poured into water and basicified with 1N NaOH till pH reached 10. The mixture was extracted EtOAc (50 mL×3). The organic layers were washed with brine, dried over $Na_2SO_4$ and concentrated. The residue was purified Prep-HPLC to give SS20308-0228-01 (40 mg, about 12% yield) as an oil. MS Calcd.: 405.2; MS Found: 406.0 $[M+H]^+$.

$^1H$ NMR (400 MHz, DMSO-$d_6$) δ 8.37 (s, 1H), 7.89 (s, 1H), 7.46-7.37 (m, 5H), 7.16-7.11 (m, 4H), 6.47 (d, J=9.2 Hz, 1H), 6.34 (d, J=8.8 Hz, 1H), 5.45 (t, J=5.8 Hz, 1H), 4.26-4.23 (m, 4H), 3.87 (t, J=6.2 Hz, 1H), 3.32-3.29 (m, 2H).

Example 23

SS20308-0229-01

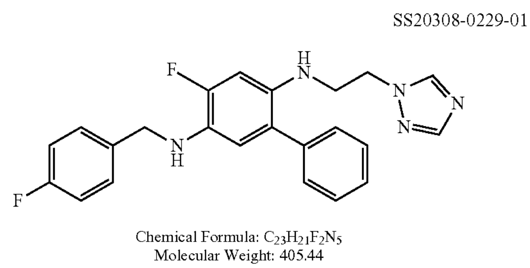 [SMILES: Fc1ccc(CNc2cc(-c3ccccc3)c(NCCn3cncn3)cc2F)cc1]

Chemical Formula: $C_{23}H_{21}F_2N_5$
Molecular Weight: 405.44

Example Route for Example 23

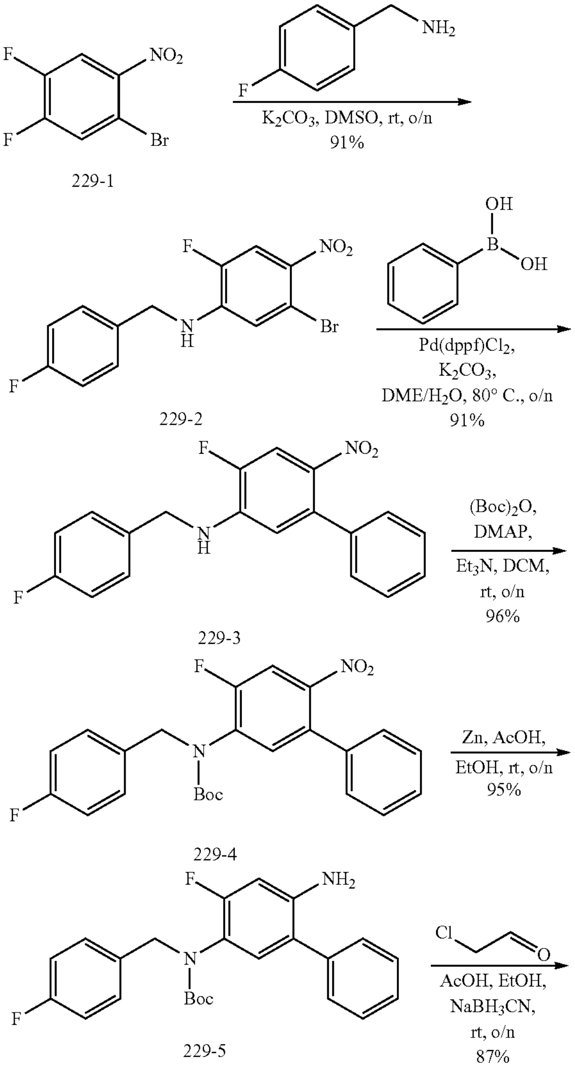

-continued

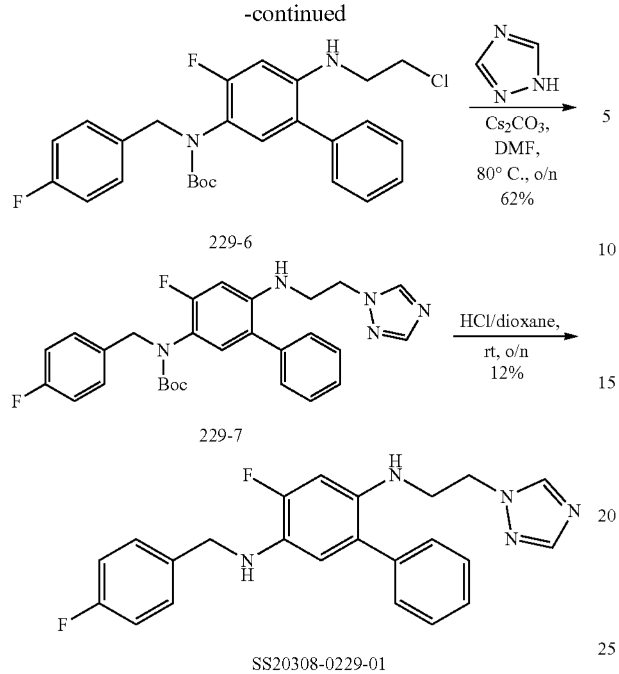

The Synthesis of 5-bromo-2-fluoro-N-(4-fluorobenzyl)-4-nitroaniline (229-2)

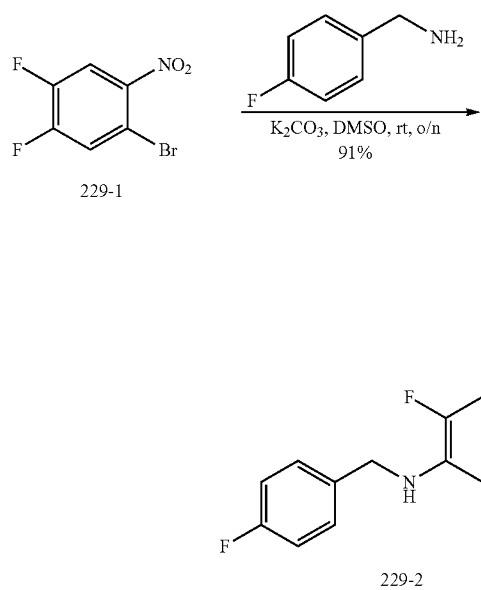

229-2

The mixture of 229-1 (2.00 g, 8.40 mmol), 4-fluorobenzylamine (2.10 g, 16.8 mmol) and $K_2CO_3$ (3.48 g, 25.2 mmol) in DMSO (50 mL) was stirred at room temperature overnight. The reaction mixture was added water (150 mL), and then the mixture was extracted ethyl acetate (150 mL×3). The organic layers were washed with brine, dried over $Na_2SO_4$ and concentrated to give 229-2 (2.64 g, about 91% yield) as a solid. MS Calcd.: 342.0; MS Found: 341.9 $[M+H]^+$.

The Synthesis of 4-fluoro-N-(4-fluorobenzyl)-6-nitrobiphenyl-3-amine (229-3)

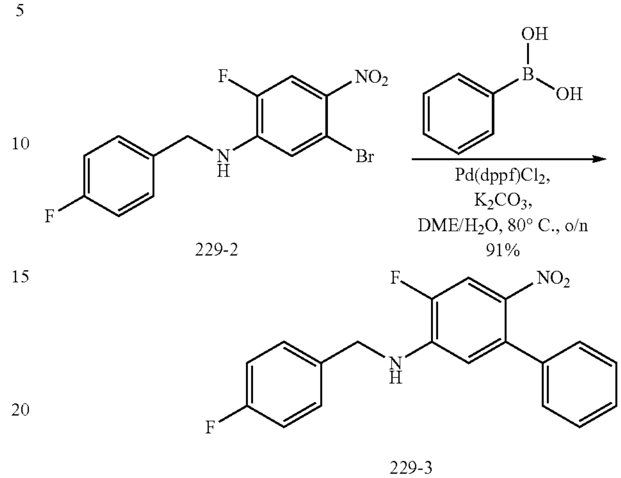

The mixture of 229-2 (2. g, 7.29 mmol), phenyl boronic acid (1.78 g, 14.6 mmol), $Pd(dppf)Cl_2$ (522 mg, 0.73 mmol) and $K_2CO_3$ (2.01 g, 14.6 mmol) in DME/$H_2O$ (60 mL, 5/1) was stirred at 80° C. overnight under $N_2$ atmosphere. After cooled to room temperature, the reaction mixture was poured into water and extracted with EtOAc (60 mL×3). The organic layers were washed with brine, dried over $Na_2SO_4$ and concentrated. The residue was purified column chromatography (petroleum ether/EtOAc=10/1) to give 229-3 (2.25 g, about 91% yield) as a solid. MS Calcd.: 292.2; MS Found: 293.3 $[M+H]^+$.

The Synthesis of tert-butyl 4-fluoro-6-nitrobiphenyl-3-yl(4-fluorobenzyl)carbamate (229-4)

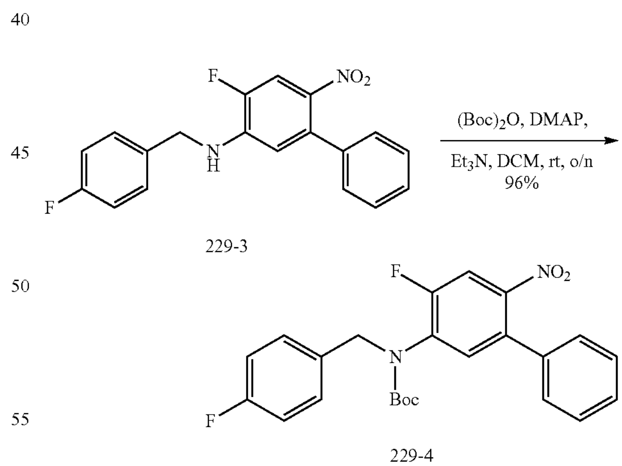

To a solution of 229-3 (2.25 g, 6.61 mmol) in DCM (50 mL) was added $(Boc)_2O$ (2.88 g, 13.2 mmol), DMAP (168 mg, 1.32 mmol) and $Et_3N$ (1.34 g, 13.2 mmol), then the reaction mixture was stirred at room temperature overnight. Then the reaction mixture was poured into water and extracted with EtOAc (30 mL×3). The organic layers were washed with brine, dried over $Na_2SO_4$ and concentrated to give 229-4 (2.81 g, about 96% yield) as a solid. MS Calcd.: 440.2; MS Found: 385.1 $[M+H]^+$.

The Synthesis of tert-butyl 6-amino-4-fluorobiphenyl-3-yl(4-fluorobenzyl)carbamate (229-5)

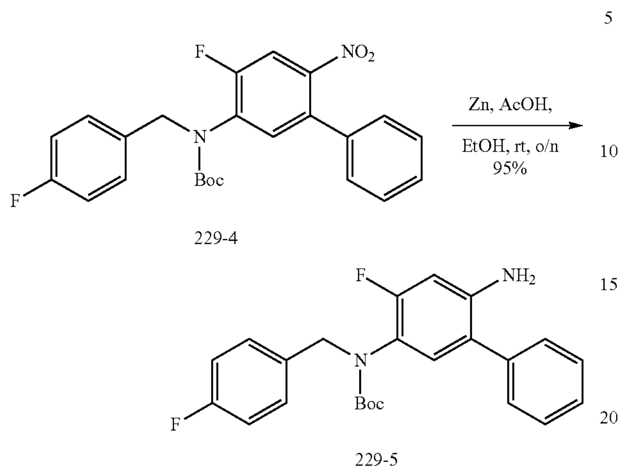

229-4

229-5

The mixture of 229-4 (2.81 g, 6.38 mmol) and Zn powder (4.15 g, 63.8 mmol in EtOH/AcOH (60 mL, 15/1) was stirred at room temperature overnight. Then the reaction mixture was filtered through celite and concentrate to give 229-5 (2.50 g, about 95% yield) as a solid. MS Calcd.: 410.2; MS Found: 355.1 $[M+H]^+$.

The Synthesis of tert-butyl 6-(2-chloroethylamino)-4-fluorobiphenyl-3-yl(4-fluorobenzyl)carbamate (229-6)

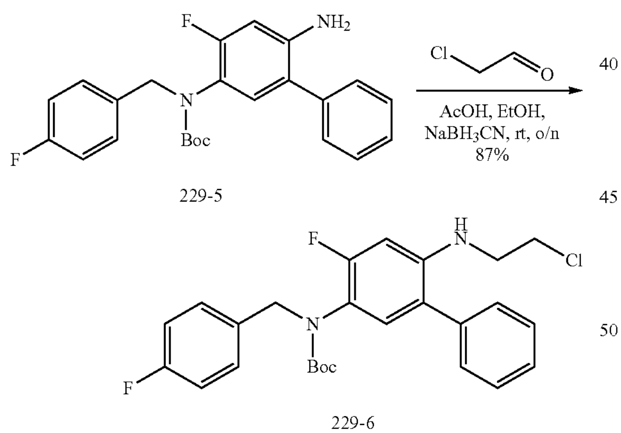

229-5

229-6

To a solution of 229-5 (2.50 g, 6.09 mmol) in EtOH (40 mL) was added 2-chloroacetaldehyde (2.39 g, 12.2 mmol, 40% in water), $NaBH_3CN$ (768 mg, 12.2 mmol) and AcOH (732 mg, 12.2 mmol), then the reaction mixture was stirred at room temperature overnight. Then the reaction mixture was poured into water and basicified with 1N NaOH till pH reached 10. The mixture was extracted with EtOAc (100 mL×3). The organic layers were washed with brine, dried over $Na_2SO_4$ and concentrated to give 229-6 (2.50 g, about 87% yield) as a solid. MS Calcd.: 472.2; MS Found: 317.3 $[M+H]^+$.

The Synthesis of tert-butyl 6-(2-(1H-1,2,4-triazol-1-yl)ethylamino)-4-fluorobiphenyl-3-yl(4-fluorobenzyl)carbamate (229-7)

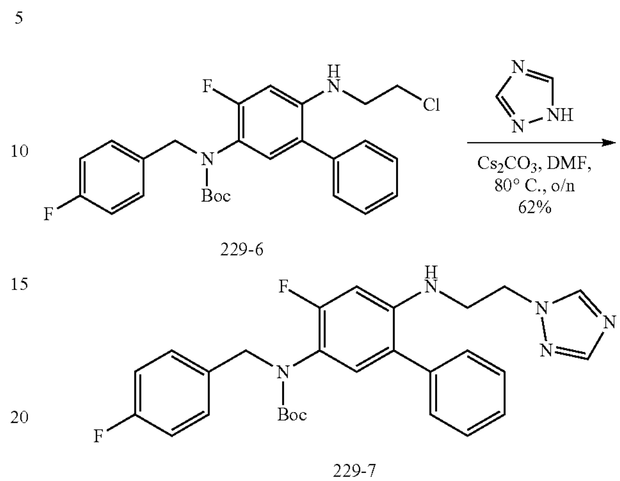

229-6

229-7

A mixture of 229-6 (600 mg, 1.27 mmol), 1H-1,2,4-triazole (175 mg, 2.54 mmol) and $Cs_2CO_3$ (825 mg, 2.54 mmol) in DMF (15 mL) was stirred at 80° C. overnight. The reaction mixture was then cooled to room temperature and filtered through celite and concentrated. The residue was purified by column chromatography (petroleum ether/EtOAc=1/2) to give 229-7 (400 mg, about 62% yield) as a solid. MS Calcd.: 505.2; MS Found: 506.2 $[M+H]^+$.

The Synthesis of $N^2$-(2-(1H-1,2,4-triazol-1-yl)ethyl)-4-fluoro-N-(4-fluorobenzyl)biphenyl-2,5-diamine (SS20308-0229-01)

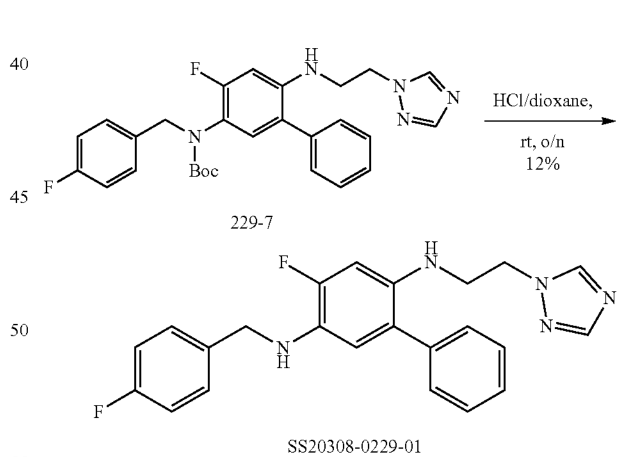

229-7

SS20308-0229-01

The 229-7 (400 mg, 1.27 mmol) was solvent in HCl/dioxane (10 mL, 1 N) and stirred at room temperature overnight. Then the reaction mixture was poured into water and basicified with 1N NaOH till pH reached 10. The mixture was extracted EtOAc (50 mL×3). The organic layers were washed with brine, dried over $Na_2SO_4$ and concentrated. The residue was purified Prep-HPLC to give SS20308-0229-01 (39 mg, about 12% yield) as an oil. MS Calcd.: 405.2; MS Found: 406.0 $[M+H]^+$.

$^1H$ NMR (400 MHz, DMSO-$d_6$) δ 8.42 (s, 1H), 7.93 (s, 1H), 7.38-7.28 (m, 5H), 7.13-7.08 (m, 4H), 6.55 (d, J=14.4

Hz, 1H), 6.36 (d, J=10.0 Hz, 1H), 5.44 (t, J=6.0 Hz, 1H), 4.28 (t, J=5.8 Hz, 3H), 4.22 (d, J=6.0 Hz, 2H), 3.38-3.34 (m, 2H).

Example 24

SS20308-0232-01

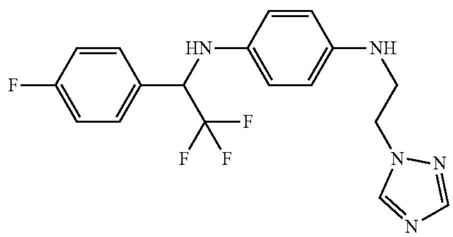

Example Route for Example 24 (SS20308-0232-01, SS20308-0275-01)

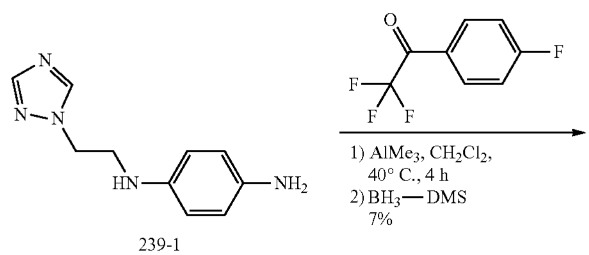

239-1

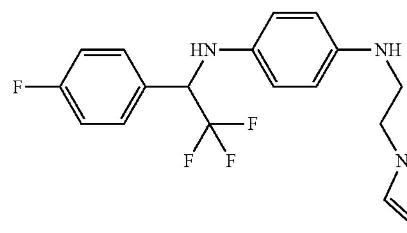

SS20308-0232-01

The Synthesis of N[1]-(2-(1H-1,2,4-triazol-1-yl) ethyl)-N[4]-(2,2,2-trifluoro-1-(4-fluorophenyl)ethyl) benzene-1,4-diamine (SS20308-0232-01)

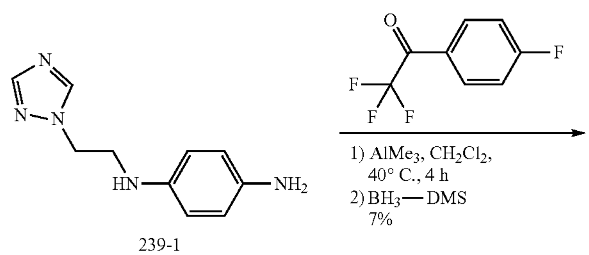

239-1

-continued

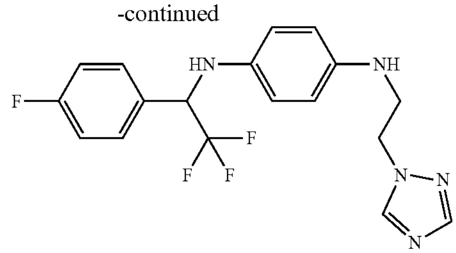

SS20308-0232-01

A solution of 239-1 (180 mg, 0.89 mmol), 2,2,2-trifluoro-1-(4-fluorophenyl)ethanone (204 mg, 1.06 mmol) in $CH_2Cl_2$ (10 ml) was added $AlMe_3$ (0.89 ml, 1.78 mmol, 2N in THF), the reaction was stirred at 40° C. under nitrogen atmosphere for 2 h. After the reaction was cooled down, the mixture was added $BH_3$-DMS (0.89 ml, 1.78 mmol, 2N in THF), and was stirred at 40° C. under nitrogen atmosphere for 2 h. After the reaction was complete, it was quenched with water and extracted with EtOAc (50 mL×3). The organic layer was separated, dried over $MgSO_4$, and concentrated in vacuum, which was purified by Prep-HPLC to give SS20308-0232-01 (23 mg, about 7% yield) as an oil. MS Calcd.: 379.1; MS Found: 380.0 $[M+H]^+$.

$^1H$ NMR (400 MHz, DMSO-$d_6$) δ 8.44 (s, 1H), 7.96 (s, 1H), 7.65-7.61 (m, 2H), 7.24-7.19 (m, 2H), 6.63 (d, J=8.4 Hz, 2H), 6.38 (d, J=8.8 Hz, 2H), 5.97 (d, J=11.2 Hz, 1H), 5.38-5.33 (m, 1H), 5.05 (t, J=6.4 Hz, 1H), 4.25 (t, J=6.0 Hz, 2H), 3.31 (t, J=6.4 Hz, 2H).

The Synthesis of N[1]-(2-(1H-1,2,4-triazol-1-yl) ethyl)-N[4]-(3,3-dimethyl-2,3-dihydro-1H-inden-1-yl) benzene-1,4-diamine (SS20308-0275-01)

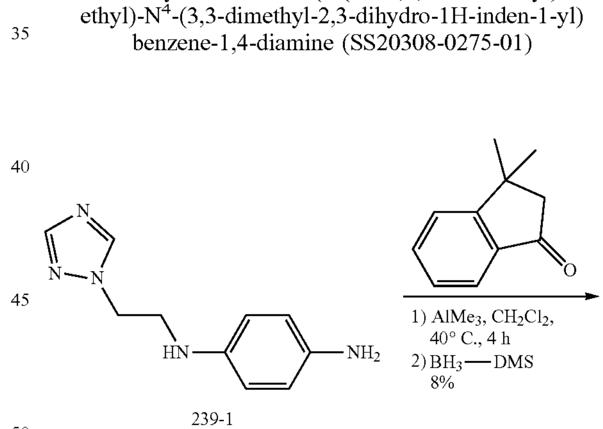

239-1

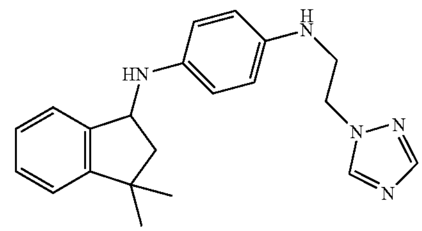

SS20308-0275-01

A solution of 239-1 (180 mg, 0.89 mmol), 3,3-dimethyl-2,3-dihydro-1H-inden-1-one (170 mg, 1.06 mmol) in $CH_2Cl_2$ (10 ml) was added $AlMe_3$ (0.89 ml, 1.78 mmol, 2N in THF), the reaction was stirred at 40° C. under nitrogen atmosphere for 2 h. After the reaction was cooled down, the mixture was added $BH_3$-DMS (0.89 ml, 1.78 mmol, 2N in THF), and was stirred at 40° C. under nitrogen atmosphere for 2 h. After the reaction was complete, it was quenched with water and extracted with EtOAc (50 mL×3). The organic layer was separated, dried over $MgSO_4$, and concentrated under vacuum, which was purified by Prep-HPLC to give SS20308-0275-01 (26 mg, about 8% yield) as an oil. MS Calcd.: 347.2; MS Found: 348.2 $[M+H]^+$.

$^1H$ NMR (400 MHz, DMSO-$d_6$) δ 8.48 (s, 1H), 7.98 (s, 1H), 7.25-7.21 (m, 3H), 7.17-7.13 (m, 1H), 6.61 (d, J=8.8 Hz, 2H), 6.46 (d, J=8.8 Hz, 2H), 5.04 (d, J=8.8 Hz, 1H), 4.96-4.87 (m, 2H), 4.31 (t, J=6.4 Hz, 2H), 3.39-3.34 (m, 2H), 2.35-2.30 (m, 1H), 1.68-1.63 (m, 1H), 1.33 (s, 3H), 1.19 (s, 3H).

Example 25

SS20308-0236-01

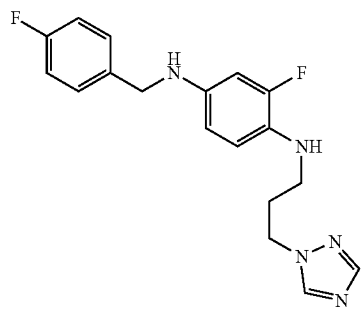

Chemical Formula: $C_{18}H_{19}F_2N_5$
Molecular Weight: 343.37

Example Route for Example 25

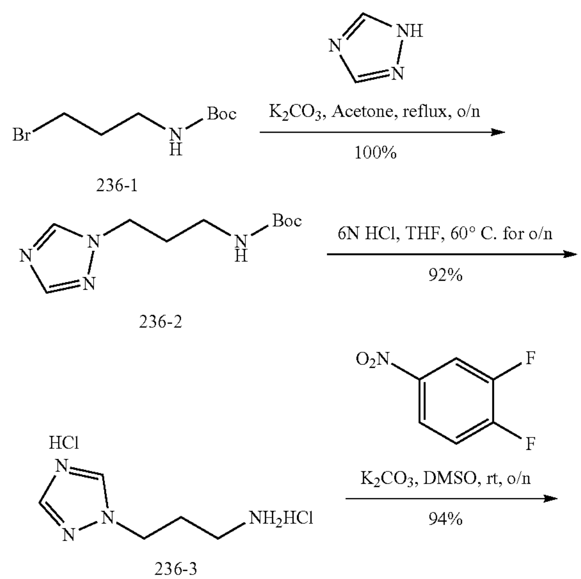

236-1

236-2

236-3

-continued

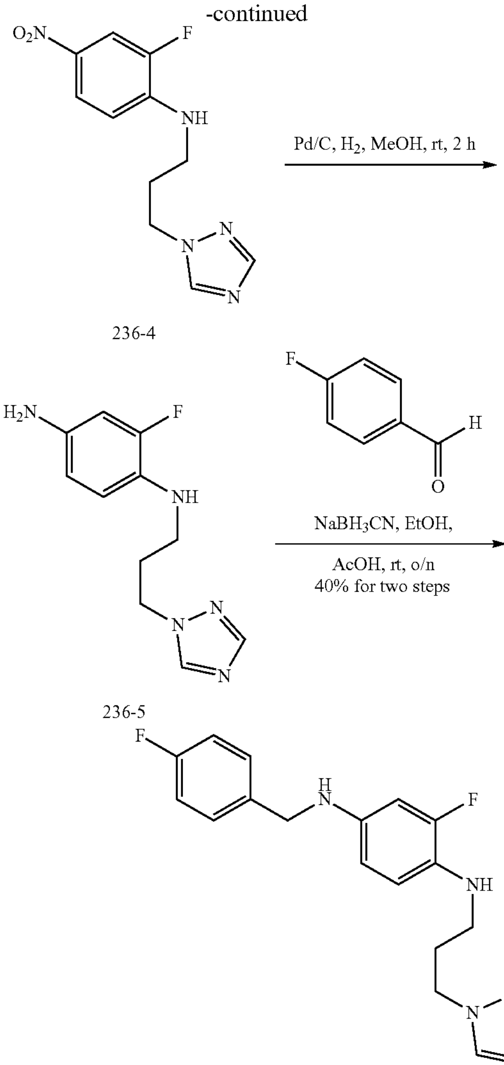

236-4

236-5

SS20308-0236-01

The Synthesis of tert-butyl 3-(1H-1,2,4-triazol-1-yl) propylcarbamate (236-2)

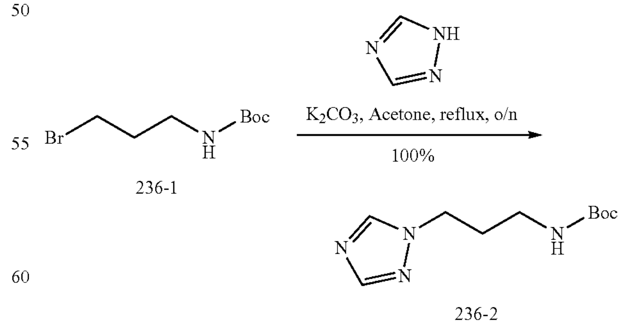

236-1

236-2

A mixture of tert-butyl (3-bromopropyl)carbamate (236-1) (5.0 g, 21.0 mmol), 1H-1,2,4-triazole (1.74 g, 25.2 mmol) and potassium carbonate (4.35 g, 31.5 mmol) in acetone (150 mL) was stirred at 60° C. for overnight. Then the reaction mixture was filtered through celite, rinsing with ethyl acetate. The filtrate was concentrated and the residue was purified by column chromatography (petroleum ether/EtOAc=1/1, dichloromethane/methanol=50/1, 20/1) to give 236-2 (4.75 g, about 100% yield) as an oil. MS Calcd.: 226.1; MS Found: 227.2 $[M+H]^+$.

$^1H$ NMR (400 MHz, $CDCl_3$) δ 8.16 (s, 1H), 7.90 (s, 1H), 4.67 (brs, 1H), 4.19 (t, J=6.6 Hz, 2H), 3.13-3.03 (m, 2H), 2.05-1.95 (m, 2H), 1.38 (s, 9H).

The Synthesis of N-(3-(1H-1,2,4-triazol-1-yl)propyl)-6-nitrobiphenyl-3-amine dihydrogen chloride (262-3)

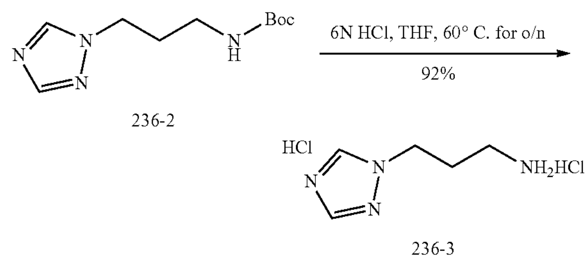

236-2

236-3

A mixture of 236-2 (4.75 g, 21.0 mmol) in THF (80 mL) and 6N HCl (20 mL) was stirred at 60° C. for overnight. The mixture was concentrated in vacuum. Ethanol was added to the residue and the mixture was concentrated again to give 236-3 (3.8 g, about 92% yield) as a solid.

$^1H$ NMR (400 MHz, DMSO-$d_6$) δ 9.16 (s, 1H), 9.06 (brs, 1H), 8.40 (s, 1H), 8.31 (brs, 3H), 4.41 (t, J=6.8 Hz, 2H), 2.83-2.72 (m, 2H), 2.19-2.10 (m, 2H).

The Synthesis of N-(3-(1H-1,2,4-triazol-1-yl)propyl)-2-fluoro-4-nitroaniline (236-4)

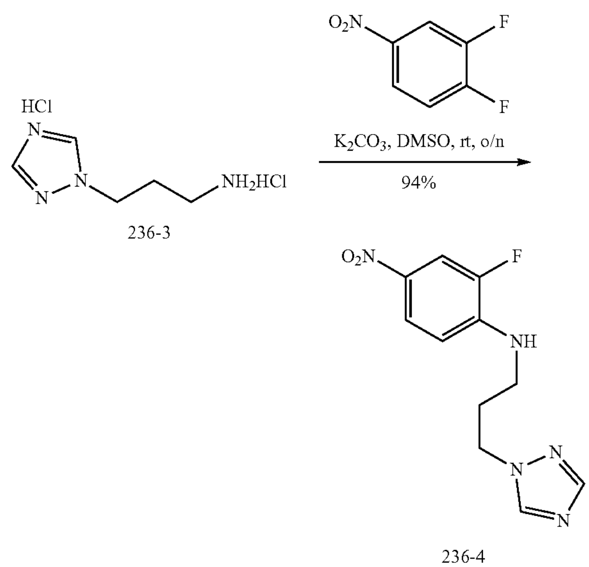

236-3

236-4

A mixture of 3,4-difluoronitrobenzene (100 mg, 0.63 mmol), 236-3 (138 mg, 0.69 mmol) and potassium carbonate (261 mg, 1.89 mmol) were suspended in DMSO (2 mL). After stirring at room temperature for overnight, the mixture was diluted with water (8 mL). The resulting solid was filtered, washed with water, dried, and concentrated to give 236-4 (157 mg, about 94% yield) as a solid. MS Calcd.: 265.1; MS Found: 266.4 $[M+H]^+$.

The Synthesis of $N^1$-(3-(1H-1,2,4-triazol-1-yl)propyl)-2-fluorobenzene-1,4-diamine (236-5)

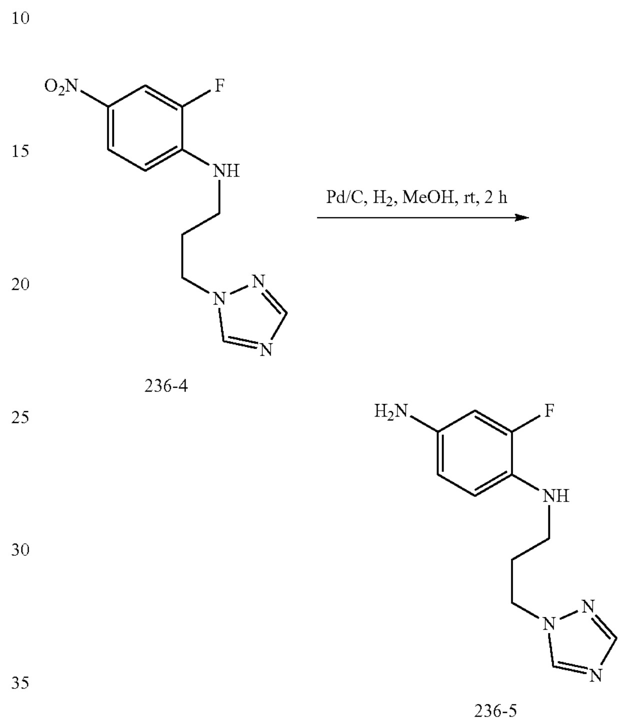

236-4

236-5

A solution of 236-4 (157 mg, 0.59 mmol) and Pd/C (30 mg, 10%) in MeOH (5 mL) was stirred at room temperature for 2 h under $H_2$. Then the reaction mixture was filtered through celite. The filtrate was concentrated to give 236-5 (140 mg) as an oil which was used for next step directly. MS Calcd.: 235.1; MS Found: 236.4 $[M+H]^+$.

The Synthesis of $N^1$-(3-(1H-1,2,4-triazol-1-yl)propyl)-2-fluoro-$N^4$-(4-fluorobenzyl)benzene-1,4-diamine (SS20308-0236-01)

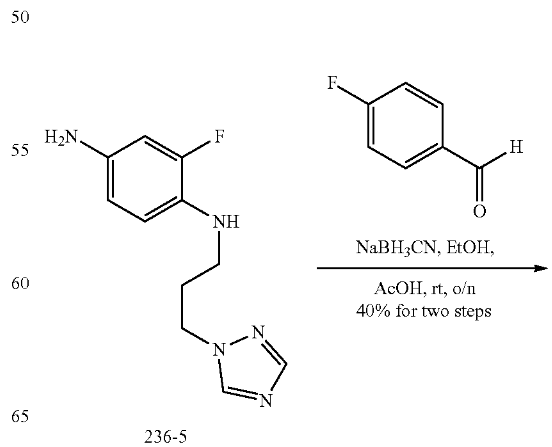

236-5

-continued

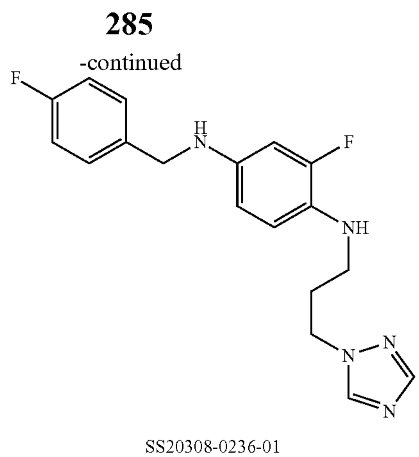

SS20308-0236-01

A solution of 236-5 (140 mg, 0.6 mmol), 4-fluorobenzaldehyde (74 mg, 0.6 mmol), $NaBH_3CN$ (56 mg, 0.89 mmol), and AcOH (0.2 mL) in EtOH (2 mL) was stirred at room temperature for overnight. The reaction mixture was basified with $NaHCO_3$ solution and extracted with EtOAc (20 mL×3). The combined organic layers were washed with water and brine, dried over $Na_2SO_4$ and concentrated. The residue was purified by Prep-TLC (EtOAc) and Prep-HPLC to give compound SS20308-0236-01 (82.3 mg, about 40% yield for two steps) as a solid. MS Calcd.: 343.2; MS Found: 344.0 $[M+H]^+$.

$^1H$ NMR (400 MHz, DMSO-$d_6$) δ 8.50 (s, 1H), 7.96 (s, 1H), 7.37 (dd, J=8.4, 5.6 Hz, 2H), 7.13 (dd, J=8.8, 8.8 Hz, 2H), 6.47 (dd, J=9.6, 8.8 Hz, 1H), 6.36 (d, J=14.4 Hz, 1H), 6.26 (d, J=8.4 Hz, 1H), 5.76 (brs, 1H), 4.58 (brs, 1H), 4.24 (t, J=6.8 Hz, 2H), 4.15 (s, 2H), 2.95-2.85 (m, 2H), 2.04-1.95 (m, 2H).

Example 26

SS20308-0237-01

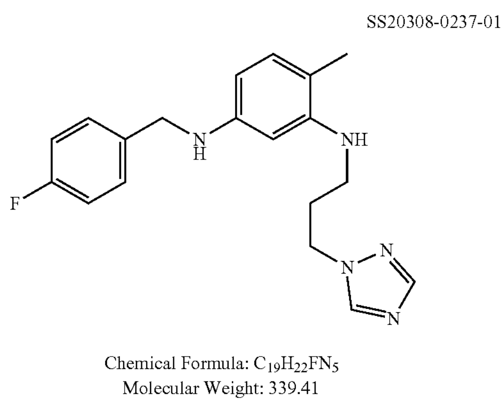 [SMILES: Cc1ccc(NCc2ccc(F)cc2)cc1NCCCn1cncn1]

Chemical Formula: $C_{19}H_{22}FN_5$
Molecular Weight: 339.41

Example Route for Example 26

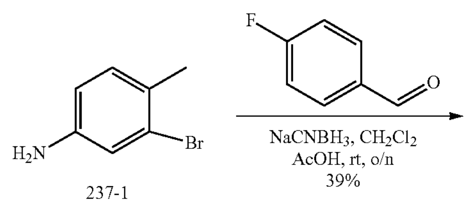

237-1

-continued

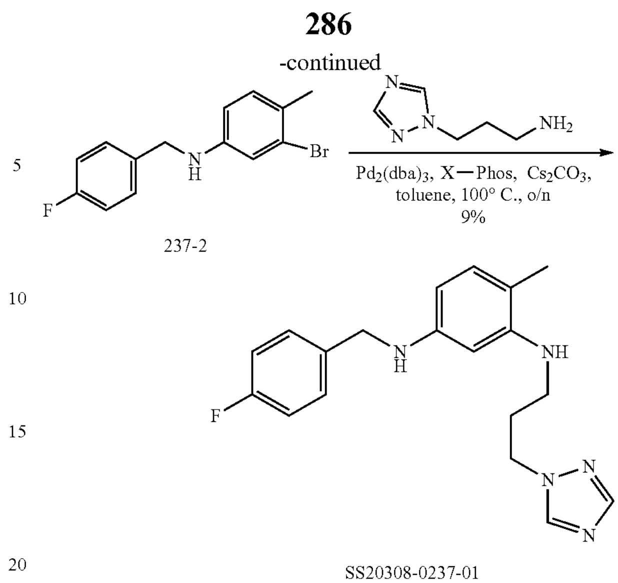

237-2

SS20308-0237-01

The Synthesis of 3-bromo-N-(4-fluorobenzyl)-4-methylaniline (237-2)

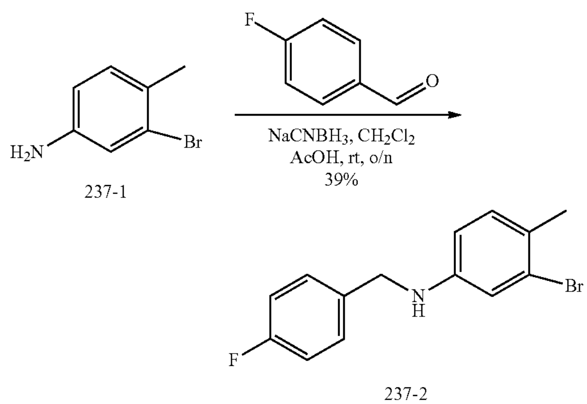

237-1

237-2

A mixture of 237-1 (200 mg, 1.3 mmol), 4-fluorobenzaldehyde (190 mg, 1.6 mmol), AcOH (a drop) and $NaCNBH_3$ (130 mg, 2.0 mmol) in $CH_2Cl_2$ (10 mL) was stirred at 80° C. overnight. The reaction mixture was cooled to room temperature and poured into water (10 mL) and extracted with EtOAc (10 mL×3). The organic layer was washed with brine and evaporated to give 237-2 (150 mg, about 39% yield) as an oil. MS Calcd.: 216.1; MS Found: 294.3 $[M+H]^+$.

The Synthesis of $N^3$-(3-(1H-1,2,4-triazol-1-yl)propyl)-$N^1$-(4-fluorobenzyl)-4-methylbenzene-1,3-diamine (SS20308-0237-01)

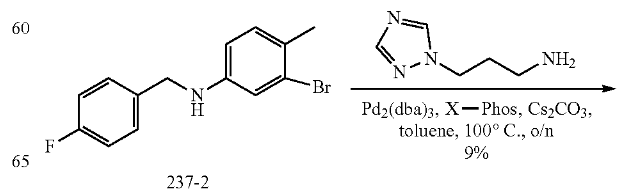

237-2

-continued

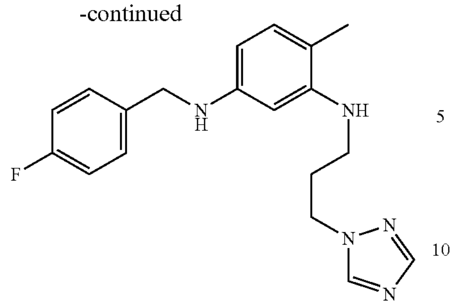

SS20308-0237-01

A mixture of 237-2 (130 mg, 0.44 mmol), 1H-1,2,4-Triazole-1-propanamine (86 mg, 0.53 mmol), $Pd_2(dba)_3$ (20 mg, 0.022 mmol), X-Phos (21 mg, 0.044 mmol) and $Cs_2CO_3$ (430 mg, 1.32 mmol) in toluene (3 mL) was stirred at reflux overnight. The reaction mixture was cooled to room temperature and poured into water (10 mL) and extracted with EtOAc (10 mL×3). The organic layer was washed with brine and evaporated, the residue crude product was purified by Prep-HPLC to give SS20308-0237-01 (13.5 mg, about 9% yield) as an oil. MS Calcd.: 339.2; MS Found: 340.0 $[M+H]^+$.

$^1H$ NMR (400 MHz, DMSO-$d_6$) δ 8.52 (s, 1H), 7.98 (s, 1H), 7.96 (dd, J=8.8, 5.6 Hz, 2H), 7.10 (t, J=8.8 Hz, 2H), 6.60 (d, J=8.0 Hz, 1H), 5.79-5.73 (m, 3H), 4.59 (t, J=5.6 Hz, 1H), 4.24 (t, J=6.8 Hz, 2H), 4.16 (d, J=6.4 Hz, 2H), 2.96-2.91 (m, 2H), 2.03-1.99 (m, 2H), 1.90 (s, 3H).

Example 27

SS20308-0239-01

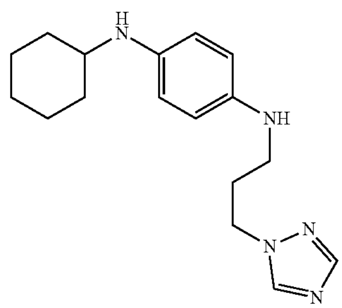

Chemical Formula: $C_{17}H_{25}N_5$
Molecular Weight: 299.41

Example Route for Example 27

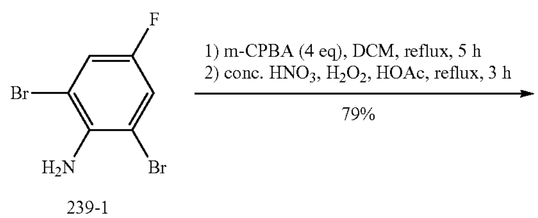

239-1

-continued

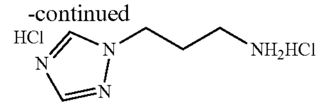

236-3

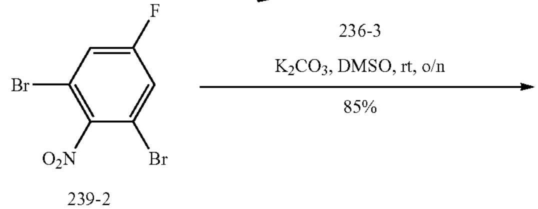

239-2

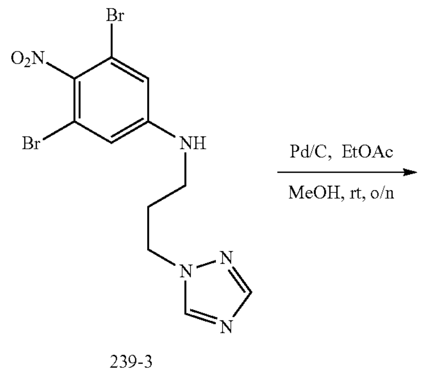

239-3

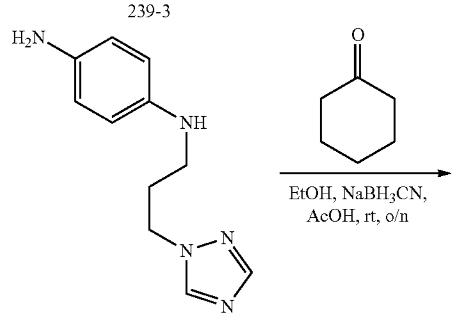

0239-4

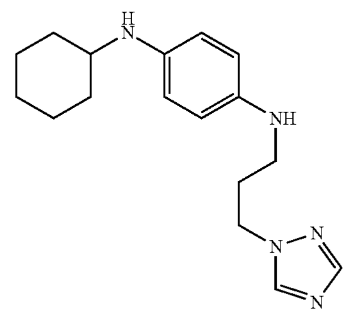

SS20308-0239-01

The Synthesis of 1,3-dibromo-5-fluoro-2-nitrobenzene (239-2)

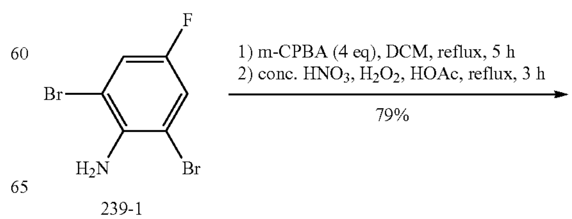

239-1

-continued

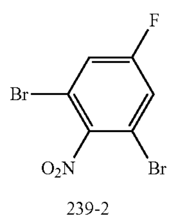

239-2

To a solution of 2,6-dibromo-4-fluoroaniline (5.0 g, 18.59 mmol) in dichloromethane (100 mL) was added 3-chloroperoxybenzoic acid (18.4 g, 90.63 mmol, 85% by weight). The mixture was heated to reflux and stirred for 5 h. The reaction mixture was cooled to 0° C. in an ice bath, and then filtered. The filtrate was then washed with 1.0 N KOH (3×75 mL), and the organic layer was concentrated in vacuo to afford a brown solid. The solid was dissolved in 50 mL of glacial acetic acid. To this solution were added 25 mL of a 30% $H_2O_2$ solution and 4 mL of concentrated nitric acid. The mixture was heated to reflux and stirred for 3 h, then poured into 250 mL of ice water and the suspension was filtered and the solid washed with water, then dried on the filter under air to give 239-2 (4.4 g, about 79% yield) as a solid. MS Calcd.: 296.8; MS Found: 298.2 $[M+H]^+$.

The Synthesis of N-(3-(1H-1,2,4-triazol-1-yl)propyl)-3,5-dibromo-4-nitroaniline (239-3)

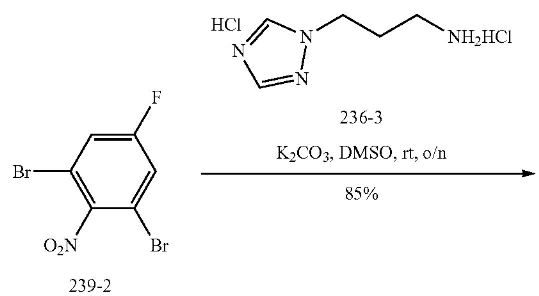

236-3

239-2

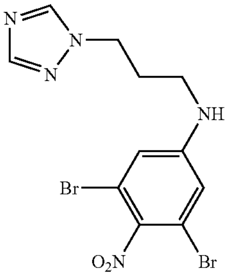

239-3

A mixture of compound 239-2 (2.0 g, 6.69 mmol), 236-3 (2.0 g, 10.04 mmol) and potassium carbonate (4.62 g, 33.46 mmol) were suspended in DMSO (20 mL). After stirring at room temperature for overnight, the mixture was diluted with water (80 mL). The resulting solid was filtered, washed with water, dried to give compound 239-3 (2.3 g, about 85% yield) as a solid. MS Calcd.: 402.9; MS Found: 403.9 $[M+H]^+$.

The Synthesis of N[1]-(3-(1H-1,2,4-triazol-1-yl)propyl)benzene-1,4-diamine (239-4)

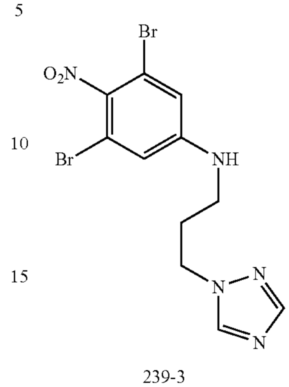

239-3

Pd/C, EtOAc

MeOH, rt, o/n

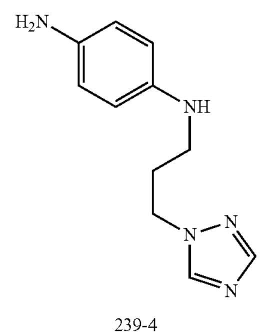

239-4

To a solution of 239-3 (1.00 g, 2.47 mmol) in MeOH (5 mL) and EtOAc (5 mL) was added Pd/C (10%, 250 mg). The resulting mixture was stirred under $H_2$ atmosphere at room temperature overnight. The mixture was filtered and concentrated to give 239-4 (700 mg) as a crude oil. MS Calcd.: 217.1; MS Found: 218.1 $[M+H]^+$.

The Synthesis of N[1]-(3-(1H-1,2,4-triazol-1-yl)propyl)-N[4]-cyclohexylbenzene-1,4-diamine (SS20308-0239-01)

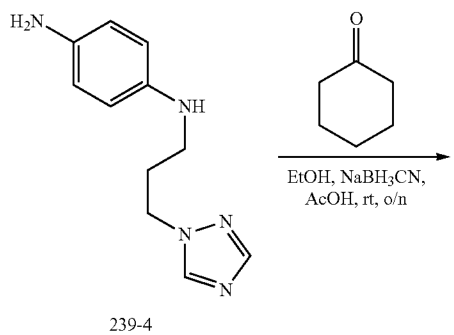

239-4

-continued

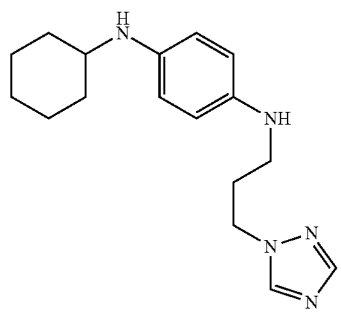

SS20308-0239-01

To a solution of 239-4 (200.00 mg, 0.92 mmol) in EtOH (3 mL) and AcOH (3 mL) was added cyclohexanone (361.37 mg, 3.68 mmol) and $NaBH_3CN$ (173.54 mg, 2.76 mmol). The resulting mixture was stirred at room temperature overnight. Then the mixture was basified with $Na_2CO_3$ (aq.) until pH reached 7-8, extracted with EtOAc. The combined organic layers were washed with brine, dried over $Na_2SO_4$, filtered and the filtrate was concentrated, the residue was purified by Prep-HPLC to give SS20308-0239-01 (15 mg, about 5% yield) as a solid. MS Calcd.: 299.2; MS Found: 300.2 $[M+H]^+$.

$^1H$ NMR (400 MHz, DMSO-$d_6$) δ 8.50 (s, 1H), 7.97 (s, 1H), 6.43-6.37 (m, 4H), 4.76 (t, J=5.8 Hz, 1H), 4.41 (d, J=8.4 Hz, 1H), 4.27 (t, J=6.8 Hz, 2H), 3.02-2.99 (m, 1H), 2.86 (q, J=12.8 Hz, 2H), 2.03-1.96 (m, 2H), 1.89-1.86 (m, 2H), 1.71-1.67 (m, 2H), 1.59-1.56 (m, 1H), 1.32-1.23 (m, 2H), 1.18-1.01 (m, 3H).

Example 28

SS20308-0240-01

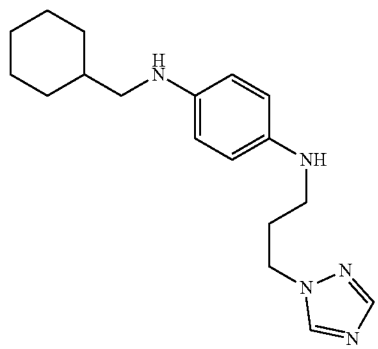

Chemical Formula: $C_{18}H_{27}FN_5$
Molecular Weight: 313.44

Example Route for Example 28

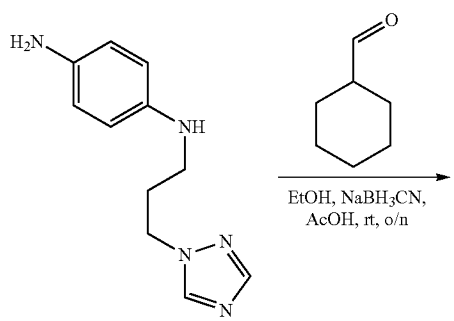

239-4

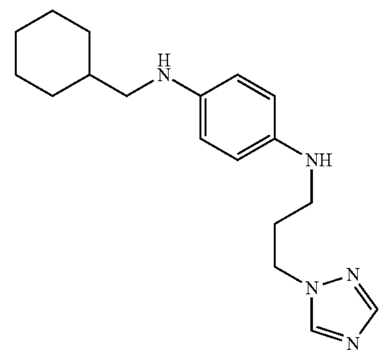

SS20308-0240-01

The Synthesis of N[1]-(3-(1H-1,2,4-triazol-1-yl)propyl)-N[4]-(cyclohexylmethyl)benzene-1,4-diamine (SS20308-0240-01)

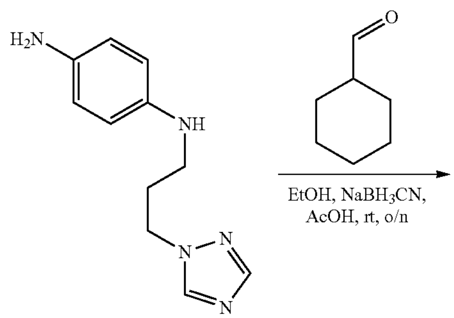

239-4

-continued

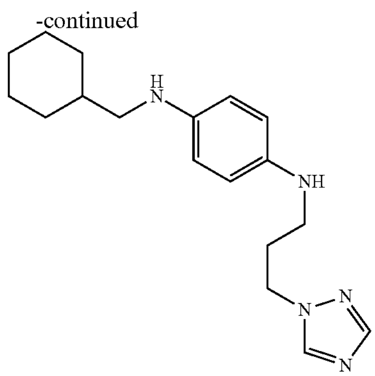

SS20308-0240-01

To a solution of 239-4 (250.00 mg, 1.15 mmol) in EtOH (3 mL) and AcOH (3 mL) was added cyclohexanecarbaldehyde (516.27 mg, 4.60 mmol) and $NaBH_3CN$ (216.93 mg, 3.45 mmol). The resulting mixture was stirred at room temperature overnight. Then the mixture was basicified with $Na_2CO_3$ (aq.) until pH reached 7-8, extracted with EtOAc. The combined organic layers were washed with brine, dried over $Na_2SO_4$, filtered and the filtrate was concentrated, the residue was purified by Prep-HPLC to give SS20308-0240-01 (40 mg, about 11% yield) as a solid. MS Calcd.: 313.4; MS Found: 314.2 $[M+H]^+$.

$^1H$ NMR (400 MHz, DMSO-$d_6$) δ 8.50 (s, 1H), 7.97 (s, 1H), 6.42-6.37 (m, 4H), 4.76-4.69 (m, 2H), 4.27 (t, J=7.0 Hz, 2H), 2.85 (q, J=6.4 Hz, 2H), 2.73 (t, J=6.2 Hz, 2H), 2.08-1.96 (m, 2H), 1.79-1.76 (m, 2H), 1.69-1.61 (m, 3H), 1.51-1.45 (m, 1H), 1.20-1.11 (m, 3H), 0.94-0.85 (m, 2H).

Example 29

SS20308-0242-01

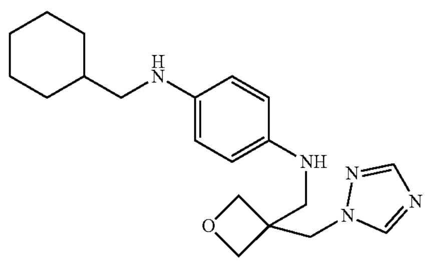

Chemical Formula: $C_{20}H_{29}N_5O$
Molecular Weight: 355.48

Example Route for Example 29

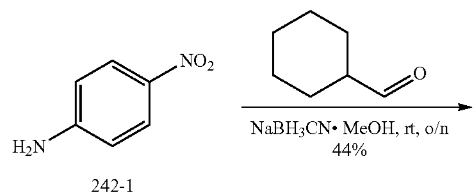

242-1

-continued

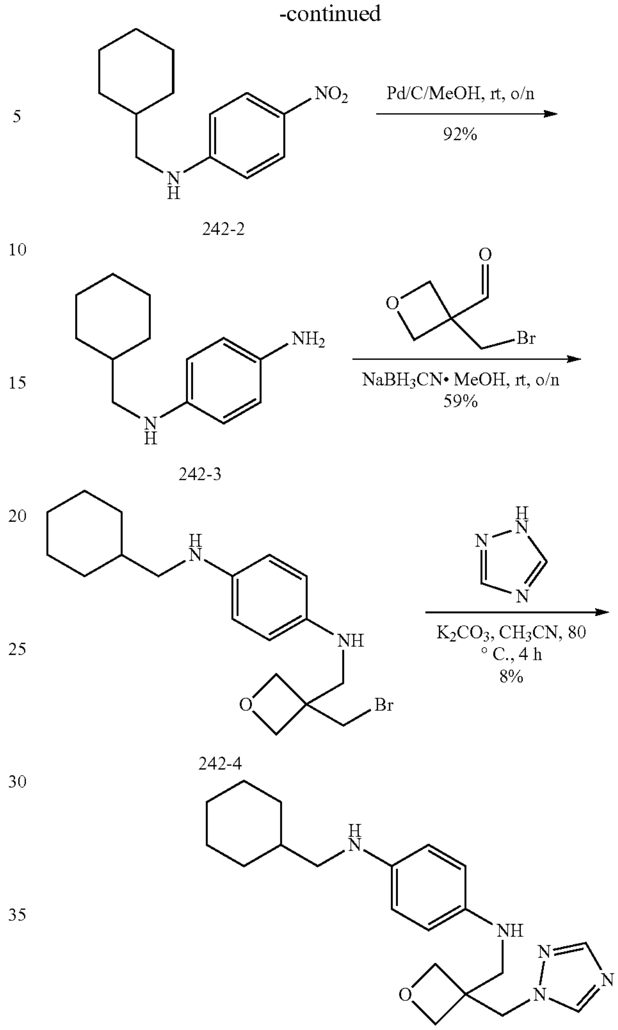

The Synthesis of N-(cyclohexylmethyl)-4-nitroaniline (242-2)

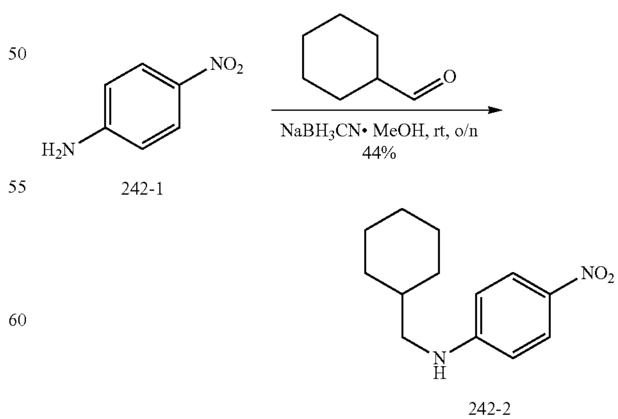

To a solution of 242-1 (2.00 g, 14.48 mmol) and cyclohexanecarbaldehyde (1.95 g, 17.38 mmol) in MeOH (25 mL) was added $NaBH_3CN$ (2.73 g, 43.44 mmol), the mixture was stirred at room temperature overnight. After the reaction was complete, the reaction was poured into water (50 mL) and extracted with EtOAc (40 mL×3). The organic layer was washed brine (2×50 mL), dried over $MgSO_4$, and concentrated in vacuum, which was purified by column chromatography (petroleum ether/EtOAc=5/1) to give 242-2 (1.5 g, about 44% yield) as a solid.

The Synthesis of N[1]-(cyclohexylmethyl)benzene-1, 4-diamine (242-3)

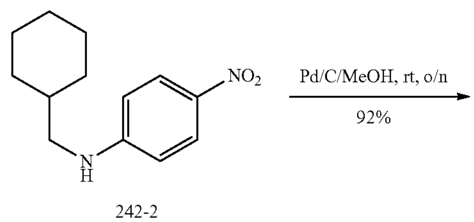

242-2

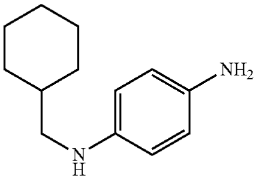

242-3

To a solution of 242-2 (1.00 g, 4.27 mmol) in MeOH (20 mL) was added Pd/C (10%, 100 mg), the mixture was stirred at room temperature under $H_2$ atmosphere overnight. After the reaction was complete, the insoluble material was removed by filtration. The organic layer was concentrated in vacuum, which was purified by column chromatography (petroleum ether/EtOAc=1/2) to give 242-3 (800 mg, about 92% yield) as a solid. MS Calcd.: 204.2; MS Found: 205.4 $[M+H]^+$.

The Synthesis of N[1]-((3-(bromomethyl)oxetan-3-yl) methyl)-N[4]-(cyclohexylmethyl)benzene-1,4-diamine (242-4)

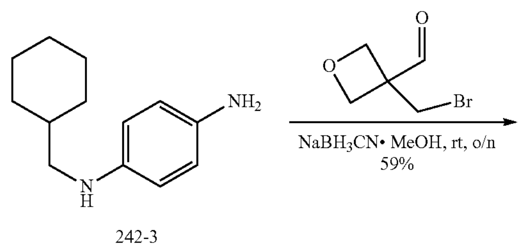

242-3

-continued

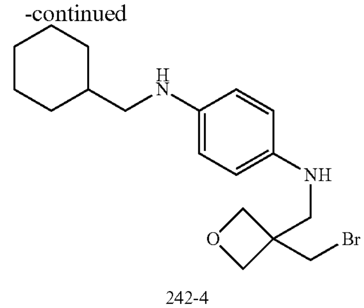

242-4

To a solution of 242-3 (150 mg, 0.73 mmol) and 3-(bromomethyl)oxetane-3-carbaldehyde (131 mg, 0.73 mmol) in MeOH (15 mL) was added $NaBH_3CN$ (138 mg, 2.20 mmol), the mixture was stirred at room temperature overnight. After the reaction was complete, the reaction was poured into water (30 mL) and extracted with EtOAc (30 mL×3). The organic layer was washed brine (2×30 mL), dried over $MgSO_4$, and concentrated under vacuum, which was obtained by simple work up to give 242-4 (160 mg, about 59% yield) as an oil. MS Calcd.: 366.1; MS Found: 367.0 $[M+H]^+$.

The Synthesis of N[1]-((3-((1H-1,2,4-triazol-1-yl) methyl)oxetan-3-yl)methyl)-N[4]-(cyclohexylmethyl) benzene-1,4-diamine (SS20308-0242-01)

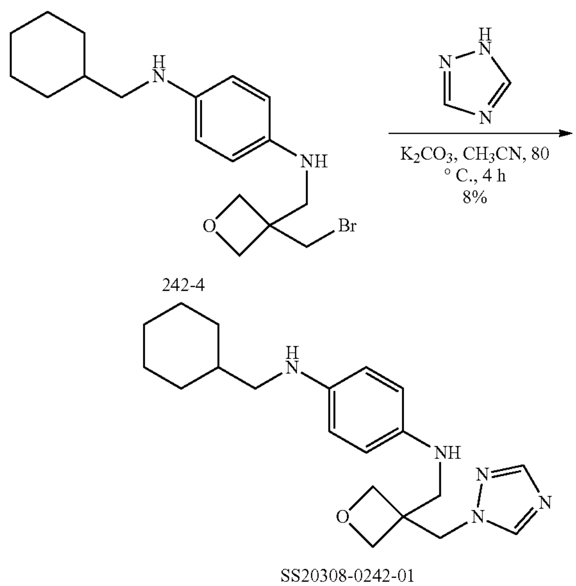

242-4

SS20308-0242-01

A mixture of 242-4 (160 mg, 0.44 mmol), 1H-1,2,4-triazole (60 mg, 0.87 mmol) and $K_2CO_3$ (180 mg, 1.31 mmol) in $CH_3CN$ (20 ml) was stirred at 80° C. under nitrogen atmosphere for 4 h. After the reaction was complete, the mixture was quenched with water and extracted with EtOAc (20 mL×3). The organic layer was separated, dried over $MgSO_4$, and concentrated under vacuum, which was purified by Prep-HPLC to give SS20308-0242-01 (13 mg, about 8% yield) as an oil. MS Calcd.: 355.2; MS Found: 356.1 $[M+H]^+$.

$^1H$ NMR (400 MHz, DMSO-$d_6$) δ 8.49 (s, 1H), 8.01 (s, 1H), 6.50-6.39 (m, 4H), 4.84 (t, J=6.8 Hz, 1H), 4.77 (t, J=5.6

Hz, 1H), 4.59 (s, 2H), 4.51 (d, J=6.0 Hz, 2H), 4.38 (d, J=6.0 Hz, 2H), 2.99 (d, J=6.4 Hz, 2H), 2.74 (t, J=6.0 Hz, 2H), 1.79-1.60 (m, 2H), 1.69-1.63 (m, 3H), 1.51-1.45 (m, 1H), 1.24-1.11 (m, 3H), 0.94-0.86 (m, 2H).

Example 30

SS20308-0245-01

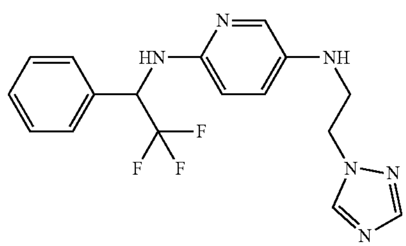

Chemical Formula: $C_{17}H_{17}N_6$
Molecular Weight: 362.35

Example Route for Example 30

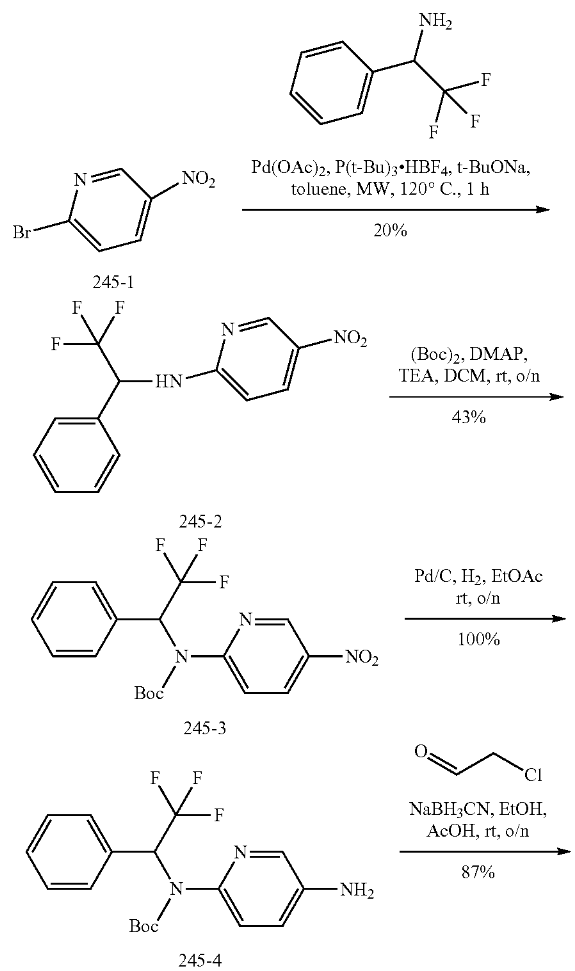

245-1

245-2

245-3

245-4

-continued

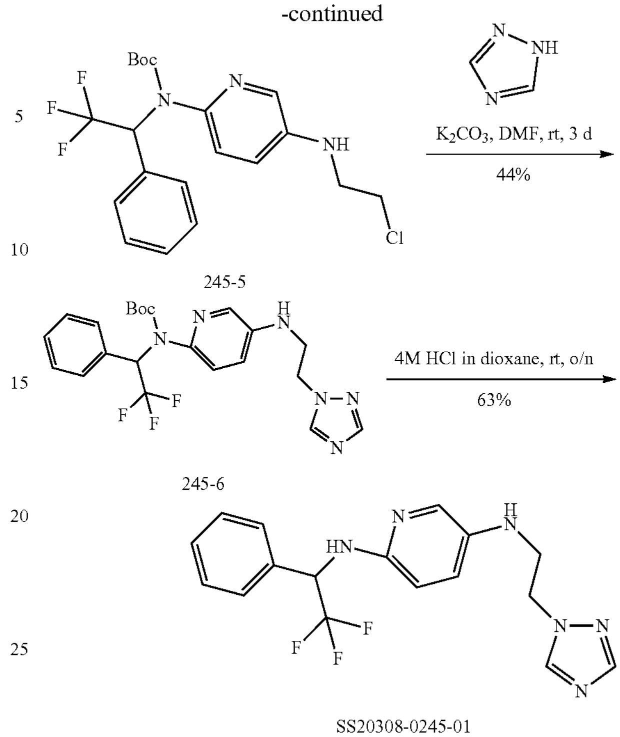

245-5

245-6

SS20308-0245-01

The Synthesis of 5-nitro-N-(2,2,2-trifluoro-1-phenylethyl)pyridin-2-amine (0245-2)

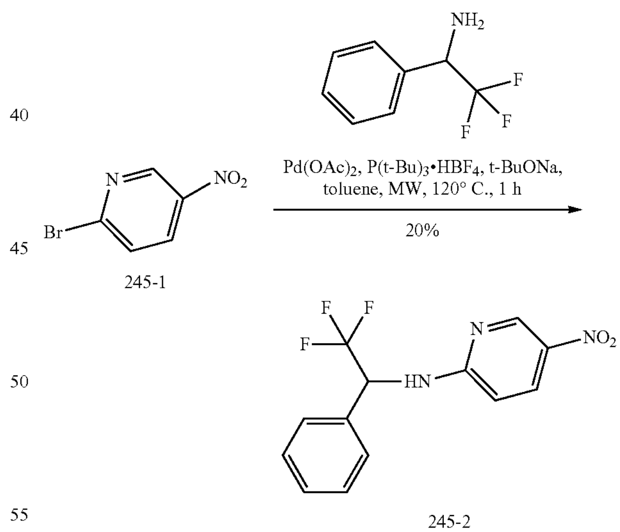

245-1

245-2

To 2-bromo-5-nitro-pyridine (245-1) (1.0 g, 4.93 mmol) in toluene (10 mL), was added 2,2,2-trifluoro-1-phenylethanamine (863 mg, 4.93 mmol), followed by palladium (II) acetate (55 mg, 0.25 mmol), tri-tert-butylphosphine tetrafluoroborate (143 mg, 0.49 mmol) and sodium tert-butoxide (710 mg, 7.39 mmol). The reaction mixture was stirred at 120° C. for 1 hr under microwave irradiation. The reaction mixture was filtered through celite and rinsed with ethyl acetate. The filtrate was concentrated and the residue was purified by silica gel column chromatography (petroleum ether/EtOAc=100/1, 50/1, 20/1) to give compound 245-2 (0.3 g, about 20% yield) as a solid. MS Calcd.: 297.1; MS Found: 298.1 $[M+H]^+$.

The Synthesis of tert-butyl 5-nitropyridin-2-yl(2,2,2-trifluoro-1-phenylethyl)carbamate (245-3)

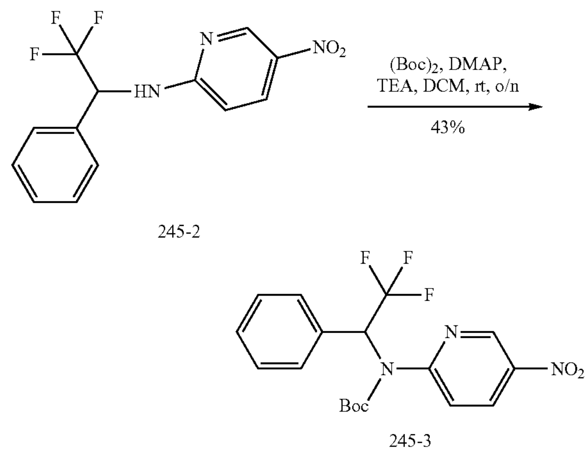

245-2

245-3

To a solution of 245-2 (300 mg, 1.01 mmol) in DCM (5 mL) was added TEA (102 mg, 1.01 mmol), $(Boc)_2O$ (440 mg, 2.02 mmol) and DMAP (62 mg, 0.50 mmol). After stirring at room temperature for overnight, the reaction mixture was concentrated and purified by Prep-TLC (petroleum ether/EtOAc=10/1) to give 245-3 (171 mg, about 43% yield) as an oil. MS Calcd.: 397.1; MS Found: 342.1 $[M-55]^+$.

The Synthesis of tert-butyl 5-aminopyridin-2-yl(2,2,2-trifluoro-1-phenylethyl)carbamate (245-4)

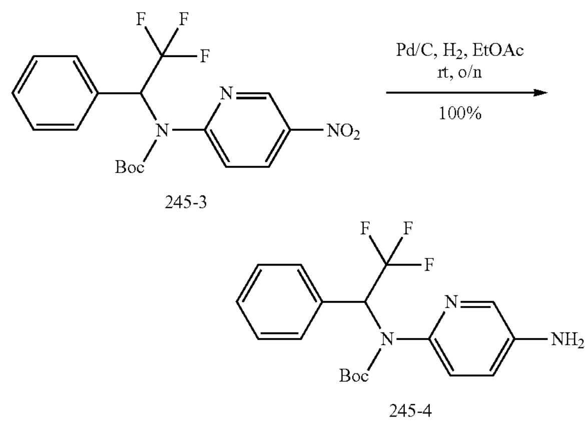

245-3

245-4

A suspension of 245-3 (166 mg, 0.42 mmol) and palladium on carbon (166 mg, 10%) in EtOAc (20 mL) is stirred vigorously under hydrogen atmosphere for 5 hr at room temperature. The reaction mixture was filtered through celite and rinsed with EtOAc. The filtrate was concentrated to give a crude product 245-4 (153 mg, about 100% yield) as a solid. MS Calcd.: 367.2; MS Found: 368.1 $[M+H]^+$.

The Synthesis of tert-butyl 5-nitropyridin-2-yl(2,2,2-trifluoro-1-phenylethyl)carbamate (245-5)

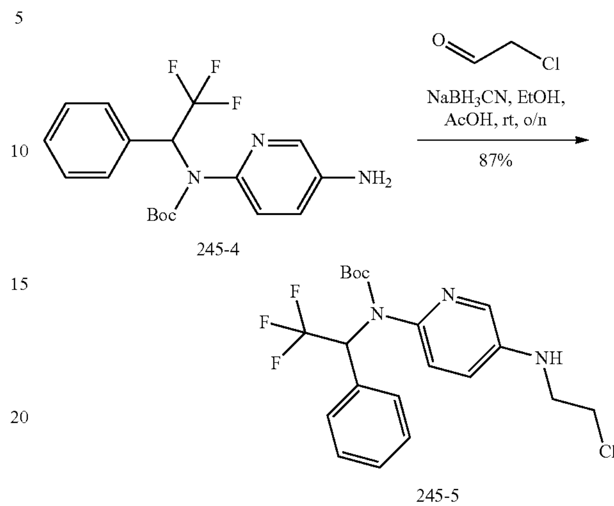

245-4

245-5

To a solution of 245-4 (159 mg, 0.43 mmol), 2-chloroacetaldehyde (255 mg, 1.30 mmol, 40% in water) and acetic acid glacial (1 mL) in ethanol (10 mL) was added $NaBH_3CN$ (55 mg, 0.87 mmol). After stirring at room temperature for 16 hr, the reaction mixture was basified with $NaHCO_3$ solution and extracted with EtOAc (10 mL×3). The organic layers were washed with water and brine, dried over $MgSO_4$ and concentrated. The residue was purified by Prep-TLC (petroleum ether/EtOAc=2/1) to give compound 245-5 (162 mg, about 87% yield) as an oil. MS Calcd.: 429.1; MS Found: 430.3 $[M+H]^+$.

The Synthesis of tert-butyl 5-(2-(1H-1,2,4-triazol-1-yl)ethylamino)pyridin-2-yl(2,2,2-trifluoro-1-phenylethyl)carbamate (245-6)

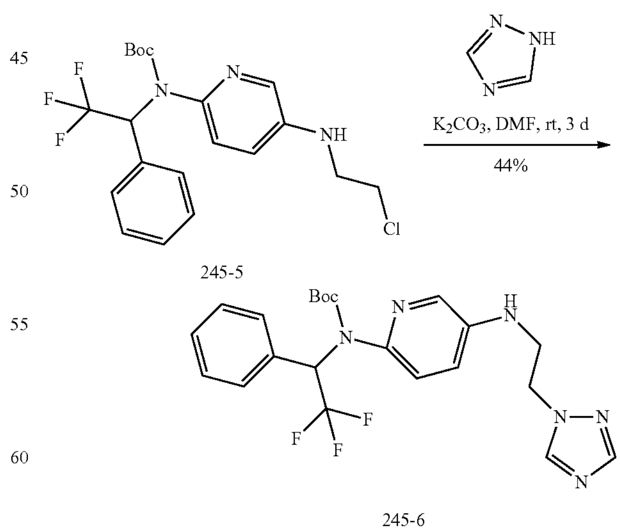

245-5

245-6

A mixture of 245-5 (162 mg, 0.38 mmol), 1H-1,2,4-triazole (52 mg, 0.75 mmol) and potassium carbonate (104 mg, 0.75 mmol) in DMF (5 mL) was stirred at room temperature for 3 d. Then the reaction mixture was poured into cool water (20 mL), extracted with EtOAc (10 mL×3). The combined organic layers were washed with brine (10 mL×2), dried over sodium sulfate, and concentrated to dryness. The residue was purified by Prep-TLC (petroleum ether/EtOAc=1/2, ethyl acetate, dichloromethane/methanol=20/1) to give compound 245-6 (77 mg, about 44% yield) as an oil. MS Calcd.: 462.2; MS Found: 463.3 $[M+H]^+$.

The Synthesis of $N^5$-(2-(1H-1,2,4-triazol-1-yl)ethyl)-$N^2$-(2,2,2-trifluoro-1-phenylethyl)pyridine-2,5-diamine (SS20308-0245-01)

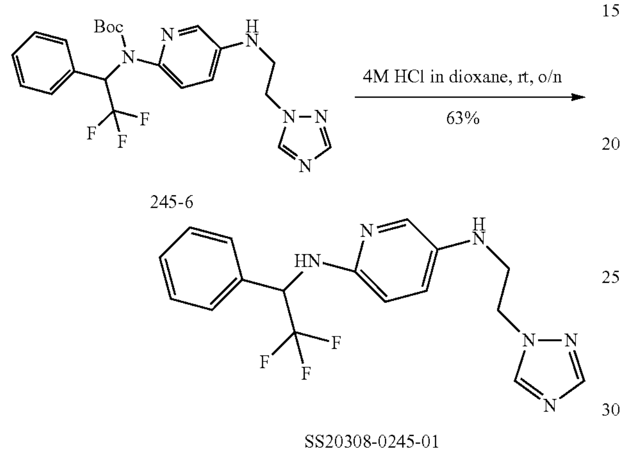

245-6

SS20308-0245-01

A suspension of 245-6 (77 mg, 0.17 mmol) in HCl (4 M in dioxane, 10 mL) is stirred for 16 hr at room temperature. The mixture was concentrated under vacuum and dissolved in water; adjust the pH to 10.0-11.0 with NaOH solution; extracted with EtOAc (10 mL×3). The combined organic layers were washed with brine (10 mL×2), dried over sodium sulfate, and concentrated to dryness. The residue was purified by Prep-TLC (dichloromethane/methanol=15/1) to give compound SS20308-0245-01 (38 mg, about 63% yield) as an oil. MS Calcd.: 362.2; MS Found: 363.3 $[M+H]^+$.

$^1$H NMR (400 MHz, DMSO-$d_6$) δ 8.43 (s, 1H), 7.94 (s, 1H), 7.54 (d, J=7.2 Hz, 2H), 7.42 (d, J=2.8 Hz, 1H), 7.39-7.29 (m, 3H), 6.99 (d, J=10.0 Hz, 1H), 6.87 (dd, J=8.8, 2.8 Hz, 1H), 6.59 (d, J=8.8 Hz, 1H), 5.97-5.86 (m, 1H), 5.10 (t, J=6.0 Hz, 1H), 4.26 (t, J=6.0 Hz, 2H), 3.37-3.30 (m, 2H).

Example 31

SS20308-0246-01

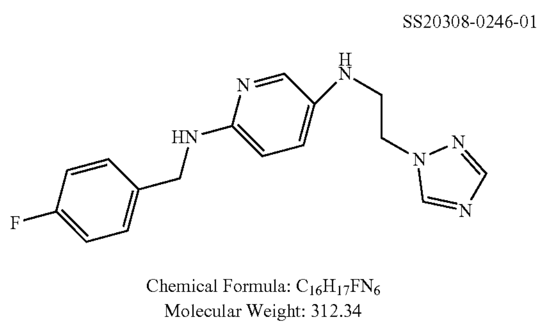 [SMILES: Fc1ccc(CNc2ccc(NCCn3cncn3)cn2)cc1]

Chemical Formula: $C_{16}H_{17}FN_6$
Molecular Weight: 312.34

Example Route for Example 31

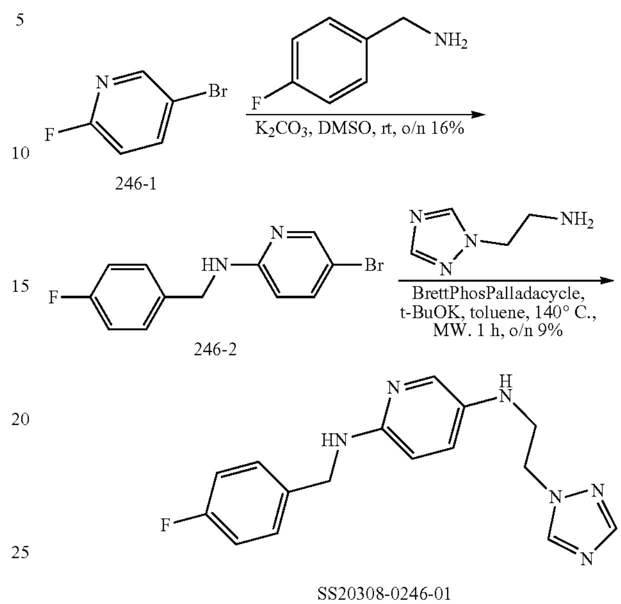

246-1

246-2

SS20308-0246-01

The Synthesis of 5-bromo-N-(4-fluorobenzyl)pyridin-2-amine (246-2):

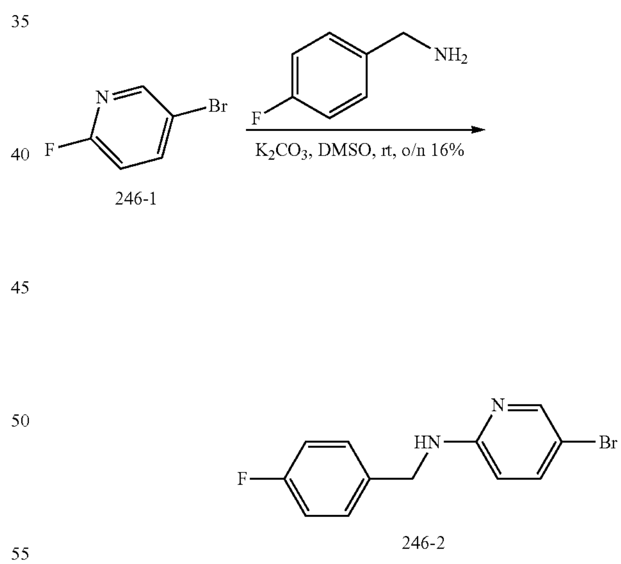

246-1

246-2

The mixture of 246-1 (2.00 g, 11.4 mmol), (4-fluorophenyl)methanamine (2.85 g, 22.8 mmol) and $K_2CO_3$ (3.15 g, 22.8 mmol) in DMSO (50 mL) was stirred at room temperature overnight. The reaction mixture was added water (150 mL), and then the mixture was extracted ethyl acetate (150 mL×3). The organic layers were washed with brine, dried over $Na_2SO_4$ and concentrated. The residue was purified by column chromatography (petroleum ether/EtOAc=10/1) to give 246-2 (500 mg, about 16% yield) as a solid. MS Calcd.: 280.0; MS Found: 281.2 $[M+H]^+$.

The Synthesis of $N^5$-(2-(1H-1,2,4-triazol-1-yl) ethyl)-$N^2$-(4-fluorobenzyl)pyridine-2,5-diamine (SS20308-0246-01)

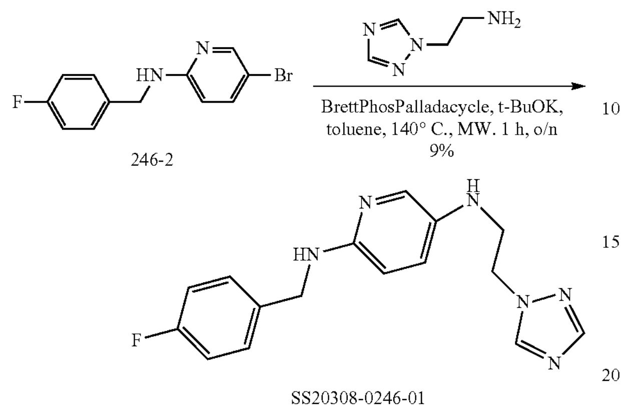

246-2

SS20308-0246-01

The mixture of 246-2 (250 mg, 0.89 mmol), 2-(1H-1,2,4-triazol-1-yl)ethanamine (199 mg, 1.78 mmol), BrettPhosPalladacycle (71 mg, 0.089 mmol), and t-BuOK (199 mg, 1.78 mmol) in toluene (5 mL) was stirred at 140° C. for one hour in a microwave reactor. The reaction mixture was then cooled to room temperature and filtered through celite and concentrated. The residue was purified by Prep-HPLC to give SS20308-0246-01 (26 mg, about 9% yield) as a solid. MS Calcd.: 312.2; MS Found: 313.1 $[M+H]^+$.

$^1H$ NMR (400 MHz, DMSO-$d_6$) δ 8.47 (s, 1H), 7.97 (s, 1H), 7.43 (d, J=2.8 Hz, 1H), 7.36-7.30 (m, 2H), 7.14-7.07 (m, 2H), 6.85 (dd, J=8.6 Hz, 3.2 Hz, 1H), 6.36 (d, J=8.8 Hz, 1H), 6.29 (t, J=6.2 Hz, 1H), 4.97 (t, J=6.2 Hz, 1H), 4.34 (d, J=6.0 Hz, 2H), 4.28 (t, J=6.2 Hz, 2H), 3.38-3.34 (m, 2H).

Example 32

SS20308-0247-01

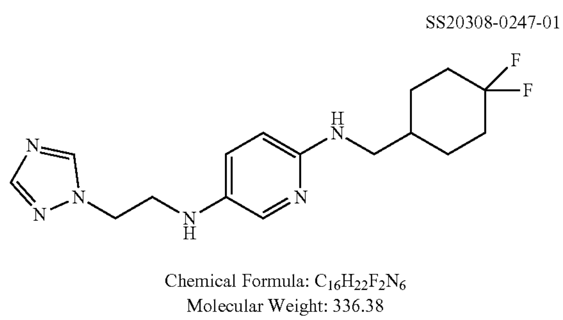 [SMILES: FC1(F)CCC(CNc2ccc(NCCn3cncn3)cn2)CC1]

Chemical Formula: $C_{16}H_{22}F_2N_6$
Molecular Weight: 336.38

Example Route for Example 32

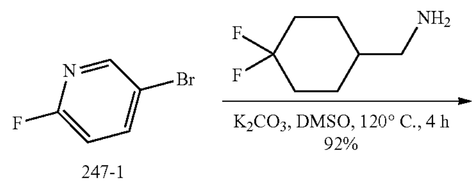

247-1

-continued

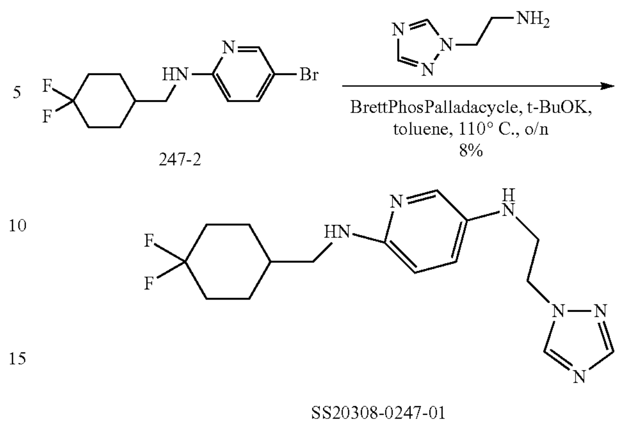

247-2

SS20308-0247-01

The Synthesis of 5-bromo-N-((4,4-difluorocyclohexyl)methyl)pyridin-2-amine (247-2)

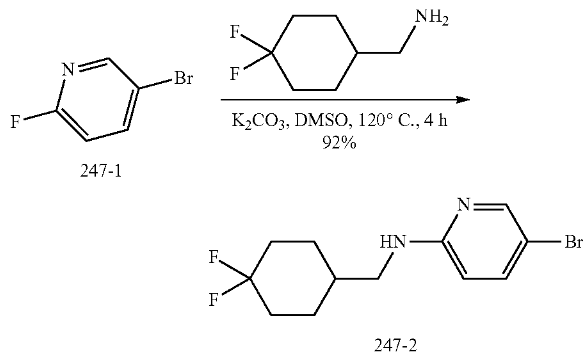

247-1

247-2

The mixture of 247-1 (50 mg, 0.28 mmol), (4,4-difluorocyclohexyl)methanamine (84 mg, 0.56 mmol) and $K_2CO_3$ (116 mg, 0.84 mmol) in DMSO (2 mL) was stirred at 120° C. 4 hours. The reaction mixture was diluted with water (10 mL) and then the mixture was extracted EtOAc (10 mL×3). The organic layers were washed with brine, dried over $Na_2SO_4$ and concentrated to give 247-2 (80 mg, about 92% yield) as an oil. MS Calcd.: 304.0; MS Found: 305.2 $[M+H]^+$.

The Synthesis of $N^5$-(2-(1H-1,2,4-triazol-1-yl) ethyl)-$N^2$-((4,4-difluorocyclohexyl)methyl)pyridine-2,5-diamine (SS20308-0247-01)

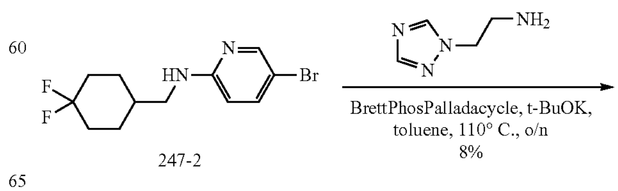

247-2

-continued

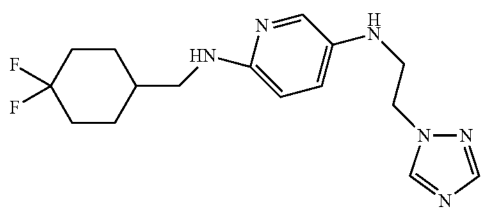

SS20308-0247-01

The mixture of 247-2 (80 mg, 0.26 mmol), 2-(1H-1,2,4-triazol-1-yl)ethanamine (58 mg, 0.52 mmol), BrettPhosPalladacycle (21 mg, 0.026 mmol), and t-BuOK (58 mg, 0.52 mmol) in toluene (3 mL) was stirred at 110° C. overnight under $N_2$ atmosphere. The reaction mixture was then cooled to room temperature and filtered through celite and concentrated. The residue was purified by Prep-HPLC to give SS20308-0247-01 (7 mg, about 8% yield) as an oil. MS Calcd.: 336.2; MS Found: 337.3 $[M+H]^+$.

$^1$H NMR (400 MHz, DMSO-$d_6$) δ 8.47 (s, 1H), 7.97 (s, 1H), 7.44-7.42 (m, 1H), 6.85-6.80 (m, 1H), 6.35 (d, J=8.8 Hz, 1H), 5.81 (t, J=6.0 Hz, 1H), 4.90 (t, J=6.4 Hz, 1H), 4.29 (t, J=6.2 Hz, 2H), 3.36 (t, J=6.0 Hz, 2H), 3.03 (t, J=6.0 Hz, 2H), 2.05-1.93 (m, 2H), 1.84-1.58 (m, 5H), 1.23-1.10 (m, 2H),

Example 33

SS20308-0249-01

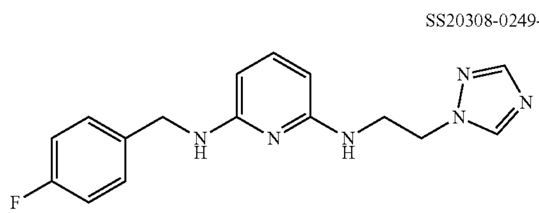

Chemical Formula: $C_{16}H_{17}FN_6$
Molecular Weight: 312.34

Example Route for Example 33

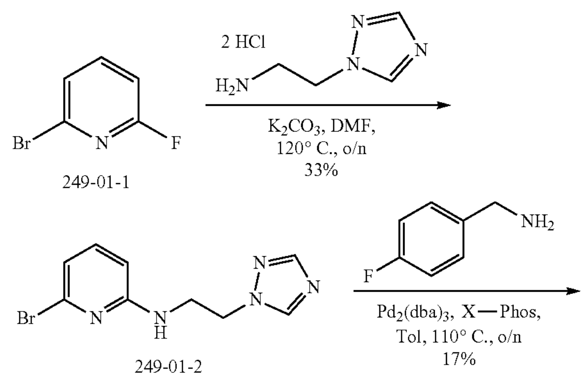

249-01-1

249-01-2

-continued

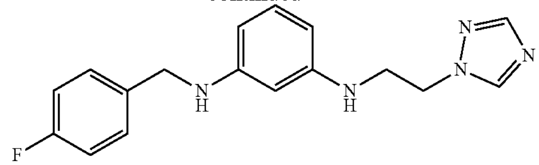

SS20308-0249-01

The Synthesis of N-(2-(1H-1,2,4-triazol-1-yl)ethyl)-6-bromopyridin-2-amine (249-2)

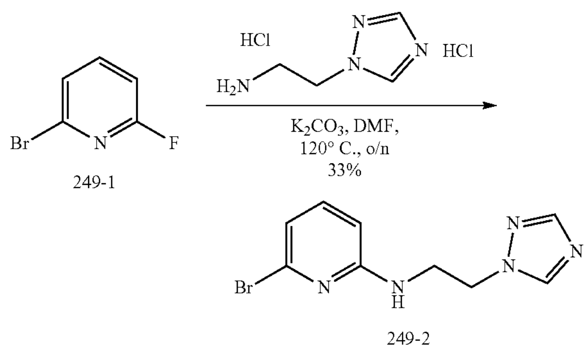

249-1

249-2

A mixture of 249-1 (600 mg, 3.41 mmol), 2-(1H-1,2,4-triazol-1-yl)ethanamine dihydrochloride (757 mg, 4.09 mmol) and $K_2CO_3$ (1.18 g, 8.52 mmol) in DMF (10 ml) was stirred at 120° C. under nitrogen atmosphere overnight. After the reaction was complete, the mixture was quenched with water and extracted with EtOAc (50 mL×3). The organic layer was separated, dried over $MgSO_4$, and concentrated under vacuum, which was purified by column chromatography (petroleum ether/EtOAc=1/1) to give 249-2 (300 mg, about 33% yield) as a solid. MS Calcd.: 267.0; MS Found: 268.0 $[M+H]^+$.

The Synthesis of $N^2$-(2-(1H-1,2,4-triazol-1-yl)ethyl)-$N^6$-(4-fluorobenzyl)pyridine-2,6-diamine (SS20308-0249-01)

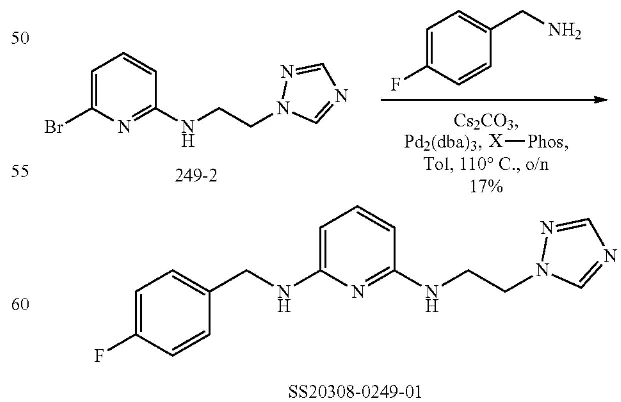

249-2

SS20308-0249-01

A mixture of 249-2 (100 mg, 0.37 mmol), (4-fluorophenyl)methanamine (56 mg, 0.45 mmol), $Pd_2(dba)_3$ (17 mg, 0.02 mmol), X-Phos (18 mg, 0.04 mmol) and $Cs_2CO_3$ (243 mg, 0.75 mmol) in toluene (10 ml) and was stirred at 110° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated under vacuum, which was purified by Prep-HPLC to give SS20308-0249-01 (20 mg, about 17% yield) as an oil. MS Calcd.: 312.2; MS Found: 313.0 $[M+H]^+$.

$^1$H NMR (400 MHz, DMSO-$d_6$) δ 8.31 (s, 1H), 7.96 (s, 1H), 7.37-7.34 (m, 2H), 7.13-7.08 (m, 2H), 7.02 (t, J=8.0 Hz, 1H), 6.68 (t, J=6.0 Hz, 1H), 6.19 (t, J=5.6 Hz, 1H), 5.66 (d, J=7.6 Hz, 1H), 5.59 (d, J=7.6 Hz, 1H), 4.39 (d, J=6.4 Hz, 2H), 4.22 (t, J=6.0 Hz, 2H), 3.53-3.49 (m, 2H).

Example 34

SS20308-0250-01

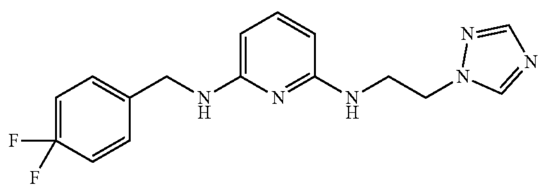

Chemical Formula: $C_{16}H_{22}F_2N_6$
Molecular Weight: 336.38

Example Route for Example 34

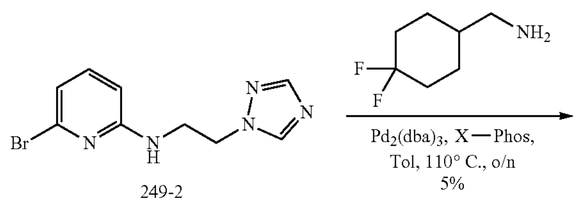

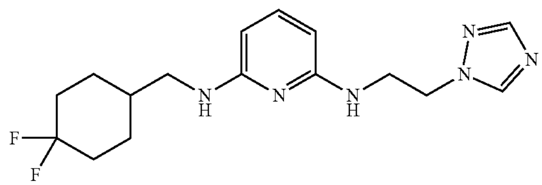

SS20308-0250-01

The Synthesis of N[2]-(2-(1H-1,2,4-triazol-1-yl)ethyl)-N[6]-((4,4-difluorocyclohexyl)methyl)pyridine-2,6-diamine (SS20308-0250-01)

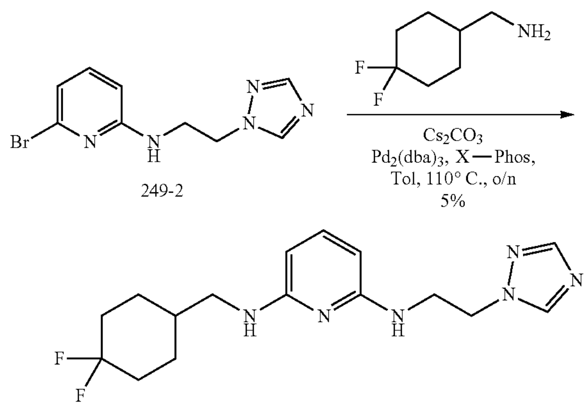

SS20308-0250-01

A mixture of 249-2 (100 mg, 0.37 mmol), (4,4-difluorocyclohexyl)methanamine (67 mg, 0.45 mmol), $Pd_2(dba)_3$ (17 mg, 0.02 mmol), X-Phos (18 mg, 0.04 mmol) and $Cs_2CO_3$ (243 mg, 0.75 mmol) in toleune (10 ml) and was stirred at 110° C. under nitrogen atmosphere overnight. After the reaction was complete, the mixture was quenched with water. The insoluble material was removed by filtration, and the filtrate was extracted with EtOAc (30 mL×3). The organic layer was separated, dried over $MgSO_4$, and concentrated in vacuum, which was purified by Prep-HPLC to give SS20308-0250-01 (6 mg, about 5% yield) as an oil. MS Calcd.: 336.2; MS Found: 337.3$[M+H]^+$.

$^1$H NMR (400 MHz, $CDCl_3$ and $D_2O$) δ 8.10 (s, 1H), 7.96 (s, 1H), 7.29-7.25 (m, 1H), 5.73 (d, J=8.0 Hz, 1H), 5.66 (d, J=8.0 Hz, 1H), 4.42 (t, J=5.2 Hz, 2H), 3.77 (t, J=5.6 Hz, 2H), 3.13 (d, J=6.8 Hz, 2H), 2.13-2.11 (m, 2H), 1.91-1.88 (m, 2H), 1.79-1.64 (m, 3H), 1.39-1.36 (m, 2H).

Example 35

SS20308-0253-01

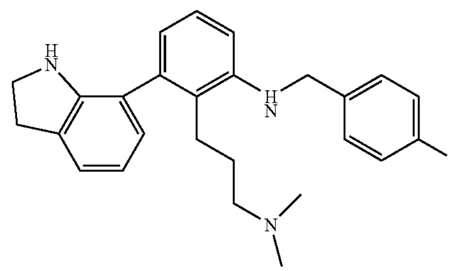

Chemical Formula: $C_{26}H_{30}FN_3$
Molecular Weight: 403.53

Example Route for Example 35

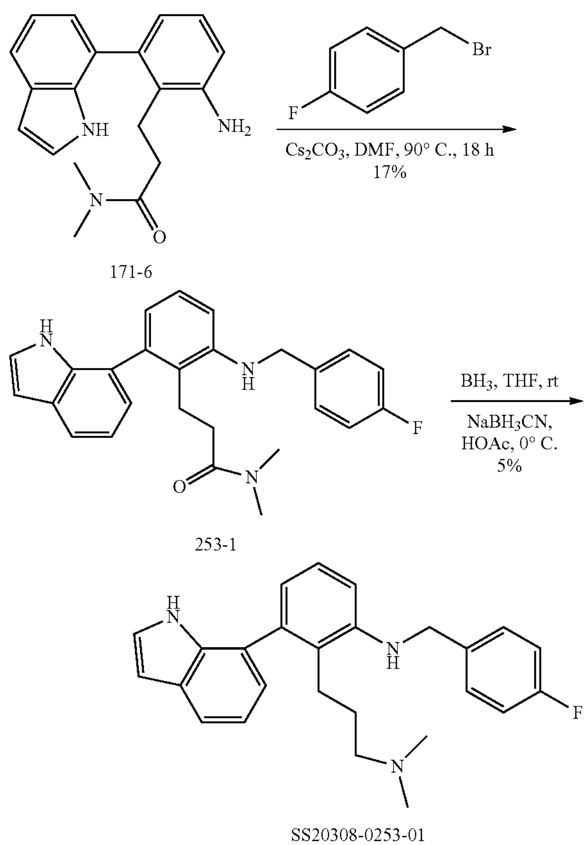

171-6

253-1

SS20308-0253-01

The Synthesis of 3-(2-(4-fluorobenzylamino)-6-(1H-indol-7-yl)phenyl)-N,N-dimethylpropanamide (253-1)

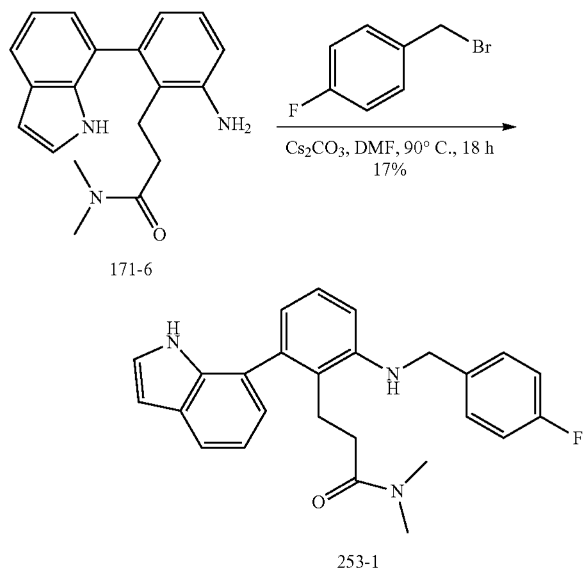

171-6

253-1

A mixture of 171-6 (200 mg, 0.7 mmol), 1-(bromomethyl)-4-fluorobenzene (120 mg, 0.7 mmol) and $Cs_2CO_3$ (180 mg, 1.4 mmol) in DMF (5 mL) was stirred at 90° C. for 18 hr. The reaction mixture was cooled to room temperature and poured into water (20 mL) and extracted with EtOAc (10 mL×3). The organic layer was washed with brine and evaporated to crude. It was purified by column chromatography (EtOAc/petroleum ether=5/1) to give 253-1 (50 mg, about 17% yield) as an oil. MS Calcd.: 415.2; MS Found: 416.4 $[M+H]^+$.

The Synthesis of 2-(3-(dimethylamino)propyl)-N-(4-fluorobenzyl)-3-(indolin-7-yl)aniline (SS20308-0253-01)

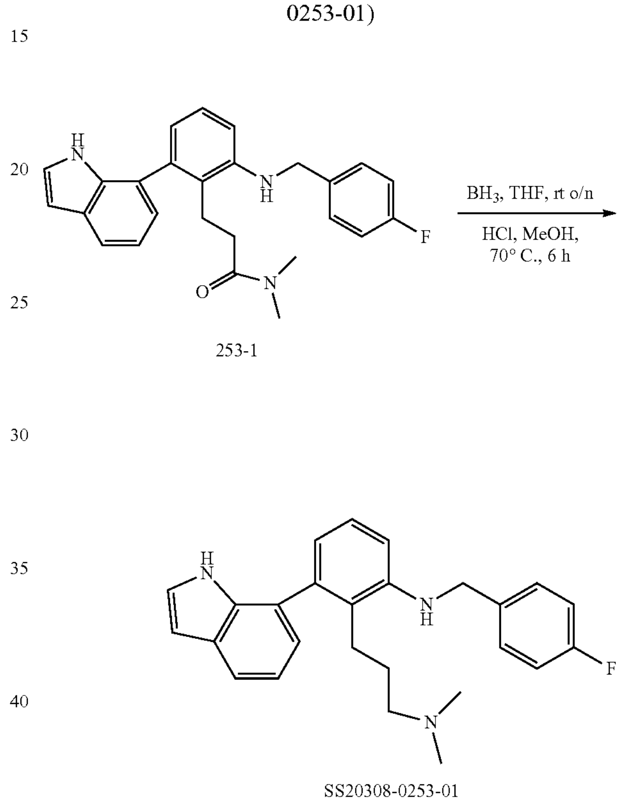

253-1

SS20308-0253-01

A mixture of 253-1 (40 mg, 100 umol) and $BH_3$ (0.5 mL) in THF (1 mL) was stirred at rt for 18 hr. To the mixture was added HCl (0.5 mL, 3 N), MeOH (1 mL) and stirred at 70° C. for 6 h. After the reaction was complete, the reaction mixture was quenched with water (10 mL), extracted with EtOAc (10 mL×3). The combined layers were dried over $Na_2SO_4$ and concentrated under vacuum to give crude, then purified with Prep-HPLC to give SS20308-0253-01 (1.84 mg, about 5% yield) as a pale solid. MS Calcd.: 403.5; MS Found: 404.3 $[M+H]^+$.

$^1H$ NMR (400 MHz, DMSO-$d_6$) δ 7.32-7.29 (m, 2H), 6.98-6.91 (m, 3H), 6.89-6.87 (m, 1H), 6.71 (d, J=8.0 Hz, 1H), 6.61 (t, J=7.2 Hz, 1H), 6.40-6.35 (m, 2H), 4.30 (s, 2H), 3.31 (t, J=8.4 Hz, 2H), 2.93 (t, J=8.0 Hz, 2H), 2.46-2.43 (m, 1H), 2.34-2.32 (m, 1H), 2.12-2.06 (m, 2H), 2.02 (s, 6H), 1.57-1.46 (m, 2H).

Example 36

SS20308-0265-01

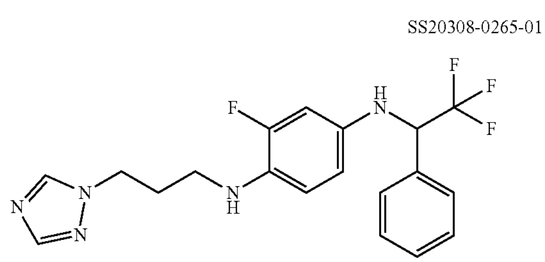

Chemical Formula: $C_{19}H_{19}F_4N_5$
Molecular Weight: 398.38

Example Route for Example 36

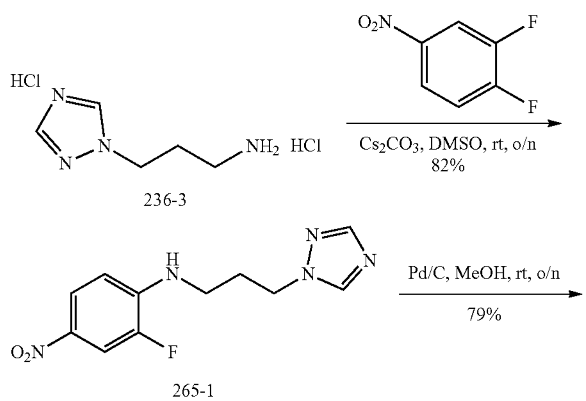

236-3

265-1

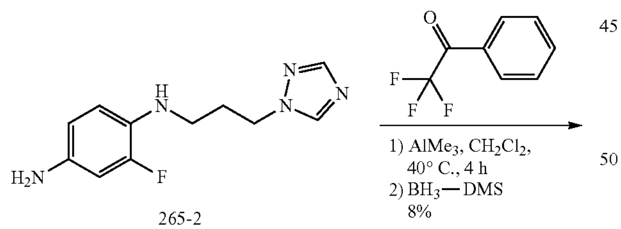

265-2

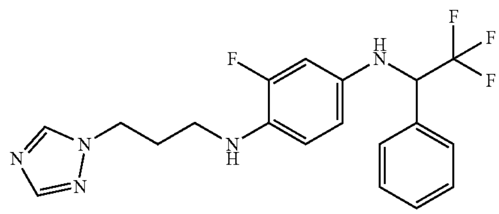

SS20308-0265-01

The Synthesis of N-(3-(1H-1,2,4-triazol-1-yl)propyl)-2-fluoro-4-nitroaniline (265-01)

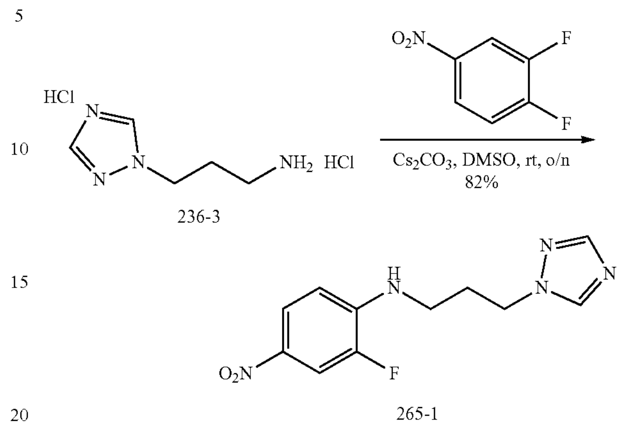

236-3

265-1

A mixture of 3,4-difluoronitrobenzene (1.60 g, 10.06 mmol), 236-3 (2.40 g, 12.07 mmol) and $K_2CO_3$ (6.55 g, 20.11 mmol) in DMSO (10 ml) was stirred at room temperature under nitrogen atmosphere overnight. After the reaction was complete, the mixture was quenched with water and extracted with EtOAc (50 mL×3). The organic layer was separated, dried over $MgSO_4$, and concentrated in vacuum, which was purified by column chromatography (PE/EtOAc=1/1) to give 265-1 (2.20 g, about 82% yield) as a solid. MS Calcd.: 265.1; MS Found: 266.1 $[M+H]^+$.

The Synthesis of $N^1$-(3-(1H-1,2,4-triazol-1-yl)propyl)-2-fluorobenzene-1,4-diamine (265-2)

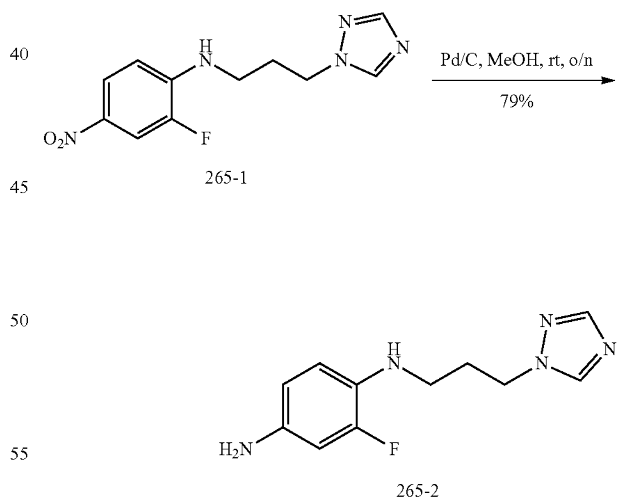

265-1

265-2

To a solution of 265-1 (1.00 g, 3.77 mmol) in MeOH (20 mL) was added Pd/C (10%, 50 mg), the mixture was stirred at room temperature under $H_2$ atmosphere overnight. After the reaction was complete, the insoluble material was removed by filtration. The organic layer was concentrated under vacuum, which was purified by column chromatography (petroleum ether/EtOAc=1/2) to give 265-01-3 (700 mg, about 79% yield) as an oil. MS Calcd.: 235.1; MS Found: 236.0 $[M+H]^+$.

The Synthesis of $N^1$-(3-(1H-1,2,4-triazol-1-yl)propyl)-2-fluoro-$N^4$-(2,2,2-trifluoro-1-phenylethyl)benzene-1,4-diamine (SS20308-0265-01)

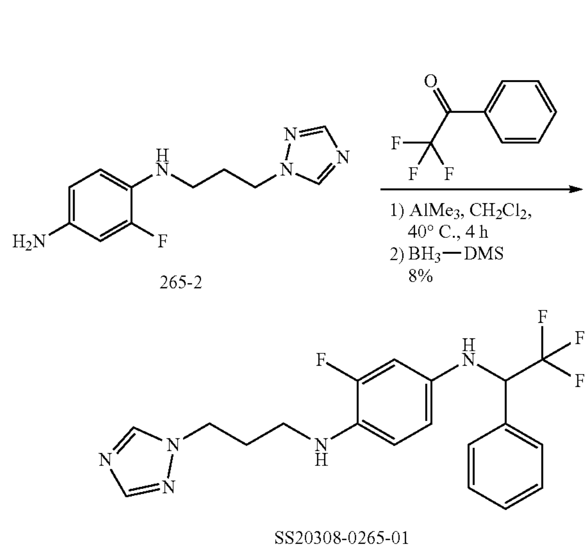

265-2

SS20308-0265-01

A solution of 265-2 (250 mg, 1.06 mmol), 2,2,2-trifluoro-1-phenylethanone (222 mg, 1.28 mmol) in $CH_2Cl_2$ (10 ml) was added $AlMe_3$ (1.06 ml, 2.12 mmol, 2N in THF), the reaction was stirred at 40° C. under nitrogen atmosphere for 2 h. After the reaction was cooled down, the mixture was added $BH_3$-DMS (1.06 ml, 2.12 mmol, 2N in THF), and was stirred at 40° C. under nitrogen atmosphere for 2 h. After the reaction was complete, it was quenched with water and extracted with EtOAc (50 mL×3). The organic layer was separated, dried over $MgSO_4$, and concentrated under vacuum, which was purified by Prep-HPLC to give SS20308-0265-01 (33 mg, about 8% yield) as an oil. MS Calcd.: 393.2; MS Found: 394.1 $[M+H]^+$.

$^1H$ NMR (400 MHz, DMSO-$d_6$) δ 8.50 (s, 1H), 7.96 (s, 1H), 7.59-7.57 (m, 2H), 7.40-7.31 (m, 3H), 6.66 (dd, J=14.4 Hz, 2.4 Hz, 1H), 6.47-6.42 (m, 2H), 6.23 (d, J=10.8 Hz, 1H), 5.42-5.33 (m, 1H), 4.71 (t, J=5.6 Hz, 1H), 4.23 (t, J=6.8 Hz, 2H), 2.93-2.88 (m, 2H), 2.02-1.95 (m, 2H).

Example 37

SS20308-0275-01

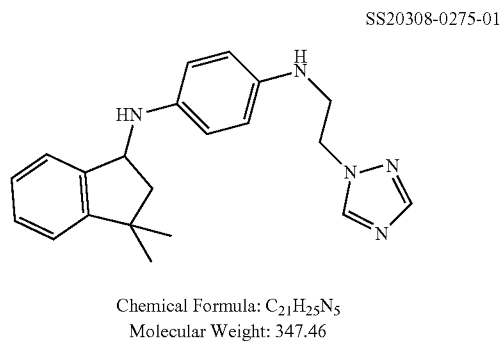 [SMILES: CC1(C)CC(Nc2ccc(NCCn3cncn3)cc2)c2ccccc21]

Chemical Formula: $C_{21}H_{25}N_5$
Molecular Weight: 347.46

Example Route for Example 37

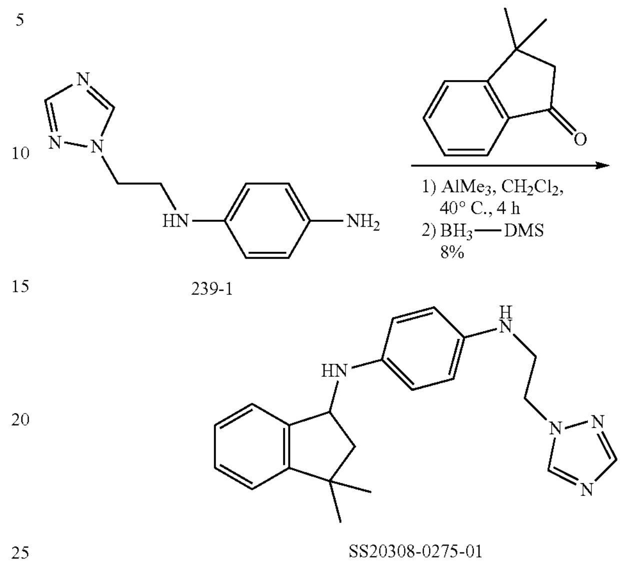

239-1

SS20308-0275-01

The Synthesis of $N^1$-(2-(1H-1,2,4-triazol-1-yl)ethyl)-$N^4$-(3,3-dimethyl-2,3-dihydro-1H-inden-1-yl)benzene-1,4-diamine (SS20308-0275-01)

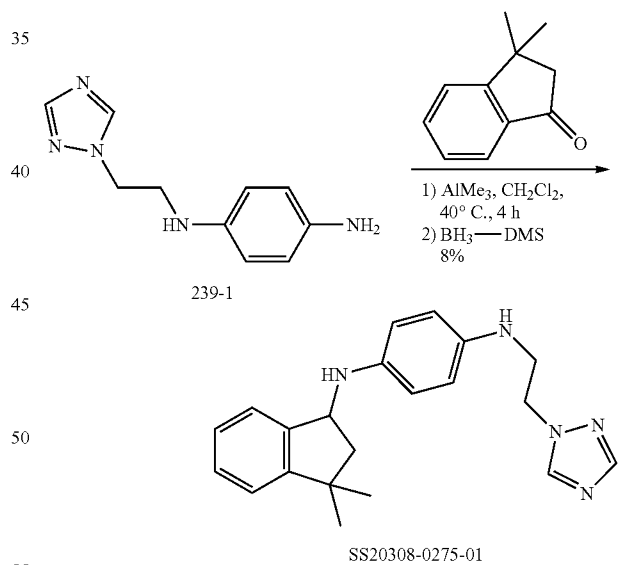

239-1

SS20308-0275-01

A solution of 239-1 (180 mg, 0.89 mmol), 3,3-dimethyl-2,3-dihydro-1H-inden-1-one (170 mg, 1.06 mmol) in $CH_2Cl_2$ (10 ml) was added $AlMe_3$ (0.89 ml, 1.78 mmol, 2N in THF), the reaction was stirred at 40° C. under nitrogen atmosphere for 2 h. After the reaction was cooled down, the mixture was added $BH_3$-DMS (0.89 ml, 1.78 mmol, 2N in THF), and was stirred at 40° C. under nitrogen atmosphere for 2 h. After the reaction was complete, it was quenched with water and extracted with EtOAc (50 mL×3). The organic layer was separated, dried over $MgSO_4$, and concentrated under vacuum, which was purified by Prep-HPLC to give SS20308-0275-01 (26 mg, about 8% yield) as an oil. MS Calcd.: 347.2; MS Found: 348.2 $[M+H]^+$.
$^1H$ NMR (400 MHz, DMSO-$d_6$) δ 8.48 (s, 1H), 7.98 (s, 1H), 7.25-7.21 (m, 3H), 7.17-7.13 (m, 1H), 6.61 (d, J=8.8 Hz, 2H), 6.46 (d, J=8.8 Hz, 2H), 5.04 (d, J=8.8 Hz, 1H), 4.96-4.87 (m, 2H), 4.31 (t, J=6.4 Hz, 2H), 3.39-3.34 (m, 2H), 2.35-2.30 (m, 1H), 1.68-1.63 (m, 1H), 1.33 (s, 3H), 1.19 (s, 3H).
Example 38
SS20308-0302-01
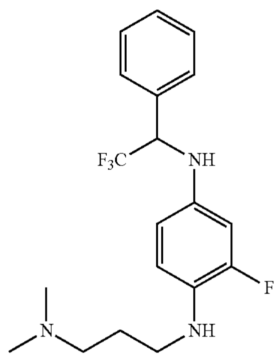
Example Route for Example 38
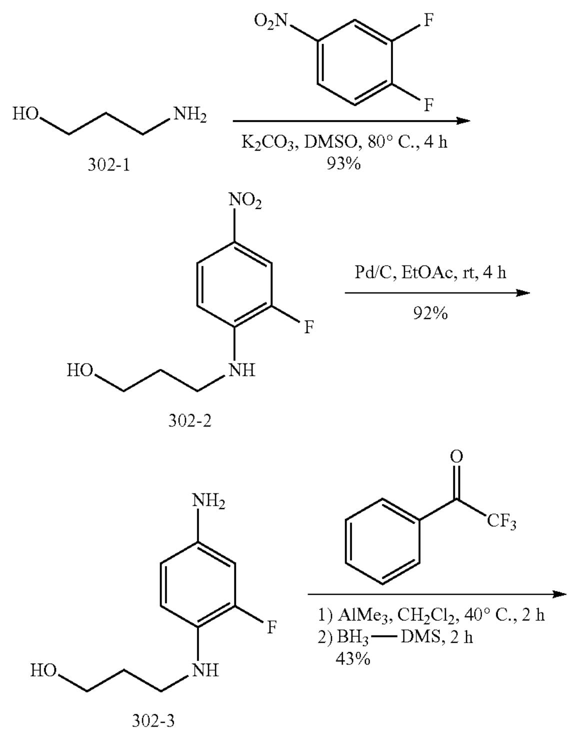
-continued
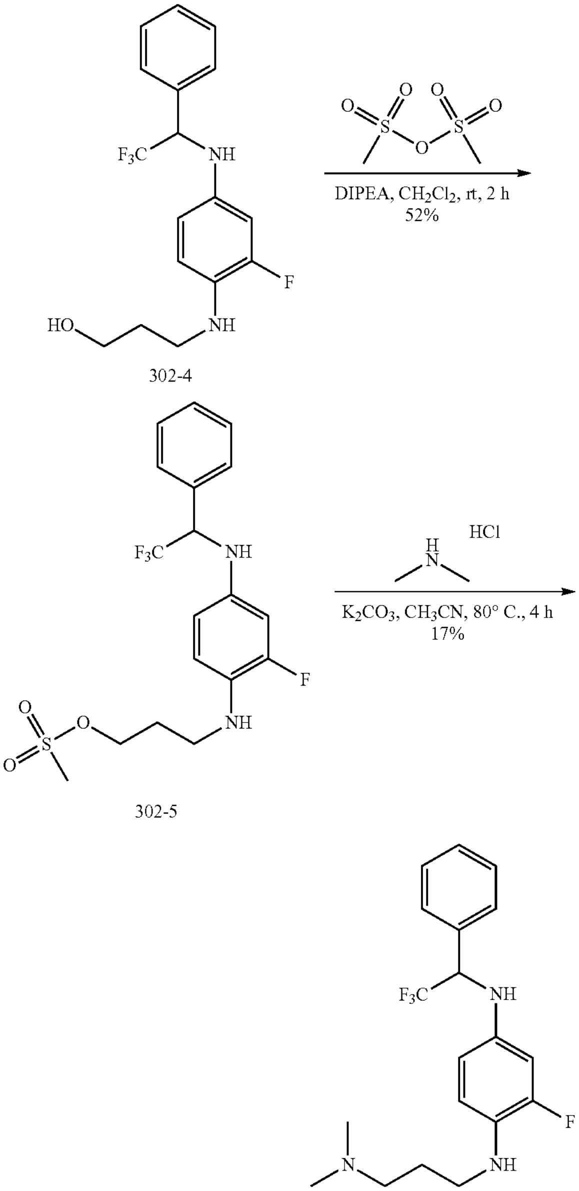
The Synthesis of 3-(2-fluoro-4-nitrophenylamino) propan-1-ol (302-2)
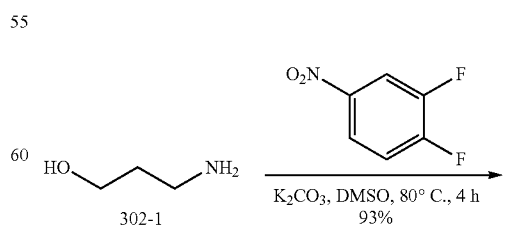

-continued

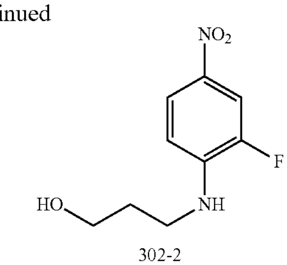

302-2

A mixture of 3,4-difluoronitrobenzene (1.60 g, 10.06 mmol), 3-aminopropan-1-ol (302-1) (906 mg, 12.07 mmol) and $K_2CO_3$ (2.78 g, 20.11 mmol) in DMSO (10 ml) was stirred at 80° C. for 4 h. After the reaction was complete, the mixture was quenched with water and extracted with EtOAc (50 mL×3). The organic layer was separated, dried over $MgSO_4$, and concentrated under vacuum, which was purified by column chromatography (petroleum ether/EtOAc=1/2) to give 302-2 (2.00 g, about 93% yield) as an oil. MS Calcd.: 214.1; MS Found: 215.2 $[M+H]^+$.

The Synthesis of 3-(4-amino-2-fluorophenylamino) propan-1-ol (302-3)

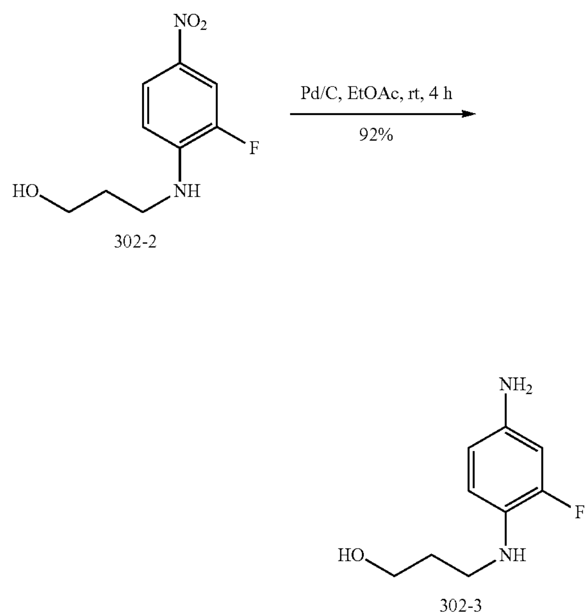

302-2

302-3

To a solution of 302-2 (1.90 g, 8.87 mmol) in EtOAc (20 mL) was added Pd/C (10%, 150 mg), the mixture was stirred at room temperature under $H_2$ atmosphere for 4 h. After the reaction was complete, the insoluble material was removed by filtration. The organic layer was concentrated under vacuum, which was purified by column chromatography (petroleum ether/EtOAc=1/2) to give 302-3 (1.5 g, about 92% yield) as an oil. MS Calcd.: 184.1; MS Found: 185.2 $[M+H]^+$.

The Synthesis of 3-(2-fluoro-4-(2,2,2-trifluoro-1-phenylethylamino)phenylamino)propan-1-ol (302-4)

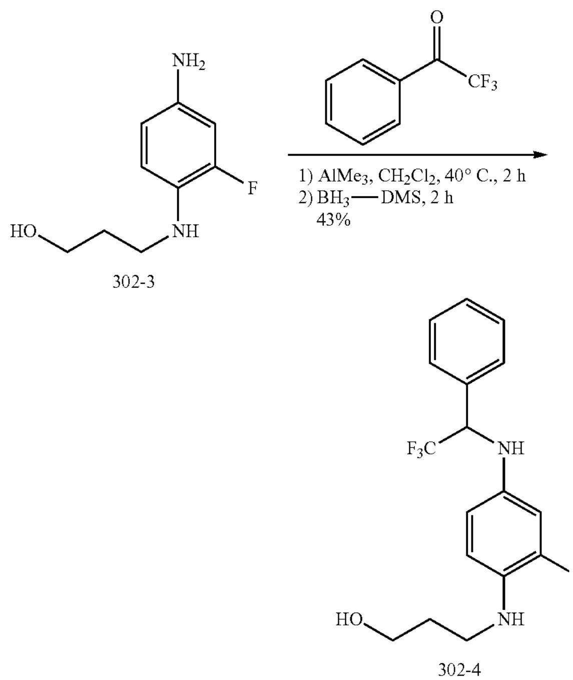

302-3

302-4

A solution of 302-3 (500 mg, 2.71 mmol), 2,2,2-trifluoro-1-phenylethanone (614 mg, 353 mmol) in $CH_2Cl_2$ (10 ml) was added $AlMe_3$ (2.71 ml, 5.42 mmol, 2N in THF), the reaction was stirred at 40° C. under nitrogen atmosphere for 2 h. After the reaction was cooled down, the mixture was added $BH_3$-DMS (2.71 ml, 5.42 mmol, 2N in THF), and was stirred at 40° C. under nitrogen atmosphere for 2 h. After the reaction was complete, it was quenched with water and extracted with EtOAc (50 mL×3). The organic layer was separated, dried over $MgSO_4$, and concentrated in vacuum, which was purified by Prep-HPLC to give 302-4 (400 mg, about 43% yield) as an oil. MS Calcd.: 342.1; MS Found: 343.0 $[M+H]^+$.

The Synthesis of 3-(2-fluoro-4-(2,2,2-trifluoro-1-phenylethylamino)phenylamino)propyl methanesulfonate (302-5)

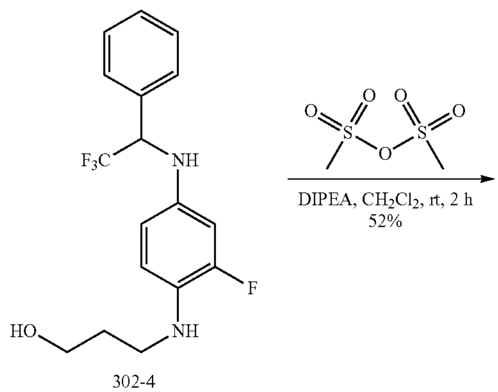

302-4

-continued

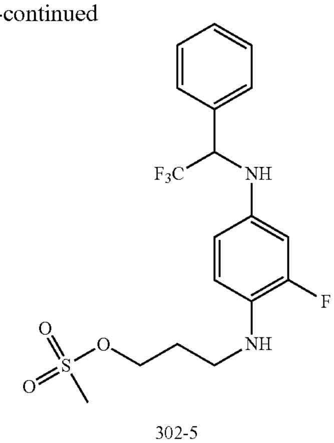

302-5

To a solution of 302-4 (250 mg, 0.73 mmol) in $CH_2Cl_2$ (20 mL) was added $Ms_2O$ (153 mg, 0.88 mmol) and DIPEA (189 mg, 1.46 mmol), the mixture was stirred at room temperature for 2 h. After the reaction was complete, it was quenched with water and extracted with $CH_2Cl_2$ (50 mL×3). The organic layer was separated, dried over $MgSO_4$, and concentrated under vacuum, which was purified by column chromatography (petroleum ether/EtOAc=1/1) to give 302-5 (160 mg, about 52% yield) as an oil. MS Calcd.: 327.1; MS Found: 328.2 $[M+H]^+$.

The Synthesis of $N^1$-(3-(dimethylamino)propyl)-2-fluoro-$N^4$-(2,2,2-trifluoro-1-phenylethyl)benzene-1,4-diamine (SS20308-0302-01)

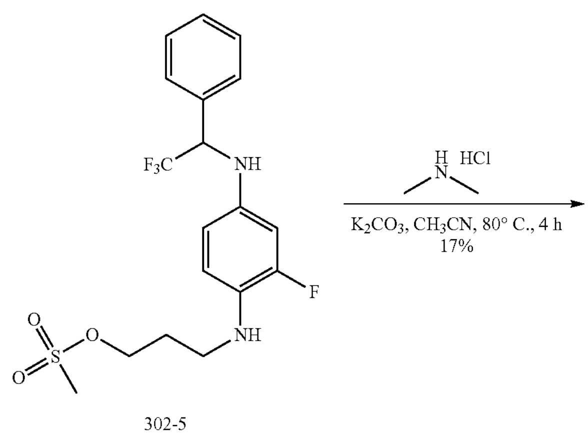

302-5

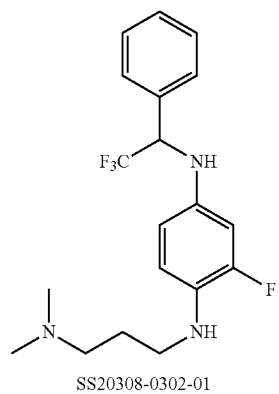 [SMILES: CN(C)CCCNc1ccc(NC(c2ccccc2)C(F)(F)F)cc1F]

SS20308-0302-01

To a solution of 302-5 (160 mg, 0.38 mmol) in $CH_3CN$ (20 mL) was added dimethylamine hydrochloride (47 mg, 0.57 mmol) and $K_2CO_3$ (210 mg, 1.52 mmol), the mixture was stirred at 80° C. for 4 h. After the reaction was complete, it was quenched with water and extracted with EtOAc (50 mL×3). The organic layer was separated, dried over $MgSO_4$, and concentrated in vacuum, which was purified by Prep-HPLC to give SS20308-0302-01 (24 mg, about 17% yield) as an oil. MS Calcd.: 369.2; MS Found: 370.2 $[M+H]^+$.

$^1H$ NMR (400 MHz, DMSO-$d_6$) δ 7.54-7.56 (m, 2H), 7.29-7.37 (m, 3H), 6.60-6.64 (m, 1H), 6.43-6.50 (m, 2H), 6.15 (d, J=10.8 Hz, 1H), 5.31-5.36 (m, 1H), 4.63 (t, J=5.2 Hz, 1H), 2.90-2.95 (m, 2H), 2.20-2.23 (m, 2H), 2.08 (s, 6H), 1.55-1.62 (m, 2H).

Example 39

SS20308-0315-01

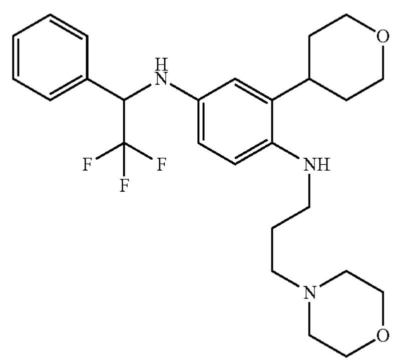

Chemical Formula: $C_{26}H_{34}F_3N_3O_2$
Molecular Weight: 477.56

Example Route for Example 39

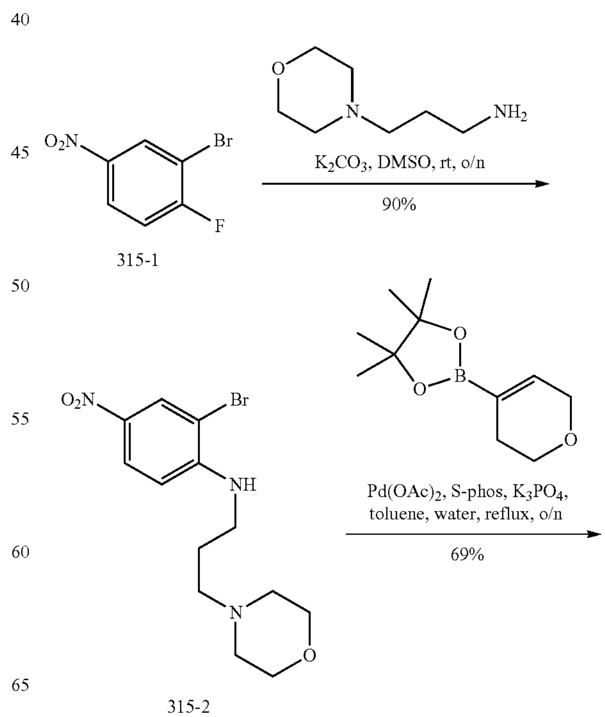

315-1

315-2

-continued

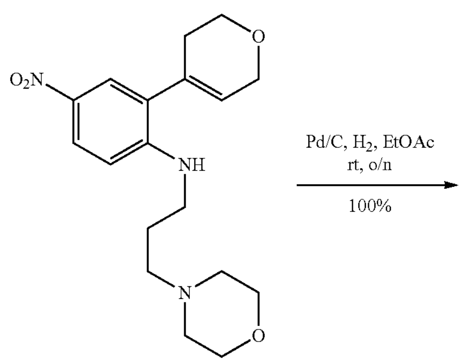

315-3

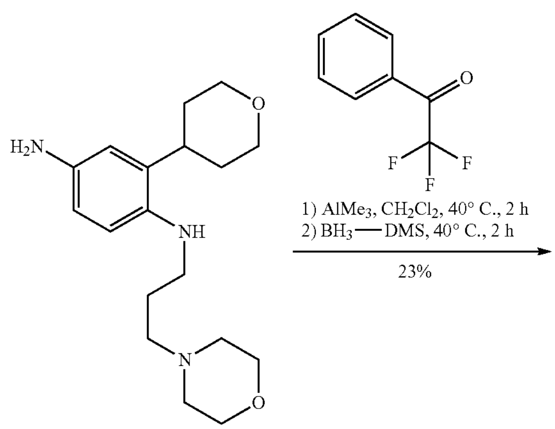

315-4

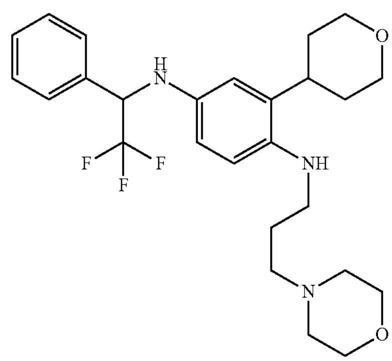

SS20308-0315-01

The Synthesis of 2-bromo-N-(3-morpholinopropyl)-4-nitroaniline (315-2)

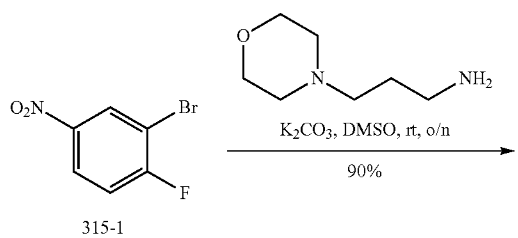

315-1

-continued

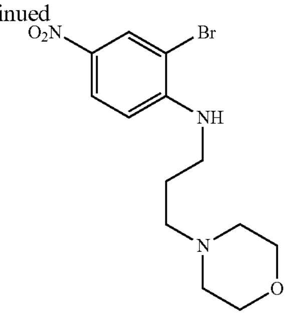

315-2

A mixture of 3-morpholinopropan-1-amine (1.31 g, 9.09 mmol), 315-1 (1 g, 4.55 mmol) and potassium carbonate (1.26 g, 9.09 mmol) were suspended in DMSO (10 mL). After stirring at room temperature for overnight, the mixture was diluted with water (40 mL). The resulting solid was filtered, washed with water, dried, and concentrated to give compound 0315-2 (1.4 g, about 89% yield) as a solid. MS Calcd.: 343.1; MS Found: 344.0 $[M+H]^+$.

The Synthesis of 2-(3,6-dihydro-2H-pyran-4-yl)-N-(3-morpholinopropyl)-4-nitroaniline (315-3)

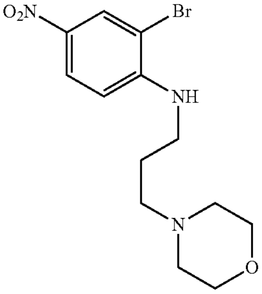

315-2

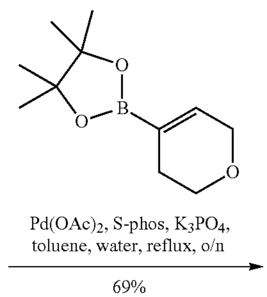

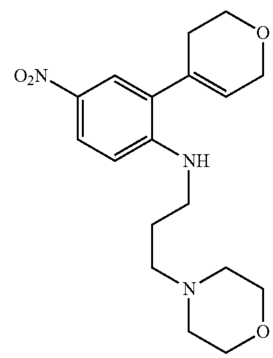

315-3

The mixture of 315-2 (1 g, 2.91 mmol), Palladium (II) acetate (33 mg, 0.15 mmol), S-phos (120 mg, 0.29 mmol), 2-(3,6-dihydro-2H-pyran-4-yl)-4,4,5,5-tetramethyl-1,3,2-dioxaborolane (672 mg, 3.20 mmol), and potassium phosphate (2.16 g, 10.17 mmol) in toluene (40 mL) was added water (2 mL) and stirred at 110° C. for 16 hr under $N_2$. The reaction mixture was filtered through celite, and rinsed with EtOAc. The filtrate was concentrated and the residue was purified by column chromatography (petroleum ether/EtOAc=1/1, 100% EtOAc, DCM/methanol=50/1) to give compound 0315-3 (700 mg, about 69% yield) as a solid. MS Calcd.: 347.2; MS Found: 348.3 $[M+H]^+$.

The Synthesis of $N^1$-(3-morpholinopropyl)-2-(tetrahydro-2H-pyran-4-yl)benzene-1,4-diamine (315-4)

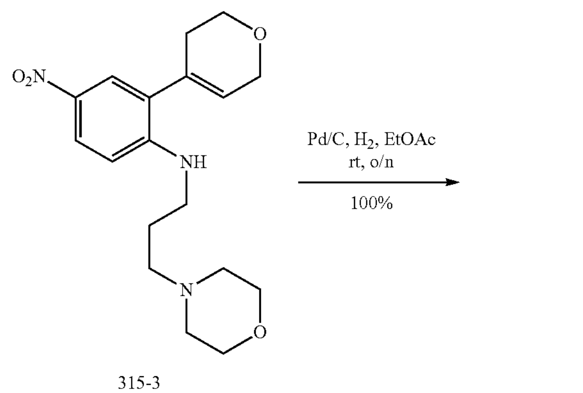

315-3

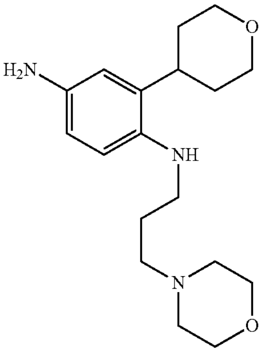

315-4

A suspension of 315-3 (650 mg, 1.87 mmol) and Palladium on activated carbon (10%, 130 mg) in EtOAc (20 mL) was stirred vigorously under hydrogen gas (balloon) for 16 hr at room temperature. The reaction mixture was filtered through celite, and rinsed with EtOAc. The filtrate was concentrated to give a crude product 315-4 (597 mg, about 100% yield) as an oil. MS Calcd.: 319.2; MS Found: 320.3 $[M+H]^+$.

The Synthesis of $N^1$-(3-morpholinopropyl)-2-(tetrahydro-2H-pyran-4-yl)-$N^4$-(2,2,2-trifluoro-1-phenylethyl)benzene-1,4-diamine (SS20308-0315-01)

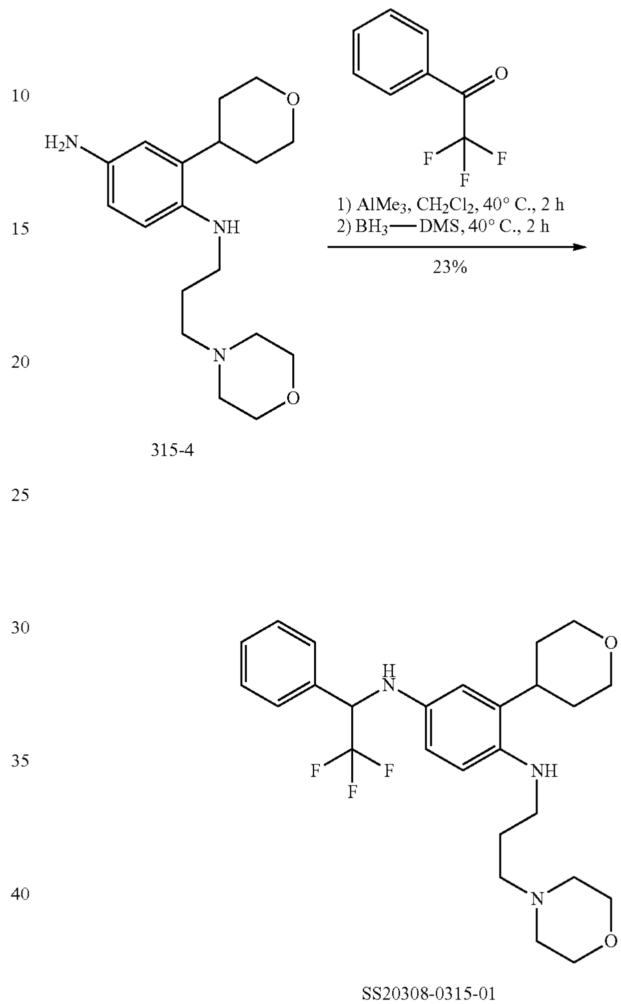

315-4

SS20308-0315-01

The mixture of 315-4 (100 mg, 0.31 mmol) and trimethylaluminium (2M in hexane) (0.23 mL, 0.46 mmol) in dichloromethane (10 mL) was heated to 40° C. for 2 hr. The reaction mixture was cooled down to room temperature and added borane-methyl sulfide complex (2M in THF) (0.31 mL, 0.62 mmol). After stirring at 40° C. for 2 hr, the reaction mixture was quenched with methanol at 0° C., and then concentrated. The residue was basified with $NaHCO_3$ solution, and extracted with EtOAc (10 mL×3). The combined organic layers were washed with water and brine, dried over $Na_2SO_4$ and concentrated. The residue was purified by Prep-TLC (DCM/methanol=20/1) to give compound SS20308-0315-01 (33.8 mg, about 23% yield) as a solid. MS Calcd.: 477.3; MS Found: 478.3 $[M+H]^+$.

$^1H$ NMR (400 MHz, DMSO-$d_6$) δ 7.59 (d, J=7.2 Hz, 2H), 7.40-7.29 (m, 3H), 6.66 (d, J=2.0 Hz, 1H), 6.53 (dd, J=8.4, 2.0 Hz, 1H), 6.35 (d, J=8.4 Hz, 1H), 5.88 (d, J=10.8 Hz, 1H), 5.38-5.27 (m, 1H), 4.38 (brs, 1H), 3.96-3.87 (m, 2H), 3.60-3.53 (m, 4H), 3.50-3.40 (m, 2H), 2.99-2.90 (m, 2H), 2.86-2.76 (m, 1H), 2.37-2.28 (m, 6H), 1.72-1.46 (m, 6H).

Example 40
SS20308-0317-01
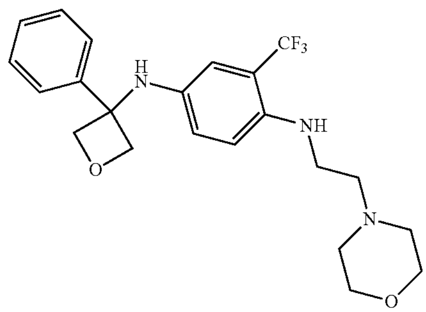
Chemical Formula: $C_{22}H_{26}F_3N_3O_2$
Molecular Weight: 421.46
Example 41
SS20308-0325-01
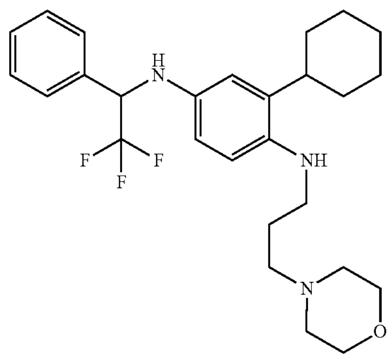
Chemical Formula: $C_{27}H_{36}F_3N_3O$
Molecular Weight: 475.59
Example Route for Example 41
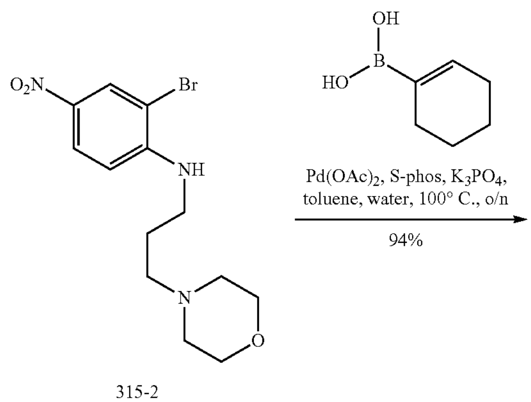
315-2
-continued
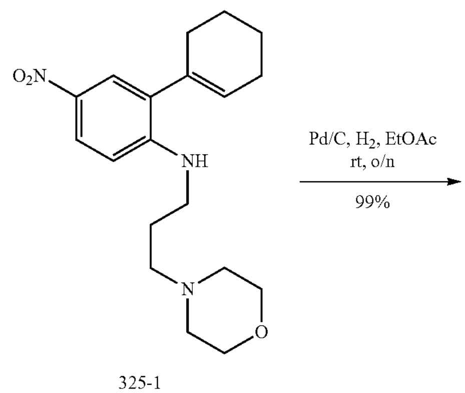
325-1
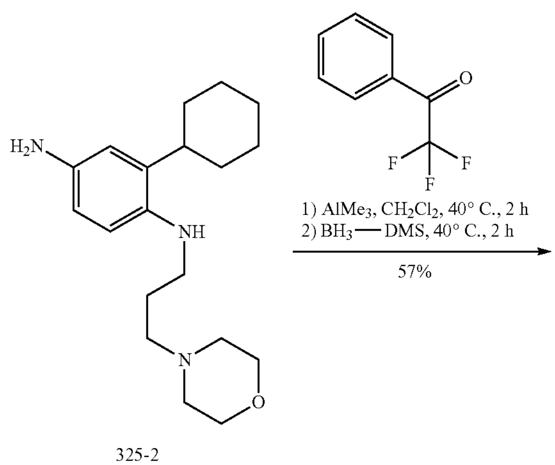
325-2
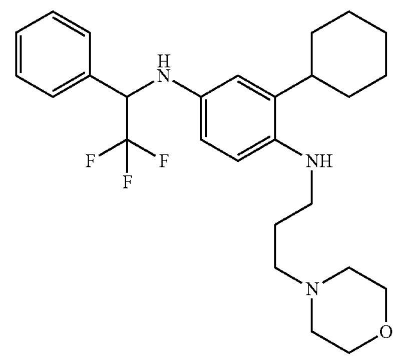
SS20308-0325-01

The Synthesis of 2-cyclohexenyl-N-(3-morpholinopropyl)-4-nitroaniline (325-1)

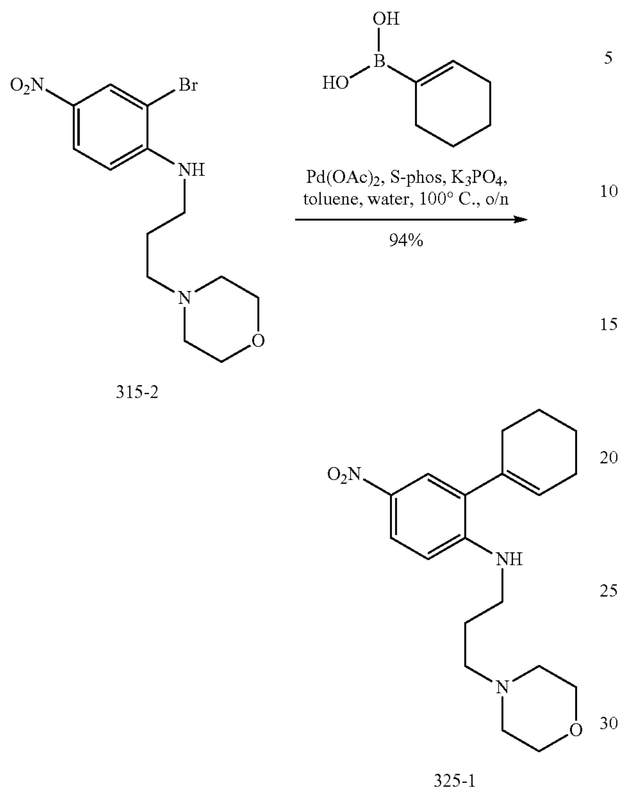

315-2

325-1

To the mixture of 315-2 (580 mg, 1.69 mmol), cyclohexen-1-ylboronic acid (429 mg, 3.41 mmol), palladium (II) acetate (19 mg, 0.085 mmol), S-phos (70 mg, 0.17 mmol) and potassium phosphate (1.25 g, 5.90 mmol) in toluene (20 mL) was added water (1 mL). After stirring at 100° C. for 16 hr under $N_2$ (g), the reaction mixture was filtered through celite, and rinsed with EtOAc. The filtrate was concentrated and the residue was purified by column chromatography (petroleum ether/EtOAc=1/1, 100% EtOAc) to give compound 325-1 (548 mg, about 94% yield) as an oil. MS Calcd.: 345.2; MS Found: 346.2 $[M+H]^+$.

The Synthesis of 2-cyclohexyl-$N^1$-(3-morpholinopropyl)benzene-1,4-diamine (325-2)

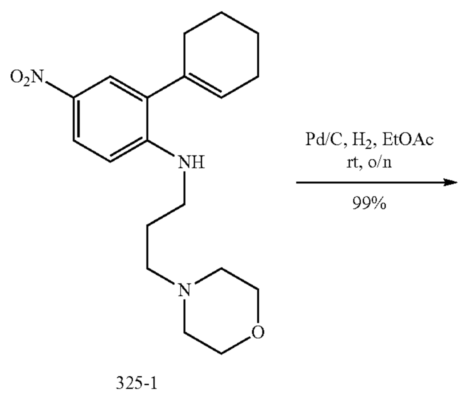

325-1

-continued

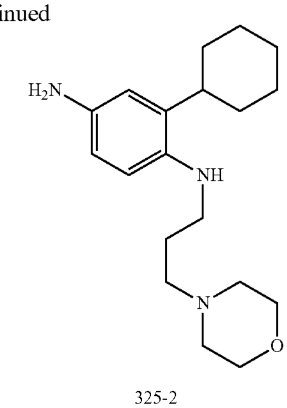

325-2

A suspension of 325-1 (550 mg, 1.59 mmol) and palladium on activated carbon (10%, 55 mg) in EtOAc (10 mL) is stirred vigorously under hydrogen gas (balloon) for 16 hr at room temperature. The reaction mixture was filtered through celite, and rinsed with EtOAc. The filtrate was concentrated to give a crude product 325-2 (498 mg, about 99% yield) as an oil. MS Calcd.: 317.3; MS Found: 318.3 $[M+H]^+$.

The Synthesis of 2-cyclohexyl-$N^1$-(3-morpholinopropyl)-$N^4$-(2,2,2-trifluoro-1-phenylethyl)benzene-1,4-diamine (SS20308-0325-01)

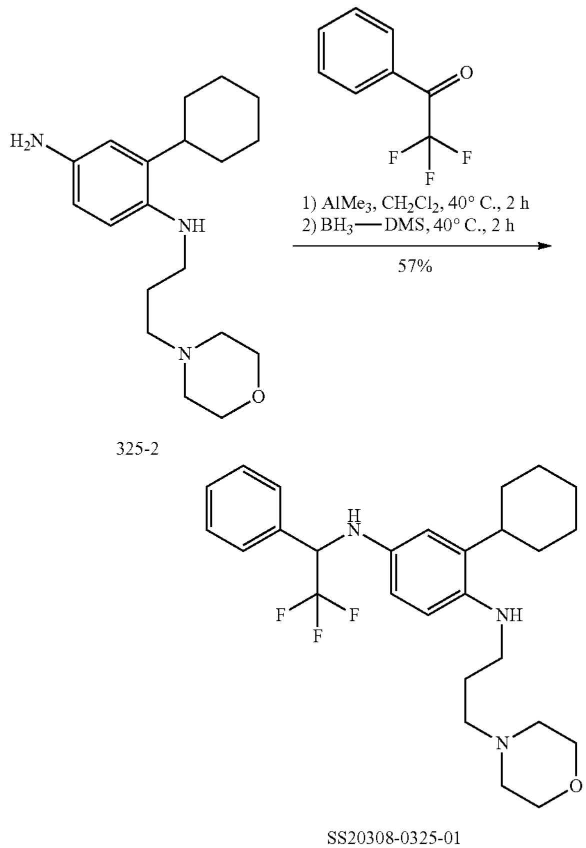

325-2

SS20308-0325-01

The mixture of 325-2 (100 mg, 0.31 mmol) and trimethylaluminium (2M in hexane) (0.24 mL, 0.48 mmol) in dichloromethane (10 mL) was heated to 40° C. for 2 hr. The reaction mixture was cooled down to room temperature and added borane-methyl sulfide complex (2M in THF) (0.8 mL, 1.6 mmol). After stirring at 40° C. for 2 hr, the reaction mixture was quenched with methanol at 0° C., and then concentrated. The residue was basified with $NaHCO_3$ solution, and extracted with EtOAc (10 mL×3). The combined organic layers were washed with water and brine, dried over $Na_2SO_4$ and concentrated. The residue was purified by Prep-TLC (DCM/methanol=20/1) to give compound SS20308-0325-01 (85.4 mg, about 57% yield) as a solid. MS Calcd.: 475.3; MS Found: 476.4 $[M+H]^+$.

$^1H$ NMR (400 MHz, DMSO-$d_6$) δ 7.59 (d, J=6.8 Hz, 2H), 7.39-7.29 (m, 3H), 6.65 (d, J=2.4 Hz, 1H), 6.48 (dd, J=8.6, 2.6 Hz, 1H), 6.32 (d, J=8.8 Hz, 1H), 5.84 (d, J=10.8 Hz, 1H), 5.32-5.21 (m, 1H), 4.27 (brs, 1H), 3.61-3.53 (m, 4H), 3.32-3.29 (m, 1H), 2.95 (t, J=6.8 Hz, 2H), 2.39-2.27 (m, 6H), 1.80-1.60 (m, 6H), 1.45-1.15 (m, 6H).

Example 42

SS20308-0326-01

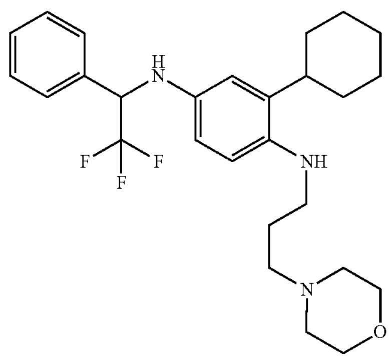

Chemical Formula: $C_{27}H_{36}F_3N_3O$
Molecular Weight: 475.59

Example Route for Example 42

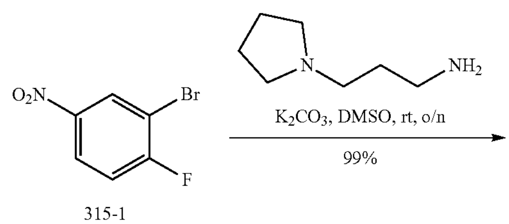

315-1

-continued

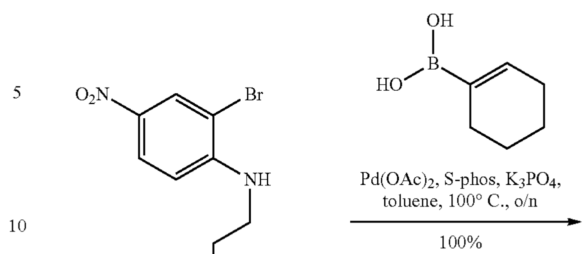

326-1

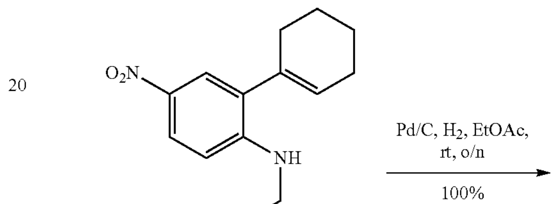

326-2

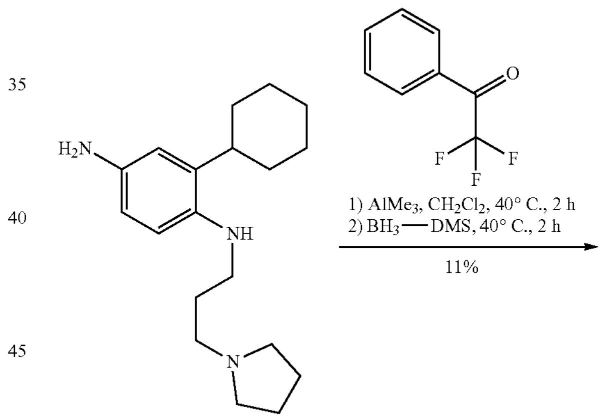

326-3

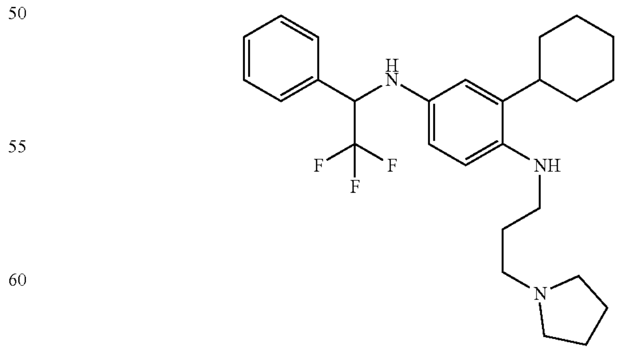

SS20308-0326-01

The Synthesis of 2-bromo-N-(3-morpholinopropyl)-4-nitroaniline (326-1)

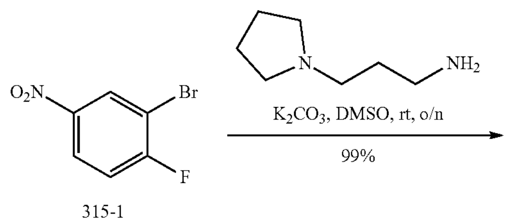

315-1

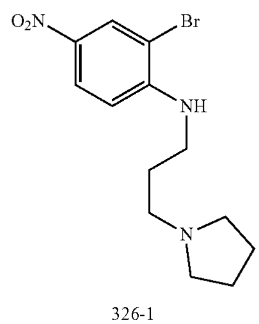

326-1

A mixture of compound 3-pyrrolidin-1-ylpropan-1-amine (2.33 g, 18.18 mmol), 315-1 (2.00 g, 9.09 mmol) and potassium carbonate (2.51 g, 18.18 mmol) were suspended in DMSO (20 mL). After stirring at room temperature for overnight, the mixture was diluted with water (80 mL). The resulting solid was filtered, washed with water, dried, and concentrated to give compound 326-1 (2.95 g, about 99% yield) as a solid. MS Calcd.: 327.1; MS Found: 328.0 $[M+H]^+$.

The Synthesis of 2-cyclohexenyl-4-nitro-N-(3-(pyrrolidin-1-yl)propyl)aniline (326-2)

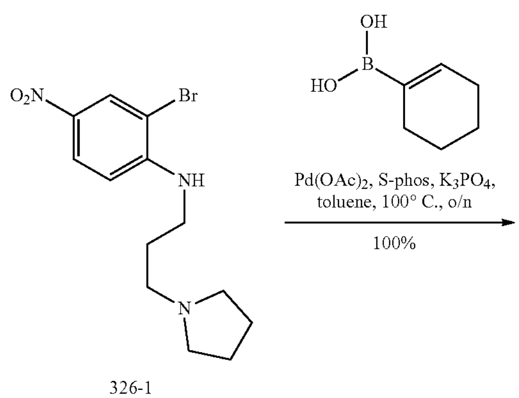

326-1

-continued

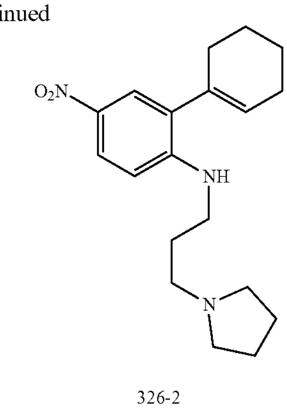

326-2

The mixture of 326-1 (1.00 g, 3.05 mmol), cyclohexen-1-ylboronic acid (780 mg, 6.19 mmol), palladium (II) acetate (34 mg, 0.15 mmol), S-phos (125 mg, 0.30 mmol) and potassium phosphate (2.26 g, 10.66 mmol) in toluene (40 mL) was added water (2 mL). After stirring at 100° C. for 3 hr under $N_2$, the reaction mixture was filtered through celite, and rinsed with EtOAc. The filtrate was concentrated and the residue was purified by CC (petroleum ether/EtOAc=1/1, 100% EtOAc, DCM/methanol=20/1) to give compound 326-2 (1.0 g, about 100% yield) as an oil. MS Calcd.: 329.2; MS Found: 330.3 $[M+H]^+$.

The Synthesis of 2-cyclohexyl-$N^1$-(3-(pyrrolidin-1-yl)propyl)benzene-1,4-diamine (0326-3)

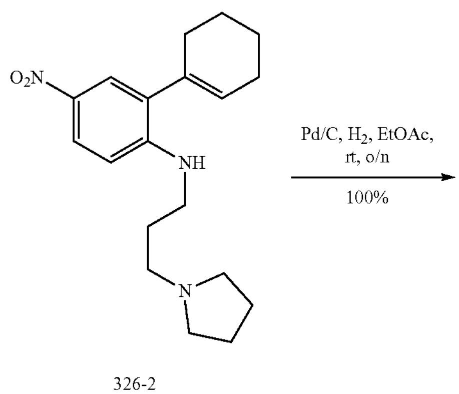

326-2

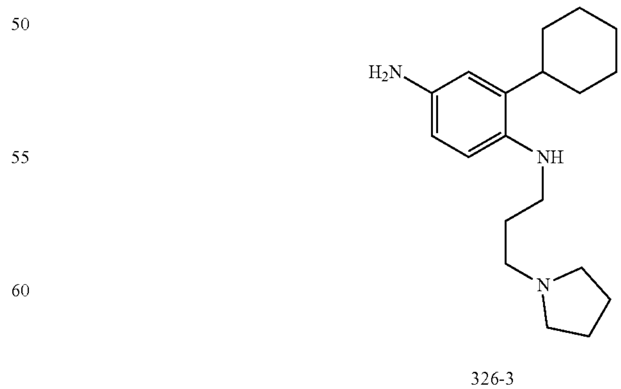

326-3

A suspension of 326-2 (1.00 g, 3.04 mmol) and palladium on activated carbon (10%, 110 mg) in EtOAc (15 mL) is stirred vigorously under hydrogen gas (balloon) for 16 hr at room temperature. The reaction mixture was filtered through celite, rinsing with EtOAc. The filtrate was concentrated to give a crude product 326-3 (915 mg, about 100% yield) as an oil. MS Calcd.: 301.3; MS Found: 302.2 $[M+H]^+$.

The Synthesis of 2-cyclohexyl-$N^1$-(3-(pyrrolidin-1-yl)propyl)-$N^4$-(2,2,2-trifluoro-1-phenylethyl)benzene-1,4-diamine (SS20308-0326-01)

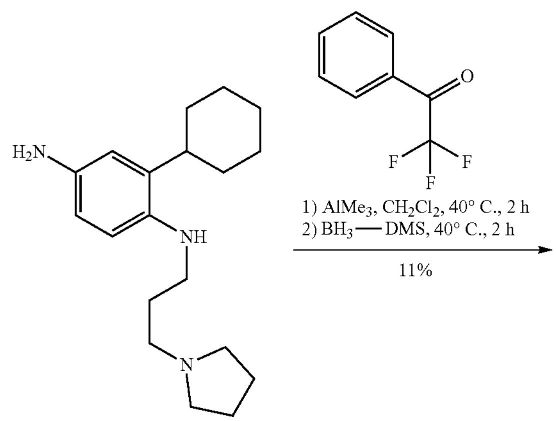

326-3

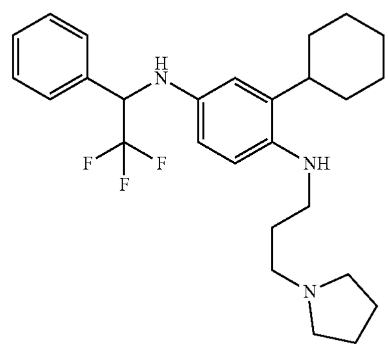

SS20308-0326-01

The mixture of 326-3 (100 mg, 0.33 mmol) and trimethylaluminium (2M in hexane) (0.25 mL, 0.50 mmol) in dichloromethane (10 mL) was heated to 40° C. for 2 hr. The reaction mixture was cooled down to room temperature and added borane-methyl sulfide complex (2M in THF) (0.9 mL, 1.80 mmol). After stirring at 40° C. for 2 hr, the reaction mixture was quenched with methanol at 0° C., and then concentrated. The residue was basified with $NaHCO_3$ solution, and extracted with EtOAc (10 mL×3). The combined organic layers were washed with water and brine, dried over $Na_2SO_4$ and concentrated. The residue was purified by Prep-TLC (DCM/methanol=10/1) to give compound SS20308-0326-01 (16.3 mg, about 11% yield) as an oil. MS Calcd.: 459.3; MS Found: 460.3 $[M+H]^+$.

$^1$H NMR (400 MHz, $CD_3OD$) δ 7.52 (d, J=6.8 Hz, 2H), 7.40-7.33 (m, 3H), 6.64 (d, J=2.4 Hz, 1H), 6.57 (d, J=8.4 Hz, 1H), 6.51 (dd, J=8.8, 2.8 Hz, 1H), 4.99 (q, J=8.0 Hz, 1H), 3.10 (t, J=6.8 Hz, 2H), 2.74-2.62 (m, 6H), 2.59-2.50 (m, 1H), 1.90-1.67 (m, 10H), 1.50-1.25 (m, 6H).

Example 43

SS20308-0033-01

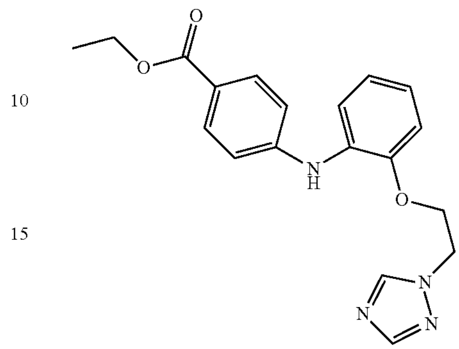

Chemical Formula: $C_{19}H_{20}N_4O_3$
Molecular Weight: 352.39

Example Route for Example 43

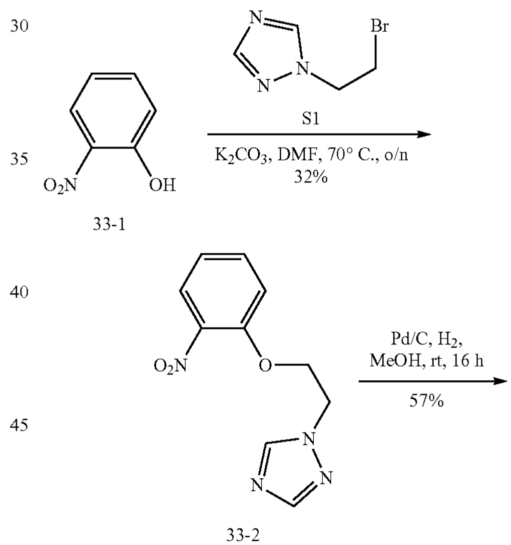

33-1

33-2

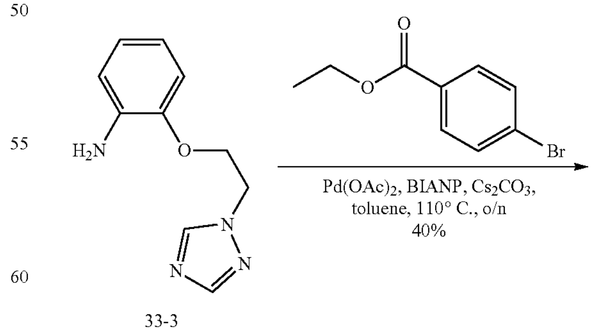

33-3

-continued

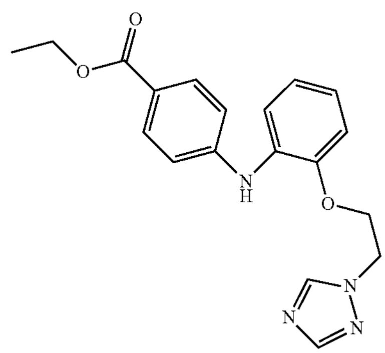

SS20308-0033-01

The Synthesis of 1-(2-(2-nitrophenoxy)ethyl)-1H-1,2,4-triazole (33-2)

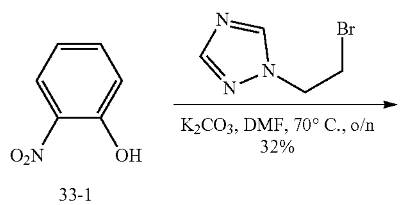

33-1

33-2

A mixture of 33-1 (3.7 g, 26.60 mmol), 1-(2-bromoethyl)-1H-1,2,4-triazole (7.0 g, 39.90 mmol) and $K_2CO_3$ (7.4 g, 53.20 mmol) in DMF (70 mL) was stirred at 70° C. overnight. The reaction mixture was cooled to room temperature and poured into water (150 mL) and extracted with EtOAc (100 mL×3). The organic layer was washed with brine and concentrated. The crude product was purified by column chromatography ($CH_2Cl_2$/MeOH=100/1-30/1) to give 0016-01-3 (2.0 g, about 32% yield) as a solid. MS Calcd.: 234.1; MS Found: 235.2 $[M+H]^+$.

The Synthesis of 2-(2-(1H-1,2,4-triazol-1-yl)ethoxy) aniline (33-3)

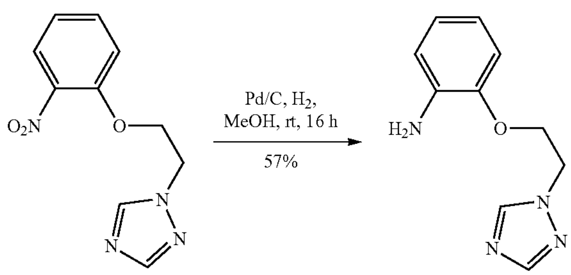

33-2

33-3

To a solution of 33-2 (2.0 g, 8.54 mmol) in MeOH (20 mL) was added Pd/C (200 mg, 10%) and the reaction mixture was stirred at room temperature for 16 h. The reaction mixture was filtered and the filtrate was concentrated to remove the solvent. The residue was purified by column chromatography ($CH_2Cl_2$/MeOH=100/1-20/1) to give 33-3 (1.0 g, about 57% yield) as an oil. MS Calcd.: 204.1; MS Found: 205.3 $[M+H]^+$.

The Synthesis of ethyl 4-(2-(2-(1H-1,2,4-triazol-1-yl)ethoxy)phenylamino)benzoate (SS20308-0033-01)

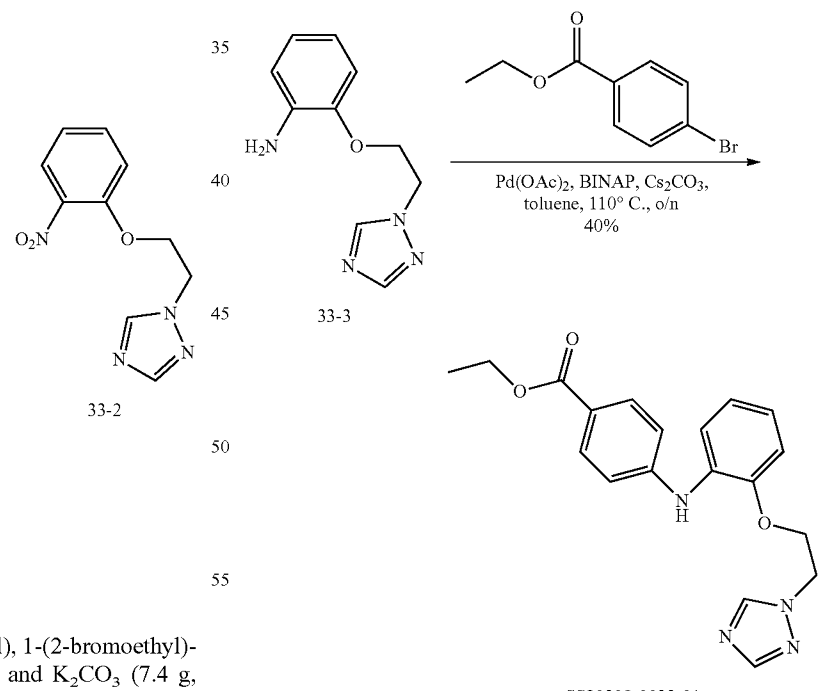

33-3

SS20308-0033-01

A solution of 33-3 (1.0 g, 4.90 mmol), ethyl 4-bromobenzoate (1.4 g, 5.88 mmol), $Pd(OAc)_2$ (110 mg, 0.49 mmol), BINAP (610 mg, 0.98 mmol) and $Cs_2CO_3$ (2.4 g, 7.34 mmol) in toluene (150 mL) was stirred at 110° C. overnight. The reaction was poured into water (500 mL) and extracted with EtOAc (500 mL). The organic layer was washed with water (300 mL), brine (2×300 mL) and the solvent evaporated to give a solid, which was purified by column chromatography ($CH_2Cl_2$/MeOH=100/1-20/1) and Prep-HPLC to give SS20308-0033-01 (700 mg, about 40% yield) as a solid. MS Calcd.: 352.2; MS Found: 353.3 $[M+H]^+$.

$^1$H NMR (400 MHz, $CDCl_3$) δ 8.08 (s, 1H), 7.99 (s, 1H), 7.96-7.93 (m, 2H), 7.38-7.36 (m, 1H), 7.04-6.99 (m, 2H), 7.98-7.94 (m, 2H), 6.90-6.98 (m, 1H), 6.29 (s, 1H), 4.57 (t, J=5.2 Hz, 2H), 4.41 (t, J=5.0 Hz, 2H), 4.57 (q, J=7.2 Hz, 2H), 1.38 (t, J=7.0 Hz, 3H).

Example 44

SS20308-0055-01

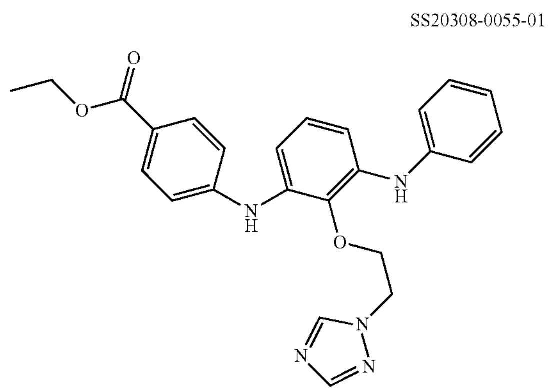

Chemical Formula: $C_{25}H_{25}N_5O_3$
Molecular Weight: 443.50

Example Route for Example 44

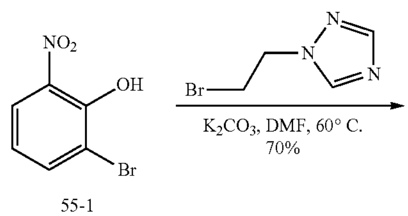

55-1

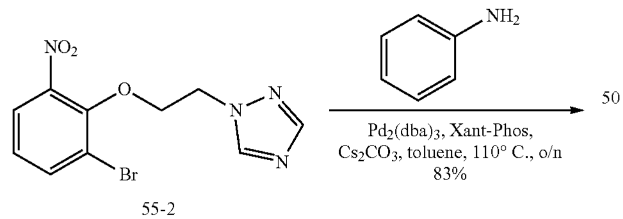

55-2

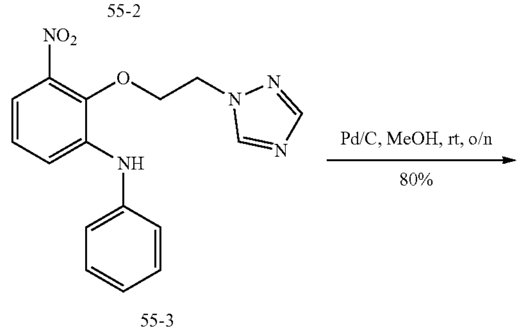

55-3

-continued

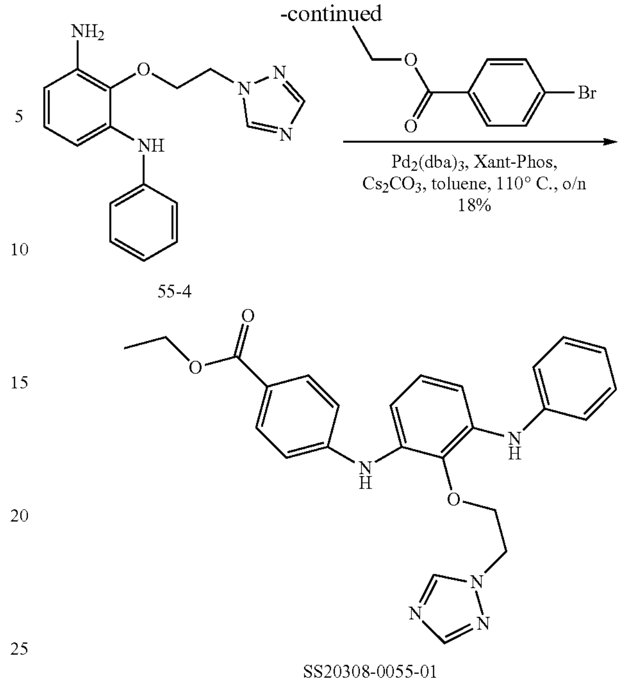

55-4

SS20308-0055-01

The Synthesis of 1-(2-(2-bromo-6-nitrophenoxy)ethyl)-1H-1,2,4-triazole (55-2)

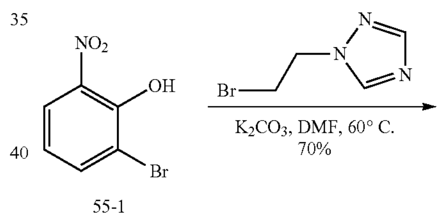

55-1

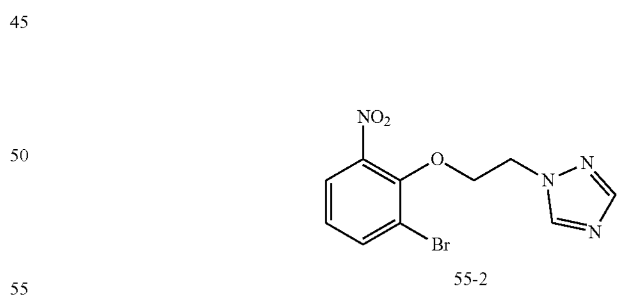

55-2

A mixture of 55-1 (2.2 g, 10.09 mmol), 1-(2-bromoethyl)-1H-1,2,4-triazole (2.1 g, 12.11 mmol) and $K_2CO_3$ (2.1 g, 15.14 mmol) in DMF (50 mL) was stirred at 60° C. overnight. The reaction mixture was cooled to room temperature and poured into water (100 mL) and extracted with EtOAc (70 mL×3). The organic layer was washed with brine and concentrated. The residue was purified by column chromatography ($CH_2Cl_2$/MeOH=100/1-20/1) to give 55-2 (2.2 g, about 70% yield) as an oil. MS Calcd.: 312.0; MS Found: 313.0$[M+H]^+$.

The Synthesis of 2-(2-(1H-1,2,4-triazol-1-yl) ethoxy)-3-nitro-N-phenylaniline (55-3)

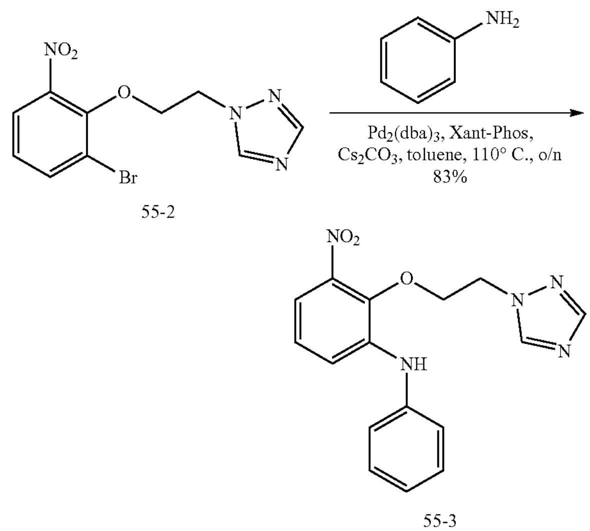

55-2

55-3

A solution of 55-2 (1.1 g, 3.51 mmol), aniline (393 mg, 4.22 mmol), $Pd_2(dba)_3$ (321 mg, 0.35 mmol), Xant-Phos (203 mg, 0.35 mmol) and $Cs_2CO_3$ (1.7 g, 5.27 mmol) in toluene (30 mL) was stirred at 110° C. under nitrogen atmosphere overnight. Then the reaction was poured into water (100 mL) and extracted with EtOAc (40 mL×4). The organic layer was washed with water (50 mL), brine (2×50 mL) and the solvent evaporated to give a solid, which was purified by column chromatography ($CH_2Cl_2$/MeOH=100/1-20/1) to give 55-3 (700 mg, about 83% yield) as an oil. MS Calcd.: 325.1; MS Found: 326.2 $[M+H]^+$.

The Synthesis of 2-(2-(1H-1,2,4-triazol-1-yl) ethoxy)-$N^1$-phenylbenzene-1,3-diamine (55-4)

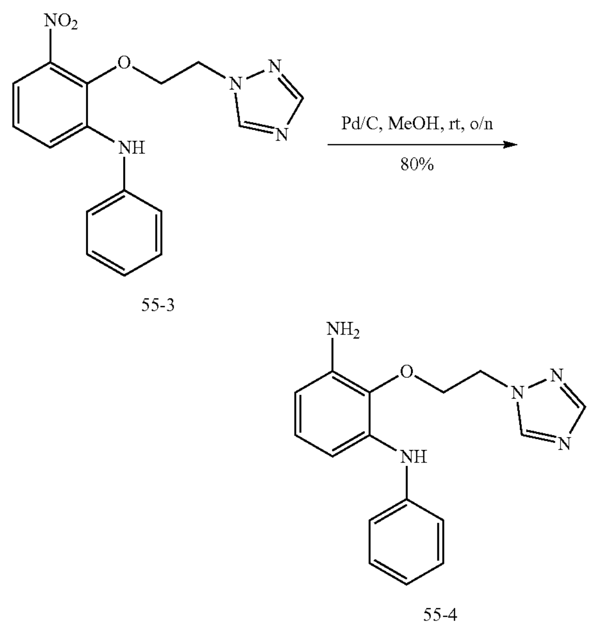

55-3

55-4

To a solution of 55-3 (550 mg, 1.69 mmol) in MeOH (20 mL) was added Pd/C (10%; 100 mg) and stirred at room temperature overnight. The reaction mixture was filtered and washed with methanol (10 mL×4) concentrated the solvent and purified by column chromatography ($CH_2Cl_2$/MeOH=100/1-20/1) to give 55-4 (400 mg, about 80% yield) as a solid. MS Calcd.: 295.1; MS Found: 296.1 $[M+H]^+$.

The Synthesis of ethyl 4-(2-(2-(1H-1,2,4-triazol-1-yl)ethoxy)-3-(phenylamino)phenylamino)benzoate (SS20308-0055-01)

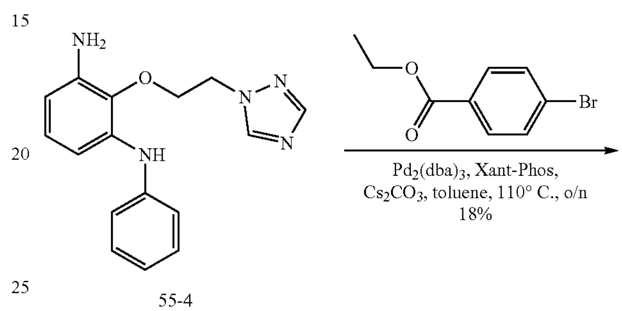

55-4

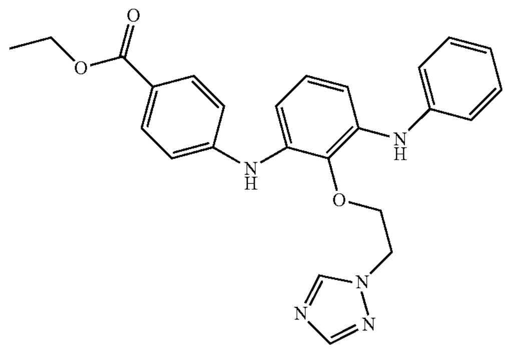

SS20308-0055-01

A solution of 55-4 (250 mg, 0.85 mmol), ethyl 4-bromobenzoate (291 mg, 1.27 mmol), $Pd_2(dba)_3$ (78 mg, 0.085 mmol), Xant-Phos (49 mg, 0.085 mmol) and $Cs_2CO_3$ (552 mg, 1.69 mmol) in toluene (6 mL) was stirred at 110° C. under nitrogen atmosphere overnight. Then the reaction was poured into water (15 mL) and extracted with EtOAc (10 mL×5). The organic layer was washed with water (10 mL), brine (2×10 mL) and the solvent evaporated to give a solid, which was purified by column chromatography ($CH_2Cl_2$/MeOH=80/1-30/1) and Prep-HPLC to give 55-3 (67 mg, about 18% yield) as a solid. MS Calcd.: 443.2; MS Found: 444.2 $[M+H]^+$.

$^1H$ NMR (400 MHz, $CDCl_3$) δ 8.39 (s, 1H), 8.16 (s, 1H), 7.99 (s, 1H), 7.78 (d, J=8.8 Hz, 1H), 7.47 (s, 1H), 7.24 (dd, J=7.6, 7.6 Hz, 1H), 7.08 (d, J=8.0 Hz, 1H), 6.97-6.90 (m, 4H), 6.86 (t, J=7.2 Hz, 1H), 6.80 (dd, J=7.6 Hz, 1.6 Hz, 1H), 4.40 (t, J=4.8 Hz, 2H), 4.25-4.20 (m, 2H), 4.12 (t, J=4.8 Hz, 2H), 1.27 (t, J=7.0 Hz, 3H).

Example 45
SS20308-0072-01
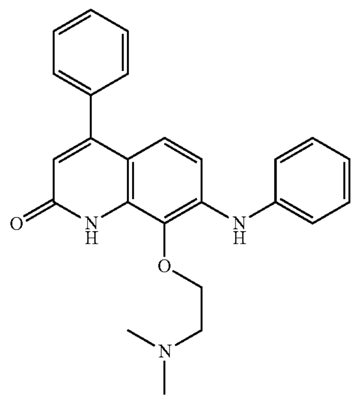
Chemical Formula: $C_{25}H_{25}N_3O_2$
Molecular Weight: 399.48
Example Route for Example 45
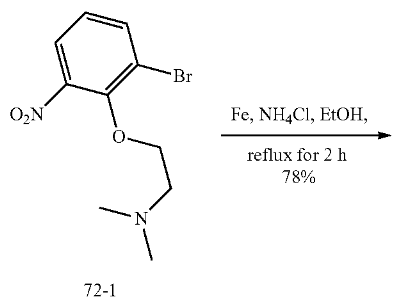
72-1
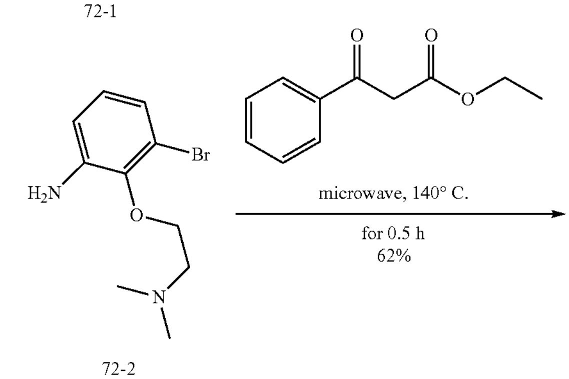
72-2
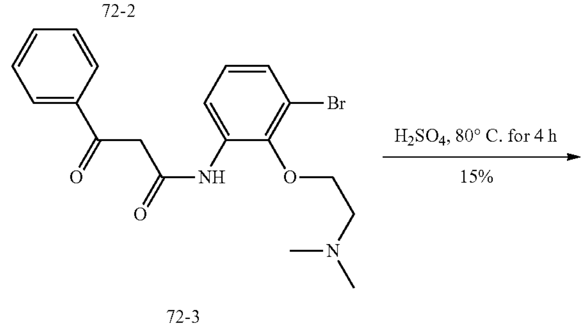
72-3
-continued
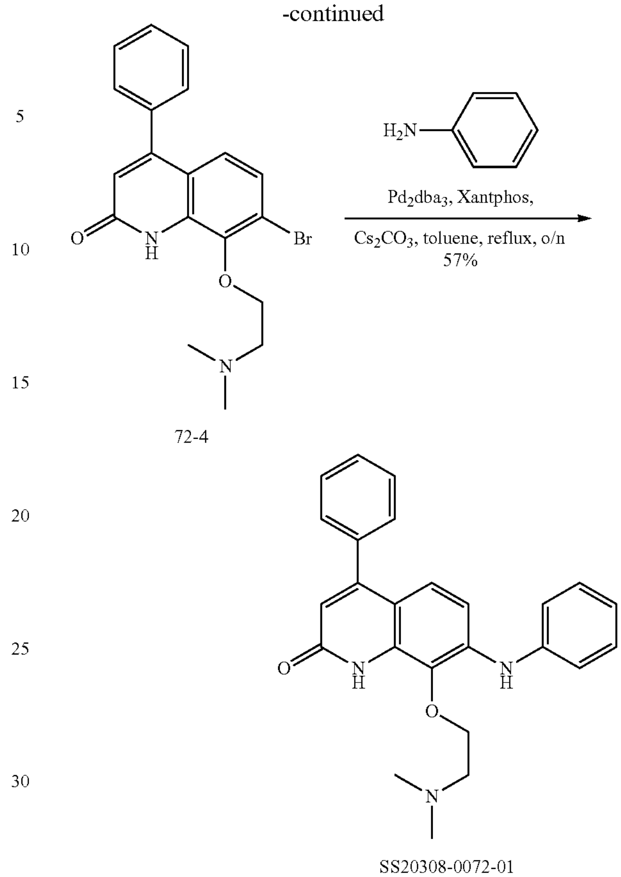
72-4
SS20308-0072-01
The Synthesis of 3-bromo-2-(2-(dimethylamino) ethoxy)aniline (72-2)
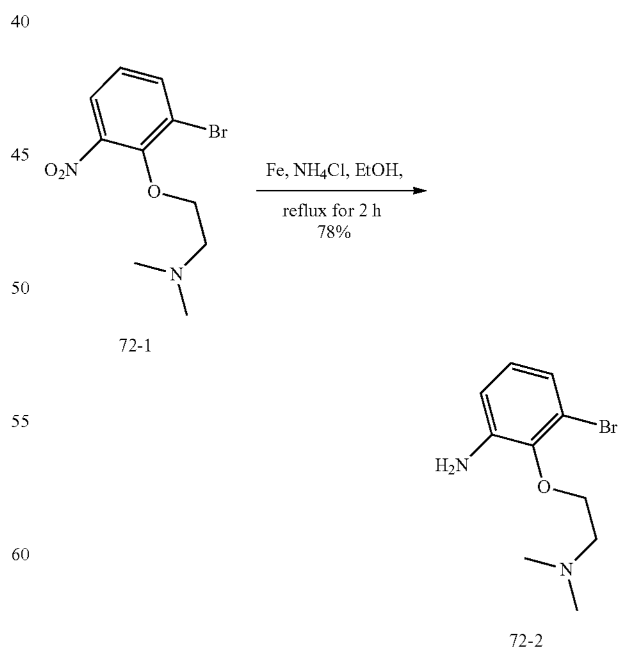
72-1
72-2
A mixture of 72-1 (1.0 g, 3.46 mmol), iron powder (1.9 g, 34.59 mmol) and $NH_4Cl$ (93 mg, 1.74 mmol) in ethanol (16 mL) and water (4 mL) was stirred at 85° C. for 2 h. Then the reaction mixture was filtered through celite. The filtrate was basified with NaOH solution until the pH value reached 10.0-11.0 and extracted with DCM (20 mL×3). The combined organic layers were washed with brine (10 mL×2), dried over sodium sulfate, and concentrated to give 72-2 (0.7 g, about 78% yield) as a solid. MS Calcd.: 258.0; MS Found: 259.2 $[M+H]^+$.

The Synthesis of N-(3-bromo-2-(2-(dimethylamino)ethoxy)phenyl)-3-oxo-3-phenylpropanamide (72-3)

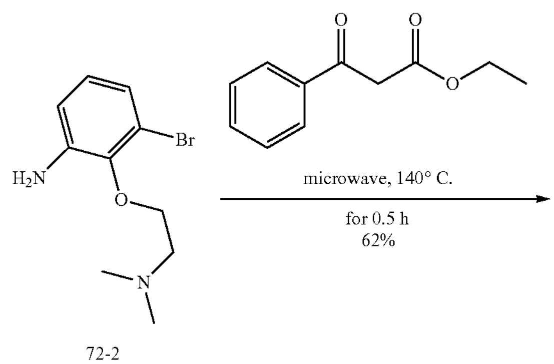

72-2

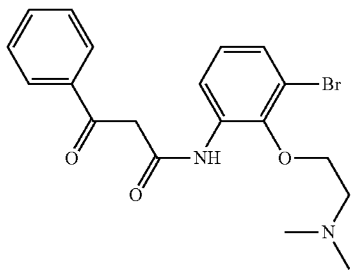

72-3

A mixture of 72-2 (410 mg, 1.58 mmol) and ethyl 3-oxo-3-phenylpropanoate (760 mg, 3.95 mmol) was stirred and heated to 140° C. for 0.5 h under microwave irradiation and nitrogen atmosphere. The reaction mixture was purified by silica gel column chromatography (petroleum ether/EtOAc=10/1, 5/1, 3/1, 1/1, $CH_2Cl_2$/MeOH=20/1) to give 72-3 (400 mg, about 62% yield) as a solid. MS Calcd.: 404.1; MS Found: 405.3 $[M+H]^+$.

The Synthesis of 7-bromo-8-(2-(dimethylamino)ethoxy)-4-phenylquinolin-2(1H)-one (72-4)

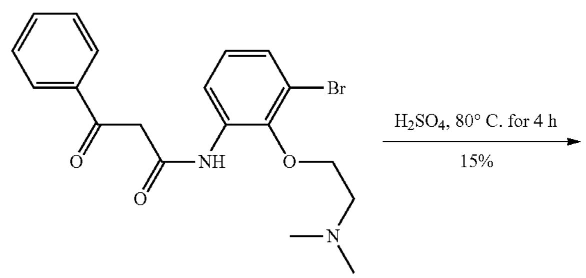

72-3

-continued

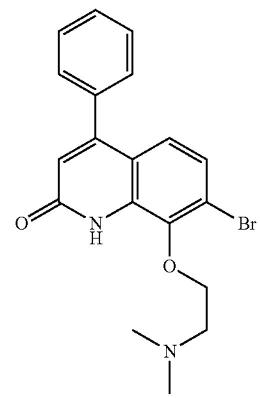

72-4

A mixture of 72-3 (500 mg, 1.23 mmol) in $H_2SO_4$ (5 mL) was stirred and heated to 80° C. for 4 h. The reaction mixture was cooled down to room temperature and poured into ice, basified with NaOH (40%) solution until the pH value reached 9.0-10.0 and extracted with EtOAc (20 mL×3). The combined organic layers were washed with brine (10 mL×2), dried over sodium sulfate, and concentrated to dryness. The residue was purified by Prep-TLC ($CH_2Cl_2$/MeOH=20/1) to give 72-4 (70 mg, about 15% yield) as an oil. MS Calcd.: 386.1; MS Found: 387.2 $[M+H]^+$.

The Synthesis of 8-(2-(dimethylamino)ethoxy)-4-phenyl-7-(phenylamino)quinolin-2(1H)-one (SS20308-0072-01)

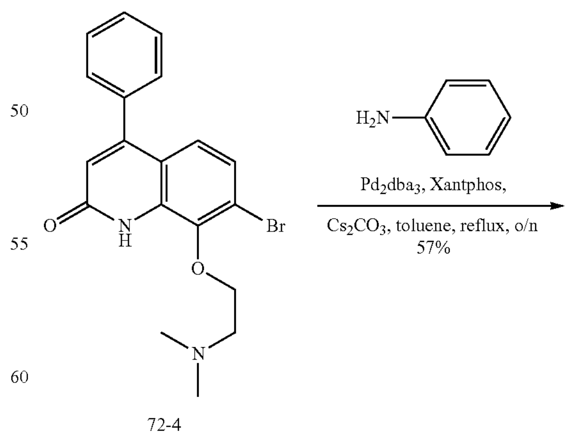

72-4

-continued

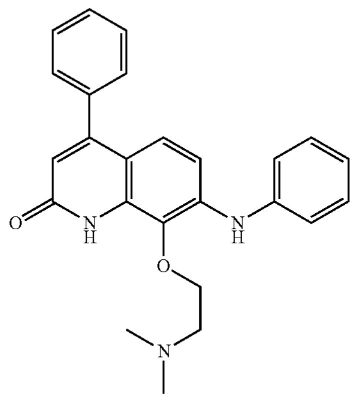

SS20308-0072-01

A solution of 72-4 (60 mg, 0.15 mmol), aniline (73 mg, 0.78 mmol), Xantphos (9 mg, 0.016 mmol), $Pd_2(dba)_3$ (7 mg, 0.0076 mmol), and anhydrous cesium carbonate (76 mg, 0.23 mmol) were suspended in toluene (2 mL). The reaction mixture was heated overnight at reflux under nitrogen atmosphere and then filtered, and rinsed with EtOAc. The filtrate was concentrated and purified by Prep-TLC ($CH_2Cl_2$/MeOH=20/1) to give SS20308-0072-01 (35 mg, about 57% yield) as a solid. MS Calcd.: 399.2; MS Found: 400.4 $[M+H]^+$.

$^1H$ NMR (400 MHz, DMSO-$d_6$) δ 12.67 (brs, 1H), 8.33 (s, 1H), 7.55-7.44 (m, 5H), 7.28 (dd, J=8.0, 7.6 Hz, 2H), 7.19 (d, J=7.6 Hz, 2H), 7.04-6.99 (m, 2H), 6.95 (dd, J=7.2, 7.2 Hz, 1H), 6.14 (s, 1H), 4.08 (t, J=4.2 Hz, 2H), 2.66 (t, J=4.2 Hz, 2H), 2.38 (s, 6H).

Example 46

SS20308-0095-01

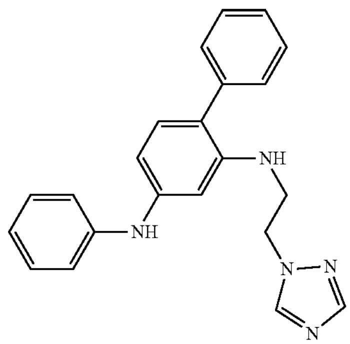

Chemical Formula: $C_{22}H_{21}N_5$
Molecular Weight: 355.44

Example Route for Example 46

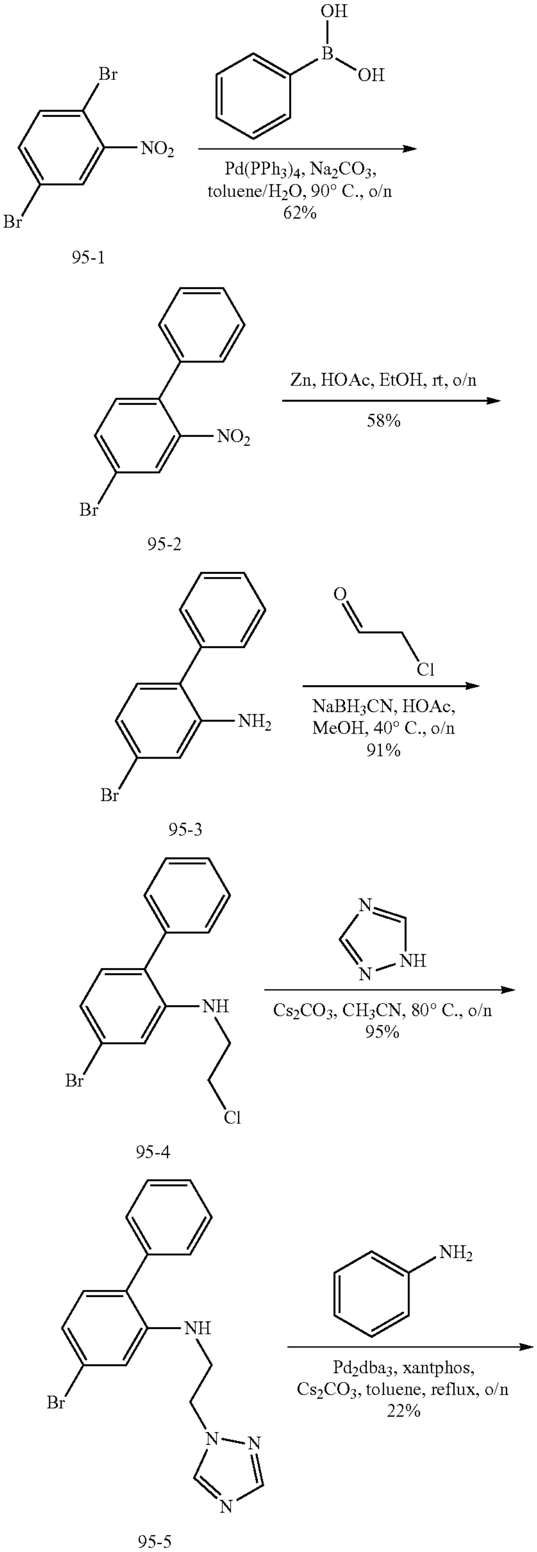

-continued

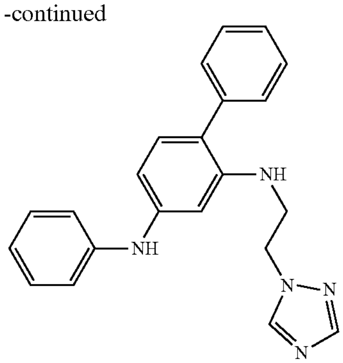

SS20308-0095-01

The Synthesis of 4-bromo-2-nitrobiphenyl (95-2)

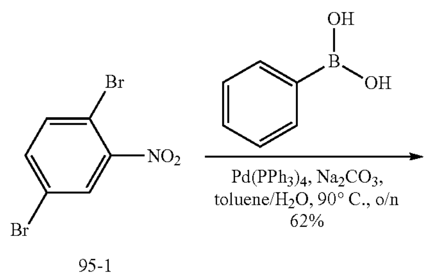

95-1

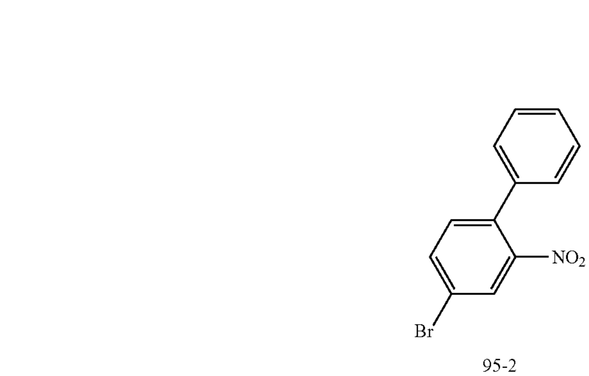

95-2

The mixture of 95-1 (6.00 g, 21.36 mmol), phenylboronic acid (2.60 g, 21.36 mmol), $Pd(PPh_3)_4$ (1.23 g, 1.07 mmol) and $Na_2CO_3$ (7.90 g, 74.76 mmol) in toluene/$H_2O$ (60 mL, 5/1) was stirred at 90° C. overnight under $N_2$ atmosphere. After cooled to room temperature, the reaction mixture was poured into water and extracted with EtOAc (60 mL×3). The organic layers were washed with brine, dried over $Na_2SO_4$ and concentrated. The residue was purified column chromatography (petroleum ether) to give 95-2 (3.70 g, about 62% yield) as an oil.

$^1H$ NMR (400 MHz, $CDCl_3$) δ 8.00 (d, J=2.0 Hz, 1H), 7.75 (dd, J=8.4 Hz, 2.0 Hz, 1H), 7.45-7.40 (m, 3H), 7.33 (d, J=8.4 Hz, 1H), 7.31-7.27 (m, 2H).

The Synthesis of 4-bromobiphenyl-2-amine (95-3)

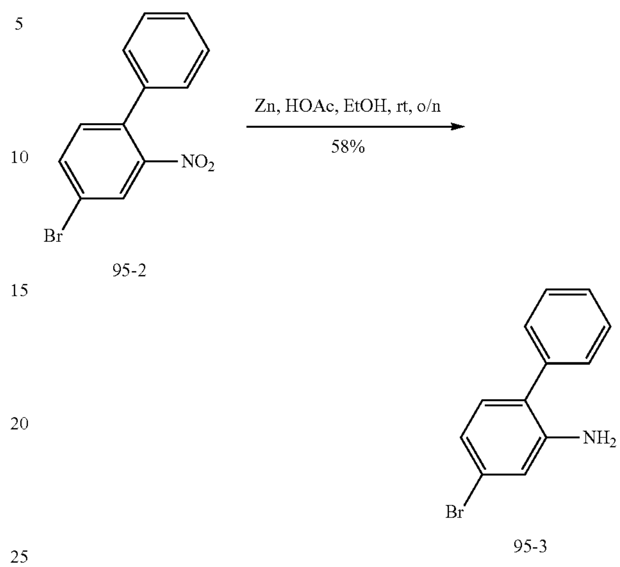

95-2

95-3

The mixture of 95-2 (3.70 g, 13.30 mmol), Zn powder (8.70 g, 133.00 mmol) and HOAc (3.5 mL) in EtOH (35 mL) was stirred at room temperature overnight. Then the reaction mixture was concentrated and poured into water. The mixture was basified with 40% NaOH till pH reached 10. The resulting mixture was filtrated through diatomite and washed with MeOH. The filtrate was extracted with EtOAc (50 mL×3). The organic layers were washed with brine, dried over $Na_2SO_4$ and concentrated. The residue was purified column chromatography (petroleum ether/EtOAc=20/1) to give 95-3 (1.90 g, about 58% yield) as an oil. MS Calcd.: 247.0; MS Found: 248.1 $[M+H]^+$.

The Synthesis of 4-bromo-N-(2-chloroethyl)biphenyl-2-amine (95-4)

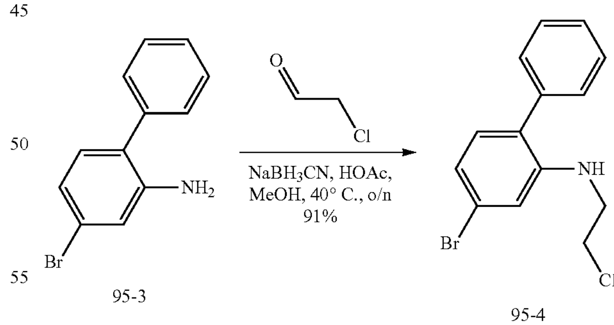

95-3

95-4

To a solution of 95-3 (1.75 g, 7.05 mmol) in MeOH (20 mL) was added 2-chloroacetaldehyde (2.77 g, 14.11 mmol, 40% in water), AcOH (846 mg, 14.11 mmol), and $NaBH_3CN$ (887 mg, 14.11 mmol), then the reaction mixture was stirred at 40° C. overnight. Then the reaction mixture was poured into water and basified with 1N NaOH till pH reached 10. The mixture was extracted with EtOAc (50 mL×3). The organic layers were washed with brine, dried over $Na_2SO_4$ and concentrated. The residue was purified column chromatography (petroleum ether/EtOAc=20/1) to give 95-4 (2.00 g, about 91% yield) as an oil. MS Calcd.: 309.0; MS Found: 309.8 [M+H]+.

The Synthesis of N-(2-(1H-1,2,4-triazol-1-yl)ethyl)-4-bromobiphenyl-2-amine (95-5)

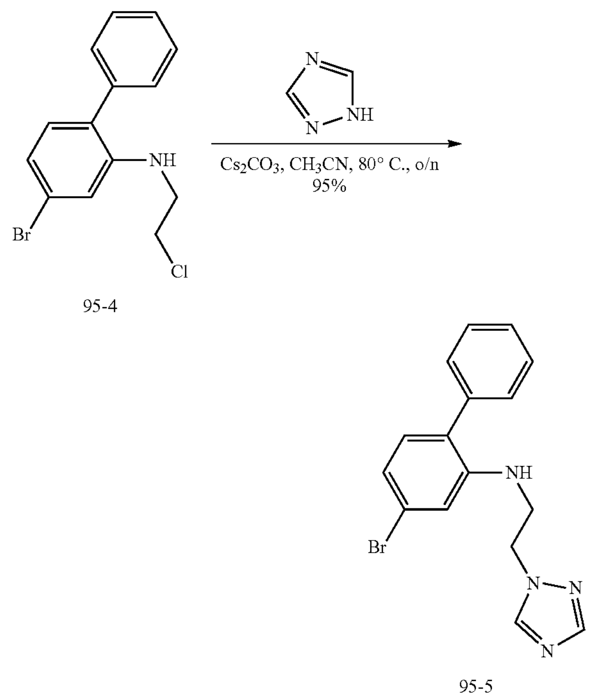

95-4

95-5

A mixture of 95-4 (2.00 g, 6.44 mmol), 1H-1,2,4-triazole (677 mg, 9.66 mmol) and $Cs_2CO_3$ (4.20 g, 12.88 mmol) in $CH_3CN$ (40 mL) was stirred at 80° C. overnight. The reaction mixture was then cooled to room temperature and filtered through celite and concentrated. The residue was purified by column chromatography (petroleum ether/EtOAc=2/1) to give 95-5 (2.10 g, about 95% yield) as an oil. MS Calcd.: 342.1; MS Found: 342.8 [M+H]+.

The Synthesis of $N^2$-(2-(1H-1,2,4-triazol-1-yl)ethyl)-$N^4$-phenylbiphenyl-2,4-diamine (SS20308-0095-01)

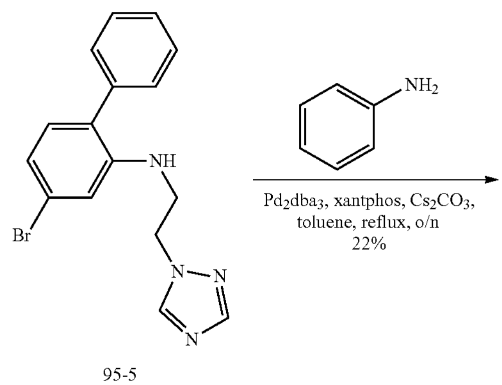

95-5

-continued

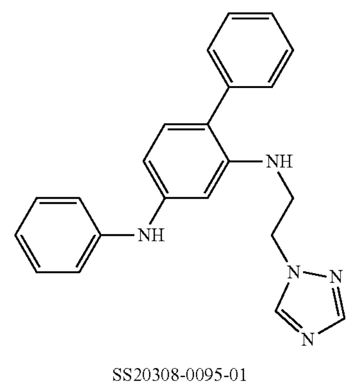 [SMILES: c1ccc(Nc2ccc(-c3ccccc3)c(NCCn3cncn3)c2)cc1]

SS20308-0095-01

The mixture of 95-5 (200 mg, 0.58 mmol), aniline (65 mg, 0.70 mmol), $Pd_2dba_3$ (53 mg, 0.06 mmol), Xantphos (67 mg, 0.12 mmol) and $Cs_2CO_3$ (378 mg, 1.16 mmol) in toluene (20 mL) was stirred at 110° C. overnight under $N_2$ atmosphere. The reaction mixture was then cooled to room temperature and filtered through celite and concentrated. The residue was purified by Prep-HPLC to give SS20308-0095-01 (45 mg, about 22% yield) as a solid. MS Calcd.: 355.2; MS Found: 356.1 [M+H]+.

$^1H$ NMR (400 MHz, $CDCl_3$) δ 7.95 (s, 1H), 7.88 (s, 1H), 7.43-7.37 (m, 2H), 7.34-7.23 (m, 5H), 7.14 (dd, J=8.4 Hz, 1.2 Hz, 2H), 7.02-6.93 (m, 2H), 6.54 (dd, J=8.0 Hz, 2.0 Hz, 1H), 6.39 (d, J=2.0 Hz, 1H), 5.75 (s, 1H), 4.32 (t, J=6.0 Hz, 2H), 4.18 (t, J=6.0 Hz, 1H), 3.60-3.54 (m, 2H).

Example 47

SS20308-0129

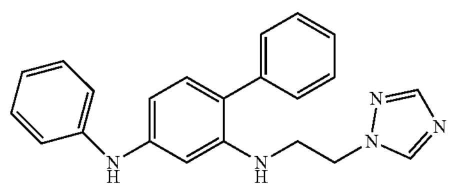

Example Route for Example 47

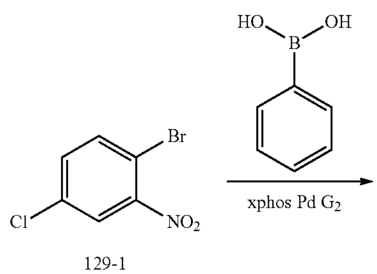

129-1

-continued

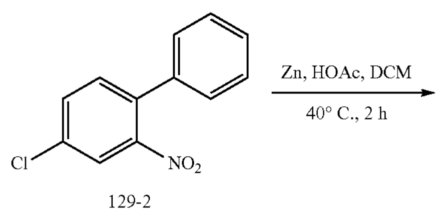

129-2

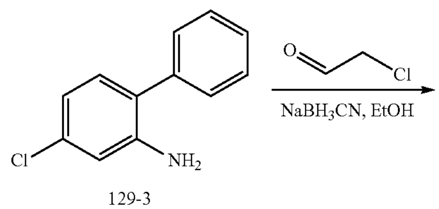

129-3

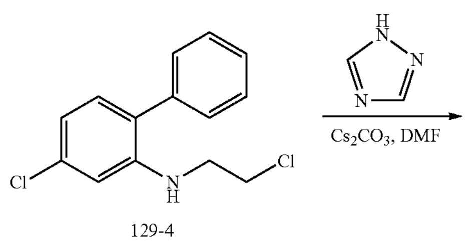

129-4

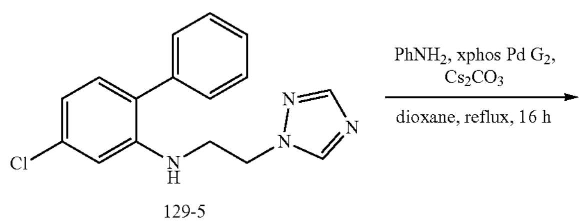

129-5

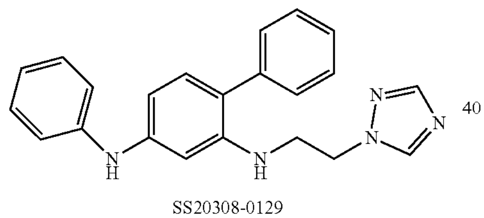

SS20308-0129

The Synthesis of 4-chloro-2-nitro-1,1'-biphenyl (129-2)

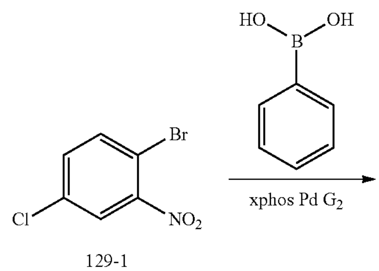

129-1

-continued

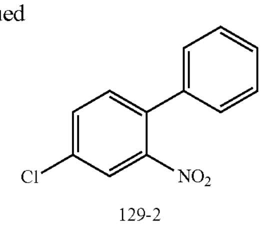

129-2

To a mixture of 129-1 (2.36 g, 10 mmol) and phenylboronic acid (1.22 g, 10 mmol) in toluene/$H_2O$ (50 mL/5 mL) was added $Cs_2CO_3$ (6.52 g, 20 mmol) and Xphos Pd $G_2$ (200 mg). The mixture was heated to reflux for 6 h. The mixture was diluted with ethyl acetate (50 mL). The organic layer was successively washed with water (50 mL) and brine (50 mL). The organic layer was then dried with $MgSO_4$, filtered and concentrated under reduced pressure. The crude product was purified by column chromatography on silica gel (hexanes/EtOAc=15/1) to give 129-2 (1.2 g, about 51% yield) as an oil. MS Calcd.: 233.0; MS Found: 234.2 $[M+H]^+$ The Synthesis of 4-chloro-[1,1'-biphenyl]-2-amine (129-3)

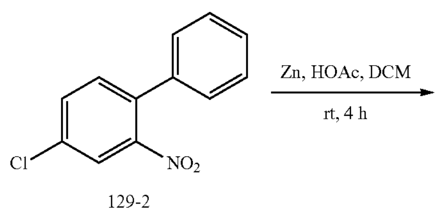

129-2

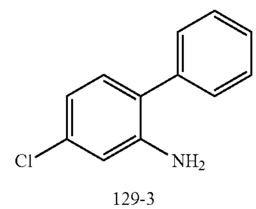

129-3

To a mixture of 129-2 (1.2 g, 4.3 mmol) in DCM (50 mL) was added HOAc (5 mL) and Zn powder (500 mg) at room temperature. Then the mixture was stirred at rt for 4 h. The reaction mixture was filtered and the organic layer was concentrated under reduced pressure. The crude product was purified by column chromatography on silica gel (hexanes/EtOAc=5/1) to give 129-3 (800 mg, about 77% yield) as an oil. MS Calcd: 203.1; MS Found: 204.2 $[M+H]^+$ The Synthesis of 4-chloro-N-(2-chloroethyl)-[1,1'-biphenyl]-2-amine (129-4)

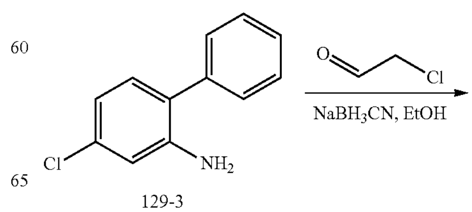

129-3

-continued

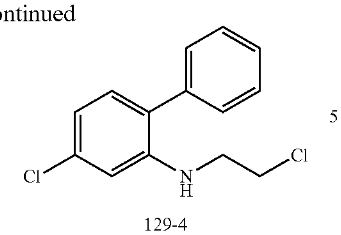

129-4

To a mixture of 129-3 (406 mg, 2 mmol) in EtOH (50 mL) was added 2-chloroacetaldehyde (5 mL, 40% in water) and HOAc (2 mL) at room temperature. To this mixture $NaBH_3CN$ (0.5 g) was added and resulting was stirred at rt for 6 h. The mixture was filtered. The filtrate was concentrated and purified by column chromatography on silica gel (hexanes/EtOAc=3/1) to give 129-4 (380 mg, about 71% yield) as a colorless oil. MS Calcd.: 265.0; MS Found: 266.2 $[M+H]^+$ The Synthesis of N-(2-(1H-1,2,4-triazol-1-yl)ethyl)-4-chloro-[1,1'-biphenyl]-2-amine (129-5)

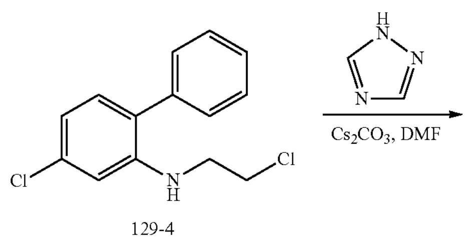

129-4

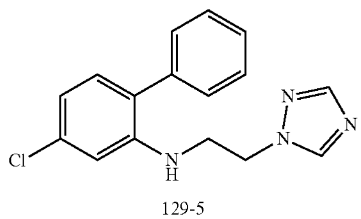

129-5

To a mixture of 129-4 (380 mg, 1.4 mmol) in DMF (10 mL) was added 1H-1,2,4-triazole (193 mg, 2.8 mmol) and $Cs_2CO_3$ (913 mg, 2.8 mmol) at room temperature, The mixture was stirred at 80° C. for 8 h. The mixture was diluted with DCM (30 mL). The mixture was successively washed with $H_2O$ (40 mL) and brine (40 mL). The organic layer was then dried with $MgSO_4$, filtered and concentrated under reduced pressure. The crude product was purified by column chromatography on silica gel (hexanes/EtOAc=1/5) to give 129-5 (260 mg, about 61% yield) as a solid. MS Calcd.: 298.1; MS Found: 299.2 $[M+H]^+$ The Synthesis of N2-(2-(1H-1,2,4-triazol-1-yl)ethyl)-N4-phenyl-[1,1'-biphenyl]-2,4-diamine (SS20308-0129)

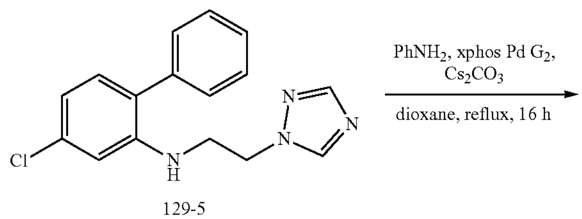

129-5

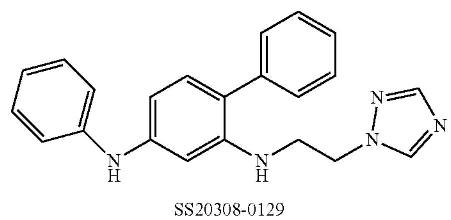

SS20308-0129

To a mixture of 129-5 (130 mg, 0.4 mmol) in dioxane (5 mL) was added aniline (74.4 mg, 0.8 mmol), $Cs_2CO_3$ (326 g, 1 mmol) and Xphos Pd $G_2$ (30 mg) at room temperature. The mixture was heated to reflux for 12 h under nitrogen. The reaction mixture was cooled to room temperature, filtered and washed with EtOAc (80 mL). The filtrate was successively washed with water (100 mL) and brine (100 mL). The organic layer was then dried with $MgSO_4$, filtered and concentrated under reduced pressure. The crude product was purified by column chromatography on silica gel (hexanes/EtOAc=5/1 to 1/5) to give SS20308-0129 (20 mg, about 13% yield) as an oil. MS Calcd.: 355.2; MS Found: 356.2 $[M+H]^+$ $^1H$ NMR (400 MHz, DMSO-$d_6$) δ 3.36-3.44 (m, 2H), 4.30 (t, J=6.02 Hz, 2H), 4.34-4.38 (m, 1H), 4.71 (br t, J=5.77 Hz, 1H), 6.24 (t, J=2.01 Hz, 1H), 6.39-6.51 (m, 2H), 6.77-6.89 (m, 2H), 7.08-7.17 (m, 2H), 7.19-7.32 (m, 5H), 7.34-7.46 (m, 3H), 7.67 (d, J=2.01 Hz, 1H), 8.07 (s, 1H).

Example 48

SS20308-0130

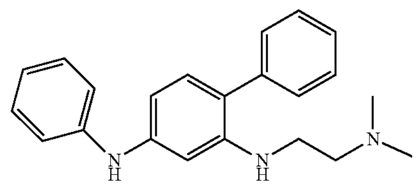

Example Route for Example 48

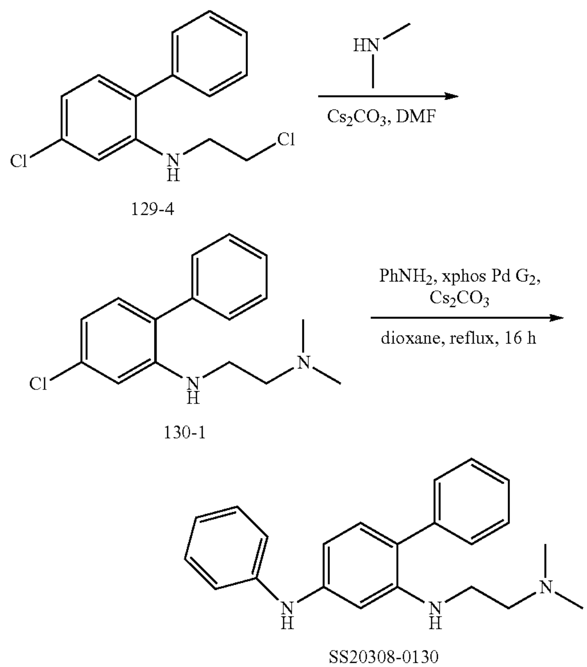

129-4

130-1

SS20308-0130

The Synthesis of N1-(4-chloro-[1,1'-biphenyl]-2-yl)-N2,N2-dimethylethane-1,2-diamine (130-1)

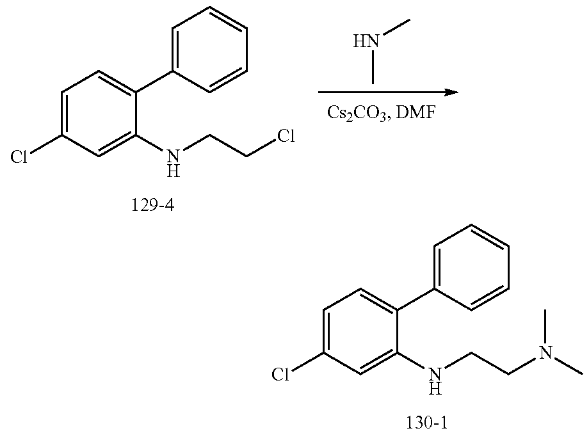

129-4

130-1

To a mixture of 129-4 (380 mg, 1.4 mmol) in DMF (10 mL) was added dimethylamine (7 mL, 14 mmol) and $Cs_2CO_3$ (913 mg, 2.8 mmol) at room temperature, then the mixture was stirred at 80° C. for 8 h. The mixture was diluted with DCM (30 mL). The mixture was successively washed with $H_2O$ (40 mL) and brine (40 mL). The organic layer was then dried with $MgSO_4$, filtered and concentrated under reduced pressure. The crude product was purified by column chromatography on silica gel (hexanes/EtOAc=1/5) to give 130-1 (220 mg, about 56% yield) as an oil. MS Calcd.: 274.1; MS Found: 275.2 $[M+H]^+$

The Synthesis of N2-(2-(dimethylamino)ethyl)-N4-phenyl-[1,1'-biphenyl]-2,4-diamine (SS20308-0130)

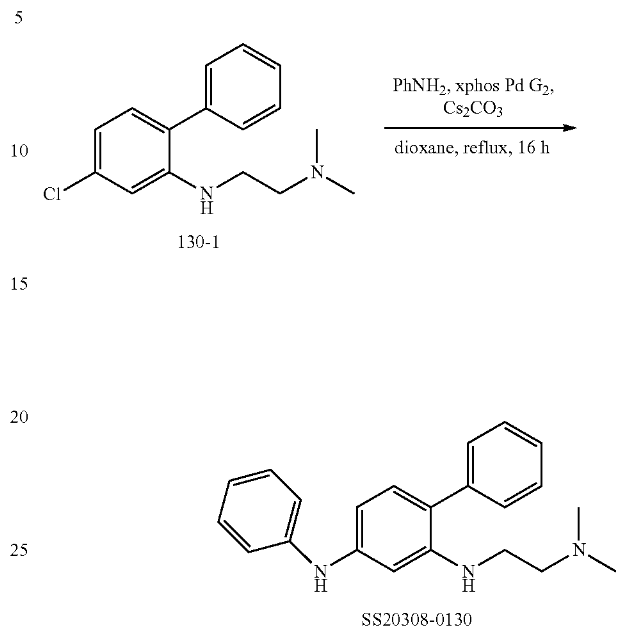

130-1

SS20308-0130

To a mixture of 130-1 (137 mg, 0.5 mmol) in dioxane (5 mL) was added aniline (74.4 mg, 0.8 mmol), $Cs_2CO_3$ (326 g, 1 mmol) and xphos Pd $G_2$ (30 mg) at room temperature. The mixture was heated to reflux for 12 h under nitrogen. The reaction mixture was cooled to room temperature. The mixture was filtered, and washed with EtOAc (40 mL). The filtrate was successively washed with water (40 mL) and brine (40 mL). The organic layer was then dried with $MgSO_4$, filtered and concentrated under reduced pressure. The crude product was purified by column chromatography on silica gel (DCM/MeOH=20/1 to 4/1) to give SS20308-0130 (10 mg, about 13% yield) as a solid. MS Calcd.: 331.2; MS Found: 332.2 $[M+H]^+$ $^1H$ NMR (400 MHz, DMSO-$d_6$) δ 2.81 (s, 6H), 3.17-3.27 (m, 2H), 3.36-3.44 (m, 2H), 6.47 (d, J=2.01 Hz, 1H), 6.53 (s, 1H), 6.82 (s, 1H), 6.91 (d, J=8.28 Hz, 1H), 7.08-7.16 (m, 2H), 7.20-7.27 (m, 2H), 7.29-7.36 (m, 1H), 7.39-7.47 (m, 4H).

Example 49

SS20308-0131

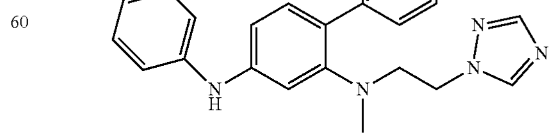

Example Route for Example 49

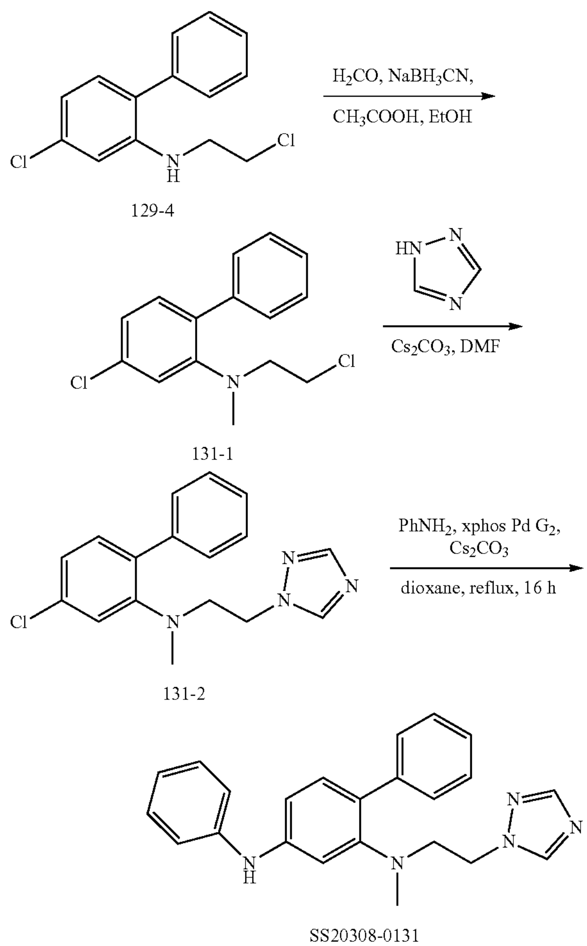

129-4

131-1

131-2

SS20308-0131

The Synthesis of 4-chloro-N-(2-chloroethyl)-N-methyl-[1,1'-biphenyl]-2-amine (131-1)

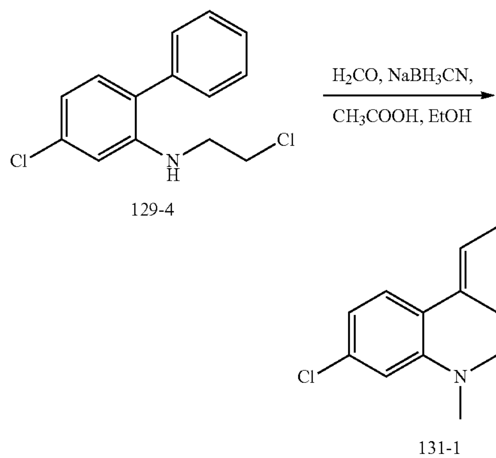

129-4

131-1

To a mixture of 129-4 (266 mg, 1 mmol) in EtOH (30 mL) was added HCHO (aq) (3 mL) and HOAc (2 mL) at room temperature, then $NaBH_3CN$ (0.5 g) was added, the mixture was stirred at rt for 6 h. The mixture was filtered. The filtrate was concentrated and purified by column chromatography on silica gel (hexanes/EtOAc=1/1) to give 131-1 (180 mg, about 64% yield) as an oil. MS Calcd.: 279.1; MS Found: 280.2 $[M+H]^+$ The Synthesis of N-(2-(1H-1,2,4-triazol-1-yl)ethyl)-4-chloro-N-methyl-[1,1'-biphenyl]-2-amine (131-2)

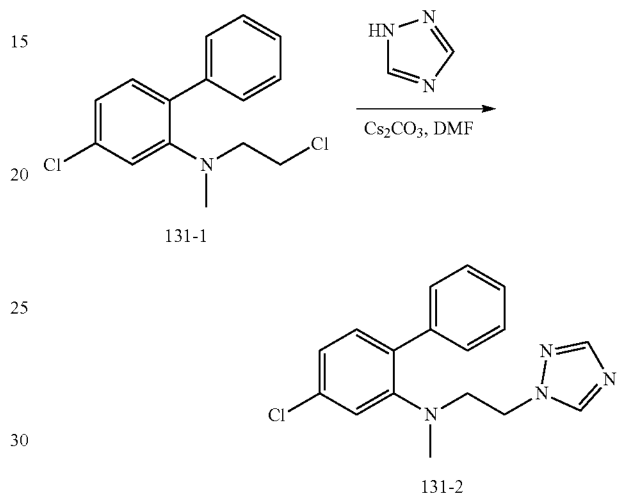

131-1

131-2

To a mixture of 131-1 (180 mg, 0.6 mmol) in DMF (10 mL) was added 1H-1,2,4-triazole (138 mg, 2 mmol) and $Cs_2CO_3$ (652 mg, 2 mmol) at room temperature. The mixture was stirred at 80° C. for 8 h. The mixture was diluted with DCM (30 mL), washed with saturated $H_2O$ (40 mL) and brine (40 mL). The organic layer was then dried with $MgSO_4$, filtered and concentrated under reduced pressure. The crude product was purified by column chromatography on silica gel (hexanes/EtOAc=1/6) to give 131-2 (120 mg, about 60% yield) as an oil. MS Calcd.: 312.1; MS Found: 313.2 $[M+H]^+$ The Synthesis of N2-(2-(1H-1,2,4-triazol-1-yl)ethyl)-N2-methyl-N4-phenyl-[1,1'-biphenyl]-2,4-diamine (SS20308-0131)

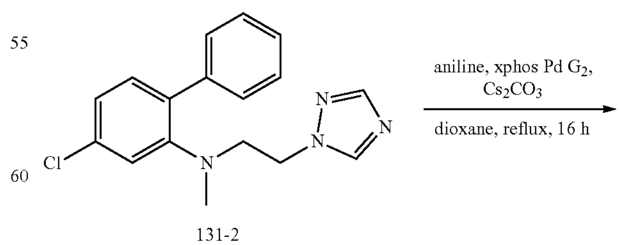

131-2

-continued

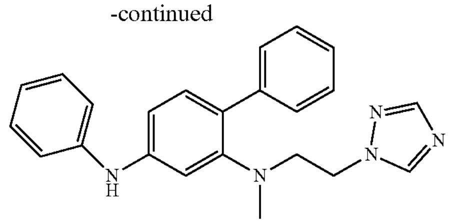

SS20308-0131-01

To a mixture of 131-2 (120 mg, 0.4 mmol) in toluene (15 mL) was added aniline (74.4 mg, 0.8 mmol), $Cs_2CO_3$ (326 g, 1 mmol) and xphos Pd $G_2$ (30 mg) at room temperature. The mixture was heated to reflux for 12 h under nitrogen. The reaction mixture was cooled to room temperature, filtered and washed with EtOAc (40 mL). The filtrate was washed with water (50 mL) and brine (50 mL). The organic layer was then dried with $MgSO_4$, filtered and concentrated under reduced pressure. The crude product was purified by column chromatography on silica gel (hexanes/EtOAc=5/1 to 1/4) to give SS20308-0131 (28 mg, about 20% yield) as a solid. MS Calcd.: 369.2; MS Found: 370.2 $[M+H]^+$ $^1$H NMR (400 MHz, DMSO-$d_6$) δ 2.45 (s, 3H), 3.24 (s, 2H), 4.16-4.24 (m, 2H), 6.72-6.78 (m, 1H), 6.79 (t, J=2.13 Hz, 1H), 6.81-6.87 (m, 1H), 7.00 (d, J=8.03 Hz, 1H), 7.07-7.15 (m, 2H), 7.17-7.35 (m, 6H), 7.95 (s, 1H), 8.20 (s, 1H), 8.33 (s, 1H).

Example 50

SS20308-0132

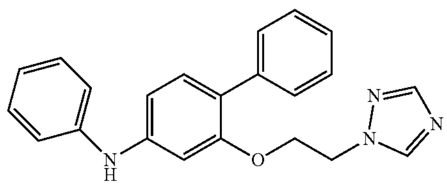

Example Route for Example 50

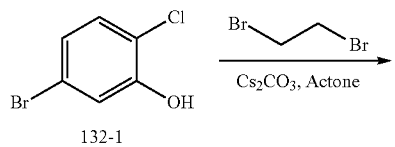

132-1

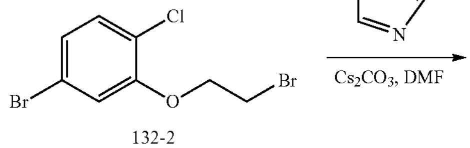

132-2

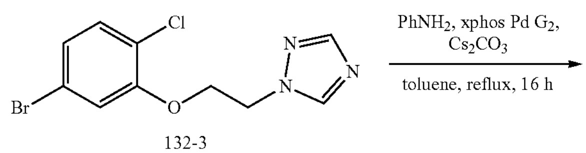

132-3

-continued

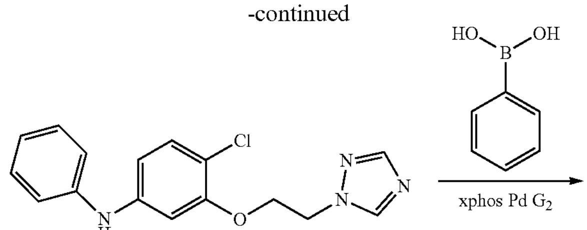

132-4

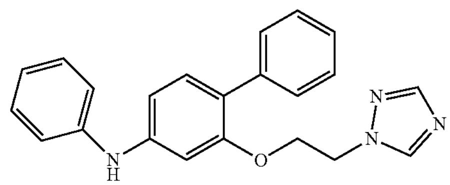

SS20308-0132

The Synthesis of 4-bromo-2-(2-bromoethoxy)-1-chlorobenzene (132-2)

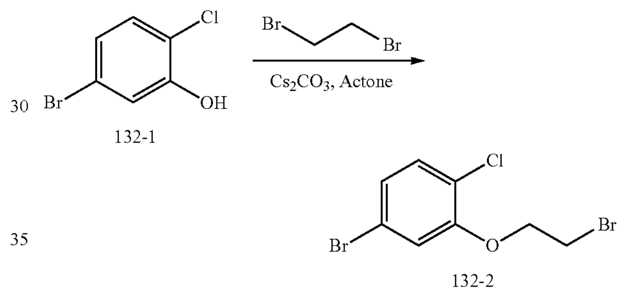

132-1

132-2

To a mixture of 132-1 (412 mg, 2 mmol) in acetone (50 mL) was added 1,2-dibromoethane (744 mg, 4 mmol) and $Cs_2CO_3$ (1.3 g, 4 mmol) at room temperature. The mixture was stirred at 70° C. for 8 h. The mixture was filtered and the filtrate was concentrated under reduced pressure. The crude product was purified by column chromatography on silica gel (hexanes/EtOAc=20/1) to give 132-2 (380 mg, about 61% yield) as an oil. MS Calcd.: 311.9; MS Found: 312.9 $[M+H]^+$

The Synthesis of 1-(2-(5-bromo-2-chlorophenoxy)ethyl)-1H-1,2,4-triazole (132-3)

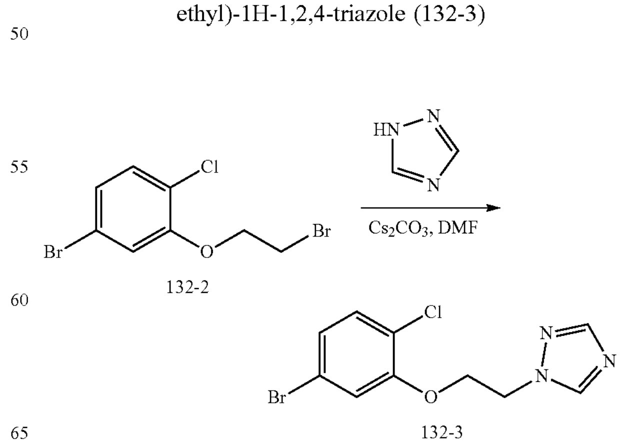

132-2

132-3

To a mixture of 132-2 (312 mg, 1.0 mmol) in DMF (10 mL) was added 1H-1,2,4-triazole (138 mg, 2.0 mmol) and $Cs_2CO_3$ (652 mg, 2.0 mmol) at room temperature. The mixture was stirred at 80° C. for 8 h. The mixture was diluted with DCM (30 mL), and was successively washed with $H_2O$ (40 mL) and brine (40 mL). The organic layer was then dried with $MgSO_4$, filtered and concentrated under reduced pressure. The crude product was purified by column chromatography on silica gel (hexanes/EtOAc=1/3) to give 132-3 (220 mg, about 73% yield) as an oil. MS Calcd.: 301.0; MS Found: 302.2 $[M+H]^+$ The Synthesis of 3-(2-(1H-1,2,4-triazol-1-yl)ethoxy)-4-chloro-N-phenylaniline (132-4)

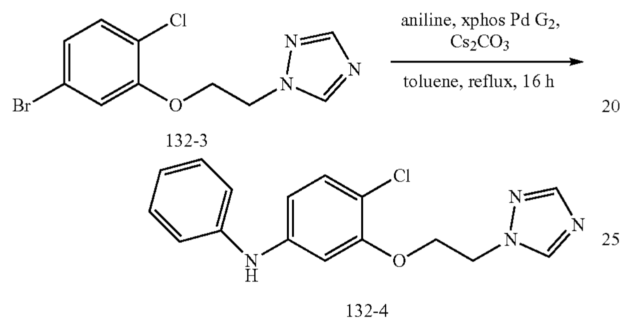

132-3

132-4

To a mixture of 132-3 (220 mg, 0.7 mmol) in toluene (10 mL) was added aniline (65 mg, 0.7 mmol), $Cs_2CO_3$ (326 g, 1 mmol) and Xphos Pd $G_2$ (30 mg) at room temperature, the mixture was heated to reflux for 12 h under nitrogen. The reaction mixture was cooled to room temperature, the mixture was filtered and washed with EtOAc (40 mL). The filtrate was washed with water (40 mL) and brine (40 mL). The organic layer was then dried with $MgSO_4$ filtered and concentrated under reduced pressure. The crude product was purified by column chromatography on silica gel (hexanes/EtOAc=5/1 to 1/5) to give 132-4 (80 mg, about 35% yield) as an oil. MS Calcd.: 314.1; MS Found: 315.1 $[M+H]^+$ The Synthesis of 2-(2-(1H-1,2,4-triazol-1-yl)ethoxy)-N-phenyl-[1,1'-biphenyl]-4-amine (SS20308-0132)

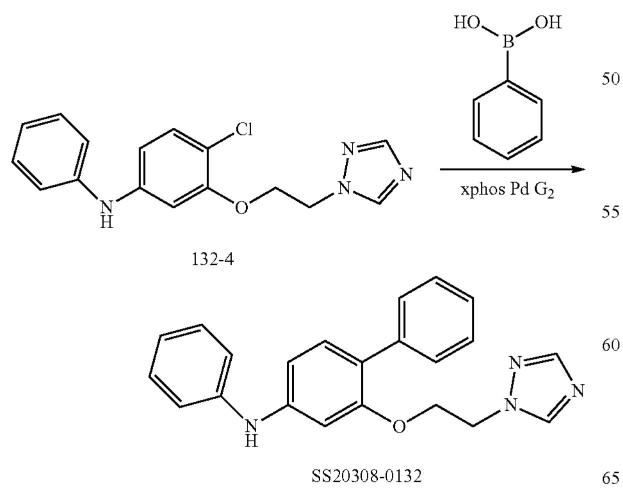

132-4

SS20308-0132

To a mixture of 132-4 (80 mg, 0.25 mmol) and phenylboronic acid (61 mg, 0.5 mmol) in toluene/$H_2O$ (15 mL/3 mL) was added $Cs_2CO_3$ (326 mg, 1 mmol) and xphos Pd $G_2$ (15 mg). The mixture was heated to reflux for 6 h. The mixture was diluted with ethyl acetate (50 mL), the organic layer was washed with water (30 mL) and brine (30 mL), dried with $MgSO_4$, filtered and concentrated under reduced pressure. The crude product was purified by column chromatography on silica gel (DCM/MeOH=10/1) to give SS20308-0132 (15 mg, about 16% yield) as a solid. MS Calcd.: 356.2; MS Found: 357.2 $[M+H]^+$ $^1H$ NMR (400 MHz, DMSO-$d_6$) δ 4.32 (t, J=5.02 Hz, 2H), 4.55 (t, J=5.02 Hz, 2H), 6.75 (s, 1H), 6.76 (d, J=6.00 Hz, 2H), 6.87 (t, J=7.07 Hz, 1H), 7.13-7.32 (m, 11H), 8.01 (s, 1H), 8.30-8.34 (m, 2H).

Example 51

SS20308-0133

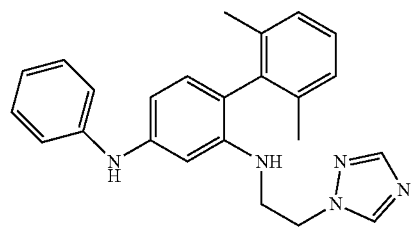

Example Route for Example 51

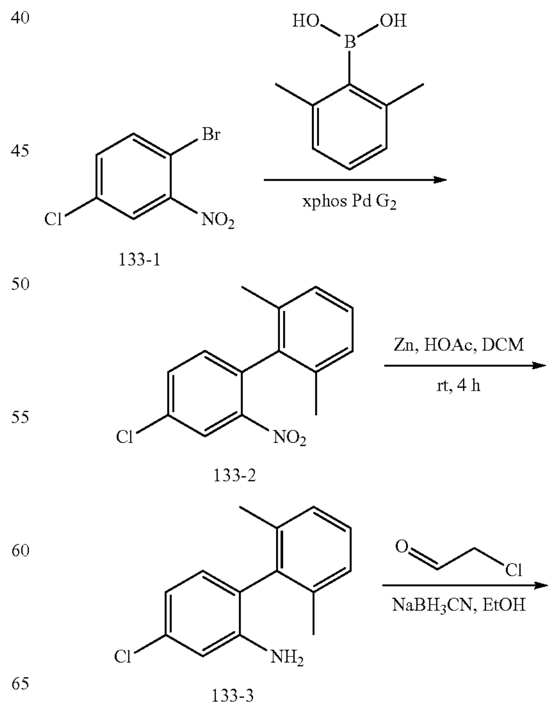

133-1

133-2

133-3

-continued

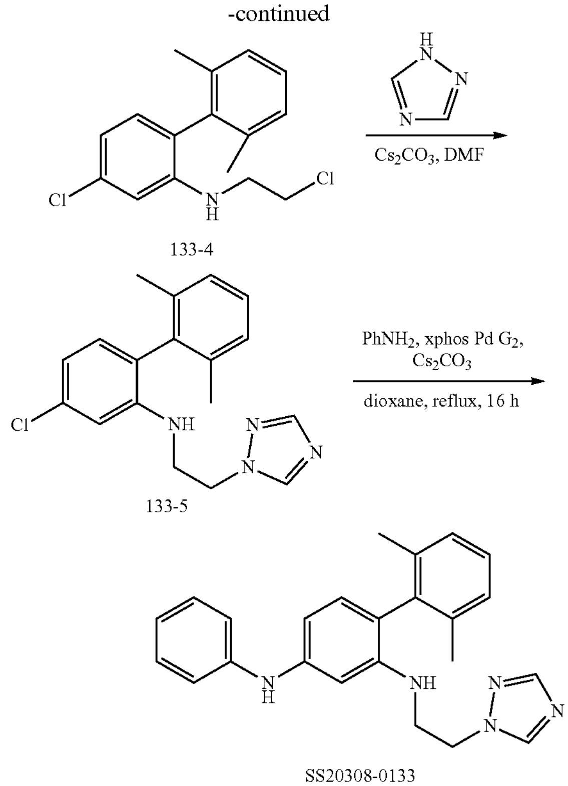

133-4

133-5

SS20308-0133

The Synthesis of 4-chloro-2',6'-dimethyl-2-nitro-1,1'-biphenyl (133-2)

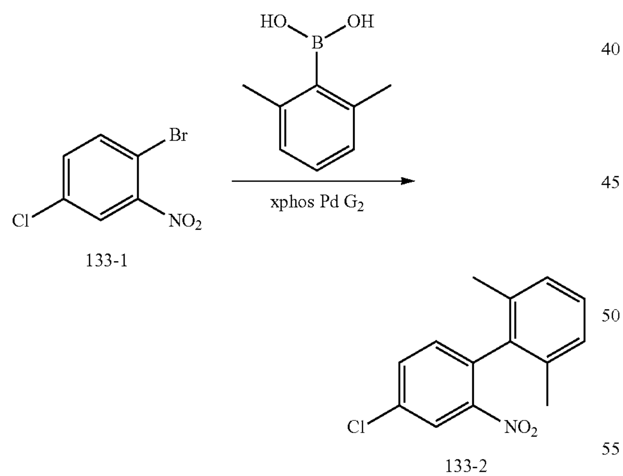

133-1

133-2

To a mixture of 133-1 (235 mg, 1 mmol) and (2,6-dimethylphenyl)boronic acid (180 mg, 1.2 mmol) in toluene/$H_2O$ (15 mL/3 mL) was added $Cs_2CO_3$ (652 mg, 2 mmol) and Xphos Pd $G_2$ (20 mg), the mixture was heated to reflux for 6 h. The solution was cooled to rt and diluted with ethyl acetate (30 mL), the organic layer was washed with water (30 mL) and brine (30 mL). The organic layer was dried with $MgSO_4$, filtered and concentrated under reduced pressure. The crude product was purified by column chromatography on silica gel (hexanes/EtOAc=15/1) to give 133-2 (90 mg, about 35% yield) as an oil. MS Calcd.: 261.1; MS Found: 262.2 $[M+H]^+$ The Synthesis of 4-chloro-2',6'-dimethyl-[1,1'-biphenyl]-2-amine (133-3)

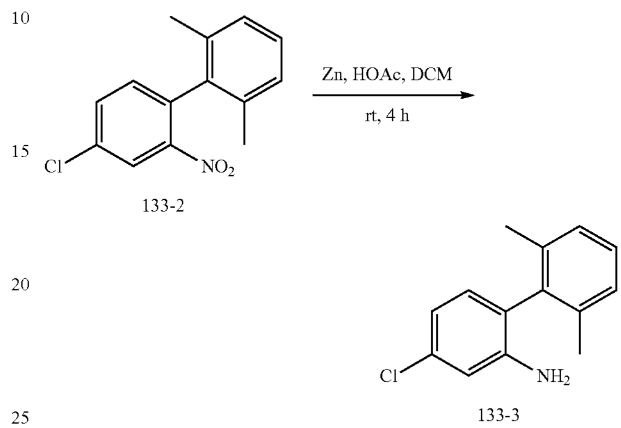

133-2

133-3

To a mixture of 133-2 (261 mg, 1 mmol) in DCM (50 mL) was added HOAc (5 mL) and Zn powder (150 mg) at room temperature. The mixture was stirred at rt for 4 h, filtered and the organic layer was concentrated under reduced pressure. The crude product was purified by column chromatography on silica gel (hexanes/EtOAc=4/1) to give 133-3 (200 mg, about 86% yield) as an oil. MS Calcd.: 231.1; MS Found: 232.2 $[M+H]^+$ The Synthesis of 4-chloro-N-(2-chloroethyl)-2',6'-dimethyl-[1,1'-biphenyl]-2-amine (133-4)

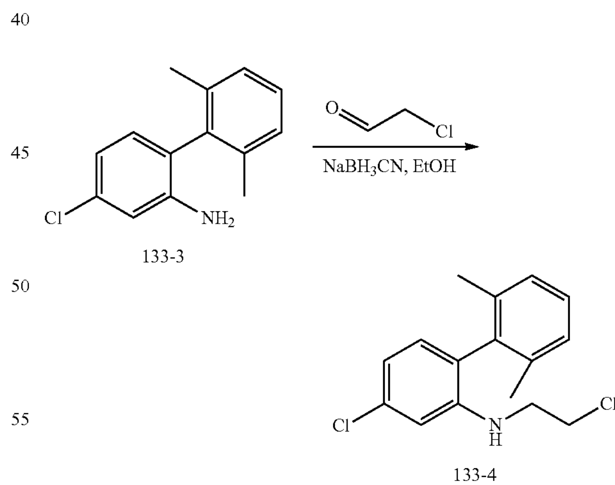

133-3

133-4

To a mixture of 133-3 (200 mg, 2 mmol) in EtOH (30 mL) was added 2-chloroacetaldehyde (1 mL, 40% in water) and HOAc (1 mL) at room temperature, then $NaBH_3CN$ (0.3 g) was added, the mixture was stirred at rt for 6 h. The solution was filtrated, the filtrate was concentrated and purified by column chromatography on silica gel (hexanes/EtOAc=1/1) to give 133-4 (160 mg, about 63% yield) as a colorless oil. MS Calcd.: 293.1; MS Found: 293.2 $[M+H]^+$ The Synthesis of N-(2-(1H-1,2,4-triazol-1-yl)ethyl)-4-chloro-2',6'-dimethyl-[1,1'-biphenyl]-2-amine (133-5)

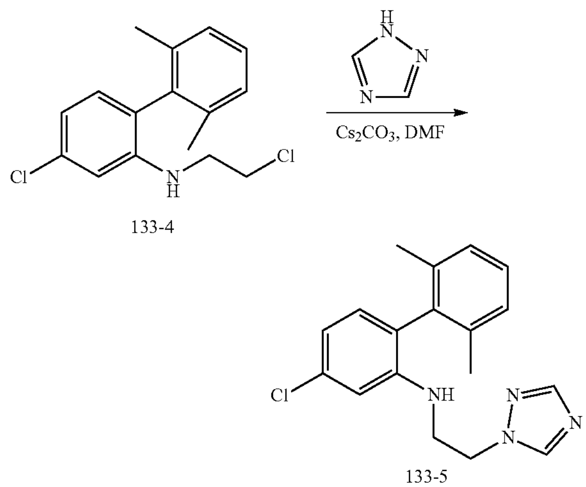

133-4

133-5

To a mixture of 133-4 (160 mg, 0.5 mmol) in DMF (10 mL) was added 1H-1,2,4-triazole (69 mg, 1 mmol) and $Cs_2CO_3$ (326 mg, 1 mmol) at room temperature. The mixture was stirred at 80° C. for 8 h, diluted with DCM (30 mL), washed by $H_2O$ (40 mL) and brine (40 mL). The organic layer was dried with $MgSO_4$, filtered and concentrated under reduced pressure. The crude product was purified by column chromatography on silica gel (hexanes/EtOAc=1/3) to give 133-5 (120 mg, about 67% yield) as a solid. MS Calcd.: 326.1; MS Found: 327.2 $[M+H]^+$ The Synthesis of N2-(2-(1H-1,2,4-triazol-1-yl)ethyl)-2',6'-dimethyl-N4-phenyl-[1,1'-biphenyl]-2,4-diamine (SS20308-0133)

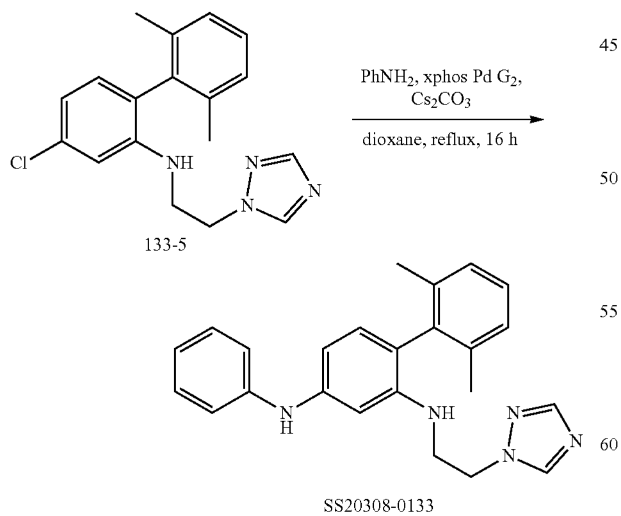

133-5

SS20308-0133

To a mixture of 133-5 (120 mg, 0.37 mmol) in dioxane (15 mL) was added aniline (74.4 mg, 0.8 mmol), $Cs_2CO_3$ (326 g, 1 mmol) and Xphos Pd $G_2$ (20 mg) at room temperature. The mixture was heated to reflux for 12 h under nitrogen. The reaction mixture was cooled to room temperature, filtered and washed with EtOAc (40 mL). The filtrate was washed with water (40 mL) and brine (40 mL). The organic layer was dried with $MgSO_4$, filtered and concentrated under reduced pressure. The crude product was purified by column chromatography on silica gel (DCM/MeOH=10/1) to give SS20308-0133 (37 mg, about 26% yield) as a solid. MS Calcd.: 383.2; MS Found: 384.2 $[M+H]^+$ $^1H$ NMR (400 MHz, DMSO-$d_6$) δ 1.89 (s, 6H), 3.39-3.47 (m, 2H), 3.97 (s, 1H), 4.30 (t, J=6.02 Hz, 2H), 6.39-6.52 (m, 2H), 6.62 (d, J=7.78 Hz, 1H), 6.76-6.85 (m, 1H), 7.04-7.18 (m, 5H), 7.23 (t, J=7.14 Hz, 2H), 7.86 (s, 1H), 8.02 (s, 1H), 8.36 (s, 1H).

Example 52

SS20308-0134

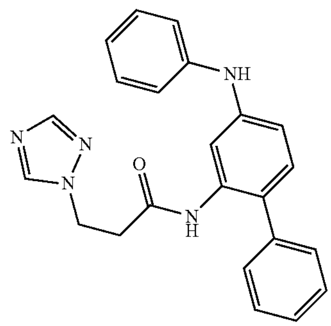

Example Route for Example 52

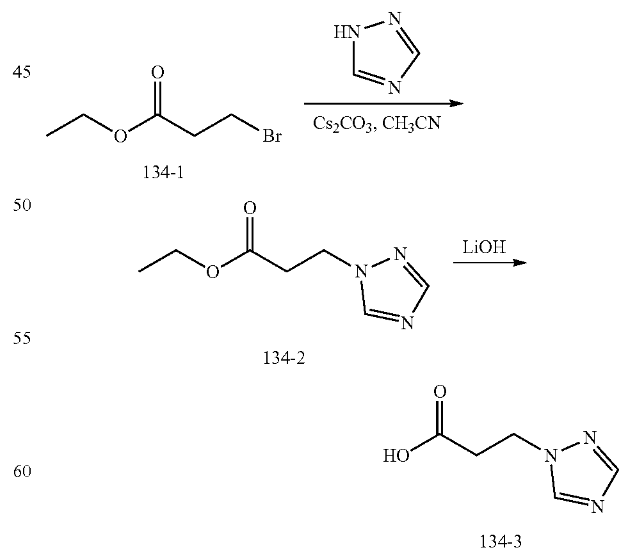

134-1

134-2

134-3

-continued

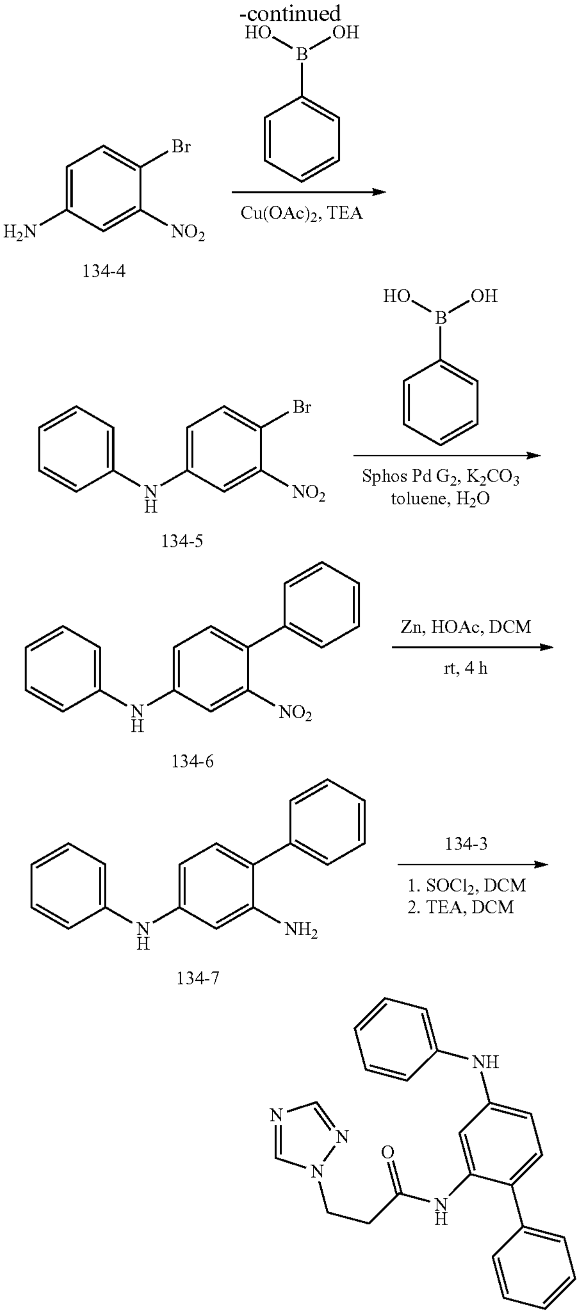

Cu(OAc)$_2$, TEA 134-4

Sphos Pd $G_2$, $K_2CO_3$ toluene, $H_2O$ 134-5

Zn, HOAc, DCM rt, 4 h 134-6

134-3

1. $SOCl_2$, DCM
2. TEA, DCM 134-7

SS20308-0134

The Synthesis of ethyl 3-(1H-1,2,4-triazol-1-yl)propanoate (134-2)

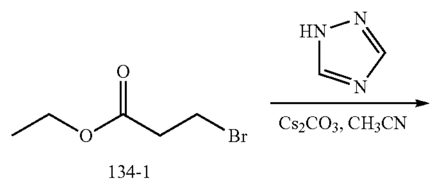

134-1

-continued

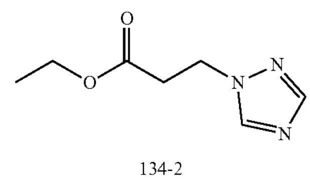

134-2

To a mixture of 134-1 (500 mg, 2.8 mmol) in $CH_3CN$ (50 mL) was added 1H-1,2,4-triazole (241 mg, 3.5 mmol) and $Cs_2CO_3$ (1.6 g, 5 mmol) at room temperature. The mixture was stirred at 80° C. for 8 h. The solution was filtered and the solid was washed with DCM (50 mL). The organic layer was dried with $MgSO_4$ and concentrated under reduced pressure. The crude product was purified by column chromatography on silica gel (hexanes/EtOAc=1/5) to give 134-2 (300 mg, about 64% yield) as a colorless oil. MS Calcd.: 169.1; MS Found: 170.2 $[M+H]^+$ The Synthesis of 3-(1H-1,2,4-triazol-1-yl)propanoic acid (34-3)

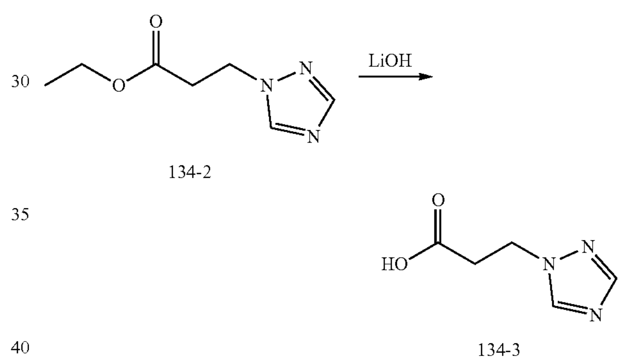

134-2

134-3

To a mixture of 134-2 (300 mg, 1.8 mmol) in MeOH (30 mL) was added LiOH (228 mg, 6 mmol). The mixture was stirred at rt for 6 h. The solution was added HCl (2 M) to pH=3-4, the mixture was concentrated under reduced pressure to give crude 134-2 (400 mg, about 80% yield) as a colorless oil, which was used in the next step without further purification. MS Calcd.: 141.1; MS Found: 142.2 $[M+H]^+$ The Synthesis of 4-bromo-3-nitro-N-phenylaniline (134-5)

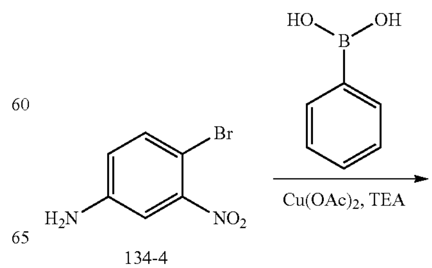

134-4

-continued

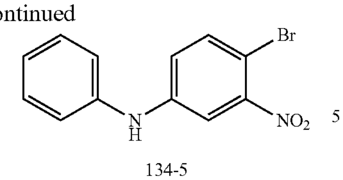

134-5

To a mixture of 134-4 (432 mg, 2 mmol) in DCM (50 mL) was added phenylboronic acid (268 mg, 2.2 mmol), $Cu(OAc)_2$ (362 g, 2 mmol) and TEA (300 mg, 3 mmol) at room temperature. The mixture was stirred at rt for 12 h under nitrogen. The reaction mixture was concentrated under reduced pressure and the crude product was purified by column chromatography on silica gel (hexanes/EtOAc=15/1 to 3/1) to give 134-5 (256 mg, about 44% yield) as an oil. MS Calcd.: 292.0; MS Found: 293.2 $[M+H]^+$ The Synthesis of 2-nitro-N-phenyl-[1,1'-biphenyl]-4-amine (134-6)

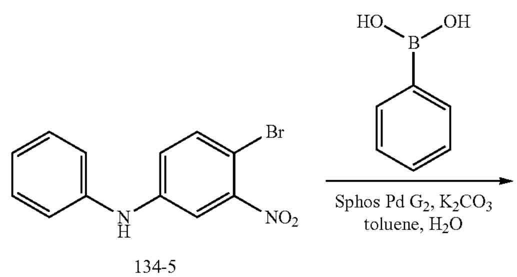

134-5

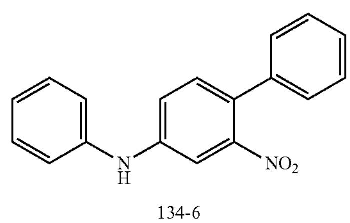

134-6

To a mixture of 134-5 (292 mg, 1 mmol) and phenylboronic acid (146 mg, 1.2 mmol) in toluene/$H_2O$ (25 mL/5 mL) was added $K_2CO_3$ (276 mg, 2 mmol) and Sphos Pd $G_2$ (40 mg). The mixture was heated to reflux for 6 h. The mixture was diluted with EtOAc (30 mL), the organic layer was washed with water (30 mL) and brine (30 mL). The organic layer was dried with $MgSO_4$, filtered and concentrated under reduced pressure. The crude product was purified by column chromatography on silica gel (hexanes/EtOAc=2/1) to give 134-6 (220 mg, about 76% yield) as a solid. MS Calcd.: 290.1; MS Found: 291.2 $[M+H]^+$ The Synthesis of N4-phenyl-[1,1'-biphenyl]-2,4-diamine (134-7)

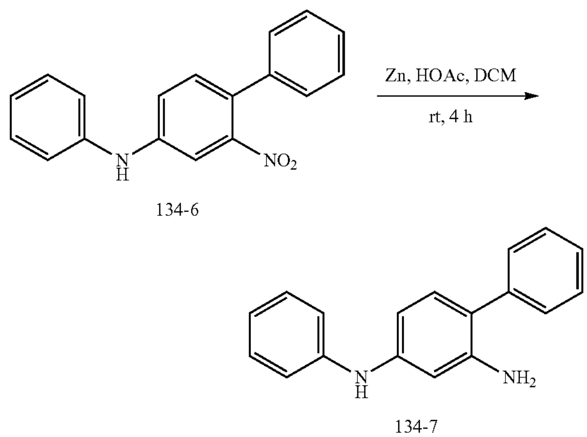

134-6

134-7

To a mixture of 134-6 (220 mg, 0.76 mmol) in DCM (50 mL) was added HOAc (5 mL) and Zn powder (150 mg) at room temperature. The mixture was stirred at rt for 4 h. The reaction mixture was filtered and the organic layer was concentrated under reduced pressure. The crude product was purified by column chromatography on silica gel (hexanes/EtOAc=1/2) to give 134-7 (140 mg, about 71% yield) as an oil. MS Calcd.: 260.1; MS Found: 261.2 $[M+H]^+$ The Synthesis of N-(4-(phenylamino)-[1,1'-biphenyl]-2-yl)-3-(1H-1,2,4-triazol-1-yl)propanamide (SS20308-0134)

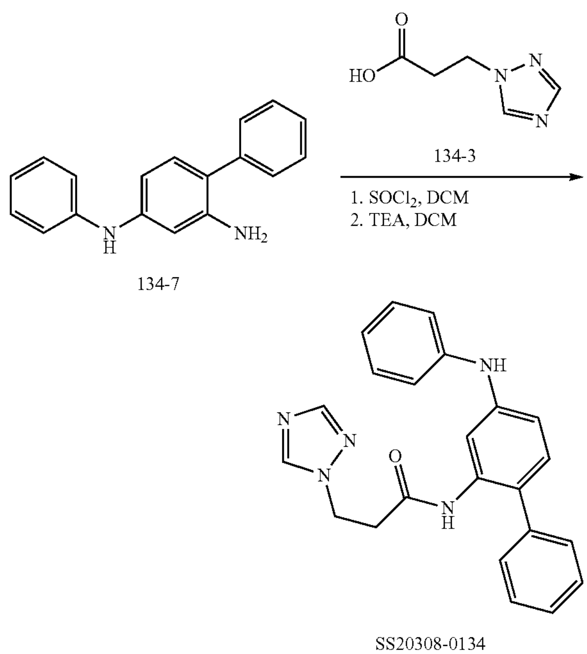

134-3

134-7

SS20308-0134

To a solution of 134-3 (140 mg, 1 mmol) in DCM (50 mL) was added $SOCl_2$ (3 mL). The mixture was stirred at 50° C. for 2 h. The mixture was concentrated and added DCM (50 mL), 134-7 (130 mg, 0.5 mmol) and TEA (151 mg, 1.5 mmol) was added. The solution was stirred at rt for 3 h, the mixture was washed by $H_2O$ (40 mL) and brine (40 mL). The organic layer was dried with $MgSO_4$, filtered and concentrated under reduced pressure. The crude product was purified by column chromatography on silica gel (hexanes/EtOAc=5/1 to 1/5) to give SS20308-0134 (40 mg, about 21% yield) as a solid. MS Calcd.: 383.5; MS Found: 384.2 $[M+H]^+$ $^1$H NMR (400 MHz, DMSO-$d_6$) δ 2.77 (t, J=6.65 Hz, 2H), 4.41 (t, J=6.53 Hz, 2H), 6.87 (t, J=6.94 Hz, 1H), 6.97 (dd, J=8.41, 2.13 Hz, 1H), 7.12 (d, J=7.53 Hz, 2H), 7.16-7.23 (m, 2H), 7.24-7.32 (m, 5H), 7.35-7.40 (m, 2H), 7.98 (s, 1H), 8.33 (s, 1H), 8.41 (s, 1H), 9.30 (s, 1H).

Example 53

SS20308-0141-01

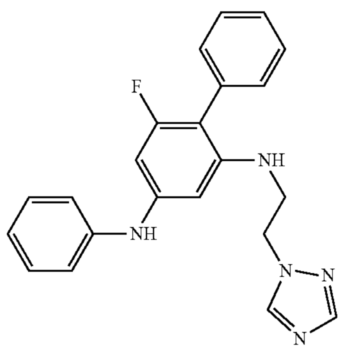

Chemical Formula: $C_{22}H_{20}FN_5$
Molecular Weight: 373.43

Example Route for Example 53

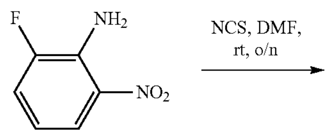

141-1

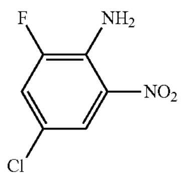

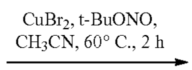

141-2

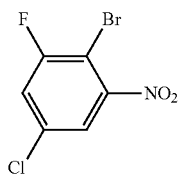

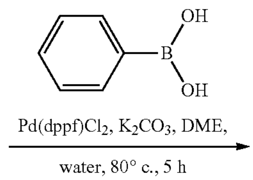

141-3

-continued

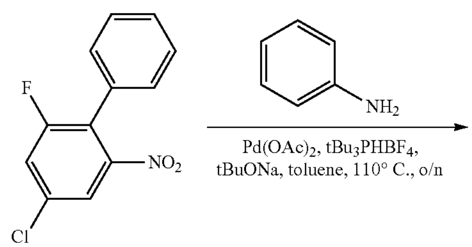

141-4

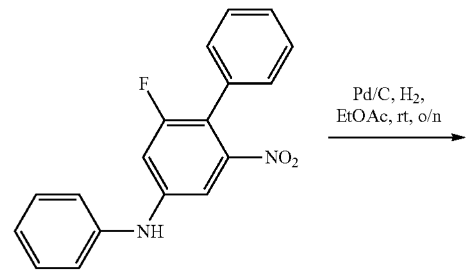

141-5

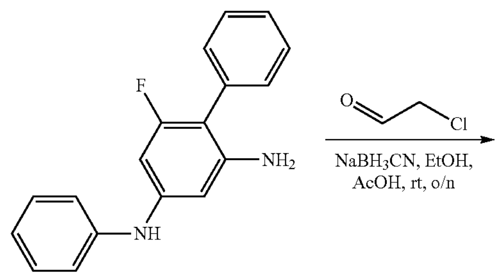

141-6

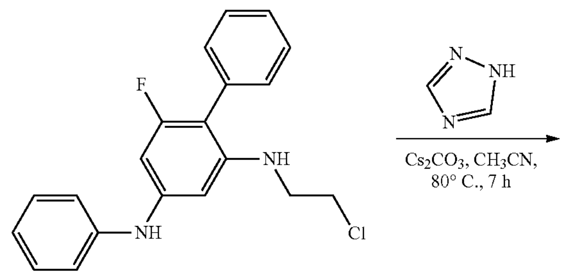

141-7

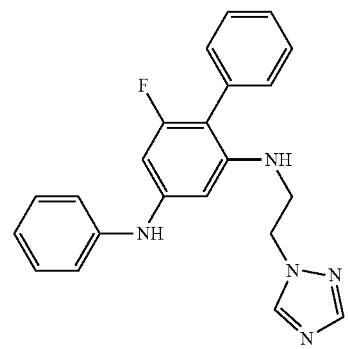

SS20308-0141-01

The Synthesis of 4-chloro-2-fluoro-6-nitroaniline (141-2)

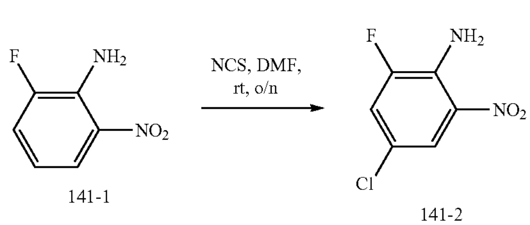 [SMILES: Nc1c(F)cccc1[N+](=O)[O-] ; Nc1c(F)cc(Cl)cc1[N+](=O)[O-]]

141-1

141-2

To a solution of 141-1 (5.0 g, 32.1 mmol) in DMF (40 mL) was added NCS (4.5 g, 33.7 mmol) at room temperature. The mixture was stirred at room temperature overnight. The mixture was diluted with water (100 mL). The solid was obtained by filtration, washed by water and dried in vacuum to give 141-2 (4.5 g, about 74% yield) as a solid.

The Synthesis of 2-bromo-5-chloro-1-fluoro-3-nitrobenzene (141-3)

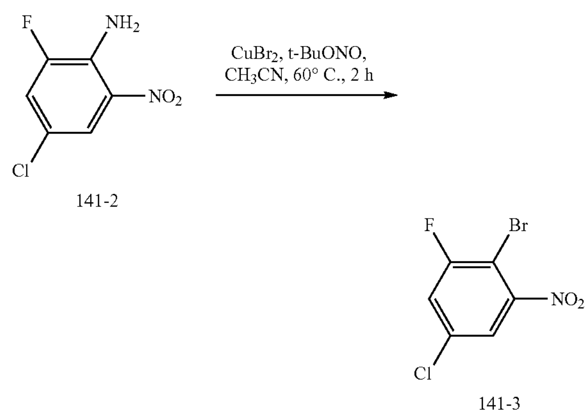

141-2

141-3

To the solution of 141-2 (900 mg, 4.7 mmol) in $CH_3CN$ (10 mL) was added $CuBr_2$ (2.1 g, 9.4 mmol) at room temperature. Then t-BuONO (2.4 g, 23.5 mmol) was added dropwise at 60° C.; the mixture was stirred at 60° C. for 2 h under nitrogen. Filtered and washed with EtOAc; the filtrate was concentrated to a crude oil, which was purified by column chromatography on silica gel (petroleum ether/EtOAc=1/20) to give 141-3 (620 mg, about 52% yield) as an oil.

The Synthesis of 4-chloro-2-fluoro-6-nitrobiphenyl (141-4)

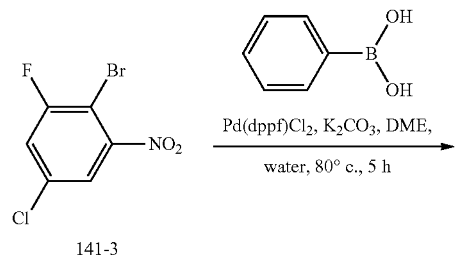

141-3

-continued

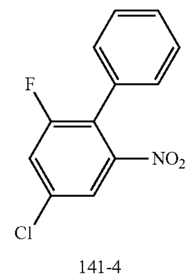

141-4

To a mixture of 141-3 (620 mg, 2.44 mmol) and phenylboronic acid (328 mg, 2.69 mmol) in DME (10 mL) and water (2 mL) was added $PdCl_2$(dppf) (58 mg, 0.1 mmol), $K_2CO_3$ (673 mg, 4.88 mmol) at room temperature, then the mixture was heated to 80° C. for 5 h under nitrogen. The reaction mixture was cooled to room temperature. The mixture was filtered, and washed with EtOAc. The filtrate was concentrated to oil, which was purified by column chromatography on silica gel (petroleum ether/EtOAc=1/10) to give 141-4 (750 mg, about 60% yield) as an oil.

The Synthesis of 2-fluoro-6-nitro-N-phenylbiphenyl-4-amine (141-5)

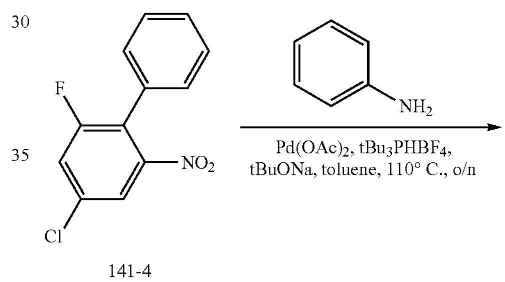

141-4

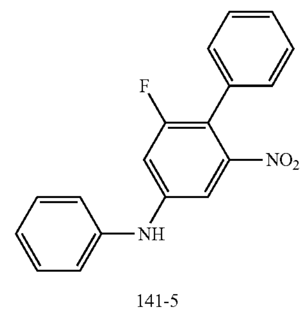

141-5

The mixture of 141-4 (590 mg, 2.35 mmol), aniline (230 mg, 2.47 mmol), Pd(OAc)2 (45 mg, 0.2 mmol), $tBu_3PHBF_4$ (58 mg, 0.2 mmol), tBuONa (564 mg, 5.88 mmol) in toluene (15 mL) was heated to 110° C. overnight under hydrogen. The mixture was cooled to room temperature, the mixture was filtrated, and washed with EtOAc. The filtrate was concentrated to oil, which was purified by column chromatography on silica gel (petroleum ether/EtOAc=1/8) to give 141-5 (180 mg, about 25% yield) as an oil. MS Calcd.: 308.1; MS Found: 309.3 $[M+H]^+$.

The Synthesis of 6-fluoro-N4-phenylbiphenyl-2,4-diamine (141-6)

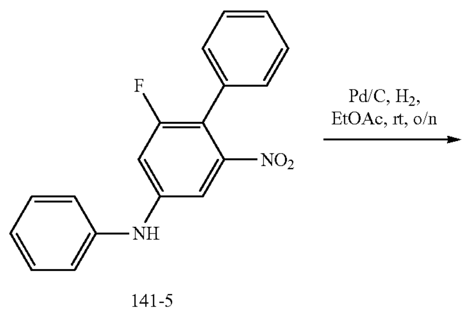

141-5

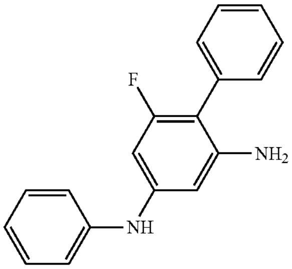

141-6

To the solution of 141-5 (240 mg, 0.79 mmol) in EtOAc (10 mL) was added Pd/C (10%, 30 mg) at room temperature, the mixture was stirred at room temperature overnight under hydrogen gas (1 atm). The mixture was filtered and washed with EtOAc. The filtrate was concentrated to oil to give 141-6 (170 mg, about 78% yield) as an oil. MS Calcd.: 278.1; MS Found: 279.1 $[M+H]^+$.

The Synthesis of 6-fluoro-N4-phenylbiphenyl-2,4-diamine (141-7)

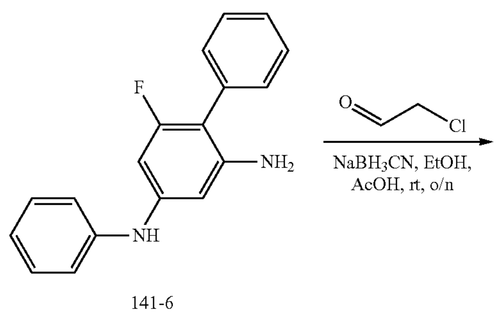

141-6

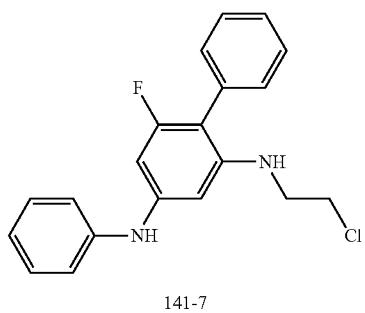

141-7

To the solution of 141-6 (170 mg, 0.61 mmol) and 2-chloroacetaldehyde (143 mg, 1.83 mmol, 40% in water) in EtOH (5 mL) and HOAc (0.2 mL) was added $NaBH_3CN$ (77 mg, 1.22 mmol) at room temperature, the mixture was stirred at room temperature overnight. The mixture was diluted with water, extracted with DCM, then DCM phase was dried with $Na_2SO_4$. Filtered and concentrated the filtrate to an oil, which was purified by Prep-TLC to give 141-7 (58 mg, about 28% yield) as an oil. MS Calcd.: 340.1; MS Found: 341.0 $[M+H]^+$.

The Synthesis of N2-(2-(1H-1,2,4-triazol-1-yl) ethyl)-6-fluoro-N4-phenylbiphenyl-2,4-diamine (SS20308-0141-01)

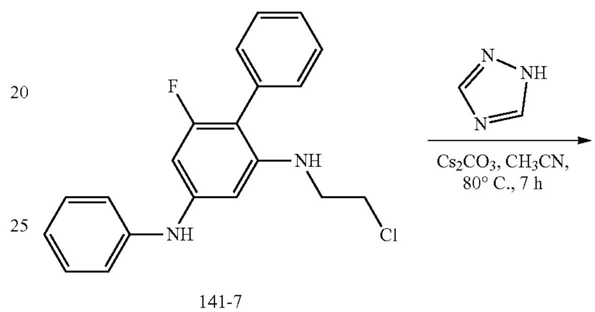

141-7

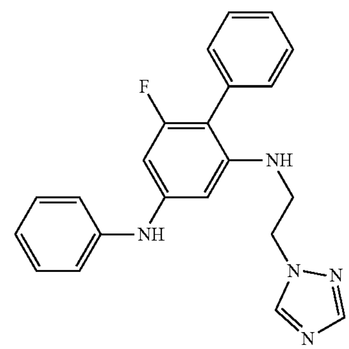

SS20308-0141-01

To the solution of 141-7 (48 mg, 0.14 mmol), 1H-1,2,4-triazole (10 mg, 0.14 mmol) in $CH_3CN$ (8 mL) was added $Cs_2CO_3$ (91 mg, 0.28 mmol) at room temperature, then the mixture was heated to 80° C. for 7 h. was diluted with water, extracted with EtOAc, then EtOAc phase was dried with $Na_2SO_4$. Filtered and concentrated the filtrate to an oil, which was purified by Prep-HPLC to give SS20308-0141-01 (12 mg, about 23% yield) as a solid. MS Calcd.: 373.2; MS Found: 374.3 $[M+H]^+$.

1H NMR (400 MHz, DMSO-$d_6$) δ 8.43 (s, 1H), 8.30 (s, 1H), 7.93 (s, 1H), 7.45-7.39 (m, 2H), 7.37-7.32 (m, 1H), 7.30-7.24 (m, 2H), 7.17-7.11 (m, 4H), 6.88 (t, J=7.4 Hz, 1H), 6.23-6.18 (m, 2H), 4.64 (t, J=6.0, 1H), 4.33 (t, J=6.0, 2H), 3.44-3.38 (m, 2H).

Example 54

SS20308-0142-01

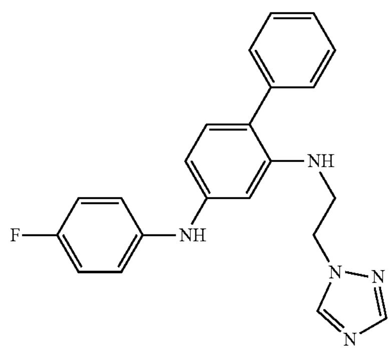

Chemical Formula: $C_{22}H_{20}FN_5$
Molecular Weight: 373.43

Example Route for Example 54

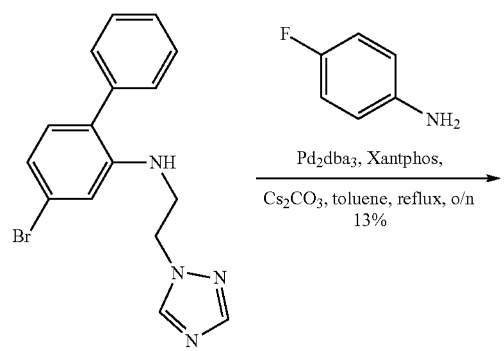

95-5

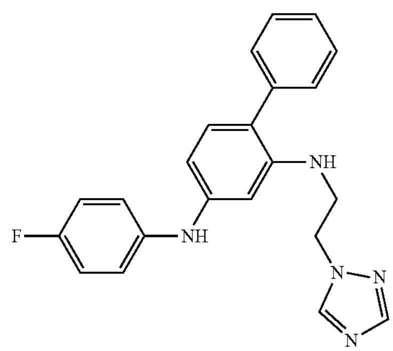

SS20308-0142-01

The Synthesis of $N^2$-(2-(1H-1,2,4-triazol-1-yl) ethyl)-$N^4$-(4-fluorophenyl)biphenyl-2,4-diamine (SS20308-0142-01)

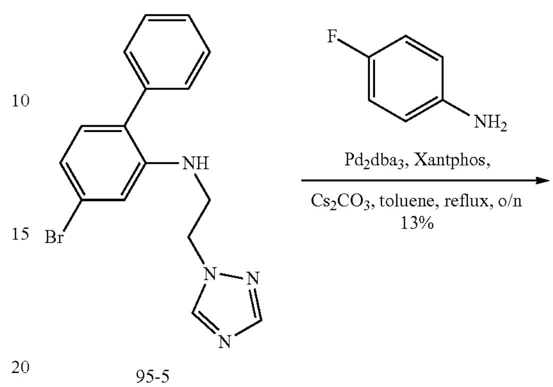

95-5

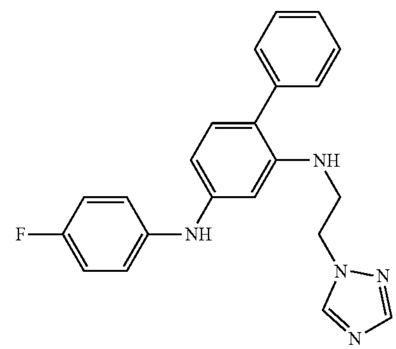

SS20308-0142-01

The mixture of 95-5 (100 mg, 0.29 mmol), 4-fluoroaniline (39 mg, 0.35 mmol), $Pd_2(dba)_3$ (26 mg, 0.029 mmol), Xantphos (34 mg, 0.058 mmol) and $Cs_2CO_3$ (189 mg, 0.58 mmol) in toluene (10 mL) was stirred at 110° C. overnight under $N_2$ atmosphere. The reaction mixture was then cooled to room temperature and filtered through celite, the filtrate was concentrated to crude oil, which was purified by Prep-HPLC to give SS20308-0142-01 (14.3 mg, about 13% yield) as a solid. MS Calcd.: 373.2; MS Found: 374.2 $[M+H]^+$.

$^1H$ NMR (400 MHz, DMSO-$d_6$) δ 8.45 (s, 1H), 8.04 (s, 1H), 7.95 (s, 1H), 7.39 (dd, J=7.6, 7.2 Hz, 2H), 7.31-7.26 (m, 1H), 7.25-7.20 (m, 2H), 7.14-7.05 (m, 4H), 6.85 (d, J=8.0 Hz, 1H), 6.40 (dd, J=8.4, 2.0 Hz, 1H), 6.35 (d, J=2.0 Hz, 1H), 4.74 (t, J=5.8 Hz, 1H), 4.37 (t, J=6.0 Hz, 2H), 3.46-3.39 (m, 2H).

Example 55
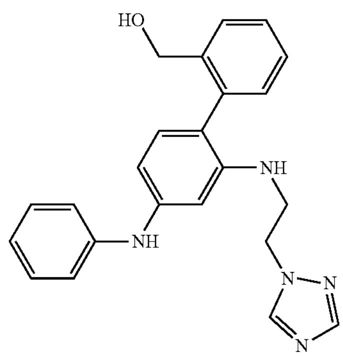
SS20308-0143-01
Example Route for Example 55
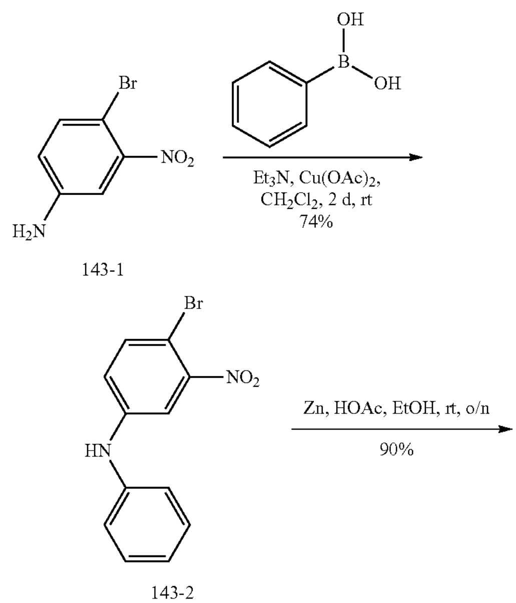
143-1
143-2
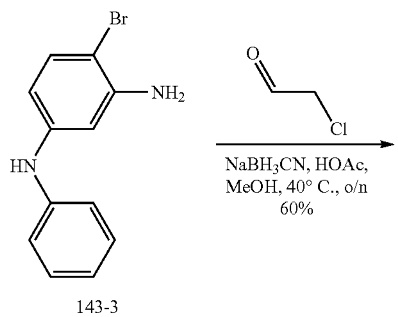
143-3
-continued
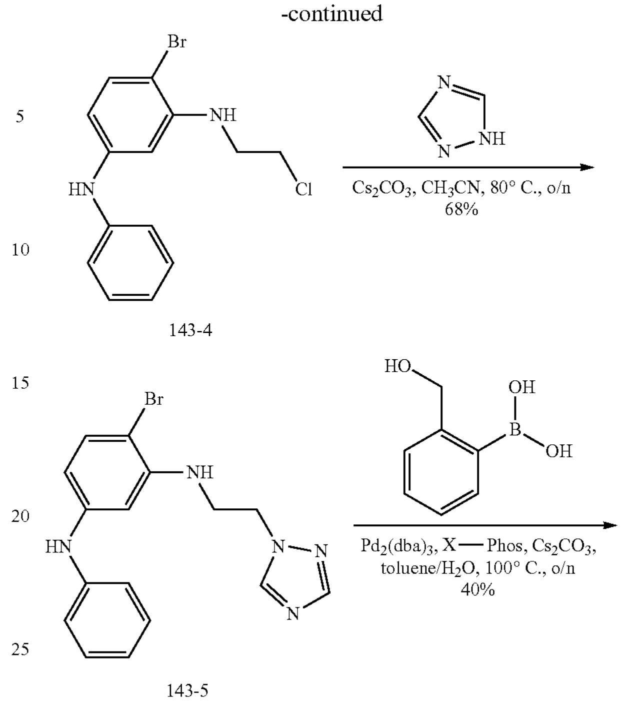
143-4
143-5
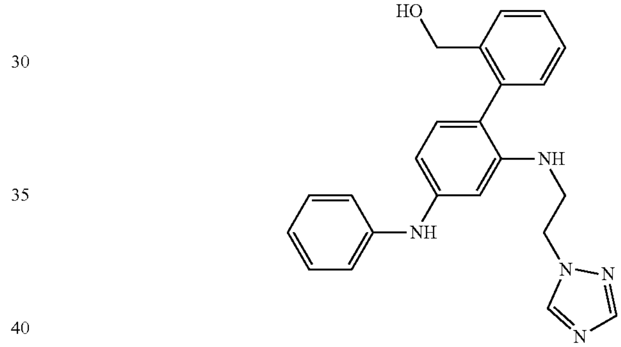
SS20308-0143-01
The Synthesis of 4-bromo-3-nitro-N-phenylaniline (143-2)
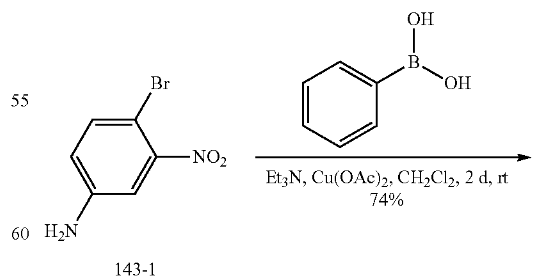
143-1

-continued

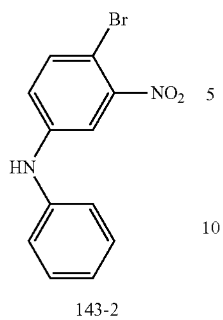

143-2

A mixture of 143-1 (1.0 g, 4.6 mmol), phenylboronic acid (1.1 g, 9.2 mmol) and $Cu(OAc)_2$ (833 mg, 4.6 mmol), $Et_3N$ (2.3 g, 23 mmol) in $CH_2Cl_2$ (100 mL) was stirred at rt for 2 d. After the reaction was complete, the insoluble material was removed by filtration. The filtrate was poured into water (100 mL) and extracted with EtOAc (100 mL×3). The combined layers were dried over $Na_2SO_4$, and concentrated under vacuum. The residue was purified by column chromatography to give 143-2 (1.0 g, about 74% yield) as a solid.

The Synthesis of 4-bromo-$N^1$-phenylbenzene-1,3-diamine (143-3)

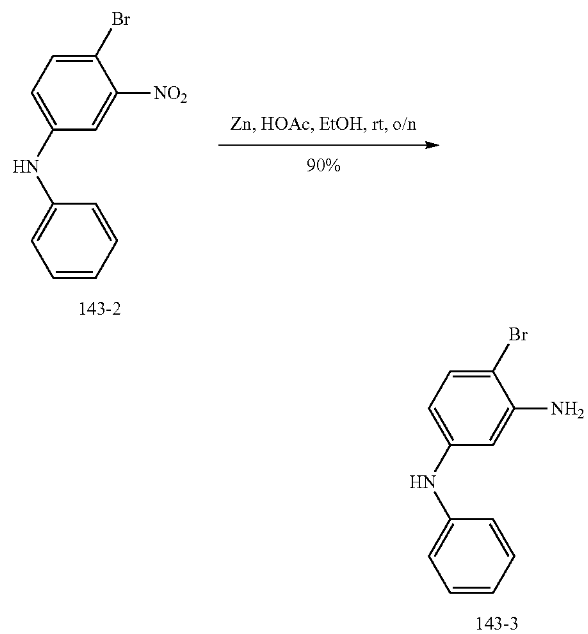

143-2

143-3

A mixture of 143-2 (1.0 g, 3.4 mmol), Zn (1.1 g, 17 mmol) and HOAc (1.0 g, 17 mmol) in EtOH (50 mL) was stirred at rt overnight. After the reaction was complete, the insoluble material was removed by filtration. The filtrate was poured into water (100 mL) and extracted with EtOAc (100 mL×3). The combined layers were dried over $Na_2SO_4$, and concentrated in vacuum. The residue was purified by column chromatography (petroleum ether/EtOAc=5/1) to give 143-3 (800 mg, about 90% yield) as a solid. MS Found: 263.2 $[M+H]^+$.

The Synthesis of 4-bromo-$N^3$-(2-chloroethyl)-$N^1$-phenylbenzene-1,3-diamine (143-4)

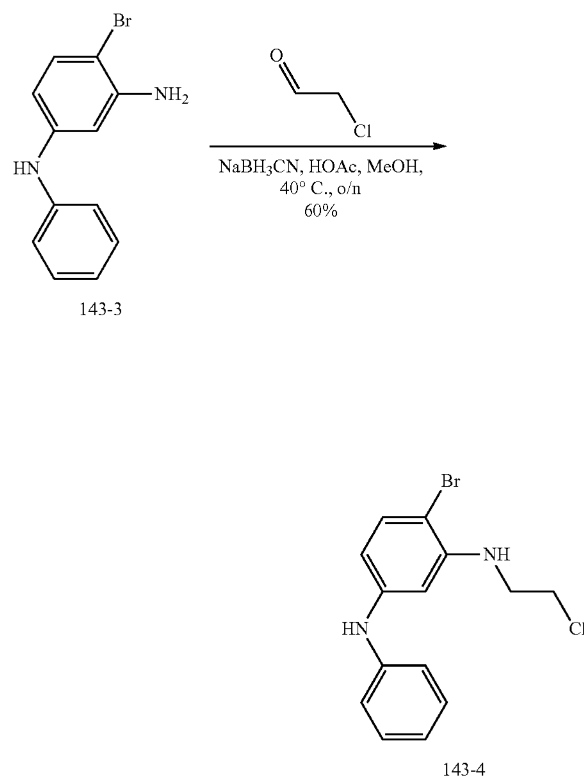

143-3

143-4

A mixture of the 143-3 (800 mg, 3.1 mmol), 2-chloroacetaldehyde (242 mg, 3.1 mmol, 40% in water) and $NaBH_3CN$, (1.3 g, 6.2 mmol) and HOAc (2 drops) in MeOH (50 mL) was stirred at 40° C. overnight. After the reaction was complete, the reaction mixture was quenched with water (100 mL), extracted with EtOAc (50 mL×3). The combined layers were dried over $Na_2SO_4$ and concentrated in vacuum. The residue was purified by reverse phase column chromatography (EtOAc) to give 143-4 (600 mg, about 60% yield) as a solid. MS Calcd.: 324.0; MS Found: 325.0 $[M+H]^+$.

The Synthesis of $N^3$-(2-(1H-1,2,4-triazol-1-yl)ethyl)-4-bromo-$N^1$-phenylbenzene-1,3-diamine (143-01-4)

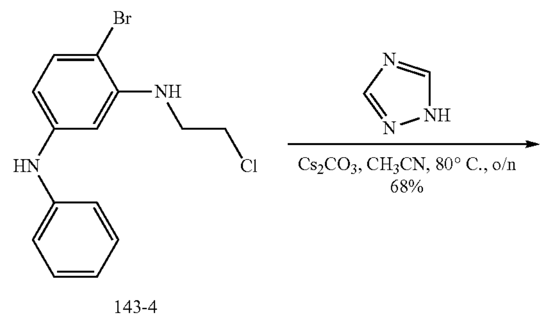

143-4

-continued

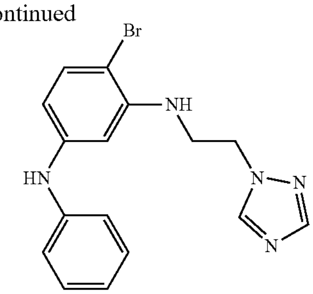

143-5

A mixture of the 143-4 (600 mg, 1.85 mmol), 1H-1,2,4-triazole (192 mg, 2.78 mmol) and $Cs_2CO_3$ (1.2 g, 3.7 mmol) in acetone (20 mL) was stirred at 80° C. overnight. After the reaction was complete, the reaction mixture was quenched with water (50 mL), extracted with EtOAc (30 mL×3). The combined layers were dried over $Na_2SO_4$ and concentrated in vacuum. The residue was purified by reverse phase (silica) column chromatography (DCM/EtOH=20/1) to give 143-5 (450 mg, about 68% yield) as a solid. MS Calcd.: 357.1; MS Found: 358.3 $[M+H]^+$.

The Synthesis of (2'-(2-(1H-1,2,4-triazol-1-yl)ethylamino)-4'-(phenylamino)biphenyl-2-yl)methanol (SS20308-143-01)

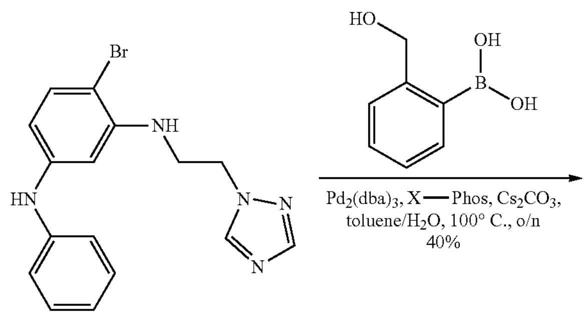

143-5

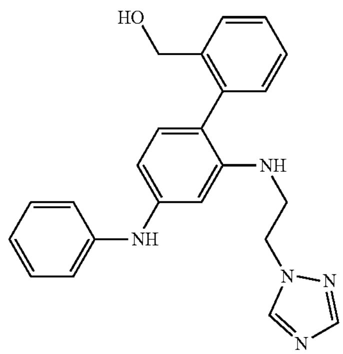

SS20308-0143-01

A mixture of 143-5 (100 mg, 0.28 mmol), 2-hydroxymethylphenylboronic acid (51 mg, 0.34 mmol), $Pd_2(dba)_3$ (13 mg, 0.014 mmol) and X-Phos (613 mg, 0.028 mmol), $Cs_2CO_3$ (183 mg, 0.56 mmol) in toluene/water (3/0.3 mL) was stirred at reflux overnight. The reaction mixture was cooled to room temperature and poured into water (50 mL) and extracted with EtOAc (50 mL×3). The organic layer was washed with brine and concentrated. The residue crude product was purified by Prep-HPLC to give SS20308-143-01 (43.6 mg, about 40% yield) as a solid. MS Calcd.: 385.5; MS Found: 386.2 $[M+H]^+$.

$^1H$ NMR (400 MHz, DMSO-$d_6$) δ 8.38 (s, 1H), 8.06 (s, 1H), 7.89 (s, 1H), 7.56 (d, J=7.2 Hz, 1H), 7.36-7.33 (m, 1H), 7.28-7.21 (m, 3H), 7.12-7.10 (m, 2H), 6.99-6.97 (m, 1H), 6.80 (t, J=7.2 Hz, 1H), 6.72 (d, J=8.0 Hz, 1H), 6.46-6.42 (m, 1H), 6.41 (s, 1H), 4.93 (t, J=5.6 Hz, 1H), 4.31-4.26 (m, 2H), 4.22-4.20 (m, 2H), 4.17 (t, J=6.0 Hz, 1H), 3.42-3.38 (m, 2H).

Example 56

SS20308-0144-01

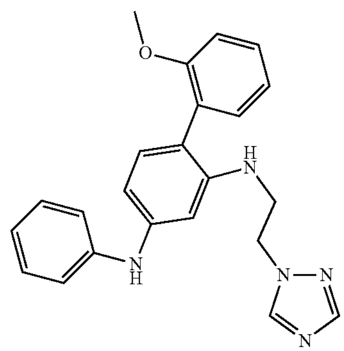

The Synthesis of $N^2$-(2-(1H-1,2,4-triazol-1-yl)ethyl)-2'-methoxy-$N^4$-phenylbiphenyl-2,4-diamine (SS20308-144-01)

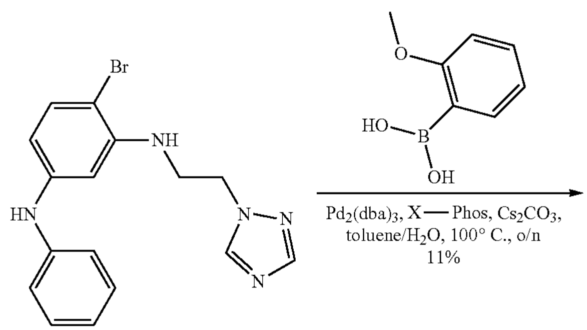

143-5

-continued

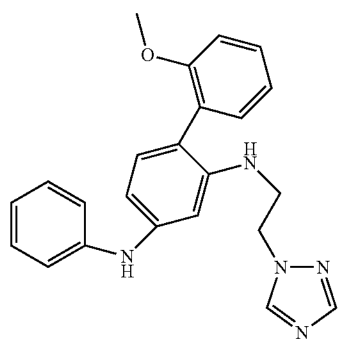

SS20308-0144-01

A mixture of 143-5 (50 mg, 0.14 mmol), 2-methoxyphenylboronic acid (32 mg, 0.21 mmol), $Pd(PPh_3)_4$ (6 mg, 0.007 mmol), X-Phos (7 mg, 0.014 mmol) and $Cs_2CO_3$ (91 mg, 0.28 mmol) in toluene/water (2/0.2 mL) was stirred at reflux overnight. The reaction mixture was cooled to room temperature and poured into water (10 mL) and extracted with EtOAc (10 mL×3). The organic layer was washed with brine and evaporated, the residue crude product was purified by column chromatography (petroleum ether/EtOAc=30/1-5/1) to give SS20308-0144-01 (6.22 mg, about 11% yield) as a solid. MS Calcd.: 385.2; MS Found: 386.2 $[M+H]^+$.

$^1H$ NMR (400 MHz, DMSO-$d_6$) δ 8.41 (s, 1H), 8.04 (s, 1H), 7.92 (s, 1H), 7.32-7.30 (m, 1H), 7.22 (t, J=8.4 Hz, 2H), 7.10 (d, J=7.6 Hz, 2H), 7.05-7.02 (m, 2H), 6.99-6.97 (m, 1H), 6.81-6.75 (m, 2H), 6.45-6.38 (m, 2H), 4.33-4.25 (m, 3H), 3.64 (s, 3H), 3.44-3.41 (m, 2H).

Example 57

SS20308-0147-01

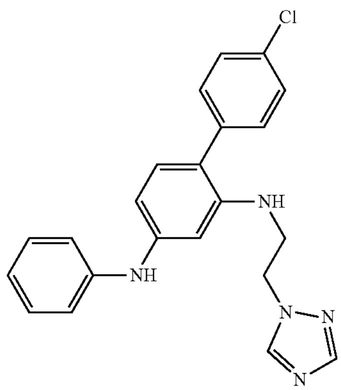

Chemical Formula: $C_{22}H_{20}ClN_5$
Molecular Weight: 389.88

Example Route for Example 57

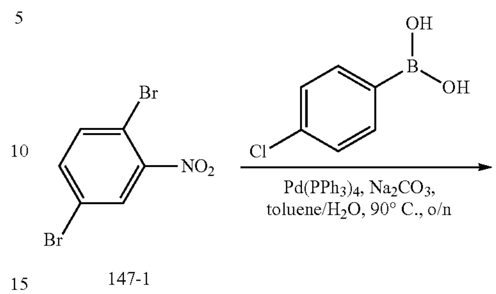

147-1

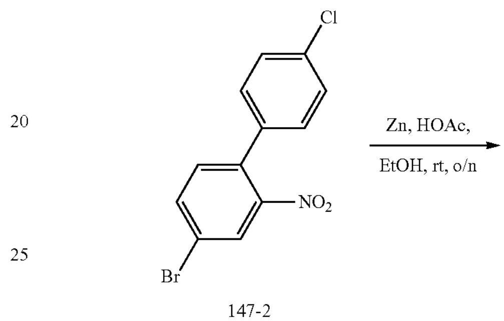

147-2

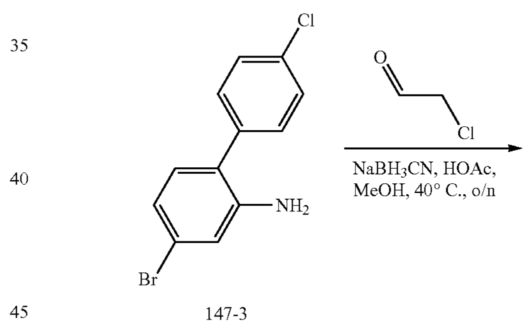

147-3

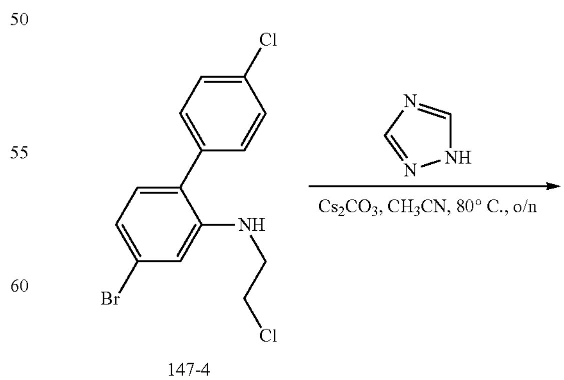

147-4

-continued

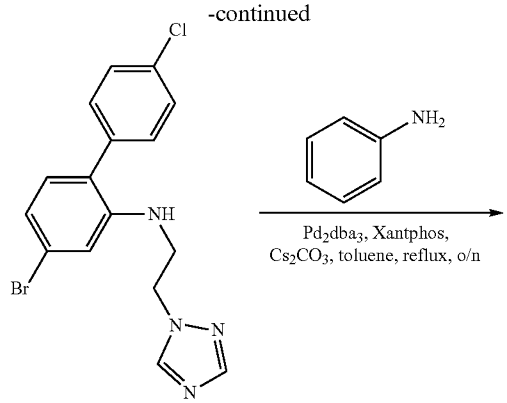

147-5

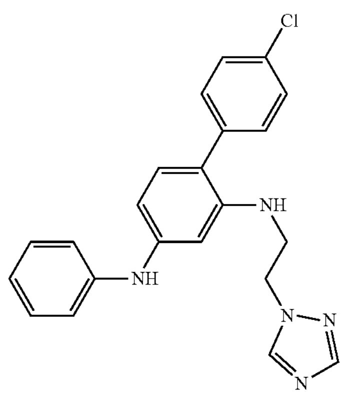

SS20308-0147-01

The Synthesis of 4-bromo-4'-chloro-2-nitrobiphenyl (147-2)

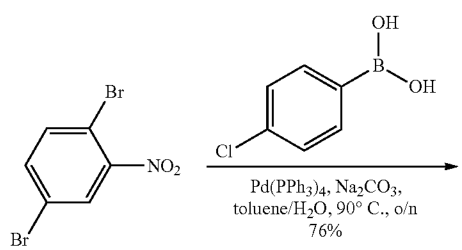

147-1

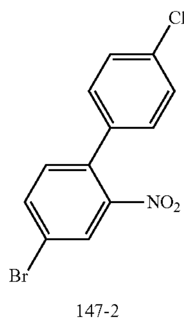

147-2

The mixture of 147-1 (2.00 g, 7.12 mmol), 4-chloro boronic acid (1.11 g, 7.12 mmol), $Pd(PPh_3)_4$ (0.42 g, 0.36 mmol) and $Na_2CO_3$ (1.51 g, 14.24 mmol) in toluene/$H_2O$ (30 mL, 5/1) was stirred at 90° C. overnight under $N_2$ atmosphere. After cooled to room temperature, the reaction mixture was poured into water and extracted with EtOAc (40 mL×3). The organic layers were washed with brine, dried over $Na_2SO_4$ and concentrated. The residue was purified via column chromatography (petroleum ether) to give 147-2 (1.70 g, about 76% yield) as a solid.

$^1$H NMR (400 MHz, $CDCl_3$) δ 7.96 (d, J=2.0 Hz, 1H), 7.70 (dd, J=8.4, 2.0 Hz, 1H), 7.34 (d, J=8.8 Hz, 2H), 7.23 (d, J=8.0 Hz, 1H), 7.15 (d, J=8.8 Hz, 2H).

The Synthesis of 4-bromo-4'-chlorobiphenyl-2-amine (147-3)

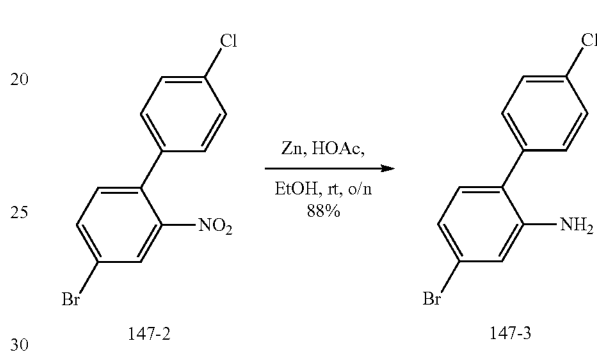

147-2 147-3

The mixture of 147-2 (1.50 g, 4.80 mmol), Zn powder (3.14 g, 48.00 mmol) and HOAc (3. mL) in EtOH (30 mL) was stirred at room temperature overnight. Then the reaction mixture was concentrated and poured into water. The mixture was basified with 40% NaOH till pH reached 10. The resulting mixture was filtered through celite and washed with EtOAc. The filtrate was extracted with EtOAc (40 mL×3). The organic layers were washed with brine, dried over $Na_2SO_4$ and concentrated. The residue was purified by column chromatography (petroleum ether/EtOAc=20/1) to give 147-3 (1.20 g, about 88% yield) as a solid. MS Calcd.: 280.96; MS Found: 282.0 $[M+H]^+$.

The Synthesis of 4-bromo-4'-chloro-N-(2-chloroethyl)biphenyl-2-amine (147-4)

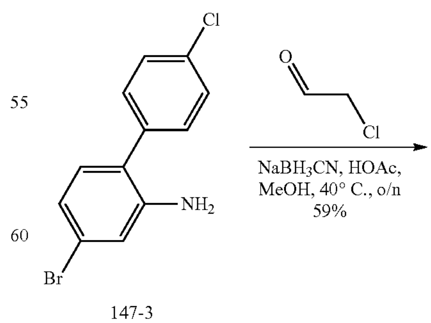

147-3

-continued

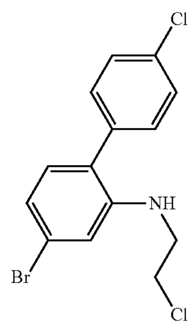

147-4

To a solution of 147-3 (1.00 g, 3.54 mmol) in MeOH (20 mL) was added 2-chloroacetaldehyde (1.11 g, 14.16 mmol, 40%), AcOH (844 mg, 14.16 mmol), and $NaBH_3CN$ (890 mg, 14.16 mmol), then the reaction mixture was stirred at 40° C. overnight. Then the reaction mixture was poured into water and basified with 1N NaOH till pH reached 10. The mixture was extracted with EtOAc (50 mL×3). The organic layers were washed with brine, dried over $Na_2SO_4$ and concentrated. The residue was purified by column chromatography (petroleum ether/EtOAc=20/1) to give 147-4 (710 mg, about 59% yield) as an oil. MS Calcd.: 343.0; MS Found: 344.0 $[M+H]^+$.

The Synthesis of N-(2-(1H-1,2,4-triazol-1-yl)ethyl)-4-bromo-4'-chlorobiphenyl-2-amine (147-5)

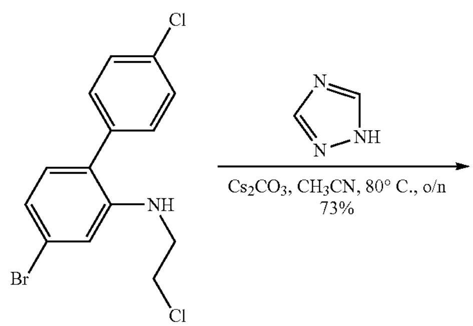

147-4

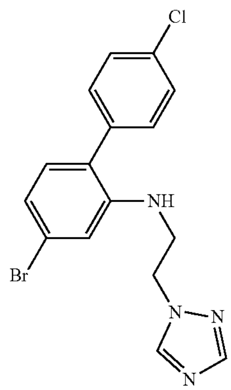

147-5

A mixture of 147-4 (670 mg, 1.94 mmol), 1H-1,2,4-triazole (201 mg, 2.91 mmol) and $Cs_2CO_3$ (1.26 g, 3.88 mmol) in $CH_3CN$ (10 mL) was stirred at 80° C. overnight. The reaction mixture was then cooled to room temperature and filtered through celite and concentrated. The residue was purified by column chromatography (petroleum ether/EtOAc=1/1) to give 147-5 (537 mg, about 73% yield) as an oil. MS Calcd.: 376.01; MS Found: 379.0 $[M+H]^+$.

The Synthesis of $N^2$-(2-(1H-1,2,4-triazol-1-yl)ethyl)-4'-chloro-$N^4$-phenylbiphenyl-2,4-diamine (SS20308-0147-01)

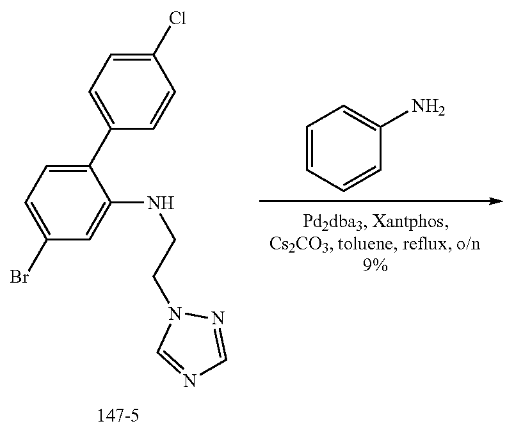

147-5

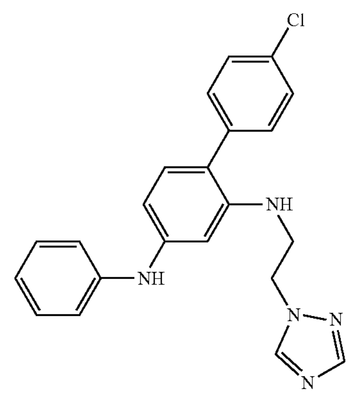

SS20308-0147-01

The mixture of 147-5 (150 mg, 0.40 mmol), aniline (45 mg, 0.48 mmol), $Pd_2dba_3$ (37 mg, 0.04 mmol), Xantphos (46 mg, 0.08 mmol) and $Cs_2CO_3$ (261 mg, 0.80 mmol) in toluene (30 mL) was stirred at 100° C. overnight under $N_2$ atmosphere. The reaction mixture was then cooled to room temperature and filtered through celite and concentrated. The residue was purified by Prep-HPLC to give SS20308-0147-01 (15 mg, about 9% yield) as an oil. MS Calcd.: 389.1; MS Found: 390.3 $[M+H]^+$.

$^1H$ NMR (400 MHz, $CDCl_3$) δ 8.46 (s, 1H), 8.12 (s, 1H), 7.97 (s, 1H), 7.42 (d, J=8.4 Hz, 2H), 7.28-7.21 (m, 4H), 7.13-7.08 (m, 2H), 6.86 (d, J=8.0 Hz, 1H), 6.84-6.79 (m, 1H), 6.46 (dd, J=8.4, 2.0 Hz, 1H), 6.40 (d, J=1.6 Hz, 1H), 4.84 (t, J=5.6 Hz, 1H), 4.37 (t, J=6.0 Hz, 2H), 3.44-3.38 (m, 2H).

Example 58
SS20308-0148-01
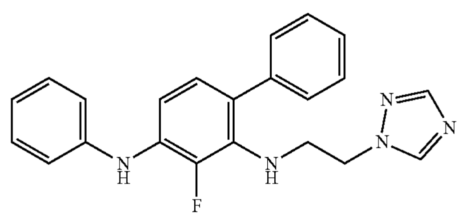
Chemical Formula: $C_{22}H_{20}FN_5$
Molecular Weight: 373.43
Example Route for Example 58
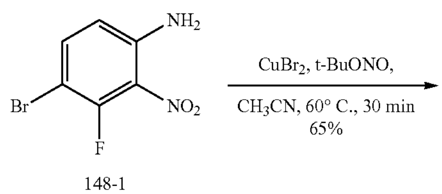
148-1
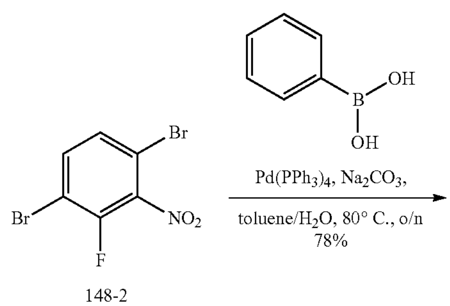
148-2
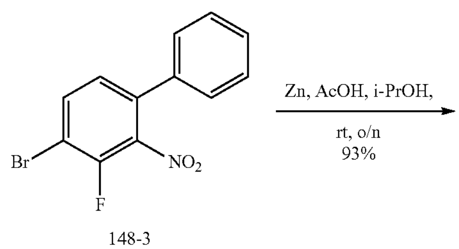
148-3
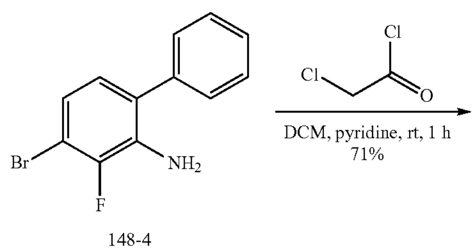
148-4
-continued
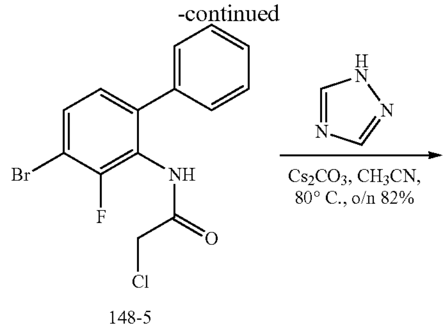
148-5
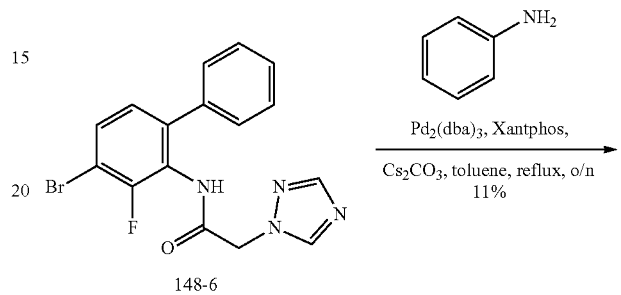
148-6
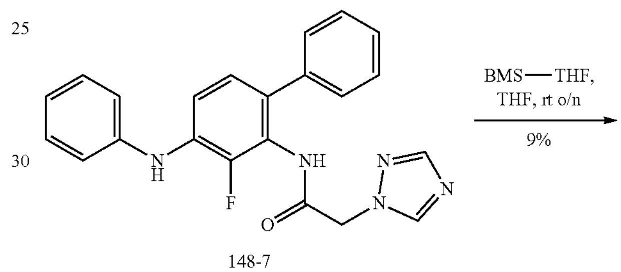
148-7
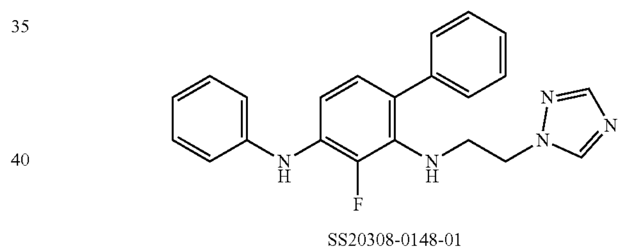
SS20308-0148-01
The Synthesis of 1,4-dibromo-2-fluoro-3-nitrobenzene (148-2)
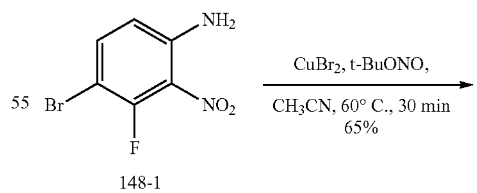
148-1
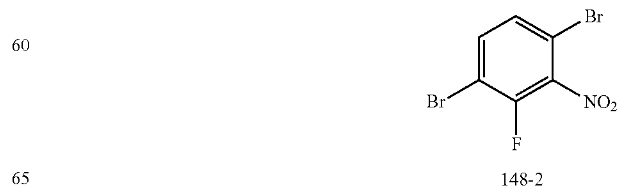
148-2

The mixture of 148-1 (1.0 g, 4.26 mmol) and cupric bromide (1.43 g, 6.38 mmol) in $CH_3CN$ (20 mL) was stirred at 60° C. for 10 min; tert-butyl nitrite (2.19 g, 21.28 mmol) was added slowly. The mixture was stirred at 60° C. for 0.5 h and then poured into water (100 mL). The mixture was extracted with EtOAc (20 mL×3). The combined organic layers were washed with brine (10 mL×2), dried over sodium sulfate, and concentrated to dryness. The residue was purified by silica gel column chromatography (petroleum ether/EtOAc=20/1) to give 148-2 (820 mg, about 65% yield) as a solid.

The Synthesis of 4-bromo-3-fluoro-2-nitrobiphenyl (148-3)

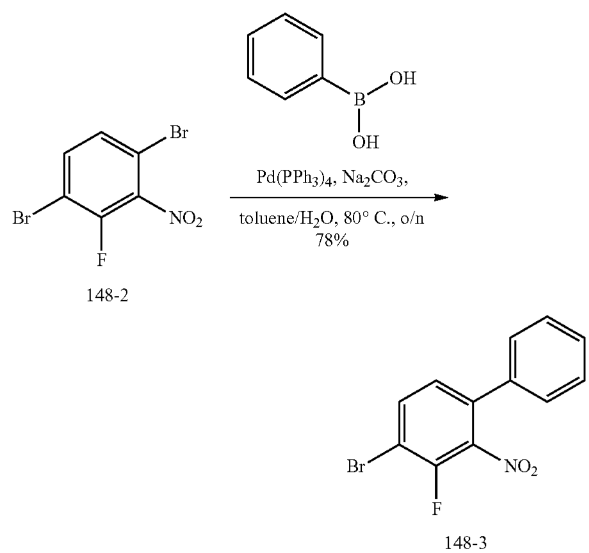

148-2

148-3

A solution of 148-2 (810 mg, 2.71 mmol), phenylboronic acid (331 mg, 2.71 mmol), $Pd(PPh_3)_4$ (157 mg, 0.136 mmol), and sodium carbonate (1.01 g, 9.49 mmol) were suspended in toluene (20 mL) and water (4 mL). The reaction mixture was heated to 80° C. for overnight and then filtered, rinsing with EtOAc. The filtrate was concentrated and the residue was purified by silica gel column chromatography (petroleum ether/EtOAc=100/1) to give compound 148-3 (622 mg, about 78% yield) as an oil.

The Synthesis of 4-bromo-3-fluorobiphenyl-2-amine (148-4)

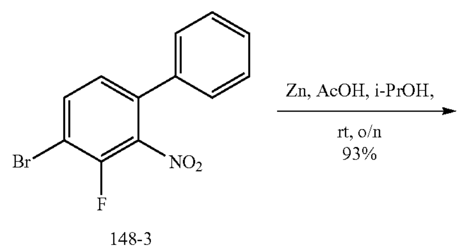

148-3

-continued

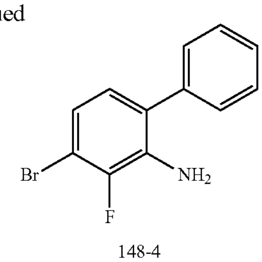

148-4

A mixture of 148-3 (622 mg, 2.10 mmol), and zinc powder (825 mg, 12.61 mmol) in isopropanol (15 mL), acetic acid (1.5 mL) was stirred at room temperature for overnight. Then the reaction mixture was filtered through celite. The filtrate was concentrated and the residue was purified by silica gel column chromatography (petroleum ether/EtOAc=100/1) to give compound 148-4 (622 mg, about 93% yield) as an oil. MS Calcd.: 265.0; MS Found: 266.2 $[M+H]^+$.

The Synthesis of N-(4-bromo-3-fluorobiphenyl-2-yl)-2-chloroacetamide (148-5)

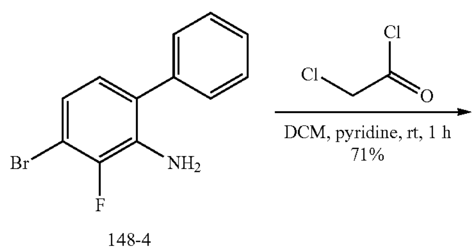

148-4

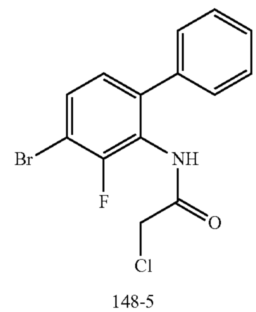

148-5

A solution of 148-4 (470 mg, 1.0 mmol), pyridine (168 mg, 1.2 mmol) and chloroacetyl chloride (220 mg, 1.1 mmol) in DCM (10 mL) was heated at room temperature for 1 h and then washed with brine, dried over sodium sulfate, and concentrated to give 148-5 (428 mg, about 71% yield) as a solid. MS Calcd.: 341.0; MS Found: 342.2 $[M+H]^+$.

The Synthesis of N-(4-bromo-3-fluorobiphenyl-2-yl)-2-(1H-1,2,4-triazol-1-yl)acetamide (148-6)

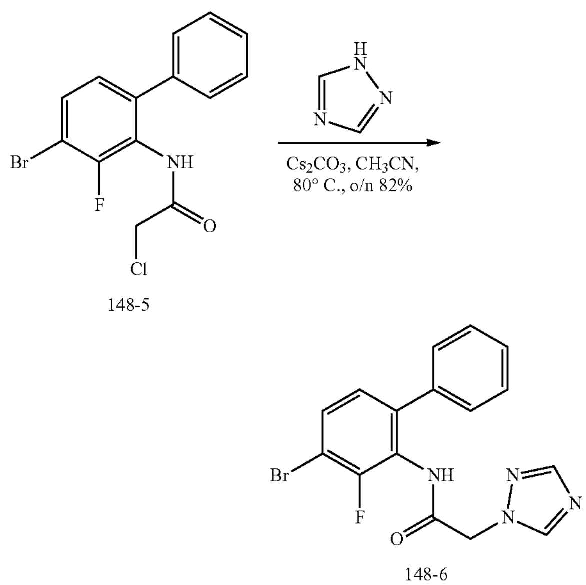

148-5

148-6

A mixture of 148-5 (430 mg, 1.25 mmol), 1H-1,2,4-triazole (130 mg, 1.88 mmol) and $Cs_2CO_3$ (611 mg, 1.88 mmol) in $CH_3CN$ (20 mL) was stirred at 80° C. for overnight. Then the reaction mixture was cooled down to room temperature and filtered. The filtrate was concentrated and purified by column chromatography (EtOAc/petrol ether=1/5, 1/1) to give 148-6 (386 mg, about 82% yield) as an oil. MS Calcd.: 374.0; MS Found: 375.0 $[M+H]^+$.

The Synthesis of N-(3-fluoro-4-(phenylamino)biphenyl-2-yl)-2-(1H-1,2,4-triazol-1-yl)acetamide (148-7)

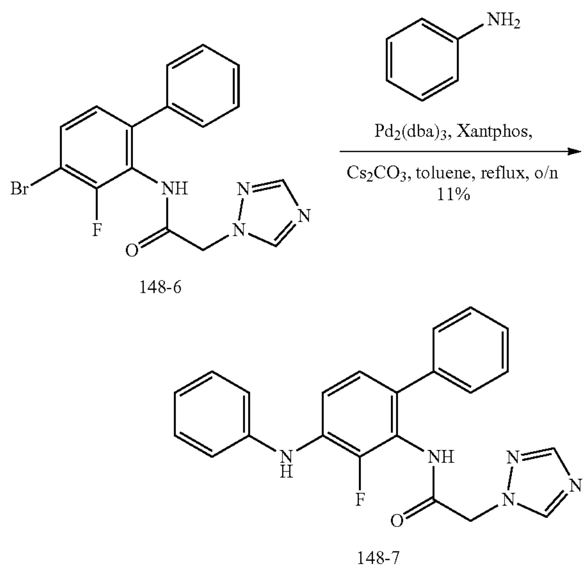

148-6

148-7

A solution of 148-6 (386 mg, 1.03 mmol), aniline (288 mg, 3.09 mmol), Xantphos (119 mg, 0.21 mmol), $Pd_2(dba)_3$ (95 mg, 0.10 mmol), and anhydrous cesium carbonate (503 mg, 1.54 mmol) were suspended in toluene (10 mL). The reaction mixture was heated to 120° C. for overnight under $N_2$ and then filtered, and rinsed with EtOAc. The filtrate was concentrated and purified by silica gel column chromatography (petroleum ether/EtOAc=5/1, 1/1) to give 148-7 as an oil. MS Calcd.: 387.2; MS Found: 388.3 $[M+H]^+$.

The Synthesis of $N^2$-(2-(1H-1,2,4-triazol-1-yl)ethyl)-3-fluoro-$N^4$-phenylbiphenyl-2,4-diamine (SS20308-0148-01)

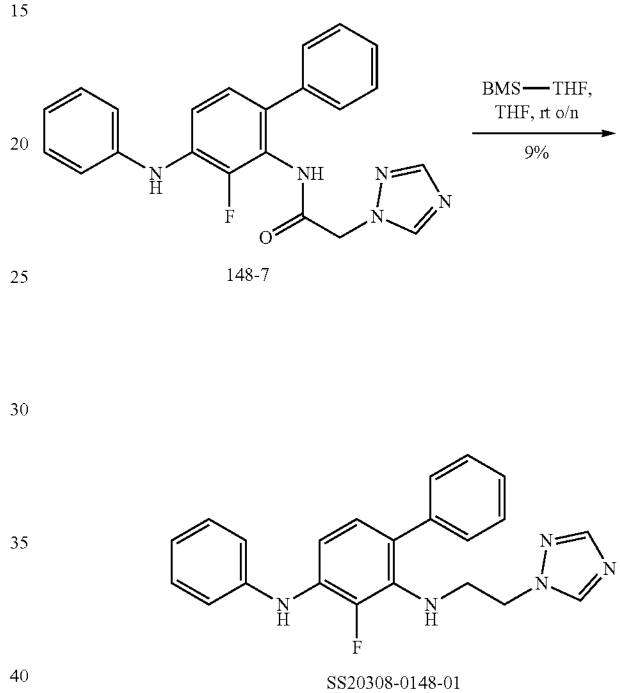

148-7

SS20308-0148-01

To a solution of 148-7 (44 mg, 0.26 mmol) in THF (5 mL) was added borane-dimethyl sulfide complex (10 mL, 2M in THF) slowly. The reaction mixture was stirred at room temperature for overnight and then quenched with MeOH, acidified with 1N HCl to pH~1. Then the reaction mixture was heated to 60° C. and stirred for overnight. After cooling to room temperature, the reaction mixture was basicified $NaHCO_3$ solution, and extracted with EtOAc (20 mL×3). The combined organic layers were washed with water and brine, dried over $Na_2SO_4$ and concentrated. The residue was purified by Prep-TLC (EtOAc) to give SS20308-0148-01 (3.8 mg, about 9% yield) as a solid. MS Calcd.: 373.2; MS Found: 374.3 $[M+H]^+$.

$^1$H NMR (400 MHz, DMSO-$d_6$) δ 8.33 (s, 1H), 7.89 (brs, 1H), 7.88 (s, 1H), 7.39 (dd, J=7.2, 7.2 Hz, 2H), 7.35-7.27 (m, 3H), 7.23 (dd, J=8.4, 7.2 Hz, 2H), 7.04 (d, J=8.0 Hz, 2H), 6.84 (dd, J=7.2, 7.2 Hz, 1H), 6.78-6.73 (m, 2H), 4.50-4.43 (m, 1H), 4.20 (t, J=6.0 Hz, 2H), 3.33-3.27 (m, 2H).

Example 59

SS20308-0149-01

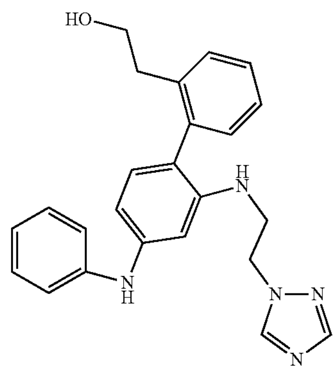

Example Route for Example 59: The Synthesis of methyl 2-(2-(4,4,5,5-tetramethyl-1,3,2-dioxaborolan-2-yl)phenyl)acetate (149-2)

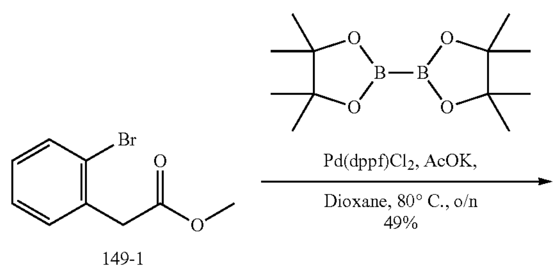

149-1

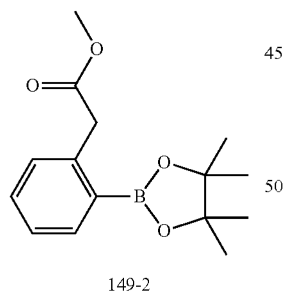

149-2

A mixture of 149-1 (300 mg, 1.32 mmol), 4,4,4',4',5,5,5',5'-octamethyl-2,2'-bi(1,3,2-dioxaborolane) (368 mg, 1.45 mmol), Pd(dppf)$Cl_2$ (48 mg, 0.07 mmol) and AcOK (259 mg, 2.64 mmol) in 1,4 dioxane (5 mL) was stirred at 80° C. overnight. The reaction mixture was cooled to room temperature and poured into water (100 mL) and extracted with EtOAc (60 mL×3). The organic layer was washed with brine and concentrated. The crude product was purified by column chromatography (petroleum ether/EtOAc=10/1) to give 149-2 (180 mg, about 49% yield) as a solid. MS Calcd.: 276.2; MS Found: 277.4 $[M+H]^+$.

The Synthesis of methyl 2-(2'-(2-(1H-1,2,4-triazol-1-yl)ethylamino)-4'-(phenylamino)biphenyl-2-yl) acetate (149-3)

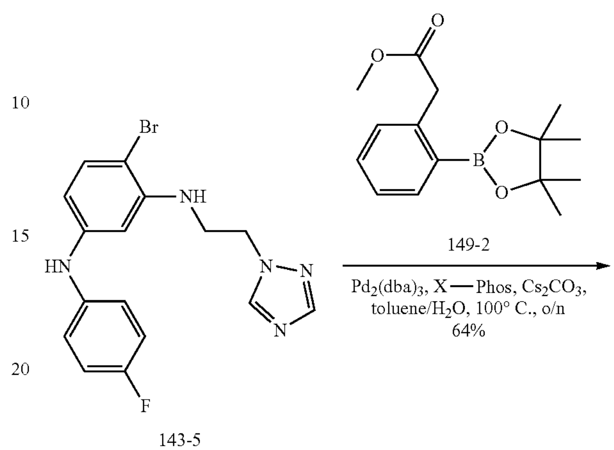

143-5

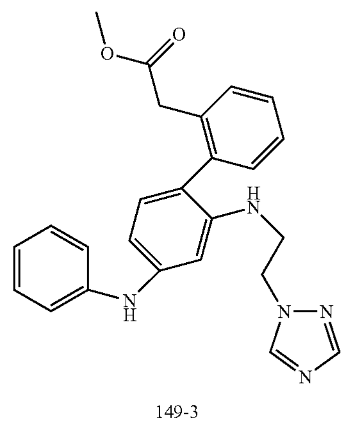

149-3

A mixture of 143-5 (80 mg, 0.22 mmol), 149-2 (91 mg, 0.33 mmol), $Pd(PPh_3)_4$ (10 mg, 0.011 mmol), X-Phos (10 mg, 0.022 mmol) and $Cs_2CO_3$ (143 mg, 0.44 mmol) in toluene/water (2/0.2 mL) was stirred at reflux overnight. The reaction mixture was cooled to room temperature and poured into water (10 mL) and extracted with EtOAc (10 mL×3). The organic layer was washed with brine and evaporated, the residue crude product was purified by column chromatography (petroleum ether/EtOAc=30/1-5/1) to give 149-3 (60 mg, about 64% yield) as a solid. MS Calcd.: 427.2; MS Found: 428.3 $[M+H]^+$ The Synthesis of 2-(2'-(2-(1H-1,2,4-triazol-1-yl)ethylamino)-4'-(phenylamino)biphenyl-2-yl)ethanol (SS20308-0149-01)

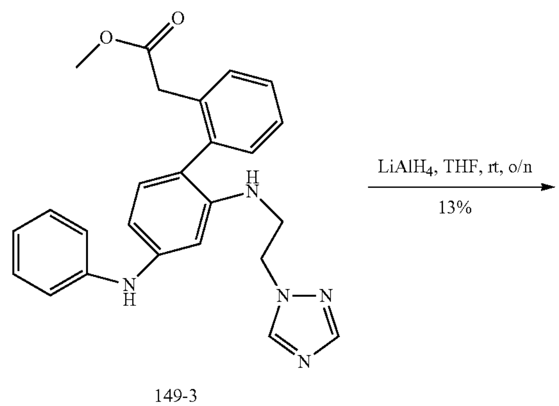

149-3

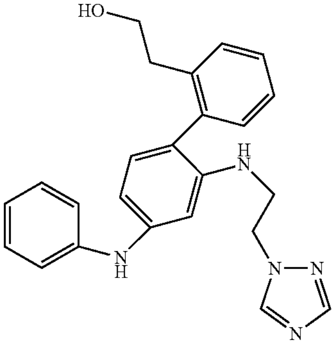

SS20308-0149-01

A mixture of 149-3 (60 mg, 0.14 mmol) and $LiAlH_4$ (27 mg, 0.7 mmol) in THF (3 mL) was stirred at rt overnight. After the reaction was complete, crude reaction mixture was poured onto wet $Na_2SO_4$ (s) and the insoluble material was removed by filtration, and rinsed with $Et_2O$. The filtrate was concentrated under vacuum. The residue was purified by Prep-HPLC to give SS20308-0149-01 (7.2 mg, about 13% yield) as a solid. MS Calcd.: 399.2; MS Found: 400.3 $[M+H]^+$.

$^1H$ NMR (400 MHz, DMSO-$d_6$) δ 8.38 (s, 1H), 8.06 (s, 1H), 7.88 (s, 1H), 7.32-7.19 (m, 6H), 7.11 (d, J=7.6 Hz, 2H), 6.98-6.96 (m, 1H), 6.80 (t, J=7.2 Hz, 1H), 6.73 (d, J=8.0 Hz, 1H), 6.48-6.42 (m, 1H), 6.41 (s, 1H), 4.48 (t, J=5.2 Hz, 1H), 4.29 (t, J=6.0 Hz, 2H), 4.12 (t, J=5.6 Hz, 1H), 3.44-3.30 (m, 5H).

Example 60

SS20308-0151-01

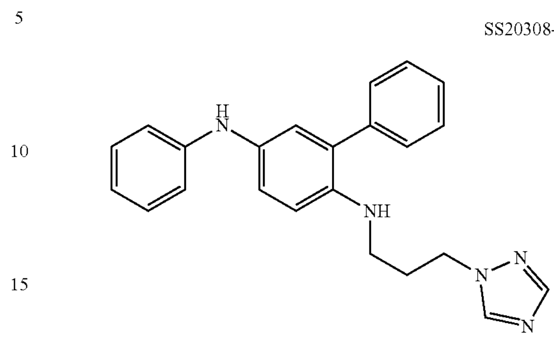

Example Route for Example 60

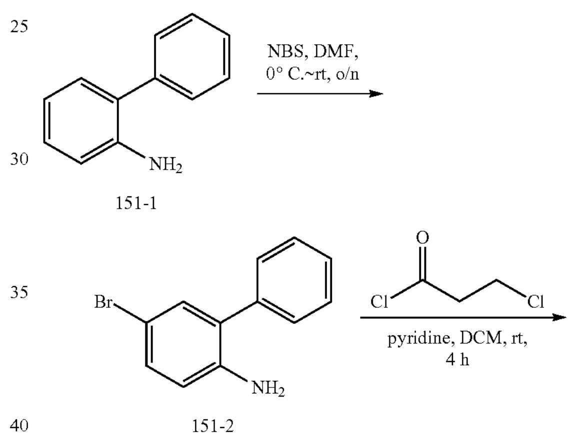

151-1

151-2

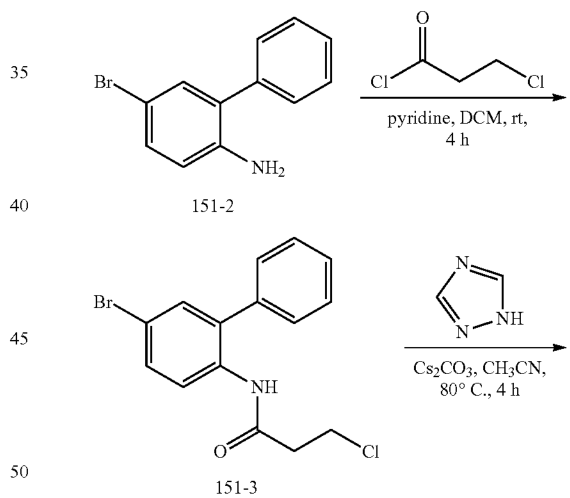

151-3

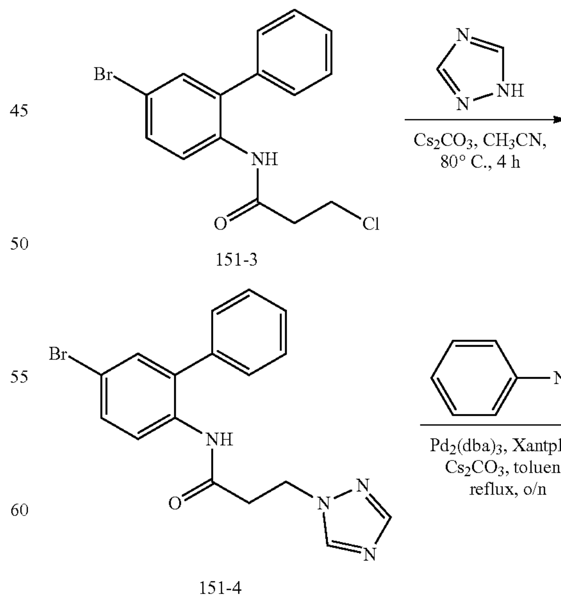

151-4

-continued

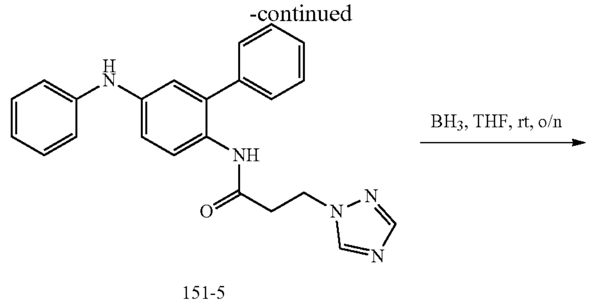

151-5

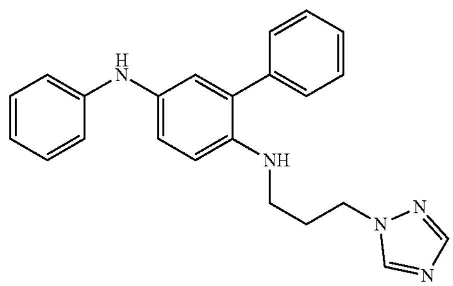

SS20308-0151-01

The Synthesis of 5-bromobiphenyl-2-amine (151-2)

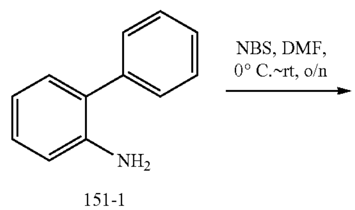

151-1

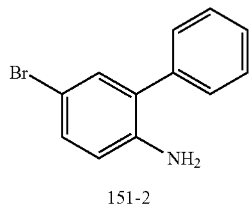

151-2

The mixture of 151-1 (6.40 g, 37.82 mmol) and NBS (6.70 g, 37.82 mmol) in DMF (10 mL) was stirred at 0° C. overnight. Then mixture was poured into water and extracted with EtOAc (30 mL×3) and the organic layers were washed with brine, dried over $MgSO_4$ and concentrated. The residue was purified by column chromatography (petroleum ether/EtOAc=20/1) to give 151-2 (5.7 g, about 57.6% yield) as an oil. MS Calcd.: 247.0; MS Found: 248.2 $[M+H]^+$.

The Synthesis of N-(5-bromobiphenyl-2-yl)-3-chloropropanamide (151-3)

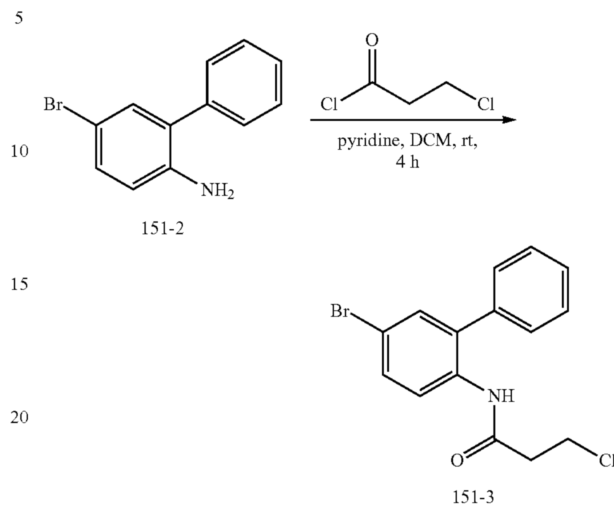

151-2

151-3

The mixture of 151-2 (5.70 g, 22.97 mmol), 3-chloropropanoyl chloride (3.50 g, 27.56 mmol) and pyridine (0.181 g, 2.3 mmol) in DCM (10 mL) was stirred at rt for 4 h. The resulting mixture was extracted with ethyl acetate (30 mL×3) and the organic layers were washed with brine, dried over $MgSO_4$ and concentrated. The residue was purified by column chromatography (petroleum ether/EtOAc=1/1) to give 151-3 (5.0 g, about 64% yield) as a solid. MS Calcd.: 337.0; MS Found: 3380.2 $[M+H]^+$.

The Synthesis of N-(5-bromobiphenyl-2-yl)-3-(1H-1,2,4-triazol-1-yl)propanamide (151-4)

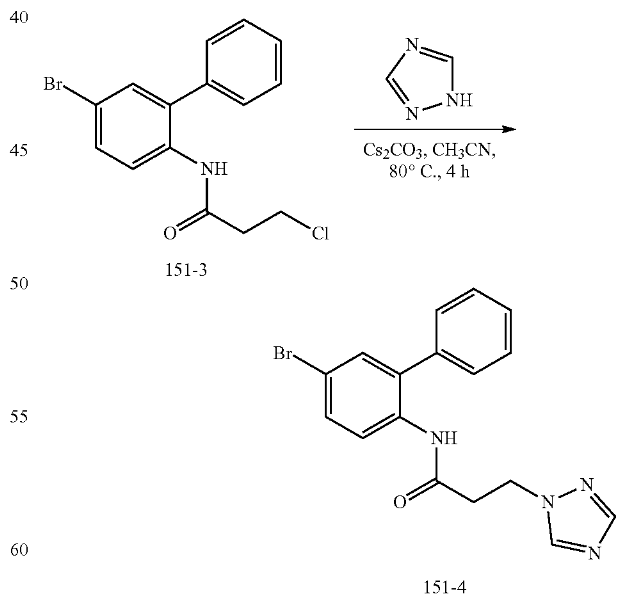

151-3

151-4

The mixture of 151-3 (5.00 g, 14.77 mmol), 1H-1,2,4-triazole (1.22 g, 17.72) and $Cs_2CO_3$ (14.43 g, 44.29 mmol) in $CH_3CN$ (15 mL) was stirred at 80° C. for 4 h. Then the mixture was poured into water and extracted with $CH_2Cl_2$ (3×30 mL). The combined organic layers were washed with brine, dried over $Na_2SO_4$ and concentrated. The residue was purified by column chromatography (petroleum ether/EtOAc=1/2) to give 151-4 (3.3 g, about 60% yield) as a solid. MS Calcd.: 370.0; MS Found: 372.3 [M+H]$^+$.

The Synthesis of N-(5-(phenylamino)biphenyl-2-yl)-3-(1H-1,2,4-triazol-1-yl)propanamide (151-5)

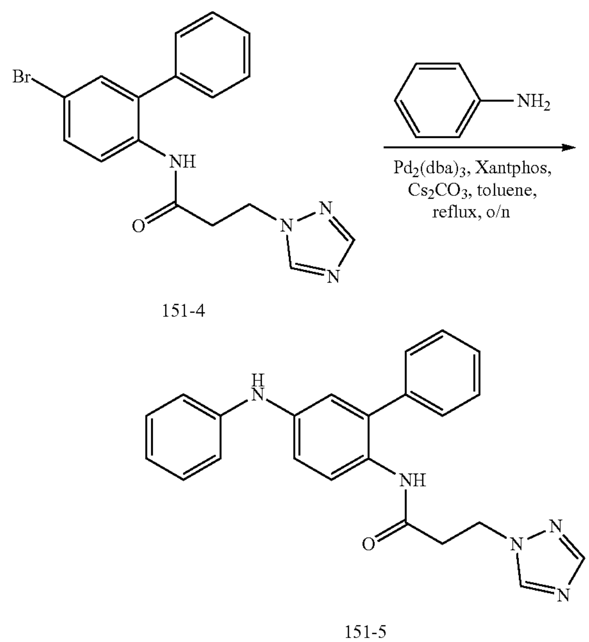

151-4

151-5

The mixture of 151-4 (1.00 g, 2.69 mmol), aniline (752 mg, 8.08 mmol), $Pd_2(dba)_3$ (247 mg, 0.27 mmol), Xantphos (312 mg, 0.54 mmol) and $Cs_2CO_3$ (378 mg, 8.07 mmol) in toluene (5 mL) was stirred at 110° C. under $N_2$ atmosphere overnight. Then mixture was poured into water and extracted with ethyl acetate (30 mL×3) and the organic layers were washed with brine, dried over $MgSO_4$ and concentrated. The residue was purified by column chromatography (petroleum ether/EtOAc=1/2) to give 151-5 (810 mg, about 60% yield) as an oil. MS Calcd.: 383.2; MS Found: 384.3 [M+H]$^+$.

The Synthesis of N$^2$-(3-(1H-1,2,4-triazol-1-yl)propyl)-N$^5$-phenylbiphenyl-2,5-diamine (SS20308-0151-01)

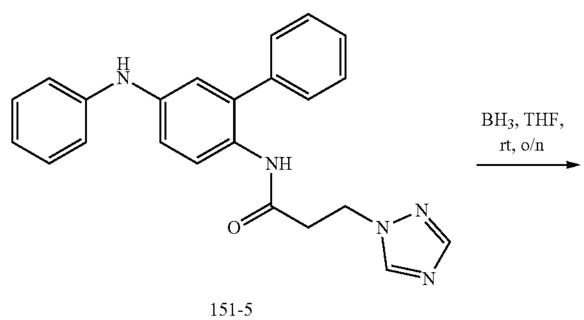

151-5

-continued

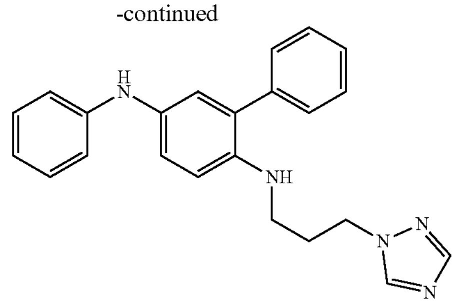

SS20308-0151-01

The mixture of 151-5 (50 mg, 0.13 mmol), and BMS (2.5 M in THF) (5 mL) was stirred at rt overnight. Then mixture was poured into water and extracted with ethyl acetate (30 mL×3) and the organic layers were washed with brine, dried over $MgSO_4$ and concentrated. The residue was purified by Prep-TLC (petroleum ether/EtOAc=1/2) to give SS20308-0151-01 (30 mg, about 62% yield) as a solid. MS Calcd.: 369.2; MS Found: 370.3 [M+H]$^+$.

$^1$H NMR (400 MHz, DMSO-d$_6$) δ 8.49 (s, 1H), 7.93 (s, 1H), 7.65 (s, 1H), 7.40-7.48 (m, 4H), 7.34-7.38 (m, 1H), 7.12 (m, 2H), 6.97 (m, 1H), 6.86 (d, J=7.6 Hz, 2H), 6.79 (d, J=7.6 Hz, 1H), 6.61-6.66 (m, 2H), 4.36 (t, J=6.0 Hz, 1H), 4.21 (t, J=6.8 Hz, 2H), 3.00 (q, J=6.8 Hz, 2H), 2.00 (t, J=6.8 Hz, 2H).

Example 61

SS20308-0153-01

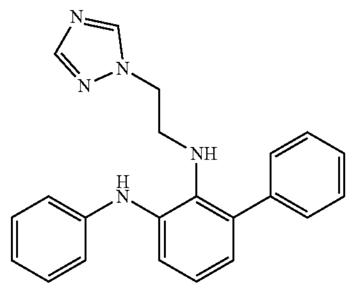

Chemical Formula: $C_{22}H_{21}N_5$
Molecular Weight: 355.44

Example Route for Example 61

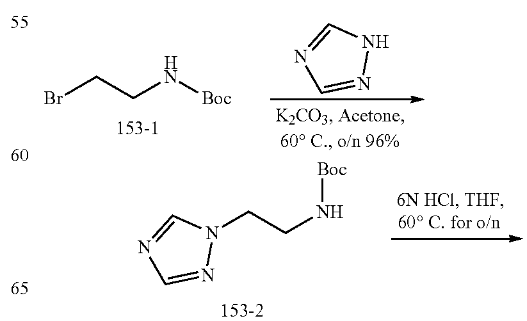

153-1

153-2

-continued

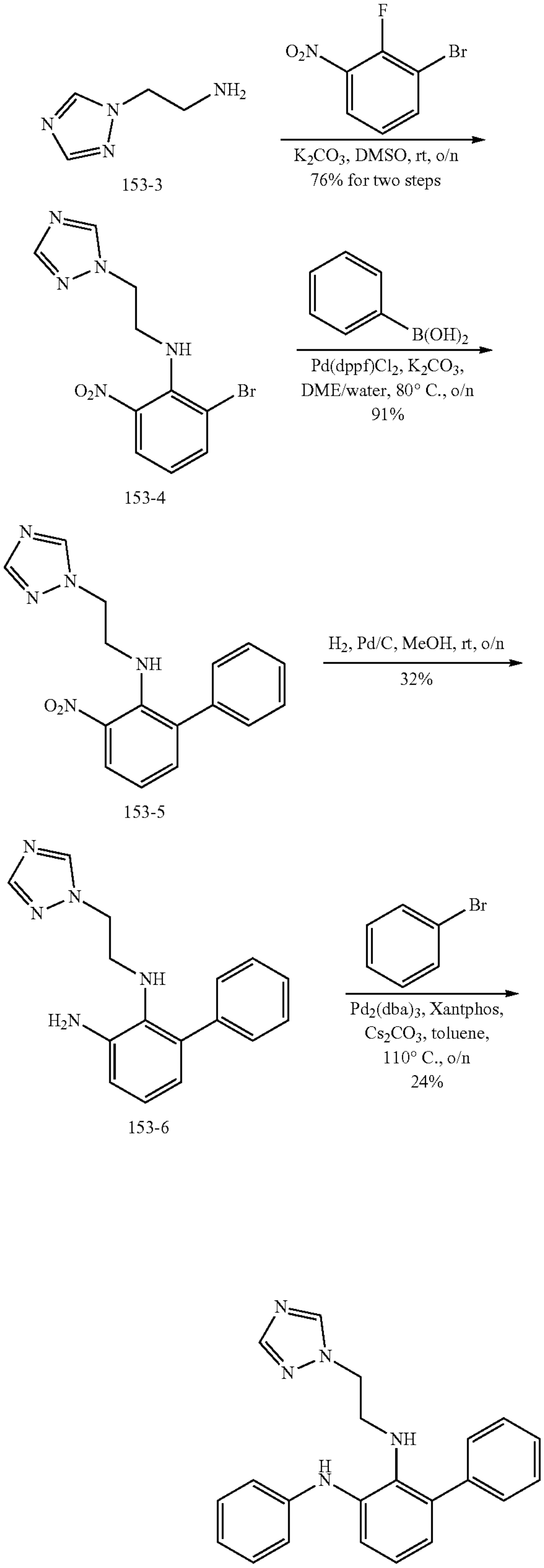

153-3

153-4

153-5

153-6

SS20308-0153-01

The Synthesis of tert-butyl 2-(1H-1,2,4-triazol-1-yl) ethylcarbamate (153-2)

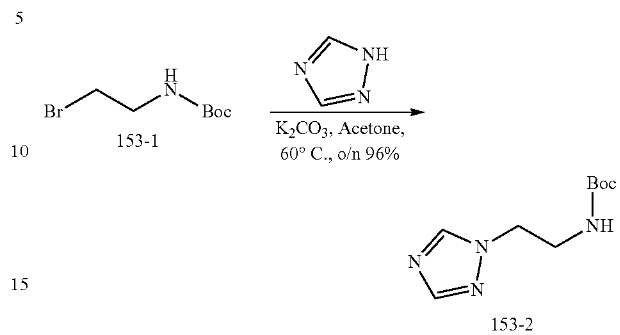

153-1

153-2

To a mixture of 153-1 (2.2 g, 9.82 mmol) and $K_2CO_3$ (2.7 g, 19.63 mmol) in acetone (30 mL) was added 1H-1,2,4-triazole (1.0 g, 14.73 mmol), then stirred at 60° C. overnight. The reaction mixture was purified by column chromatography (petroleum ether/EtOAc=10/1) to give 153-2 (2.0 g, about 96% yield) as an oil. MS Calcd.: 212.1; MS Found: 213.2 $[M+H]^+$.

The Synthesis of N-(2-(1H-1,2,4-triazol-1-yl)ethyl)-2-bromo-6-nitroaniline (153-4)

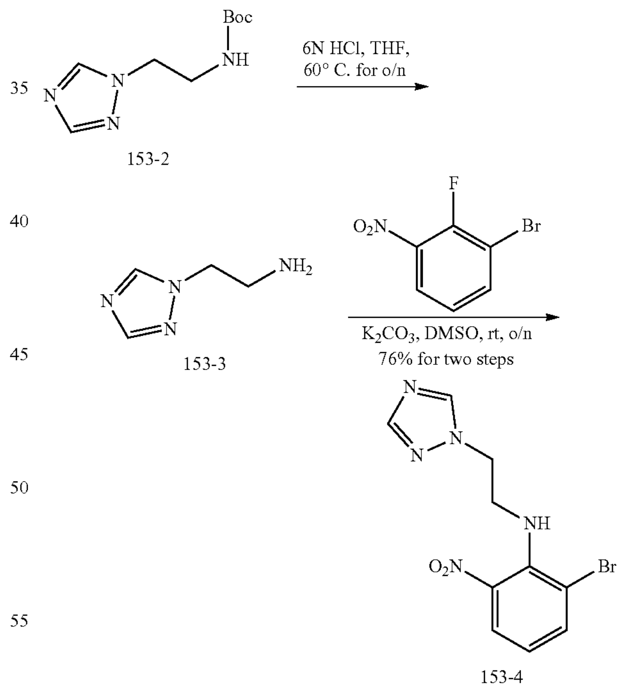

153-2

153-3

153-4

To a solution of 153-2 (424 mg, 2.00 mmol) and in THF (10 mL) was added HCl (6 N, 5 mL), then stirred at room temperature overnight. The reaction mixture was concentrated to dryness several times then dissolved in DMSO (10 mL) and 1-bromo-2-fluoro-3-nitrobenzene (440 mg, 2.00 mmol), $K_2CO_3$ (552 mg, 4.00 mmol) was added above. The mixture was stirred at room temperature overnight. The reaction mixture was diluted with water (40 mL) and then extracted with EtOAc (20 mL×3). The organic layer was washed with brine and concentrated to dryness. The residue was purified by purified by column chromatography (petroleum ether/EtOAc=5/1-3/1) to give 153-4 (474 mg, about 76% yield for two steps) as an oil. MS Calcd.: 311.0; MS Found: 312.0 $[M+H]^+$.

The Synthesis of N-(2-(1H-1,2,4-triazol-1-yl)ethyl)-3-nitrobiphenyl-2-amine (153-5)

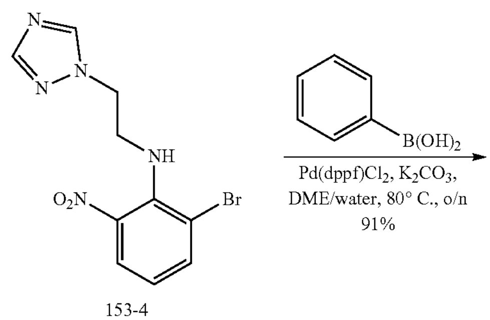

153-4

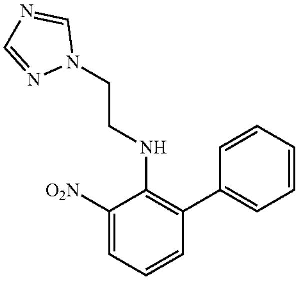

153-5

To a solution of 153-4 (443 mg, 1.42 mmol) in DME/water (10/1, 15 mL) was added phenylboronic acid (260 mg, 2.13 mmol), Pd(dppf)$Cl_2$ (102 mg, 0.14 mmol) and $K_2CO_3$ (392 mg, 2.84 mmol), then the reaction mixture was stirred at 80° C. overnight. The reaction mixture was cooled to room temperature and filtered through celite. The filtrate was diluted with water (30 mL) and then extracted with EtOAc (20 mL×3). The organic layer was washed with brine and concentrated to dryness. The residue was purified by purified by column chromatography (petroleum ether/EtOAc=10/1-4/1) to give 153-5 (400 mg, about 91% yield) as a solid. MS Calcd.: 309.1; MS Found: 310.0 $[M+H]^+$.

The Synthesis of $N^2$-(2-(1H-1,2,4-triazol-1-yl)ethyl)biphenyl-2,3-diamine (153-6)

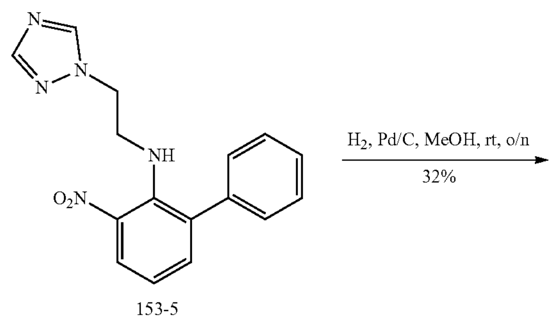

153-5

-continued

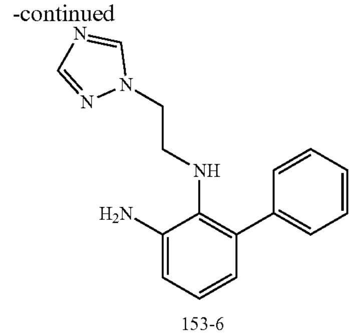

153-6

To a solution of 153-5 (350 mg, 1.13 mmol) in MeOH (5 mL) was added Pd/C (35 mg, 10%), then the reaction mixture was stirred at room temperature overnight. The reaction mixture was filtered through celite. The filtrate was purified by Prep-TLC (EtOAc) to give 153-6 (100 mg, about 32% yield) as a solid. MS Calcd.: 279.1; MS Found: 280.1 $[M+H]^+$.

The Synthesis of $N^2$-(2-(1H-1,2,4-triazol-1-yl)ethyl)-$N^3$-phenylbiphenyl-2,3-diamine (SS20308-0153-01)

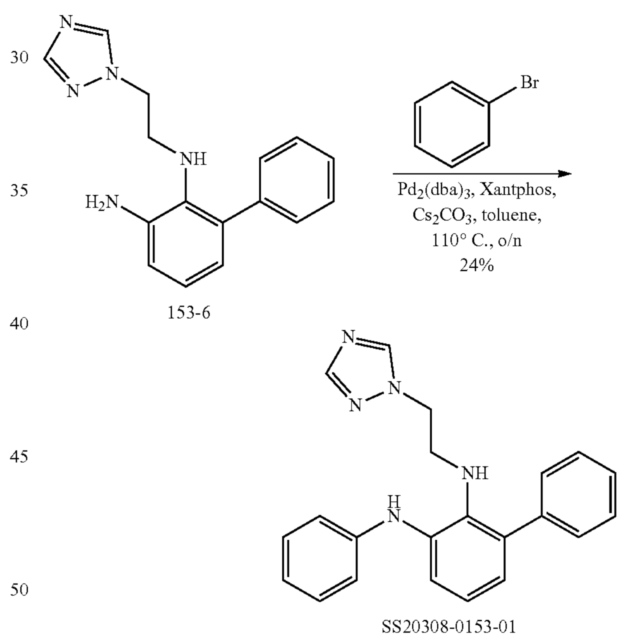

153-6

SS20308-0153-01

To a solution of 153-6 (100 mg, 0.36 mmol) in toluene (10 mL) was added bromobenzene (84 mg, 0.54 mmol), $Pd_2(dba)_3$ (30 mg, 0.03 mmol), Xantphos (29 mg, 0.06 mmol) and $Cs_2CO_3$ (233 mg, 0.72 mmol), then the reaction mixture was stirred at 110° C. overnight. The reaction mixture was cooled to room temperature and filtered through celite. The filtrate was diluted with water (20 mL) and then extracted with EtOAc (10 mL×3). The organic layer was washed with brine and concentrated to dryness. The residue was purified by purified by Prep-TLC (petroleum ether/EtOAc=1/1) to give SS20308-0153-01 (31 mg, about 24% yield) as an oil. MS Calcd.: 355.2; MS Found: 356.0 $[M+H]^+$.

$^1H$ NMR (400 MHz, DMSO-$d_6$) δ 8.15 (s, 1H), 7.82 (s, 1H), 7.43-7.32 (m, 5H), 7.23-7.10 (m, 3H), 7.11 (d, J=6.4

Hz, 1H), 6.90 (t, J=7.6 Hz, 1H), 6.84-6.82 (m, 3H), 6.75 (t, J=7.2 Hz, 1H), 4.22-4.18 (m, 1H), 4.01 (t, J=6.0 Hz, 2H), 3.03-2.98 (m, 2H).

Example 62

SS20308-0165-01

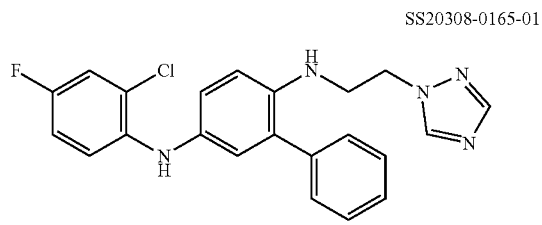

Chemical Formula: $C_{22}H_{19}ClFN_5$
Molecular Weight: 407.87

Example Route for Example 62

The Synthesis of $N^2$-(2-(1H-1,2,4-triazol-1-yl) ethyl)-$N^5$-(2-chloro-4-fluorophenyl)biphenyl-2,5-diamine (SS20308-0165-01)

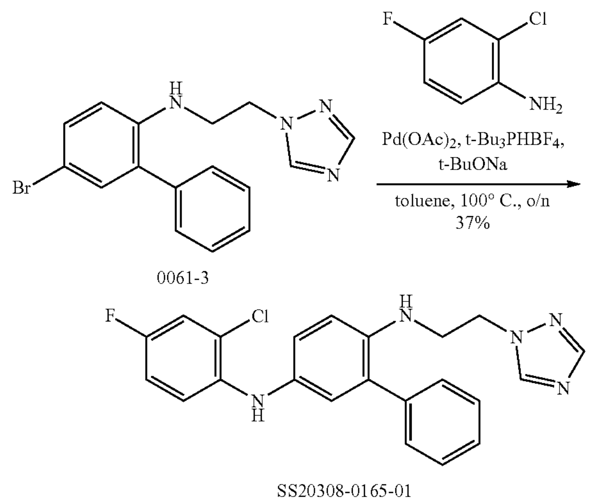

0061-3

SS20308-0165-01

A solution of 0061-3 1.0 g, 2.91 mmol), 2-chloro-4-fluoroaniline (637 mg, 4.38 mmol), t-$Bu_3PHBF_4$ (169 mg, 0.583 mmol), $Pd(OAc)_2$ (66 mg, 0.294 mmol), and t-BuONa (840 mg, 8.74 mmol) were suspended in toluene (20 mL). The reaction mixture was heated for overnight at reflux under $N_2$ and then filtered, and rinsed with EtOAc. The filtrate was concentrated and purified by silica gel column chromatography (petroleum ether/EtOAc=5/1, 3/1, 1/1) to give SS20308-0165-01 (440 mg, about 37% yield) as an oil. MS Calcd.: 407.1; MS Found: 408.0 $[M+H]^+$.

$^1H$ NMR (400 MHz, DMSO-$d_6$) δ 8.46 (s, 1H), 7.96 (s, 1H), 7.45-7.39 (m, 2H), 7.37-7.30 (m, 2H), 7.29-7.26 (m, 2H), 7.14 (s, 1H), 7.03-6.93 (m, 3H), 6.79 (d, J=2.8 Hz, 1H), 6.71 (d, J=8.8 Hz, 1H), 4.59 (t, J=6.0 Hz, 1H), 4.35 (t, J=5.8 Hz, 2H), 3.50-3.44 (m, 2H).

The Synthesis of $N^3$-(2-(1H-1,2,4-triazol-1-yl) ethyl)-4-(1H-indol-7-yl)-$N^1$-phenylbenzene-1,3-diamine (166-1)

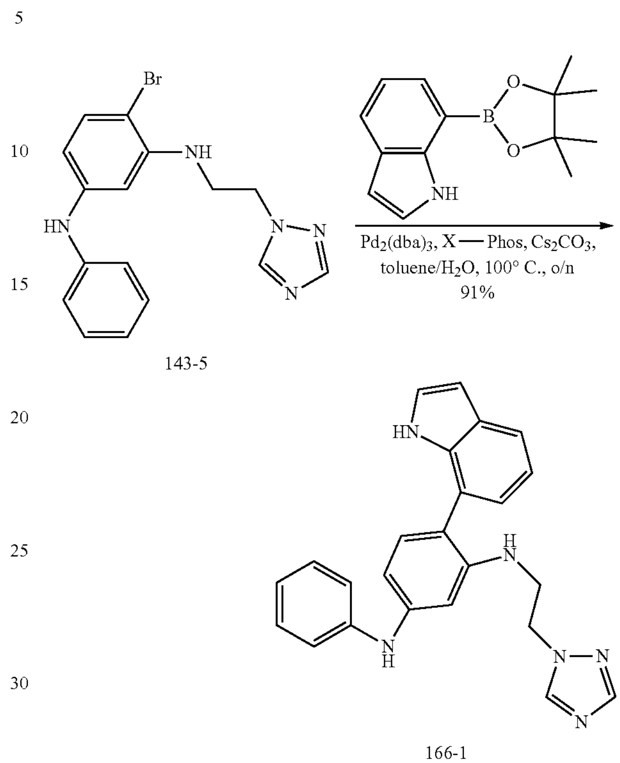

143-5

166-1

A mixture of 143-5 (50 mg, 0.14 mmol), 7-(4,4,5,5-Tetramethyl-1,3,2-dioxaborolan-2-yl)-1H-indole (51 mg, 0.21 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (100 mL) and extracted with EtOAc (60 mL×3). The organic layer was washed with brine and concentrated, the residue crude product was purified by column chromatography (petroleum ether/EtOAc=5/1) to give 166-1 (50 mg, about 91% yield) as a solid. MS Calcd.: 394.2; MS Found: 395.2 $[M+H]^+$.

Example 63

SS20308-0166-01

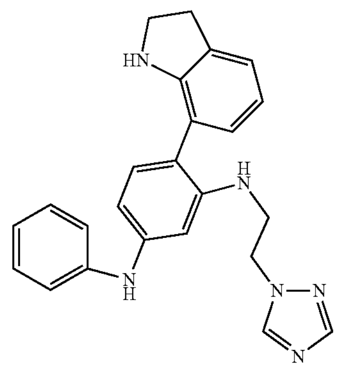

The Synthesis of $N^3$-(2-(1H-1,2,4-triazol-1-yl)ethyl)-4-(indolin-7-yl)-$N^1$-phenylbenzene-1,3-diamine (SS20308-0166-01)

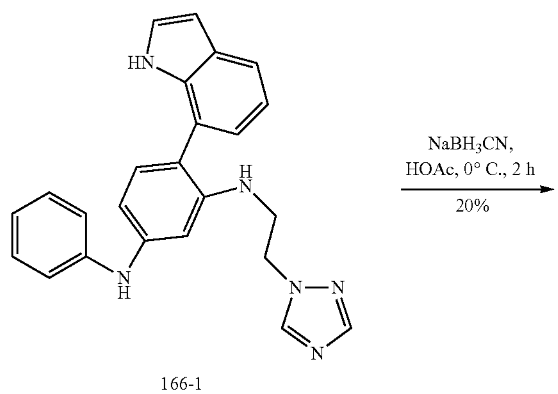

166-1

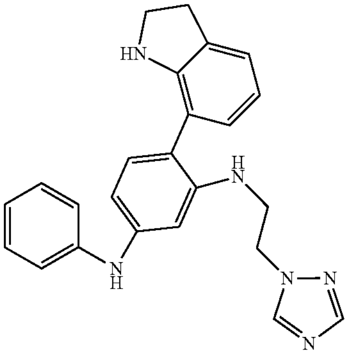

SS20308-0166-01

A mixture of 166-1 (50 mg, 0.13 mmol) and $NaBH_3CN$ (25 mg, 0.39 mmol) in AcOH (1 mL) was stirred at 0° C. for 2 h. After the reaction was complete, the reaction mixture was quenched with water (10 mL), extracted with EtOAc (30 mL×3). The combined layers were dried over $Na_2SO_4$ and concentrated in vacuum. The residue was purified by Prep-HPLC to give SS20308-0166-01 (10.3 mg, about 20% yield) as a solid. MS Calcd.: 396.5; MS Found: 397.3 $[M+H]^+$.

$^1$H NMR (400 MHz, DMSO-$d_6$) δ 8.49 (s, 1H), 8.08 (s, 1H), 7.96 (s, 1H), 7.23 (t, J=8.4 Hz, 2H), 7.10 (d, J=7.6 Hz, 2H), 7.00 (d, J=6.8 Hz, 1H), 6.90 (d, J=8.0 Hz, 1H), 6.82-6.76 (m, 2H), 6.61 (t, J=7.2 Hz, 1H), 6.50-6.45 (m, 2H), 4.67 (s, 1H), 4.62-4.61 (m, 1H), 4.39-4.36 (m, 2H), 3.48-3.47 (m, 2H), 2.29-2.28 (m, 2H), 2.96-2.92 (m, 2H).

Example 64

SS20308-0171-01

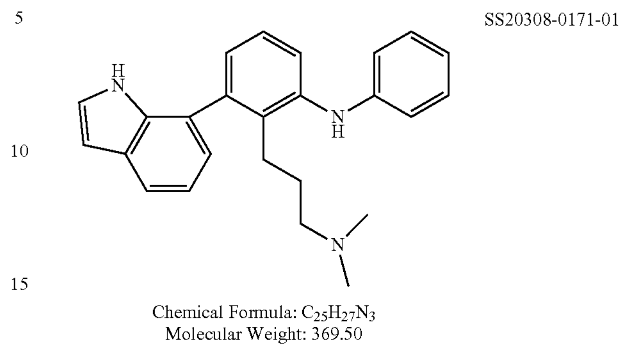

Chemical Formula: $C_{25}H_{27}N_3$
Molecular Weight: 369.50

The Synthesis of 2-(3-(dimethylamino)propyl)-3-(1H-indol-7-yl)-N-phenylaniline (SS20308-0171-01)—See below for synthesis of SS20308-0172-01

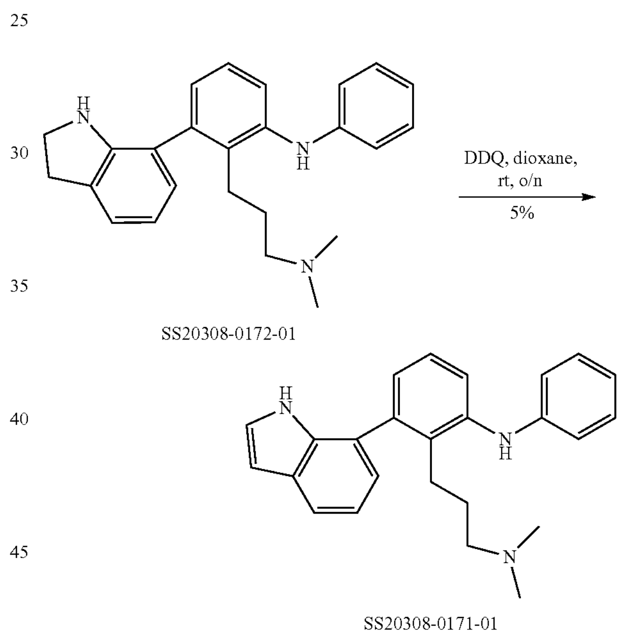

SS20308-0172-01

SS20308-0171-01

A mixture of SS20308-0172-01 (50 mg, 0.13 mmol) and DDQ (59 mg, 0.58 mmol) in dioxane (2 mL) was stirred at room temperature overnight. The reaction mixture was poured into water (5 mL) and extracted with EtOAc (5 mL×3). The organic layer was washed with brine and evaporated, the residue crude product was purified by Prep-HPLC to give SS20308-0171-01 (2.5 mg, about 5% yield) as a solid. MS Calcd.: 369.5; MS Found: 370.3 $[M+H]^+$.

$^1$H NMR (400 MHz, DMSO-$d_6$) δ 10.59 (s, 1H), 8.19 (s, 1H), 7.53 (d, J=8.0 Hz, 1H), 7.30 (d, J=7.2 Hz, 1H), 7.29-7.17 (m, 4H), 7.05 (t, J=6.8 Hz, 1H), 6.95 (d, J=7.6 Hz, 2H), 6.90 (d, J=7.2 Hz, 1H), 6.86-6.85 (m, 1H), 6.73 (t, J=7.2 Hz, 1H), 6.48-6.46 (m, 1H), 2.36-2.30 (m, 2H), 1.93 (s, 6H), 1.89-1.86 (m, 2H), 1.29-1.23 (m, 2H).

Example 65
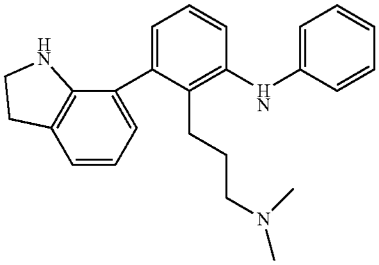
SS20308-0172-01
Chemical Formula: $C_{25}H_{29}N_3$
Molecular Weight: 371.52
Example Route for Example 65 (SS20308-0172-01 and SS20308-0171-01)
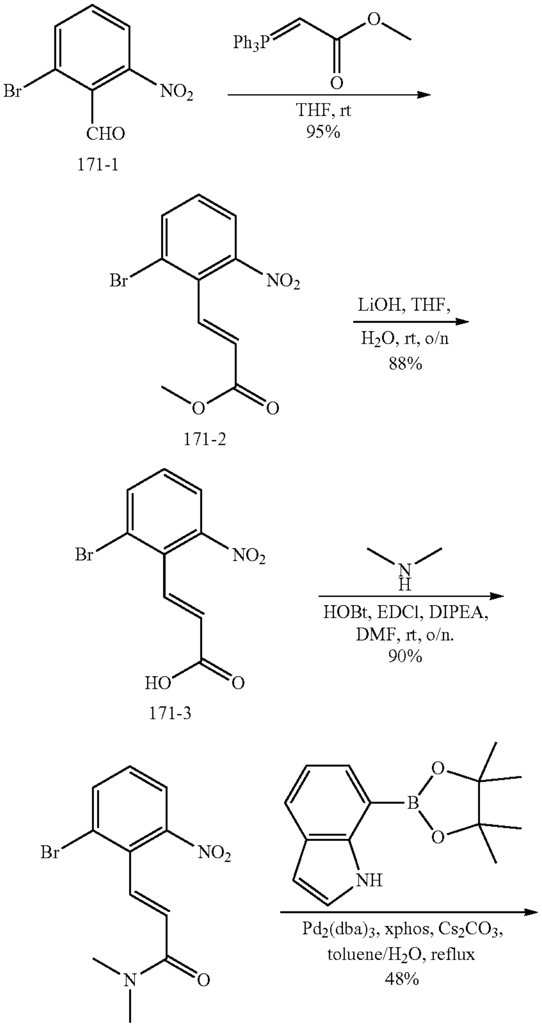
171-1
171-2
171-3
171-4
-continued
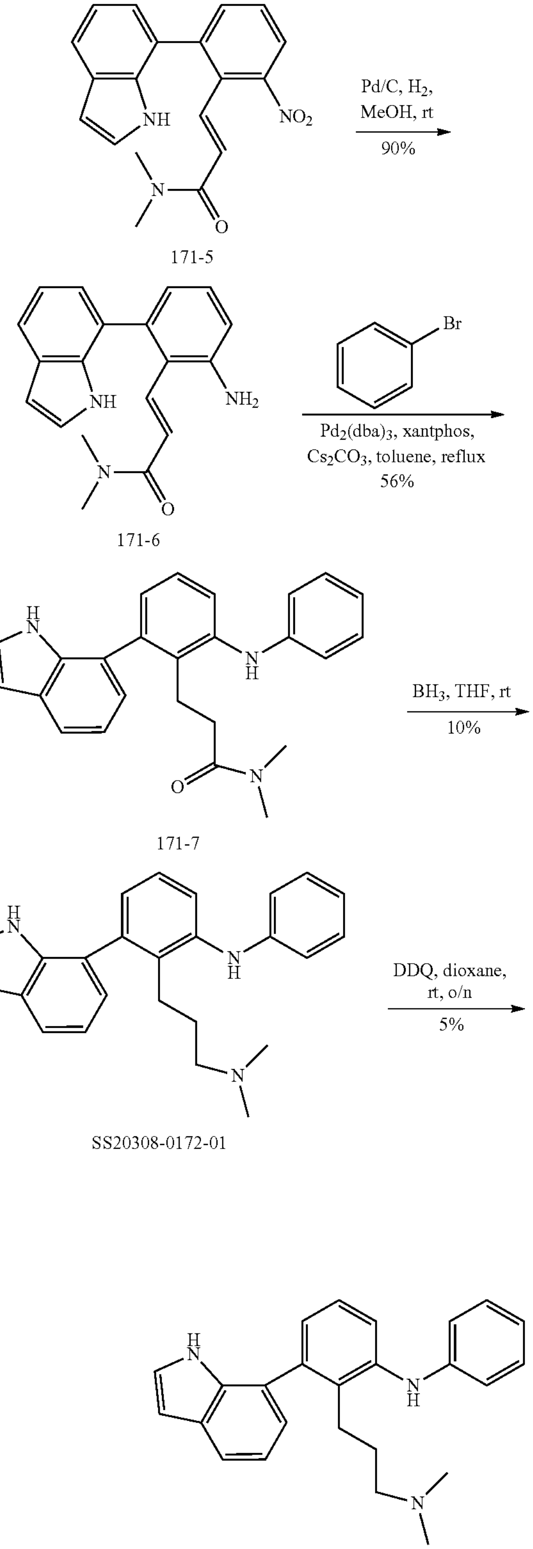
171-5
171-6
171-7
SS20308-0172-01
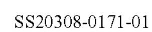
SS20308-0171-01

The Synthesis of (E)-methyl 3-(2-bromo-6-nitrophenyl)acrylate (171-2)

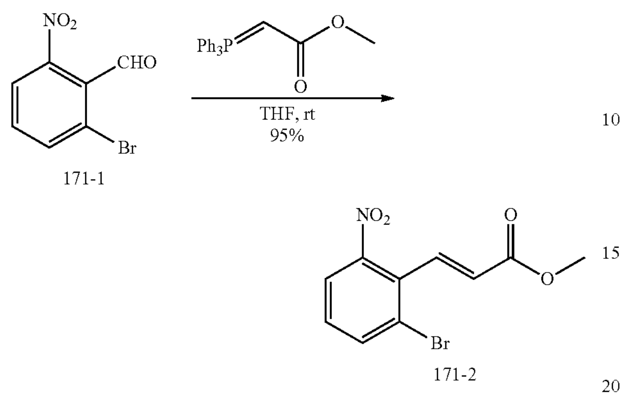

A mixture of 171-1 (1.0 g, 4.4 mmol) and methyl (triphenylphosphoranylidene)acetate (2.2 g, 6.6 mmol) in THF (50 mL) was stirred at rt overnight. The reaction mixture was cooled to room temperature and poured into water (100 mL) and extracted with EtOAc (60 mL×3). The organic layer was washed with brine and concentrated. The crude product was purified by column chromatography (petroleum ether/EtOAc=5/1) to give 171-2 (1.2 g, about 95% yield) as a solid. MS Calcd.: 285.0; MS Found: 303.0 $[M+18]^+$.

The Synthesis of (E)-3-(2-bromo-6-nitrophenyl) acrylic acid (171-3)

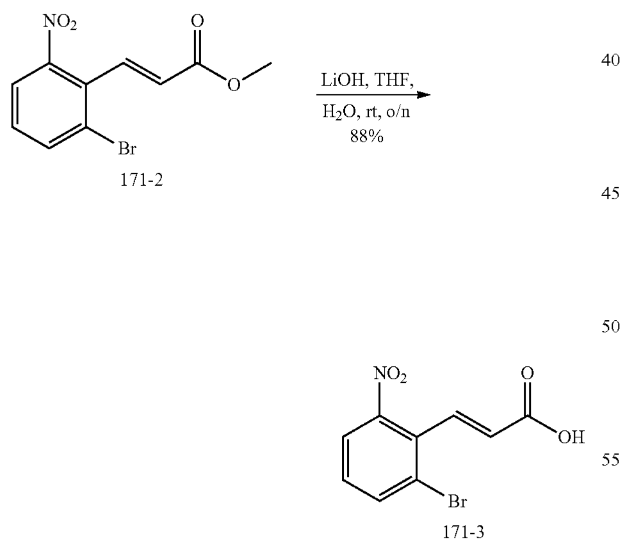

A mixture of 171-2 (600 mg, 2.1 mmol) and LiOH (100 mg, 4.2 mmol) in THF (5 mL) and $H_2O$ (2 mL) was stirred at rt overnight. The reaction mixture was poured into water (10 mL) and extracted with EtOAc (10 mL×3). The organic layer was washed with brine and concentrated to give 171-3 (500 mg, about 88% yield) as a solid. MS Calcd.: 271.0; MS Found: 289.0 $[M+18]^+$.

The Synthesis of (E)-3-(2-bromo-6-nitrophenyl)-N,N-dimethylacrylamide (171-4)

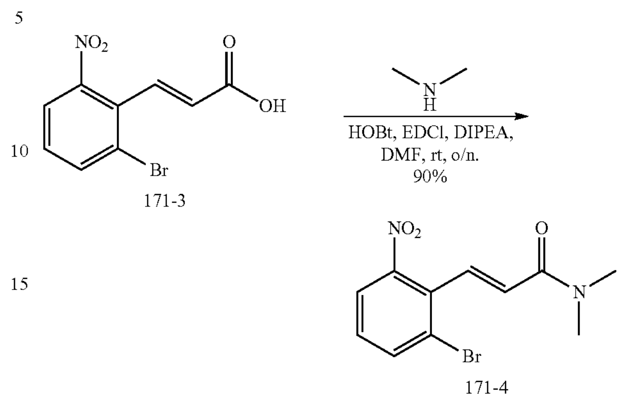

A mixture of 171-3 (500 mg, 1.85 mmol), dimethylamine (225 mg, 2.78 mmol), HOBt (300 mg, 2.22 mmol), EDCI (424 mg, 2.22 mmol) and DIPEA (525 mg, 4.07 mmol) in DMF (10 mL) was stirred at room temperature overnight. The reaction mixture was cooled to room temperature and poured into water (10 mL) and extracted with EtOAc (10 mL×3). The organic layer was washed with brine and concentrated. The crude product was purified by column chromatography (petroleum ether/EtOAc=5/1) to give 171-4 (500 mg, about 90% yield) as a solid. MS Calcd.: 298.0; MS Found: 299.0 $[M+H]^+$.

The Synthesis of (E)-3-(2-(1H-indol-7-yl)-6-nitrophenyl)-N,N-dimethylacrylamide (171-5)

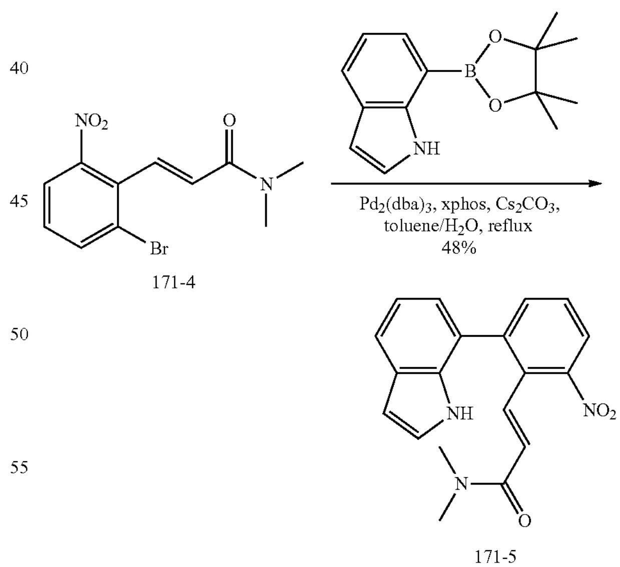

A mixture of 171-4 (500 mg, 1.4 mmol), 7-(4,4,5,5-tetramethyl-1,3,2-dioxaborolan-2-yl)-1H-indole (610 mg, 1.7 mmol), $Pd_2(dba)_3$ (80 mg, 0.07 mmol), X-Phos (80 mg, 0.14 mmol) and $Cs_2CO_3$ (1.1 mg, 2.8 mmol) in toluene (10 mL) and $H_2O$ (1 mL) was stirred at reflux overnight. The reaction mixture was cooled to room temperature and poured into water (10 mL) and extracted with EtOAc (10 mL×3). The organic layer was washed with brine and concentrated. The crude product was purified by column chromatography (EtOAc) to give 171-5 (450 mg, about 48% yield) as a solid. MS Calcd.: 335.1; MS Found: 336.4 $[M+H]^+$.

The Synthesis of 3-(2-amino-6-(1H-indol-7-yl)phenyl)-N,N-dimethylpropanamide (171-5)

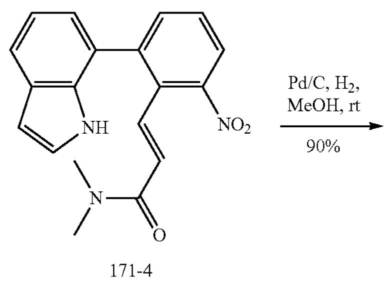

171-4

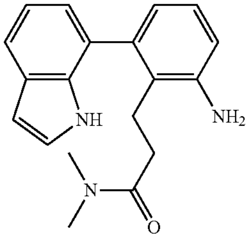

171-5

A mixture of 171-4 (600 mg, 1.4 mmol) and Pd/C (10%; 100 mg) in MeOH (10 mL) was stirred at room temperature overnight under $H_2$(g). The reaction mixture was filtered and purified by column chromatography (EtOAc) to give 171-5 (450 mg, about 90% yield) as a solid. MS Calcd.: 307.2; MS Found: 308.4 $[M+H]^+$.

The Synthesis of 3-(2-(1H-indol-7-yl)-6-(phenylamino)phenyl)-N,N-dimethylpropanamide (171-6)"

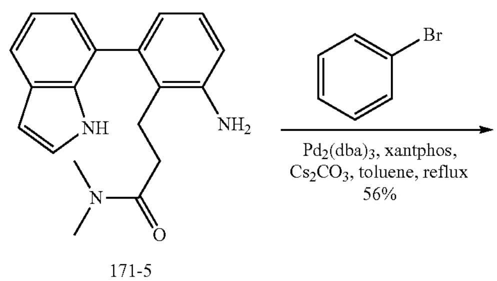

171-5

-continued

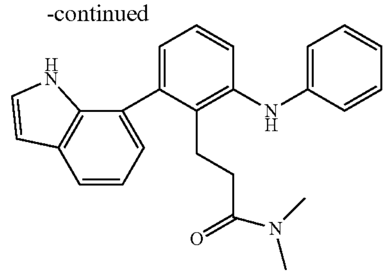

171-6

A mixture of 171-5 (450 mg, 1.5 mmol), bromobenzene (281 mg, 1.8 mmol), $Pd_2(dba)_3$ (38.7 mg, 0.075 mmol), xant-Phos (72 mg, 0.15 mmol) and $Cs_2CO_3$ (978 mg, 3.0 mmol) in toluene (5 mL) was stirred at reflux overnight. The reaction mixture was cooled to room temperature and poured into water (10 mL) and extracted with EtOAc (10 mL×3). The organic layer was washed with brine and concentrated. The crude product was purified by column chromatography (EtOAc) to give 171-6 (320 mg, about 56% yield) as a solid. MS Calcd.: 383.2; MS Found: 384.3 $[M+H]^+$.

The Synthesis of 2-(3-(dimethylamino)propyl)-3-(indolin-7-yl)-N-phenylaniline (SS20308-0172-01)

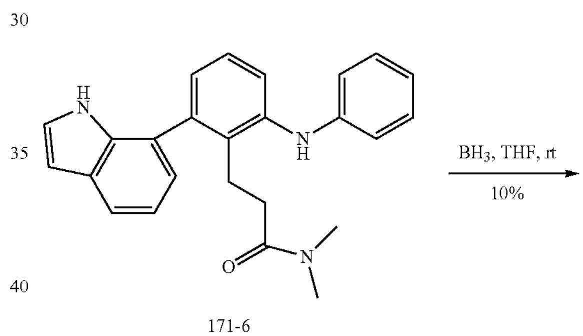

171-6

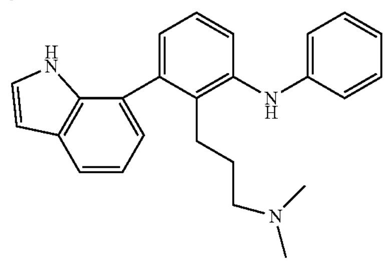

SS20308-0172-01

A mixture of 171-6 (50 mg, 0.13 mmol), $BH_3$ (0.5 mL, 1M in THF) in THF (2 mL) was stirred at room temperature overnight. Then HCl (1N, 2 mL) and MeOH (2 mL) was added, the final mixture was stirred at room temperature overnight. The reaction mixture was poured into water (10 mL) and extracted with EtOAc (10 mL×3). The organic layer was washed with brine and concentrated. The crude product was purified by Prep-HPLC to give SS20308-0172-01 (5.1 mg, about 10% yield) as a solid. MS Calcd.: 371.5; MS Found: 372.4 $[M+H]^+$.

$^1H$ NMR (400 MHz, $CDCl_3$) δ 10.64 (brs, 1H), 7.37-7.34 (m, 1H), 7.31-7.29 (m, 2H), 7.20-7.11 (m, 5H), 7.03-7.00 (m, 2H), 6.79 (t, J=7.2 Hz, 1H), 3.75-3.73 (m, 2H), 3.35-

3.27 (m, 2H), 2.91-2.80 (m, 2H), 2.76-2.68 (m, 2H), 2.54 (s, 3H), 2.45 (s, 3H), 1.73-1.67 (m, 2H).

Example 66

SS20308-0173-01

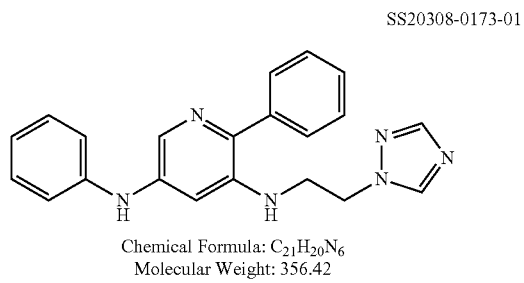 [SMILES: c1ccc(Nc2cnc(-c3ccccc3)c(NCCn3cncn3)c2)cc1]

Chemical Formula: $C_{21}H_{20}N_6$
Molecular Weight: 356.42

Example Route for Example 66 (SS20308-0173-01 and SS20308-0219-01)

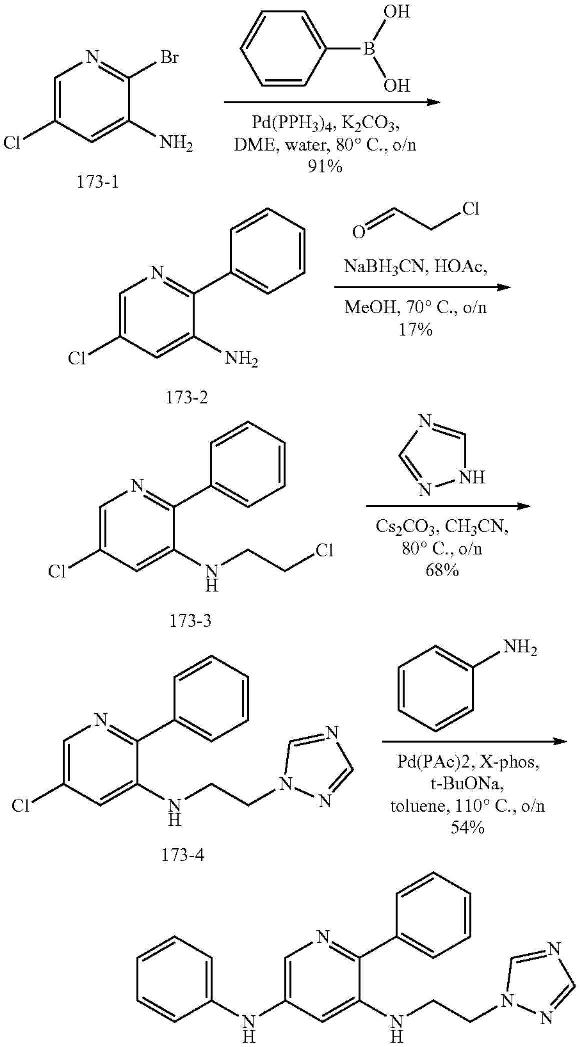

173-1

173-2

173-3

173-4

SS20308-0173-01

The Synthesis of 5-chloro-2-phenylpyridin-3-amine (173-2)

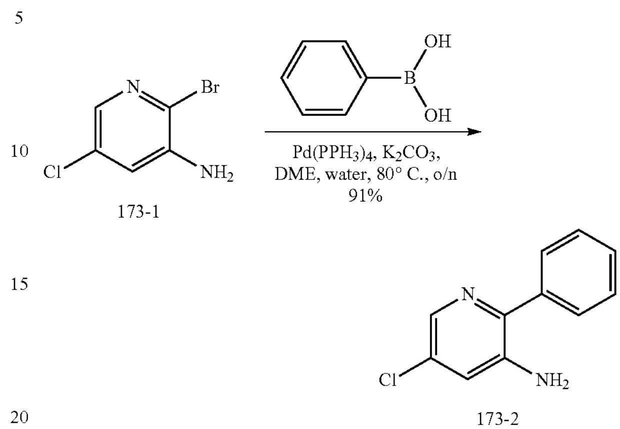

173-1

173-2

The mixture of 173-1 (500 mg, 2.42 mmol), phenylboronic acid (590 mg, 4.84 mmol), $Pd(PPh_3)_4$ (277 mg, 0.24 mmol), $K_2CO_3$ (668 mg, 4.84 mmol) in DME (10 mL) and water (1 mL) was stirred at 80° C. overnight under N2 atmosphere. The reaction mixture was then cooled to room temperature and filtered through celite and concentrated. The residue was purified by Prep-TLC (petroleum ether/EtOAc=10/1) to give 173-2 (440 mg, about 91% yield) as an oil. MS Calcd.: 204.0; MS Found: 205.1 $[M+H]^+$.

The Synthesis of 5-chloro-N-(2-chloroethyl)-2-phenylpyridin-3-amine (173-3)

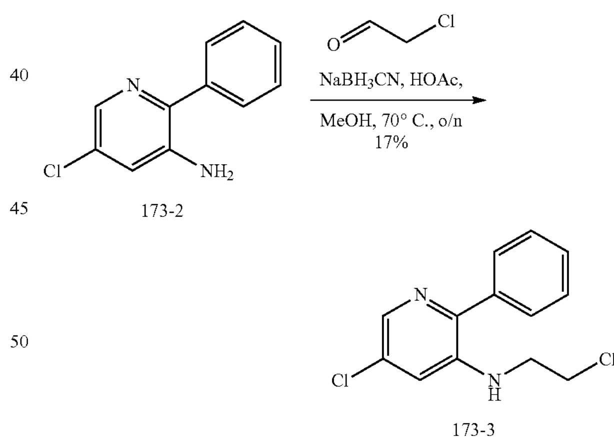

173-2

173-3

To a solution of 173-2 (450 mg, 2.20 mmol) in MeOH (10 mL) was added 2-chloroacetaldehyde (432 mg, 4.40 mmol, 40% in water), AcOH (264 mg, 4.40 mmol), and $NaBH_3CN$ (275 mg, 4.40 mmol), then the reaction mixture was stirred at room temperature overnight. Then the reaction mixture was poured into water and basicified with 1N NaOH till pH reached 10. The mixture was extracted with EtOAc (30 mL×3). The organic layers were washed with brine, dried over $Na_2SO_4$ and concentrated. The residue was purified via column chromatography (petroleum ether/EtOAc=10/1) to give 173-3 (100 mg, about 17% yield) as a solid. MS Calcd.: 266.0; MS Found: 237.1 $[M+H]^+$.

The Synthesis of N-(2-(1H-1,2,4-triazol-1-yl)ethyl)-5-chloro-2-phenylpyridin-3-amine (173-4)

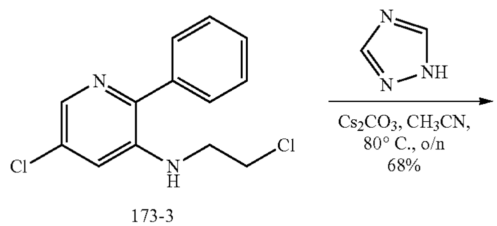

173-3

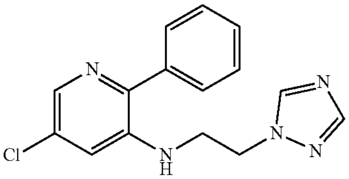

173-4

A mixture of 173-3 (100 ng, 0.37 mmol), 1H-1,2,4-triazole (52 mg, 0.74 mmol) and $Cs_2CO_3$ (240 mg, 0.74 mmol) in $CH_3CN$ (10 mL) was stirred at 80° C. overnight. The reaction mixture was then cooled to room temperature and filtered through celite and concentrated. The residue was purified by column chromatography (petroleum ether/EtOAc=1/1) to give 173-4 (77 mg, about 68% yield) as a solid. MS Calcd.: 299.1; MS Found: 300.2 $[M+H]^+$.

The Synthesis of $N^3$-(2-(1H-1,2,4-triazol-1-yl)ethyl)-$N^5$,2-diphenylpyridine-3,5-diamine (SS20308-0173-01)

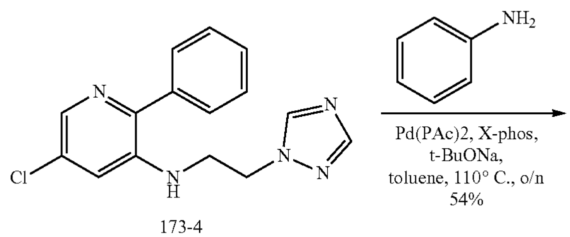

173-4

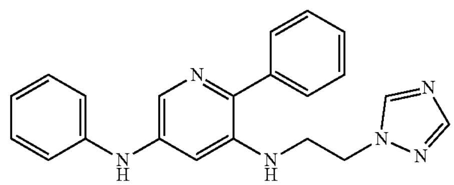

SS20308-0173-01

The mixture of 173-4 (20 mg, 0.67 mmol), aniline (13 mg, 0.14 mmol), $Pd(OAc)_2$ (32 mg, 0.14 mmol), X-phos (138 mg, 0.28 mmol) and t-BuONa (13 mg, 0.14 mmol) in toluene (2 mL) was stirred at 110° C. overnight under $N_2$ atmosphere. The reaction mixture was then cooled to room temperature and filtered through celite and concentrated. The residue was purified by Prep-TLC (petroleum ether/EtOAc=1/3) and Prep-HPLC to give SS20308-0173-01 (13 mg, about 54% yield) as a solid. MS Calcd.: 356.2; MS Found: 357.3 $[M+H]^+$.

$^1$H NMR (400 MHz, DMSO-$d_6$) δ 8.48 (s, 1H), 8.25 (s, 1H), 7.95 (s, 1H), 6.68 (d, J=2.4 Hz, 1H), 7.47-7.45 (m, 2H), 4.36 (t, J=7.4 Hz, 2H), 7.34-7.25 (m, 3H), 7.14 (d, J=7.6 Hz, 2H), 4.36 (t, J=7.2 Hz, 1H), 7.14 (d, J=2.0 Hz, 1H), 5.17 (t, J=6.0 Hz, 1H), 4.36 (t, J=6.0 Hz, 2H), 3.46 (dd, J=12.0, 6.0 Hz, 2H).

Example 67

SS20308-0175-01

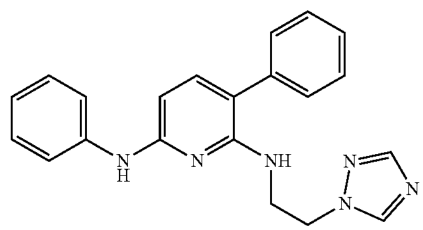

Example Route for Example 67

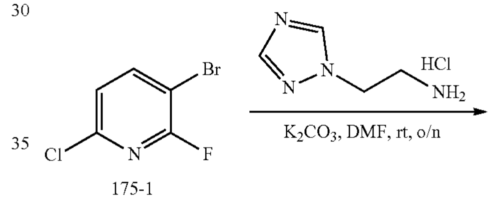

175-1

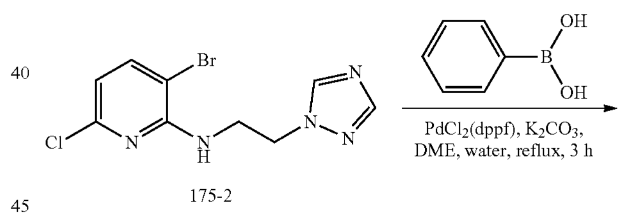

175-2

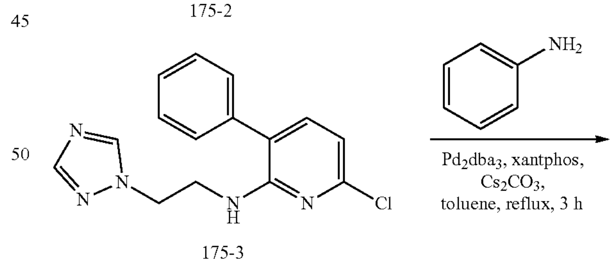

175-3

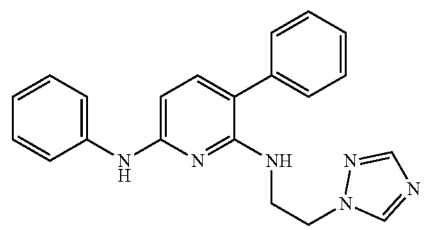

SS20308-0175-01

The Synthesis of N-(2-(1H-1,2,4-triazol-1-yl)ethyl)-3-bromo-6-chloropyridin-2-amine (175-2)

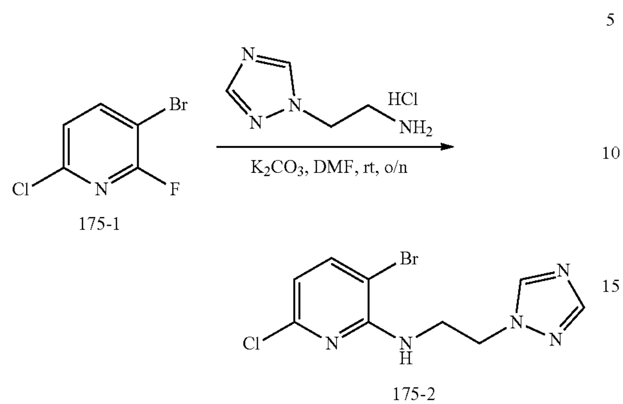

175-1

175-2

The mixture of 175-1 (1.00 g, 4.75 mmol), 2-(1H-1,2,4-triazol-1-yl)ethanamine hydrochloride (847 mg, 5.70 mmol), and $K_2CO_3$ (1.97 g, 14.25 mmol) in DMF (10 mL) was stirred at rt overnight. Then mixture was poured into water and extracted with EtOAc (30 mL×3) and the organic layers were washed with brine, dried over $MgSO_4$ and concentrated. The residue was purified by column chromatography (petroleum ether/EtOAc=1/1) to give 175-2 (1.0 g, about 71% yield) as a solid. MS Calcd.: 301.0; MS Found: 302.0 $[M+H]^+$.

The Synthesis of N-(2-(1H-1,2,4-triazol-1-yl)ethyl)-6-chloro-3-phenylpyridin-2-amine (175-3)

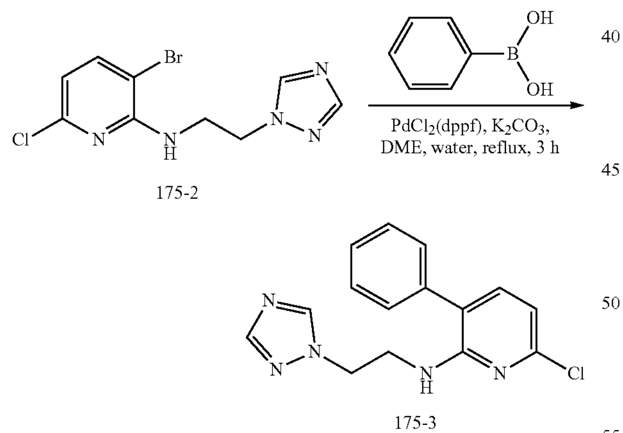

175-2

175-3

The mixture of 175-2 (300 mg, 0.99 mmol), phenylboronic acid (145 mg, 1.19 mmol), Pd(dppf)$Cl_2$ (7.3 mg, 0.01 mmol) and $K_2CO_3$ (410 mg, 2.97 mmol) in DME (5 mL) was stirred at 80° C. for 4 h under $N_2$ atmosphere. The resulting mixture was extracted with ethyl acetate (30 mL×3) and the organic layers were washed with brine, dried over $MgSO_4$ and concentrated. The residue was purified by column chromatography (petroleum ether/EtOAc=1/2) to give 175-3 (250 mg, about 84% yield) as a solid. MS Calcd.: 299.1; MS Found: 300.2 $[M+H]^+$ The Synthesis of $N^2$-(2-(1H-1,2,4-triazol-1-yl)ethyl)-$N^6$,3-diphenylpyridine-2,6-diamine (SS20308-0175-01)

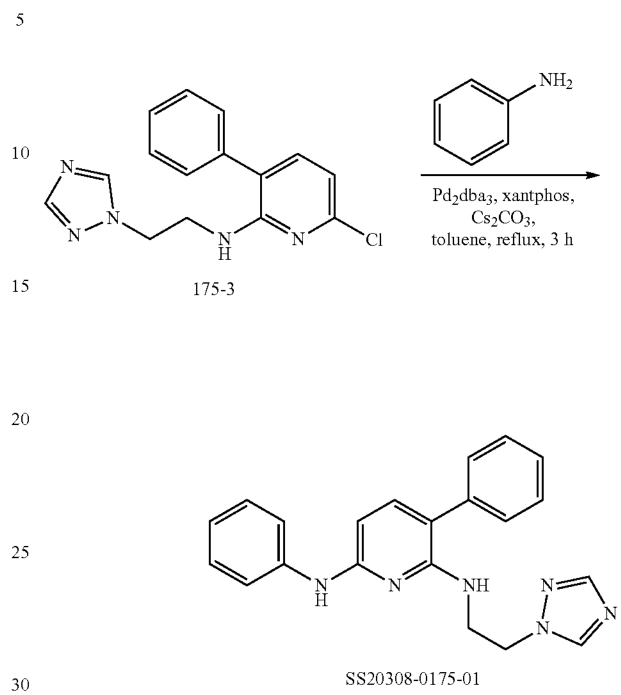

175-3

SS20308-0175-01

The mixture of 175-3 (50 mg, 0.17 mmol), aniline (47 mg, 0.50 mmol) and $Cs_2CO_3$ (162 mg, 0.50 mmol), $Pd_2(dba)_3$ (16 mg, 0.017 mmol) and Xantphos (20 mg, 0.034 mmol) in toluene (3 mL) was stirred at 110° C. for 3 h under N2 atmosphere. The reaction mixture was then cooled to room temperature and was purified by Prep-HPLC to give SS20308-0175-01 (44 mg, about 72% yield) as a solid. MS Calcd.: 356.2; MS Found: 357.3 $[M+H]^+$.

$^1H$ NMR (400 MHz, DMSO-$d_6$) δ 8.82 (s, 1H), 8.43 (s, 1H), 7.98 (s, 1H), 7.68 (d, J=8.8 Hz, 2H), 7.38-7.42 (m, 2H), 7.29-7.31 (m, 3H), 7.22-7.26 (m, 2H), 7.18 (d, J=8.0 Hz, 1H), 6.85 (t, J=7.2 Hz, 1H), 6.17 (d, J=8.0 Hz, 1H) 5.80 (t, J=5.4 Hz, 1H), 4.42 (t, J=6.0 Hz, 2H), 3.75 (q, J=6.0 Hz, 2H).

Example 68

SS20308-0177-01

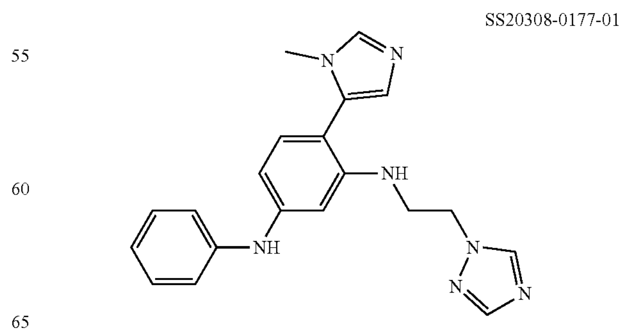

Example Route for Example 68

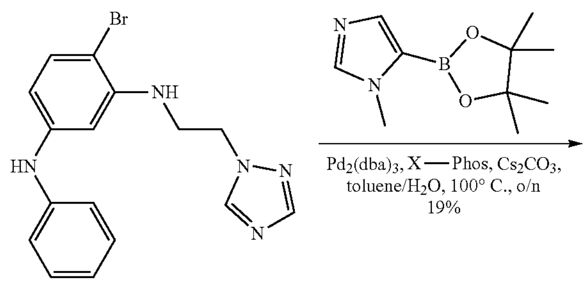

143-5

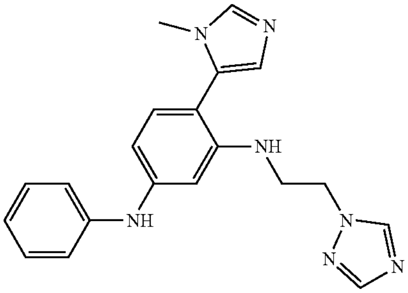

SS20308-0177-01

The Synthesis of N[3]-(2-(1H-1,2,4-triazol-1-yl) ethyl)-4-(1-methyl-1H-imidazol-5-yl)-N[1]-phenylbenzene-1,3-diamine (SS20308-177-01)

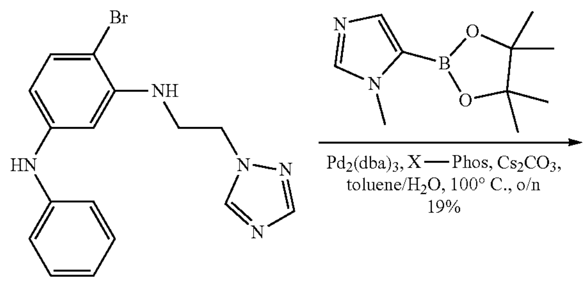

143-5

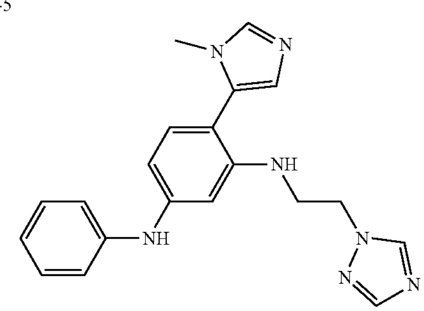

SS20308-0177-01

A mixture of 143-5 (70 mg, 0.20 mmol), 1-methyl-5-(4,4,5,5-tetramethyl-1,3,2-dioxaborolan-2-yl)-1H-imidazole (63 mg, 0.30 mmol), $Pd_2(dba)_3$ (9 mg, 0.01 mmol) and X-Phos (9 mg, 0.02 mmol), $Cs_2CO_3$ (130 mg, 0.40 mmol) in toluene/water (2/0.2 mL) was stirred at reflux overnight. The reaction mixture was cooled to room temperature and poured into water (50 mL) and extracted with EtOAc (30 mL×3). The organic layer was washed with brine and concentrated. The crude product was purified by Prep-HPLC to give SS20308-177-01 (14 mg, 19% yield) as a solid. MS Calcd.: 359.4; MS Found: 360.3 $[M+H]^+$.

$^1H$ NMR (400 MHz, DMSO-$d_6$) δ 8.43 (s, 1H), 8.16 (s, 1H), 7.93 (s, 1H), 7.66 (s, 1H), 7.24 (t, J=8.4 Hz, 2H), 7.12 (d, J=7.6 Hz, 2H), 6.85-6.82 (m, 2H), 6.74 (s, 1H), 6.43-6.39 (m, 2H), 4.74 (t, J=5.6 Hz, 1H), 4.35 (t, J=6.0 Hz, 2H), 3.45-3.41 (m, 2H), 3.28 (s, 3H).

Example 69

SS20308-0178-01

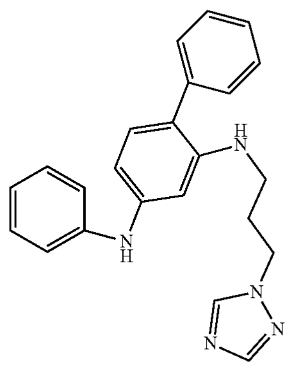

Example Route for Example 69

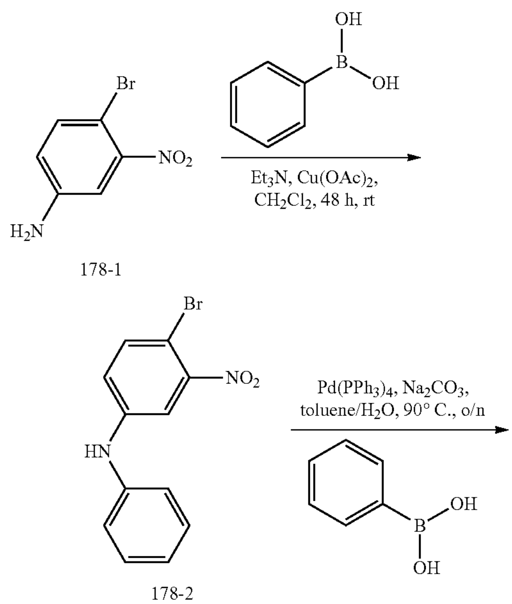

178-1

178-2

-continued

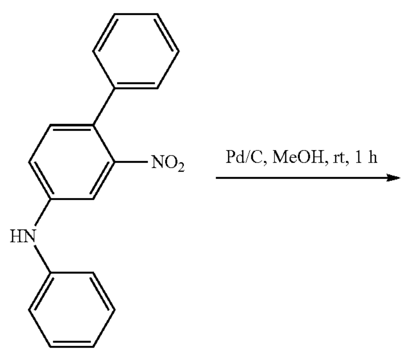

178-3

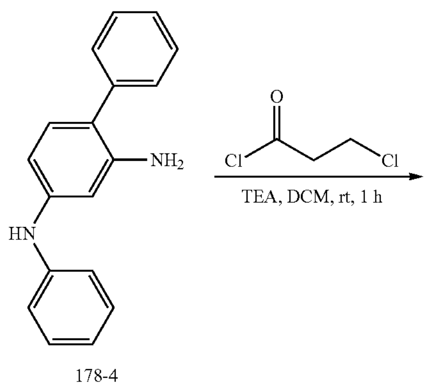

178-4

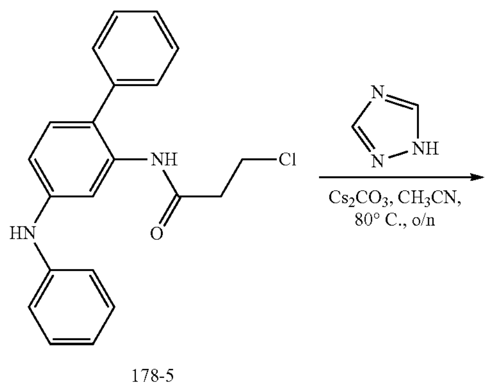

178-5

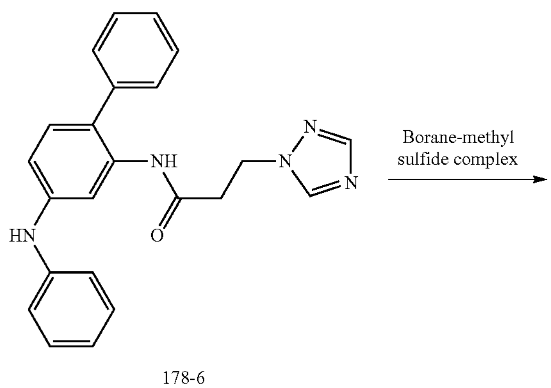

178-6

-continued

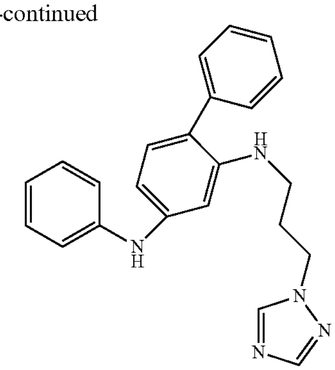

SS20308-0178-01

The Synthesis of 4-bromo-3-nitro-N-phenylaniline (178-2)

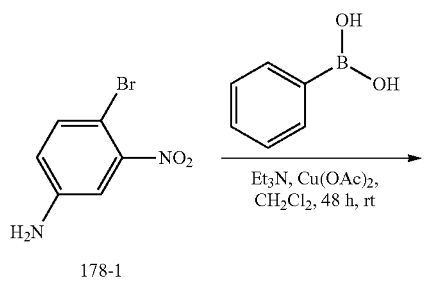

178-1

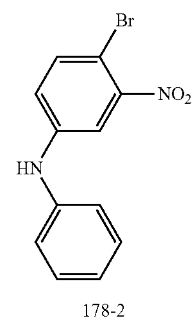

178-2

The mixture of 178-1 (1.00 g, 4.61 mmol), phenylboronic acid (674 mg, 5.53 mmol), $Et_3N$ (560 mg, 5.53 mmol) and $Cu(OAc)_2$ (837 mg, 4.61 mmol) in DCM (10 mL) was stirred at rt for 48 h. Then mixture was poured into water and extracted with EtOAc (30 mL×3) and the organic layers were washed with brine, dried over $MgSO_4$ and concentrated. The residue was purified by column chromatography (petroleum ether/EtOAc=5/1) to give 178-2 (500 mg, about 37% yield) as a solid.

$^1$H NMR (400 MHz, $CDCl_3$) δ 7.42-7.49 (m, 1H), 7.37 (d, J=2.8 Hz, 1H), 7.26-7.31 (m, 2H), 7.02-7.06 (m, 3H), 6.93-6.96 (m, 1H) 5.84 (brs, 1H).

The Synthesis of 2-nitro-N-phenylbiphenyl-4-amine (178-3)

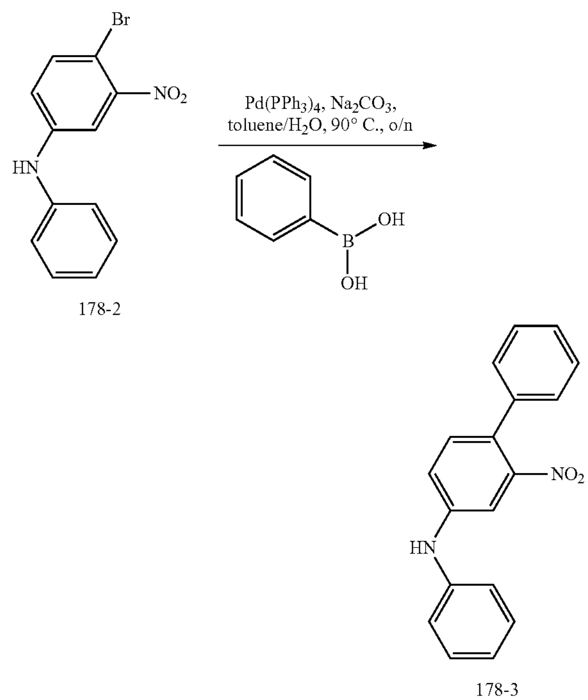

178-2

178-3

The mixture of 178-2 (500 mg, 1.71 mmol), phenylboronic acid (250 mg, 2.05 mmol), $Pd(PPh_3)_4$ (196 mg, 0.17 mmol) and $Na_2CO_3$ (544 mg, 5.13 mmol) in DME/$H_2O$ (5 mL, 5/1) was stirred at 90° C. overnight under N2 atmosphere. The resulting mixture was extracted with ethyl acetate (30 mL×3) and the organic layers were washed with brine, dried over $MgSO_4$ and concentrated. The residue was purified by column chromatography (petroleum ether/EtOAc=2/1) to give 178-3 (400 mg, about 81% yield) as a solid. MS Calcd.: 290.1; MS Found: 291.1 $[M+H]^+$.

The Synthesis of $N^4$-phenylbiphenyl-2,4-diamine (178-4)

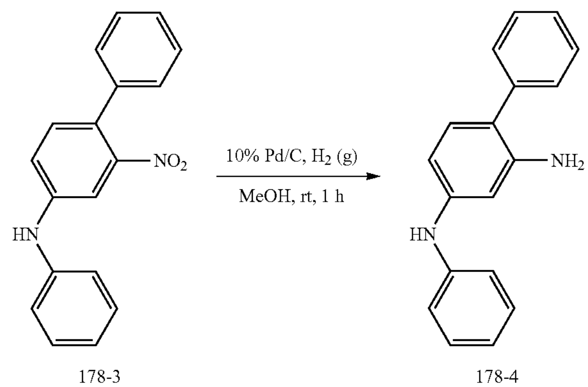 [SMILES: O=[N+]([O-])c1cc(Nc2ccccc2)ccc1-c1ccccc1 ; Nc1cc(Nc2ccccc2)ccc1-c1ccccc1]

178-3 178-4

The mixture of 178-3 (400 mg, 1.38 mmol), and 10% Pd/C (47 mg, 1.38 mmol) in MeOH (5 mL) was stirred at rt for 1 h under $H_2$ (g) (1 atm). The reaction mixture was then cooled to room temperature and was purified by Prep-TLC to give 178-4 (320 mg, about 89% yield) as a solid. MS Calcd.: 260.1; MS Found: 261.4 $[M+H]^+$ The Synthesis of 3-chloro-N-(4-(phenylamino)biphenyl-2-yl)propanamide (178-5)

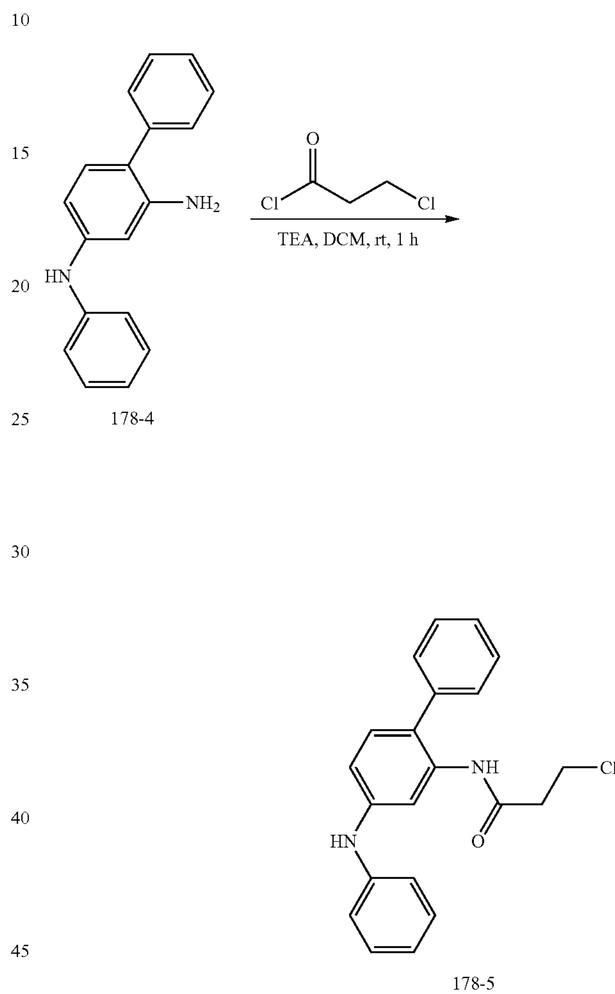

178-4

178-5

The mixture of 178-4 (330 mg, 1.27 mmol), 3-chloropropanoyl chloride (161 mg, 1.27 mmol), and TEA (128 mg, 1.27 mmol) in DCM (10 mL) was stirred at rt for 1 h. Then the mixture was poured into water and extracted with $CH_2Cl_2$ (3×30 mL). The combined organic layers were washed with water and brine, dried over $Na_2SO_4$ and concentrated. The residue was purified by column chromatography (petroleum ether/EtOAc=1/1) to give 178-5 (350 mg, about 79% yield) as a solid. MS Calcd.: 350.1; MS Found: 351.3 $[M+H]^+$.

The Synthesis of N-(4-(phenylamino)biphenyl-2-yl)-3-(1H-1,2,4-triazol-1-yl)propanamide (178-6)

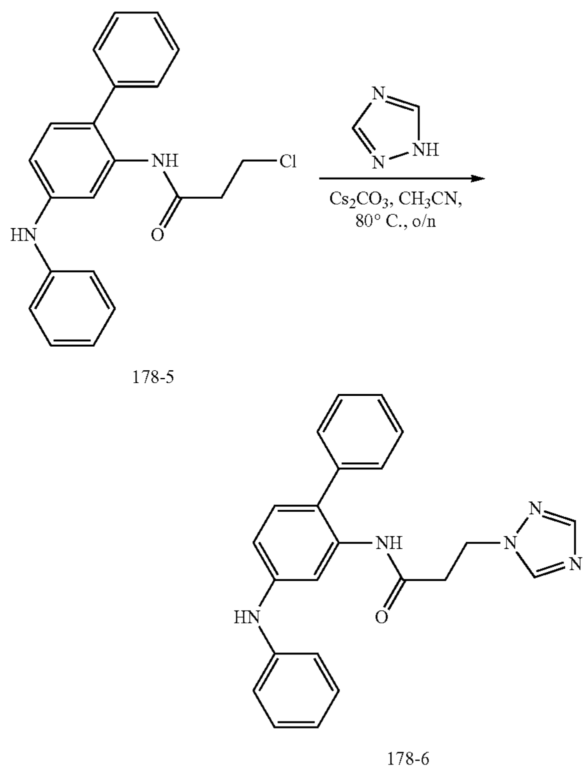

178-5

178-6

The mixture of 178-5 (350 mg, 1.00 mmol), 1H-1,2,4-triazole (207 mg, 3.00 mmol) and $Cs_2CO_3$ (975 mg, 3.00 mmol) in $CH_3CN$ (10 mL) was stirred at 80° C. overnight. Then mixture was poured into water and extracted with ethyl acetate (30 mL×3) and the organic layers were washed with brine, dried over $MgSO_4$ and concentrated. The residue was purified by column chromatography (petroleum ether/EtOAc=1/2) to give 178-6 (300 mg, 78% yield) as a solid. MS Calcd.: 383.2; MS Found: 384.3 $[M+H]^+$.

The Synthesis of $N^2$-(3-(1H-1,2,4-triazol-1-yl)propyl)-$N^4$-phenylbiphenyl-2,4-diamine (SS20308-0178-01)

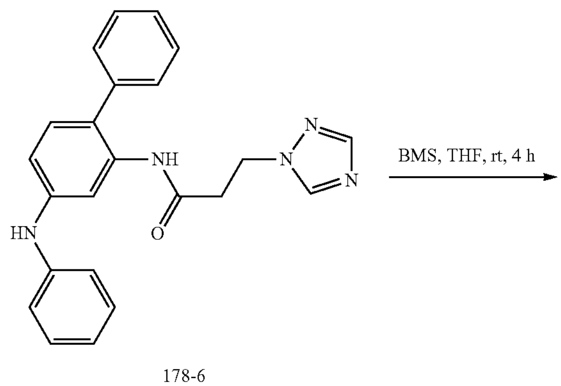

178-6

-continued

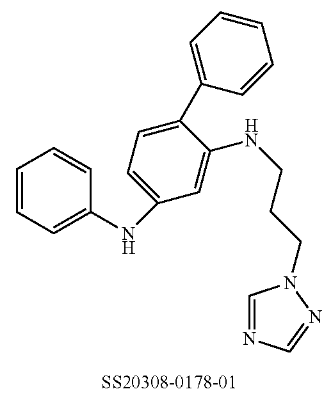

SS20308-0178-01

The mixture of 178-6 (50 mg, 0.13 mmol) and Borane-Methyl Sulfide (2.5 M in THF) (5 mL) was stirred at rt overnight. Then mixture was poured into water and extracted with ethyl acetate (30 mL×3) and the organic layers were washed with brine, dried over $MgSO_4$ and concentrated. The residue was purified by Prep-MPLC (petroleum ether/EtOAc=1/2) to give SS20308-0178-01 (28 mg, about 59% yield) as a solid. MS Calcd.: 369.2; MS Found: 370.0 $[M+H]^+$.

$^1H$ NMR (400 MHz, DMSO-$d_6$) δ 8.49 (s, 1H), 8.07 (s, 1H), 7.91 (s, 1H), 7.37-7.45 (m, 4H), 7.28-7.32 (m 1H), 7.20-7.24 (t, 2H) 7.08 (d, J=7.2 Hz, 2H), 6.86 (d, J=8.0 Hz, 1H), 6.79 (t, J=7.2 Hz, 1H), 6.44-6.46 (m, 1H), 6.35 (d, J=2.0 Hz, 1H), 4.64 (t, J=5.6 Hz, 1H), 4.22 (t, J=6.8 Hz, 2H), 2.98-3.03 (m, 2H), 2.02-2.08 (m, 2H).

Example 70

SS20308-0181-01

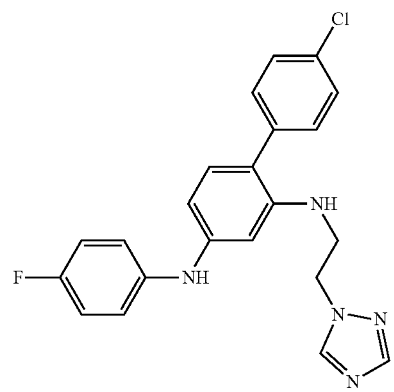

Chemical Formula: $C_{22}H_{19}ClFN_5$
Molecular Weight: 407.87

Example Route for Example 70

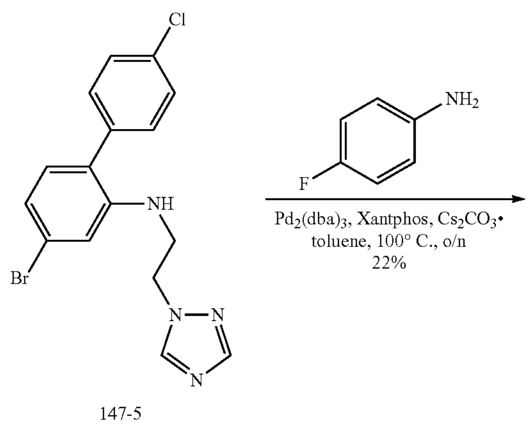

147-5

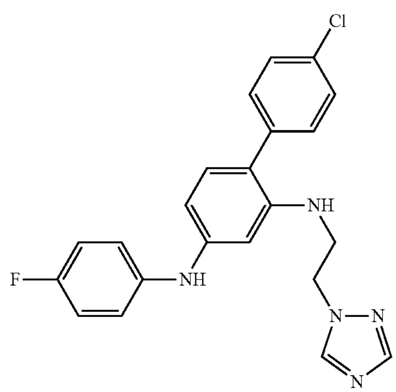

SS20308-0181-01

The Synthesis of $N^2$-(2-(1H-1,2,4-triazol-1-yl) ethyl)-4'-chloro-$N^4$-(4-fluorophenyl)biphenyl-2,4-diamine (SS20308-0181-01)

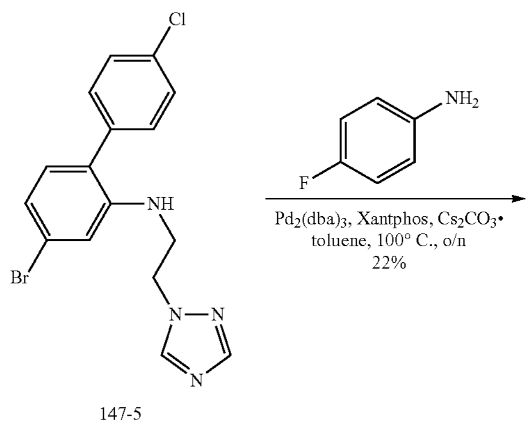

147-5

-continued

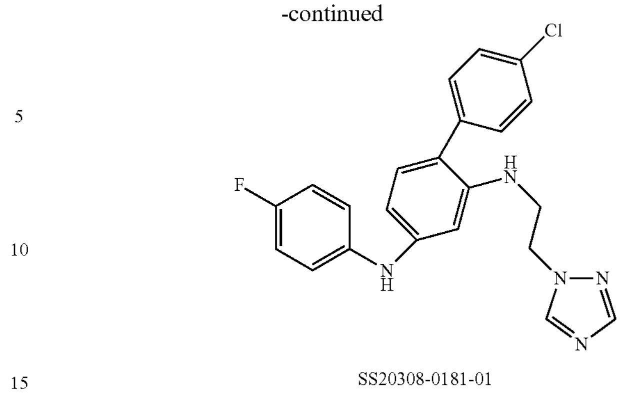

SS20308-0181-01

The mixture of 147-5 (50 mg, 0.13 mmol), 4-fluoroaniline (22 mg, 0.20 mmol), $Pd_2dba_3$ (26 mg, 0.29 mmol), Xantphos (34 mg, 0.058 mmol) and $Cs_2CO_3$ (189 mg, 0.58 mmol) in toluene (2 mL) was stirred at 100° C. overnight under $N_2$ atmosphere. The reaction mixture was then cooled to room temperature and filtered through celite and concentrated. The residue was purified by Prep-HPLC to give SS20308-0181-01 (14.3 mg, about 13% yield) as a solid. MS Calcd.: 407.1; MS Found: 408.2 $[M+H]^+$.

$^1$H NMR (400 MHz, DMSO-$d_6$) δ 8.46 (s, 1H), 8.07 (s, 1H), 7.97 (s, 1H), 7.43 (d, J=8.4 Hz, 2H), 7.26 (d, J=8.4 Hz, 2H), 7.14-7.05 (m, 4H), 6.85 (d, J=8.0 Hz, 1H), 6.39 (dd, J=8.0, 2.0 Hz, 1H), 6.33 (d, J=2.0 Hz, 1H), 4.85 (t, J=5.8 Hz, 1H), 4.36 (t, J=6.0 Hz, 2H), 3.37-3.43 (m, 2H).

Example 71

SS20308-0184-01

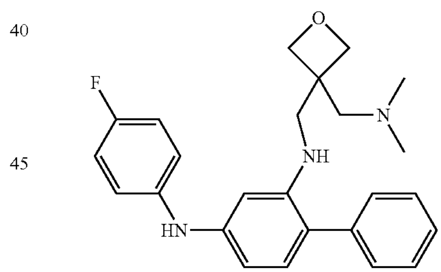

Example Route for Example 71

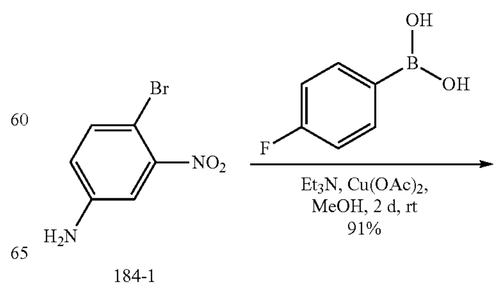

184-1

-continued

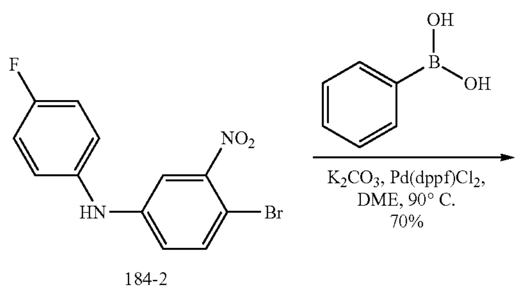

184-2

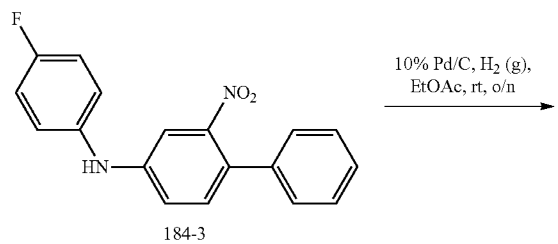

184-3

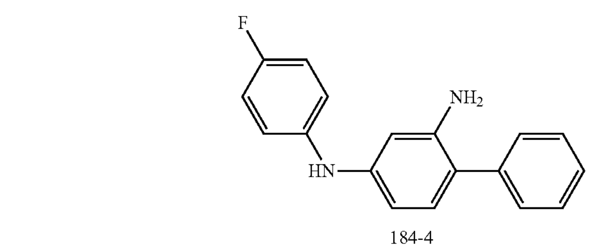

184-4

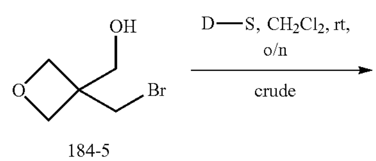

184-5

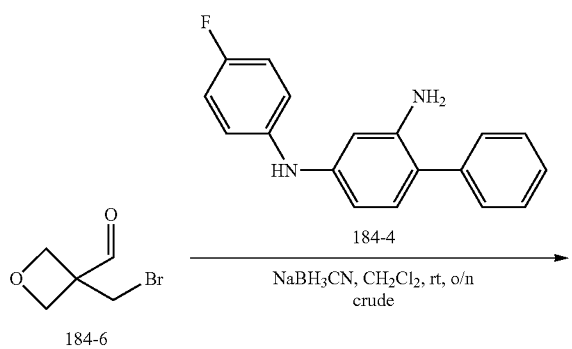

184-6

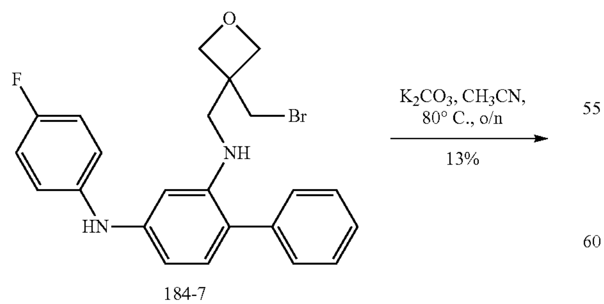

184-7

-continued

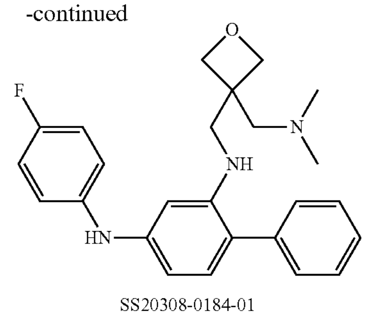

SS20308-0184-01

The Synthesis of 4-bromo-N-(4-fluorophenyl)-3-nitroaniline (184-2)

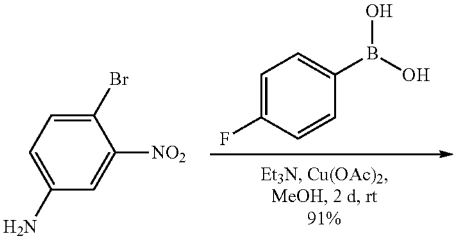

Et3N, Cu(OAc)2,
MeOH, 2 d, rt
91%

184-1

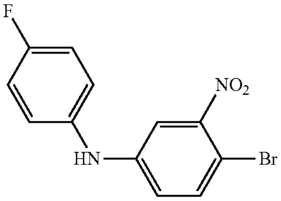

184-2

A mixture of 184-1 (500 mg, 2.30 mmol), 4-fluorophenylboronic acid (322 mg, 2.30 mmol), $Et_3N$ (466 mg, 4.61 mmol), $Cu(OAc)_2$ (418 mg, 2.30 mmol) in MeOH (20 ml) was stirred at room temperature for 48 h. After the reaction was complete, the reaction mixture was poured into water (500 mL) and extracted with EtOAc (40 mL×3). The organic layer was washed brine (2×50 mL), dried over $MgSO_4$, and concentrated under vacuum, which was purified by column chromatography (petroleum ether/EtOAc=1/1) to give 184-2 (650 mg, about 91% yield) as a solid. MS Calcd.: 310.0; MS Found: 311.0 $[M+H]^+$.

The Synthesis of N-(4-fluorophenyl)-2-nitrobiphenyl-4-amine (184-3)

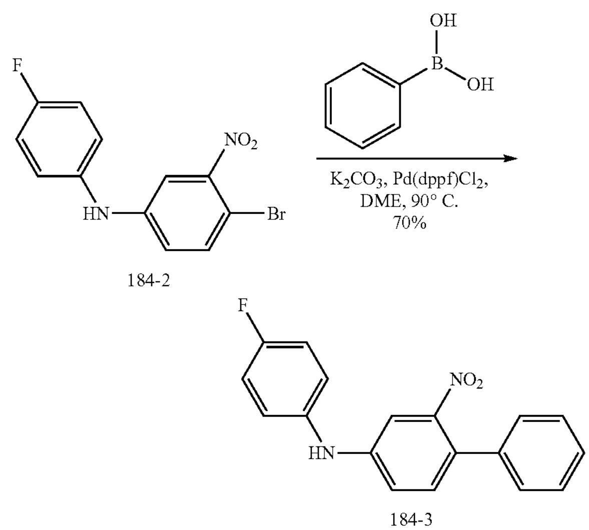

184-2

184-3

A mixture of 184-2 (650 mg, 2.09 mmol), phenylboronic acid (255 mg, 2.09 mmol), Pd(dppf)$Cl_2$ (76 mg, 0.10 mmol), $K_2CO_3$ (578 mg, 4.18 mmol) in DME (20 ml) was stirred at 90° C. under nitrogen atmosphere overnight. After the reaction was complete, the reaction mixture was poured into water (50 mL) and extracted with EtOAc (4 mL×3). The organic layer was washed brine (2×50 mL), dried over $MgSO_4$, and concentrated under vacuum, which was purified by column chromatography (petroleum ether/EtOAc=1/1) to give 184-3 (450 mg, about 70% yield) as a solid. MS Calcd.: 308.1; MS Found: 309.0 $[M+H]^+$.

The Synthesis of $N^4$-(4-fluorophenyl)biphenyl-2,4-diamine (184-4)

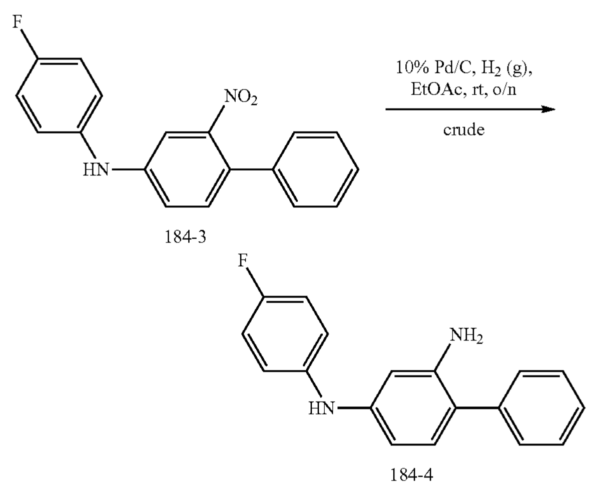

184-3

184-4

To a solution 184-3 (3.00 g, 9.31 mmol) in EtOAc (50 mL) was added 10% Pd/C (6.09 g, 93.13 mmol). The mixture was stirred at room temperature under $H_2$ (g) (1 atm) overnight. After the reaction was complete, the insoluble material was removed by filtration, and the filtrate was concentrated under vacuum. This crude product was used in the next step without further purification. MS Calcd.: 278.1; MS Found: 279.2 $[M+H]^+$.

The Synthesis of $N^2$-((3-(bromomethyl)oxetan-3-yl)methyl)-$N^4$-(4-fluorophenyl)biphenyl-2,4-diamine (184-7)

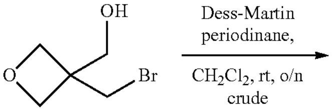

184-5

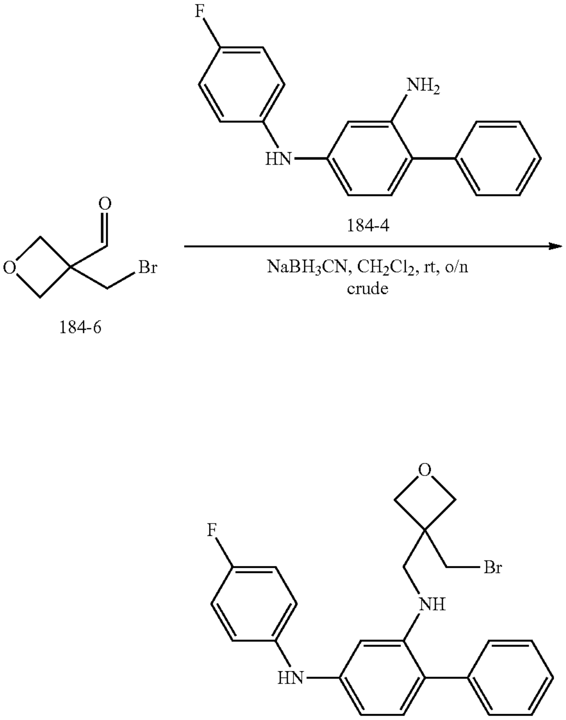

184-4

184-6

184-7

To a solution of 184-5 (200 mg, 1.10 mmol) in $CH_2Cl_2$ (10 mL) was added Dess-Martin periodinane (937 mg, 2.21 mmol). The mixture was stirred at room temperature for overnight. After the reaction was complete, the insoluble material was removed by filtration, and the filtrate was added 184-4 (307 mg, 1.10 mmol) and $NaBH_3CN$ (139 mg, 2.21 mmol), the mixture was stirred at room temperature overnight. After the reaction was complete, the reaction mixture was poured into water (50 mL) and extracted with EtOAc (50 mL×3). The organic layer was washed brine (2×50 mL), dried over $MgSO_4$, and concentrated under vacuum. The resulting crude product was used in the next step without further purification.

The Synthesis of $N^2$-((3-((dimethylamino)methyl)oxetan-3-yl)methyl)-$N^4$-(4-fluorophenyl)biphenyl-2,4-diamine (SS20308-0184-01)

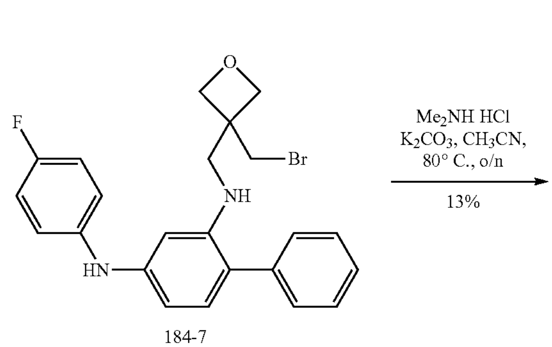

184-7

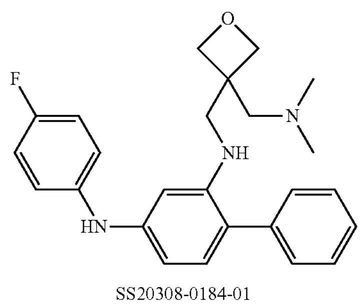

SS20308-0184-01

A mixture of 184-7 (50 mg, 0.11 mmol), dimethylamine hydrochloride (18 mg, 0.23 mmol), and $K_2CO_3$ (63 mg, 0.45 mmol) in $CH_3CN$ (20 ml) was stirred at 80° C. under nitrogen atmosphere overnight. After the reaction was complete, the reaction mixture was poured into water (50 mL) and extracted with EtOAc (4 mL×3). The organic layer was washed with brine (2×50 mL), dried over $MgSO_4$, and concentrated under vacuum. The crude product was purified by Prep-HPLC to give SS20308-0184-01 (6 mg, about 13% yield) as a solid. MS Calcd.: 405.2; MS Found: 406.0 $[M+H]^+$.

$^1H$ NMR (400 MHz, DMSO-$d_6$) δ 8.05 (s, 1H), 7.43-7.40 (m, 2H), 7.34-7.27 (m, 3H), 7.13-7.05 (m, 4H), 6.85 (d, J=8.0 Hz, 1H), 6.48 (d, J=2.0 Hz, 1H), 6.41 (dd, J=8.0 Hz, 2.0 Hz, 1H), 5.48 (t, J=5.6 Hz, 1H), 4.33 (d, J=6.0 Hz, 2H), 4.25 (d, J=6.4 Hz, 2H), 3.41 (d, J=6.0 Hz, 2H), 2.48 (d, J=6.0 Hz, 2H), 1.81 (s, 6H).

Example 72

SS20308-0189-01

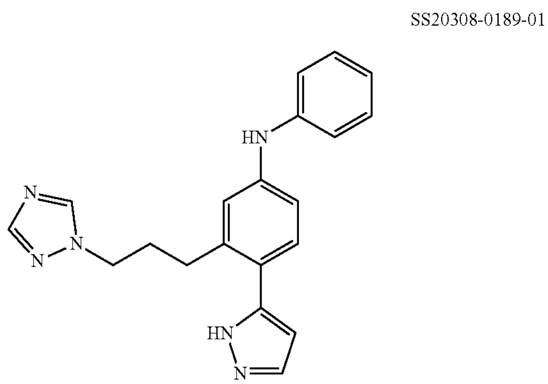 [SMILES: c1ccc(Nc2ccc(-c3ccn[nH]3)c(CCCn3cncn3)c2)cc1]

Example Route for Example 72 (SS20308-0189-01 and SS20308-0223-01)

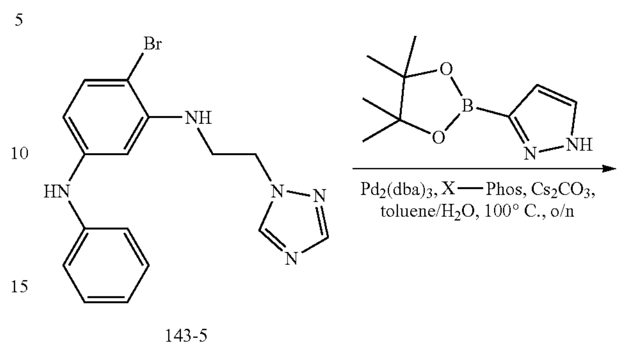

143-5

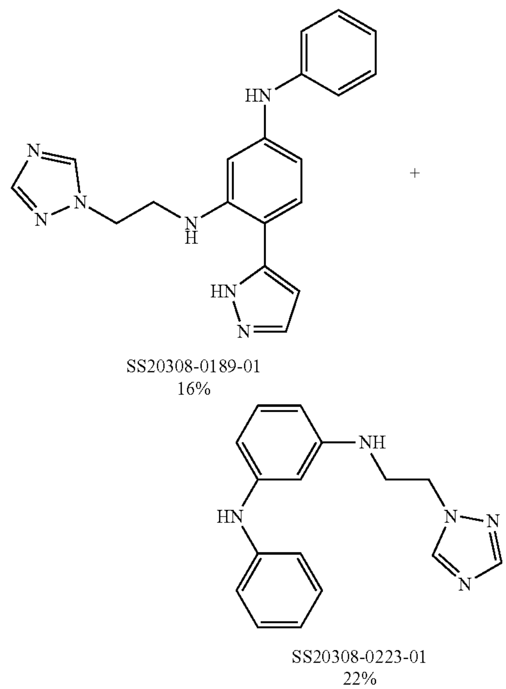

SS20308-0189-01
16%

SS20308-0223-01
22%

A mixture of 143-5 (50 mg, 0.14 mmol), 3-(4,4,5,5-tetramethyl-1,3,2-dioxaborolan-2-yl)-1H-pyrazole (41 mg, 0.21 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (50 mL) and extracted with EtOAc (30 mL×3). The organic layer was washed with brine and evaporated, the residue crude product was purified by Prep-HPLC to give SS20308-189-01 (7.04 mg, about 16% yield) as a solid, MS Calcd.: 345.4; MS Found: 346.3 $[M+H]^+$;

$^1H$ NMR (400 MHz, DMSO-$d_6$) δ 12.69 (s, 1H), 8.47 (s, 1H), 8.12 (s, 1H), 7.97 (s, 1H), 7.86 (t, J=6.0 Hz, 1H), 7.73 (d, J=1.6 Hz, 1H), 7.45 (d, J=8.8 Hz, 1H), 7.23 (t, J=8.4 Hz, 2H), 7.11 (d, J=7.6 Hz, 2H), 6.81 (t, J=7.2 Hz, 1H), 6.60-6.59 (m, 1H), 6.43-6.41 (m, 2H), 4.45 (t, J=6.0 Hz, 2H), 3.63-3.58 (m, 2H). and SS20308-223-01 (8.59 mg, about 22% yield) as a solid, MS Calcd.: 279.3; MS Found: 280.0 $[M+H]^+$.

$^1H$ NMR (400 MHz, DMSO-$d_6$) δ 8.47 (s, 1H), 7.97 (s, 1H), 7.91 (s, 1H), 7.19 (t, J=8.4 Hz, 2H), 7.03 (d, J=7.6 Hz, 2H), 6.93 (d, J=7.6 Hz, 1H), 6.77 (t, J=7.6 Hz, 1H), 6.32-6.30 (m, 2H), 6.10-6.08 (m, 1H), 5.67 (t, J=2.0 Hz, 1H), 4.32 (t, J=6.4 Hz, 2H), 3.44-3.40 (m, 2H).

Examples 73 to 78 follow all follow the same initial syntheses steps shown below and will not be repeated for each individual example:

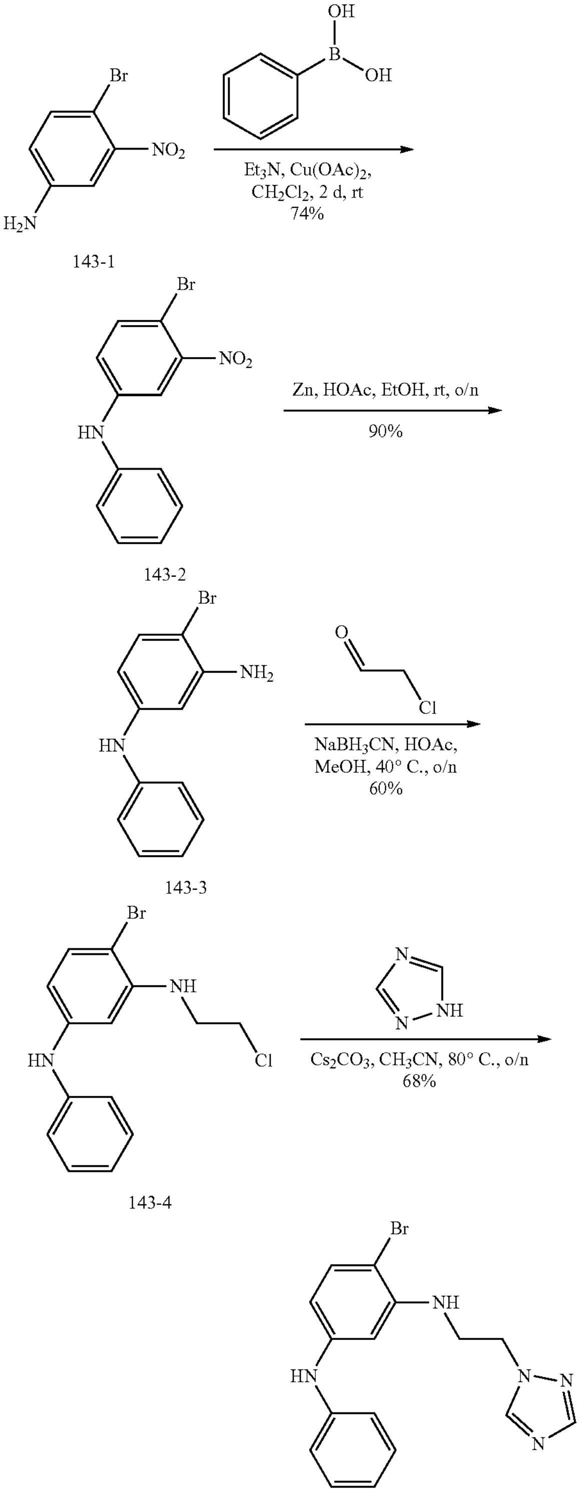

143-1

143-2

143-3

143-4

143-5

The Synthesis of 4-bromo-3-nitro-N-phenylaniline (143-2)

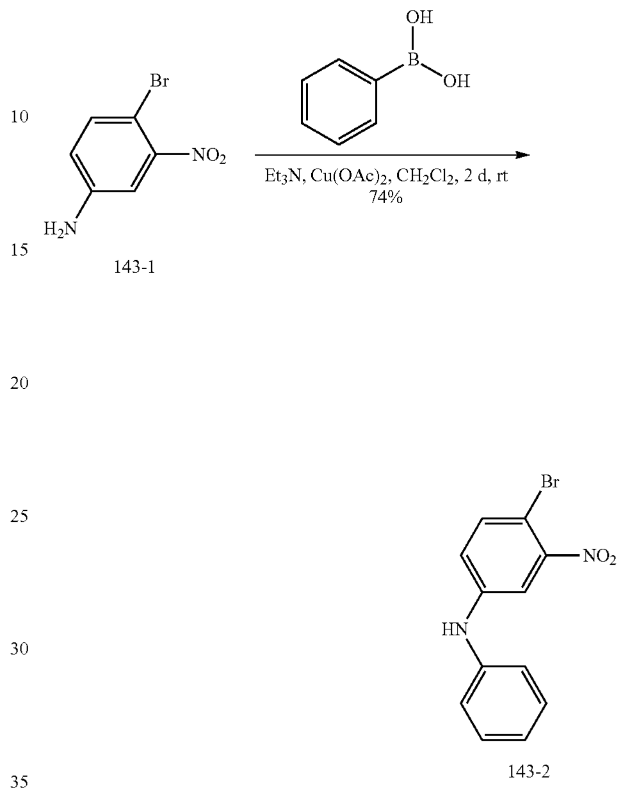

143-1

143-2

A mixture of 143-1 (1.0 g, 4.6 mmol), phenylboronic acid (1.1 g, 9.2 mmol) and $Cu(OAc)_2$ (833 mg, 4.6 mmol), $Et_3N$ (2.3 g, 23 mmol) in $CH_2Cl_2$ (100 mL) was stirred at rt for 2 d. After the reaction was complete, the insoluble material was removed by filtration. The filtrate was poured into water (100 mL) and extracted with EtOAc (100 mL×3). The combined layers were dried over $Na_2SO_4$, and concentrated under vacuum. The residue was purified by column chromatography to give 143-2 (1.0 g, about 74% yield) as a solid.

The Synthesis of 4-bromo-$N^1$-phenylbenzene-1,3-diamine (143-3)

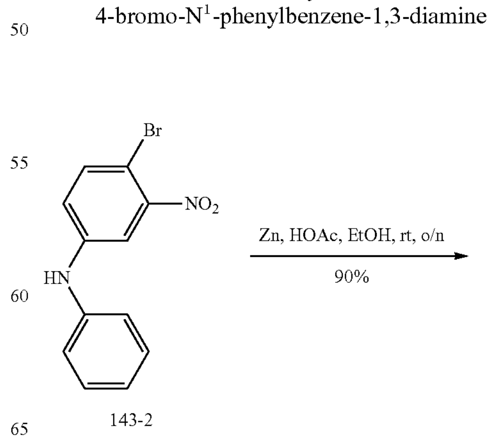

143-2

-continued

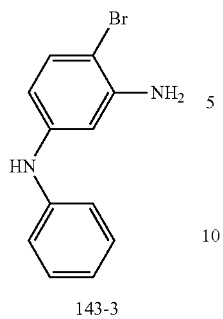

143-3

A mixture of 143-2 (1.0 g, 3.4 mmol), Zn powder (1.1 g, 17 mmol) and HOAc (1.0 g, 17 mmol) in EtOH (50 mL) was stirred at rt overnight. After the reaction was complete, the insoluble material was removed by filtration. The filtrate was poured into water (100 mL) and extracted with EtOAc (100 mL×3). The combined layers were dried over $Na_2SO_4$, and concentrated under vacuum. The residue was purified by column chromatography (petroleum ether/EtOAc=5/1) to give 143-3 (800 mg, about 90% yield) as a solid. MS Found: 263.2 $[M+H]^+$.

The Synthesis of 4-bromo-$N^3$-(2-chloroethyl)-$N^1$-phenylbenzene-1,3-diamine (143-4)

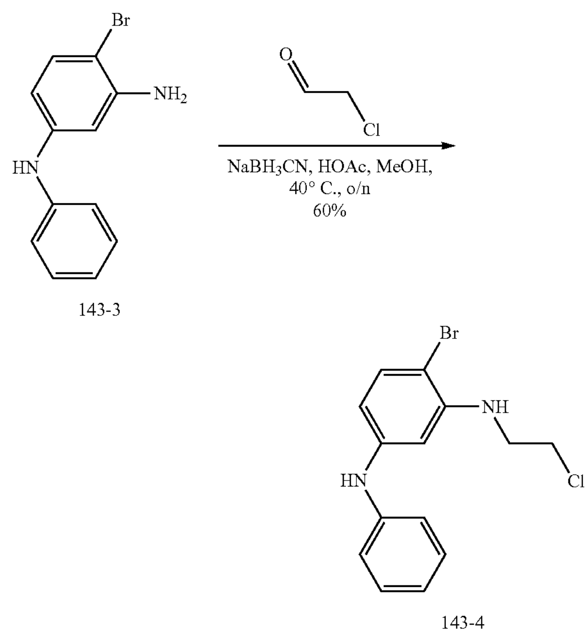

143-3

143-4

A mixture of the 143-3 (800 mg, 3.1 mmol), 2-chloroacetaldehyde (242 mg, 3.1 mmol, 40% in water) and $NaBH_3CN$, (1.3 g, 6.2 mmol) and HOAc (2 drops) in MeOH (50 mL) was stirred at 40° C. overnight. After the reaction was complete, the reaction mixture was quenched with water (100 mL), extracted with EtOAc (50 mL×3). The combined layers were dried over $Na_2SO_4$ and concentrated under vacuum. The residue was purified by reverse phase column chromatography (EtOAc) to give 143-4 (600 mg, about 60% yield) as a solid. MS Calcd.: 324.0; MS Found: 325.0 $[M+H]^+$.

The Synthesis of $N^3$-(2-(1H-1,2,4-triazol-1-yl)ethyl)-4-bromo-$N^1$-phenylbenzene-1,3-diamine (143-5)

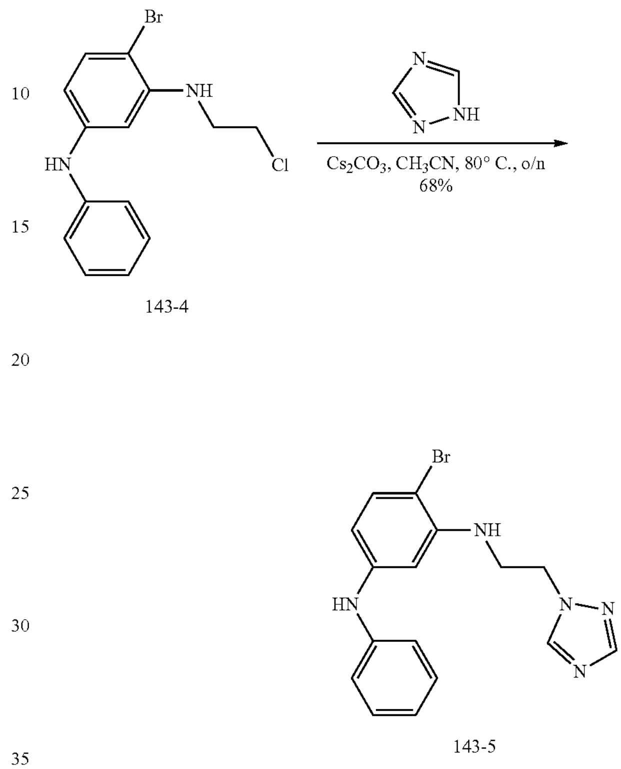

143-4

143-5

A mixture of the 143-4 (600 mg, 1.85 mmol), 1H-1,2,4-triazole (192 mg, 2.78 mmol) and $Cs_2CO_3$ (1.2 g, 3.7 mmol) in acetone (20 mL) was stirred at 80° C. overnight. After the reaction was complete, the reaction mixture was quenched with water (50 mL), extracted with EtOAc (30 mL×3). The combined layers were dried over $Na_2SO_4$ and concentrated under vacuum. The residue was purified by reverse phase column chromatography (DCM/EtOH=20/1) to give 143-5 (450 mg, about 68% yield) as a solid. MS Calcd.: 357.1; MS Found: 358.3 $[M+H]^+$.

Example 73

SS20308-0190-01

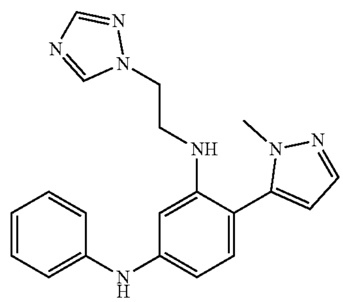

The Synthesis of $N^3$-(2-(1H-1,2,4-triazol-1-yl) ethyl)-4-(1-methyl-1H-pyrazol-5-yl)-$N^1$-phenylbenzene-1,3-diamine (SS20308-190-01)

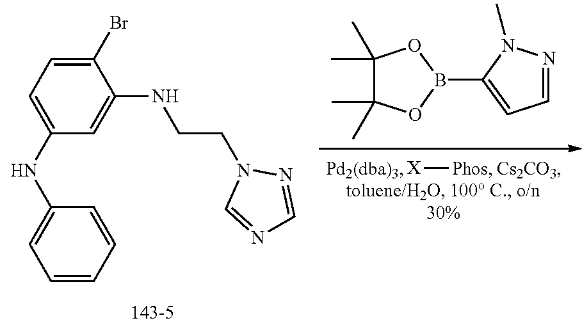

143-5

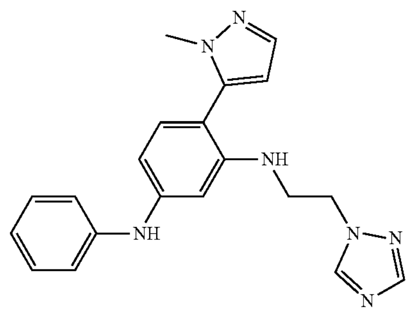

SS20308-0190-01

A mixture of 143-5 (50 mg, 0.14 mmol), 1-methyl-5-(4,4,5,5-tetramethyl-1,3,2-dioxaborolan-2-yl)-1H-pyrazole (44 mg, 0.21 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (50 mL) and extracted with EtOAc (30 mL×3). The organic layer was washed with brine and concentrated. The crude product was purified by Prep-HPLC to give SS20308-190-01 (14.9 mg, about 30% yield) as a solid. MS Calcd.: 359.4; MS Found: 360.3 $[M+H]^+$.

$^1H$ NMR (400 MHz, DMSO-$d_6$) δ 8.44 (s, 1H), 8.20 (s, 1H), 7.93 (s, 1H), 7.45 (d, J=1.6 Hz, 1H), 7.25 (t, J=8.8 Hz, 2H), 7.13 (d, J=7.6 Hz, 2H), 6.86-6.83 (m, 2H), 6.45-6.40 (m, 2H), 6.10 (s, 1H), 4.70 (t, J=5.6 Hz, 1H), 4.35 (t, J=6.0 Hz, 2H), 3.52 (s, 3H), 3.46-3.42 (m, 2H).

Example 74

SS20308-0191-01

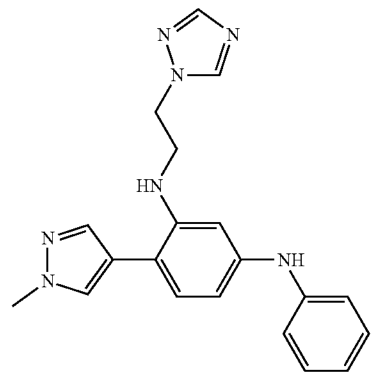

The Synthesis of $N^3$-(2-(1H-1,2,4-triazol-1-yl) ethyl)-4-(1-methyl-1H-pyrazol-4-yl)-$N^1$-phenylbenzene-1,3-diamine (SS20308-191-01)

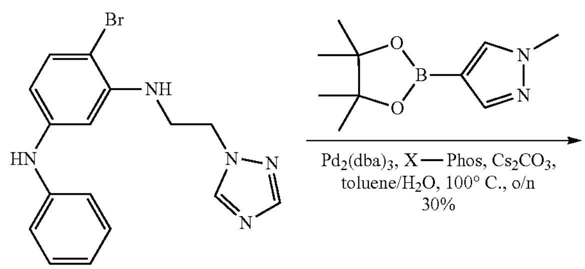

143-5

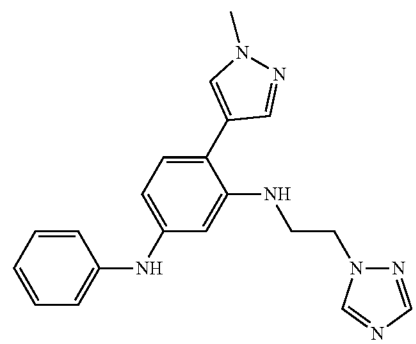

SS20308-0191-01

A mixture of 143-5 (50 mg, 0.14 mmol), 1-methyl-4-(4,4,5,5-tetramethyl-1,3,2-dioxaborolan-2-yl)-1H-pyrazole (44 mg, 0.21 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (50 mL) and extracted with EtOAc (30 mL×3). The organic layer was washed with brine and concentrated, the crude product was purified by Prep-HPLC to give SS20308-191-01 (15 mg, about 30% yield) as a solid. MS Calcd.: 359.4; MS Found: 360.3 $[M+H]^+$.

$^1H$ NMR (400 MHz, DMSO-$d_6$) δ 8.52 (s, 1H), 8.04 (s, 1H), 7.93 (s, 1H), 7.68 (s, 1H), 7.45 (s, 1H), 7.21 (t, J=8.4

Hz, 2H), 7.07 (d, J=7.6 Hz, 2H), 6.96 (d, J=8.0 Hz, 1H), 6.78 (t, J=7.2 Hz, 1H), 6.44-6.39 (m, 2H), 4.84 (t, J=6.4 Hz, 1H), 4.42 (t, J=6.0 Hz, 2H), 3.86 (s, 3H), 3.46-3.41 (m, 2H).

Example 75

SS20308-0192-01

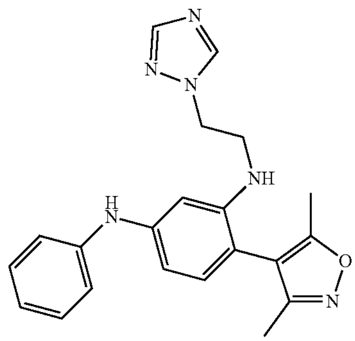

The Synthesis of $N^3$-(2-(1H-1,2,4-triazol-1-yl) ethyl)-4-(3,5-dimethylisoxazol-4-yl)-$N^1$-phenylbenzene-1,3-diamine (SS20308-192-01)

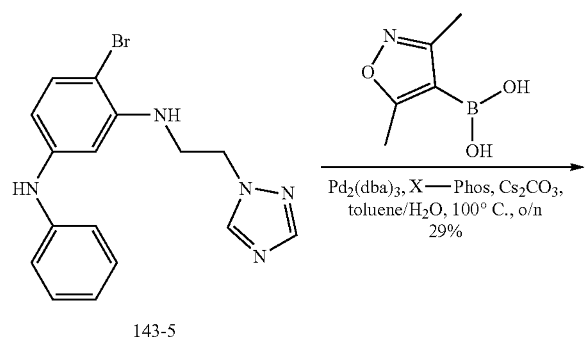

143-5

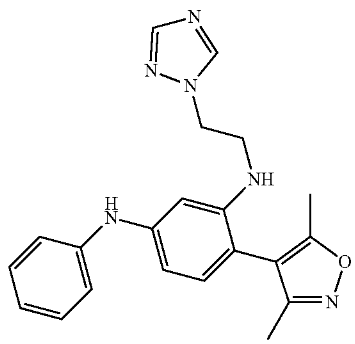

SS20308-0192-01

A mixture of 143-5 (50 mg, 0.14 mmol), 3,5-dimethylisoxazole-4-boronic acid (24 mg, 0.17 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (50 mL) and extracted with EtOAc (30 mL×3). The organic layer was washed with brine and concentrated, the crude product was purified by Prep-HPLC to give SS20308-192-01 (14.6 mg, about 29% yield) as a solid. MS Calcd.: 374.4; MS Found: 375.3 $[M+H]^+$.

$^1H$ NMR (400 MHz, DMSO-$d_6$) δ 8.43 (s, 1H), 8.11 (s, 1H), 7.93 (s, 1H), 7.24 (t, J=8.4 Hz, 2H), 7.13-7.10 (m, 2H), 6.82 (t, J=7.2 Hz, 1H), 6.77 (d, J=8.4 Hz, 1H), 6.42 (dd, J=8.0, 2.0 Hz, 1H), 6.39 (d, J=1.6 Hz, 1H), 4.80 (t, J=6.0 Hz, 1H), 4.34 (t, J=6.0 Hz, 2H), 3.45-3.41 (m, 2H), 2.10 (s, 3H), 1.93 (s, 3H).

Example 76

SS20308-0193-01

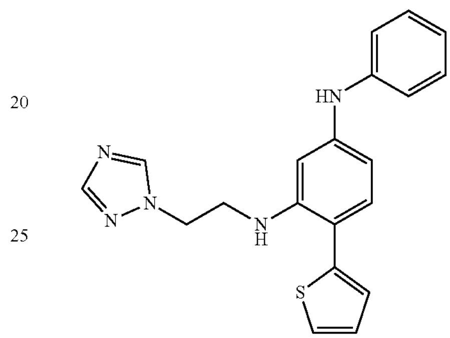

The Synthesis of $N^3$-(2-(1H-1,2,4-triazol-1-yl) ethyl)-$N^1$-phenyl-4-(thiophen-2-yl)benzene-1,3-diamine (SS20308-193-01)

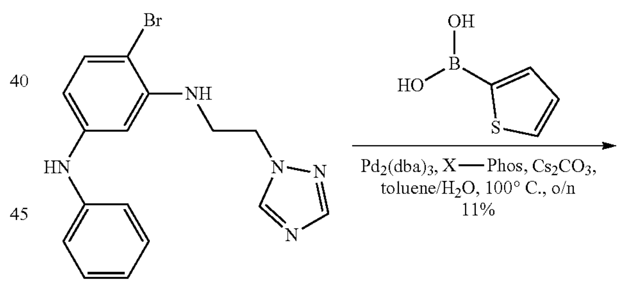

143-5

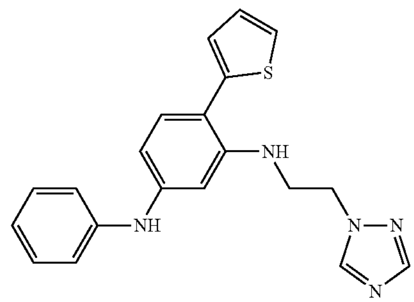

SS20308-0193-01

A mixture of 143-5 (50 mg, 0.14 mmol), 2-thiophene boronic acid (22 mg, 0.17 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (50 mL) and extracted with EtOAc (30 mL×3). The organic layer was washed with brine and concentrated, the crude product was purified by Prep-HPLC to give SS20308-193-01 (5.6 mg, about 11% yield) as a solid. MS Calcd.: 361.5; MS Found: 362.1 $[M+H]^+$.

$^1$H NMR (400 MHz, MeOD-$d_4$) δ 8.36 (s, 1H), 7.94 (s, 1H), 7.36-7.35 (m, 1H), 7.34-7.24 (m, 2H), 7.16-7.14 (m, 2H), 7.08-7.03 (m, 2H), 6.94-6.93 (m, 1H), 6.89 (t, J=7.6 Hz, 1H), 6.49 (dd, J=8.4, 2.0 Hz, 1H), 6.45-6.44 (m, 1H), 4.44 (t, J=6.0 Hz, 2H), 3.61 (t, J=6.0 Hz, 2H).

Example 77

SS20308-0194-01

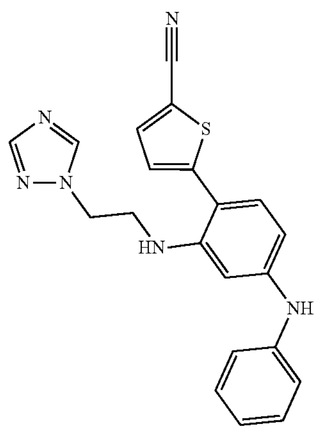

The Synthesis of 5-(2-(2-(1H-1,2,4-triazol-1-yl)ethylamino)-4-(phenylamino)phenyl)thiophene-2-carbonitrile (SS20308-194-01)

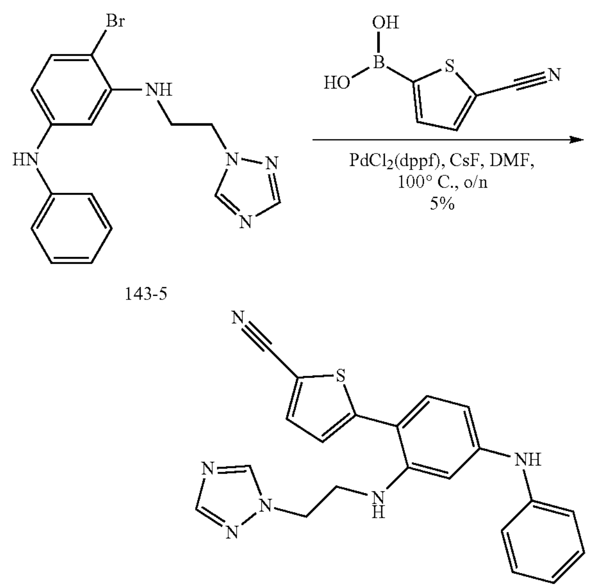

143-5

SS20308-0194-01

A mixture of 143-5 (100 mg, 0.28 mmol), (5-cyanothiophen-2-yl)boronic acid (86 mg, 0.56 mmol), PdCl$_2$(dppf) (20 mg, 0.028 mmol) and CsF (85 mg, 0.5 mmol) in DMF (3 mL) was stirred at 100° C. overnight. The reaction mixture was cooled to room temperature and poured into water (50 mL) and extracted with EtOAc (30 mL×3). The organic layer was washed with brine and concentrated. The crude product was purified by Prep-HPLC to give SS20308-194-01 (5.65 mg, about 5% yield) as a solid. MS Calcd.: 386.5; MS Found: 387.3 $[M+H]^+$.

$^1$H NMR (400 MHz, DMSO-$d_6$) δ 8.50 (s, 1H), 8.36 (s, 1H), 7.97 (s, 1H), 7.92 (d, J=4.4 Hz, 1H), 7.29-7.25 (m, 2H), 7.19 (d, J=3.6 Hz, 1H), 7.16-7.13 (m, 3H), 6.90-6.87 (m, 1H), 6.49-6.44 (m, 2H), 5.38 (t, J=6.0 Hz, 1H), 4.43 (t, J=6.0 Hz, 2H), 3.46-3.42 (m, 2H).

Example 78

SS20308-0195-01

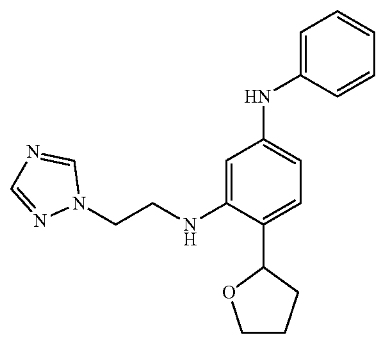

The Synthesis of $N^3$-(2-(1H-1,2,4-triazol-1-yl)ethyl)-4-(2,5-dihydrofuran-2-yl)-$N^1$-phenylbenzene-1,3-diamine (195-01-1)

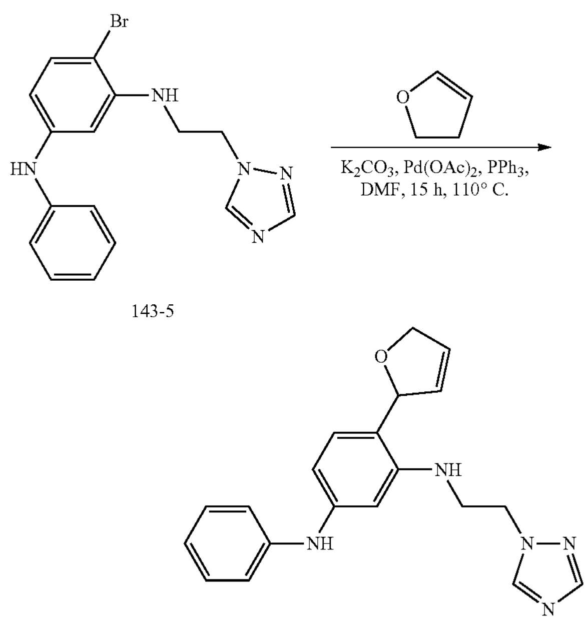

143-5

195-1

A mixture of 143-5 (100 mg, 0.28 mmol), 2,3-dihydrofuran (59 mg, 0.84 mmol), $Pd(OAc)_2$ (6 mg, 0.028 mmol), $PPh_3$ (15 mg, 0.056 mmol) and $K_2CO_3$ (77 mg, 0.56 mmol) in DMF (3 mL) was stirred at 110° C. overnight. The reaction mixture was cooled to room temperature and poured into water (50 mL) and extracted with EtOAc (30 mL×3). The organic layer was washed with brine and concentrated. The crude product was used next step directly without further purification. MS Calcd.: 347.2; MS Found: 348.4 $[M+H]^+$.

The Synthesis of $N^3$-(2-(1H-1,2,4-triazol-1-yl)ethyl)-$N^1$-phenyl-4-(tetrahydrofuran-2-yl)benzene-1,3-diamine (SS20308-0195-01)

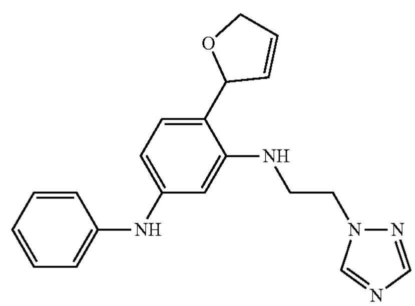

195-1

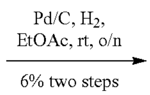

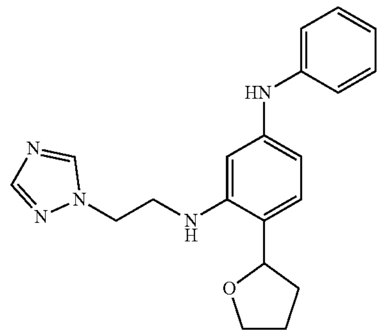

SS20308-0195-01

A mixture of 195-01-1 (crude, 0.28 mmol) and Pd/C (10%, 100 mg) in EtOAc (2 mL) was stirred at rt overnight under $H_2$. After the reaction was complete, the insoluble material was removed by filtration. The filtrate was concentrated under vacuum. The residue was purified by Prep-HPLC to give SS20308-0195-01 (5.74 mg, about 6% yield) as a solid. MS Calcd.: 349.4; MS Found: 350.2 $[M+H]^+$.

$^1$H NMR (400 MHz, DMSO-$d_6$) δ 8.51 (s, 1H), 7.99 (s, 1H), 7.97 (s, 1H), 7.22-7.18 (m, 2H), 7.05 (d, J=7.6 Hz, 2H), 6.93 (d, J=7.6 Hz, 1H), 6.77 (t, J=7.6 Hz, 1H), 6.37-6.36 (m, 1H), 6.35-6.34 (m, 1H), 5.13 (t, J=5.6 Hz, 1H), 4.63-4.59 (m, 1H), 4.41 (t, J=6.0 Hz, 2H), 3.94-3.89 (m, 1H), 3.70-3.65 (m, 1H), 3.47-3.43 (m, 2H), 2.07-1.90 (m, 1H), 1.88-1.85 (m, 2H), 1.69-1.62 (m, 1H).

Example 79

SS20308-0197-01

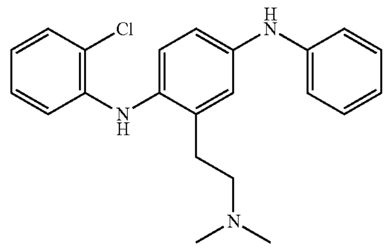

Chemical Formula: $C_{22}H_{24}ClN_3$
Molecular Weight: 365.90

Example Route for Example 79

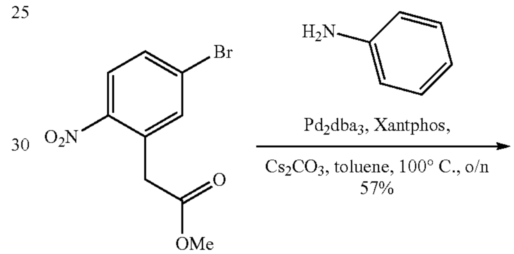

197-1

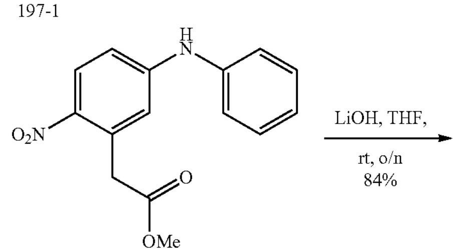

197-2

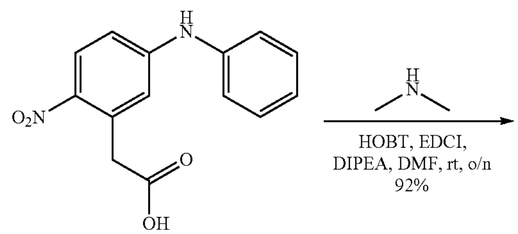

197-3

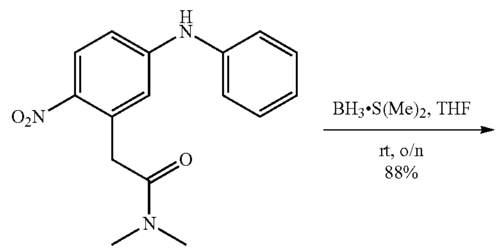

197-4

-continued

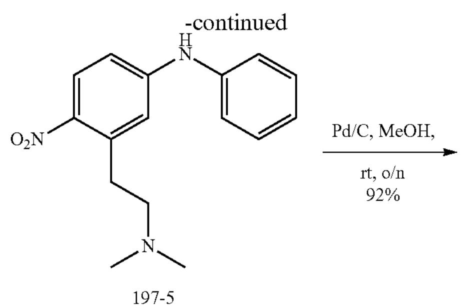

197-5

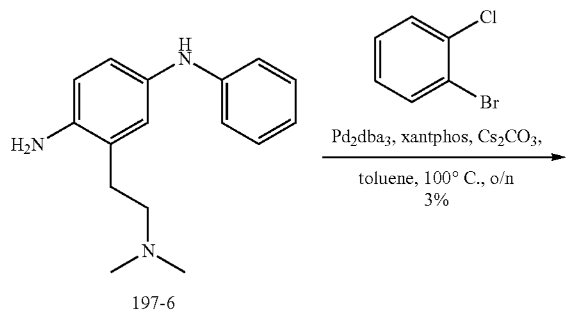

197-6

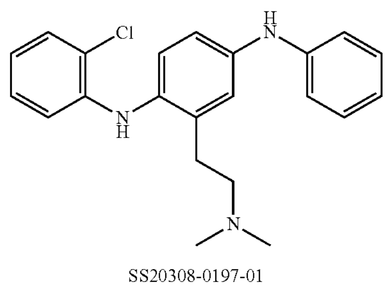

SS20308-0197-01

The Synthesis of methyl 2-(2-nitro-5-(phenylamino) phenyl)acetate (197-2)

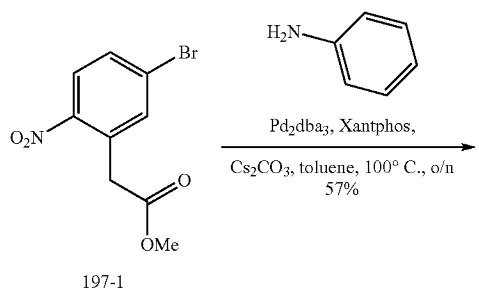

197-1

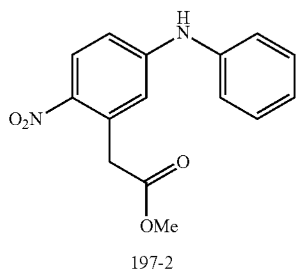

197-2

The mixture of 197-1 (2.00 g, 7.30 mmol), aniline (1.36 g, 14.60 mmol), $Pd_2(dba)_3$ (668 mg, 0.73 mmol), Xantphos (854 mg, 1.46 mmol) and $Cs_2CO_3$ (4.74 g, 14.60 mmol) in toluene (60 mL) was stirred at 100° C. overnight under N2 atmosphere. After cooled to room temperature, the reaction mixture was filtered through diatomite and concentrate. The residue was purified by column chromatography (petroleum ether/ethyl acetate=5/1) to give 197-2 (1.20 g, 57% yield) as yellow oil. MS Calcd.: 286.1; MS Found: 287.4.

The Synthesis of 2-(2-nitro-5-(phenylamino)phenyl) acetic acid (197-3)

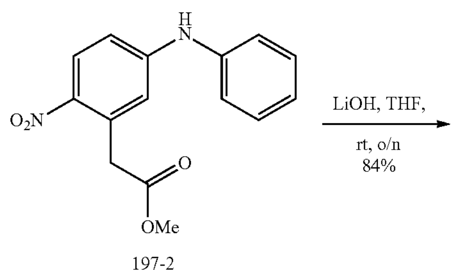

197-2

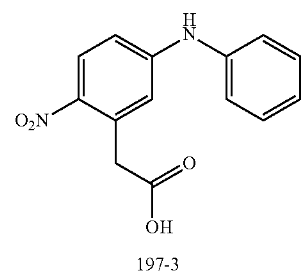

197-3

The mixture of 197-2 (500 mg, 1.75 mmol) and LiOH (147 mg, 3.50 mmol) in THF (30 mL) was stirred at room temperature overnight. Then the reaction mixture was basicified with saturated $NaHCO_3$ aq till pH reached 10. The resulting mixture was extracted with EtOAc (80 mL×3). The organic layers were washed with brine, dried over $Na_2SO_4$ and concentrated to give 197-3 (400 mg, about 84% yield) as an oil. MS Calcd.: 272.1; MS Found: 273.4 $[M+H]^+$.

The Synthesis of 2-(2-nitro-5-(phenylamino)phenyl) acetic acid (197-4)

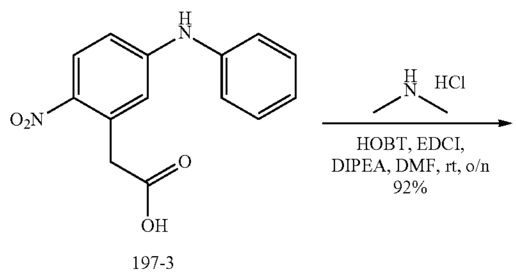

197-3

-continued

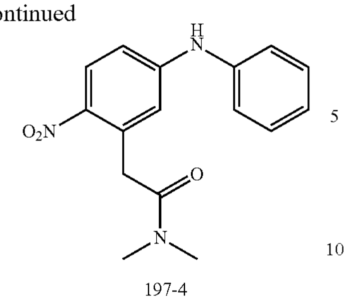

197-4

The mixture of 197-3 (400 mg, 1.47 mmol), dimethylamine hydrochloride (132 mg, 2.94 mmol), HOBT (397 mg, 2.94 mmol), EDCI (564 mg, 2.94 mmol) and DIPEA (379 mg, 2.94 mmol) in DMF (20 mL) was stirred at room temperature overnight. Then the reaction mixture was concentrated and poured into water (100 mL). The resulting mixture was extracted with EtOAc (80 mL×3). The organic layers were washed with brine, dried over $Na_2SO_4$ and concentrated to give 197-4 (405 mg, about 92% yield) as an oil. MS Calcd.: 299.1; MS Found: 300.1 $[M+H]^+$.

The Synthesis of 3-(2-(dimethylamino)ethyl)-4-nitro-N-phenylaniline (197-5)

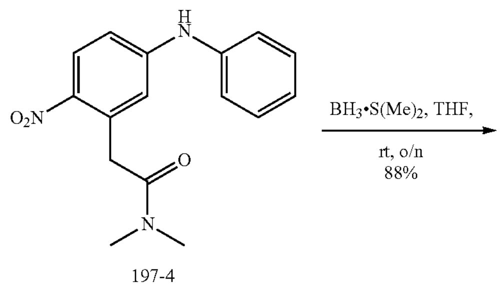

197-4

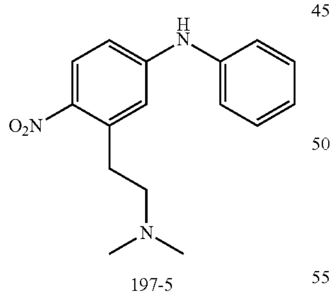

197-5

The mixture of 197-4 (405 mg, 1.35 mmol) and $BH_3·S(Me)_2$ (2.7 mL, 2.7 mmol) in THF (5 mL) was stirred at room temperature overnight. Then the reaction mixture was concentrated and dropped into MeOH. The resulting mixture was acidulated with 1N HCl till pH reached 1 and stirred at 80° C. overnight. Then the mixture was extracted with EtOAc (50 mL×3). The organic layers were washed with brine, dried over $Na_2SO_4$ and concentrated to give 197-5 (340 mg, about 88% yield) as an oil. MS Calcd.: 285.1; MS Found: 286.2 $[M+H]^+$.

The Synthesis of 3-(2-(dimethylamino)ethyl)-$N^1$-phenylbenzene-1,4-diamine (197-6)

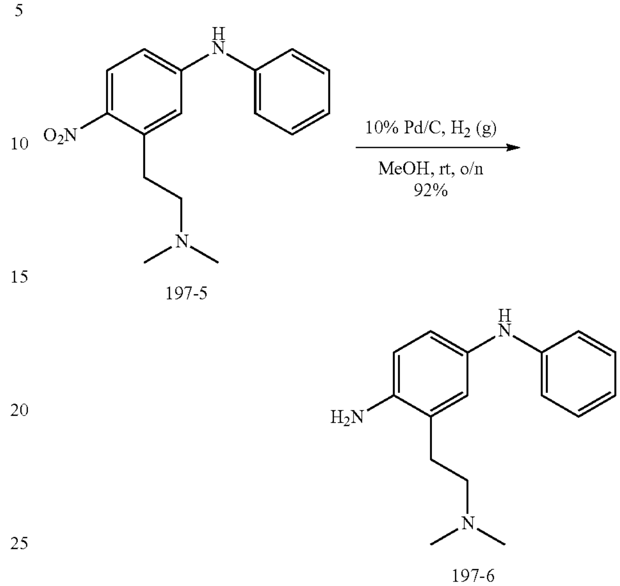

197-5

197-6

The mixture of 197-5 (340 mg, 1.19 mmol) and 10% Pd/C (34 mg) in MeOH (5 mL) was stirred at room temperature overnight under $N_2$ atmosphere. Then the reaction mixture was filtered and concentrated to give 197-6 (280 mg, about 92% yield) as an oil. MS Calcd.: 255.2; MS Found: 256.2 $[M+H]^+$.

The Synthesis of $N^1$-(2-chlorophenyl)-2-(2-(dimethylamino)ethyl)-$N^4$-phenylbenzene-1,4-diamine (SS20308-0197-01)

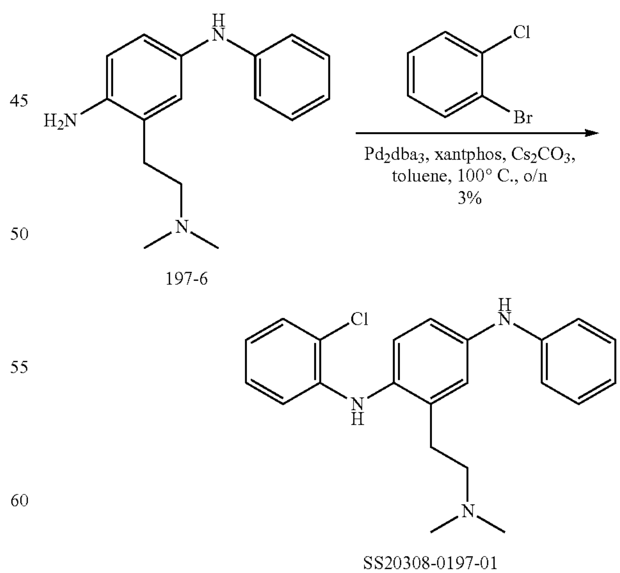

197-6

SS20308-0197-01

The mixture of 197-6 (130 mg, 0.51 mmol), 2-chloro-1-bromobenzene (195 mg, 1.02 mmol), $Pd_2(dba)_3$ (46 mg, 0.05 mmol), Xantphos (57.8 mg, 0.10 mmol) and $Cs_2CO_3$ (332 mg, 1.02 mmol) in toluene (4 mL) was stirred at 100° C. overnight under $N_2$ atmosphere. After cooled to room temperature, the reaction mixture was filtered through celite and concentrated. The residue was purified by column chromatography (petroleum ether/EtOAc=1/2) and Prep-HPLC to give SS20308-0197-01 (6 mg, yield 3% yield) as an oil. MS Calcd.: 365.2; MS Found: 366.3 $[M+H]^+$.

$^1$H NMR (400 MHz, DMSO-$d_6$) δ 8.08 (s, 1H), 7.57 (s, 1H), 7.32 (dd, J=8.0 Hz, 1.2 Hz, 1H), 7.23 (t, J=8.0 Hz, 2H), 7.06-7.02 (m, 5H), 6.96-6.94 (m, 1H), 6.80 (t, J=7.2 Hz, 1H), 6.67-6.63 (m, 1H), 6.56 (dd, J=8.0 Hz, 1.2 Hz, 1H), 2.60 (t, J=6.8 Hz, 2H), 2.44-2.43 (m, 2H), 2.13 (s, 6H).

Example 80

SS20308-0198-01

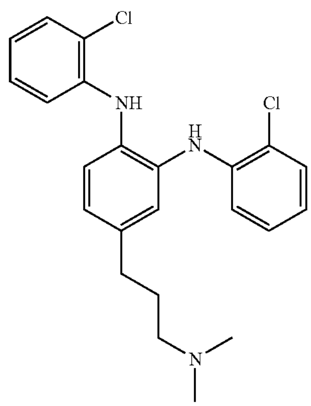

Chemical Formula: $C_{23}H_{25}Cl_2N_3$
Molecular Weight: 414.37

Example Route for Example 80

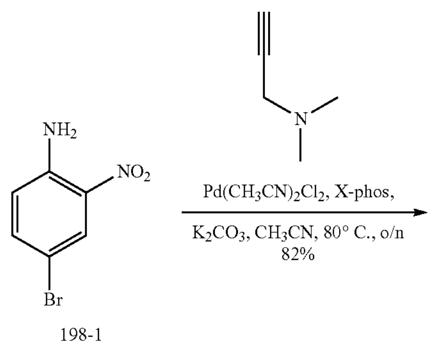

198-1

-continued

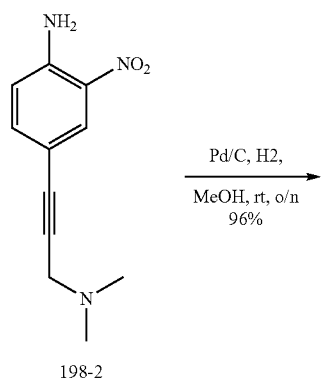

198-2

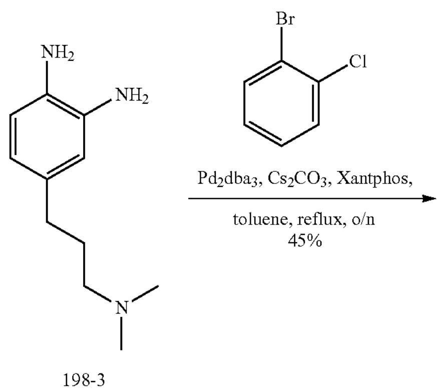

198-3

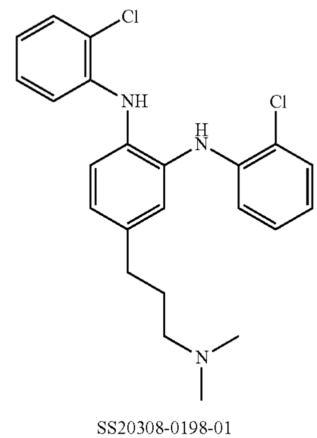

SS20308-0198-01

The Synthesis of 4-(3-(dimethylamino)prop-1-ynyl)-2-nitroaniline (198-2)

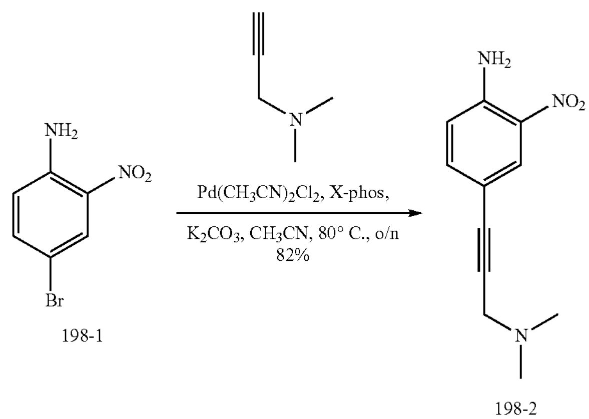

198-1

198-2

A solution of 0155-1 (1.0 g, 4.61 mmol), N,N-dimethyl-prop-2-yn-1-amine (1.92 g, 23.04 mmol), X-phos (110 mg, 0.23 mmol), $Pd(CH_3CN)_2Cl_2$ (48 mg, 0.19 mmol), and potassium carbonate (1.27 g, 9.22 mmol) were suspended in $CH_3CN$ (20 mL). The reaction mixture was heated at reflux for overnight under N2 and then filtered, and rinsed with EtOAc. The filtrate was concentrated and the residue was purified by silica gel column chromatography (petroleum ether/EtOAc=5/1, 3/1, 1/1) to give compound 198-2 (0.83 g, about 92% yield) as a solid. MS Calcd.: 219.1; MS Found: 219.6 $[M+H]^+$.

The Synthesis of 4-(3-(dimethylamino)propyl)benzene-1,2-diamine (198-3)

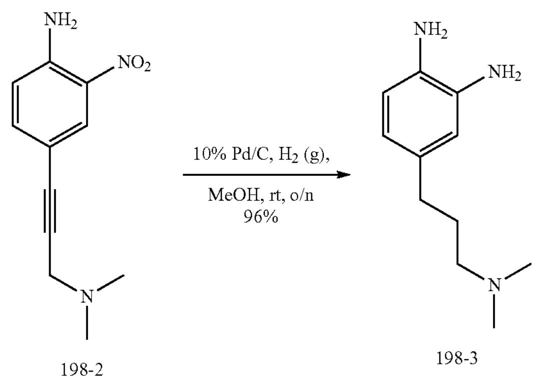 [SMILES: CN(C)CC#Cc1ccc(N)c([N+](=O)[O-])c1 ; CN(C)CCCc1ccc(N)c(N)c1]

198-2

198-3

A solution of 198-2 (830 mg, 3.79 mmol) and 10% Pd/C (83 mg) in MeOH (20 mL) was stirred at room temperature for overnight under $H_2$ (g). Then the reaction mixture was filtered through celite. The filtrate was concentrated to give 198-3 (700 mg, 96% yield) as a brown oil. MS Calcd.: 193.2; MS Found: 194.4 $[M+H]^+$.

The Synthesis of $N^1$,$N^2$-bis(2-chlorophenyl)-4-(3-(dimethylamino)propyl)benzene-1,2-diamine (SS20308-0198-01)

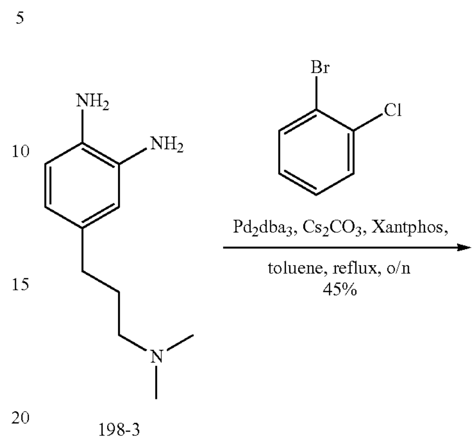

198-3

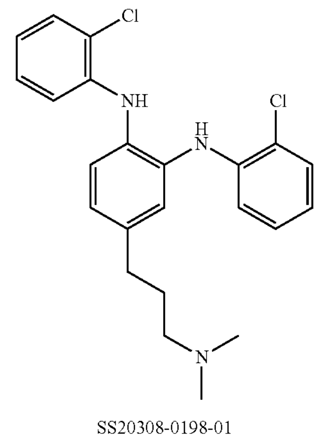

SS20308-0198-01

A solution of 198-3 (520 mg, 2.69 mmol), 1-bromo-2-chlorobenzene (3.09 g, 16.14 mmol), Xantphos (312 mg, 0.54 mmol), $Pd_2(dba)_3$ (247 mg, 0.27 mmol), and anhydrous cesium carbonate (2.63 g, 8.07 mmol) were suspended in toluene (20 mL). The reaction mixture was heated to 120° C. for overnight under $N_2$ and then filtered, rinsing with EtOAc. The filtrate was concentrated and purified by silica gel column chromatography (petroleum ether/EtOAc=5/1, 1/1, 100% EtOAc, DCM/MeOH=20/1) as an oil. MS Calcd.: 413.1; MS Found: 414.2 $[M+H]^+$.

$^1H$ NMR (400 MHz, DMSO-$d_6$) δ 7.37-7.28 (m, 2H), 7.20-7.00 (m, 6H), 6.96-6.88 (m, 2H), 6.81-6.69 (m, 3H), 2.55 (t, J=7.6 Hz, 2H), 2.20 (t, J=7.0 Hz, 2H), 2.11 (s, 6H), 1.73-1.63 (m, 2H).

Example 81

SS20308-0199-01

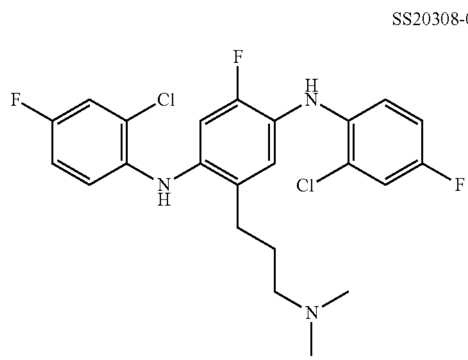

Chemical Formula: $C_{23}H_{22}Cl_2F_3N_3$
Molecular Weight: 468.34

Example Route for Example 81

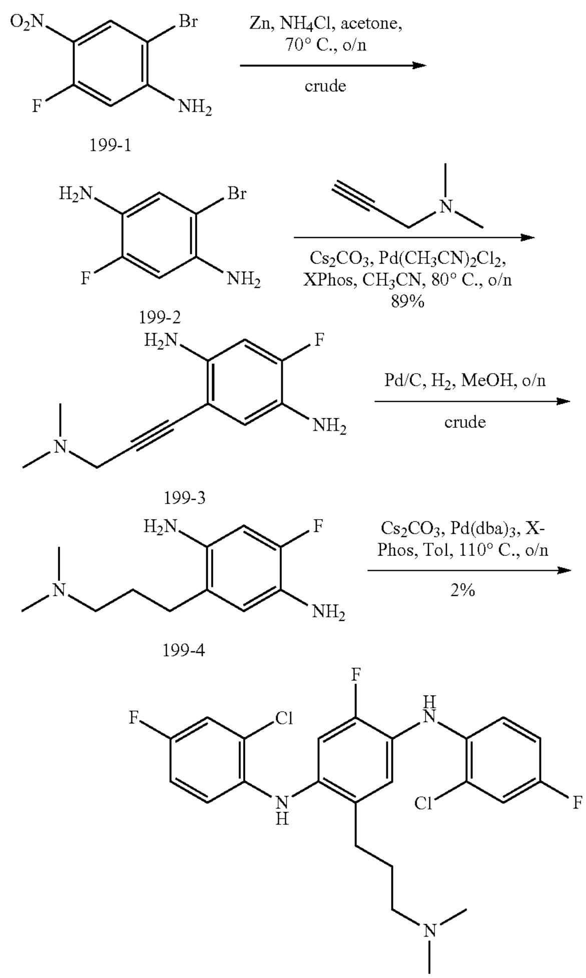

199-1

199-2

199-3

199-4

SS20308-0199-1

The Synthesis of 2-bromo-5-fluorobenzene-1,4-diamine (199-2)

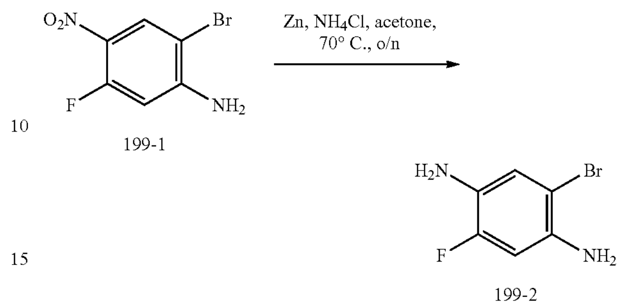

199-1

199-2

To a solution of 199-1 (300 mg, 1.28 mmol) in acetone (30 mL) was added Zn powder (417 mg, 6.38 mmol) and $NH_4Cl$ (341 mg, 6.38 mmol), the mixture was stirred at 70° C. for 16 h. After the reaction was complete, the insoluble material was removed by filtration. The filtrate was poured into water (50 mL) and extracted with EtOAc (40 mL×3). The organic layer was washed brine (2×50 mL), dried over $MgSO_4$, and concentrated in vacuum, which was used next step without purification.

The Synthesis of 2-(3-(dimethylamino)prop-1-ynyl)-5-fluorobenzene-1,4-diamine (199-3)

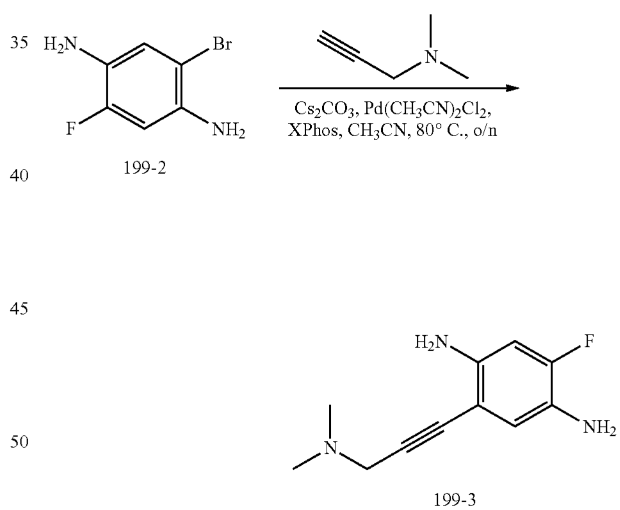

199-2

199-3

A mixture of 199-2 (500 mg, 2.44 mmol), N, N-dimethylprop-2-yn-1-amine (2.03 g, 24.39 mmol), $Pd(CH_3CN)_2Cl_2$ (63 mg, 0.24 mmol), $Cs_2CO_3$ (1.59 g, 4.88 mmol) and X-Phos (232 mg, 0.49 mmol) in $CH_3CN$ (20 ml) was stirred at 80° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated in vacuum, which was purified by column chromatography (petroleum ether/EtOAc=1/1) to give 163-01-3 (450 mg, 89% yield) as a yellow oil. MS Calcd.: 207.1; MS Found: 208.1 $[M+H]^+$.

The Synthesis of 2-(3-(dimethylamino)propyl)-5-fluorobenzene-1,4-diamine (199-4)

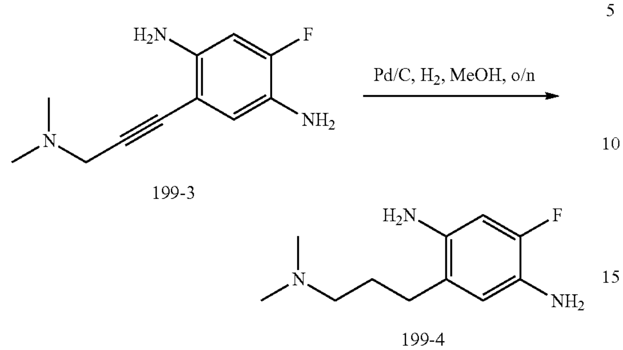

199-3

199-4

To a solution of 199-3 (250 mg, 1.21 mmol) in MeOH (30 mL) was added 10% Pd/C (50 mg), the mixture was stirred at room temperature under hydrogen atmosphere overnight for 16 h. After the reaction was complete, the insoluble material was removed by filtration. And the filtrate was poured into water (50 mL) and extracted with EtOAc (40 mL×3). The organic layer was washed brine (2×50 mL), dried over $MgSO_4$, and concentrated in vacuum, which was used in the next step without further purification.

The Synthesis of $N^1$,$N^4$-bis(2-chloro-4-fluorophenyl)-2-(3-(dimethylamino)propyl)-5-fluorobenzene-1,4-diamine (SS20308-0199-01)

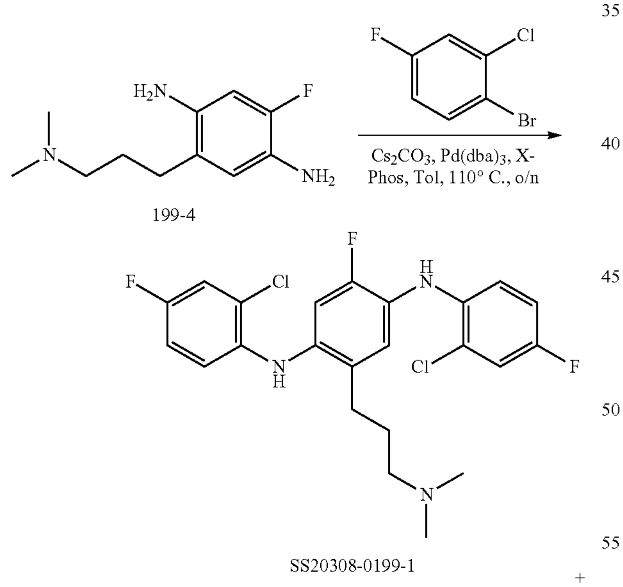

199-4

SS20308-0199-1

A mixture of 199-4 (120 mg, 0.57 mmol), 1-bromo-2-chloro-4-fluorobenzene (357 mg, 1.70 mmol), $Pd_2(dba)_3$ (52 mg, 0.06 mmol), $Cs_2CO_3$ (555 mg, 1.70 mmol) and X-Phos (54 mg, 0.11 mmol) in toluene (10 ml) was stirred at 110° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated under vacuum. The crude product was purified by Prep-HPLC to give SS20308-0199-01 (6 mg, 2% yield) as a yellow oil. MS Calcd.: 467.1; MS Found: 467.9 $[M+H]^+$.

$^1$H NMR (400 MHz, $CDCl_3$) δ 7.11-6.97 (m, 5H), 6.93-6.88 (m, 1H), 6.82-6.79 (m, 1H), 6.77-6.73 (m, 2H), 5.73 (s, 1H), 2.66-2.60 (m, 4H), 2.56 (s, 6H), 2.00-1.97 (m, 2H).

Example 82

SS20308-0200-01

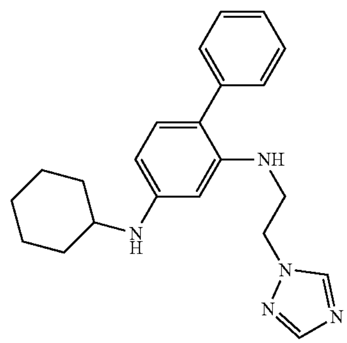

Chemical Formula: $C_{22}H_{27}N_5$

Molecular Weight: 361.48

Example Route for Example 82

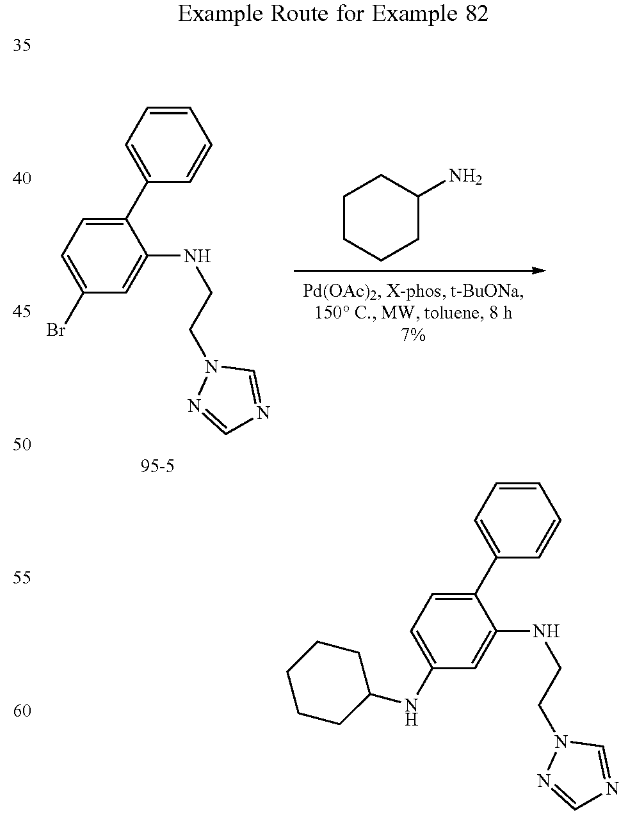

95-5

SS20308-0200-01

The Synthesis of $N^2$-(2-(1H-1,2,4-triazol-1-yl) ethyl)-$N^4$-cyclohexylbiphenyl-2,4-diamine (SS20308-0200-01)

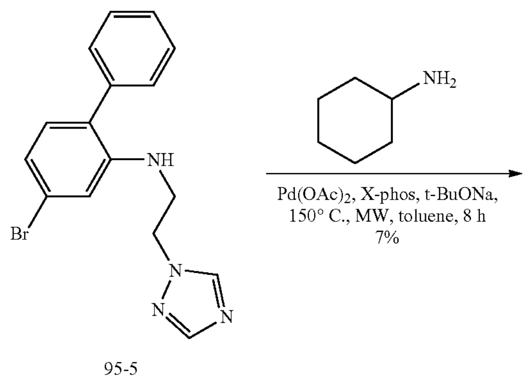

95-5

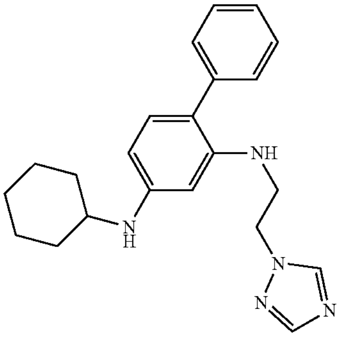

SS203080-0200-01

The mixture of 95-5 (60 mg, 0.18 mmol), cyclohexylamine (36 mg, 0.36 mmol), $Pd(OAc)_2$ (9 mg, 0.036 mmol), X-phos (52 mg, 0.072 mmol) and t-BuONa (36 mg, 0.36 mmol) in toluene (2 mL) was stirred at 150° C. 8 hours in a microwave reactor. The reaction mixture was then cooled to room temperature and filtered through celite. The filtrate was concentrated to a crude oil, which was purified by Prep-HPLC to give SS20308-0200-01 (4.3 mg, about 7% yield) as an oil. MS Calcd.: 361.2; MS Found: 362.3 $[M+H]^+$.

$^1H$ NMR (400 MHz, DMSO-$d_6$) δ 8.46 (s, 1H), 7.96 (s, 1H), 7.34 (t, J=7.6 Hz, 2H), 7.24-7.17 (m, 3H), 6.72-7.70 (m, 1H), 5.97-5.95 (m, 2H), 5.28 (d, J=8.4 Hz, 1H), 4.56 (t, J=6.0 Hz, 1H), 4.35 (t, J=6.0 Hz, 2H), 3.44 (q, J=6.0 Hz, 2H), 3.22-3.15 (m, 1H), 1.95-1.92 (m, 2H), 1.73-1.70 (m, 2H), 1.61-1.58 (m, 1H), 1.39-1.29 (m, 2H), 1.22-1.09 (m, 3H).

Example 83

SS20308-0201-01

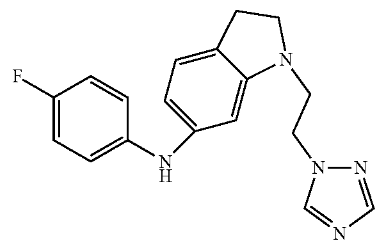

Chemical Formula: $C_{18}H_{18}FN_5$
Molecular Weight: 323.37

Example Route for Example 83

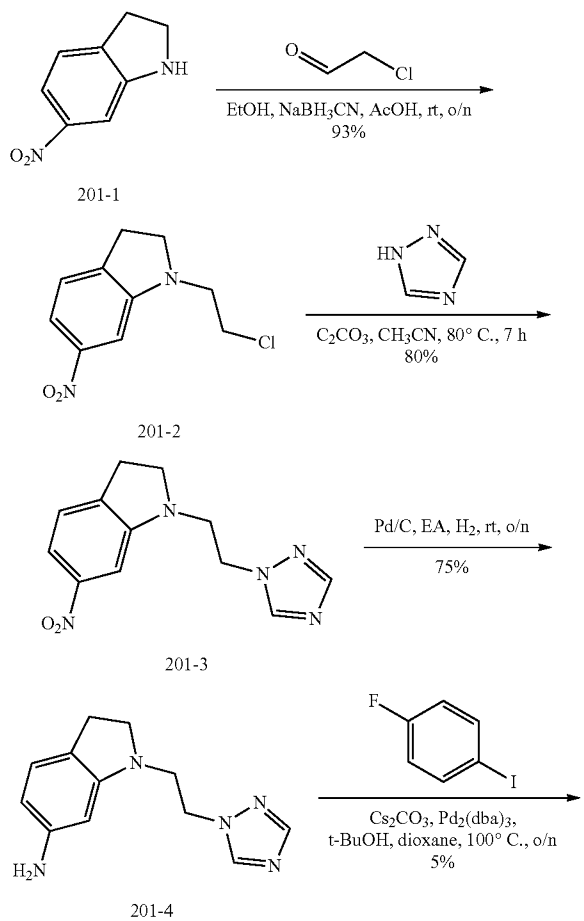

201-1

201-2

201-3

201-4

-continued

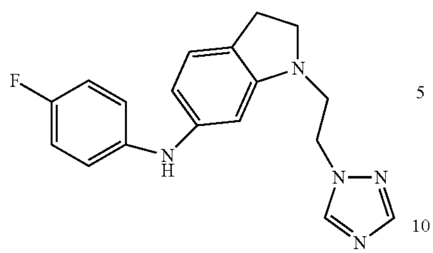

SS20308-0201-01

-continued

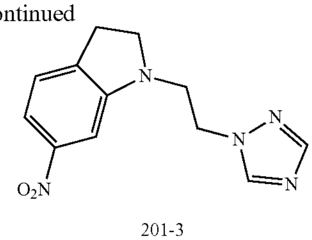

201-3

To a mixture of 201-2 (1.20 g, 5.29 mmol) and $Cs_2CO_3$ (5.17 g, 15.88 mmol) in $CH_3CN$ (60 mL) was added 1H-1,2,4-triazole (0.55 g, 7.94 mmol) and stirred at 80° C. for 7 h. The reaction mixture was diluted with water then extracted with EtOAc (3×100 mL). The organic layer was washed with brine and concentrated to dryness to give crude, which was purified by column chromatography (petroleum ether/EtOAc=10/1-1/1) to give 201-3 (1.10 g, about 80% yield) as a solid. MS Calcd.: 259.1; MS Found: 260.1 $[M+H]^+$.

The Synthesis of 1-(2-chloroethyl)-6-nitroindoline (201-2)

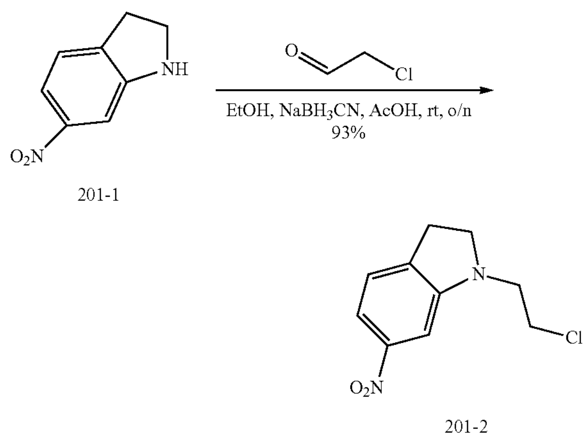

201-1

201-2

To a solution of 201-1 (1.64 g, 10.0 mmol) in EtOH (50 mL) was added 2-chloroacetaldehyde (4.71 g, 60.0 mmol), $NaBH_3CN$ (2.51 g, 40.0 mmol) and AcOH (10 mL), then stirred at room temperature overnight. The reaction mixture was diluted with water and extracted with EtOAc (3×100 mL). The organic layer was washed with brine and concentrated to dryness to give crude, which was purified by column chromatography (petroleum ether/EtOAc=10/1-1/1) to give 201-2 (2.10 g, about 93% yield) as a solid. MS Calcd.: 226.1; MS Found: 227.4 $[M+H]^+$.

The Synthesis of 1-(2-(1H-1,2,4-triazol-1-yl)ethyl)-6-nitroindoline (201-3)

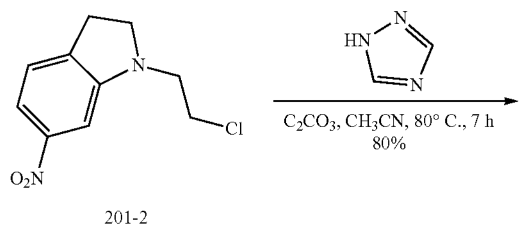

201-2

The Synthesis of 1-(2-(1H-1,2,4-triazol-1-yl)ethyl)indolin-6-amine (201-4)

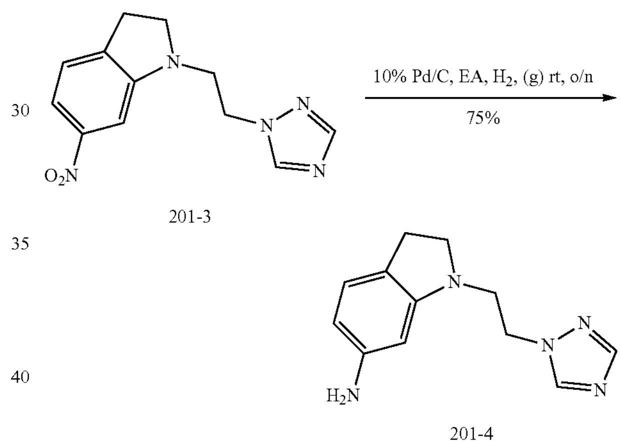

201-3

201-4

To a solution of 201-2 (390 mg, 1.51 mmol) in EtOAc (15 mL) was added Pd/C (10%) and the mixture was stirred at room temperature overnight. The mixture was filtered through a pad of Celite and washed with EtOAc, concentrated, and purified by Prep-HPLC to give 201-3 (260 mg, about 75% yield) as a solid. MS Calcd.: 229.1; MS Found: 230.2 $[M+H]^+$.

The Synthesis of 1-(2-(1H-1,2,4-triazol-1-yl)ethyl)-N-(4-fluorophenyl)indolin-6-amine (SS20308-0201-01)

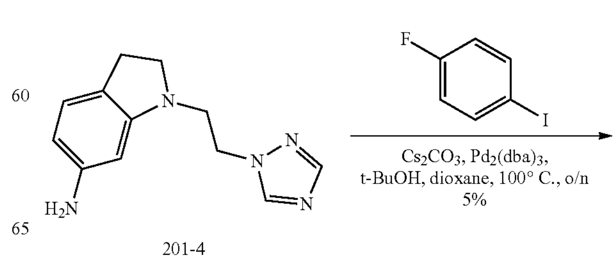

201-4

-continued

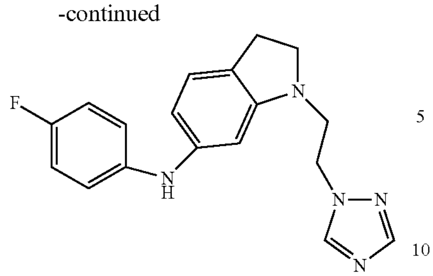

SS20308-0201-01

To a solution of 201-4 (187 mg, 0.82 mmol) in dioxane/t-BuOH (16/8 mL) was added $Cs_2CO_3$ (531 mg, 1.63 mmol), $Pd_2(dba)_3$ (73 mg, 0.08 mmol) and 1-fluoro-4-iodobenzene (272 mg, 1.22 mmol) stirred at 100° C. overnight. The residue was purified by Prep-HPLC to give SS20308-0201-01 (14 mg, about 5% yield) as a solid. MS Calcd.: 323.2; MS Found: 324.0 $[M+H]^+$.

$^1H$ NMR (400 MHz, DMSO-$d_6$) δ 8.52 (s, 1H), 7.97 (s, 1H), 7.81 (s, 1H), 7.05-7.01 (m, 2H), 6.98-6.94 (m, 2H), 6.84 (d, J=8.0 Hz, 1H), 6.24 (dd, J=7.6 Hz, 2.0 Hz, 1H), 6.06 (d, J=1.69 Hz, 1H), 4.39 (t, J=6.4 Hz, 2H), 3.41 (t, J=6.4 Hz, 2H), 3.29 (t, J=8.0 Hz, 2H), 2.78 (t, J=8.0 Hz, 2H).

Example 84

SS20308-0223-01

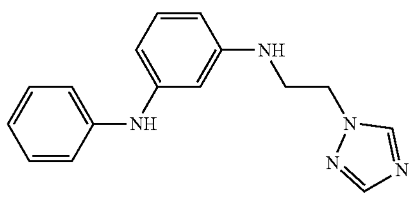

Example Route for Example 84

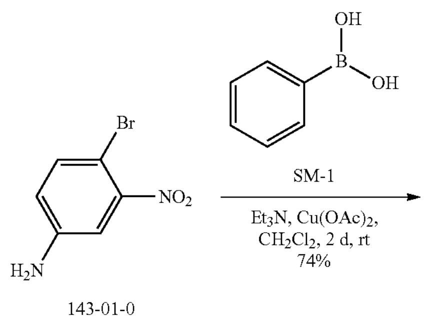

143-01-0

-continued

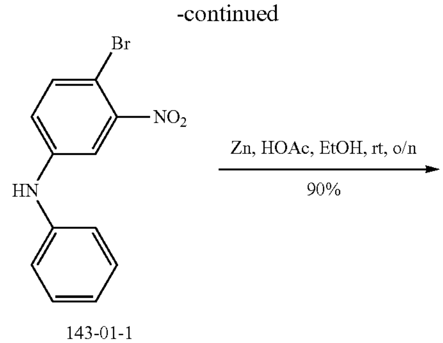

143-01-1

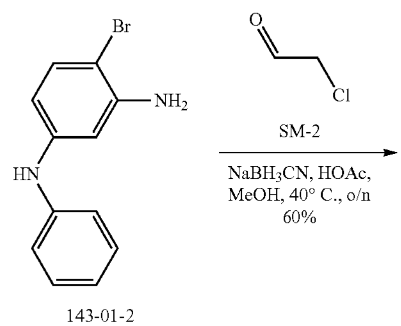

143-01-2

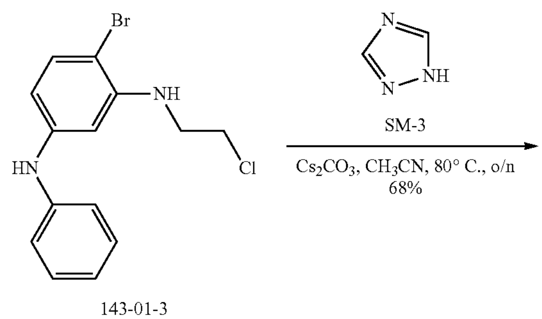

143-01-3

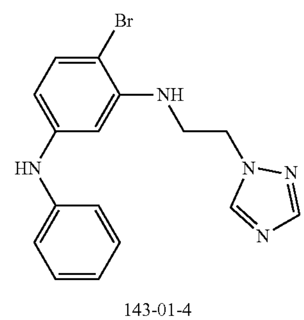

143-01-4

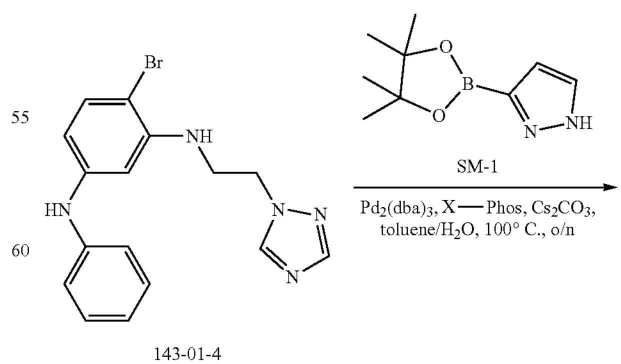

143-01-4

-continued

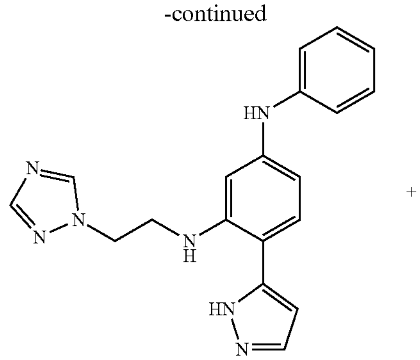

SS20308-0189-01
16%

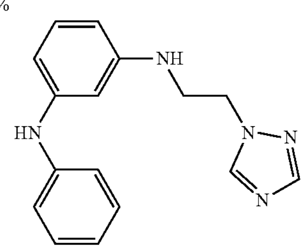

SS20308-0223-01
22%

The Synthesis of 4-bromo-3-nitro-N-phenylaniline (143-01-1)

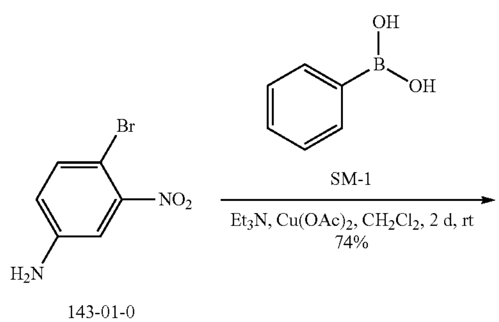

143-01-0

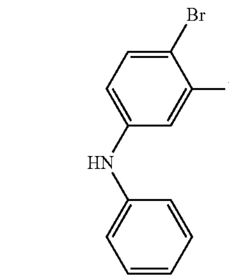

143-01-1

A mixture of 143-01-0 (1.0 g, 4.6 mmol), phenylboronic acid (1.1 g, 9.2 mmol) and $Cu(OAc)_2$ (833 mg, 4.6 mmol), $Et_3N$ (2.3 g, 23 mmol) in $CH_2Cl_2$ (100 mL) was stirred at rt for 2 d. After the reaction was complete, the insoluble material was removed by filtration. The filtrate was poured into water (100 mL) and extracted with EtOAc (100 mL×3). The combined layers were dried over $Na_2SO_4$, and concentrated in vacuum. The residue was purified by CC to give 143-01-1 (1.0 g, about 74% yield) as a solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity is about 83.1%. Rt=2.314 min; MS Calcd.: 292.0;

The Synthesis of 4-bromo-$N^1$-phenylbenzene-1,3-diamine (143-01-2)

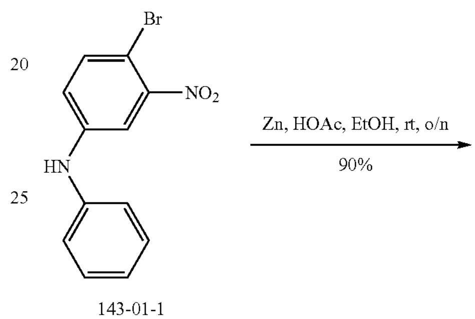

143-01-1

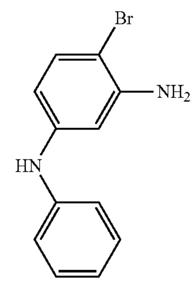

143-01-12

A mixture of 143-01-1 (1.0 g, 3.4 mmol), Zn (1.1 g, 17 mmol) and HOAc (1.0 g, 17 mmol) in EtOH (50 mL) was stirred at rt overnight. After the reaction was complete, the insoluble material was removed by filtration. The filtrate was poured into water (100 mL) and extracted with EtOAc (100 mL×3). The combined layers were dried over $Na_2SO_4$, and concentrated in vacuum. The residue was purified by CC (PE/EA=5/1) to give 143-01-2 (800 mg, about 90% yield) as a solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity is 74.0%. Rt=2.164 min; MS Found: 263.2 $[M+H]^+$.

The Synthesis of 4-bromo-$N^3$-(2-chloroethyl)-$N^1$-phenylbenzene-1,3-diamine (143-01-3)

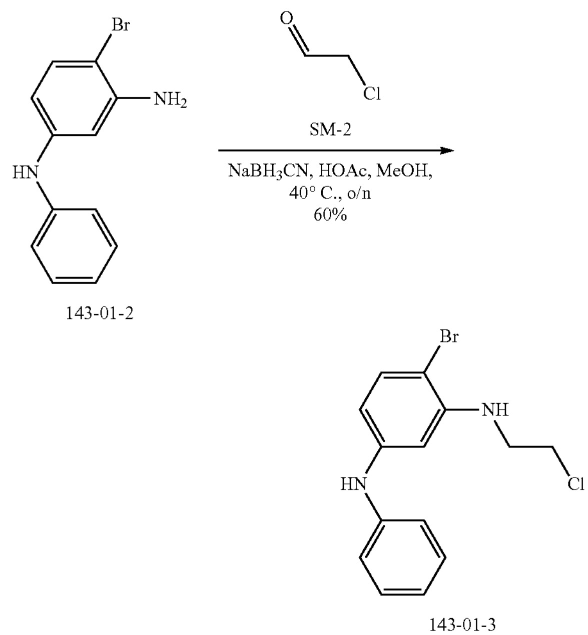

143-01-2

143-01-3

A mixture of the 143-01-2 (800 mg, 3.1 mmol), 2-chloroacetaldehyde (242 mg, 3.1 mmol) and $NaBH_3CN$, (1.3 g, 6.2 mmol) and HOAc (2 drops) in MeOH (50 mL) was stirred at 40° C. overnight. After the reaction was complete, the reaction mixture was quenched with water (100 mL), extracted with EtOAc (50 mL×3). The combined layers were dried over $Na_2SO_4$ and concentrated in vacuum. The residue was purified by reverse CC (EA) to give 143-01-3 (600 mg, about 60% yield) as a solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity is about 89.1%. Rt=2.374 min; MS Calcd.: 324.0; MS Found: 325.0 $[M+H]^+$.

The Synthesis of $N^3$-(2-(1H-1,2,4-triazol-1-yl)ethyl)-4-bromo-N-phenylbenzene-1,3-diamine (143-01-4)

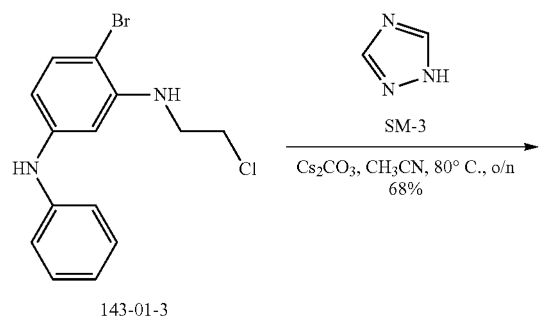

143-01-3

-continued

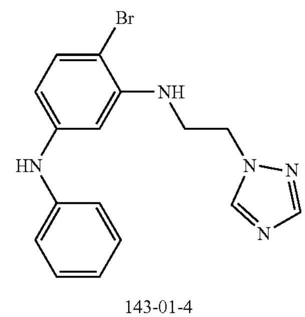

143-01-4

A mixture of the 143-01-3 (600 mg, 1.85 mmol), 1H-1,2,4-triazole (192 mg, 2.78 mmol) and $Cs_2CO_3$ (1.2 g, 3.7 mmol) in acetone (20 mL) was stirred at 80° C. overnight. After the reaction was complete, the reaction mixture was quenched with water (50 mL), extracted with EtOAc (30 mL×3). The combined layers were dried over $Na_2SO_4$ and concentrated in vacuum. The residue was purified by reverse CC (DCM/EtOH=20/1) to give 143-01-4 (450 mg, about 68% yield) as a solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity is about 100%. Rt=2.047 min; MS Calcd.: 357.1; MS Found: 358.3 $[M+H]^+$.

The Synthesis of $N^3$-(2-(1H-1,2,4-triazol-1-yl)ethyl)-$N^1$-phenyl-4-(1H-pyrazol-5-yl)benzene-1,3-diamine (SS20308-189-01), $N^1$-(2-(1H-1,2,4-triazol-1-yl)ethyl)-$N^3$-phenylbenzene-1,3-diamine (SS20308-223-01)

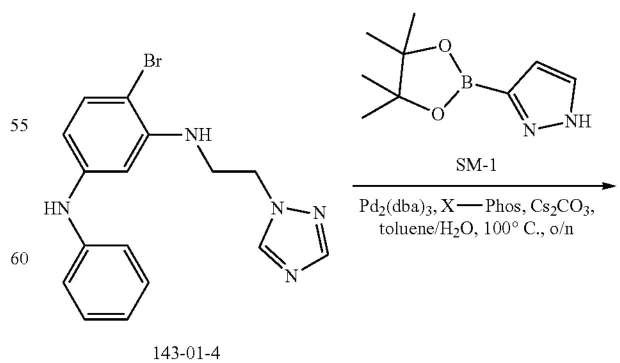

143-01-4

-continued

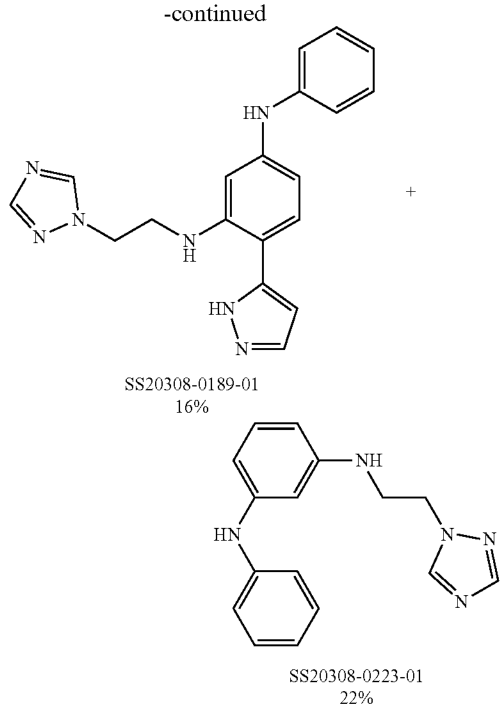

SS20308-0189-01
16%

SS20308-0223-01
22%

A mixture of 143-01-4 (50 mg, 0.14 mmol), SM-1 (41 mg, 0.21 mmol), $Pd_2(dba)_3$ (6 mg, 0.007 mmol) and X-Phos (6 mg, 0.014 mmol), $Cs_2CO_3$ (91 mg, 0.28 mmol) in toluene/water (1/0.1 mL) was stirred at reflux overnight. The reaction mixture was cooled to room temperature and poured into water (50 mL) and extracted with EtOAc (30 mL×3). The organic layer was washed with brine and evaporated, the residue crude product was purified by Prep-HPLC to give SS20308-189-01 (7.04 mg, about 16% yield) as a solid and SS20308-223-01 (8.59 mg, about 22% yield) as a solid.

SS20308-189-01: Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min. Purity is about 95.4%, Rt=2.698 min; MS Calcd.: 345.4; MS Found: 346.3 $[M+H]^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity is about 95.5%. Rt=8.519 min.

$^1H$ NMR (400 MHz, DMSO-$d_6$) δ 12.69 (s, 1H), 8.47 (s, 1H), 8.12 (s, 1H), 7.97 (s, 1H), 7.86 (t, J=6.0 Hz, 1H), 7.73 (d, J=1.6 Hz, 1H), 7.45 (d, J=8.8 Hz, 1H), 7.23 (t, J=8.4 Hz, 2H), 7.11 (d, J=7.6 Hz, 2H), 6.81 (t, J=7.2 Hz, 1H), 6.60-6.59 (m, 1H), 6.43-6.41 (m, 2H), 4.45 (t, J=6.0 Hz, 2H), 3.63-3.58 (m, 2H).

SS20308-223-01: Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 3.0 min, then under this condition for 1.0 min, finally changed to 95% [water+0.05% TFA] and 5% [$CH_3CN$+0.05% TFA] in 0.05 min and under this condition for 0.7 min. Purity is about 100%, Rt=2.076 min; MS Calcd.: 279.3; MS Found: 280.0 $[M+H]^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 10 min, then under this condition for 5 min, finally changed to 95% [water+0.05% TFA] and 5% [$CH_3CN$+0.05% TFA] in 0.1 min and under this condition for 5 min. Purity is about 96.5%. Rt=7.689 min.

$^1H$ NMR (400 MHz, DMSO-$d_6$) δ 8.47 (s, 1H), 7.97 (s, 1H), 7.91 (s, 1H), 7.19 (t, J=8.4 Hz, 2H), 7.03 (d, J=7.6 Hz, 2H), 6.93 (d, J=7.6 Hz, 1H), 6.77 (t, J=7.6 Hz, 1H), 6.32-6.30 (m, 2H), 6.10-6.08 (m, 1H), 5.67 (t, J=2.0 Hz, 1H), 4.32 (t, J=6.4 Hz, 2H), 3.44-3.40 (m, 2H).

Example 85

SS20308-0238-01

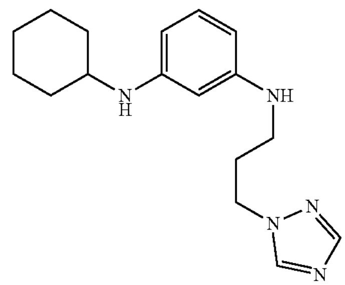

Chemical Formula: $C_{17}H_{25}N_5$
Molecular Weight: 299.41

Example Route for Example 85

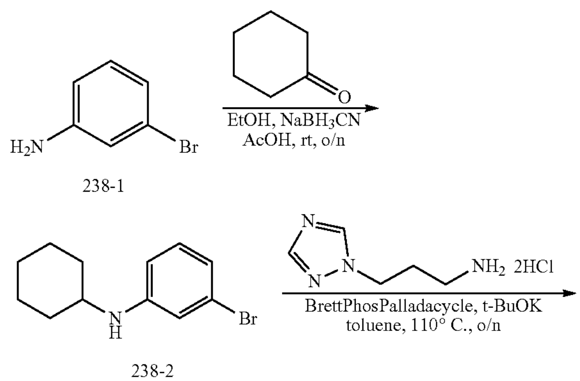

-continued

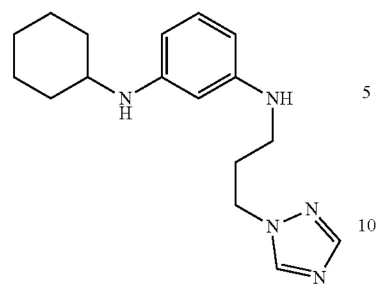

SS20308-0238-01

-continued

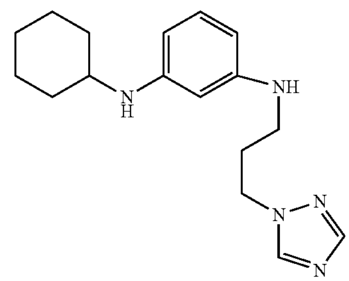

SS20308-0238-01

The Synthesis of 3-bromo-N-cyclohexylaniline (238-2):

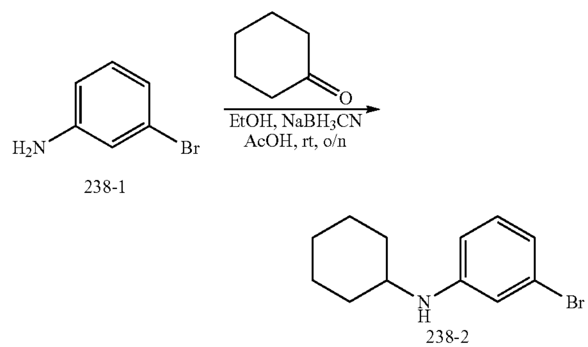

238-1

238-2

To a solution of 238-1 (1.00 g, 5.81 mmol) in EtOH (10 mL) and AcOH (10 mL) was added cyclohexanone (2.28 g, 23.25 mmol) and $NaBH_3CN$ (1.10 g, 17.44 mmol). The resulting mixture was stirred at room temperature overnight. Then the mixture was basicified with $Na_2CO_3$ (aq.) until pH reached 7-8, extracted with EtOAc. The combined organic layers were washed with brine, dried over $Na_2SO_4$, filtered and the filtrate was concentrated, the residue was purified by silica gel column chromatography (petroleum ether/EtOAc=5/1) to give 238-2 (1.32 g, about 89% yield) as an oil. MS Calcd.: 253.1; MS Found: 255.9 $[M+H]^+$.

The Synthesis of $N^1$-(3-(1H-1,2,4-triazol-1-yl)propyl)-$N^3$-cyclohexylbenzene-1,3-diamine (SS20308-0238-01)

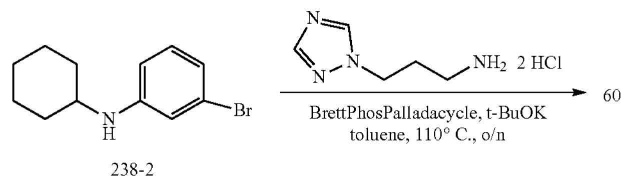

238-2

To a solution of 238-2 (300 mg, 1.18 mmol) in toluene (10 mL) was added 1H-1,2,4-Triazole-1-propanamine, hydrochloride (1:2) (352 mg, 1.77 mmol), t-BuOK (794 mg, 7.08 mmol), BrettPhosPalladacycle (94 mg, 0.11 mmol). The mixture was stirred at 110° C. overnight. After cooling to room temperature, the mixture was poured into water and extracted with EtOAc (10 mL×3), the combined organic layers were washed with brine, dried over $Na_2SO_4$, filtered and the filtrate was concentrated. The residue was purified by Prep-HPLC to give SS20308-0238-01 (150 mg, about 42% yield) as an oil. MS Calcd.: 299.2; MS Found: 300.5 $[M+H]^+$.

$^1H$ NMR (400 MHz, DMSO-$d_6$) δ 8.51 (s, 1H), 7.97 (s, 1H), 6.73 (t, J=7.8 Hz, 1H), 5.80 (d, J=8.0 Hz, 1H), 5.76-5.73 (m, 2H), 5.29 (t, J=5.6 Hz, 1H), 4.99 (d, J=8.0 Hz, 1H), 4.26 (t, J=6.8 Hz, 2H), 3.07-3.06 (m, 1H), 2.92-2.87 (m, 2H), 2.08-1.98 (m, 2H), 1.91-1.88 (m, 2H), 1.71-1.68 (m, 2H), 1.60-1.57 (m, 1H), 1.31-1.26 (m, 2H), 1.16-1.05 (m, 3H).

Example 86

SS20308-0239-01

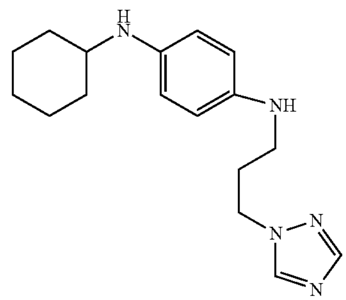

Chemical Formula: $C_{17}H_{25}N$
Molecular Weight: 299.41

Example Route for Example 86

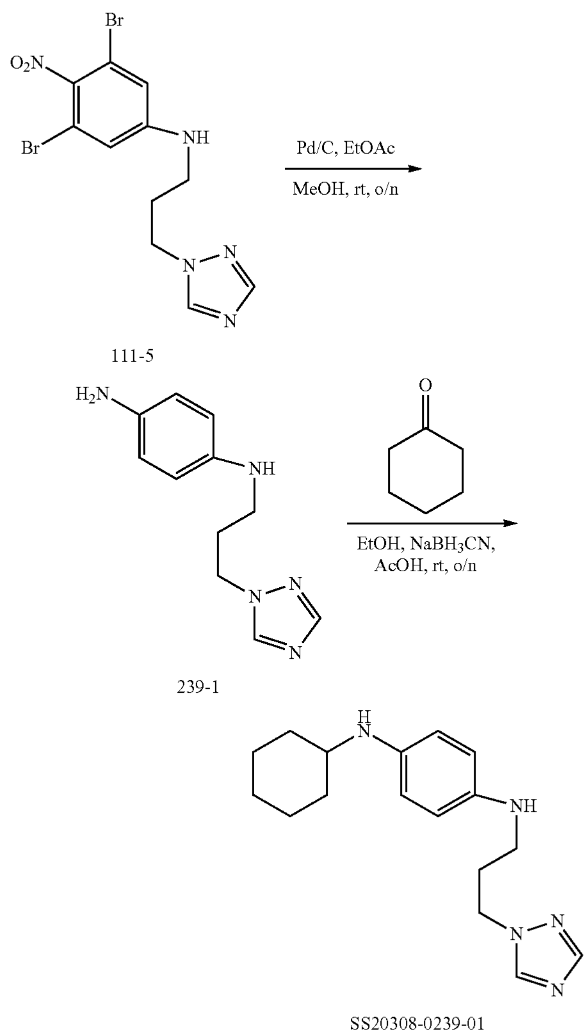

111-5

239-1

SS20308-0239-01

*The synthesis of 111-5 is described above.

The Synthesis of N[1]-(3-(1H-1,2,4-triazol-1-yl)propyl)benzene-1,4-diamine (239-1)

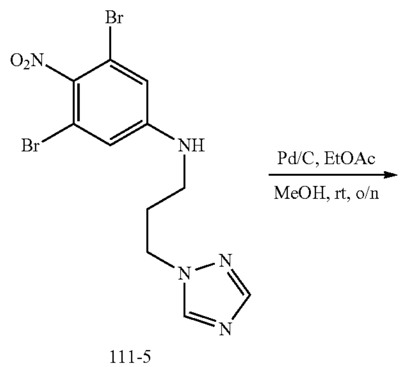

111-5

-continued

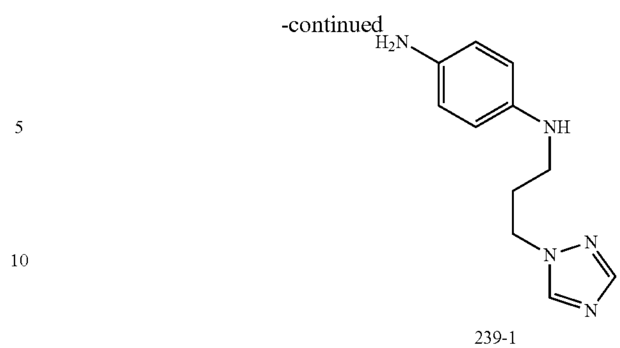

239-1

To a solution of 111-5 (1.00 g, 2.47 mmol) in MeOH (5 mL) and EtOAc (5 mL) was added Pd/C (10%, 250 mg). The resulting mixture was stirred under $H_2$ atmosphere at room temperature overnight. The mixture was filtered and concentrated to give 239-1 (700 mg) as a crude oil. MS Calcd.: 217.1; MS Found: 218.1 $[M+H]^+$.

The Synthesis of N[1]-(3-(1H-1,2,4-triazol-1-yl)propyl)-N[4]-cyclohexylbenzene-1,4-diamine (SS20308-0239-01)

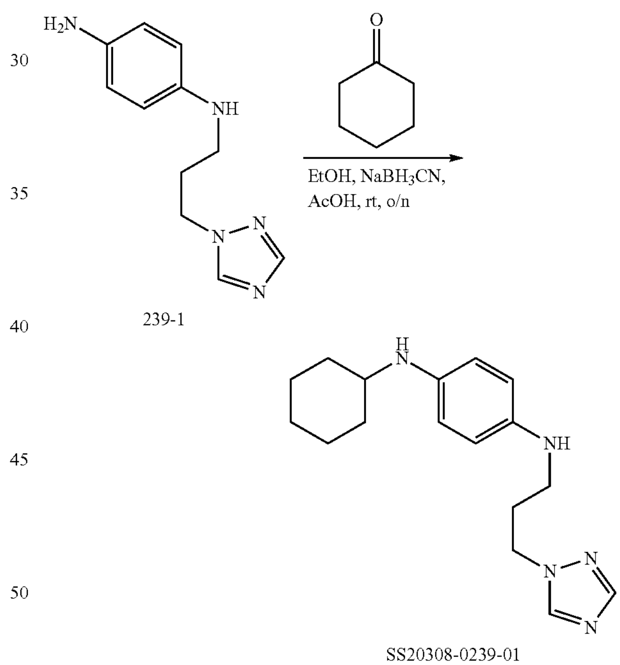

239-1

SS20308-0239-01

To a solution of 239-1 (200.00 mg, 0.92 mmol) in EtOH (3 mL) and AcOH (3 ml) was added cyclohexanone (361.37 mg, 3.68 mmol) and $NaBH_3CN$ (173.54 mg, 2.76 mmol). The resulting mixture was stirred at room temperature overnight. Then the mixture was basicified with $Na_2CO_3$ (aq.) until pH reached 7-8, extracted with EtOAc. The combined organic layers were washed with brine, dried over $Na_2SO_4$, filtered and the filtrate was concentrated, the residue was purified by Prep-HPLC to give SS20308-0239-01 (15 mg, about 5% yield) as a solid. MS Calcd.: 299.2; MS Found: 300.2 $[M+H]^+$.

$^1H$ NMR (400 MHz, DMSO-$d_6$) δ 8.50 (s, 1H), 7.97 (s, 1H), 6.43-6.37 (m, 4H), 4.76 (t, J=5.8 Hz, 1H), 4.41 (d,

J=8.4 Hz, 1H), 4.27 (t, J=6.8 Hz, 2H), 3.02-2.99 (m, 1H), 2.86 (q, J=12.8 Hz, 2H), 2.03-1.96 (m, 2H), 1.89-1.86 (m, 2H), 1.71-1.67 (m, 2H), 1.59-1.56 (m, 1H), 1.32-1.23 (m, 2H), 1.18-1.01 (m, 3H).

Example 87

SS20308-0241-01

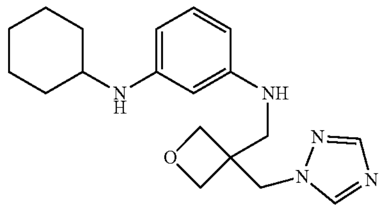

Example Route for Example 87

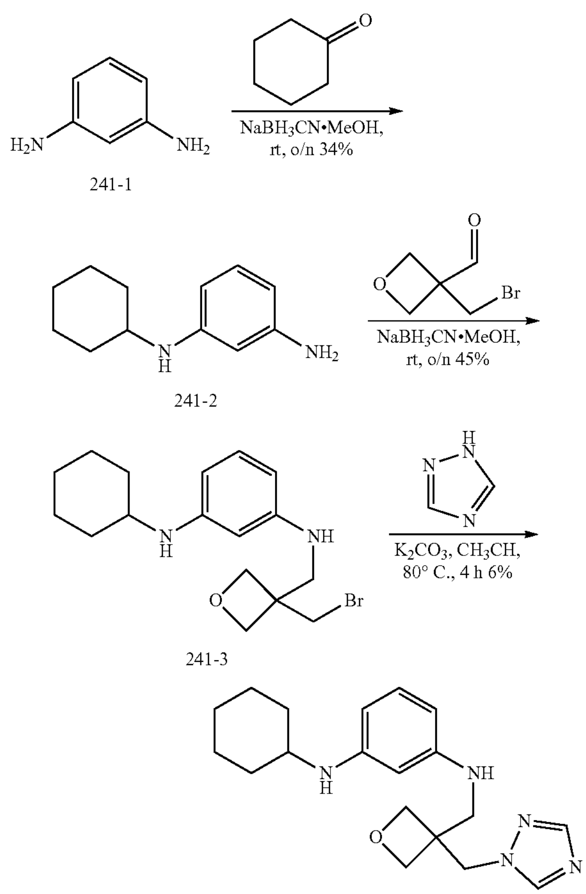

241-1

241-2

241-3

SS20308-0241-01

The Synthesis of N[1]-cyclohexylbenzene-1,3-diamine (241-2):

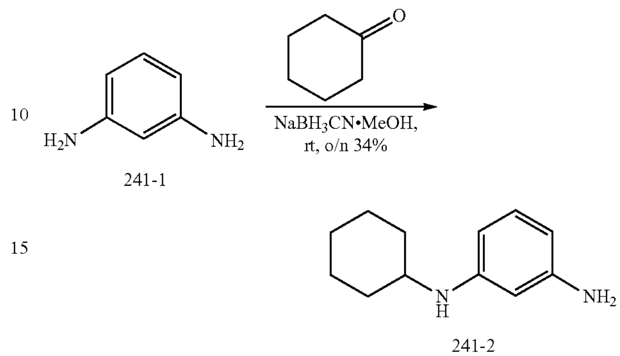

241-1

241-2

To a solution of 241-1 (1.00 g, 9.25 mmol) and cyclohexanone (908 mg, 9.25 mmol) in MeOH (25 mL) was added $NaBH_3CN$ (1.74 g, 27.74 mmol), the mixture was stirred at room temperature overnight. After the reaction was complete, the reaction was poured into water (50 mL) and extracted with EtOAc (40 mL×3). The organic layer was washed brine (2×50 mL), dried over $MgSO_4$, and concentrated in vacuum, which was purified by column chromatography (PE/EtOAc=5/1) to give 241-2 (600 mg, about 34% yield) as a solid. MS Calcd.: 190.2; MS Found: 191.4 $[M+H]^+$.

The Synthesis of N[1]-((3-(bromomethyl)oxetan-3-yl)methyl)-N[3]-cyclohexylbenzene-1,3-diamine (241-3)

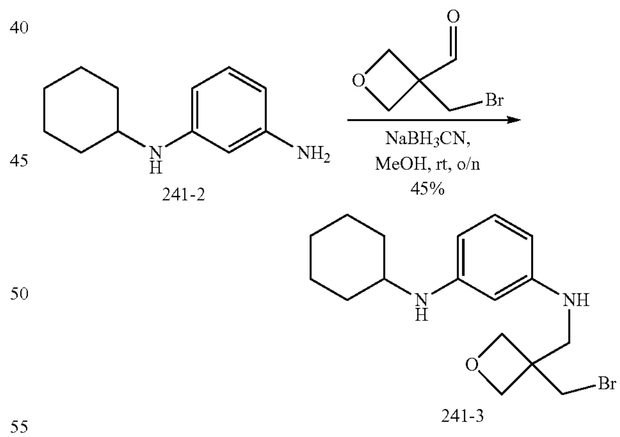

241-2

241-3

To a solution of 241-2 (190 mg, 1.00 mmol) and 3-(bromomethyl)oxetane-3-carbaldehyde (179 mg, 1.00 mmol) in MeOH (15 mL) was added $NaBH_3CN$ (188 mg, 3.00 mmol), the mixture was stirred at room temperature overnight. After the reaction was complete, the reaction was poured into water (30 mL) and extracted with EtOAc (30 mL×3). The organic layer was washed brine (2×30 mL), dried over $MgSO_4$, and concentrated in vacuum, which was obtained by simple work up to give 241-3 (160 mg, about 45% yield) as an oil. MS Calcd.: 352.1; MS Found: 353.0 $[M+H]^+$.

The Synthesis of N[1]-((3-((1H-1,2,4-triazol-1-yl)methyl)oxetan-3-yl)methyl)-N[3]-cyclohexylbenzene-1,3-diamine (SS20308-0241-01)

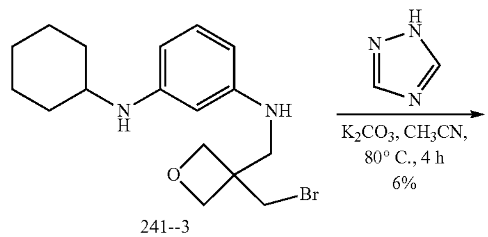

241--3

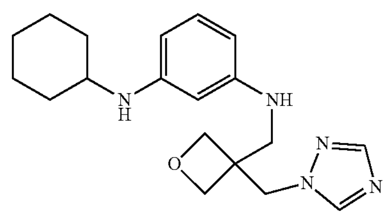

SS20308-0241-01

A mixture of 241-3 (160 mg, 0.45 mmol), 1H-1,2,4-triazole (63 mg, 0.91 mmol) and $K_2CO_3$ (188 mg, 1.36 mmol) in $CH_3CN$ (20 ml) was stirred at 80° C. under nitrogen atmosphere for 4 h. After the reaction was complete, the mixture was quenched with water and extracted with EtOAc (20 mL×3). The organic layer was separated, dried over $MgSO_4$, and concentrated in vacuum, which was purified by Prep-HPLC to give SS20308-0241-01 (9 mg, about 6% yield) as a light oil. MS Calcd.: 341.2; MS Found: 342.1 $[M+H]^+$.

$^1H$ NMR (400 MHz, DMSO-$d_6$ and $D_2O$) δ 8.50 (s, 1H), 8.02 (s, 1H), 6.76-6.73 (m, 1H), 5.86-5.75 (m, 3H), 4.59 (s, 2H), 4.51 (d, J=6.0 Hz, 2H), 4.39 (d, J=6.4 Hz, 2H), 3.08-3.03 (m, 3H), 1.90-1.87 (m, 2H), 1.71-1.68 (m, 2H), 1.60-1.57 (m, 1H), 13.4-1.25 (m, 2H), 1.19-1.05 (m, 3H).

Example 88

SS20308-0248-01

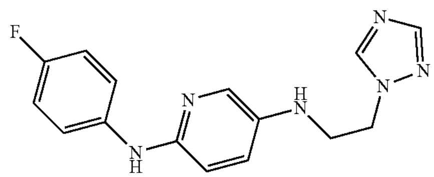

Chemical Formula: $C_{15}H_{15}FN_6$
Molecular Weight: 298.32

Example Route for Example 88

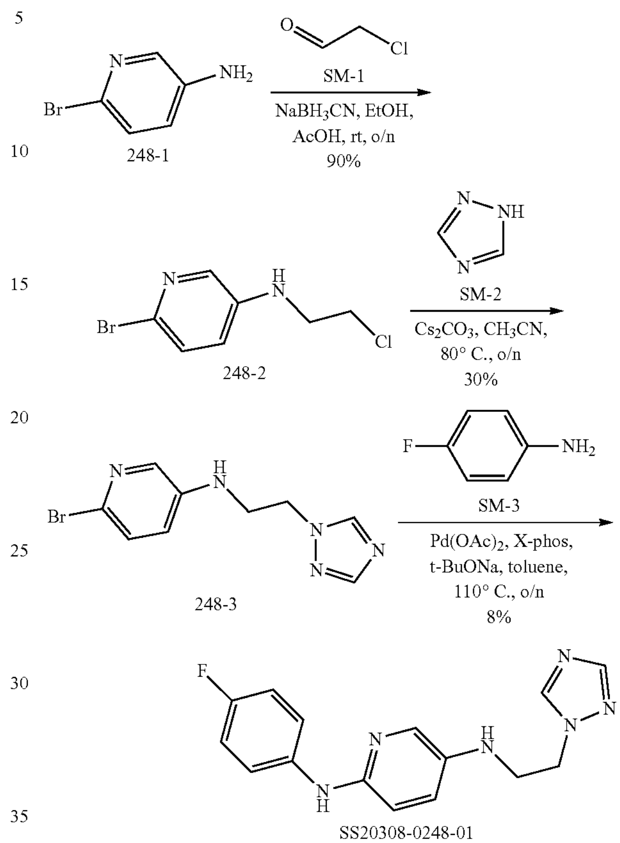

248-1 248-2 248-3

SS20308-0248-01

The Synthesis of 6-bromo-N-(2-chloroethyl)pyridin-3-amine (248-2)

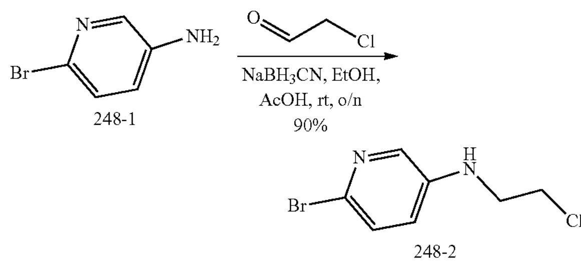

248-1

248-2

To a solution of 248-1 (5.0 g, 28.9 mmol) in EtOH (150 mL) was added 2-chloroacetaldehyde (11.3 g, 57.8 mmol, 40% in water), AcOH (3.47 g, 57.8 mmol), and $NaBH_3CN$ (3.64 g, 57.8 mmol), then the reaction mixture was stirred at room temperature overnight. Then the reaction mixture was poured into water and basified with 1N NaOH till pH reached 10. The mixture was extracted with EtOAc (150 mL×3). The organic layers were washed with brine, dried over $Na_2SO_4$ and concentrated to give 248-2 (6.10 g, about 90% yield) as a solid. MS Calcd.: 234.0; MS Found: 235.0 $[M+H]^+$.

The Synthesis of $N^4$-(bicyclo[2.2.2]octan-1-yl)biphenyl-2,4-diamine (248-3)

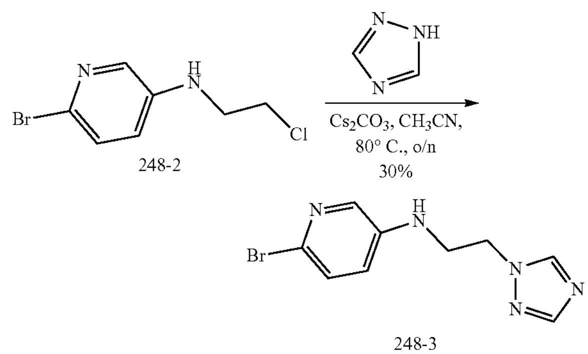

248-2

248-3

A mixture of 248-2 (6.1 g, 25.9 mmol), 1H-1,2,4-triazole (3.57 mg, 51.8 mmol) and $Cs_2CO_3$ (16.8 g, 51.8 mmol) in $CH_3CN$ (200 mL) was stirred at 80° C. overnight. The reaction mixture was then cooled to room temperature and filtered through celite and concentrated. The residue was purified by column chromatography (petroleum ether/EtOAc=1/1) to give 248-3 (2.1 g, about 30% yield) as a solid. MS Calcd.: 267.0; MS Found: 268.2 $[M+H]^+$.

The Synthesis of $N^5$-(2-(1H-1,2,4-triazol-1-yl)ethyl)-$N^2$-(4-fluorophenyl)pyridine-2,5-diamine (SS20308-0248-01)

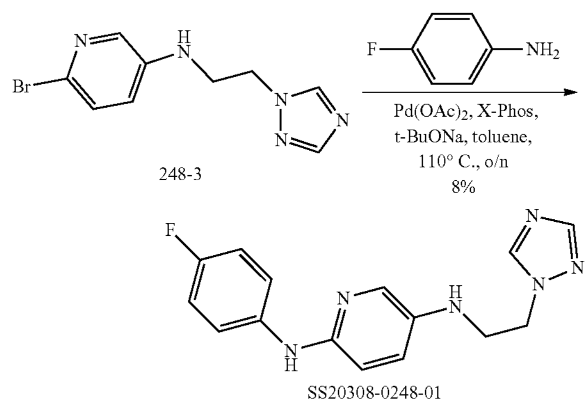

248-3

SS20308-0248-01

The mixture of 248-3 (250 mg, 0.93 mmol), 4-fluoroaniline (206 mg, 1.86 mmol), $Pd(OAc)_2$ (22 mg, 0.093 mmol), X-phos (89 mg, 0.186 mmol) and t-BuONa (179 mg, 1.86 mmol) in toluene (4 mL) was stirred at 110° C. overnight under $N_2$ atmosphere. The reaction mixture was then cooled to room temperature and filtered through diatomite and concentrated. The residue was purified by Prep-HPLC to give SS20308-0248-01 (21 mg, about 8% yield) as a solid. MS Calcd.: 298.1; MS Found: 299.2 $[M+H]^+$.

$^1H$ NMR (400 MHz, DMSO-$d_6$) δ 8.53 (s, 1H), 8.48 (s, 1H), 7.98 (s, 1H), 7.60-7.51 (m, 3H), 7.05-6.90 (m, 3H), 6.67 (d, J=8.8 Hz, 1H), 6.35 (t, J=6.2 Hz, 1H), 4.33 (t, J=6.0 Hz, 2H), 3.43 (q, J=6.0 Hz, 2H).

Example 89

SS20308-0252-01

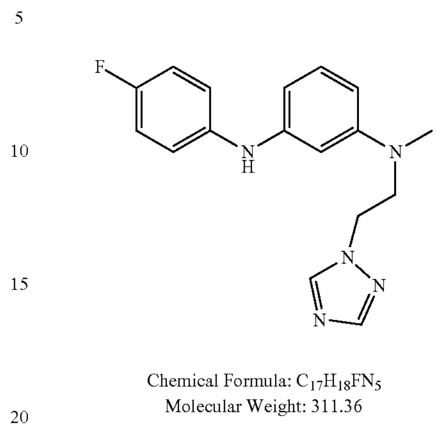

Chemical Formula: $C_{17}H_{18}FN_5$

Molecular Weight: 311.36

Example Route for Example 89

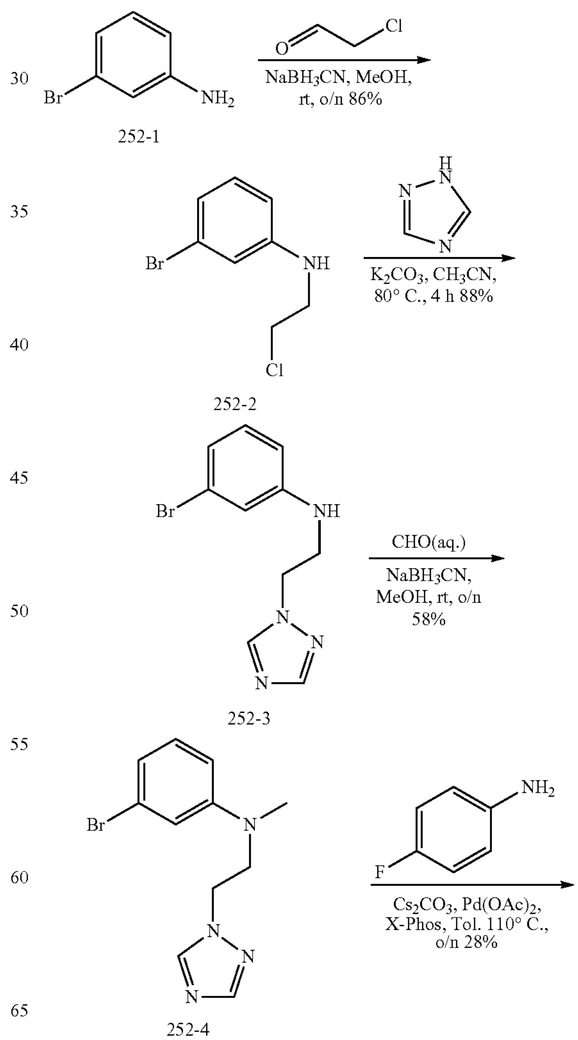

252-1

252-2

252-3

252-4

-continued

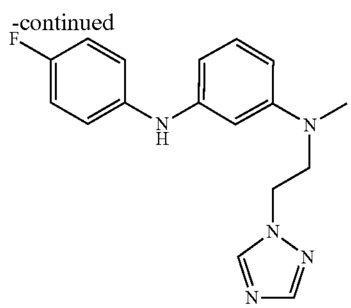

SS20308-0252-01

The Synthesis of 3-bromo-N-(2-chloroethyl)aniline (252-1):

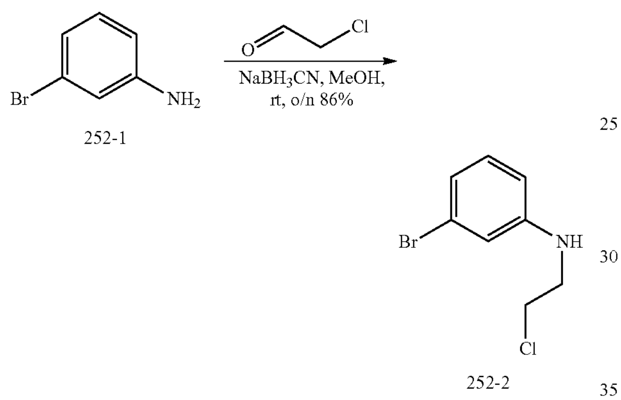

252-1

252-2

A mixture of 252-1 (1.2 g, 6.98 mmol) and 2-chloroacetaldehyde (657 mg, 8.37 mmol, 40% in water) in MeOH (20 ml) was added $NaBH_3CN$ (1.32 g, 20.93 mmol), the mixture was stirred at room temperature overnight. After the reaction was complete, the mixture was quenched with water, the insoluble material was removed by filtration, and the filtrate was extracted with EtOAc (30 mL×3). The organic layer was separated, dried over $MgSO_4$, and concentrated under vacuum, which was purified by column chromatography (petroleum ether/EtOAc=10/1) to give 252-2 (1.4 g, about 86% yield) as an oil. MS Calcd.: 233.0; MS Found: 234.0 $[M+H]^+$.

The Synthesis of N-(2-(1H-1,2,4-triazol-1-yl)ethyl)-3-bromoaniline (252-3)

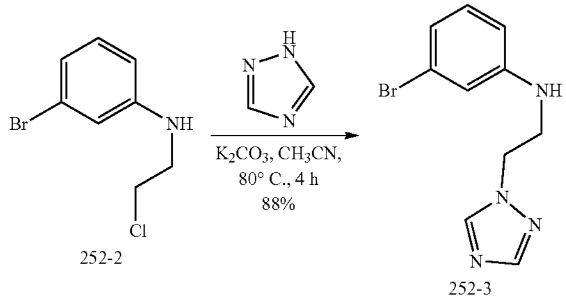 [SMILES: ClCCNc1cccc(Br)c1 ; c1nc[nH]n1 ; Brc1cccc(NCCn2cncn2)c1]

252-2

252-3

A mixture of 252-2 (1.00 g, 4.26 mmol), 1H-1,2,4-triazole (442 mg, 6.40 mmol) and $K_2CO_3$ (1.18 g, 8.53 mmol) in $CH_3CN$ (30 ml) was stirred at 80° C. under nitrogen atmosphere for 4 h. After the reaction was complete, the mixture was quenched with water and extracted with EtOAc (50 mL×3). The organic layer was separated, dried over $MgSO_4$, and concentrated in vacuum, which was purified by column chromatography (petroleum ether/EtOAc=1/1) to give 252-3 (1 g, about 88% yield) as an oil. MS Calcd.: 266.0; MS Found: 267.0 $[M+H]^+$.

The Synthesis of N-(2-(1H-1,2,4-triazol-1-yl)ethyl)-3-bromo-N-methylaniline (252-4)

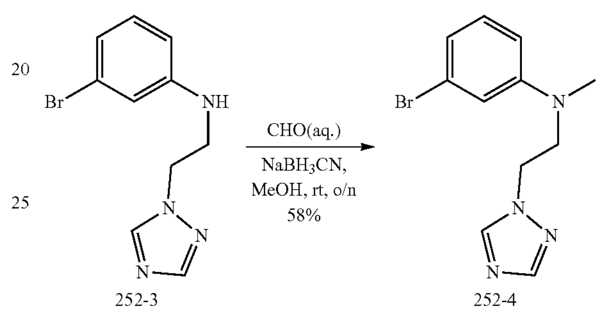

252-3

252-4

A mixture of 252-3 (900 mg, 3.37 mmol) and formaldehyde (202 mg, 6.74 mmol, 30% in water) in MeOH (20 ml) was added $NaBH_3CN$ (635 mg, 10.11 mmol), the mixture was stirred at room temperature overnight. After the reaction was complete, the mixture was quenched with water, the insoluble material was removed by filtration, and the filtrate was extracted with EtOAc (30 mL×3). The organic layer was separated, dried over $MgSO_4$, and concentrated in vacuum, which was purified by column chromatography (petroleum ether/EtOAc=3/1) to give 252-4 (550 mg, about 58% yield) as an oil. MS Calcd.: 280.0; MS Found: 281.0 $[M+H]^+$.

The Synthesis of $N^1$-(2-(1H-1,2,4-triazol-1-yl)ethyl)-$N^3$-(4-fluorophenyl)-$N^1$-methylbenzene-1,3-diamine (SS20308-0252-01)

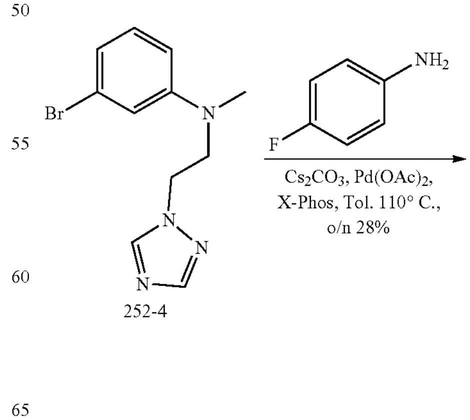

252-4

-continued

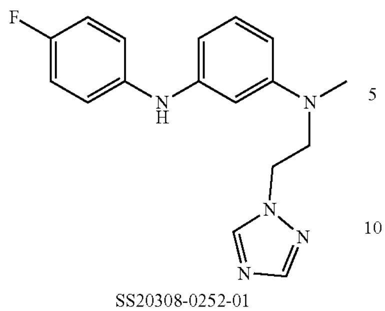

SS20308-0252-01

A mixture of 252-4 (200 mg, 0.71 mmol), 4-fluoroaniline (119 mg, 1.07 mmol), $Pd(OAc)_2$ (8 mg, 0.04 mmol), X-Phos (34 mg, 0.07 mmol) and $Cs_2CO_3$ (464 mg, 1.42 mmol) in Tol (10 ml) and was stirred at 110° C. under nitrogen atmosphere overnight. After the reaction was complete, the mixture was quenched with water, the insoluble material was removed by filtration, and the filtrate was extracted with EtOAc (30 mL×3). The organic layer was separated, dried over $MgSO_4$, and concentrated in vacuum, which was purified by Prep-HPLC to give SS20308-0252-01 (62 mg, about 28% yield) as an oil. MS Calcd.: 311.2; MS Found: 312.0 $[M+H]^+$.

$^1H$ NMR (400 MHz, DMSO-$d_6$) δ 8.43 (s, 1H), 7.97 (s, 1H), 7.94 (s, 1H), 7.06 (s, 2H), 7.04 (s, 2H), 7.00 (t, J=8.4 Hz, 1H), 6.34 (dd, J=7.6 Hz, 1.6 Hz, 1H), 6.28 (d, J=2.0 Hz, 1H), 6.15 (dd, J=8.4 Hz, 2.4 Hz, 1H), 4.35 (t, J=6.4 Hz, 2H), 3.68 (t, J=6.0 Hz, 2H), 2.69 (s, 3H).

Example 90

SS20308-0263-01

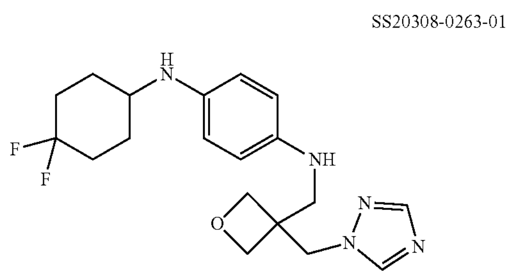

Chemical Formula: $C_{19}H_{25}F_2N_5O$
Molecular Weight: 377.43

Example Route for Example 90

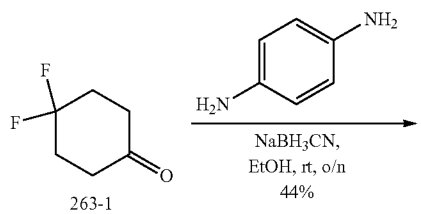

263-1

-continued

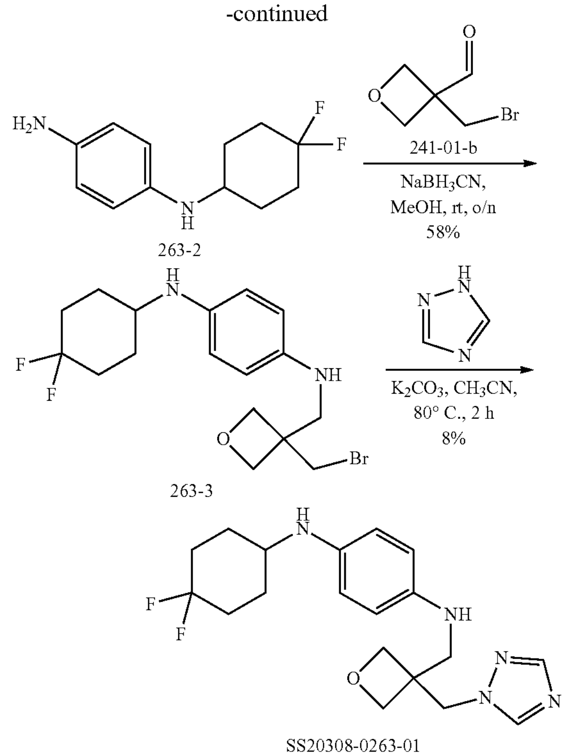

263-2

263-3

SS20308-0263-01

The Synthesis of N[1]-(4,4-difluorocyclohexyl)benzene-1,4-diamine (263-2)

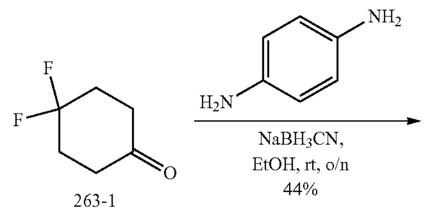

263-1

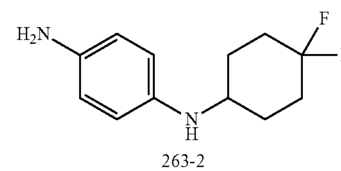

263-2

A mixture of benzene-1,4-diamine (242 mg, 2.24 mmol), 4,4-difluorocyclohexanone (263-1) (200 mg, 1.49 mmol) and $NaBH_3CN$ (143 mg, 2.24 mmol) in EtOH (20 mL) was stirred at rt for 18 hr. After the reaction was complete, the reaction mixture was concentrated and quenched with water (10 mL), extracted with EtOAc (10 mL×3). The combined layers were dried over $Na_2SO_4$ and concentrated under vacuum to give 263-2 (150 mg, about 44% yield) as a solid. MS Calcd.: 226.1; MS Found: 227.4 $[M+H]^+$.

The Synthesis of N[1]-((3-(bromomethyl)oxetan-3-yl) methyl)-N[4]-(4,4-difluorocyclohexyl)benzene-1,4-diamine (263-3)

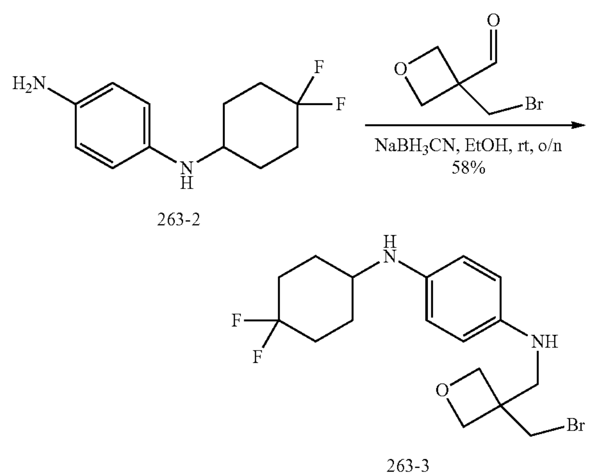

263-2

263-3

A mixture of 3-(bromomethyl)oxetane-3-carbaldehyde (79 mg, 441.96 umol), 263-2 (100 mg, 442 umol) and $NaBH_3CN$ (42 mg, 663 umol) in EtOH (2 mL) was stirred at rt overnight. After the reaction was complete, the reaction mixture was concentrated and quenched with water (10 mL), extracted with EtOAc (10 mL×3). The combined layers were dried over $Na_2SO_4$ and concentrated in vacuum to give 263-3 (100 mg, about 58% yield) as a solid. MS Calcd.: 388.1; MS Found: 389.3 $[M+H]^+$.

The Synthesis of N[1]-((3-((1H-1,2,4-triazol-1-yl) methyl)oxetan-3-yl)methyl)-N[4]-(4,4-difluorocyclohexyl) benzene-1,4-diamine (SS20308-0263-01)

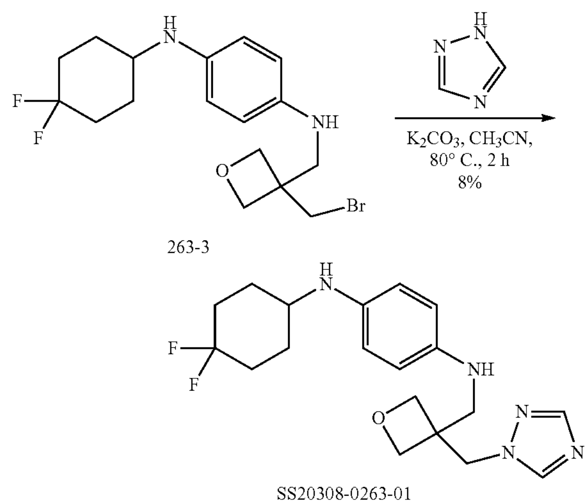

263-3

SS20308-0263-01

A mixture of 1H-1,2,4-triazole (14 mg, 206 umol), 263-3 (80 mg, 206 umol) and $K_2CO_3$ (56 mg, 412 umol) in $CH_3CN$ (1 mL) was stirred at 80° C. for 2 h. After the reaction was complete, the reaction mixture was concentrated and quenched with water (10 mL), extracted with EtOAc (10 mL×3). The combined layers were dried over $Na_2SO_4$ and concentrated in vacuum, then purified by Prep-HPLC to give SS20308-0263-01 (6.06 mg, about 8% yield) as a solid. MS Calcd.: 377.2; MS Found: 378.0 $[M+H]^+$.

$^1H$ NMR (400 MHz, DMSO-$d_6$) δ 8.49 (s, 1H), 8.01 (s, 1H), 6.48-6.41 (m, 4H), 4.90 (t, J=6.0 Hz, 1H), 4.69 (d, J=8.4 Hz, 1H), 4.59 (s, 2H), 4.52 (d, J=6.4 Hz, 2H), 4.38 (d, J=6.4 Hz, 2H), 3.30-3.27 (m, 1H), 3.00 (d, J=6.0 Hz, 2H), 2.01-1.98 (m, 2H), 1.90-1.87 (m, 4H), 1.43-1.39 (m, 2H).

Example 91

SS20308-264-01

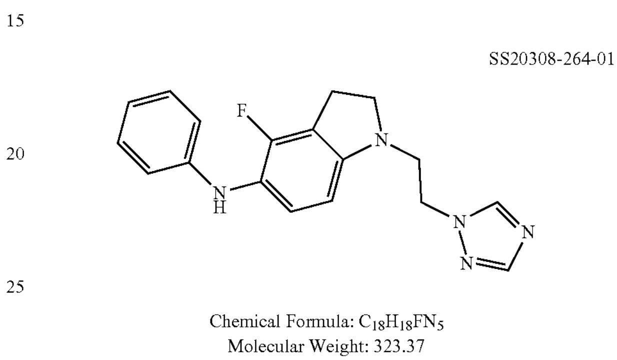

Chemical Formula: $C_{18}H_{18}FN_5$
Molecular Weight: 323.37

Example Route for Example 91

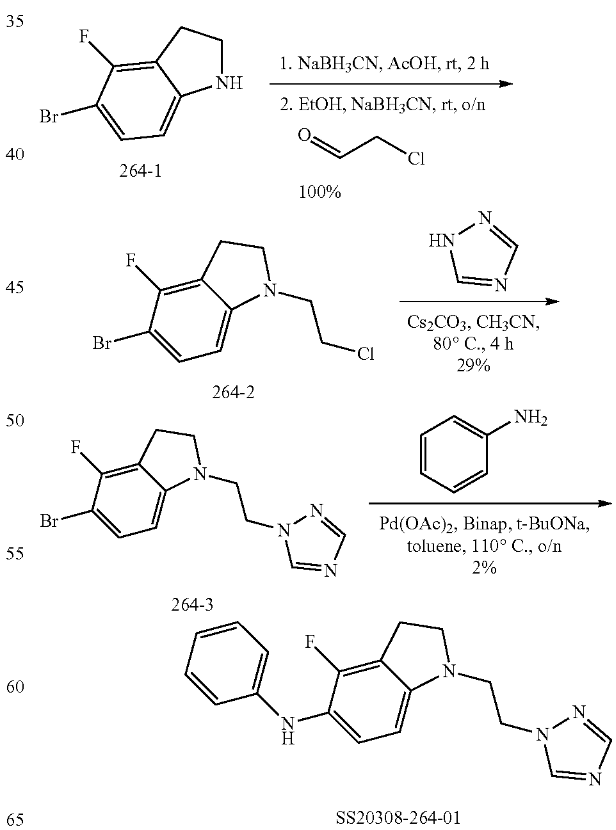

264-1

264-2

264-3

SS20308-264-01

The Synthesis of 5-bromo-1-(2-chloroethyl)-4-fluoroindoline (264-2)

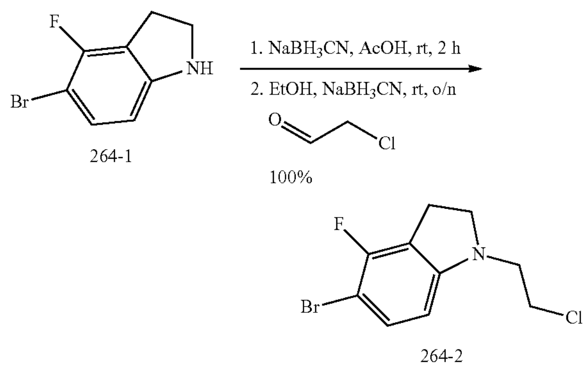

264-1

264-2

The mixture of 264-1 (3.0 g, 14.0 mmol) and $NaBH_3CN$ (1.77 g, 28.0 mmol) in AcOH (30 mL) was stirred at room temperature for 2 hours. Then the reaction mixture was added EtOH (60 mL), $NaBH_3CN$ (1.77 g, 28.0 mmol) and 2-chloroacetaldehyde (5.50 g, 28.0 mmol, 40% in water) and stirred at room temperature overnight. The reaction mixture was poured into water and basicified with 1N NaOH till pH reached 10. The mixture was extracted with EtOAc (30 mL×3). The organic layers were washed with brine, dried over $Na_2SO_4$ and concentrated to give 264-2 (7.0 g, about 100% yield, crude) as an oil. MS Calcd.: 277.0; MS Found: 278.0 $[M+H]^+$.

The Synthesis of 1-(2-(1H-1,2,4-triazol-1-yl)ethyl)-5-bromo-4-fluoroindoline (264-3)

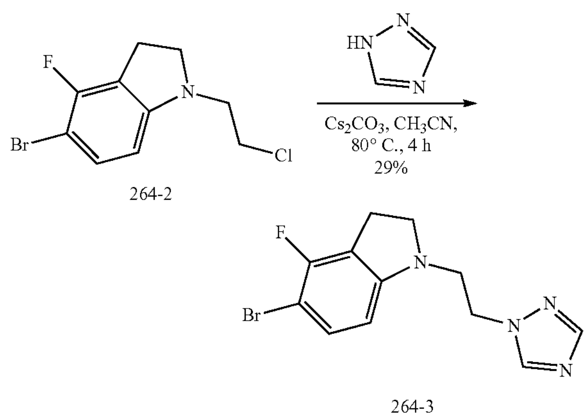

264-2

264-3

A mixture of 264-2 (7.0 g, 25.1 mmol), 1H-1,2,4-triazole (3.45 g, 50.2 mmol) and $Cs_2CO_3$ (16.3 g, 50.2 mmol) in $CH_3CN$ (150 mL) was stirred at 80° C. overnight. The reaction mixture was then cooled to room temperature and filtered through celite and concentrated. The residue was purified by column chromatography (petroleum ether/EtOAc=1/1) to give 264-3 (2.25 g, 29% yield) as a solid. MS Calcd.: 310.0; MS Found: 311.0 $[M+H]^+$.

The Synthesis of 1-(2-(1H-1,2,4-triazol-1-yl)ethyl)-4-fluoro-N-phenylindolin-5-amine (SS20308-264-01)

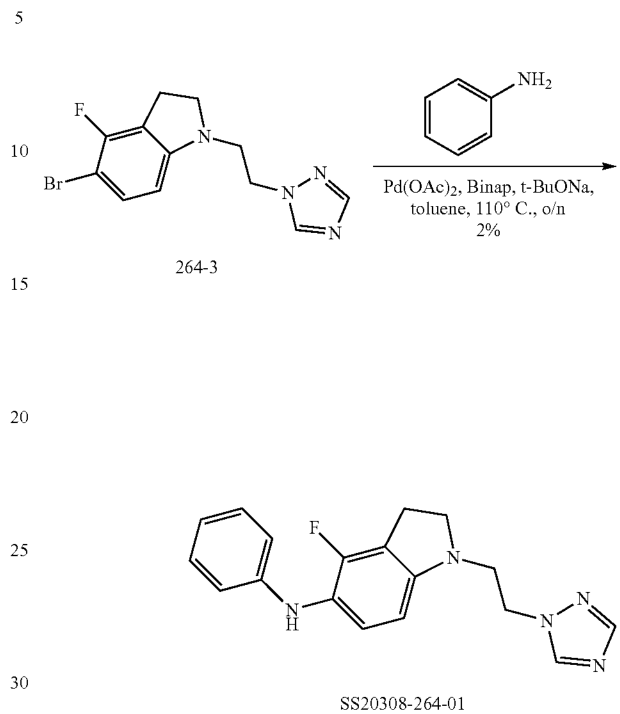

264-3

SS20308-264-01

The mixture of 264-3 (200 mg, 0.64 mmol), aniline (120 mg, 1.29 mmol), $Pd(OAc)_2$ (15 mg, 0.064 mmol), BINAP (80 mg, 0.13 mmol) and t-BuONa (123 mg, 1.29 mmol) in toluene (10 mL) was stirred at 110° C. overnight under $N_2$ atmosphere. The reaction mixture was then cooled to room temperature and filtered through celite and concentrated. The residue was purified by Prep-HPLC to give SS20308-0264-01 (5 mg, about 2% yield) as a solid. MS Calcd.: 323.1; MS Found: 324.3 $[M+H]^+$.

$^1H$ NMR (400 MHz, DMSO-$d_6$) δ 8.55 (s, 1H), 7.98 (s, 1H), 7.34 (s, 1H), 7.07 (t, J=8.0 Hz, 2H), 6.85 (t, J=8.2 Hz, 1H), 6.63-6.58 (m, 3H), 6.19 (d, J=8.0 Hz, 1H), 4.41 (t, J=6.0 Hz, 2H), 3.48 (t, J=8.0 Hz, 2H), 3.33-3.41 (m, 2H), 2.93 (d, J=8.4 Hz, 2H).

Example 92

SS20308-0272-01

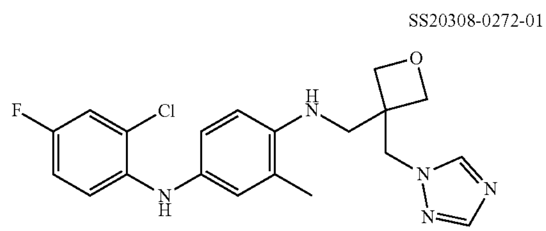

Chemical Formula: $C_{20}H_{21}ClFN_5O$
Molecular Weight: 401.87

Example Route for Example 92

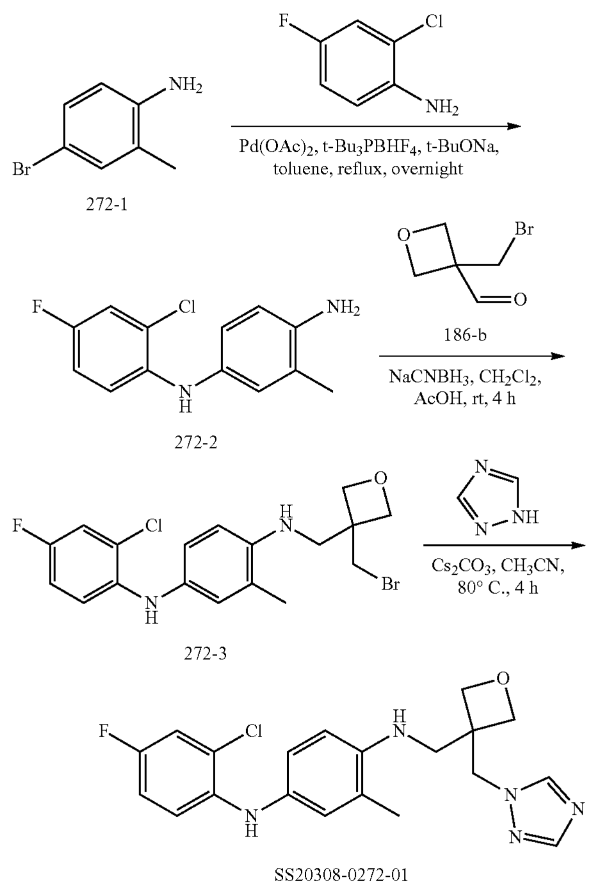

272-1

272-2

272-3

SS20308-0272-01

The Synthesis of N1-(2-chloro-4-fluorophenyl)-3-methylbenzene-1,4-diamine (272-2)

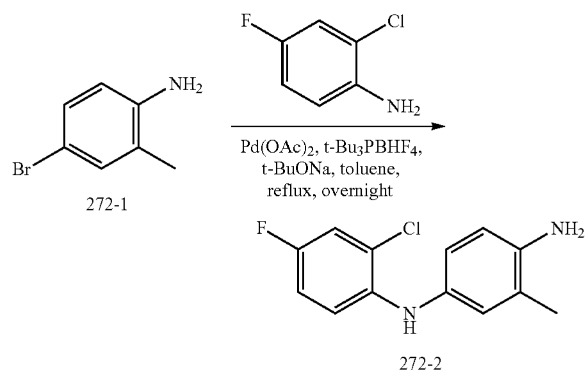

272-1

272-2

A mixture of 272-1 (3.0 g, 7.8 mmol), 2-chloro-4-fluoroaniline (2.3 g, 15.6 mmol), Pd(OAc)$_2$ (176 mg, 0.78 mmol), t-Bu$_3$PBHF$_4$ (339 mg, 1.17 mmol), t-BuONa (2.3 g, 23.4 mmol) in toluene (300 mL) was bubbled with nitrogen for 20 mins, then the reaction mixture was heated to reflux overnight under nitrogen. The mixture was cooled to room temperature, then the mixture was filtered and washed by EtOAc. The organic phase was dried with Na$_2$SO$_4$, filtered and concentrated to an oil, which was purified by column chromatography on silica gel (petroleum ether/EtOAc=1/10) to give 272-2 (750 mg, about 19% yield) as an oil. MS Calcd.: 250.1; MS Found: 251.1 [M+H]$^+$ The Synthesis of N1-((3-(bromomethyl)oxetan-3-yl)methyl)-N4-(2-chloro-4-fluorophenyl)-2-methylbenzene-1,4-diamine (272-3)

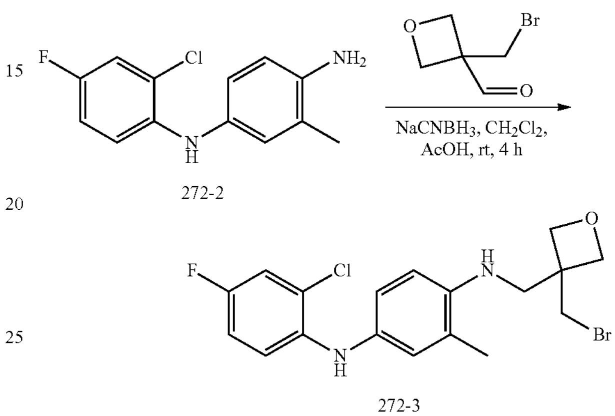

272-2

272-3

To the solution of 272-2 (750 mg, 3.0 mmol) in DCM (10 mL) was added 3-(bromomethyl)oxetane-3-carbaldehyde (534 mg, 3.0 mmol). NaCNBH$_3$ (189 mg, 3.0 mmol) in several portions. AcOH (0.1 mL) was then added and the mixture was stirred at room temperature for 4 h under nitrogen. The mixture was diluted with water and extracted with DCM. The organic extracts were dried with Na$_2$SO$_4$, filtered and concentrated to an oil, which was purified by column chromatography on silica gel (petroleum ether/EtOAc=1/5) to give 272-3 (400 mg, about 32% yield) as an oil. MS Calcd.: 412.0; MS Found: 413.9 [M+H]$^+$.

The Synthesis of N1-((3-((1H-1,2,4-triazol-1-yl)methyl)oxetan-3-yl)methyl)-N4-(2-chloro-4-fluorophenyl)-2-methylbenzene-1,4-diamine (SS20308-0272-01)

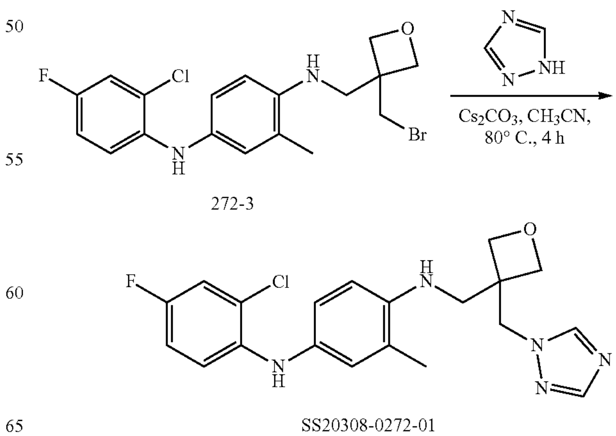

272-3

SS20308-0272-01

To a solution of 272-3 (400 mg, 0.97 mmol) in $CH_3CN$ (10 mL) was added 1H-1,2,4-triazole (69 mg, 1 mmol), $Cs_2CO_3$ (919 mg, 2.82 mmol) at room temperature, then the mixture was heated to 80° C. for 4 h under nitrogen. The reaction mixture was cooled to room temperature, filtered, and washed with EtOAc. The filtrate was concentrated to an oil, which was purified by reverse phase column chromatography to give SS20308-0272-01 (200 mg, about 51% yield) as a solid. MS Calcd.: 401.1; MS Found: 402.0 $[M+H]^+$.

$^1H$ NMR (400 MHz, DMSO-$d_6$) δ 8.54 (s, 1H), 8.03 (s, 1H), 7.30 (dd, J=8.4, 3.2 Hz, 1H), 7.00-6.93 (m, 2H), 6.84-6.76 (m, 3H), 6.44 (d, J=8.4 Hz, 1H), 4.73 (t, J=5.8 Hz, 1H), 4.65 (s, 2H), 4.54 (d, J=6.4, 2H), 4.45 (d, J=6.0, 2H), 3.17 (d, J=5.6, 2H), 2.13 (s, 3H).

Example 93: Preparation of SS20308-0233-01

The Synthesis of N-((3-((1H-1,2,4-triazol-1-yl)methyl)oxetan-3-yl)methyl)-6-fluoro-2-methyl-9H-carbazol-3-amine (SS20308-0233-01)

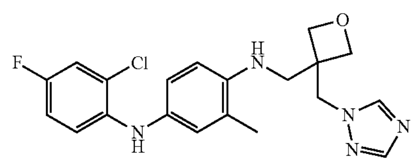

SS20308-0272-01

$Pd(OAc)_2$,
$P(t-Bu)_3•HBF_4$,
DBU,
DMA, MW,
140° C., 1 h

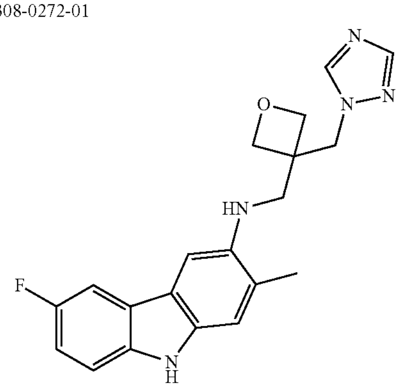

SS20308-0233-01

A mixture of SS20308-0272-01 (200 mg, 0.5 mmol), $Pd(OAc)_2$ (12 mg, 0.05 mmol), t-$Bu_3PBHF_4$ (22 mg, 0.075 mmol), DBU (304 mg, 2 mmol) in DMA (3 mL) was bubbled with nitrogen for 20 mins. The reaction mixture was heated to 140° C. for 1 h in a microwave reactor. The mixture was cooled to room temperature, filtered, and washed with EtOAc. The organic phase was dried with $Na_2SO_4$, filtered and concentrated to an oil, which was purified by Prep-TLC followed by Prep-HPLC to give SS20308-0233-01 (13 mg, about 7% yield) as a solid. MS Calcd.: 365.2; MS Found: 366.4 $[M+H]^+$.

$^1H$ NMR (400 MHz, DMSO-$d_6$ and $D_2O$) δ 8.56 (s, 1H), 8.07 (s, 1H), 7.74 (dd, J=9.6, 2.4 Hz, 1H), 7.37 (dd, J=8.8, 4.8 Hz, 1H), 7.22 (s, 1H), 7.15-7.08 (m, 2H), 4.72 (s, 2H), 4.61 (d, J=6.4, 2H), 4.53 (d, J=6.4, 2H), 3.29 (s, 2H), 2.32 (s, 3H).

Example 94

SS20308-0279-01

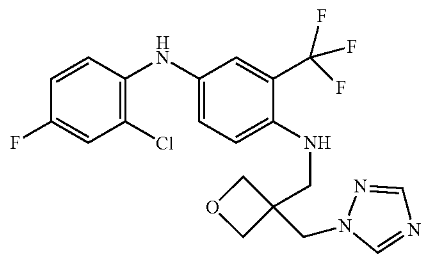

Chemical Formula: $C_{20}H_{18}ClF_4N_5O$
Molecula Weight: 455.84

Example Route for Example 94

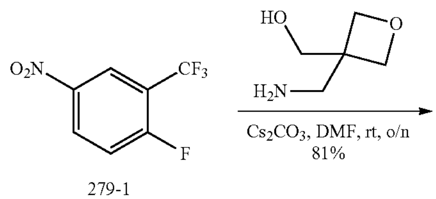

279-1

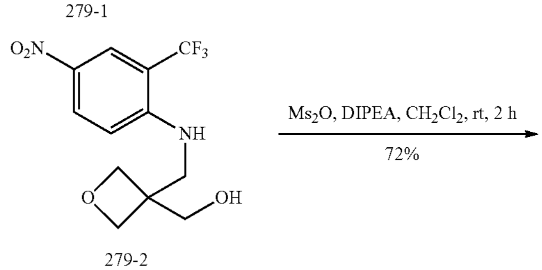

279-2

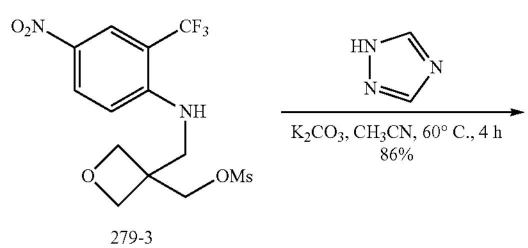

279-3

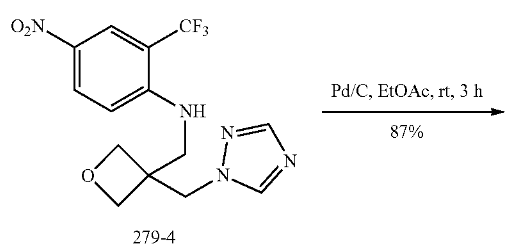

279-4

-continued

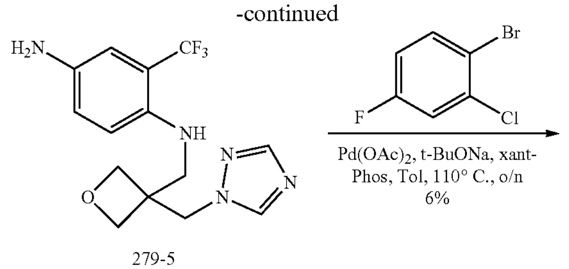

279-5

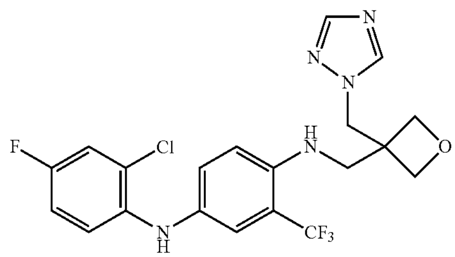

SS20308-0279-01

The Synthesis of (3-((4-nitro-2-(trifluoromethyl) phenylamino)methyl)oxetan-3-yl)methanol (279-2)

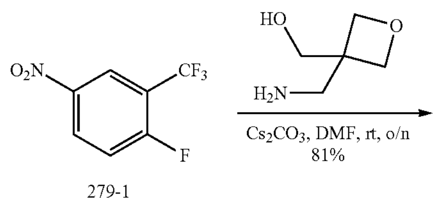

279-1

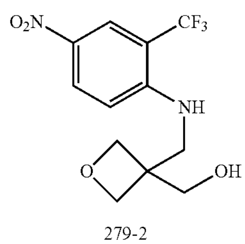

279-2

A mixture of 279-1 (1.10 g, 5.26 mmol), (3-(aminomethyl)oxetan-3-yl)methanol (616 mg, 5.26 mmol) and $Cs_2CO_3$ (3.43 g, 10.52 mmol) in DMF (10 ml) was stirred at room temperature under nitrogen atmosphere overnight. After the reaction was complete, the mixture was quenched with water and extracted with EtOAc (50 mL×3). The organic layer was separated, dried over $MgSO_4$, and concentrated under vacuum. The crude product was purified by column chromatography (petroleum ether/EtOAc=1/2) to give 279-2 (1.30 g, about 81% yield) as a solid. MS Calcd.: 306.1; MS Found: 307.0 $[M+H]^+$.

The Synthesis of (3-((4-nitro-2-(trifluoromethyl) phenylamino)methyl)oxetan-3-yl)methyl methanesulfonate (279-3)

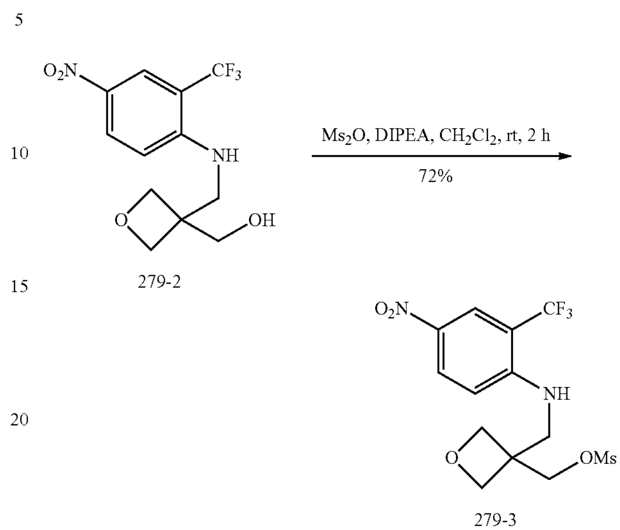

279-2

279-3

To a solution of 279-2 (1.10 g, 3.59 mmol) in $CH_2Cl_2$ (20 mL) was added $Ms_2O$ (1.25 g, 7.18 mmol) and DIPEA (928 mg, 7.18 mmol). The mixture was stirred at room temperature for 2 h. After the reaction was complete, it was quenched with water and extracted with $CH_2Cl_2$ (50 mL×3). The organic layer was separated, dried over $MgSO_4$, and concentrated under vacuum. The crude product was purified by column chromatography (petroleum ether/EtOAc=1/1) to give 279-3 (1.00 g, about 72% yield) as a solid. MS Calcd.: 384.1; MS Found: 384.8 $[M+H]^+$.

The Synthesis of N-((3-((1H-1,2,4-triazol-1-yl) methyl)oxetan-3-yl)methyl)-4-nitro-2-(trifluoromethyl) aniline (279-4)

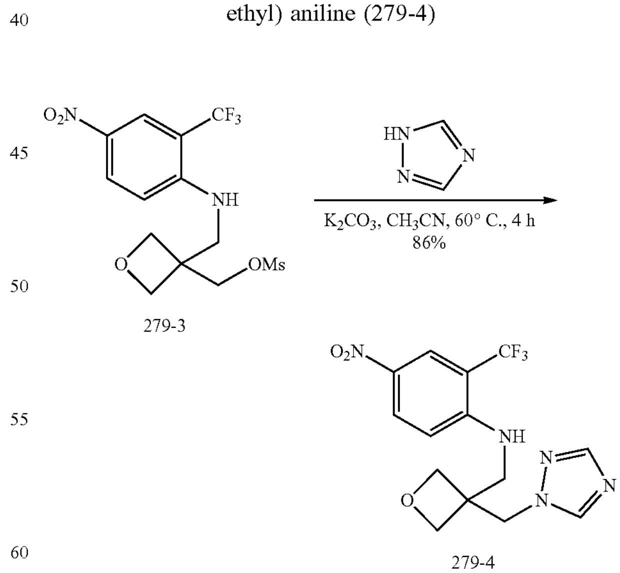

279-3

279-4

To a solution of 279-3 (1.00 g, 2.60 mmol) in $CH_3CN$ (20 mL) was added 1H-1,2,4-triazole (359 mg, 5.20 mmol) and $K_2CO_3$ (719 mg, 5.20 mmol). The mixture was stirred at 60° C. for 4 h. After the reaction was complete, it was quenched with water and extracted with EtOAc (50 mL×3). The organic layer was separated, dried over $MgSO_4$, and concentrated under vacuum. The crude product was purified by column chromatography (petroleum ether/EtOAc=1/1) to give 279-4 (0.80 g, about 86% yield) as a solid. MS Calcd.: 357.1; MS Found: 357.8 $[M+H]^+$.

The Synthesis of $N^1$-((3-((1H-1,2,4-triazol-1-yl)methyl)oxetan-3-yl)methyl)-2-(trifluoromethyl)benzene-1,4-diamine (279-5)

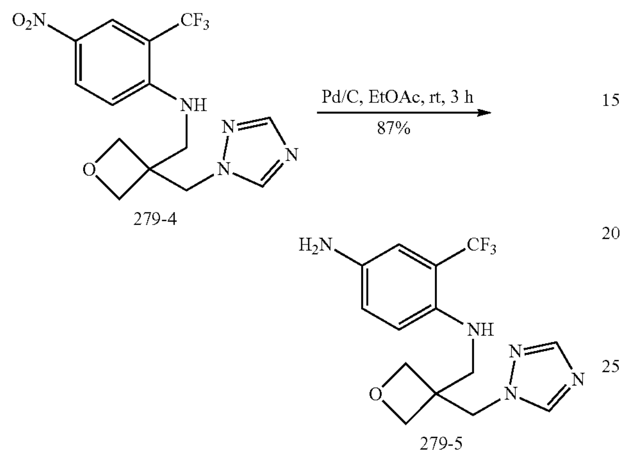

279-4

279-5

To a solution of 279-4 (250 mg, 0.70 mmol) in EtOAc (20 mL) was added Pd/C (10%, 35 mg), the mixture was stirred at room temperature under hydrogen gas (balloon) overnight. After the reaction was complete, the insoluble material was removed by filtration. The organic layer was concentrated under vacuum. The crude product was purified by column chromatography (petroleum ether/EtOAc=1/3) to give 279-5 (0.20 g, about 87% yield) as a solid. MS Calcd.: 327.1; MS Found: 328.2 $[M+H]^+$.

The Synthesis of $N^1$-((3-((1H-1,2,4-triazol-1-yl)methyl)oxetan-3-yl)methyl)-$N^4$-(2-chloro-4-fluorophenyl)-2-(trifluoromethyl)benzene-1,4-diamine (SS20308-0279-01)

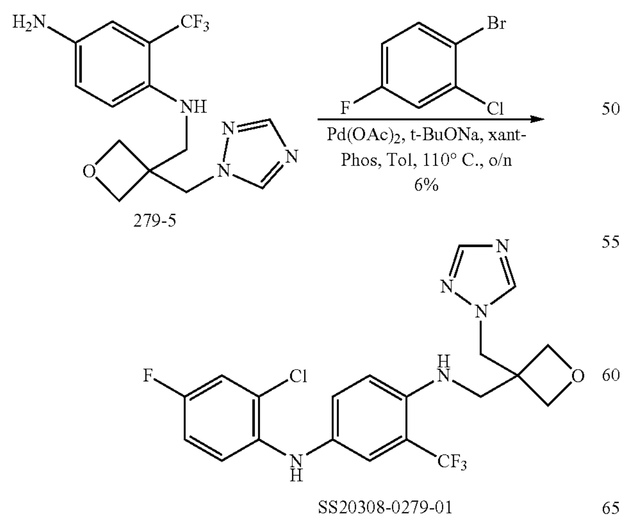

279-5

SS20308-0279-01

A mixture of 279-5 (100 mg, 0.31 mmol), 1-bromo-2-chloro-4-fluorobenzene (128 mg, 0.61 mmol), $Pd(OAc)_2$ (7 mg, 0.03 mmol), Xant-Phos (35 mg, 0.06 mmol) and t-BuONa (59 mg, 0.61 mmol) in toluene (10 ml) was stirred at 110° C. under nitrogen atmosphere overnight. After the reaction was complete, the mixture was quenched with water. The insoluble material was removed by filtration, and the filtrate was extracted with EtOAc (30 mL×3). The organic layer was separated, dried over $MgSO_4$, and concentrated under vacuum. The crude product was purified by Prep-HPLC to give SS20308-0279-01 (8 mg, about 6% yield) as a light oil. MS Calcd.: 455.1; MS Found: 456.1 $[M+H]^+$.

$^1H$ NMR (400 MHz, DMSO-$d_6$) δ 8.56 (s, 1H), 8.01 (s, 1H), 7.36-7.33 (m, 2H), 7.17 (d, J=2.4 Hz, 1H), 7.13 (d, J=8.8 Hz, 1H), 7.04-6.99 (m, 1H), 6.93-6.89 (m, 1H), 6.76 (d, J=9.2 Hz, 1H), 5.28 (t, J=6.0 Hz, 1H), 4.58 (s, 2H), 4.47 (d, J=6.4 Hz, 2H), 4.42 (d, J=6.4 Hz, 2H), 3.26 (d, J=6.0 Hz, 2H).

Example 95

SS20308-0289-01

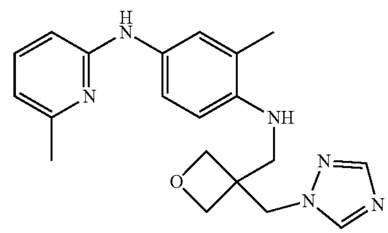

Chemical Formula: $C_{20}H_{24}N_6O$
Molecular Weight: 364.44

Example Route for Example 95

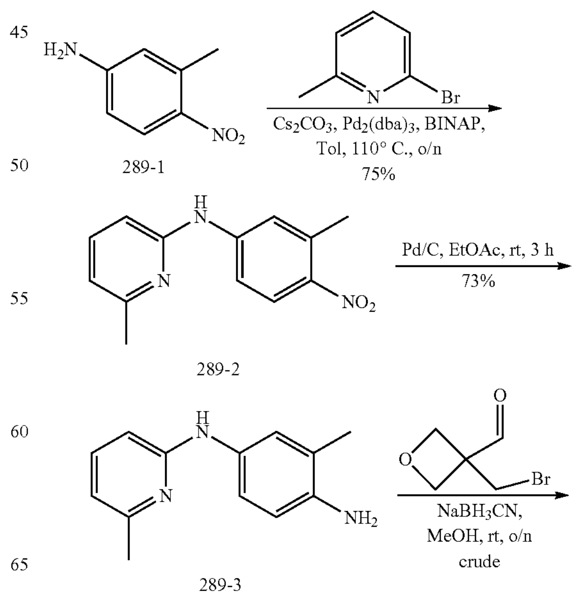

289-1

289-2

289-3

-continued

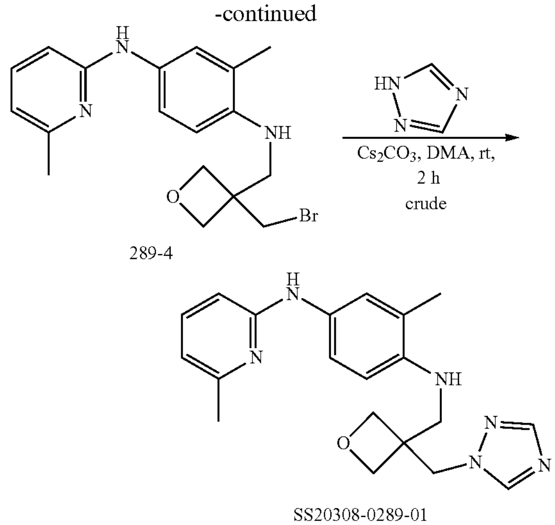

289-4

SS20308-0289-01

The Synthesis of 6-methyl-N-(3-methyl-4-nitrophenyl)pyridin-2-amine (289-2)

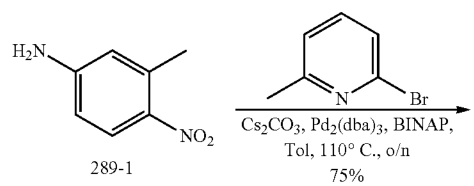

289-1

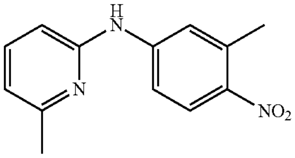

289-2

A mixture of 289-1 (1.00 g, 6.57 mmol), 2-bromo-6-methylpyridine (1.13 g, 6.57 mmol), $Pd_2(dba)_3$ (602 mg, 0.07 mmol), BINAP (818 mg, 1.31 mmol) and $Cs_2CO_3$ (4.28 g, 13.14 mmol) in toluene (10 ml) was stirred at 110° C. under nitrogen atmosphere overnight. After the reaction was complete, the mixture was quenched with water. The insoluble material was removed by filtration, and the filtrate was extracted with EtOAc (50 mL×3). The organic layer was separated, dried over $MgSO_4$, and concentrated under vacuum. The crude product was purified by column chromatography (petroleum ether/EtOAc=4/1) to give 289-2 (1.20 g, about 75% yield) as a solid. MS Calcd.: 243.1; MS Found: 244.0 $[M+H]^+$.

The Synthesis of 3-methyl-$N^1$-(6-methylpyridin-2-yl)benzene-1,4-diamine (289-3)

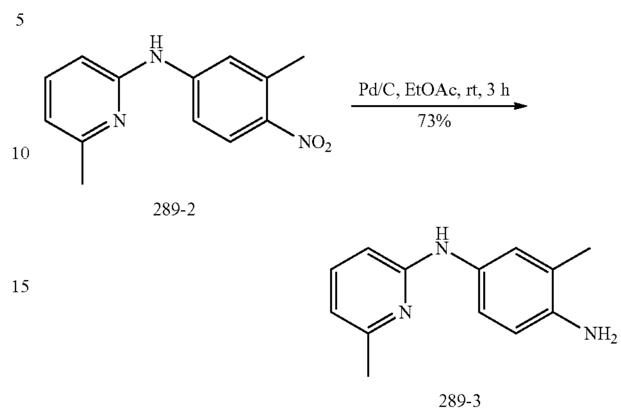

289-2

289-3

To a solution of 289-2 (500 mg, 2.06 mmol) in EtOAc (20 mL) was added Pd/C (10%, 50 mg). The mixture was stirred at room temperature under hydrogen gas (balloon) for 3 h. After the reaction was complete, the insoluble material was removed by filtration. The organic layer was concentrated under vacuum. The crude product was purified by column chromatography (petroleum ether/EtOAc=1/3) to give 289-3 (320 mg, about 73% yield) as an oil. MS Calcd.: 213.1; MS Found: 241.2 $[M+H]^+$.

The Synthesis of $N^1$-((3-(bromomethyl)oxetan-3-yl)methyl)-2-methyl-$N^4$-(6-methylpyridin-2-yl)benzene-1,4-diamine (289-4)

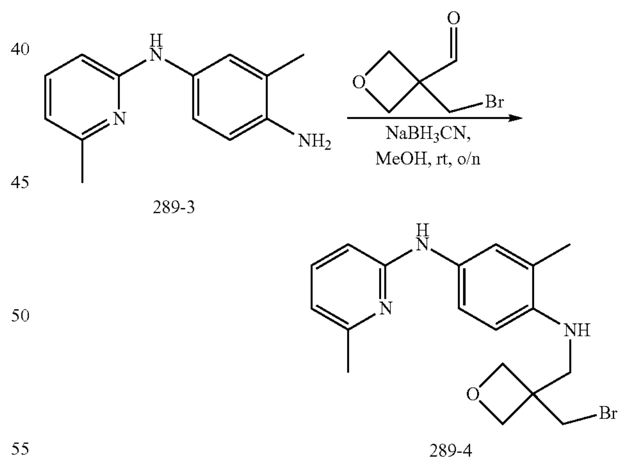

289-3

289-4

To a solution of 289-3 (320 mg, 1.50 mmol) in MeOH (20 mL) was added 3-(bromomethyl)oxetane-3-carbaldehyde (269 mg, 1.50 mmol) and $NaCNBH_3$ (189 mg, 3.00 mmol). The mixture was stirred at room temperature overnight. After the reaction was complete, it was quenched with water and extracted with $CH_2Cl_2$ (50 mL×3). The organic layer was separated, dried over $MgSO_4$, and concentrated under vacuum to afford crude 289-4. This was used in the next step without further purification. MS Calcd.: 375.1; MS Found: 375.9 $[M+H]^+$.

The Synthesis of N[1]-((3-((1H-1,2,4-triazol-1-yl)methyl)oxetan-3-yl)methyl)-2-methyl-N[4]-(6-methylpyridin-2-yl)benzene-1,4-diamine (SS20308-0289-01)

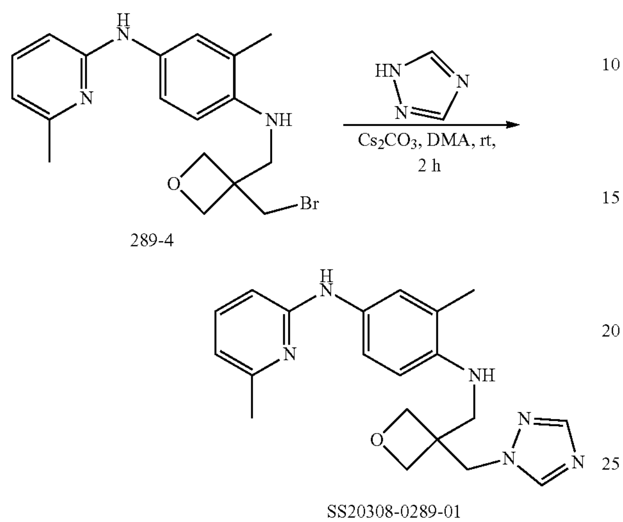

289-4

SS20308-0289-01

To a solution of 289-4 (100 mg, crude) in DMA (3 mL) was added 1H-1,2,4-triazole (37 mg, 0.53 mmol) and $Cs_2CO_3$ (173 mg, 0.53 mmol). The mixture was stirred at room temperature for 2 h. After the reaction was complete, it was quenched with water and extracted with EtOAc (50 mL×3). The organic layer was separated, dried over $MgSO_4$, and concentrated under vacuum. The crude product was purified by Prep-HPLC to give SS20308-0289-01 (8 mg) as an oil. MS Calcd.: 364.2; MS Found: 365.3 $[M+H]^+$.

$^1$H NMR (400 MHz, DMSO-$d_6$) δ 8.54 (s, 1H), 8.33 (s, 1H), 8.03 (s, 1H), 7.32 (dd, J=7.6 Hz, 1H), 7.23 (dd, J=8.8 Hz, 2.4 Hz, 1H), 7.14 (d, J=2.4 Hz, 1H), 6.46-6.40 (m, 3H), 4.65 (s, 2H), 4.59 (t, J=5.6 Hz, 1H), 4.54 (d, J=6.0 Hz, 2H), 4.45 (d, J=6.4 Hz, 2H), 3.15 (d, J=5.6 Hz, 2H), 2.29 (s, 3H), 2.13 (s, 3H).

Example 96

SS20308-0296-01

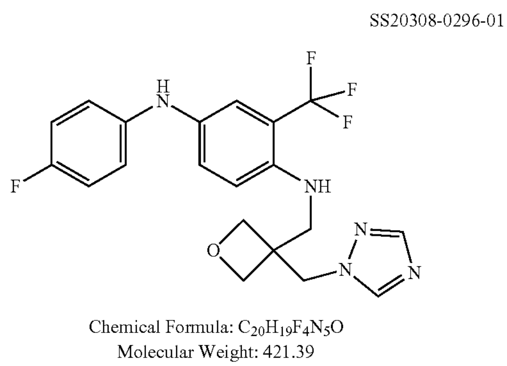 [SMILES: Fc1ccc(Nc2ccc(NCC3(Cn4cncn4)COC3)c(C(F)(F)F)c2)cc1]

Chemical Formula: $C_{20}H_{19}F_4N_5O$
Molecular Weight: 421.39

Example Route for Example 96

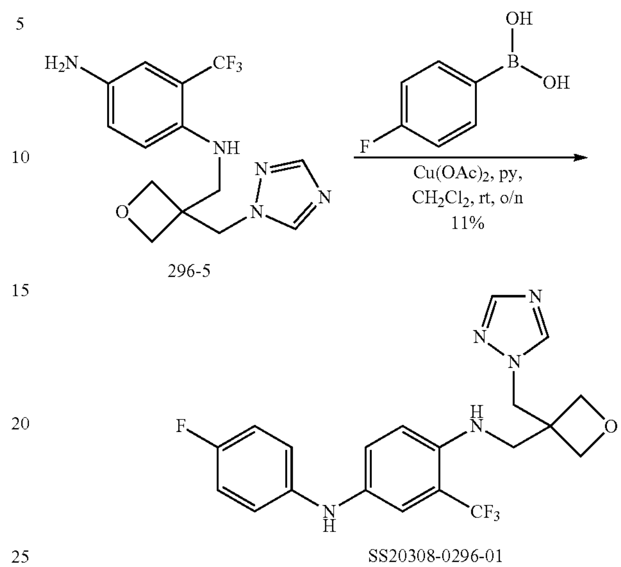

296-5

SS20308-0296-01

The synthesis of 296-5 is detailed in the synthesis for SS20308-0279-01 above.

The Synthesis of N[1]-((3-((1H-1,2,4-triazol-1-yl)methyl)oxetan-3-yl)methyl)-N[4]-(4-fluorophenyl)-2-(trifluoromethyl)benzene-1,4-diamine (SS20308-0296-01)

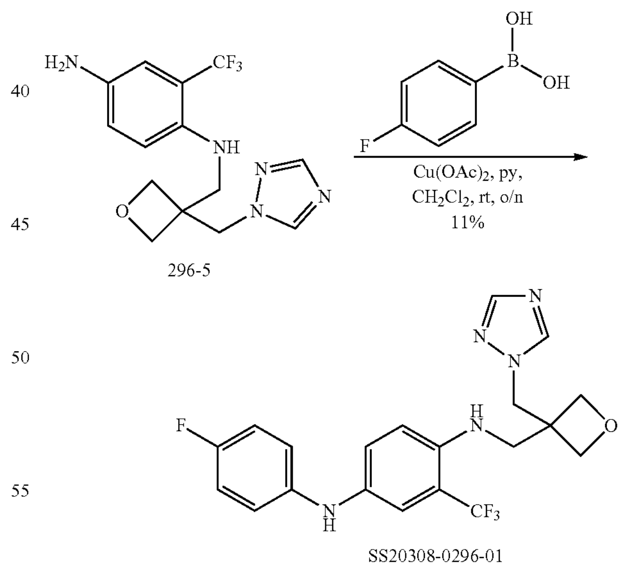

296-5

SS20308-0296-01

To a solution of 296-5 (0.15 g, 0.46 mmol) in $CH_2Cl_2$ (20 mL) was added 4-fluorophenylboronic acid (192 mg, 1.37 mmol), $Cu(OAc)_2$ (83 mg, 0.46 mmol) and pyridine (109 mg, 1.37 mmol). The mixture was stirred at room temperature overnight. After the reaction was complete, it was quenched with water and extracted with $CH_2Cl_2$ (50 mL×3). The organic layer was separated, dried over $MgSO_4$, and concentrated under vacuum. The crude product was purified by Prep-HPLC to give SS20308-0296-01 (22 mg, about 11% yield) as an oil. MS Calcd.: 421.1; MS Found: 422.1 $[M+H]^+$.

$^1H$ NMR (400 MHz, DMSO-$d_6$) δ 8.55 (s, 1H), 8.01 (s, 1H), 7.79 (s, 1H), 7.15-7.11 (m, 2H), 7.02-6.98 (m, 2H), 6.86-6.83 (m, 2H), 6.75 (d, J=8.8 Hz, 1H), 5.15 (t, J=6.0 Hz, 1H), 4.58 (s, 2H), 4.48 (d, J=6.4 Hz, 2H), 4.42 (d, J=6.4 Hz, 2H), 3.25 (d, J=6.0 Hz, 2H).

Example 97

SS20308-0307-01

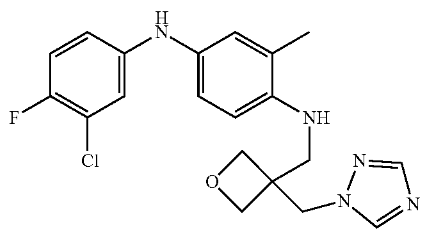

Chemical Formula: $C_{20}H_{21}ClFN_5O$
Molecular Weight: 401.87

Example Route for Example 97

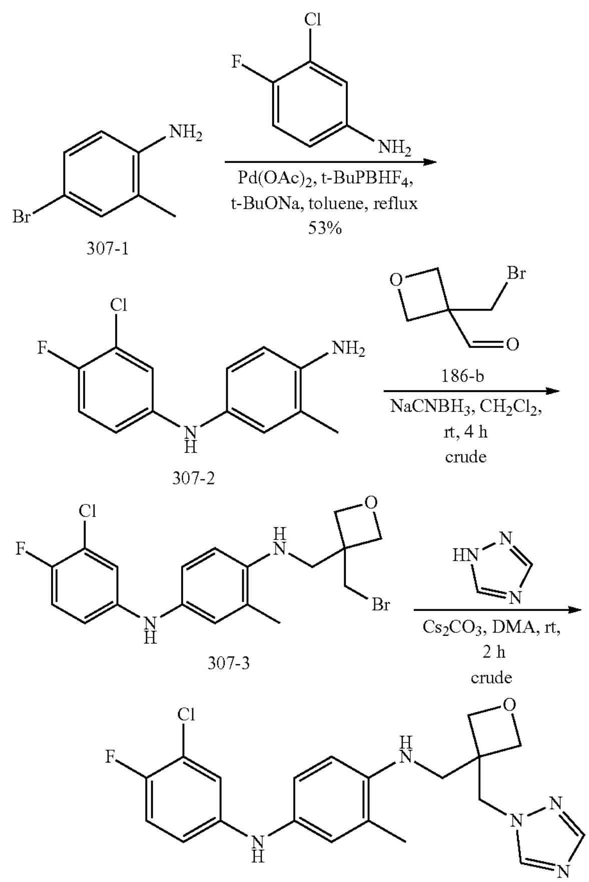

307-1

307-2

307-3

SS20308-0307-01

The Synthesis of N[1]-(3-chloro-4-fluorophenyl)-3-methylbenzene-1,4-diamine (307-2)

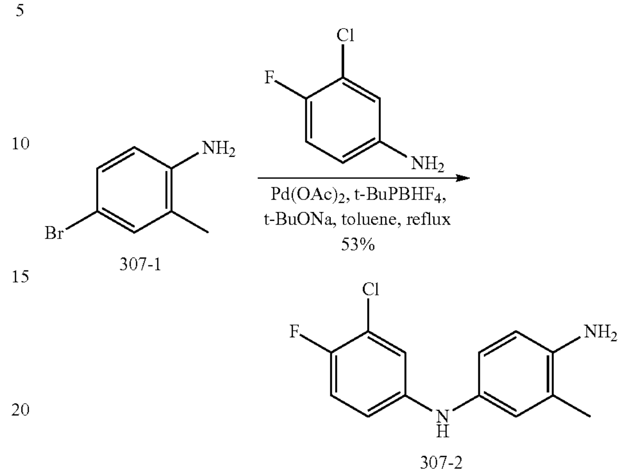

307-1

307-2

A mixture of 307-1 (2.00 g, 10.75 mmol), 4-chloro-3-fluoroaniline (1.56 g, 10.75 mmol), $Pd(OAc)_2$ (241 mg, 1.07 mmol), $P(t\text{-}Bu)_3HBF_4$ (624 mg, 2.15 mmol) and t-BuONa (2.07 mg, 21.50 mmol) in toluene (10 ml) was stirred at 110° C. under nitrogen atmosphere overnight. After the reaction was complete, the mixture was quenched with water. The insoluble material was removed by filtration, and the filtrate was extracted with EtOAc (50 mL×3). The organic layer was separated, dried over $MgSO_4$, and concentrated under vacuum. The crude product was purified by column chromatography (petroleum ether/EtOAc=4/1) to give 307-2 (1.42 g, about 53% yield) as an oil. MS Calcd.: 250.1; MS Found: 251.0 $[M+H]^+$.

The Synthesis of N[1]-((3-(bromomethyl)oxetan-3-yl)methyl)-N[4]-(3-chloro-4-fluorophenyl)-2-methylbenzene-1,4-diamine (307-3)

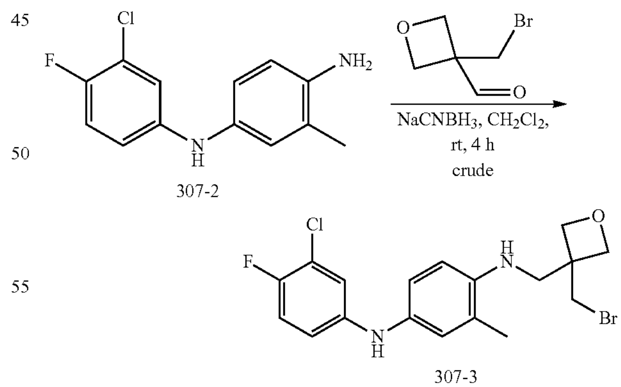

307-2

307-3

To a solution of 307-2 (350 mg, 1.40 mmol) in $CH_2Cl_2$ (20 mL) was added 3-(bromomethyl)oxetane-3-carbaldehyde (250 mg, 1.40 mmol) and $NaCNBH_3$ (263 mg, 4.19 mmol). The mixture was stirred at room temperature for 4 h. After the reaction was complete, it was quenched with water and extracted with $CH_2Cl_2$ (50 mL×3). The organic layer was separated, dried over $MgSO_4$, and concentrated under vacuum. The crude product was used in the next step without further purification. MS Calcd.: 412.0; MS Found: 413.0 [M+H]+.

The Synthesis of N[1]-((3-((1H-1,2,4-triazol-1-yl) methyl)oxetan-3-yl)methyl)-N[4]-(3-chloro-4-fluorophenyl)-2-methylbenzene-1,4-diamine (SS20308-0307-01)

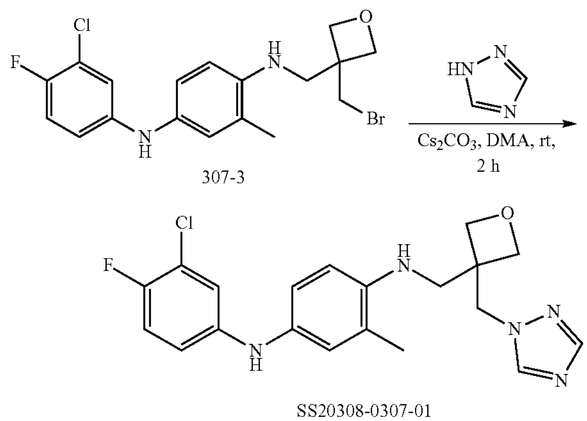

To a solution of 307-3 (150 mg, crude) in DMA (3 mL) was added 1H-1,2,4-triazole (50 mg, 0.73 mmol) and $Cs_2CO_3$ (236 mg, 0.73 mmol). The mixture was stirred at room temperature for 2 h. After the reaction was complete, it was quenched with water and extracted with EtOAc (50 mL×3). The organic layer was separated, dried over $MgSO_4$, and concentrated under vacuum. The crude product was purified by Prep-HPLC to give SS20308-0307-01 (11 mg) as a solid. MS Calcd.: 401.1; MS Found: 402.1 [M+H]+.

$^1$H NMR (400 MHz, DMSO-$d_6$) δ 8.54 (s, 1H), 8.02 (s, 1H), 7.69 (s, 1H), 7.13 (d, J=8.8 Hz, 1H), 6.81-6.76 (m, 3H), 6.73-6.69 (m, 1H), 6.45 (d, J=8.4 Hz, 1H), 4.69 (t, J=6.0 Hz, 1H), 4.65 (s, 2H), 4.54 (d, J=6.4 Hz, 2H), 4.45 (d, J=6.4 Hz, 2H), 3.17 (d, J=6.0 Hz, 2H), 2.13 (s, 3H).

Example 98

SS20308-0308-01

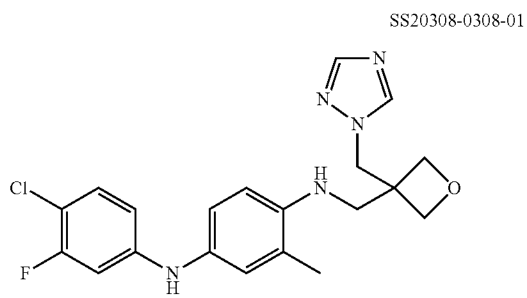

Chemical Formula: $C_{20}H_{21}ClFN_5O$
Molecular Weight: 401.87

Example Route for Example 98

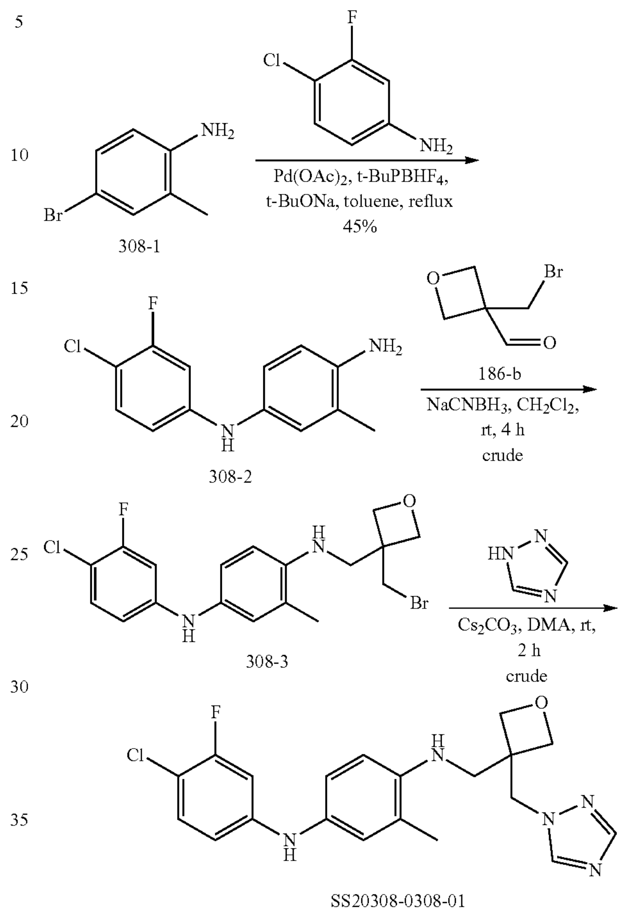

The Synthesis of N[1]-(4-chloro-3-fluorophenyl)-3-methylbenzene-1,4-diamine (308-2)

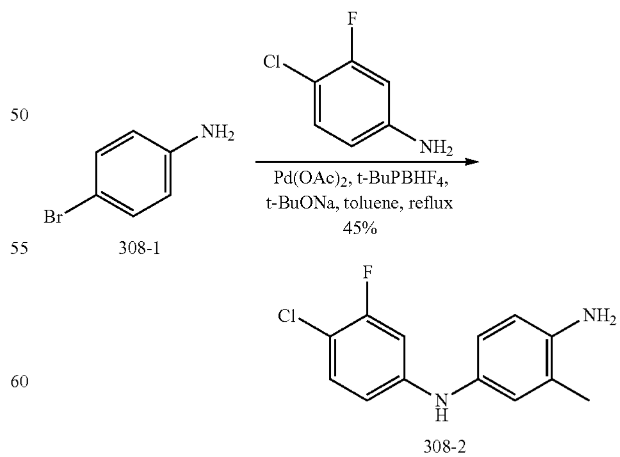

A mixture of 308-1 (2.00 g, 10.75 mmol), 4-chloro-3-fluoroaniline (1.56 g, 10.75 mmol), $Pd(OAc)_2$ (241 mg, 1.07 mmol), $P(t-Bu)_3HBF_4$ (624 mg, 2.15 mmol) and t-BuONa (2.07 mg, 21.50 mmol) in toluene (10 ml) was stirred at 110° C. under nitrogen atmosphere overnight. After the reaction was complete, the mixture was quenched with water. The insoluble material was removed by filtration, and the filtrate was extracted with EtOAc (50 mL×3). The organic layer was separated, dried over $MgSO_4$, and concentrated under vacuum. The crude product was purified by column chromatography (petroleum ether/EtOAc=4/1) to give 308-2 (1.20 g, about 45% yield) as an oil. MS Calcd.: 250.1; MS Found: 251.1 $[M+H]^+$.

The Synthesis of $N^1$-((3-(bromomethyl)oxetan-3-yl)methyl)-$N^4$-(4-chloro-3-fluorophenyl)-2-methylbenzene-1,4-diamine (308-3)

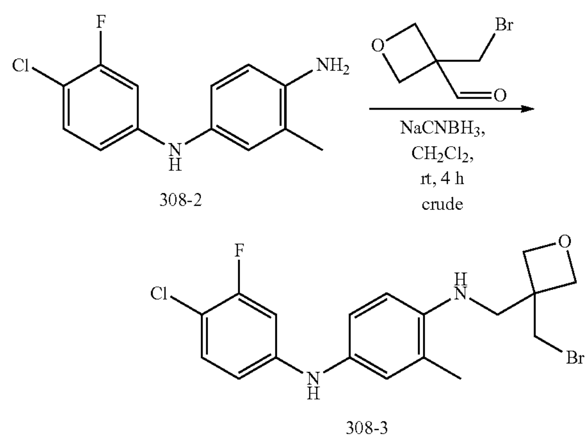

308-2

308-3

To a solution of 308-2 (350 mg, 1.40 mmol) in $CH_2Cl_2$ (20 mL) was added 3-(bromomethyl)oxetane-3-carbaldehyde (250 mg, 1.40 mmol) and $NaCNBH_3$ (263 mg, 4.19 mmol). The mixture was stirred at room temperature for 4 h. After the reaction was complete, it was quenched with water and extracted with $CH_2Cl_2$ (50 mL×3). The organic layer was separated, dried over $MgSO_4$, and concentrated under vacuum. This crude product was used in the next step without further purification. MS Calcd.: 412.0; MS Found: 413.1 $[M+H]^+$.

The Synthesis of $N^1$-((3-((1H-1,2,4-triazol-1-yl)methyl)oxetan-3-yl)methyl)-$N^4$-(4-chloro-3-fluorophenyl)-2-methylbenzene-1,4-diamine (SS20308-0308-01)

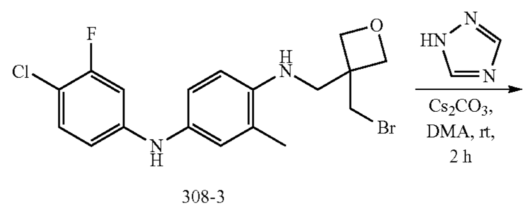

308-3

-continued

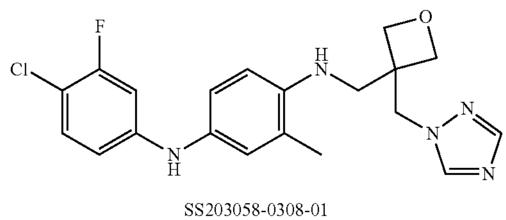

SS203058-0308-01

To a solution of 308-3 (150 mg, crude) in DMA (3 mL) was added 1H-1,2,4-triazole (50 mg, 0.73 mmol) and $Cs_2CO_3$ (236 mg, 0.73 mmol). The mixture was stirred at room temperature for 2 h. After the reaction was complete, it was quenched with water and extracted with EtOAc (50 mL×3). The organic layer was separated, dried over $MgSO_4$, and concentrated under vacuum. The crude product was purified by Prep-HPLC to give SS20308-0308-01 (10 mg) as a solid. MS Calcd.: 401.1; MS Found: 402.1 $[M+H]^+$.

$^1H$ NMR (400 MHz, DMSO-$d_6$) δ 8.52 (s, 1H), 8.01 (s, 1H), 7.95 (s, 1H), 7.20 (d, J=8.8 Hz, 1H), 6.81-6.77 (m, 2H), 6.62-6.55 (m, 2H), 6.43 (d, J=8.4 Hz, 1H), 4.71 (t, J=6.0 Hz, 1H), 4.63 (s, 2H), 4.52 (d, J=6.4 Hz, 2H), 4.43 (d, J=6.4 Hz, 2H), 3.15 (d, J=6.4 Hz, 2H), 2.12 (s, 3H).

Example 99

SS20308-0309-01

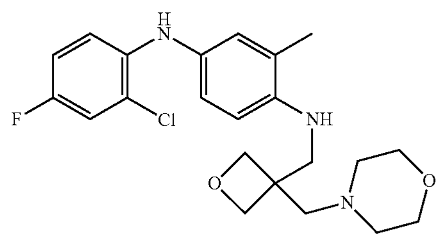

Chemical Formula: $C_{22}H_{27}ClFN_3O_2$
Molecular Weight: 419.92

Example Route for Example 99

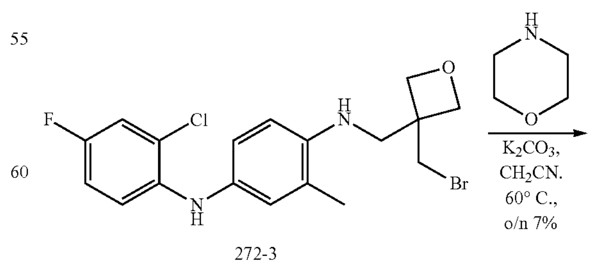

272-3

-continued

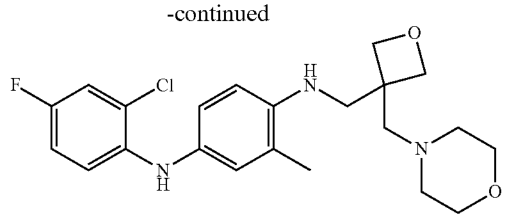

SS20308-0309-01

Note that the synthesis of 272-3 is detailed above in the description for SS20308-0272-01.

The Synthesis of N[4]-(2-chloro-4-fluorophenyl)-2-methyl-N[1]-((3-(morpholinomethyl)oxetan-3-yl) methyl) benzene-1,4-diamine (SS20308-0309-01)

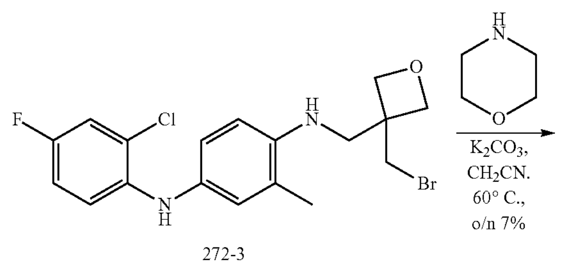

272-3

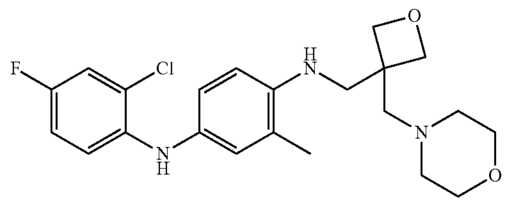

SS20308-0309-01

A mixture of 272-3 (150 mg, 0.36 mmol), morpholine (63 mg, 0.73 mmol) and $K_2CO_3$ (100 mg, 0.73 mmol) in $CH_3CN$ (10 ml) was stirred at 60° C. under nitrogen atmosphere overnight. After the reaction was complete, the mixture was quenched with water and extracted with EtOAc (50 mL×3). The organic layer was separated, dried over $MgSO_4$, and concentrated under vacuum. The crude product was purified by Prep-HPLC to give SS20308-0309-01 (10 mg, about 7% yield) as a solid. MS Calcd.: 419.2; MS Found: 420.1 $[M+H]^+$.

$^1H$ NMR (400 MHz, DMSO-$d_6$) δ 7.28 (dd, J=8.4 Hz, 2.8 Hz, 1H), 6.97-6.92 (m, 2H), 6.84-6.72 (m, 4H), 4.92 (t, J=6.4 Hz, 1H), 4.39-4.36 (m, 4H), 3.56 (t, J=4.4 Hz, 4H), 3.45 (d, J=6.0 Hz, 2H), 2.68 (s, 2H), 2.31 (t, J=4.4 Hz, 4H), 2.09 (s, 3H).

Example 100

SS20308-0310-01

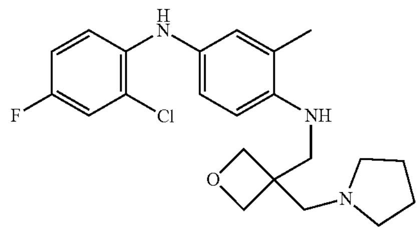

Chemical Formula: $C_{22}H_{27}ClFN_3O$
Molecular Weight: 403.92

Example Route for Example 100

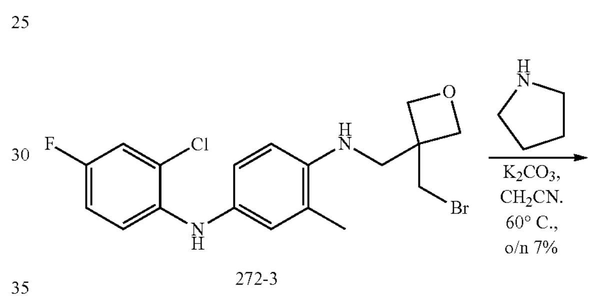

272-3

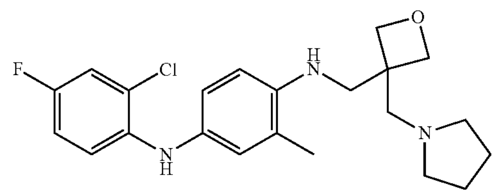

SS20308-0310-01

The Synthesis of N[4]-(2-chloro-4-fluorophenyl)-2-methyl-N[1]-((3-(pyrrolidin-1-ylmethyl)oxetan-3-yl) methyl)benzene-1,4-diamine (SS20308-0310-01)

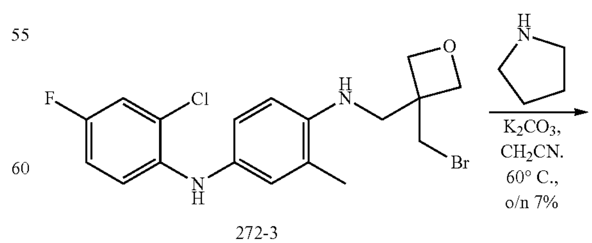

272-3

-continued

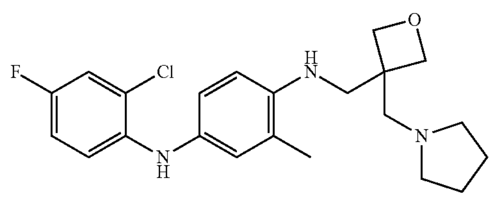

SS20308-0310-01

Synthesis of 272-3 is previously described. A mixture of 272-3 (150 mg, 0.36 mmol), pyrrolidine (52 mg, 0.73 mmol) and $K_2CO_3$ (100 mg, 0.73 mmol) in $CH_3CN$ (10 ml) was stirred at 60° C. under nitrogen atmosphere overnight. After the reaction was complete, the mixture was quenched with water and extracted with EtOAc (50 mL×3). The organic layer was separated, dried over $MgSO_4$, and concentrated under vacuum. The crude product was purified by Prep-HPLC to give SS20308-0310-01 (10 mg, about 7% yield) as a solid. MS Calcd.: 403.2; MS Found: 404.1 $[M+H]^+$.

$^1H$ NMR (400 MHz, DMSO-$d_6$) δ 7.27 (dd, J=8.4 Hz, 2.8 Hz, 1H), 6.97-6.91 (m, 2H), 6.84-6.80 (m, 2H), 6.76 (dd, J=9.2 Hz, 5.6 Hz, 1H), 6.64 (d, J=8.4 Hz, 1H), 5.56 (t, J=5.2 Hz, 1H), 4.40 (d, J=6.0 Hz, 2H), 4.33 (d, J=6.0 Hz, 2H), 3.45 (d, J=5.6 Hz, 2H), 2.86 (s, 2H), 2.46 (s, 4H), 2.01 (s, 3H), 1.69 (s, 4H).

Example 101

SS20308-0313-01

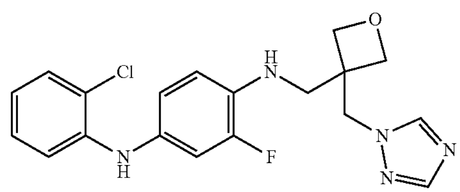

Chemical Formula: $C_{19}H_{19}ClFN_5O$
Molecular Weight: 387.84

Example Route for Example 101

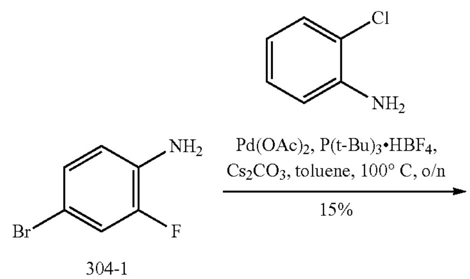

304-1

-continued

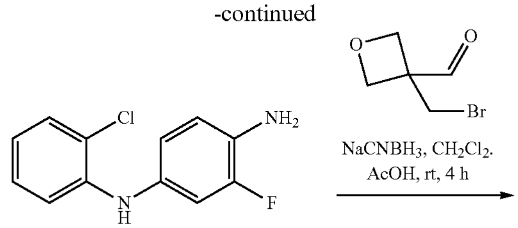

304-2

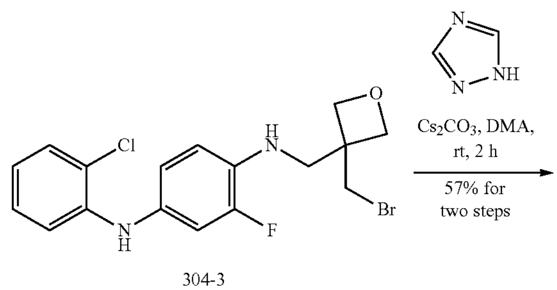

304-3

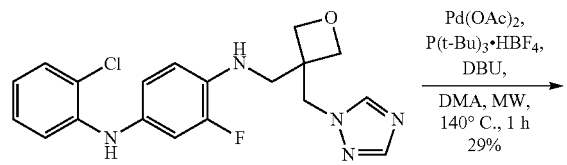

SS20308-0313-01

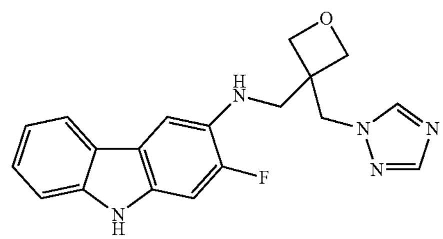

SS20308-0304-01

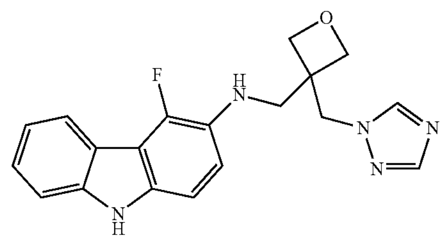

SS20308-0312-01

The synthesis of $N^1$-(2-chloropheny)-3-fluorobenzene-1,4-diamine (304-2):

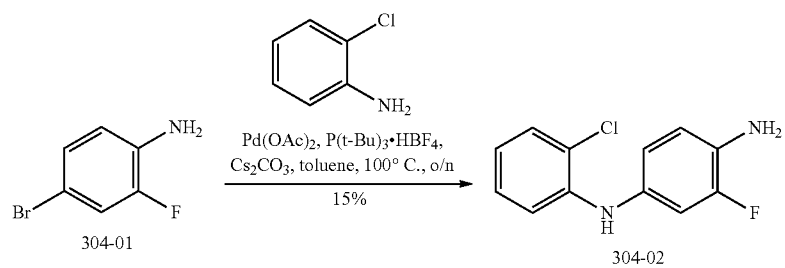 [SMILES: Nc1ccccc1Cl ; Nc1ccc(Br)cc1F ; Nc1ccc(Nc2ccccc2Cl)cc1F]

304-01

304-02

The mixture of 2-chloroaniline (2.69 g, 21.05 mmol), 4-bromo-2-fluoro-aniline (2.00 g, 10.53 mmol), Palladium (II) acetate (118 mg, 0.53 mmol), Tri-tert-butylphosphine tetrafluoroborate (304 mg, 1.05 mmol) and Cesium carbonate (5.14 g, 15.79 mmol) in toluene (40 mL) was stirred at 100° C. for 16 hr under N2. The reaction mixture was filtered through diatomite, rinsing with ethyl acetate. The filtrate was concentrated and the residue was purified by silica gel column chromatography (eluted with petroleum ether/ethyl acetate=100/1, 50/1, 20/1, 10/1) to give compound 304-2 (377 mg, about 15% yield) as an oil.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity is about 95.9%. Rt=2.084 min; MS Calcd.: 236.1; MS Found: 237.1 $[M+H]^+$.

The Synthesis of $N^1$-((3-(bromomethyl)oxetan-3-yl)methyl)-$N^4$-(2-chlorophenyl)-2-fluorobenzene-1,4-diamine (304-3)

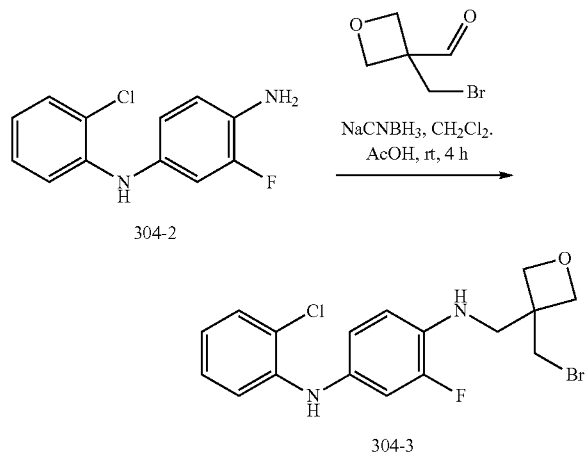

304-2

304-3

A solution of 304-2 (377 mg, 1.59 mmol), 3-(bromomethyl)oxetane-3-carbaldehyde (855 mg, 4.78 mmol) and Sodium cyanoborohydride (200 mg, 3.19 mmol) in DCM (20 mL) was stirred at room temperature for 2 hr. The reaction mixture was washed with brine, dried over $Na_2SO_4$ and concentrated. The residue was used for next step directly.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Rt=2.368 min; MS Calcd.: 398.0; MS Found: 399.0 $[M+H]^+$.

The Synthesis of $N^1$-((3-((1H-1,2,4-triazol-1-yl)methyl)oxetan-3-yl)methyl)-$N^4$-(2-chlorophenyl)-2-fluorobenzene-1,4-diamine (SS20308-0313-01)

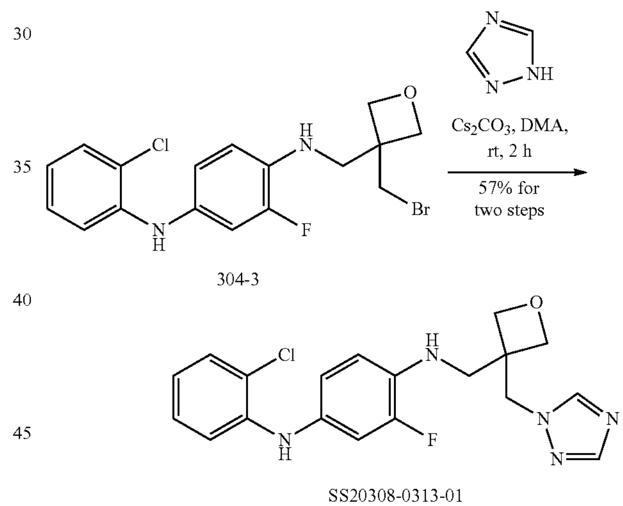

304-3

SS20308-0313-01

A mixture of 304-3 (637 mg, 2.50 mmol), 1H-1,2,4-triazole (220 mg, 3.19 mmol) and cesium carbonate (1.04 g, 3.19 mmol) in DMA (5 mL) was stirred at room temperature for 2 h. Then the reaction mixture was poured into cold water (20 mL) and extracted with ethyl acetate (10 mL×3). The combined organic layers were washed with brine (10 mL×2), dried over sodium sulfate, and concentrated to dryness. The residue was purified by Prep-TLC (petroleum ether/EtOAc=1/2) to give compound SS20308-0313-01 (355 mg, about 57% yield) as an oil. MS Calcd.: 387.1; MS Found: 388.2 $[M+H]^+$.

$^1H$ NMR (400 MHz, DMSO-$d_6$) δ 8.53 (s, 1H), 8.00 (s, 1H), 7.31 (dd, J=7.8, 1.4 Hz, 1H), 7.25 (s, 1H), 7.11-7.05 (m, 1H), 6.92 (dd, J=8.2, 1.4 Hz, 1H), 6.88 (dd, J=13.6, 2.4 Hz, 1H), 6.77 (dd, J=8.6, 2.2 Hz, 1H), 6.74-6.69 (m, 1H), 6.61 (dd, J=9.6, 8.8 Hz, 1H), 5.38 (t, J=6.0 Hz, 1H), 4.60 (s, 2H), 4.50 (d, J=6.4 Hz, 2H), 4.41 (d, J=64 Hz, 2H), 3.18 (d, J=6.4 Hz, 2H).

Example 102

SS20308-0314-01

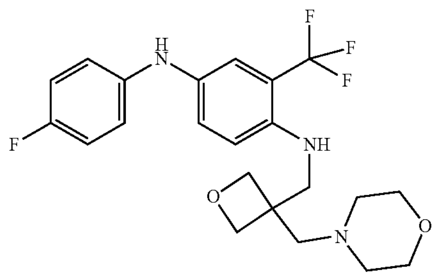

Chemical Formula: $C_{22}H_{25}F_4N_3O_2$
Molecular Weight: 439.45

Example Route for Example 102

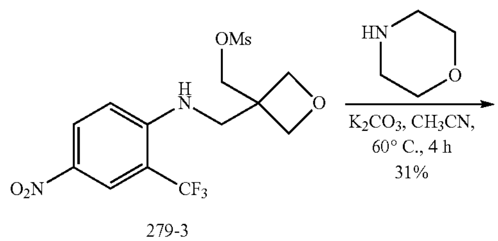

279-3

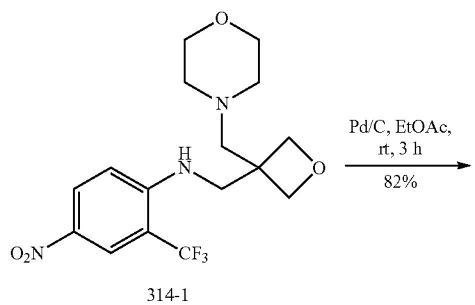

314-1

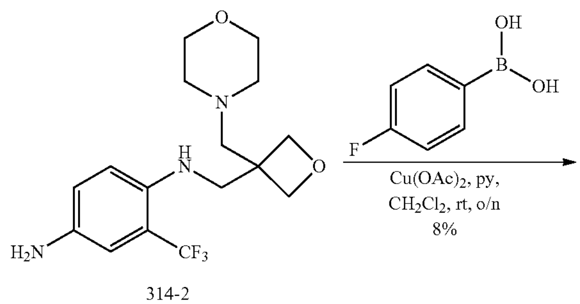

314-2

-continued

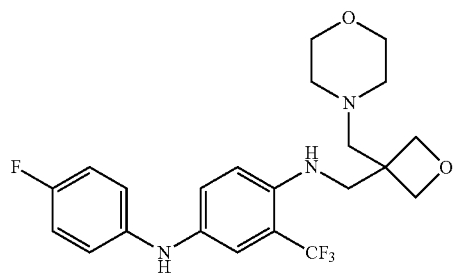

SS20308-0314-01

The Synthesis of N-((3-(morpholinomethyl)oxetan-3-yl)methyl)-4-nitro-2-(trifluoromethyl)aniline (314-01-4)

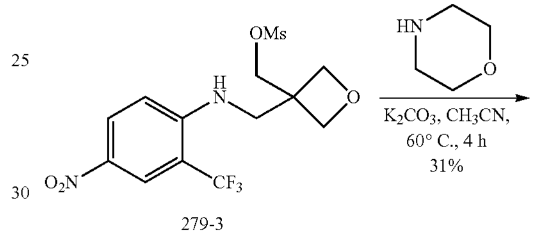

279-3

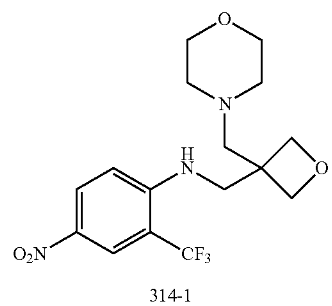

314-1

To a solution of 279-3 (400 mg, 1.04 mmol) in $CH_3CN$ (20 mL) was added morpholine (181 mg, 2.08 mmol) and $K_2CO_3$ (288 mg, 2.08 mmol). The mixture was stirred at 60° C. for 4 h. After the reaction was complete, it was quenched with water and extracted with EtOAc (50 mL×3). The organic layer was separated, dried over $MgSO_4$, and concentrated under vacuum. The crude product was purified by column chromatography (petroleum ether/EtOAc=1/1) to give 314-1 (120 mg, about 31% yield) as an oil. MS Calcd.: 375.1; MS Found: 375.9 $[M+H]^+$.

The Synthesis of $N^1$-((3-(morpholinomethyl)oxetan-3-yl)methyl)-2-(trifluoromethyl)benzene-1,4-diamine (314-2)

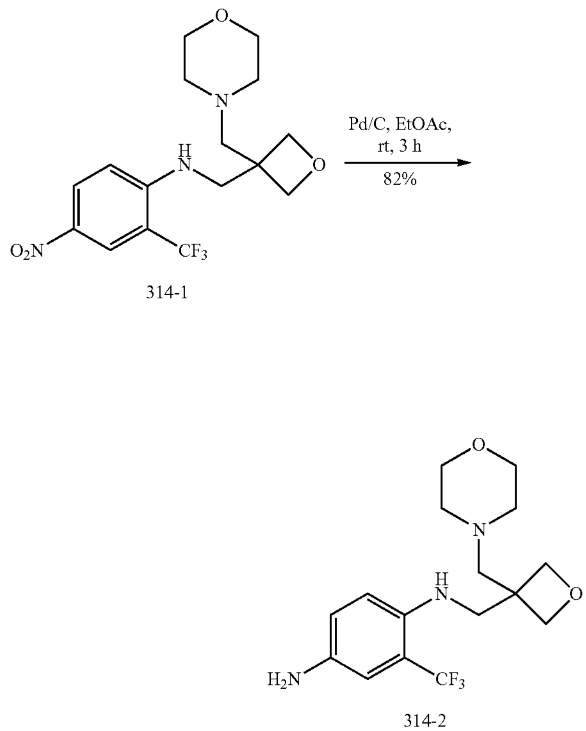

314-1

314-2

To a solution of 314-1 (120 mg, 0.32 mmol) in EtOAc (20 mL) was added Pd/C (10%, 35 mg), the mixture was stirred at room temperature under hydrogen atmosphere for 3 h. After the reaction was complete, the insoluble material was removed by filtration. The organic layer was concentrated under vacuum and was purified by column chromatography (petroleum ether/EtOAc=1/1) to give 314-2 (90 mg, about 82% yield) as an oil. MS Calcd.: 345.2; MS Found: 346.1 $[M+H]^+$.

The Synthesis of $N^1$-((3-((1H-1,2,4-triazol-1-yl)methyl)oxetan-3-yl)methyl)-$N^4$-(4-fluorophenyl)-2-(trifluoromethyl)benzene-1,4-diamine (SS20308-0314-01)

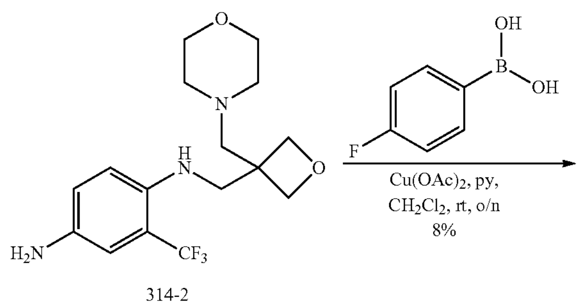

314-2

-continued

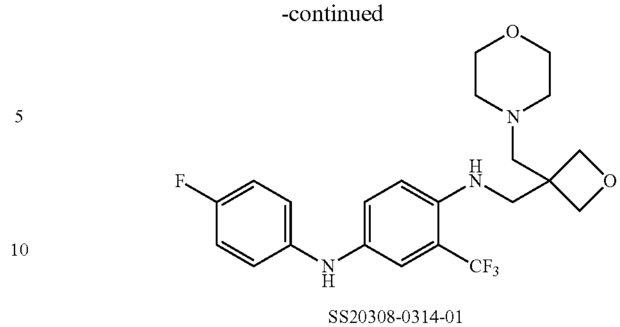

SS20308-0314-01

To a solution of 314-2 (60 mg, 0.17 mmol) in $CH_2Cl_2$ (10 mL) was added 4-fluorophenylboronic acid (49 mg, 0.35 mmol), $Cu(OAc)_2$ (16 mg, 0.09 mmol) and pyridine (41 mg, 0.52 mmol). The mixture was stirred at room temperature overnight. After the reaction was complete, it was quenched with water and extracted with $CH_2Cl_2$ (30 mL×3). The organic layer was separated, dried over $MgSO_4$, and concentrated under vacuum. The crude product was purified by Prep-HPLC to give SS20308-0314-01 (6 mg, about 8% yield) as a solid. MS Calcd.: 439.2; MS Found: 440.2 $[M+H]^+$.

$^1H$ NMR (400 MHz, DMSO-$d_6$) δ 7.81 (s, 1H), 7.22 (dd, J=8.8 Hz, 2.4 Hz, 1H), 7.13 (d, J=2.4 Hz, 1H), 7.07-7.00 (m, 3H), 6.89-6.85 (m, 2H), 5.35 (t, J=5.6 Hz, 1H), 4.41 (d, J=6.0 Hz, 2H), 4.34 (d, J=6.0 Hz, 2H), 3.57-3.55 (m, 6H), 2.68 (s, 2H), 2.31-2.28 (m, 4H).

Example 103

SS20308-0316-01

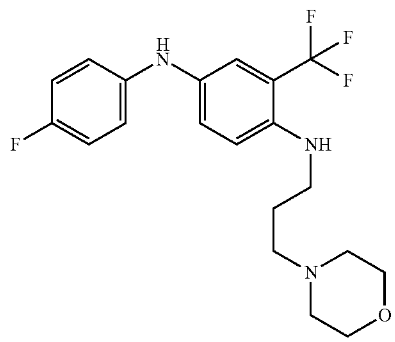

Chemical Formula: $C_{20}H_{23}F_4N_3O$
Molecular Weight: 397.41

Example Route for Example 103

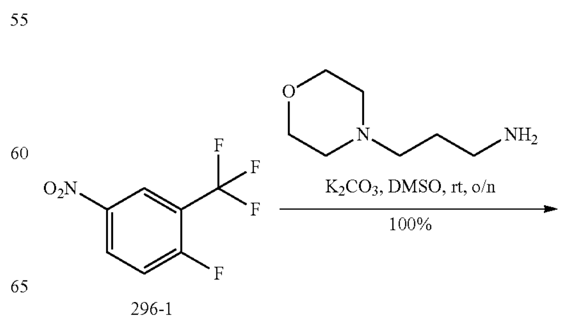

296-1

-continued

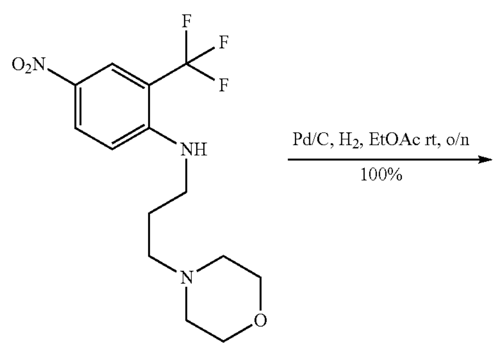

316-1

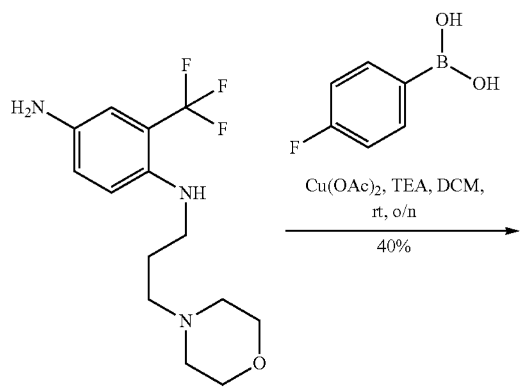

316-2

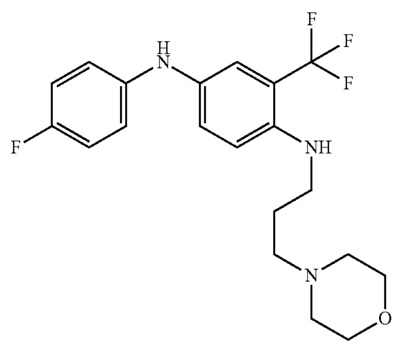

SS20308-0316-01

The Synthesis of N-(3-morpholinopropyl)-4-nitro-2-(trifluoromethyl)aniline (316-1)

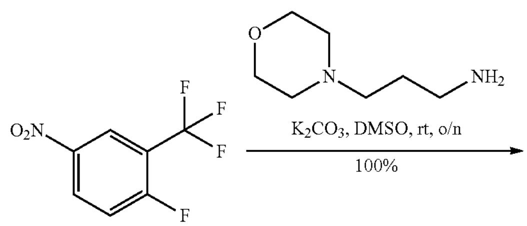

296-1

-continued

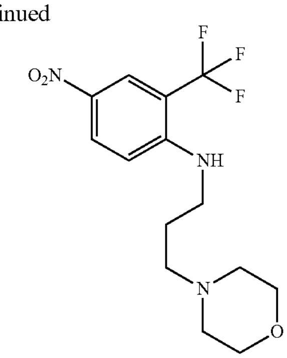

316-1

A mixture of 3-morpholinopropan-1-amine (690 mg, 4.78 mmol), 279-1 (500 mg, 2.39 mmol) and potassium carbonate (661 mg, 4.78 mmol) was suspended in DMSO (10 mL). After stirring at room temperature for overnight, the mixture was diluted with water (40 mL). The resulting solids was filtered, washed with water, dried, and concentrated to give 316-1 (797 mg, about 100% yield) as a solid. MS Calcd.: 333.1; MS Found: 334.1 $[M+H]^+$.

The Synthesis of $N^1$-(3-morpholinopropyl)-2-(trifluoromethyl)benzene-1,4-diamine (316-2)

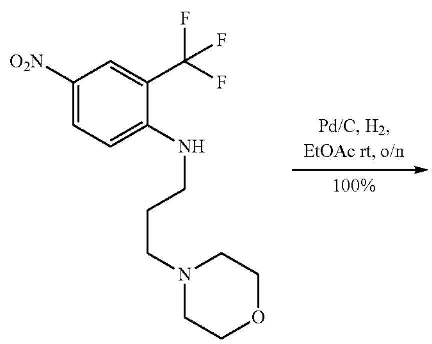

316-1

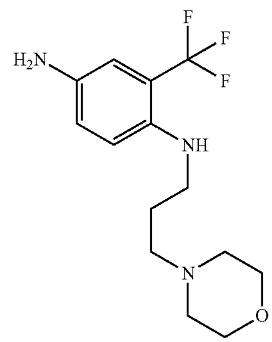

316-2

A suspension of 316-1 (780 mg, 2.34 mmol) and Palladium on activated carbon (10%, 80 mg) in ethyl acetate (20 mL) was stirred vigorously under hydrogen gas (balloon) for 16 hr at room temperature. The reaction mixture was filtered through celite and rinsed with ethyl acetate. The filtrate was concentrated to give a crude product 316-2 (709 mg, about 100% yield) as an oil. MS Calcd.: 303.2; MS Found: 304.2 $[M+H]^+$.

The Synthesis of $N^4$-(4-fluorophenyl)-$N^1$-(3-morpholinopropyl)-2-(trifluoromethyl)benzene-1,4-diamine (SS20308-0316-01)

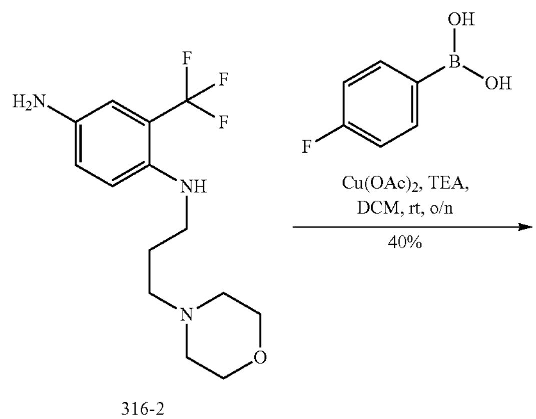

316-2

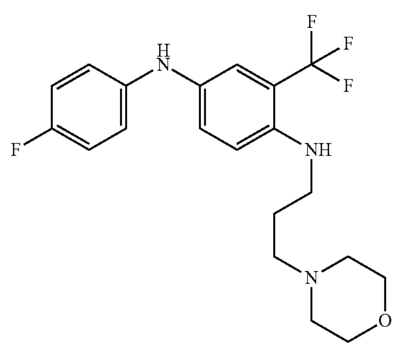

SS20308-0316-01

The mixture of (4-fluorophenyl)boronic acid (185 mg, 1.32 mmol), 316-2 (100 mg, 0.33 mmol), cupric acetate (72 mg, 0.40 mmol), and triethylamine (67 mg, 0.66 mmol) in dichloromethane (10 mL) was stirred at room temperature for 16 hr under air. The reaction mixture was filtered through celite and rinsed with ethyl acetate. The filtrate was concentrated and the residue was purified by Prep-TLC (petroleum ether/EtOAc=1/1) and reverse phase column chromatography to give SS20308-0316-01 (52.8 mg, about 40% yield) as a solid. MS Calcd.: 397.2; MS Found: 398.2 $[M+H]^+$.

$^1H$ NMR (400 MHz, DMSO-$d_6$) δ 7.71 (s, 1H), 7.17 (dd, J=8.8, 2.4 Hz, 1H), 7.09 (d, J=2.4 Hz, 1H), 6.98 (dd, J=9.2, 8.8 Hz, 2H), 6.81 (dd, J=9.0, 4.6 Hz, 2H), 6.77 (d, J=8.8 Hz, 1H), 5.42 (t, J=5.2 Hz, 1H), 3.59-3.54 (m, 4H), 3.18-3.12 (m, 2H), 2.38-2.20 (m, 6H), 1.76-1.67 (m, 2H).

Example 104

SS20308-0319-01

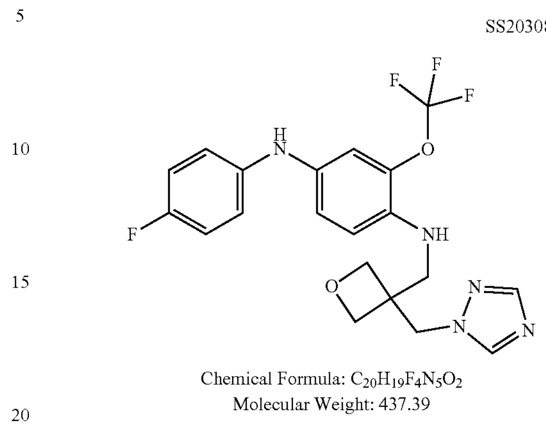

Chemical Formula: $C_{20}H_{19}F_4N_5O_2$
Molecular Weight: 437.39

Example Route for Example 104

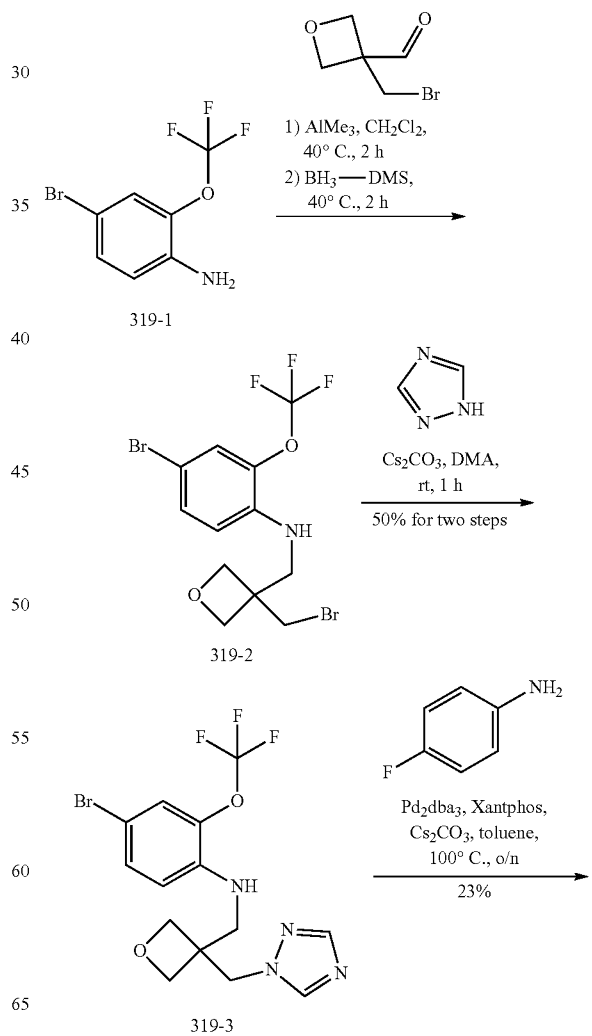

319-1

319-2

319-3

-continued

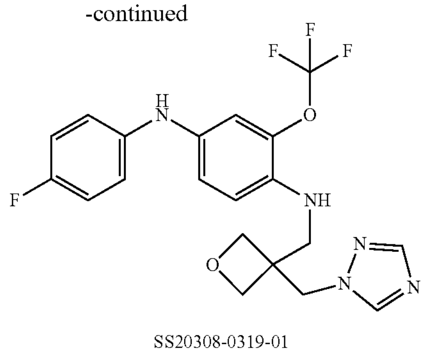

SS20308-0319-01

The Synthesis of 4-bromo-N-((3-(bromomethyl)oxetan-3-yl)methyl)-2-(trifluoromethoxy)aniline (319-2)

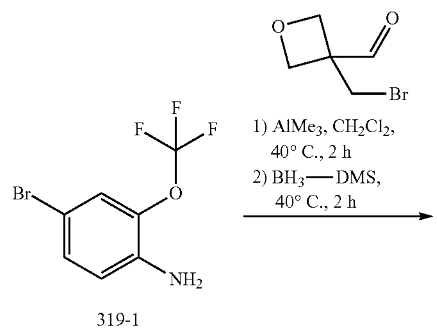

319-1

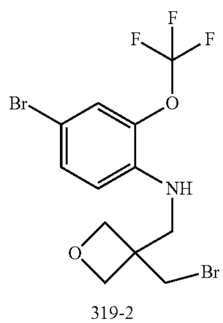

319-2

The mixture of 319-1 (70 mg, 0.27 mmol), 3-(bromomethyl)oxetane-3-carbaldehyde (54 mg, 0.30 mmol), and trimethylaluminium (2M in hexane) (0.40 mmol, 0.2 mL) in dichloromethane (10 mL) was heated to 40° C. for 2 hr. The reaction mixture was cooled down to room temperature and to this solution was added borane-methyl sulfide complex (2M in THF) (1.4 mmol, 0.7 mL). After stirring at 40° C. for 2 hr, the reaction mixture was quenched with methanol at 0° C., and then washed with brine. The organic extracts were dried over $Na_2SO_4$ and concentrated. The crude product was used for the next step without further purification. MS Calcd.: 416.9; MS Found: 418.0 $[M+H]^+$.

The Synthesis of N-((3-((1H-1,2,4-triazol-1-yl)methyl)oxetan-3-yl)methyl)-4-bromo-2-(trifluoromethoxy)aniline (319-3)

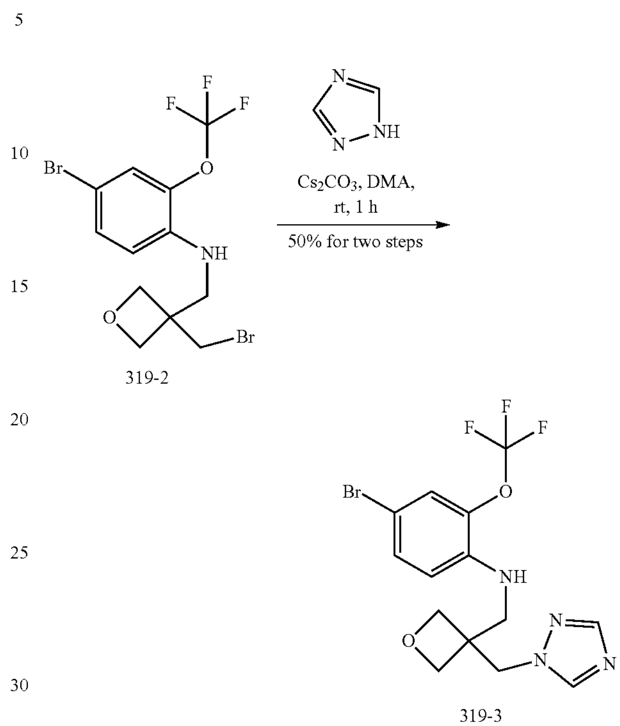

319-2

319-3

A mixture of 319-2 (115 mg, 0.27 mmol), 1H-1,2,4-triazole (38 mg, 0.55 mmol) and cesium carbonate (179 mg, 0.55 mmol) in DMA (4 mL) was stirred at room temperature for 1 hr. Then the reaction mixture was poured into cold water (20 mL) and extracted with EtOAc (10 mL×3). The combined organic layers were washed with brine (10 mL×2), dried over sodium sulfate, and concentrated to dryness. The residue was purified by Prep-TLC (EtOAc) to give 319-3 (56 mg, about 50% yield for two steps) as an oil. MS Calcd.: 406.0; MS Found: 407.0 $[M+H]^+$.

The Synthesis of $N^1$-((3-((1H-1,2,4-triazol-1-yl)methyl)oxetan-3-yl)methyl)-$N^4$-(4-fluorophenyl)-2-(trifluoromethoxy)benzene-1,4-diamine (SS20308-0319-01)

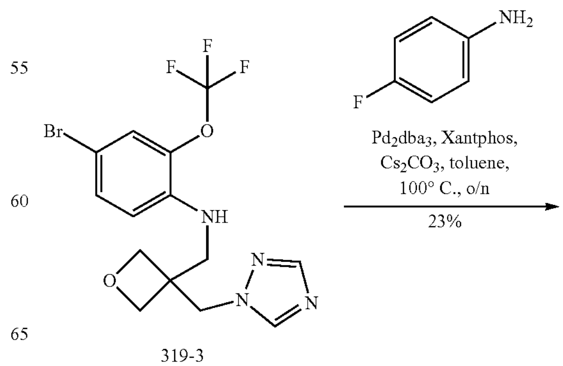

319-3

-continued

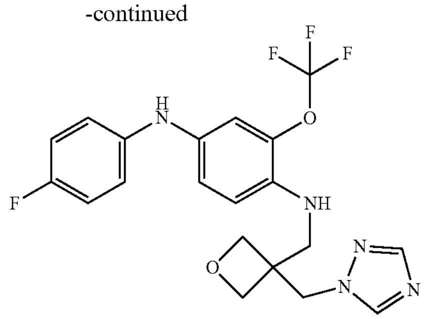

SS20308-0319-01

The mixture of 319-3 (56 mg, 0.14 mmol), 4-fluoroaniline (46 mg, 0.41 mmol), $Pd_2(dba)_3$ (13 mg, 0.014 mmol), Xantphos (16 mg, 0.028 mmol) and cesium carbonate (68 mg, 0.21 mmol) in toluene (4 mL) was stirred at 100° C. for 16 hr under $N_2$. The reaction mixture was filtered through celite and rinsed with ethyl acetate. The filtrate was concentrated and the residue was purified by Prep-TLC (100% EtOAc, dichloromethane/methanol=40/1) and reverse phase column chromatography to give SS20308-0319-01 (13.7 mg, about 23% yield) as an oil. MS Calcd.: 437.2; MS Found: 438.1 $[M+H]^+$.

$^1H$ NMR (400 MHz, DMSO-$d_6$) δ 8.52 (s, 1H), 8.02 (s, 1H), 7.78 (s, 1H), 7.01 (dd, J=9.2, 8.8 Hz, 2H), 6.92-6.84 (m, 4H), 6.66 (d, J=9.6 Hz, 1H), 5.42 (t, J=6.4 Hz, 1H), 4.61 (s, 2H), 4.49 (d, J=6.4 Hz, 2H), 4.42 (d, J=6.4 Hz, 2H), 3.20 (d, J=6.0 Hz, 2H).

Example 105

SS20308-0320-01

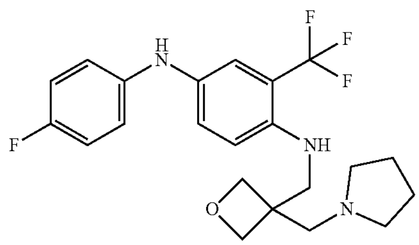

Chemical Formula: $C_{22}H_{25}F_4N_3O$
Molecular Weight: 423.45

Example Route for Example 105

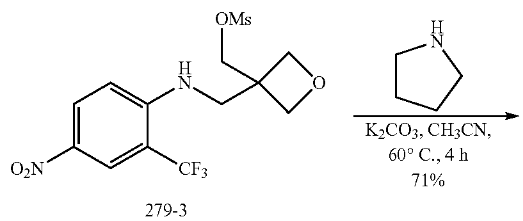

279-3

-continued

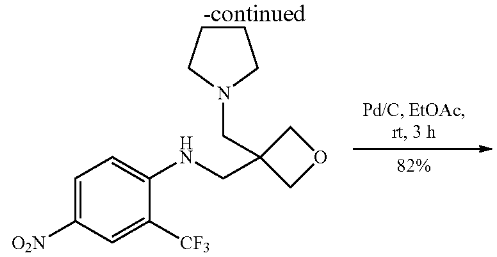

320-1

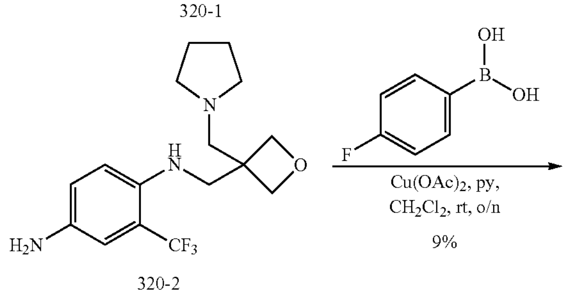

320-2

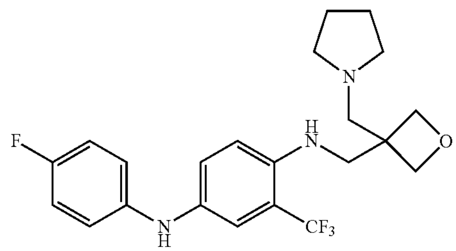

SS20308-0320-01

The Synthesis of 4-nitro-N-((3-(pyrrolidin-1-ylmethyl)oxetan-3-yl)methyl)-2-(trifluoromethyl)aniline (320-1)

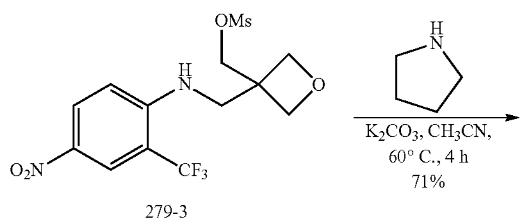

279-3

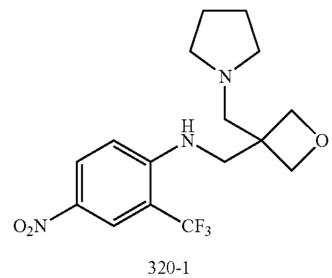

320-1

To a solution of 279-3 (300 mg, 0.78 mmol) in $CH_3CN$ (20 mL) was added pyrrolidine (111 mg, 1.56 mmol) and $K_2CO_3$ (216 mg, 1.56 mmol). The mixture was stirred at 60° C. for 4 h. After the reaction was complete, it was quenched with water and extracted with EtOAc (50 mL×3). The organic layer was separated, dried over $MgSO_4$, and concentrated under vacuum. The crude product was purified by column chromatography (petroleum ether/EtOAc=1/1) to give 320-1 (200 mg, about 71% yield) as an oil. MS Calcd.: 359.2; MS Found: 359.9 $[M+H]^+$.

The Synthesis of $N^1$-((3-(pyrrolidin-1-ylmethyl)oxetan-3-yl)methyl)-2-(trifluoromethyl)benzene-1,4-diamine (320-2)

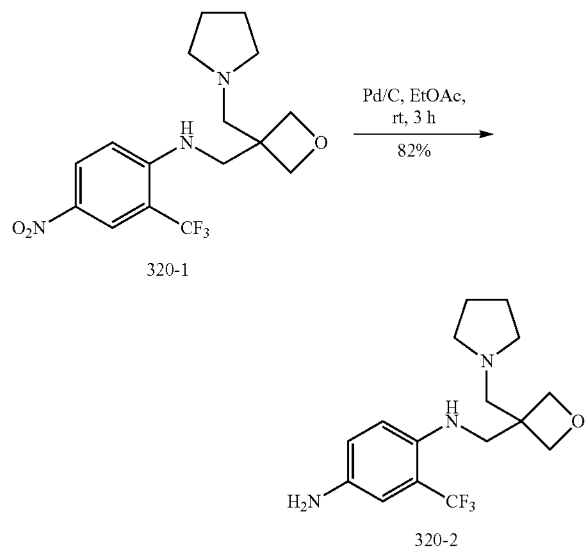

320-1

320-2

To a solution of 320-1 (200 mg, 0.56 mmol) in EtOAc (20 mL) was added Pd/C (10%, 35 mg), the mixture was stirred at room temperature under hydrogen gas (balloon) for 3 hours. After the reaction was complete, the insoluble material was removed by filtration. The organic layer was concentrated under vacuum and the crude product was purified by column chromatography (petroleum ether/EtOAc=1/1) to give 320-2 (150 mg, about 82% yield) as an oil. MS Calcd.: 329.2; MS Found: 330.2 $[M+H]^+$.

The Synthesis of $N^4$-(4-fluorophenyl)-$N^1$-((3-(pyrrolidin-1-ylmethyl)oxetan-3-yl)methyl)-2-(trifluoromethyl)benzene-1,4-diamine (SS20308-0320-01)

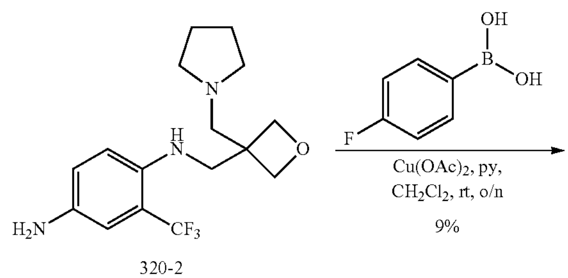

320-2

-continued

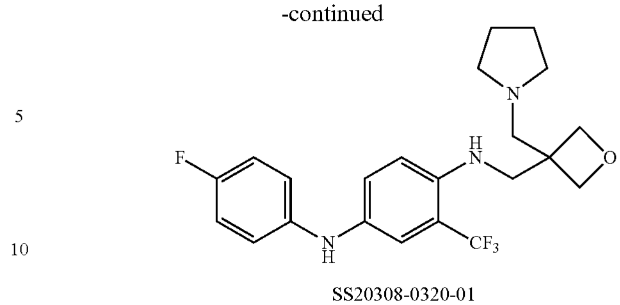

SS20308-0320-01

To a solution of 320-2 (60 mg, 0.18 mmol) in $CH_2Cl_2$ (10 mL) was added 4-fluorophenylboronic acid (51 mg, 0.36 mmol), $Cu(OAc)_2$ (17 mg, 0.09 mmol) and pyridine (43 mg, 0.55 mmol). The mixture was stirred at room temperature overnight. After the reaction was complete, it was quenched with water and extracted with $CH_2Cl_2$ (30 mL×3). The organic layer was separated, dried over $MgSO_4$, and concentrated under vacuum. The crude product was purified by Prep-HPLC to give SS20308-0320-01 (7 mg, about 9% yield) as an oil. MS Calcd.: 423.2; MS Found: 424.2 $[M+H]^+$.

$^1H$ NMR (400 MHz, DMSO-$d_6$) δ 7.78 (s, 1H), 7.22 (dd, J=8.8 Hz, 2.0 Hz, 1H), 7.12 (d, J=2.0 Hz, 1H), 7.04-6.99 (m, 2H), 6.96 (d, J=8.8 Hz, 1H), 6.87-6.84 (m, 2H), 6.20 (t, J=5.6 Hz, 1H), 4.43 (d, J=6.0 Hz, 2H), 4.30 (d, J=6.0 Hz, 2H), 3.54 (d, J=5.2 Hz, 2H), 2.87 (s, 2H), 2.45 (s, 4H), 1.70 (s, 4H).

Example 106

SS20308-0321-01

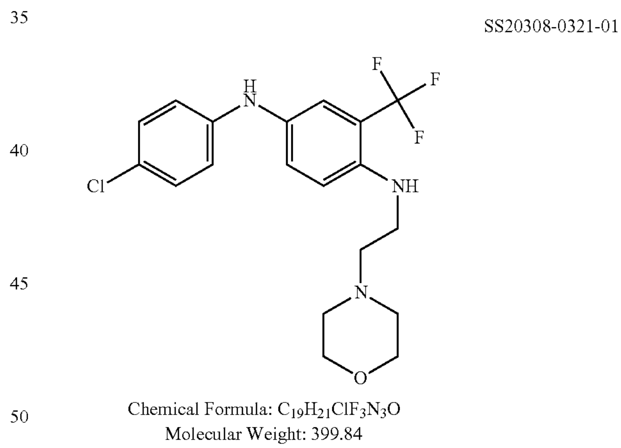

Chemical Formula: $C_{19}H_{21}ClF_3N_3O$
Molecular Weight: 399.84

Example Route for Example 106

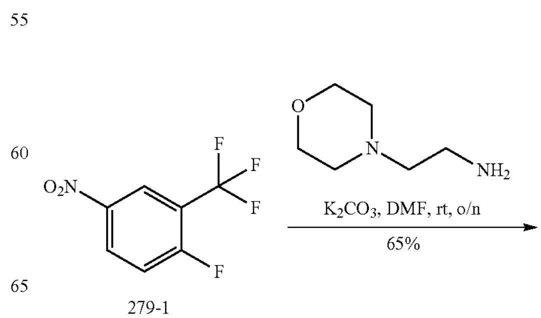

279-1

-continued

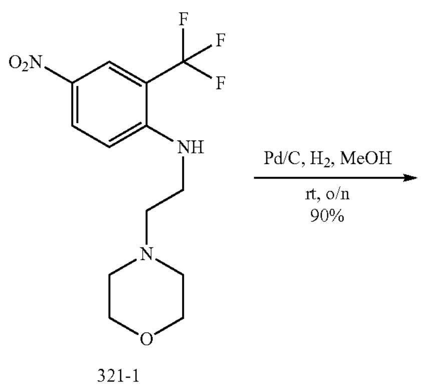

321-1

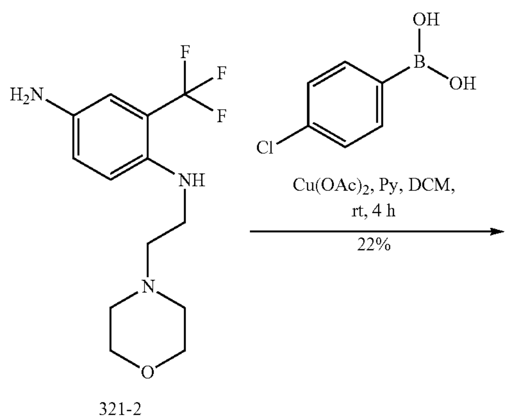

321-2

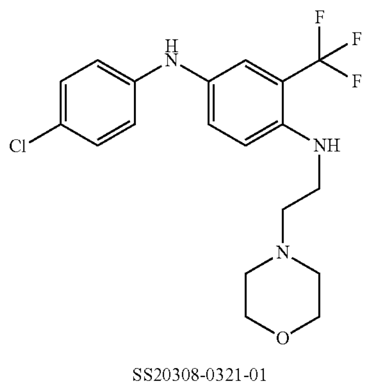

SS20308-0321-01

The Synthesis of N-(2-morpholinoethyl)-4-nitro-2-(trifluoromethyl)aniline (321-1)

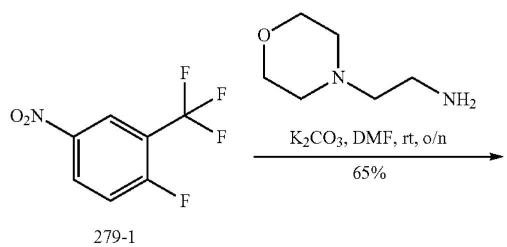

279-1

-continued

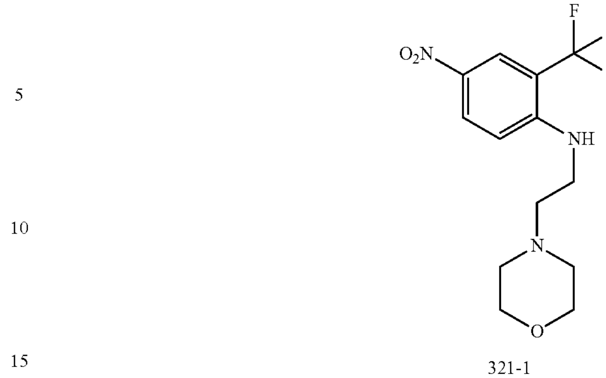

321-1

A mixture of 279-1 (1.10 g, 5.26 mmol), 2-morpholinoethanamine (1.03 g, 7.89 mmol) and $K_2CO_3$ (1.45 g, 10.52 mmol) in DMF (10 ml) was stirred at room temperature under nitrogen atmosphere overnight. After the reaction was complete, the mixture was quenched with water and extracted with EtOAc (50 mL×3). The organic layer was separated, dried over $MgSO_4$, and concentrated under vacuum. The crude product was purified by column chromatography (petroleum ether/EtOAc=1/2) to give 321-1 (1.10 g, about 65% yield) as a solid. MS Calcd.: 319.1; MS Found: 320.0 $[M+H]^+$.

The Synthesis of $N^1$-(2-morpholinoethyl)-2-(trifluoromethyl)benzene-1,4-diamine (321-2)

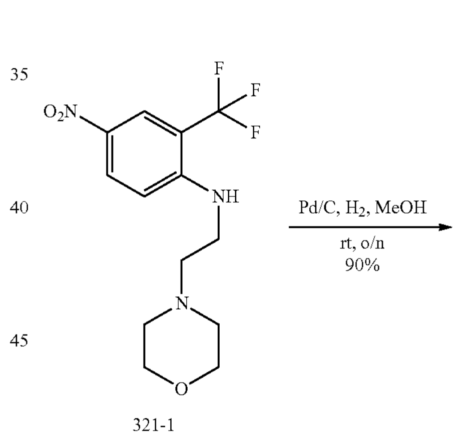

321-1

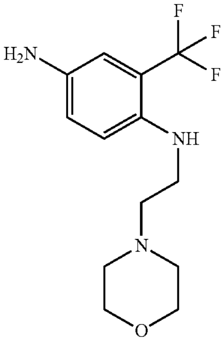

321-2

To a solution of 321-1 (1.10 g, 3.45 mmol) in MeOH (20 mL) was added Pd/C (10%, 100 mg), the mixture was stirred at room temperature under hydrogen gas (balloon) overnight. After the reaction was complete, the insoluble material was removed by filtration. The organic layer was concentrated under vacuum. The crude product was purified by column chromatography (petroleum ether/EtOAc=1/1) to give 321-2 (0.90 g, about 90% yield) as an oil. MS Calcd.: 289.1; MS Found: 290.2 $[M+H]^+$.

The Synthesis of N[4]-(4-chlorophenyl)-N[1]-(2-morpholinoethyl)-2-(trifluoromethyl)benzene-1,4-diamine (SS20308-0321-01)

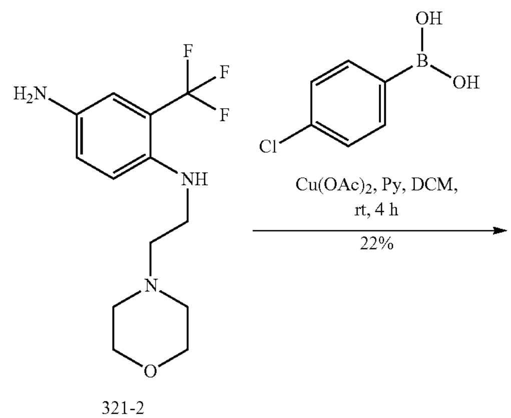

321-2

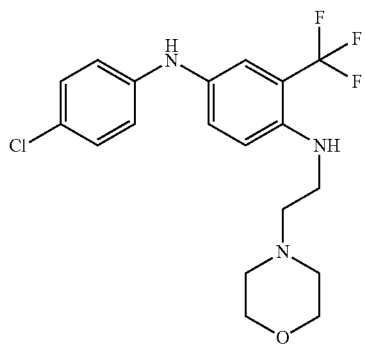

SS20308-0321-01

To a solution of 321-2 (0.15 g, 0.52 mmol) in $CH_2Cl_2$ (20 mL) was added 4-chlorophenylboronic acid (122 mg, 0.78 mmol), $Cu(OAc)_2$ (47 mg, 0.26 mmol) and pyridine (82 mg, 1.04 mmol). The mixture was stirred at room temperature overnight. After the reaction was complete, it was quenched with water and extracted with $CH_2Cl_2$ (50 mL×3). The organic layer was separated, dried over $MgSO_4$, and concentrated under vacuum. The crude product was purified by Prep-HPLC to give SS20308-0321-01 (47 mg, about 22% yield) as an oil. MS Calcd.: 399.1; MS Found: 400.2 $[M+H]^+$.

$^1H$ NMR (400 MHz, DMSO-$d_6$) δ 7.97 (s, 1H), 7.24 (dd, J=8.8 Hz, 2.4 Hz, 1H), 7.18-7.15 (m, 3H), 6.84-6.81 (m, 3H), 5.21 (t, J=4.4 Hz, 1H), 3.57 (t, J=4.4 Hz, 4H), 3.21-3.16 (m, 2H), 2.58 (t, J=6.4 Hz, 2H), 2.41 (s, 4H).

Example 107

SS20308-0322-01

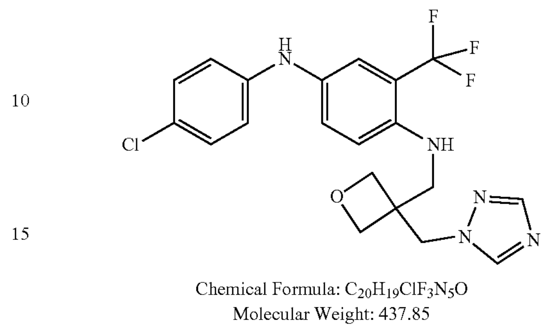

Chemical Formula: $C_{20}H_{19}ClF_3N_5O$
Molecular Weight: 437.85

Example Route Example 107

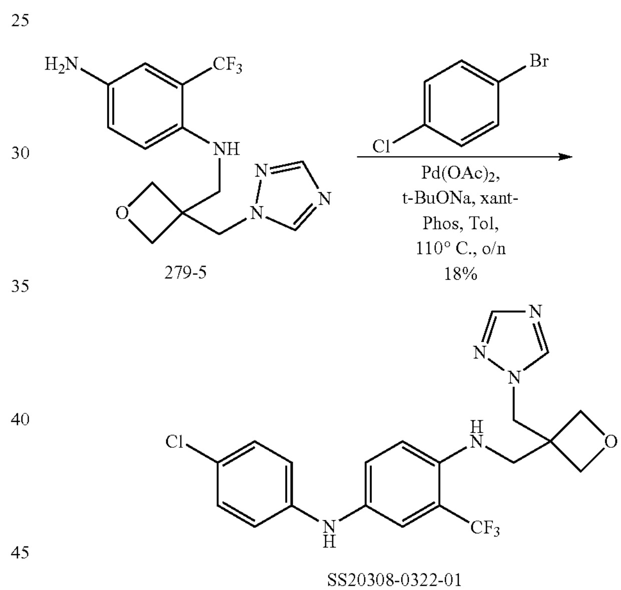

279-5

SS20308-0322-01

The Synthesis of N[1]-((3-((1H-1,2,4-triazol-1-yl)methyl)oxetan-3-yl)methyl)-N[4]-(4-chlorophenyl)-2-(trifluoromethyl)benzene-1,4-diamine (SS20308-0322-01)

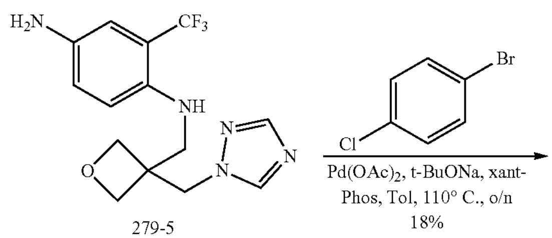

279-5

-continued

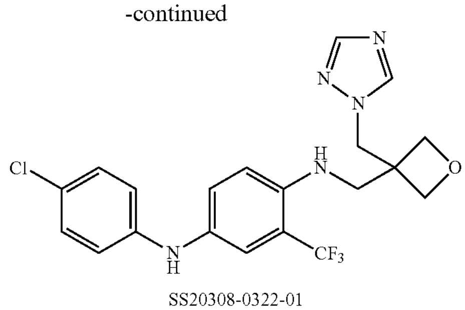

SS20308-0322-01

A mixture of 279-5 (100 mg, 0.31 mmol), 1-bromo-4-chlorobenzene (117 mg, 0.61 mmol), $Pd(OAc)_2$ (7 mg, 0.03 mmol), Xant-Phos (35 mg, 0.06 mmol) and t-BuONa (59 mg, 0.61 mmol) in toluene (10 ml) and was stirred at 110° C. under nitrogen atmosphere overnight. After the reaction was complete, the mixture was quenched with water. The insoluble material was removed by filtration, and the filtrate was extracted with EtOAc (30 mL×3). The organic layer was separated, dried over $MgSO_4$, and concentrated under vacuum. The crude product was purified by Prep-HPLC to give SS20308-0322-01 (24 mg, about 18% yield) as an oil. MS Calcd.: 437.1; MS Found: 438.2 $[M+H]^+$.

$^1H$ NMR (400 MHz, DMSO-$d_6$) δ 8.56 (s, 1H), 8.01 (s, 1H), 7.98 (s, 1H), 7.19-7.14 (m, 4H), 6.83-6.80 (m, 2H), 6.77 (d, J=8.8 Hz, 1H), 5.25 (t, J=6.0 Hz, 1H), 4.58 (s, 2H), 4.48 (d, J=6.4 Hz, 2H), 4.42 (d, J=6.4 Hz, 2H), 3.26 (d, J=6.0 Hz, 2H).

Example 108

SS20308-0323-01

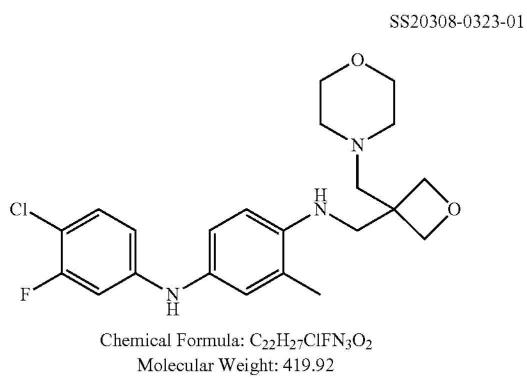 [SMILES: Cc1cc(Nc2ccc(Cl)c(F)c2)ccc1NCC1(CN2CCOCC2)COC1]

Chemical Formula: $C_{22}H_{27}ClFN_3O_2$
Molecular Weight: 419.92

Example Route for Example 108

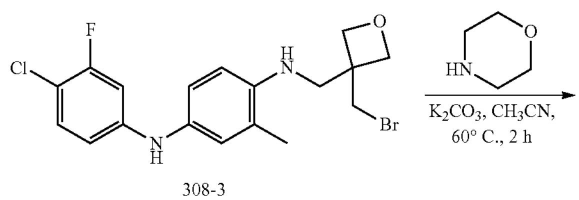

308-3

-continued

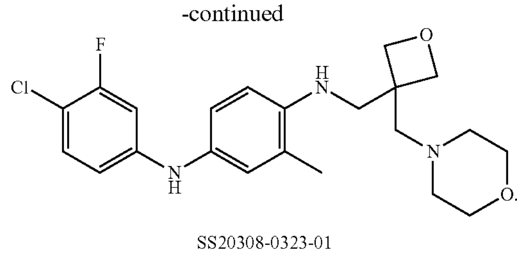

SS20308-0323-01

The Synthesis of $N^4$-(4-chloro-3-fluorophenyl)-2-methyl-$N^1$-((3-(morpholinomethyl)oxetan-3-yl) methyl) benzene-1,4-diamine (SS20308-0323-01)

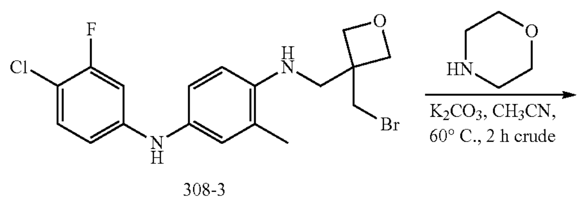

308-3

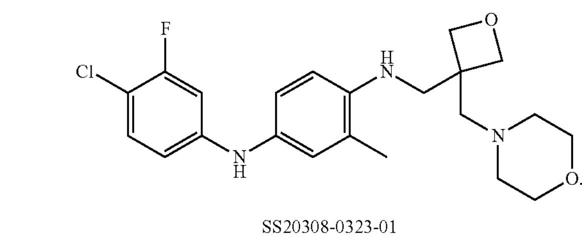

SS20308-0323-01

To a solution of 308-3 (150 mg, crude) in $CH_3CN$ (3 mL) was added morpholine (63 mg, 0.73 mmol) and $K_2CO_3$ (100 mg, 0.73 mmol). The mixture was stirred at 60° C. for 2 h. After the reaction was complete, it was quenched with water and extracted with EtOAc (50 mL×3). The organic layer was separated, dried over $MgSO_4$, and concentrated under vacuum. The crude product was purified by Prep-HPLC to give SS20308-0323-01 (5 mg) as an oil. MS Calcd.: 419.2; MS Found: 420.1 $[M+H]^+$.

$^1H$ NMR (400 MHz, DMSO-$d_6$) δ 7.91 (s, 1H), 7.22 (d, J=8.8 Hz, 1H), 6.87-6.84 (m, 2H), 6.76 (d, J=8.4 Hz, 1H), 6.64-6.57 (m, 2H), 4.97 (t, J=6.0 Hz, 1H), 4.41-4.37 (m, 4H), 3.58 (t, J=4.0 Hz, 4H), 3.47 (d, J=5.6 Hz, 2H), 2.70 (s, 2H), 2.34-2.32 (m, 4H), 2.11 (s, 3H).

Example 109

SS20308-0324-01

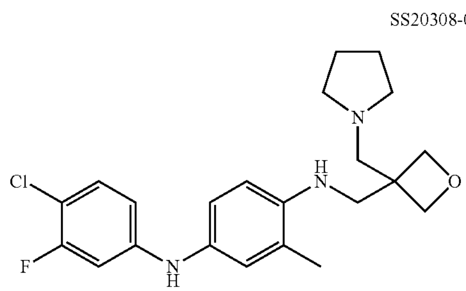

Chemical Formula: $C_{22}H_{27}ClFN_3O_2$
Molecular Weight: 403.92

Example Route for Example 109

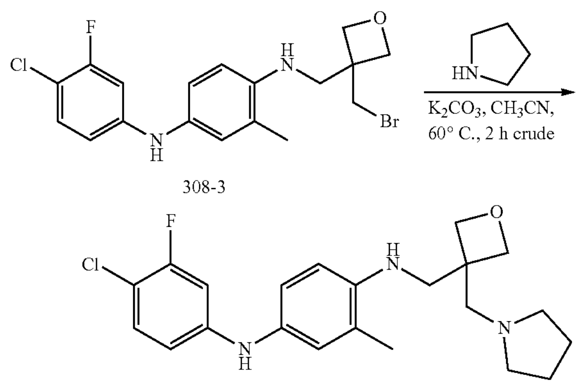

308-3

SS20308-0324-01

The Synthesis of N[4]-(4-chloro-3-fluorophenyl)-2-methyl-N[1]-((3-(pyrrolidin-1-ylmethyl)oxetan-3-yl) methyl)benzene-1,4-diamine (SS20308-0324-01)

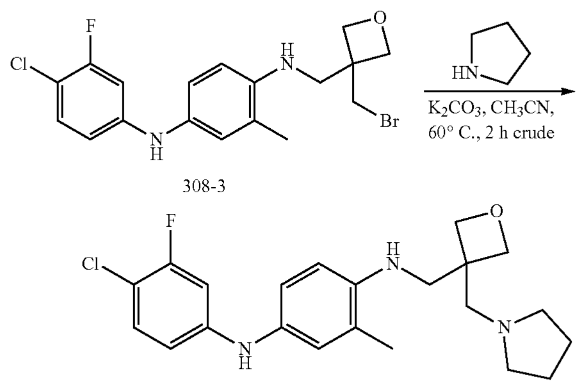

308-3

SS20308-0324-01

To a solution of 308-3 (150 mg, crude) in $CH_3CN$ (3 mL) was added pyrrolidine (52 mg, 0.73 mmol) and $K_2CO_3$ (100 mg, 0.73 mmol). The mixture was stirred at 60° C. for 2 h.

After the reaction was complete, it was quenched with water and extracted with EtOAc (50 mL×3). The organic layer was separated, dried over $MgSO_4$, and concentrated under vacuum. The crude product was purified by Prep-HPLC to give SS20308-0324-01 (18 mg) as an oil. MS Calcd.: 403.2; MS Found: 404.2 $[M+H]^+$.

$^1$H NMR (400 MHz, DMSO-$d_6$) δ 7.96 (s, 1H), 7.22 (dd, J=8.8 Hz, 1H), 6.86 (dd, J=8.4 Hz, 2.4 Hz, 1H), 6.82 (d, J=2.0 Hz, 1H), 6.67 (d, J=8.4 Hz, 1H), 6.63-6.56 (m, 2H), 5.61 (t, J=5.6 Hz, 1H), 4.42 (d, J=6.0 Hz, 2H), 4.35 (d, J=6.0 Hz, 2H), 3.47 (d, J=5.6 Hz, 2H), 2.87 (s, 2H), 2.47 (s, 4H), 2.04 (s, 3H), 1.71 (s, 4H).

Example 110

SS20308-0327-01

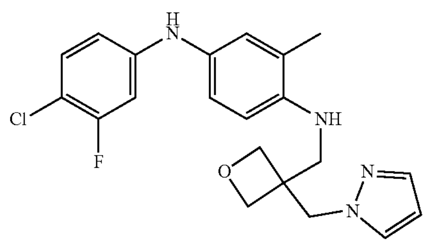

Chemical Formula: $C_{21}H_{22}ClFN_4O$
Molecular Weight: 400.88

Example Route for Example 110

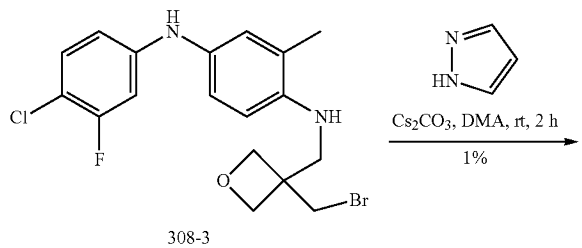

308-3

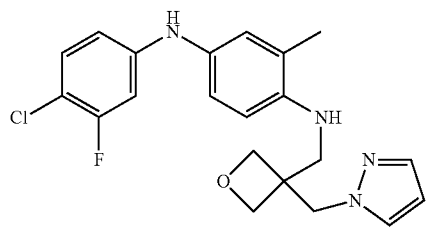

SS20308-0327-01

The Synthesis of N1-((3-((1H-pyrazol-1-yl)methyl) oxetan-3-yl)methyl)-N4-(4-chloro-3-fluorophenyl)-2-methylbenzene-1,4-diamine (SS20308-0327-01)

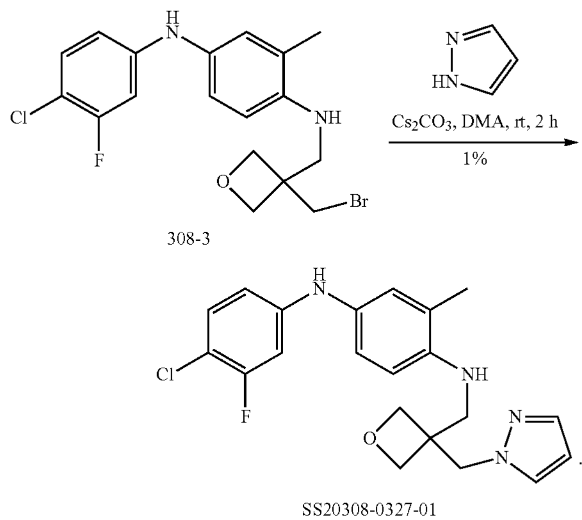

308-3

SS20308-0327-01

A mixture of 308-3 (820 mg, 1.98 mmol), 1H-pyrazole (410 mg, 6.02 mmol) and cesium carbonate (1.94 g, 5.94 mmol) in DMA (5 mL) was stirred at room temperature for 2 hr. Then the reaction mixture was poured into cold water (10 mL) and extracted with ethyl acetate (10 mL×3). The combined organic layers were washed with brine (10 mL×2), dried over sodium sulfate, and concentrated to dryness. The residue was purified by Prep-TLC (petroleum ether/EtOAc=1/1, dichloromethane/methanol=100/1) and Prep-HPLC to give compound SS20308-0327-01 (4.1 mg, about 1% yield) as a semisolid. MS Calcd.: 400.2; MS Found: 401.1 $[M+H]^+$.

$^1$H NMR (400 MHz, DMSO-$d_6$) δ 7.96 (s, 1H), 7.75 (d, J=2.0 Hz, 1H), 7.49 (d, J=1.6 Hz, 1H), 7.21 (d, J=8.8 Hz, 1H), 6.85-6.77 (m, 2H), 6.65-6.55 (m, 2H), 6.44 (d, J=8.8 Hz, 1H), 6.25 (dd, J=2.0, 2.0 Hz, 1H), 4.72 (t, J=6.2 Hz, 1H), 4.56 (s, 2H), 4.54 (d, J=6.4 Hz, 2H), 4.42 (d, J=6.0 Hz, 2H), 3.16 (d, J=6.0 Hz, 2H), 2.13 (s, 3H).

Example 111

SS20308-0328-01

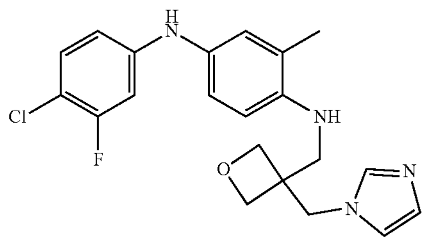

Chemical Formula: $C_{21}H_{22}ClFN_4O$
Molecular Weight: 400.88

Example Route for Example 111

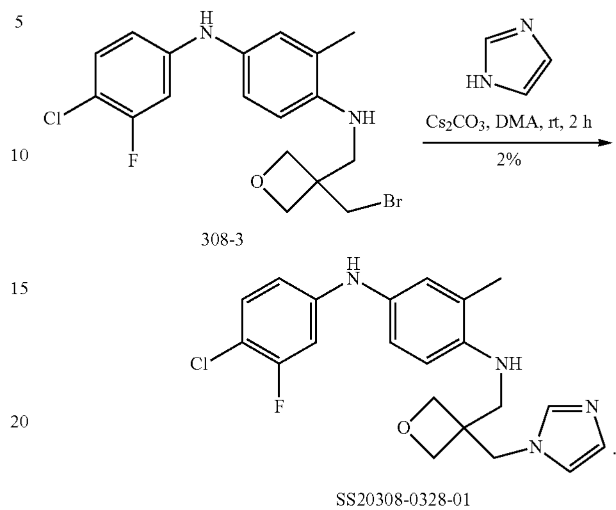

308-3

SS20308-0328-01

The Synthesis of N$^1$-((3-((1H-imidazol-1-yl)methyl) oxetan-3-yl)methyl)-N$^4$-(4-chloro-3-fluorophenyl)-2-methylbenzene-1,4-diamine (SS20308-0328-01)

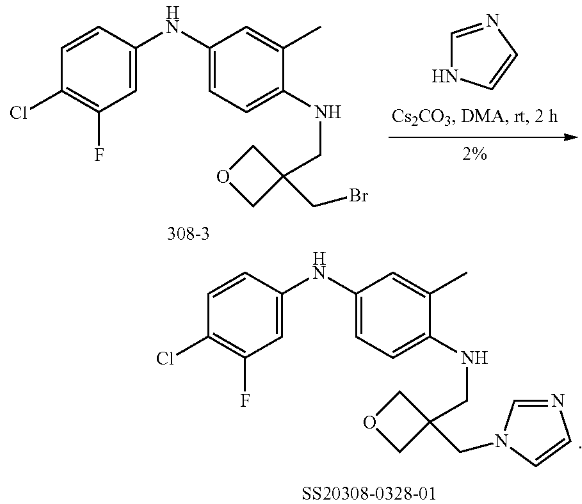

308-3

SS20308-0328-01

A mixture of 308-3 (350 mg, 0.85 mmol), imidazole (175.00 mg, 2.57 mmol) and cesium carbonate (827 mg, 2.54 mmol) in DMA (2 mL) was stirred at room temperature for 2 hr. Then the reaction mixture was poured into cold water (10 mL), and extracted with ethyl acetate (10 mL×3). The combined organic layers were washed with brine (10 mL×2), dried over sodium sulfate, and concentrated to dryness. The residue was purified by Prep-TLC (DCM/methanol=20/1), reverse phase column chromatography and Prep-HPLC to give compound SS20308-0328-01 (7.39 mg, about 2% yield) as a solid. MS Calcd.: 400.2; MS Found: 401.2 $[M+H]^+$.

$^1$H NMR (400 MHz, DMSO-$d_6$) δ 7.97 (s, 1H), 7.62 (s, 1H), 7.20 (dd, J=8.8, 8.8 Hz, 1H), 7.15 (s, 1H), 6.87 (s, 1H), 6.84-6.78 (m, 2H), 6.65-6.55 (m, 2H), 6.45 (d, J=8.4 Hz,

1H), 4.66 (t, J=5.8 Hz, 1H), 4.47 (d, J=6.4 Hz, 2H), 4.42 (s, 2H), 4.39 (d, J=6.0 Hz, 2H), 3.11 (d, J=6.0 Hz, 2H), 2.13 (s, 3H).
What is claimed is:
1. A compound, wherein the compound is selected from:
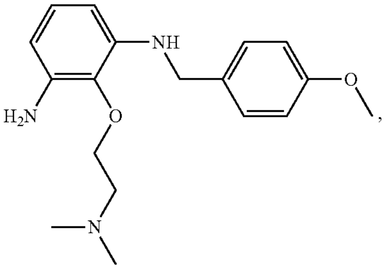
,
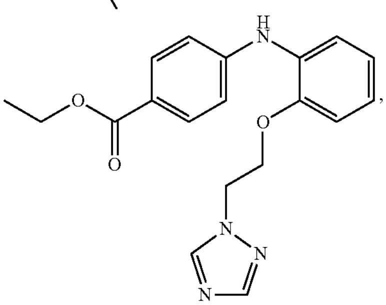
,
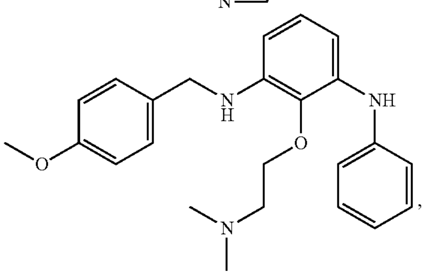
,
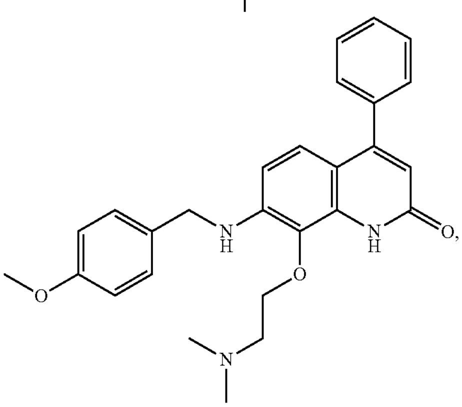
,
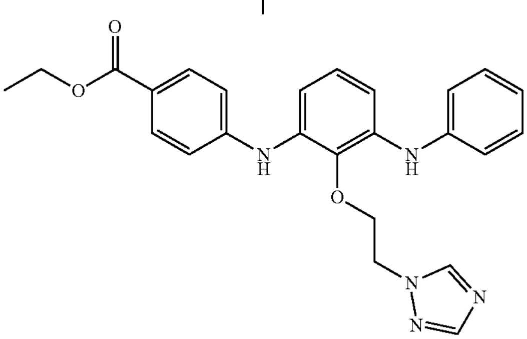
,
-continued
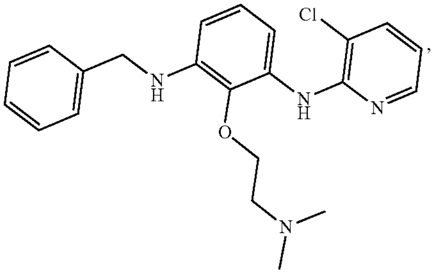
,
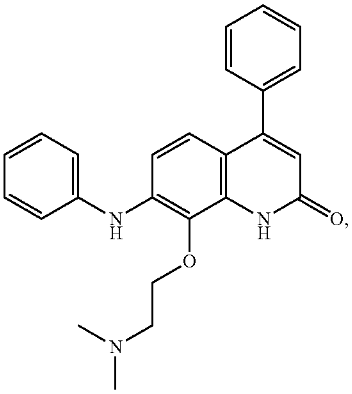
,
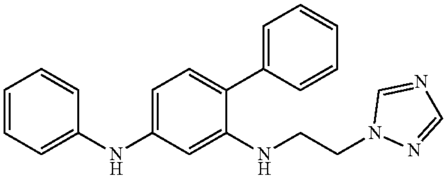
,
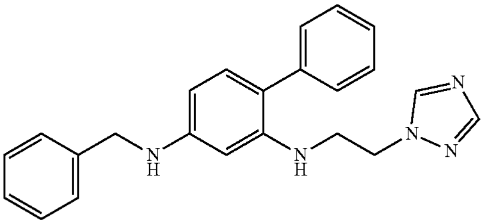
,
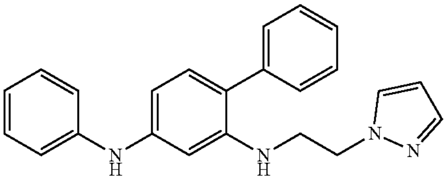
,
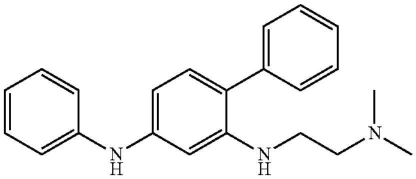
,
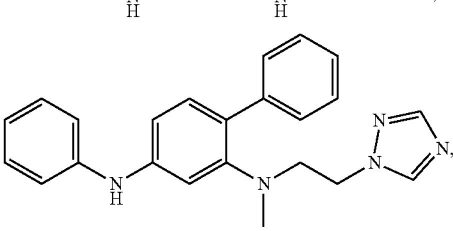
, -continued
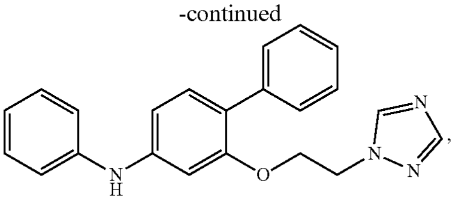
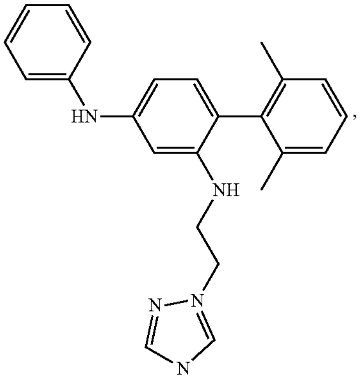
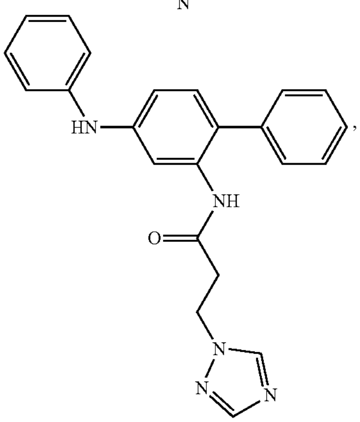
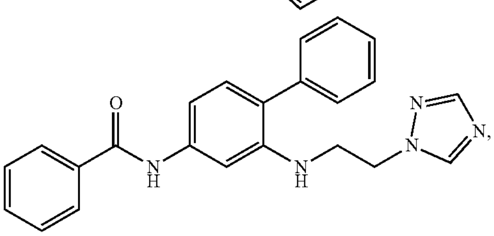
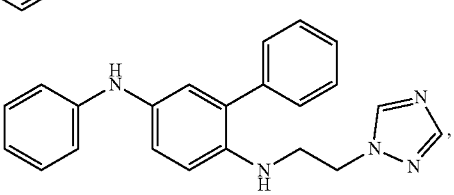
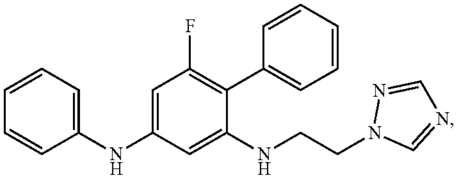
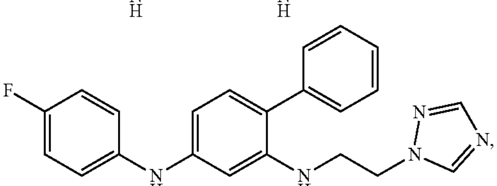
-continued
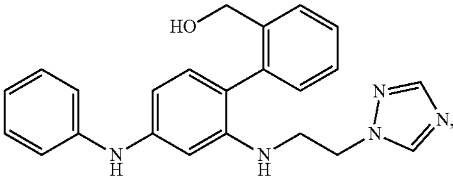
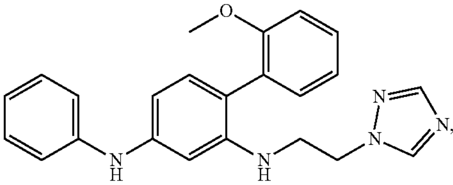
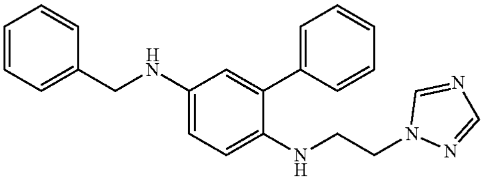
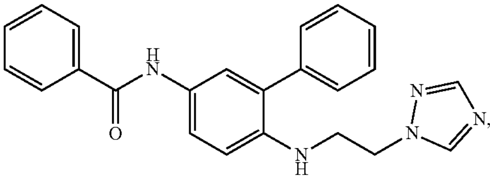
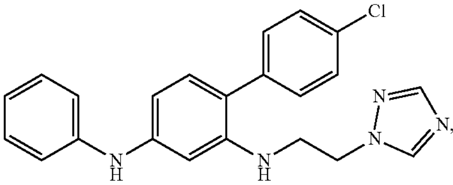
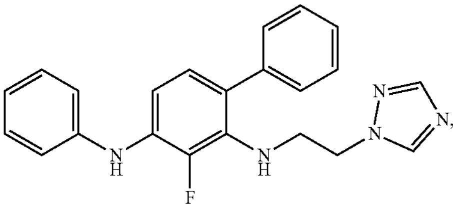
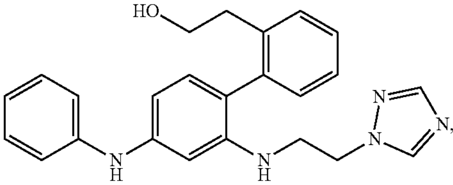
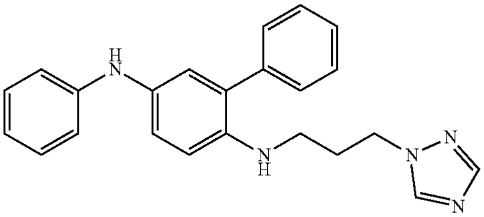

-continued
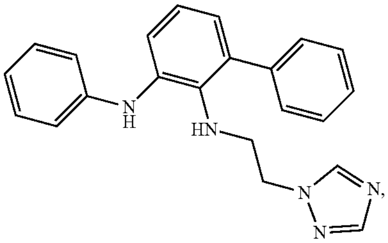
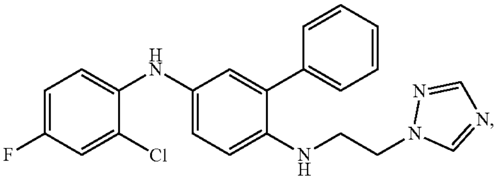
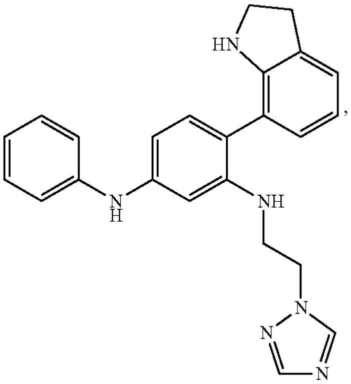
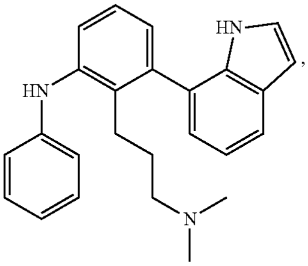
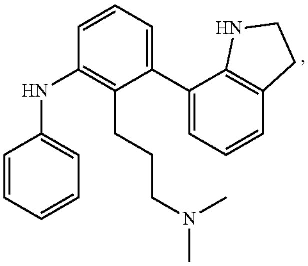
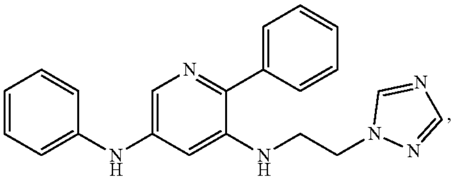
-continued
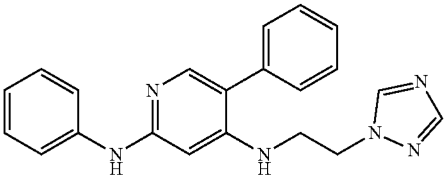
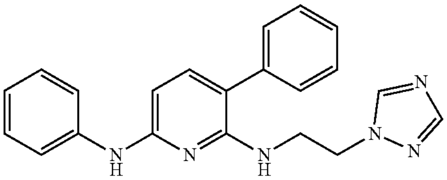
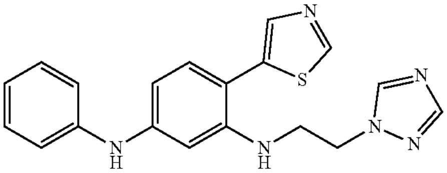
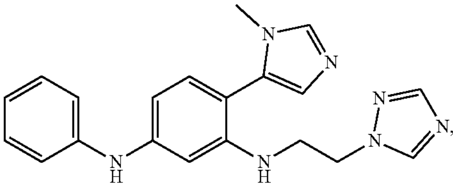
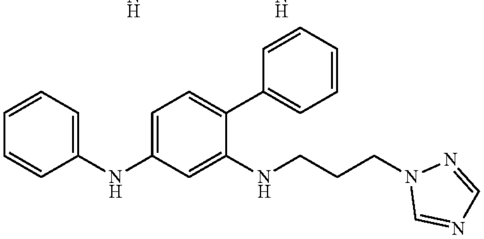
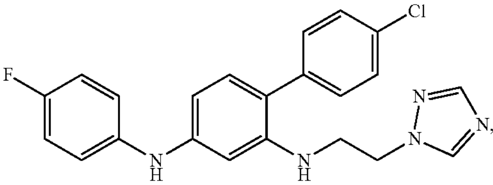
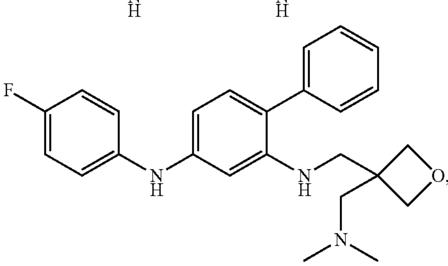
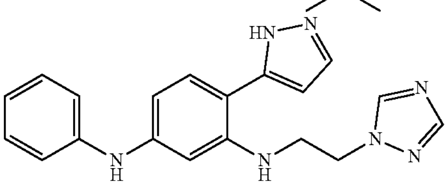
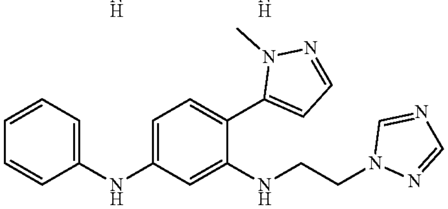

-continued
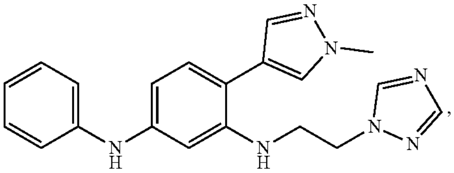
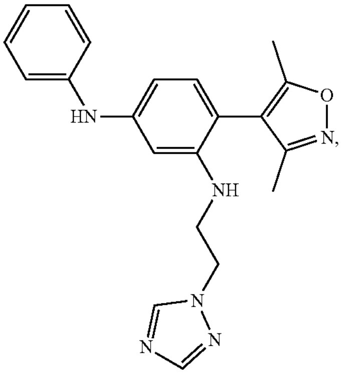
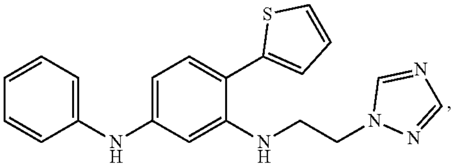
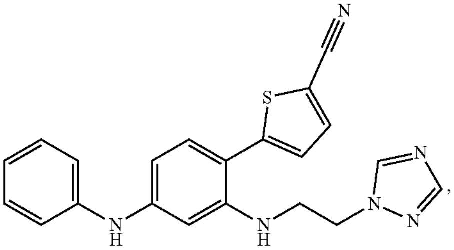
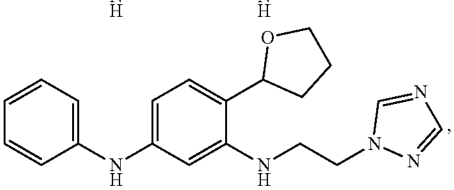
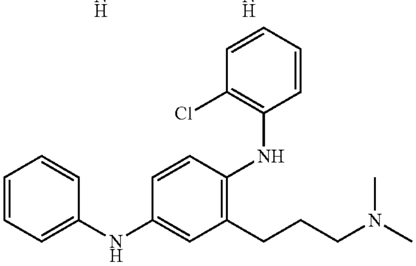
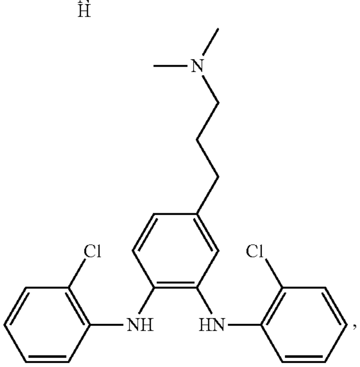
-continued
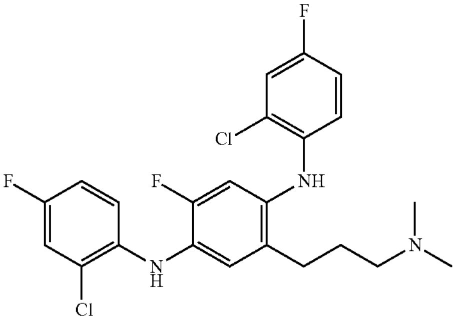
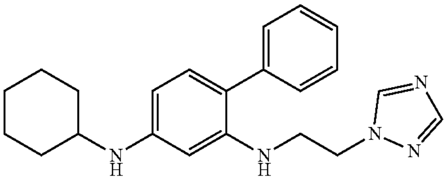
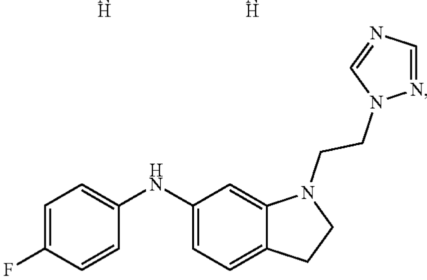
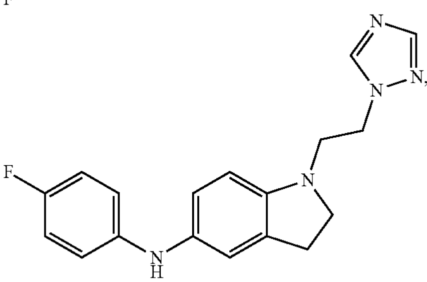
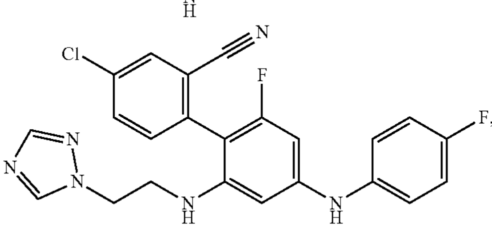
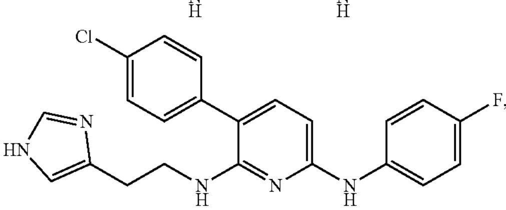
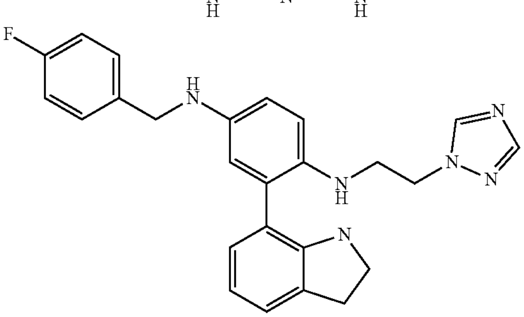

-continued
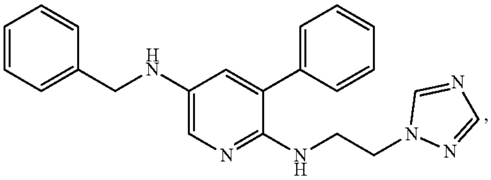
,
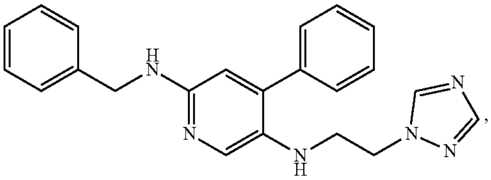
,
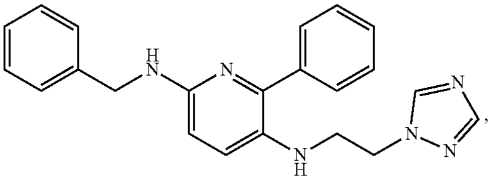
,
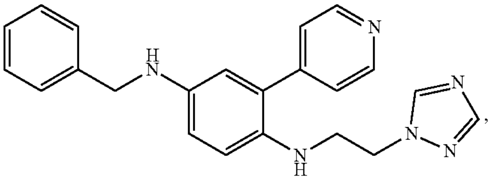
,
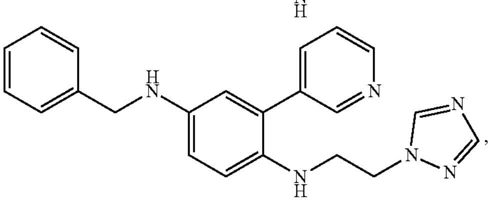
,
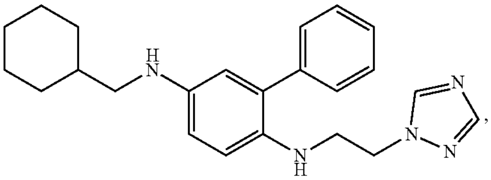
,
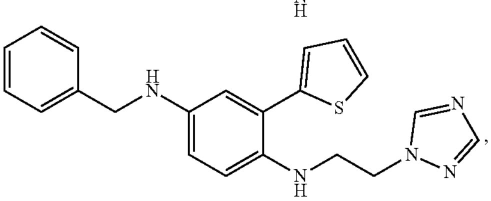
,
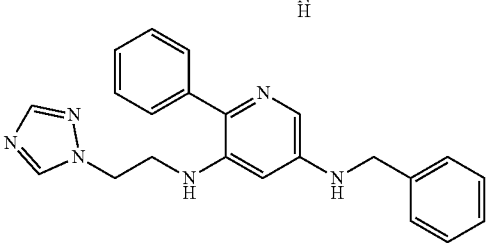
,
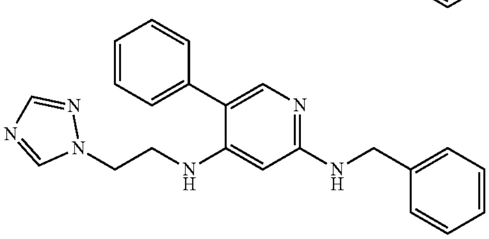
,
-continued
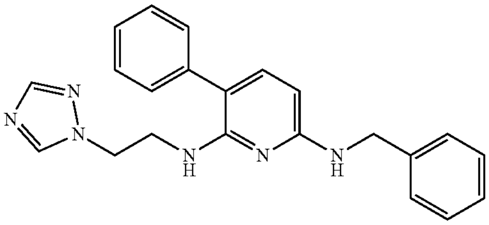
,
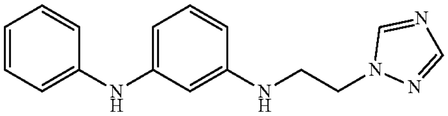
,
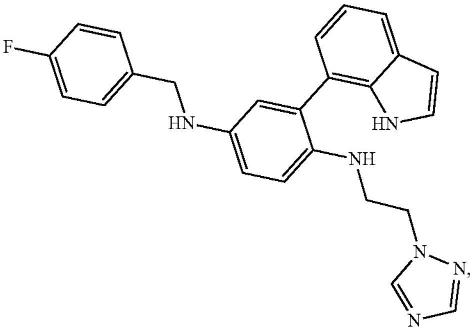
,
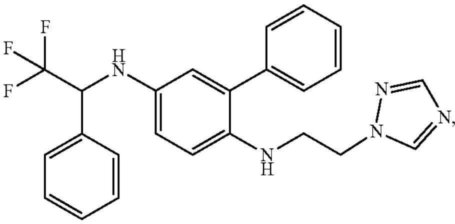
,
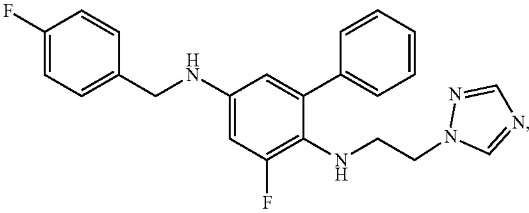
,
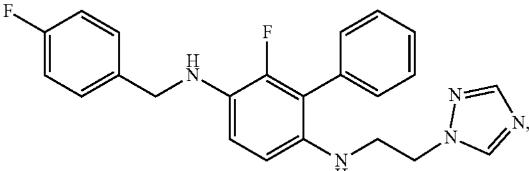
,
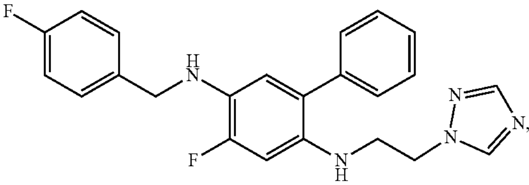
, -continued
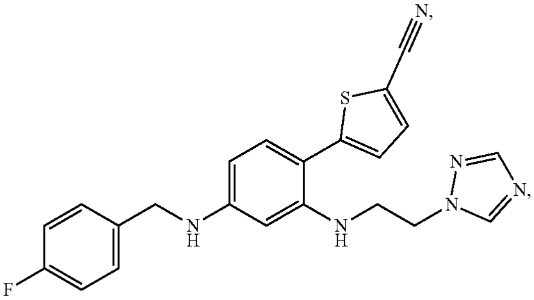 [SMILES: N#Cc1ccc(-c2ccc(NCc3ccc(F)cc3)cc2NCCn2cncn2)s1]
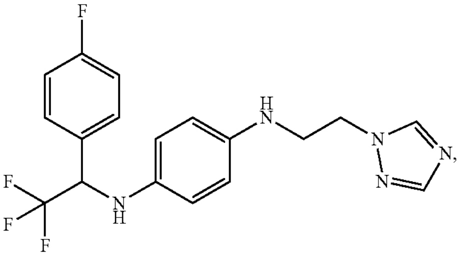
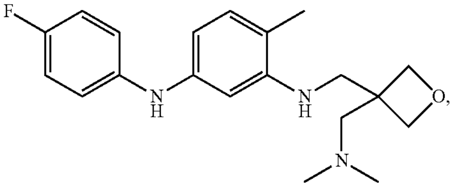
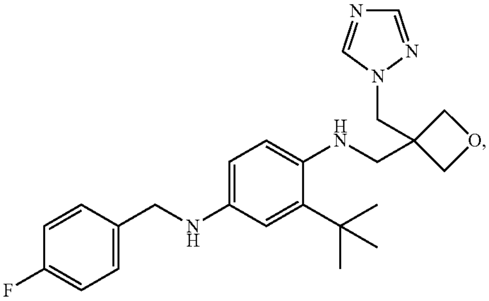
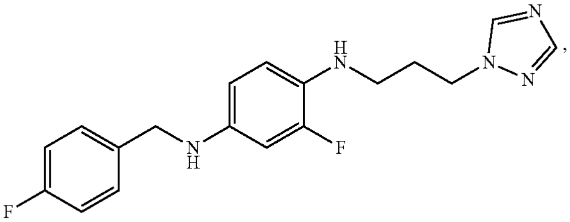
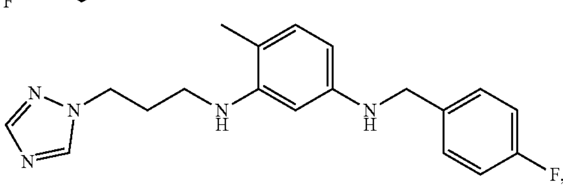
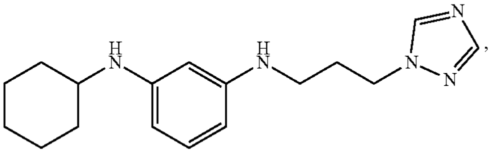
-continued
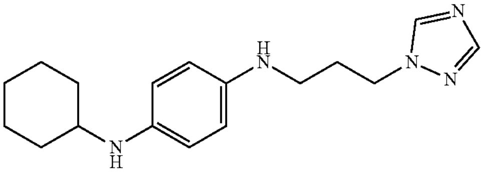
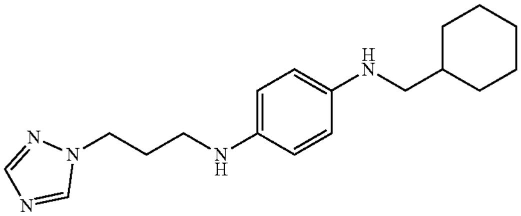
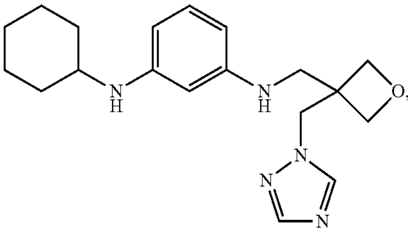
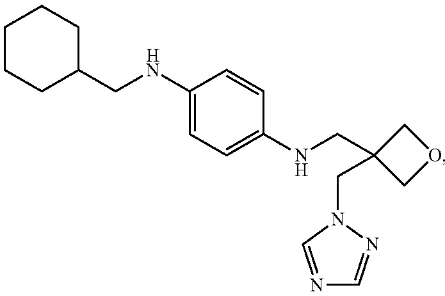
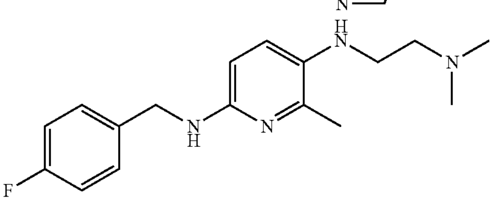
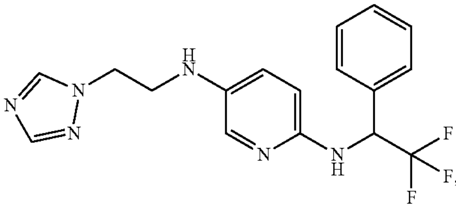
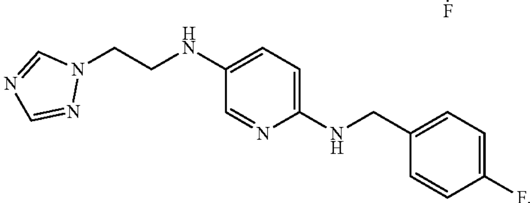
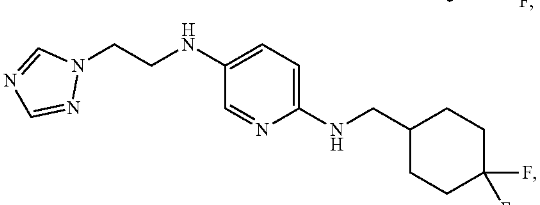

-continued
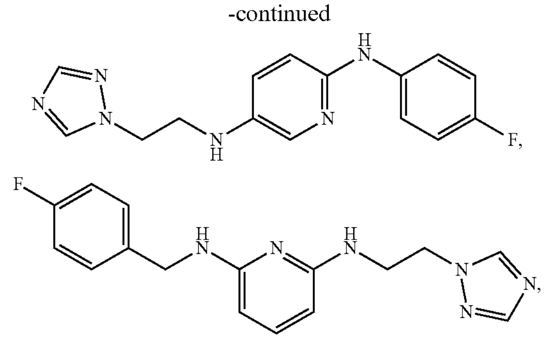
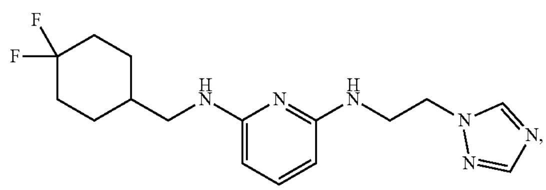
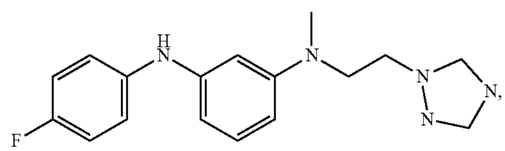
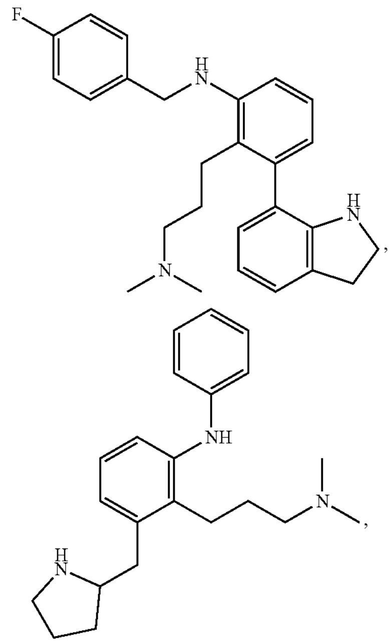
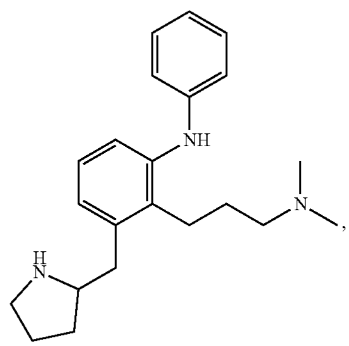
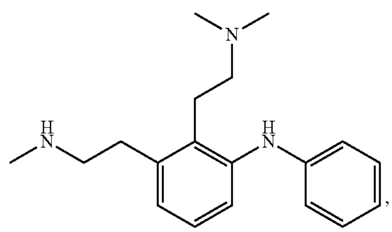
-continued
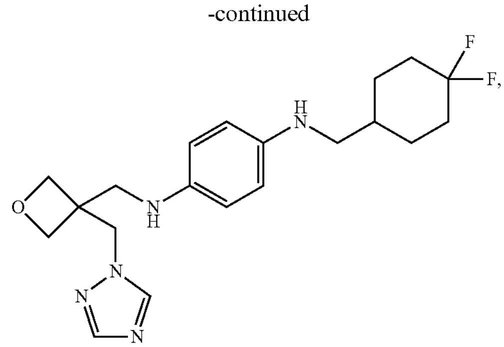
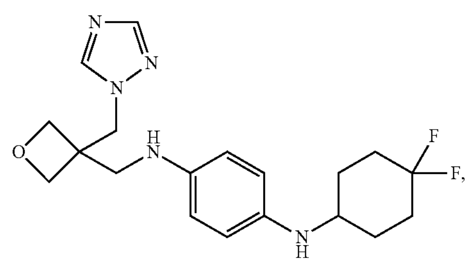
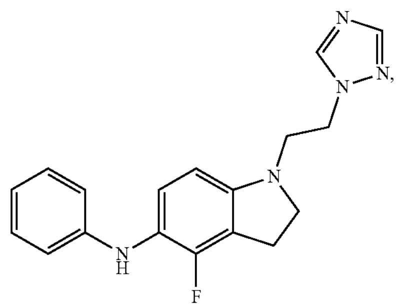
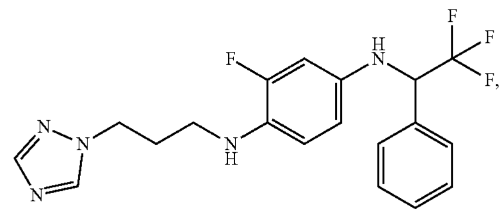
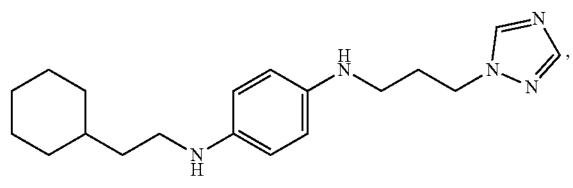
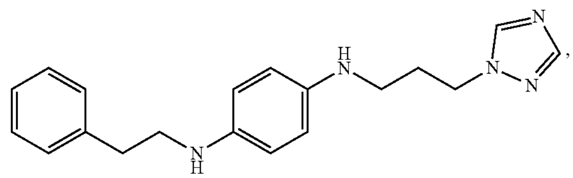
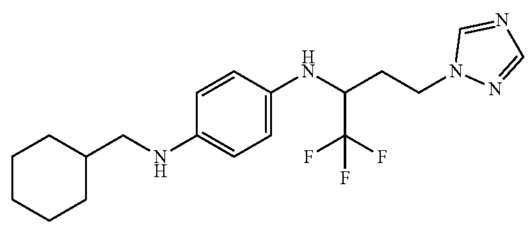

-continued
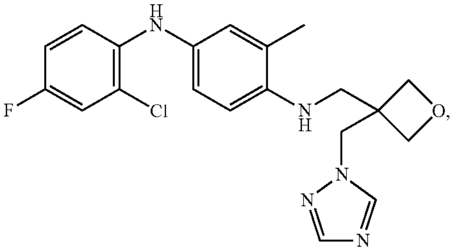
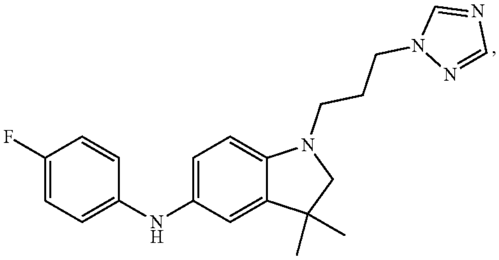
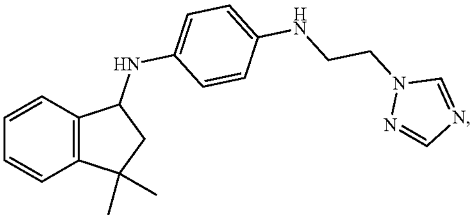
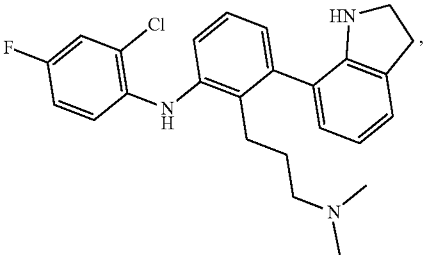
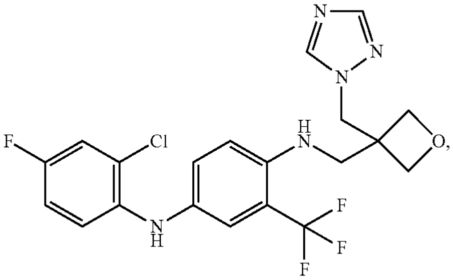
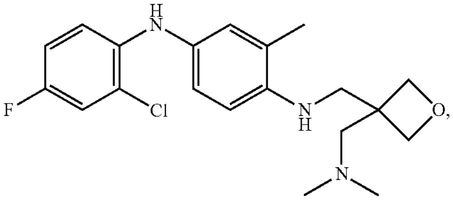
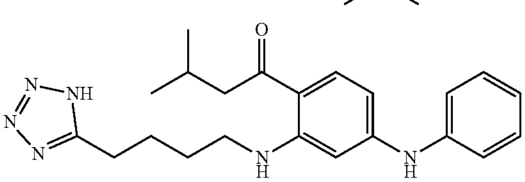
-continued
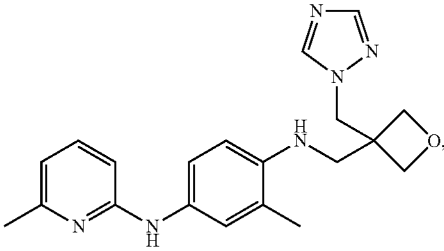
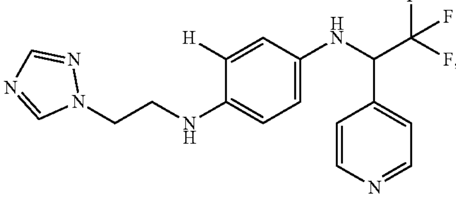
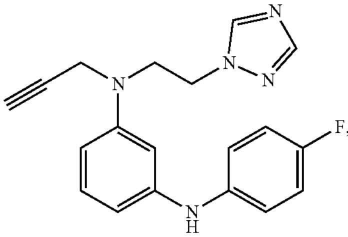
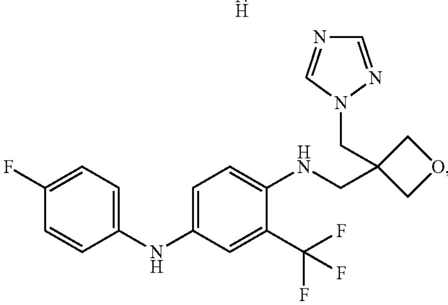
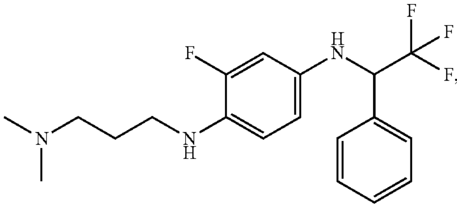
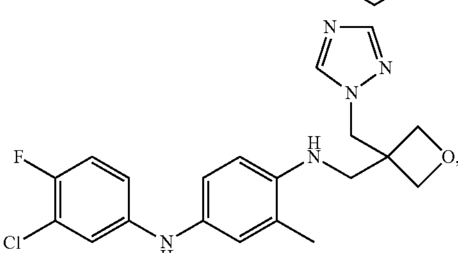
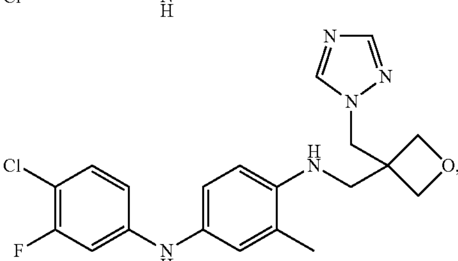

-continued
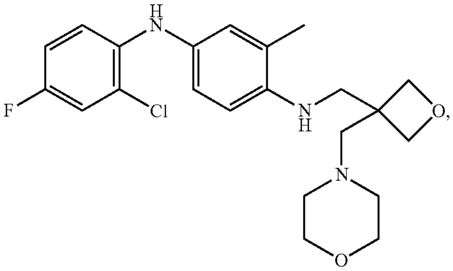
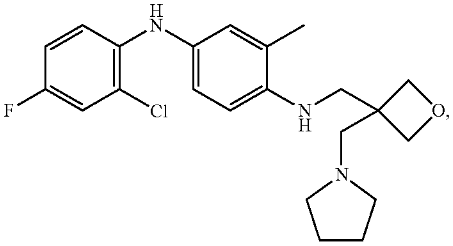
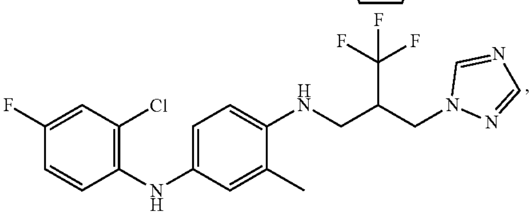
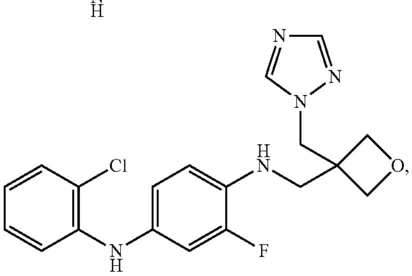
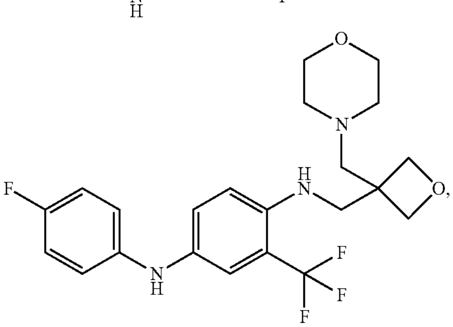
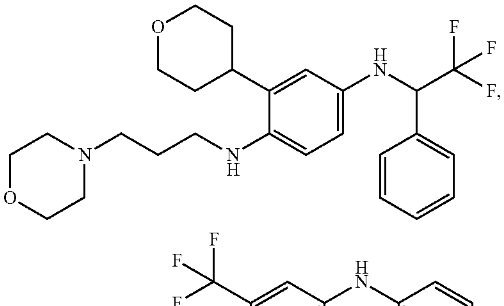
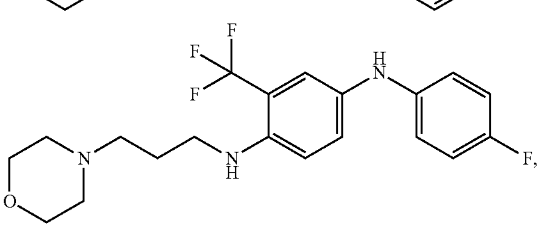
-continued
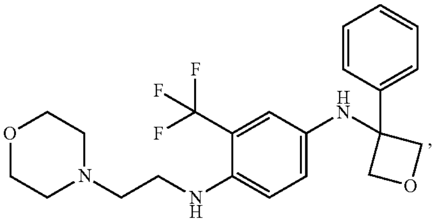
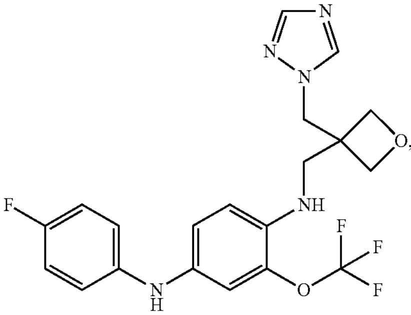
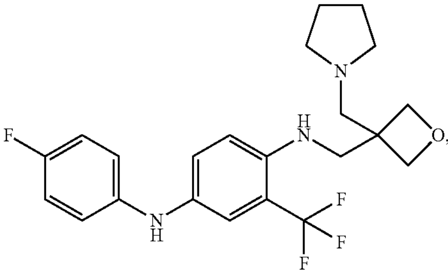
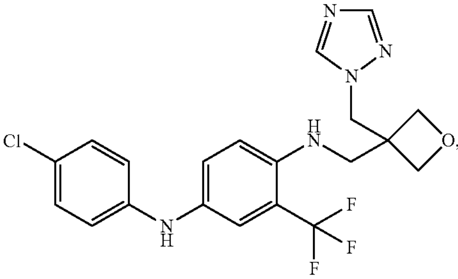
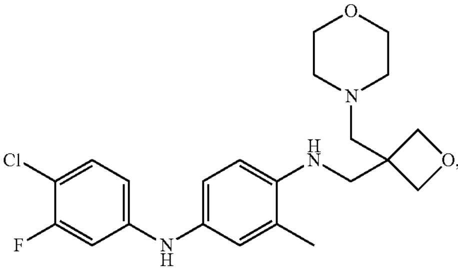
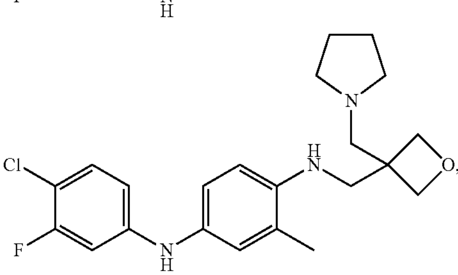

-continued
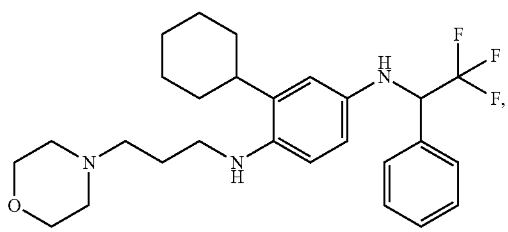
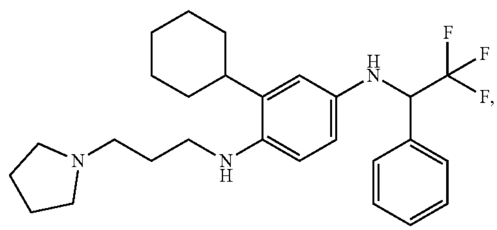
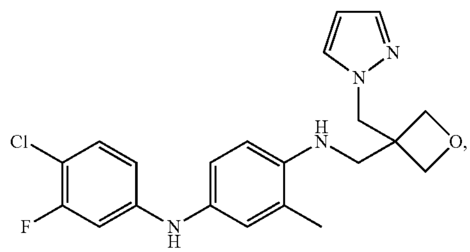
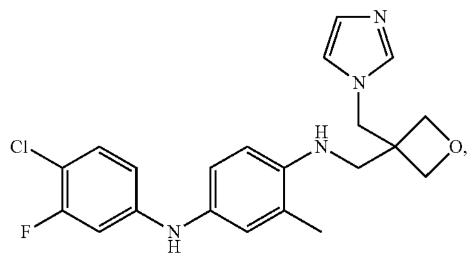
and
a pharmaceutically acceptable salt thereof.
2. The compound of claim 1, wherein the compound is selected from:
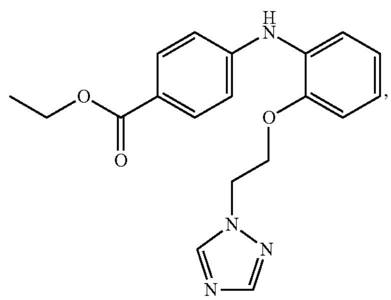
-continued
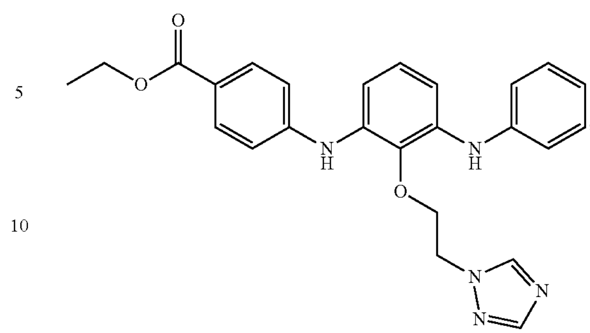
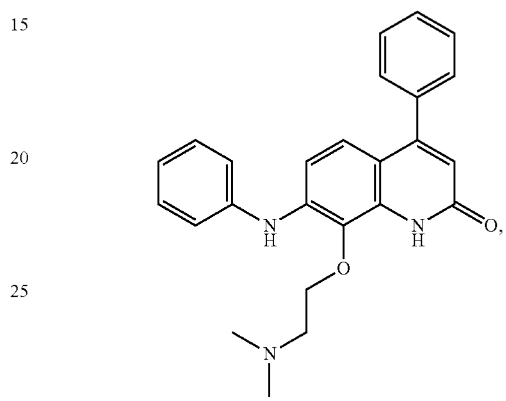
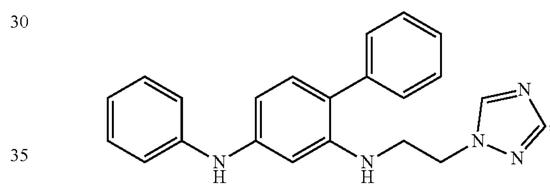
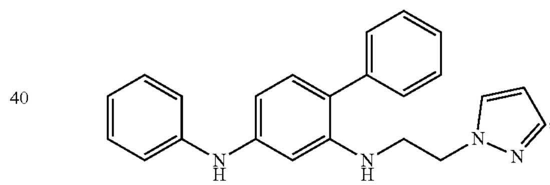
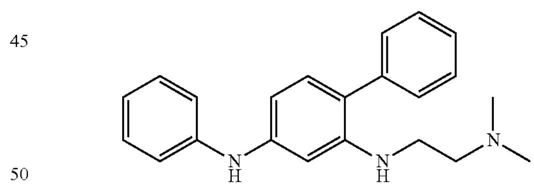
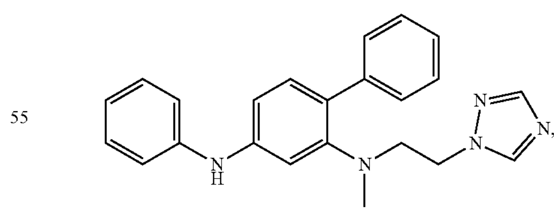
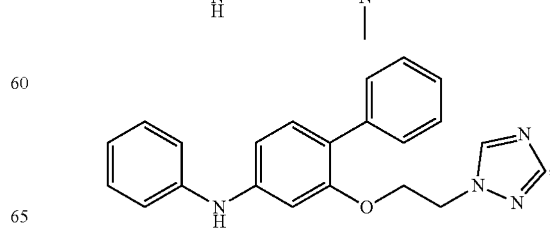

-continued
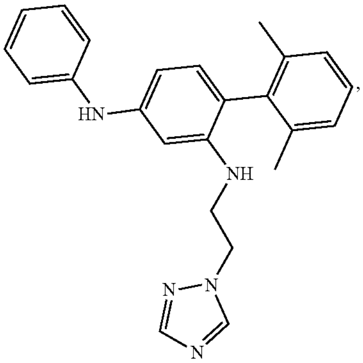
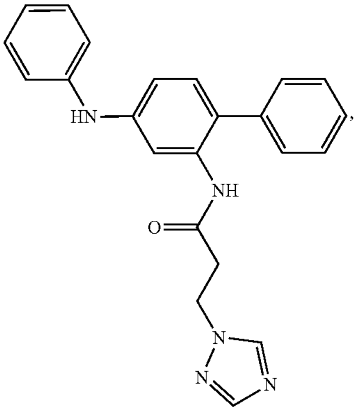
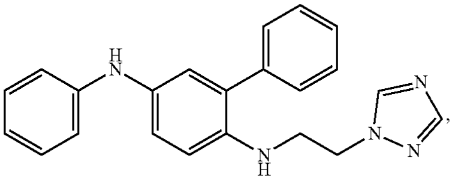
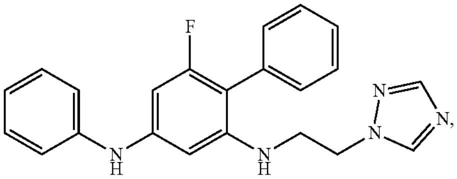
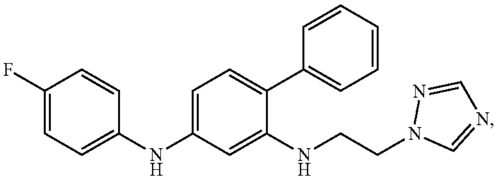
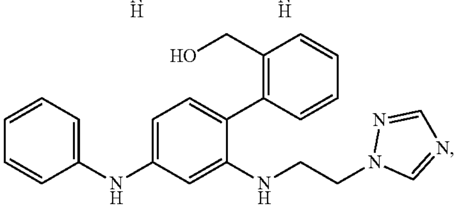
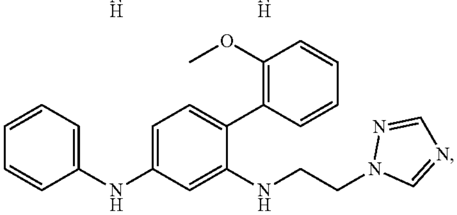
-continued
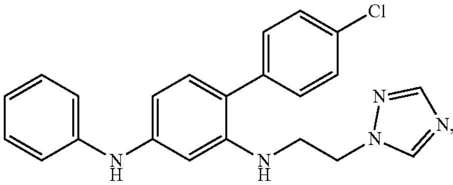
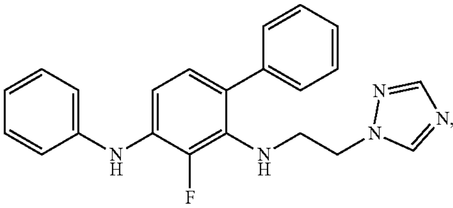
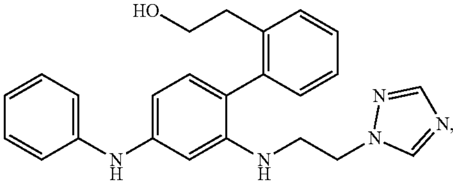
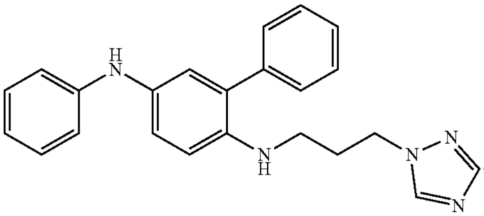
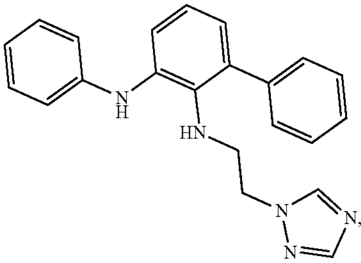
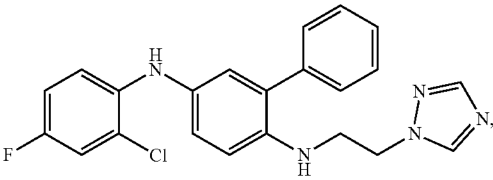
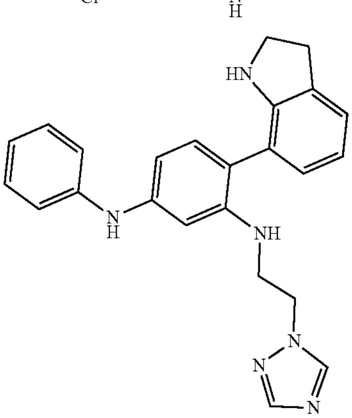

-continued
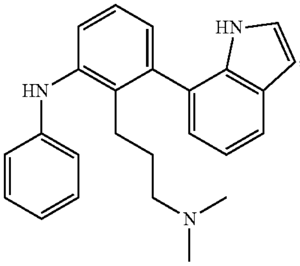
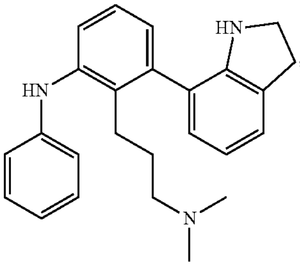
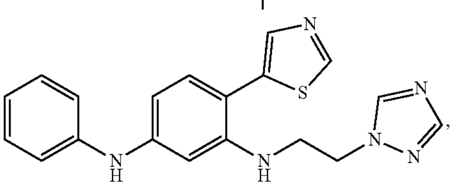
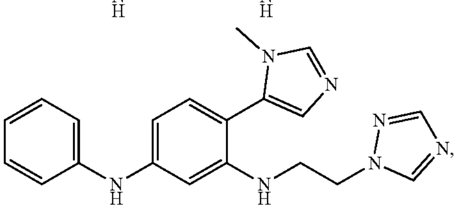
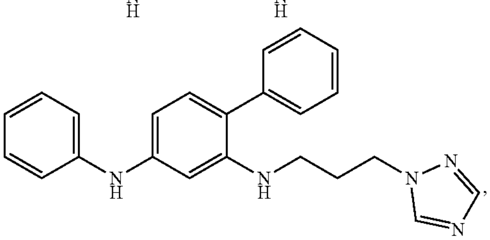
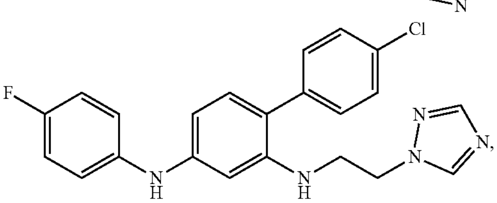
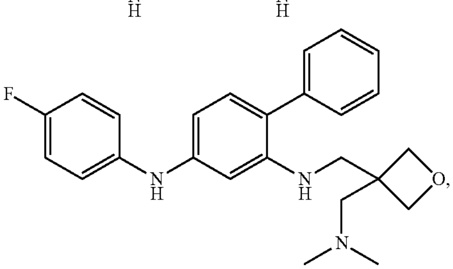
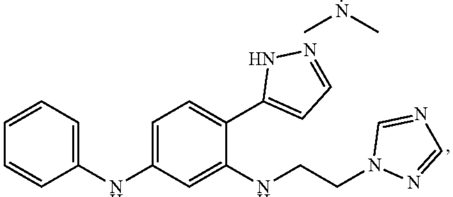
-continued
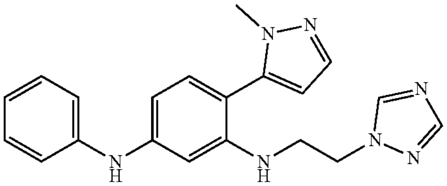
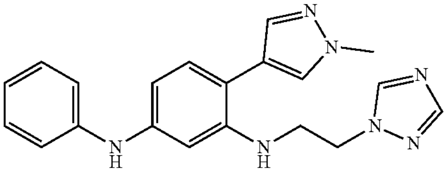
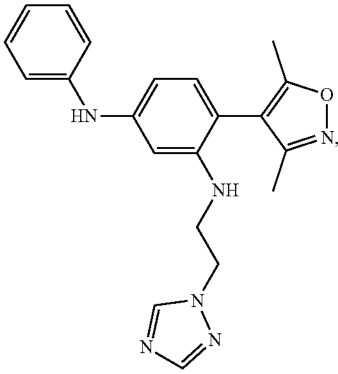
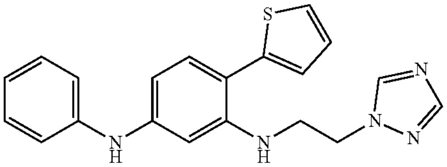
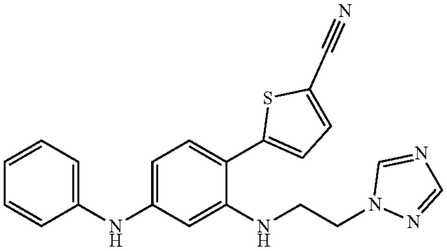
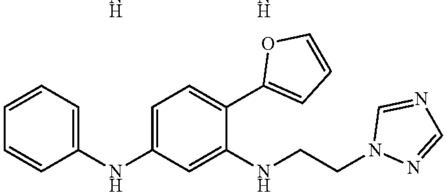
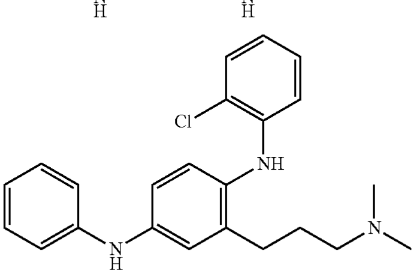

-continued
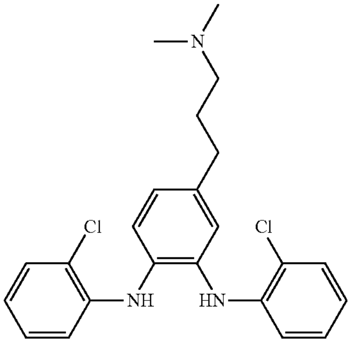
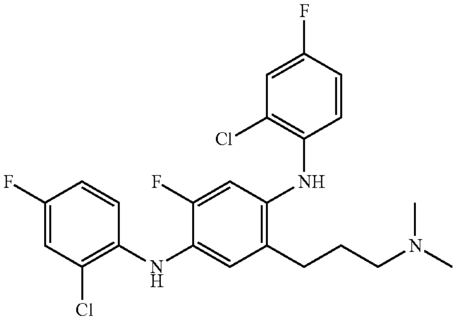
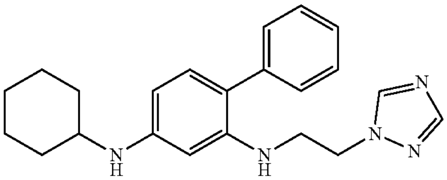
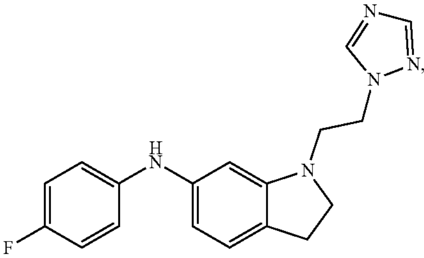
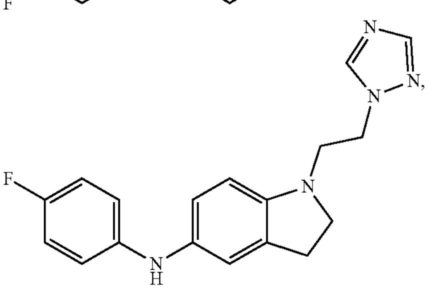
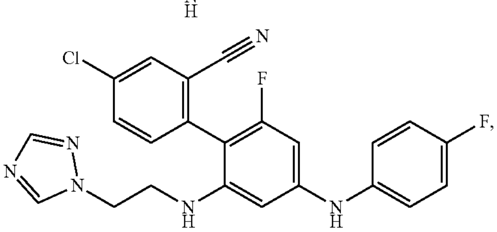
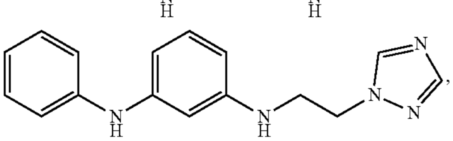
-continued
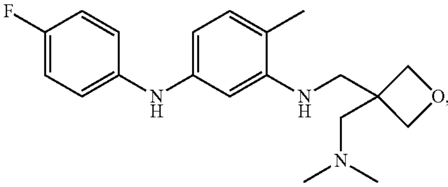
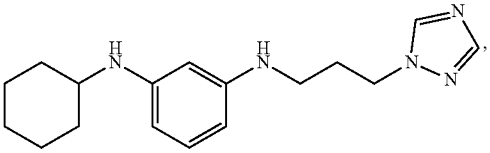
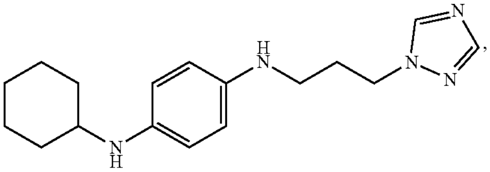
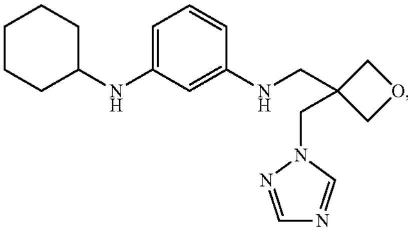
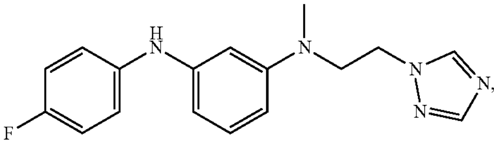
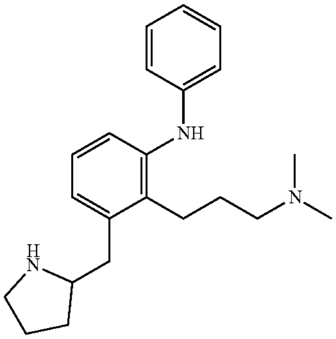
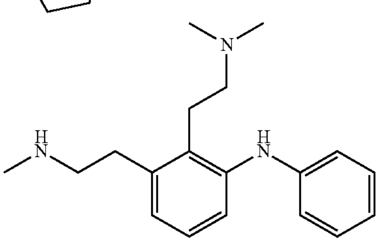
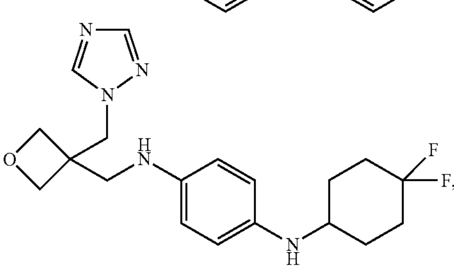

-continued
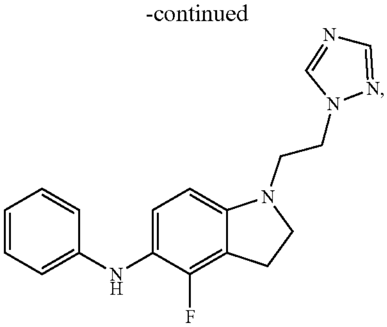
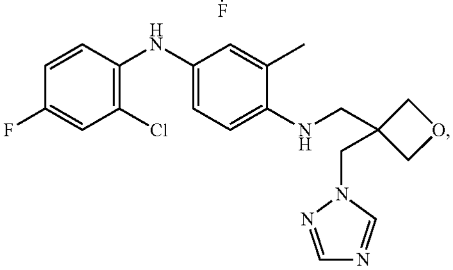
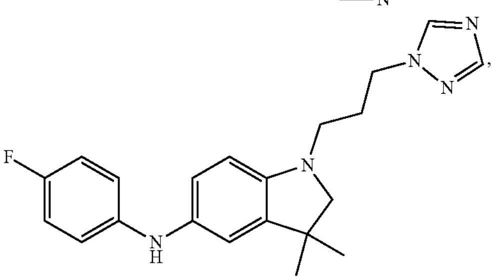
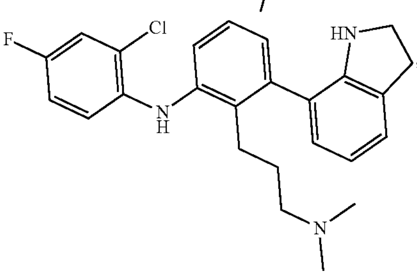
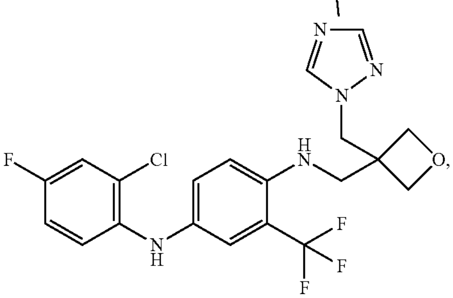
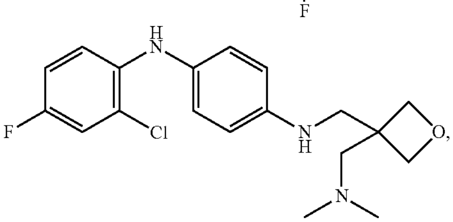
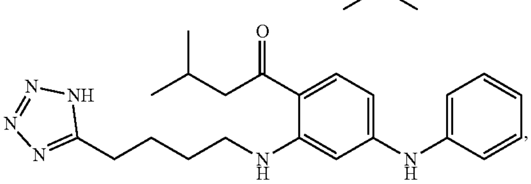
-continued
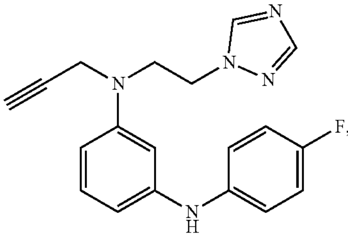
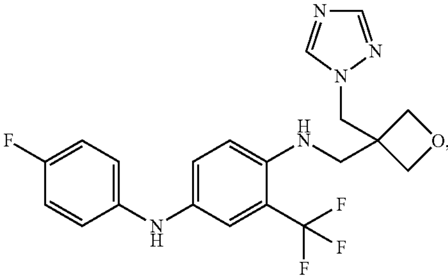
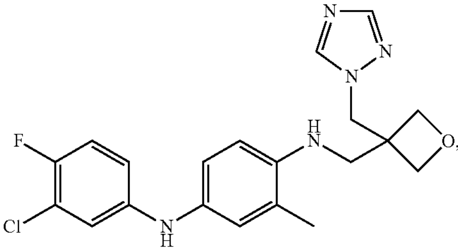
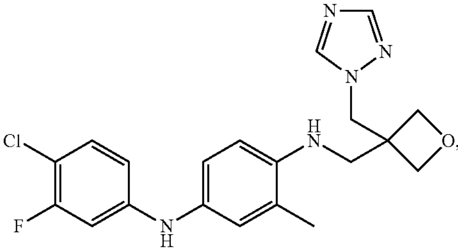
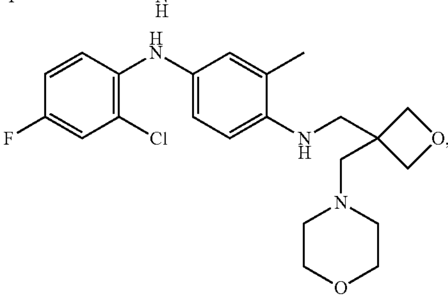
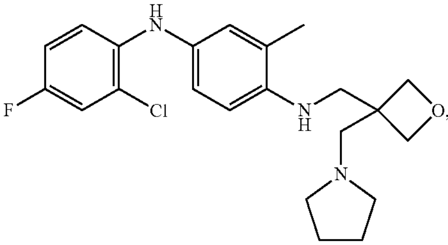

-continued
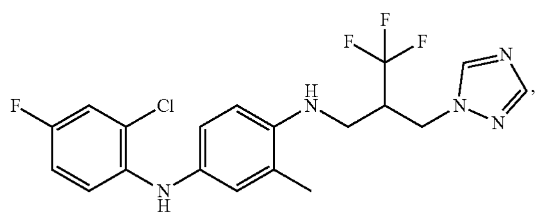
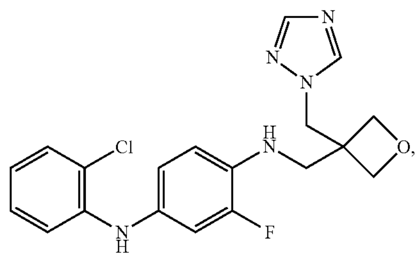
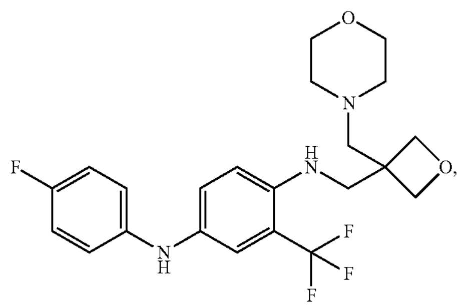
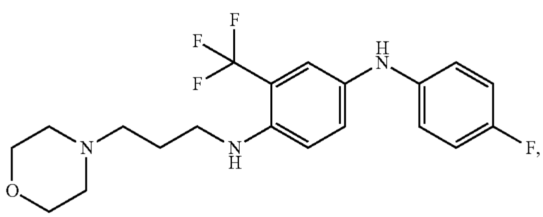
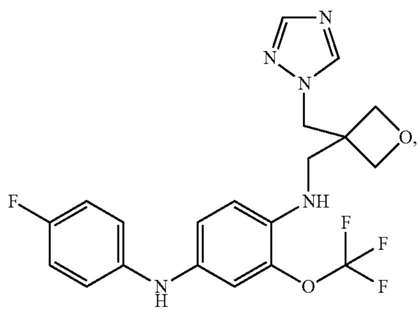
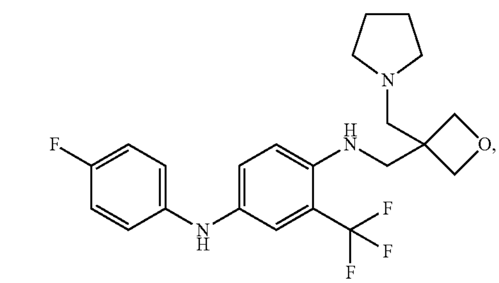
-continued
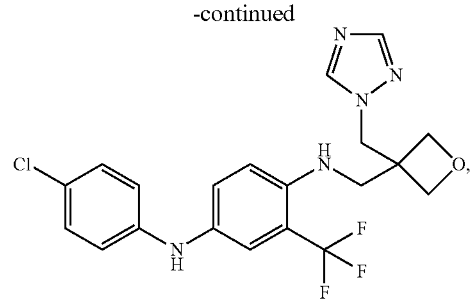
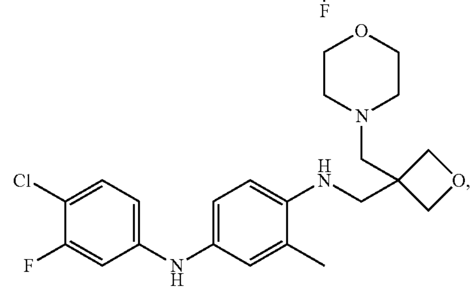
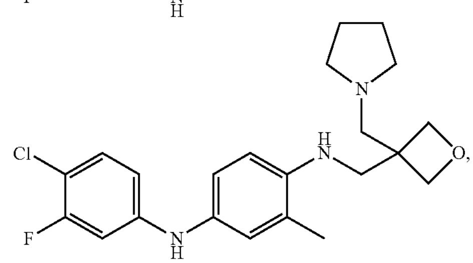
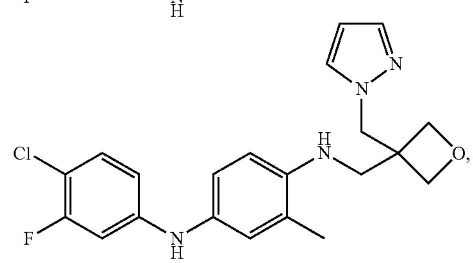
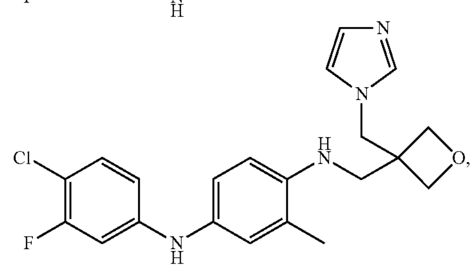
and pharmaceutically acceptable salts thereof.
3. A compound, wherein the compound is selected from:
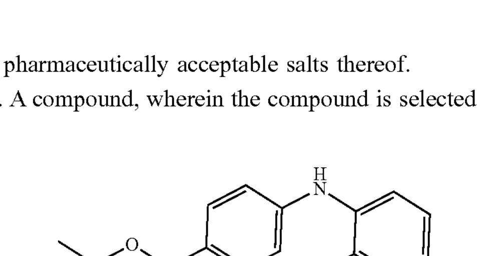
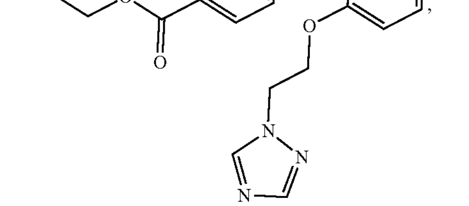

-continued
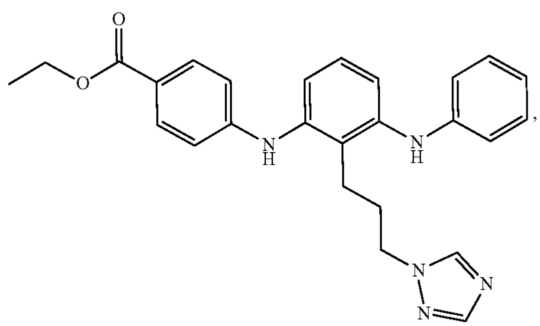
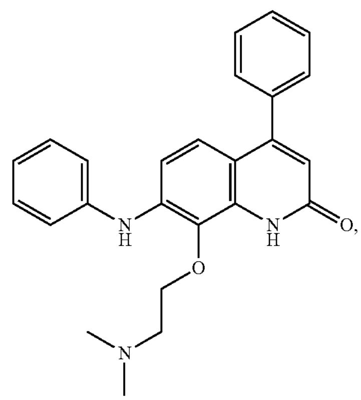
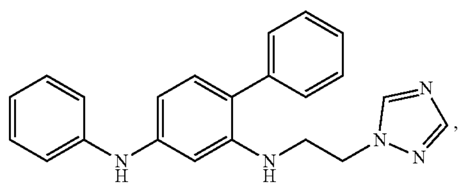
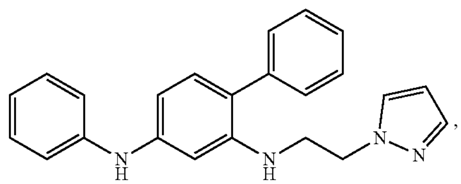
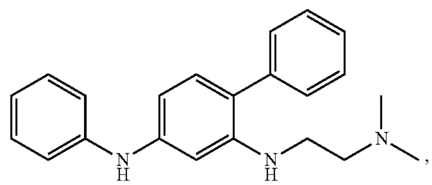
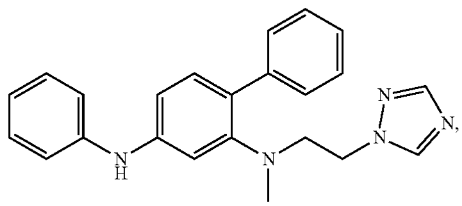
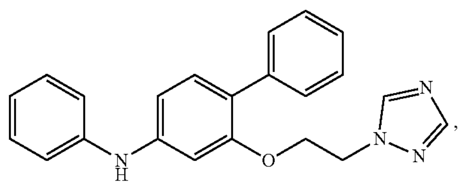
-continued
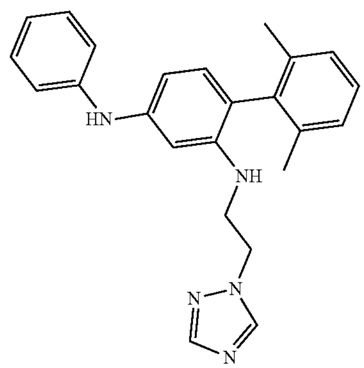
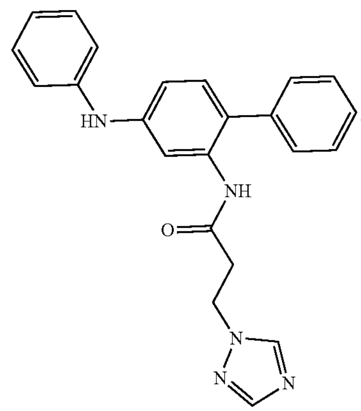
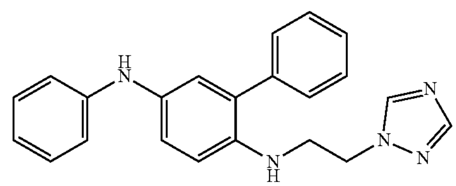
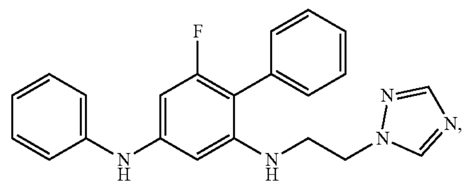
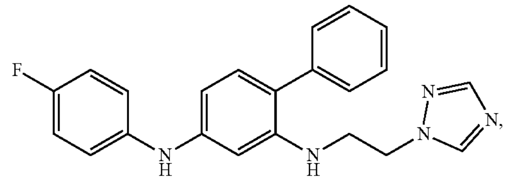
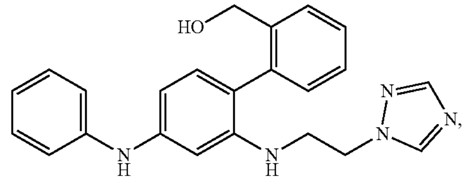
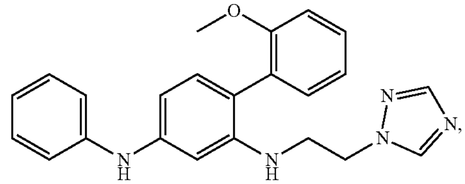 [SMILES: COc1ccccc1-c1ccc(Nc2ccccc2)cc1NCCn1cncn1]

-continued
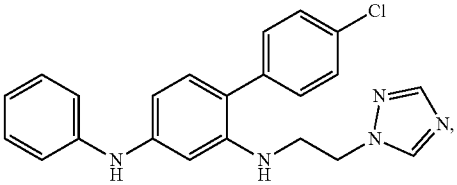
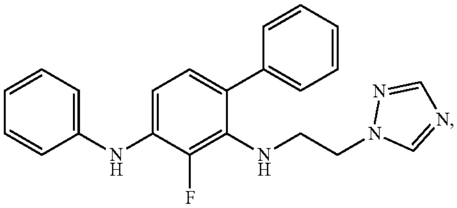
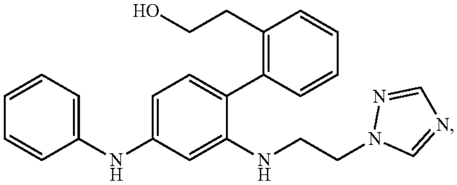
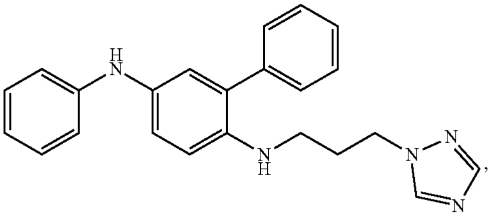
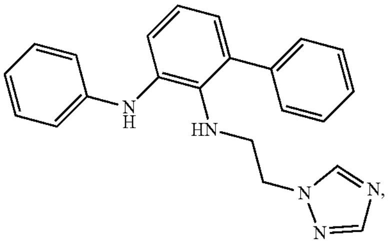
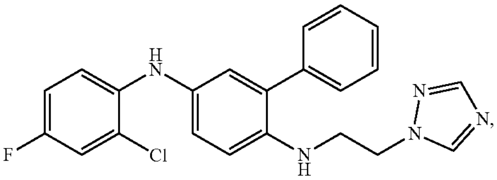
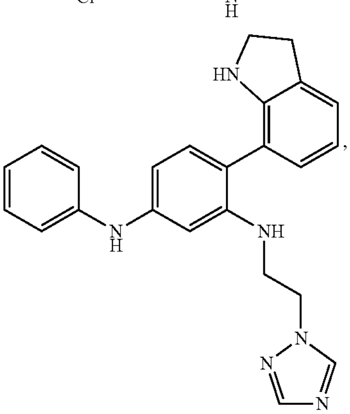
-continued
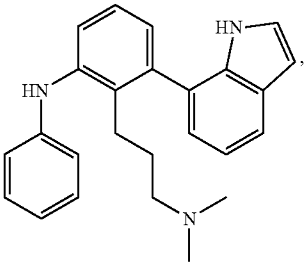
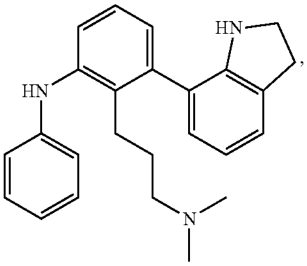
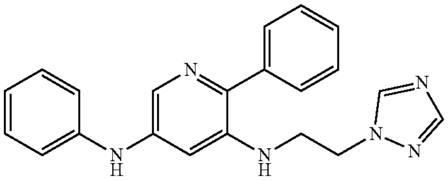
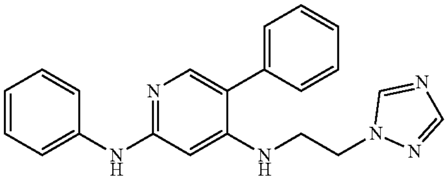
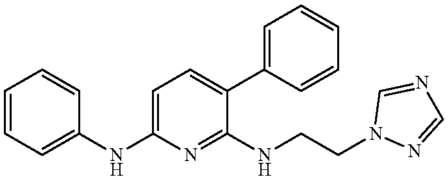
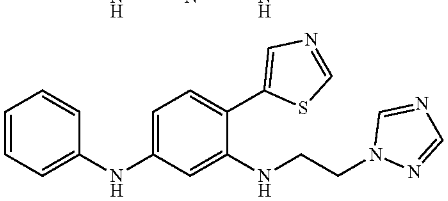
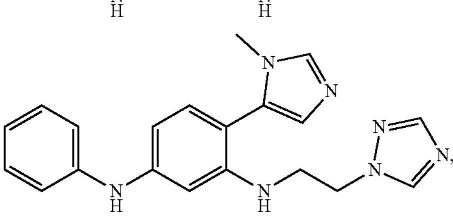
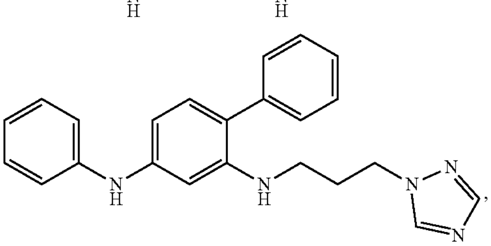

-continued
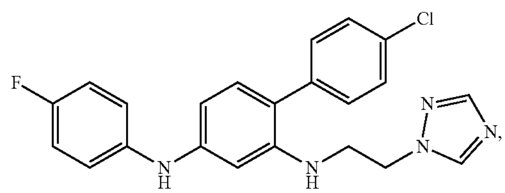
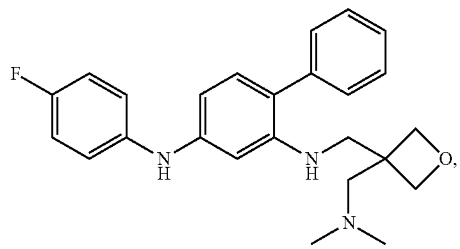
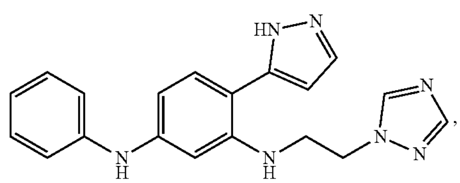
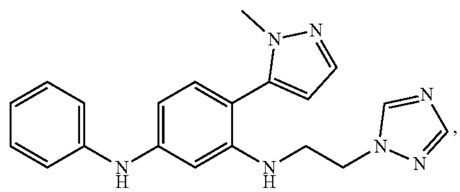
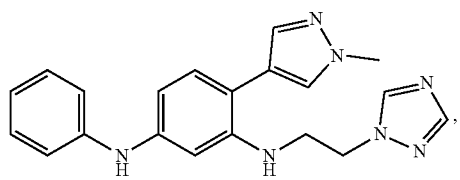
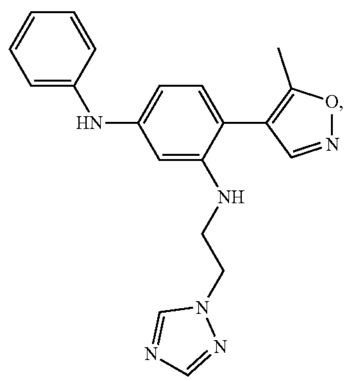
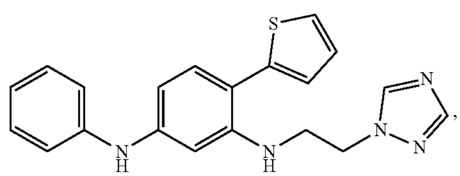
-continued
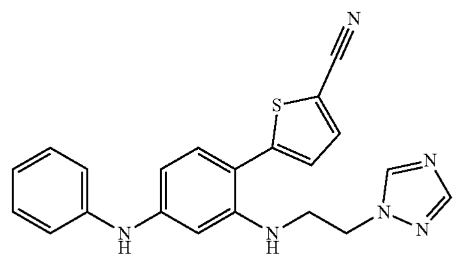
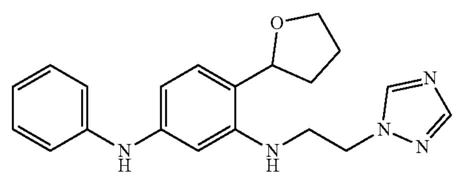
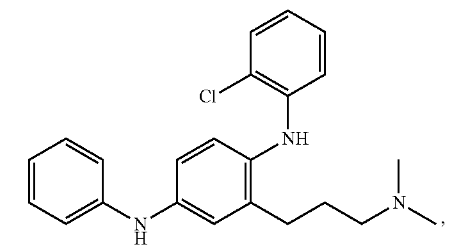
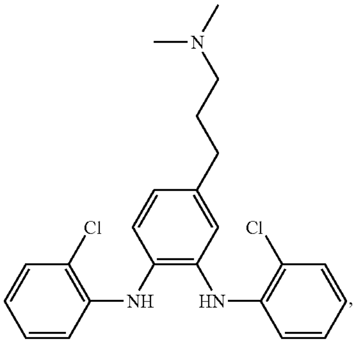
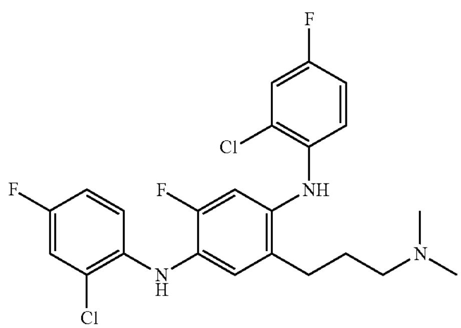
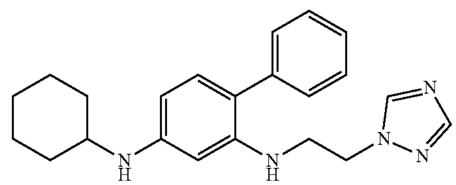

-continued
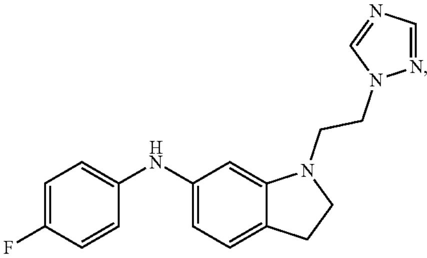 [SMILES: Fc1ccc(Nc2ccc3c(c2)N(CCn2cncn2)CC3)cc1],
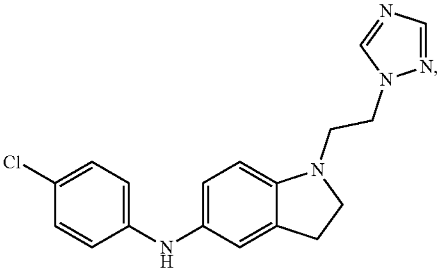,
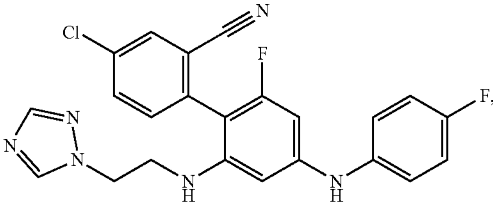,
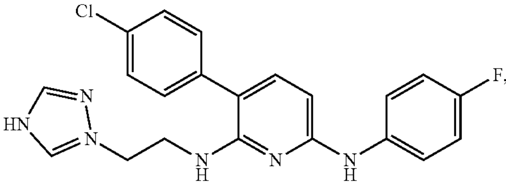,
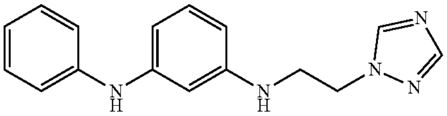,
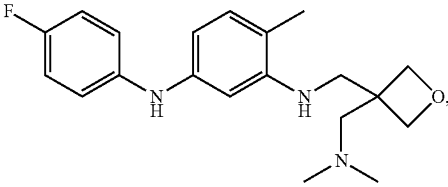,
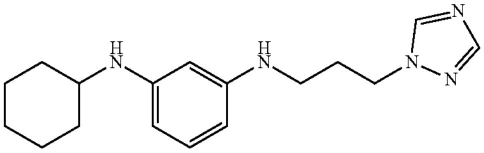,
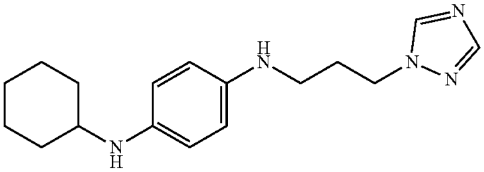,
-continued
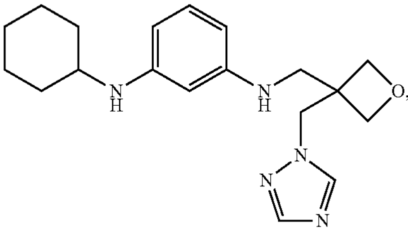,
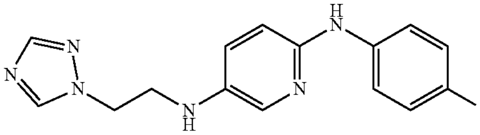,
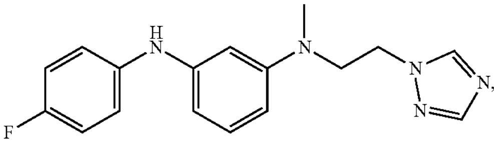,
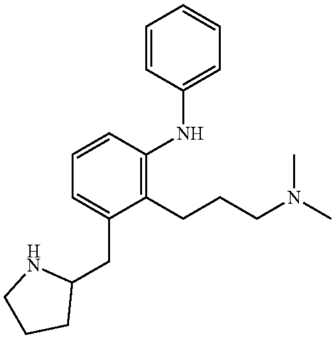,
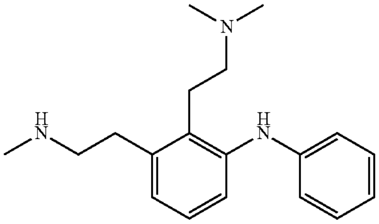,
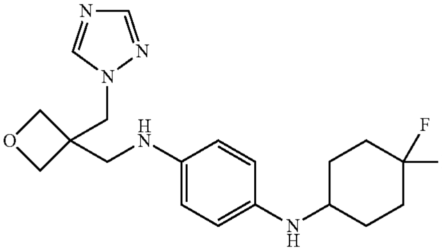,
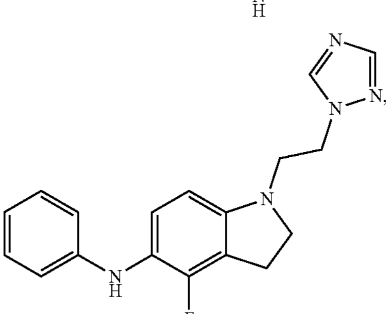, -continued
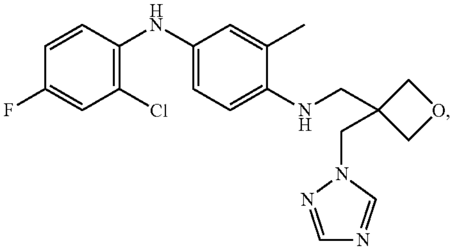
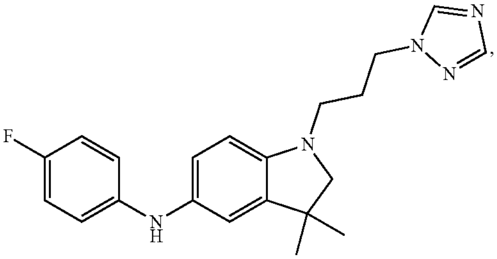
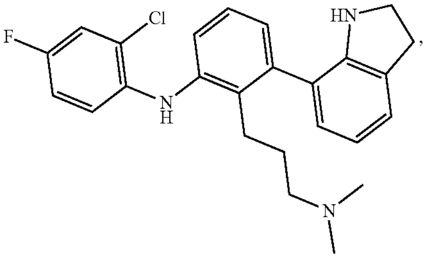
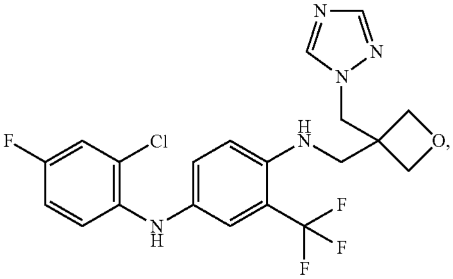
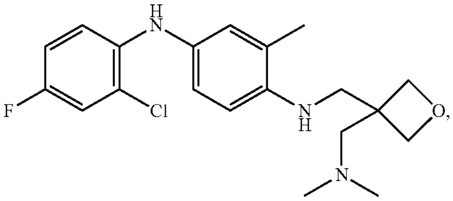
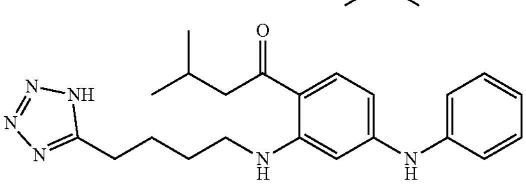
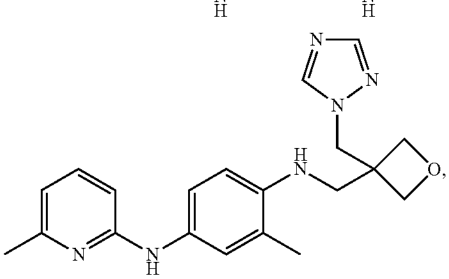
-continued
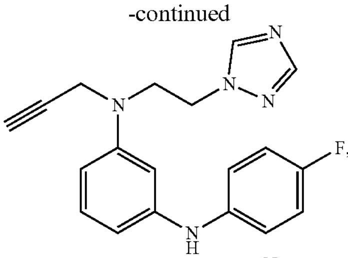
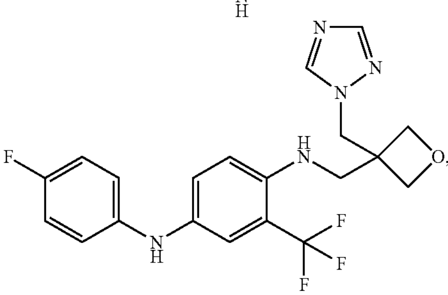
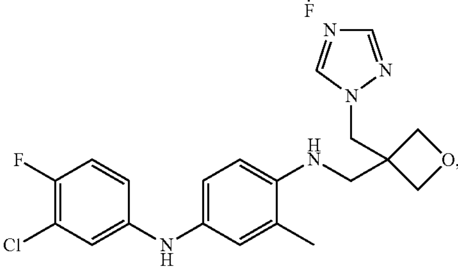
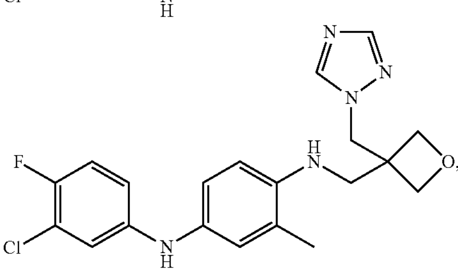
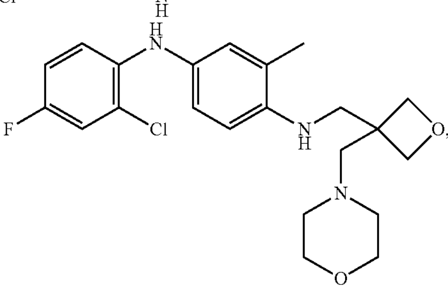
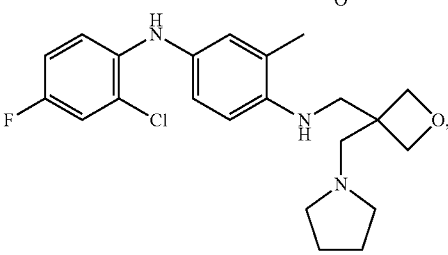
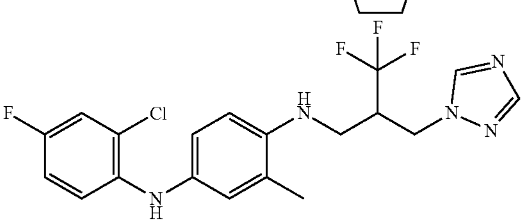

-continued
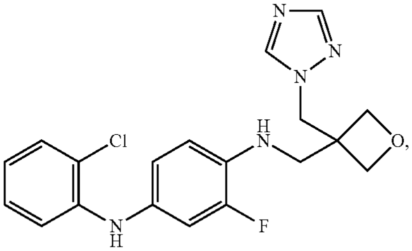
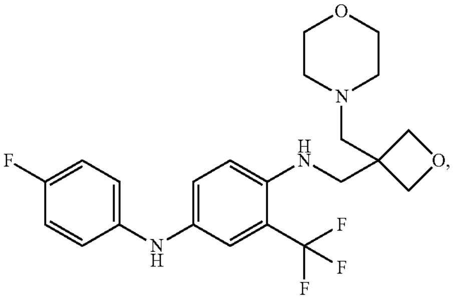
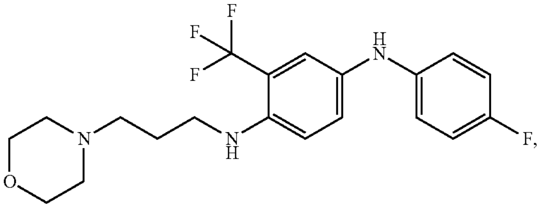
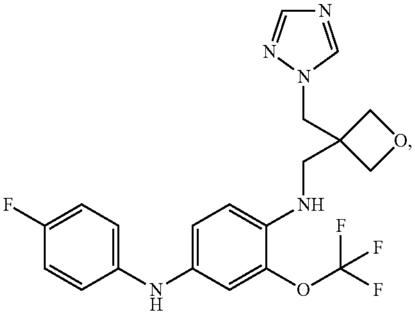
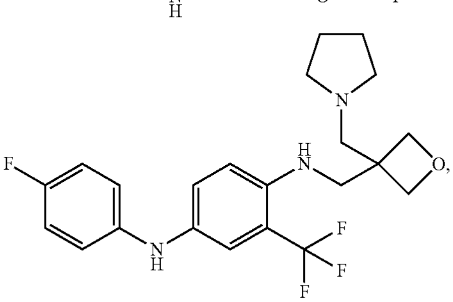
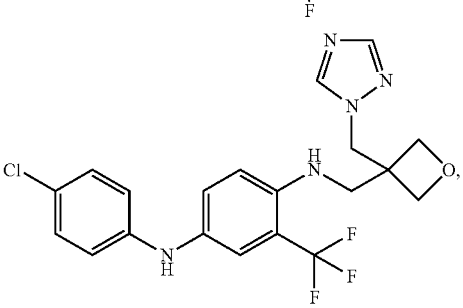
-continued
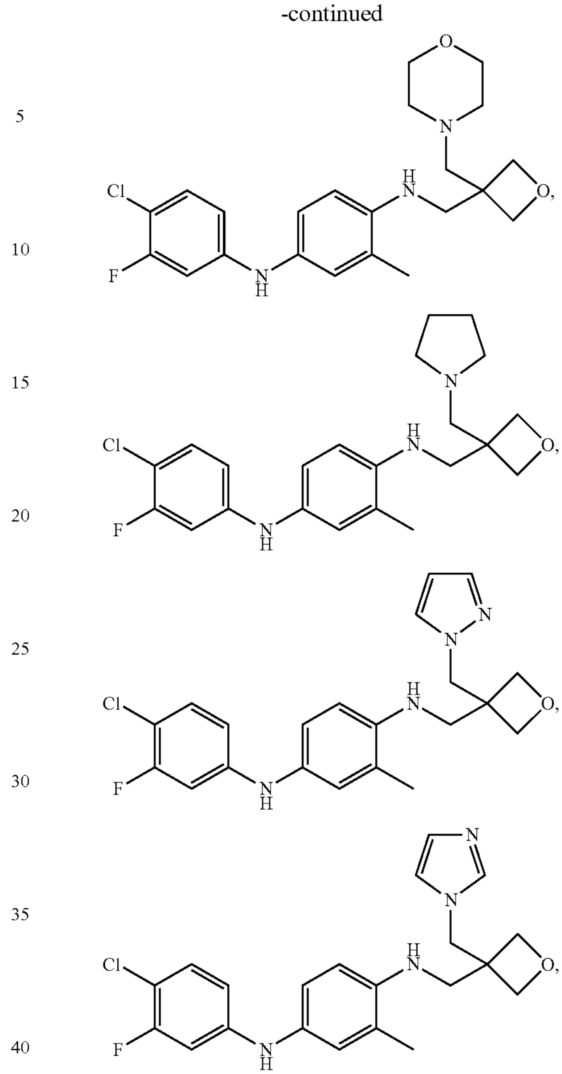
and a pharmaceutically acceptable salt thereof.
4. The compounds of claim 3, wherein the compound is selected from:
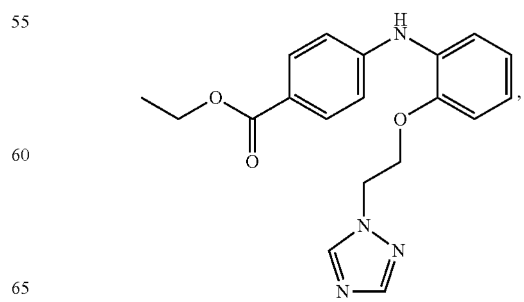

-continued
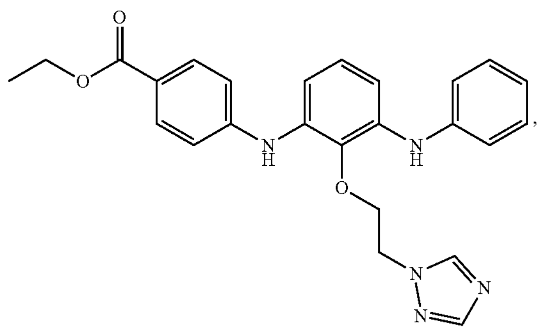
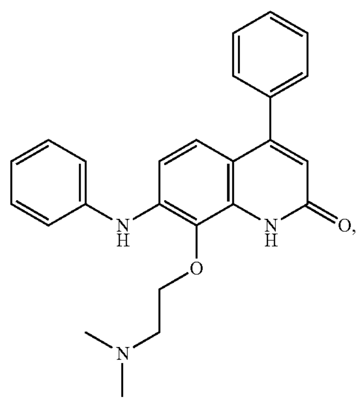
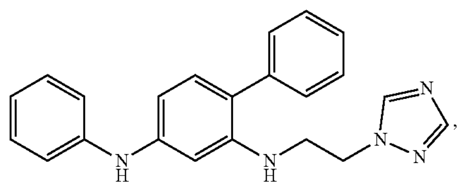
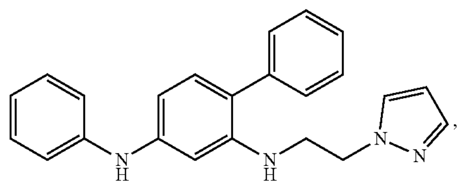
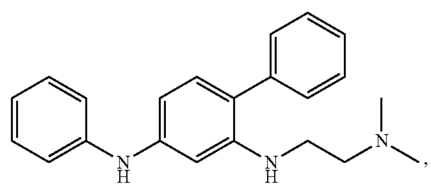
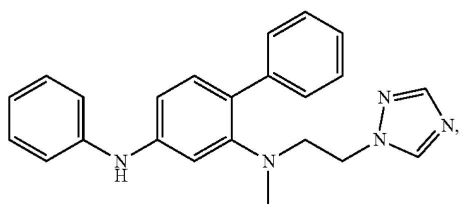
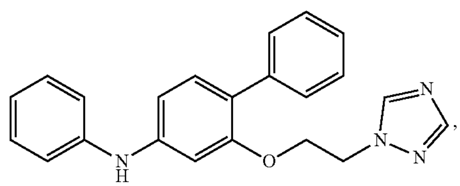
-continued
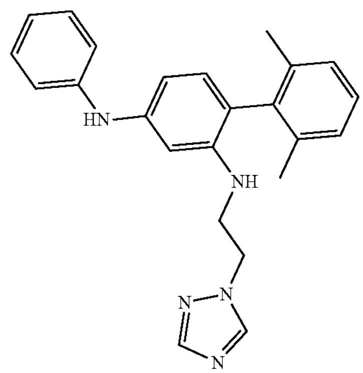
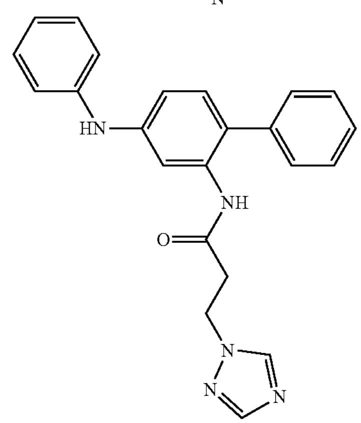
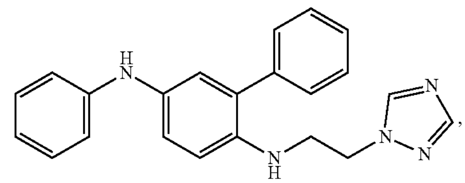
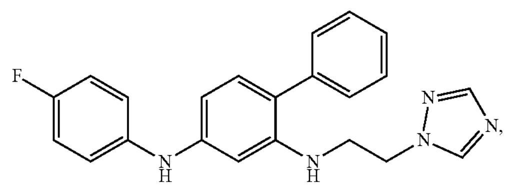
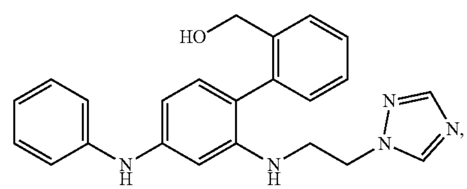
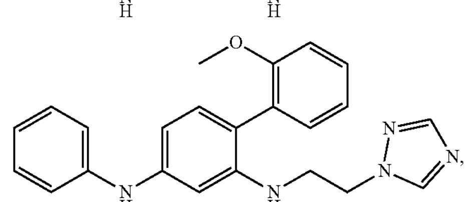
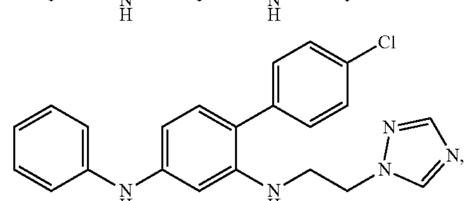

-continued
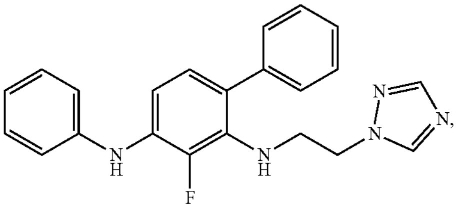
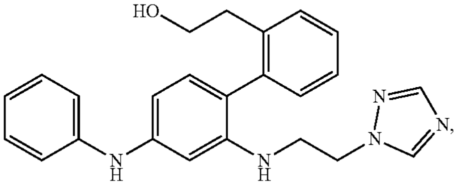
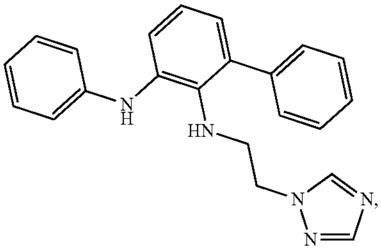
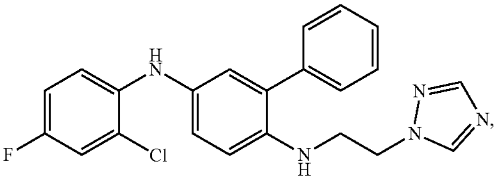
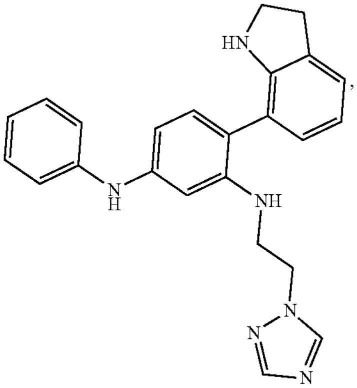
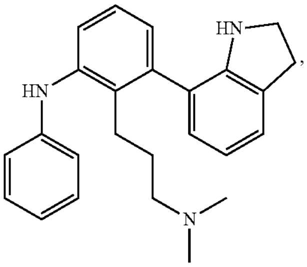
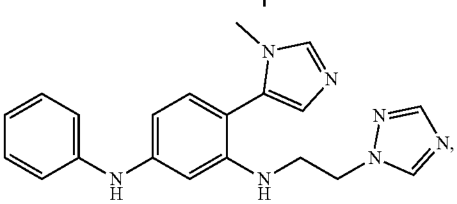
-continued
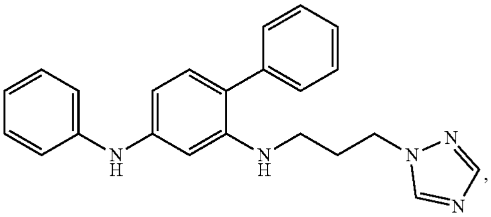
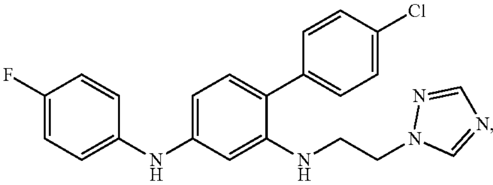
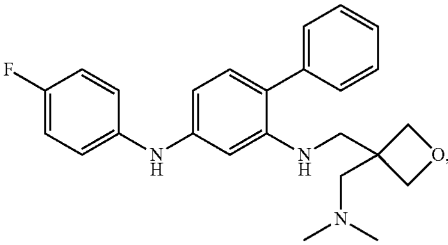
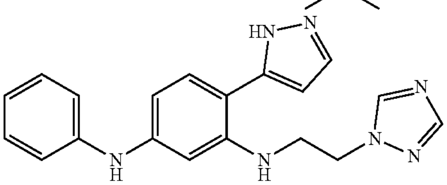
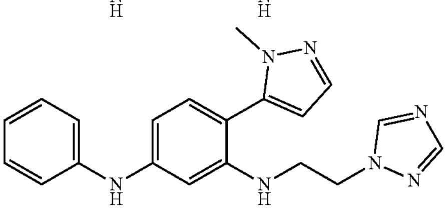
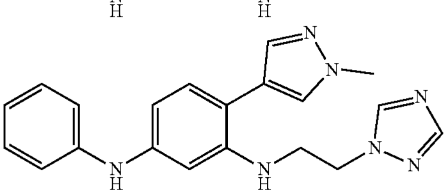
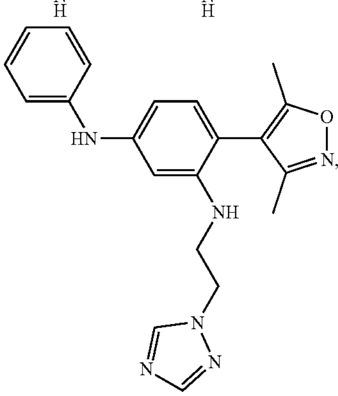
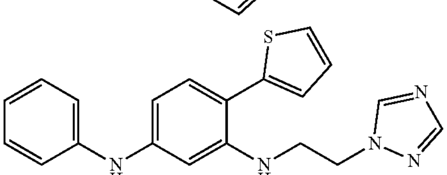

-continued
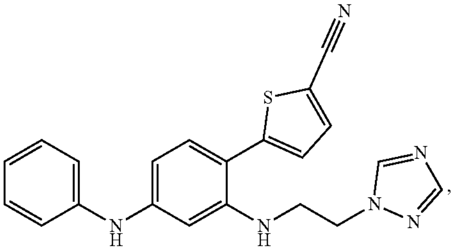
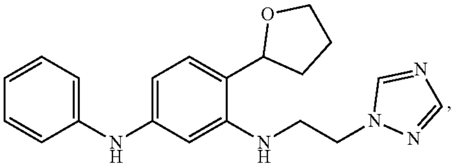
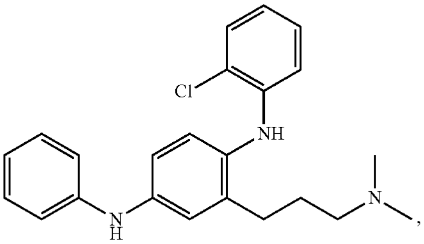
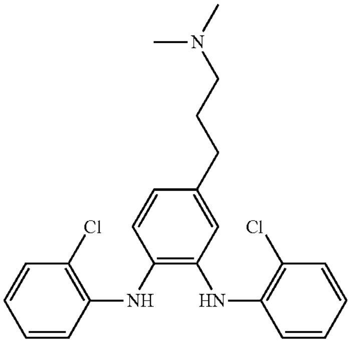
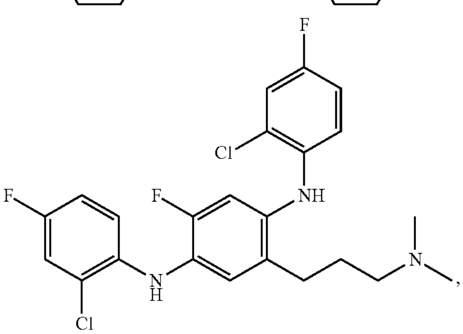
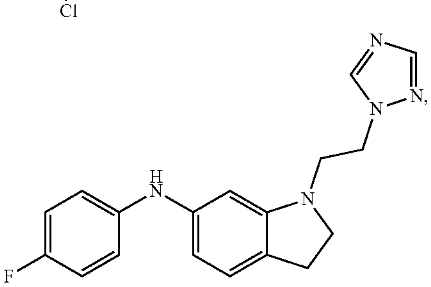
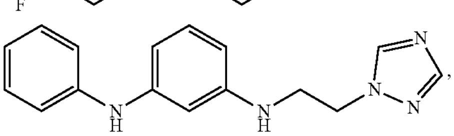
-continued
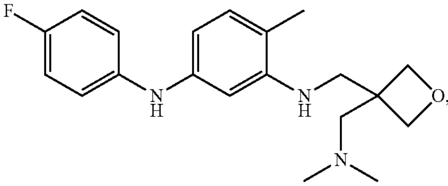
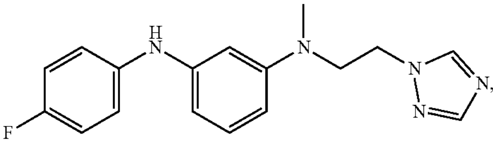
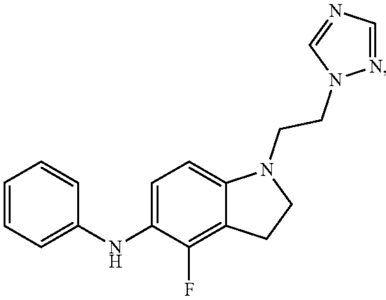
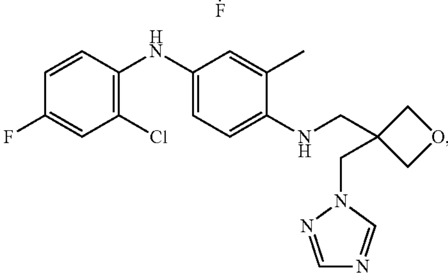
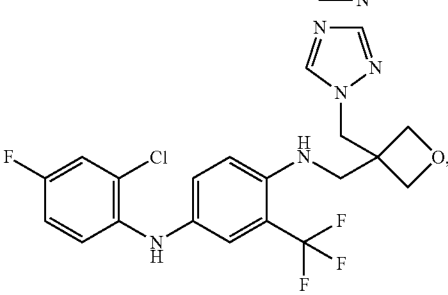
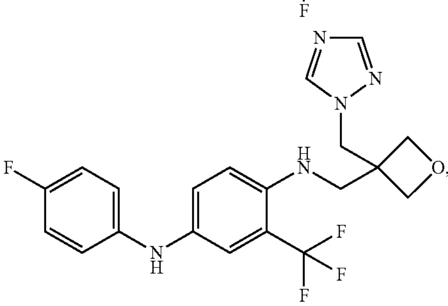
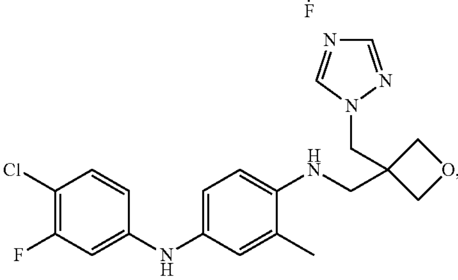

-continued
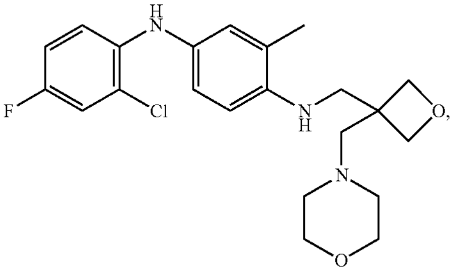
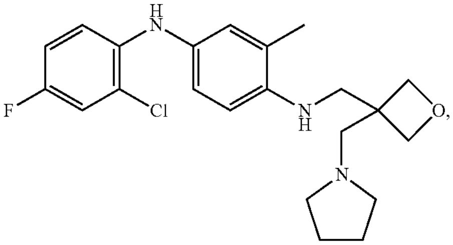
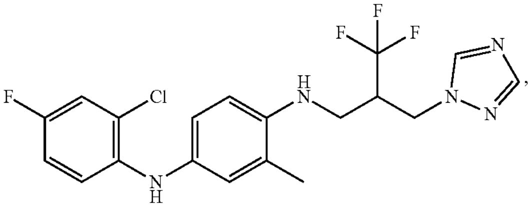
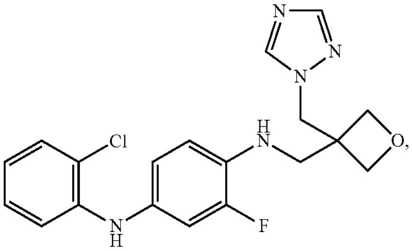
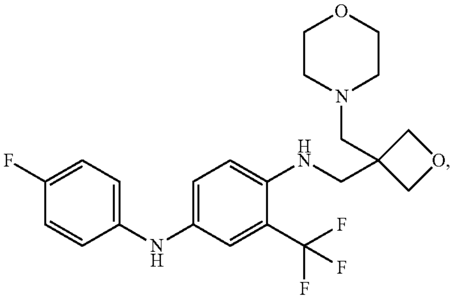
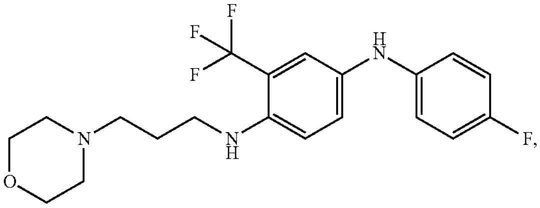
-continued
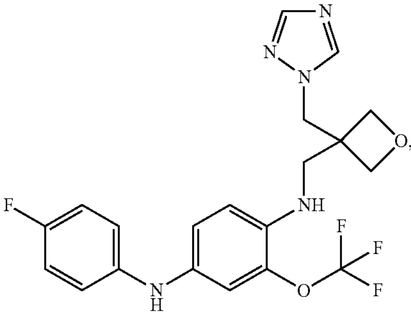
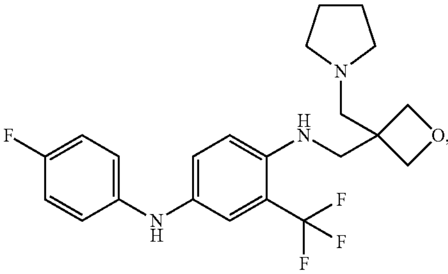
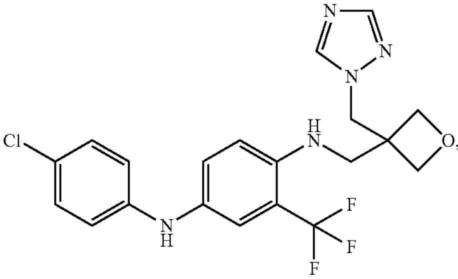
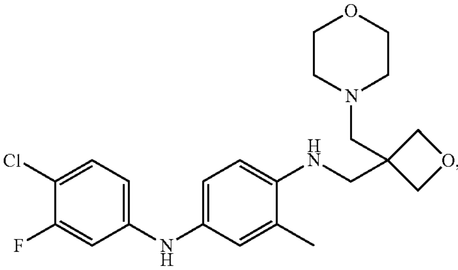
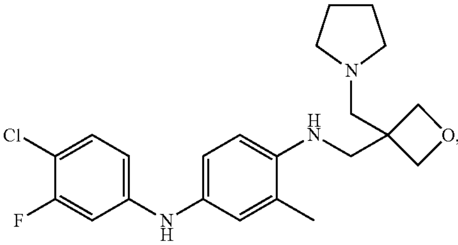
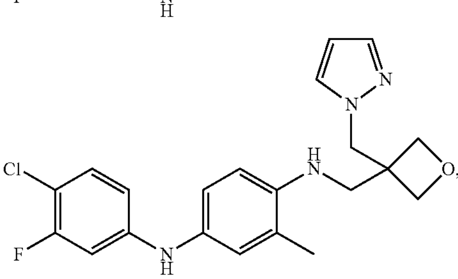

-continued
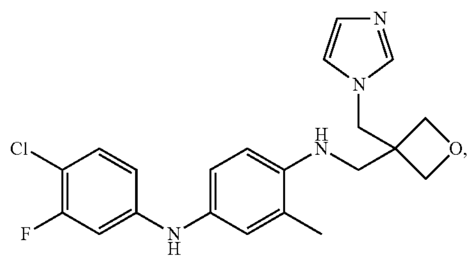
and pharmaceutically acceptable salts thereof.
5. The compound of claim 3, wherein the compound is selected from:
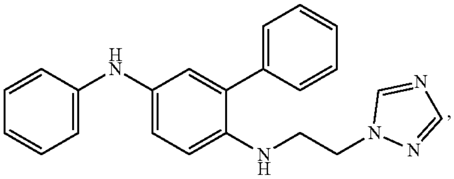
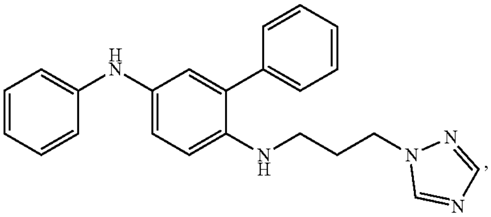
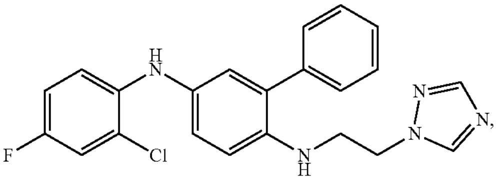
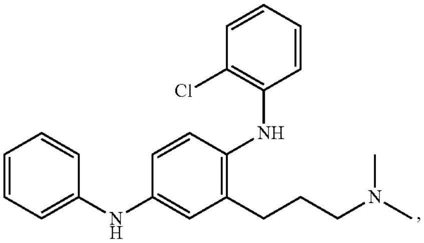
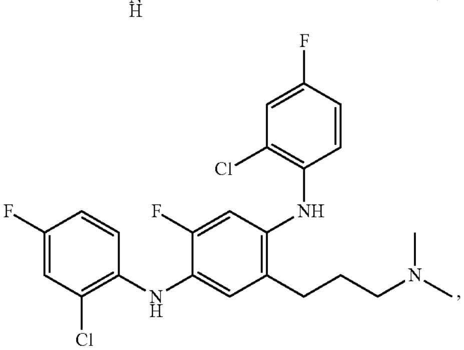
-continued
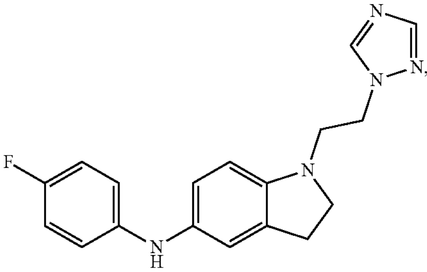
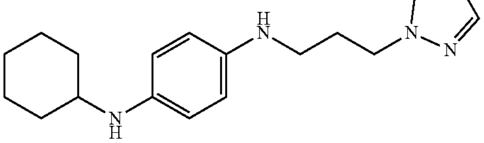
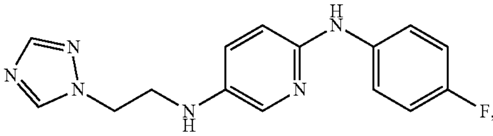
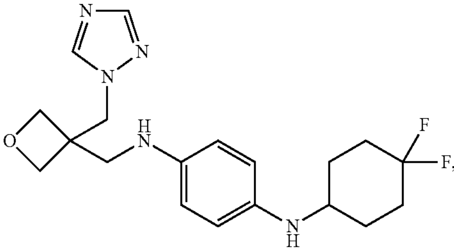
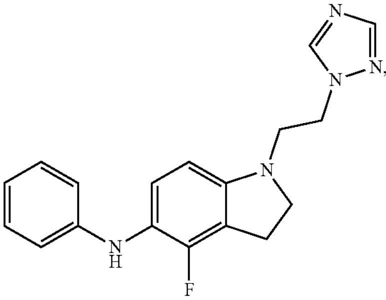
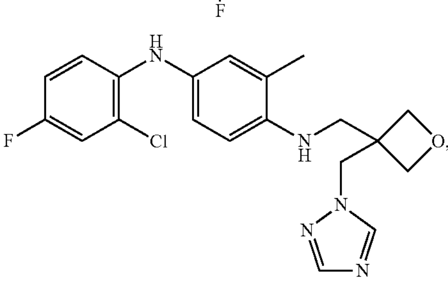
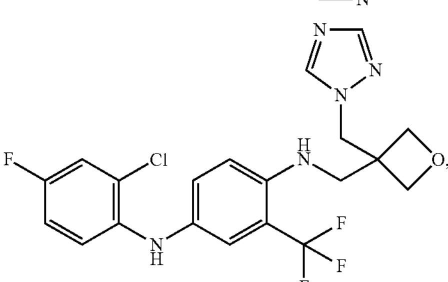

-continued
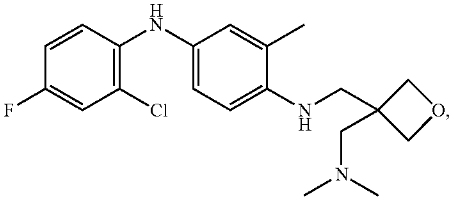
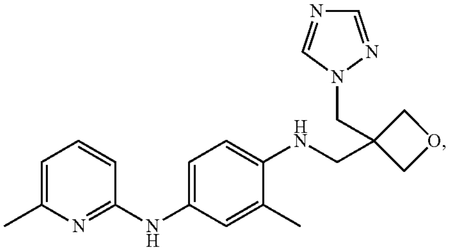
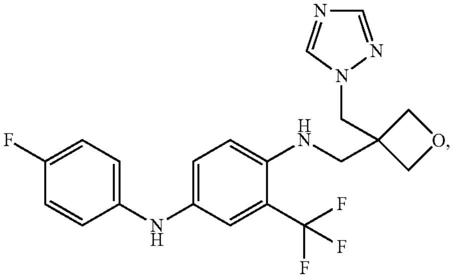
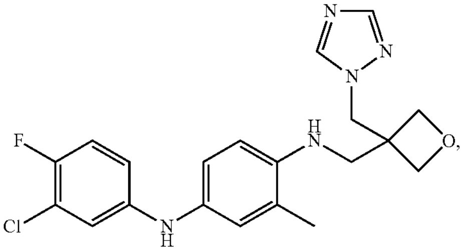
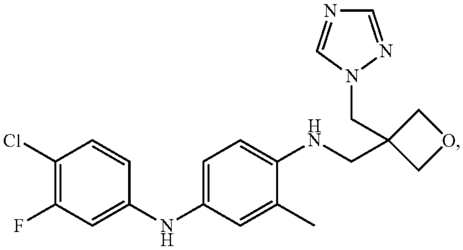
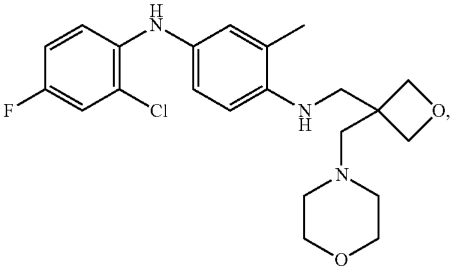
-continued
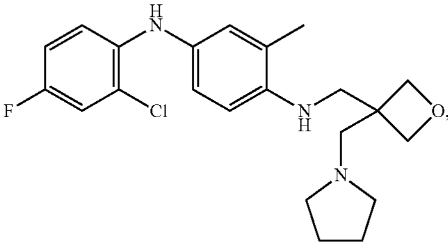
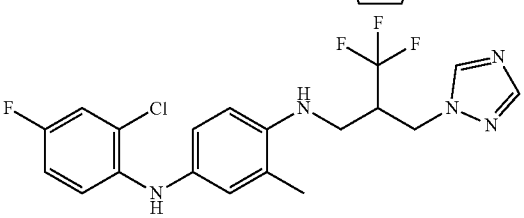
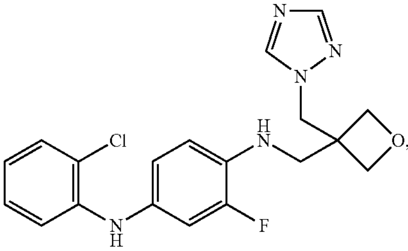
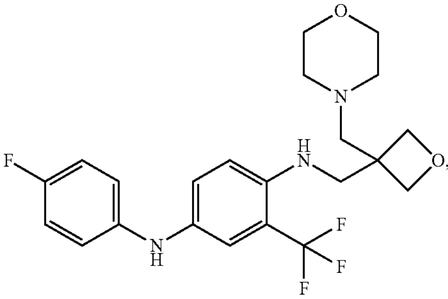
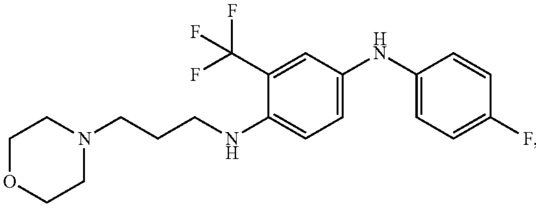
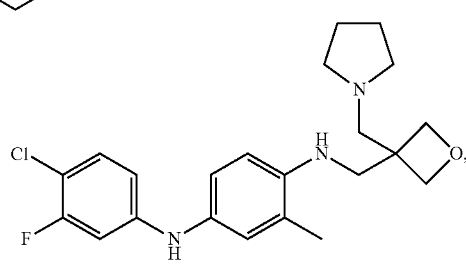
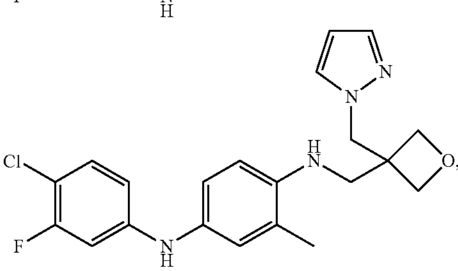

-continued
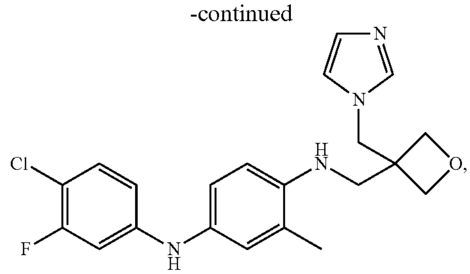
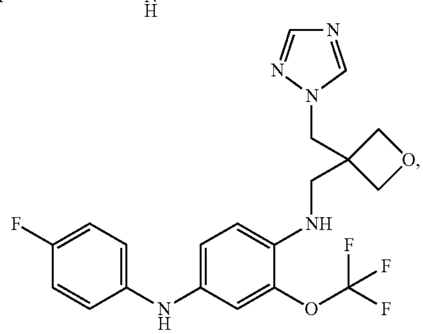
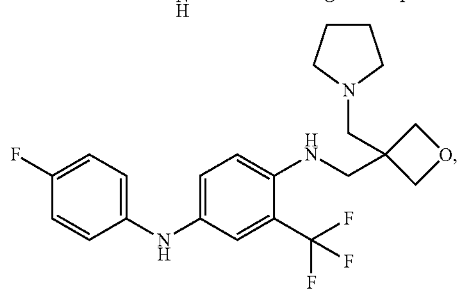
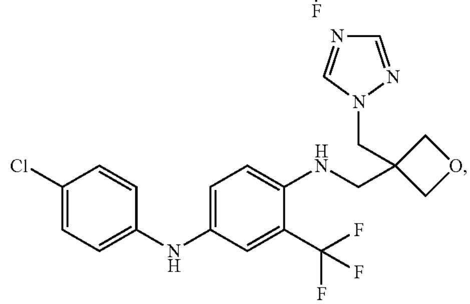
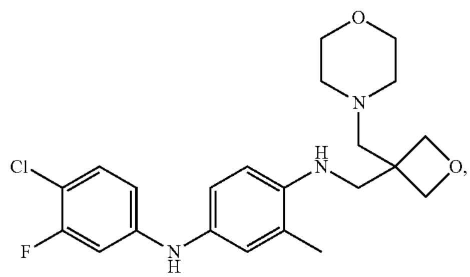
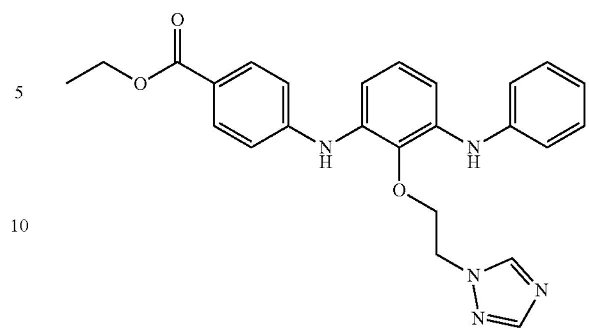
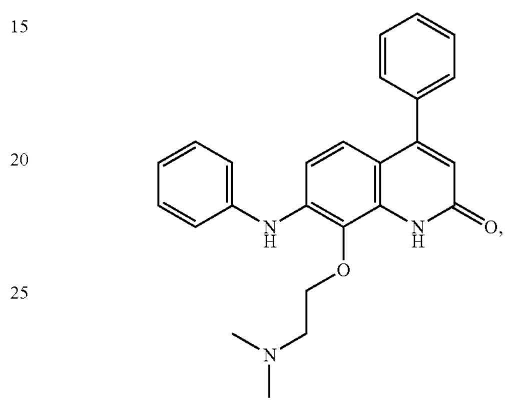
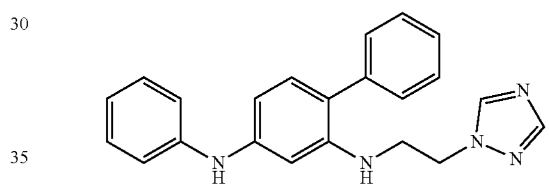
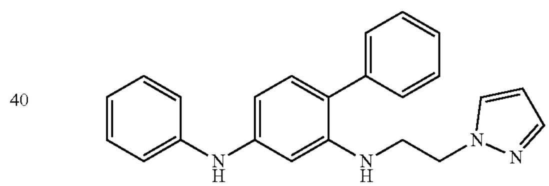
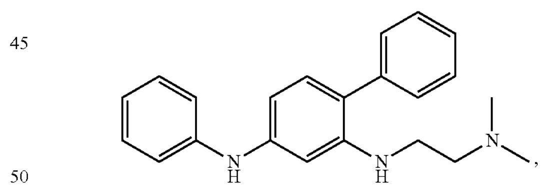
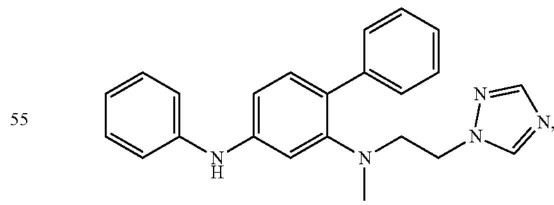
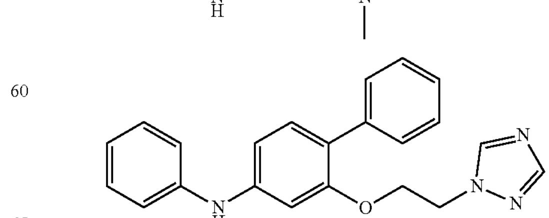
and pharmaceutically acceptable salts thereof.
6. The compound of claim 3, wherein the compound is selected from:

-continued
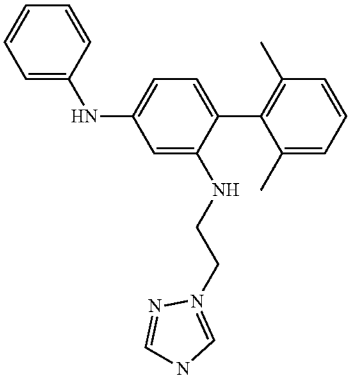
,
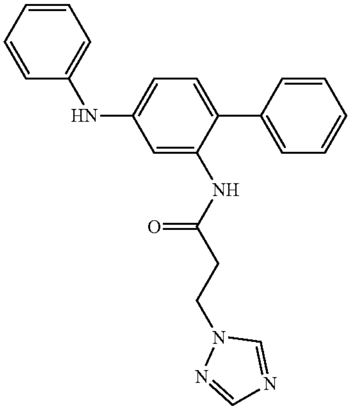
,
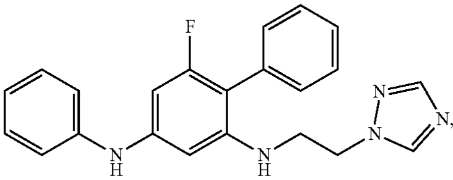
,
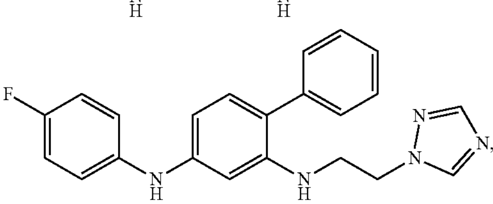
,
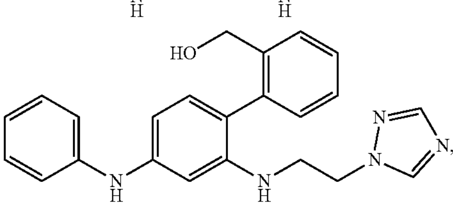
,
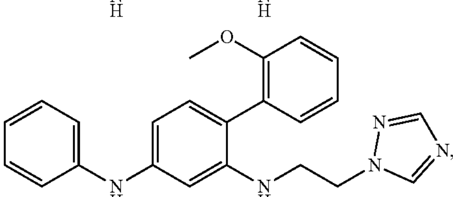
,
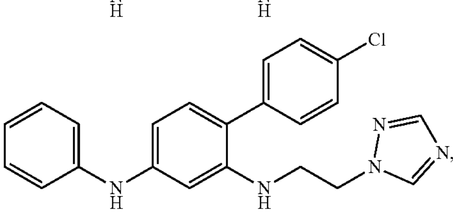
,
-continued
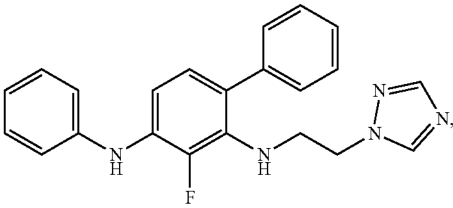
,
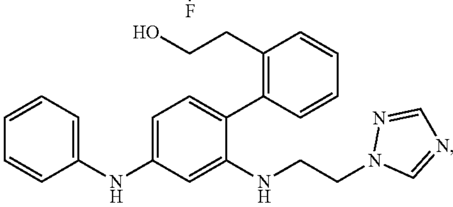
,
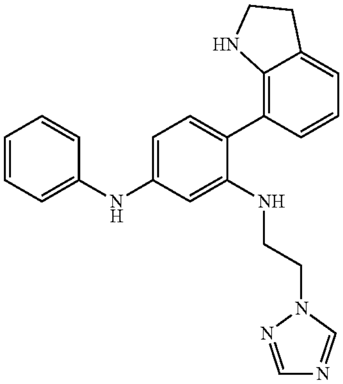
,
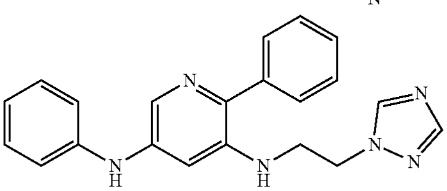
,
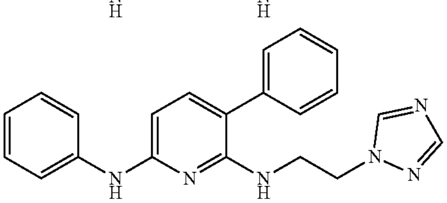
,
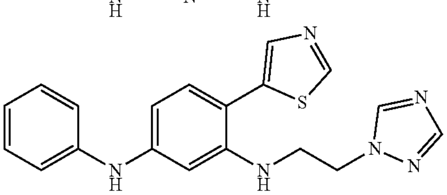
,
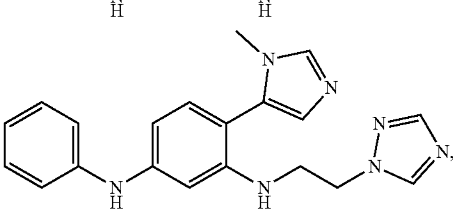
,
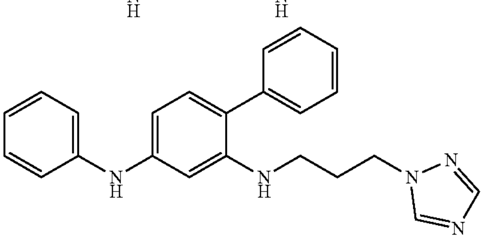
, -continued
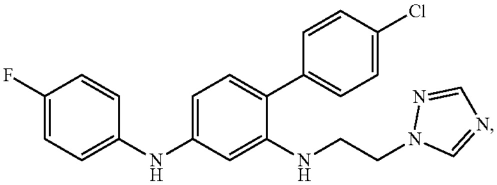
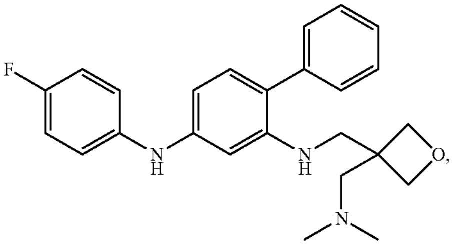
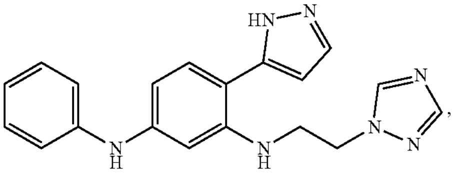
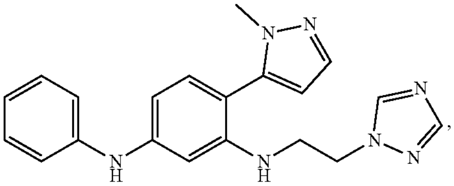
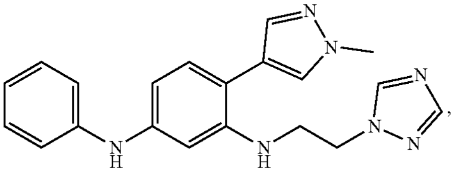
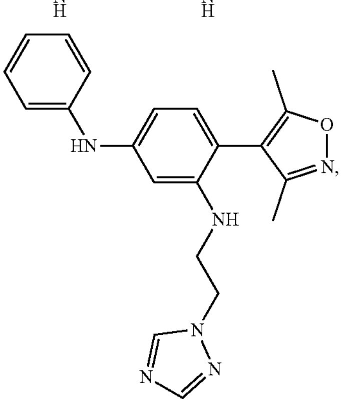
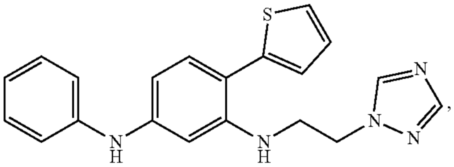
-continued
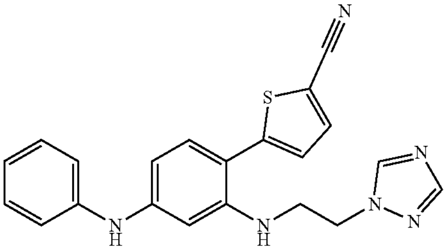
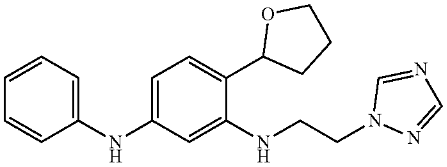
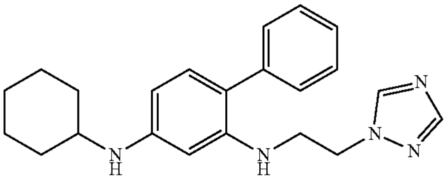
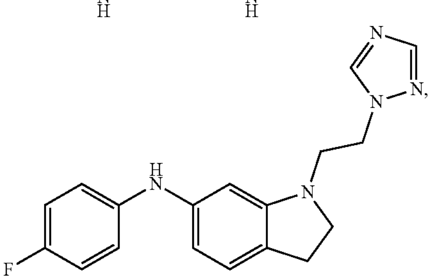
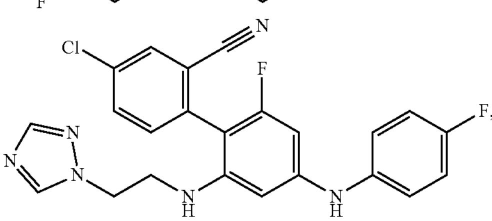
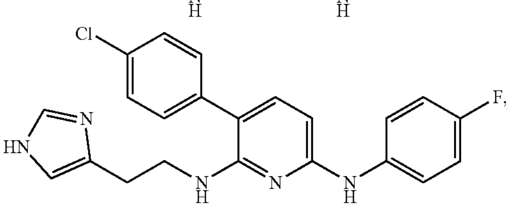
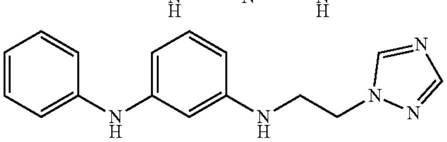
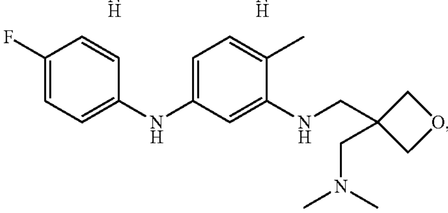
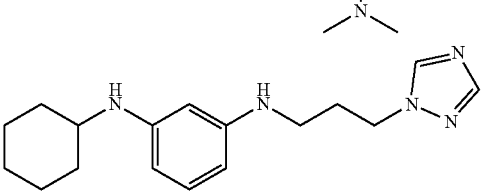

-continued
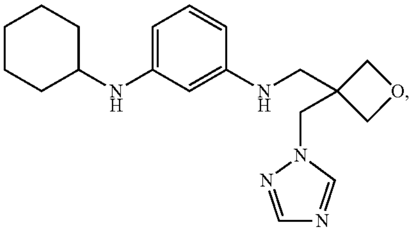
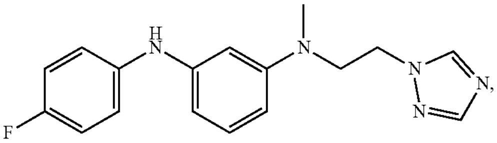
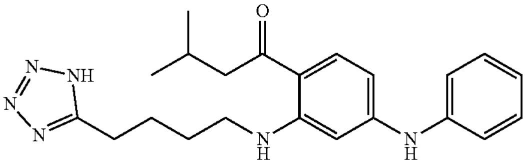
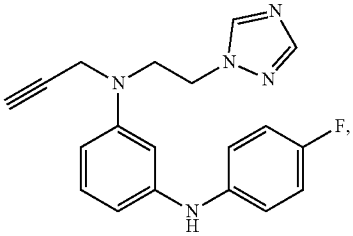
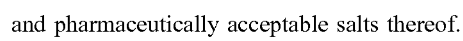
and pharmaceutically acceptable salts thereof.
7. A compound, wherein the compound is selected from:
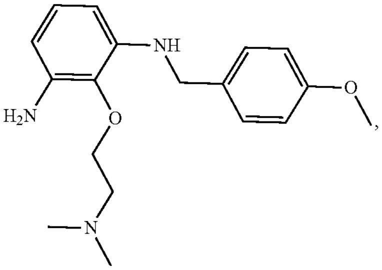
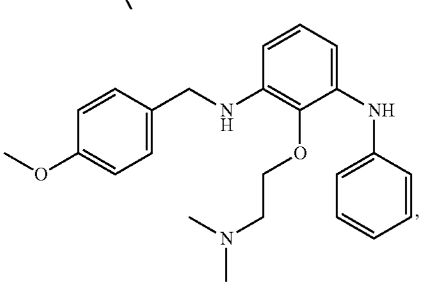
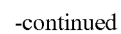
-continued
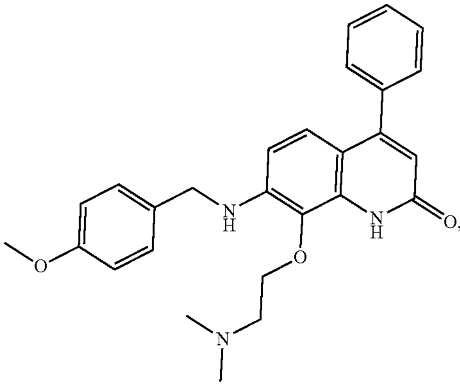
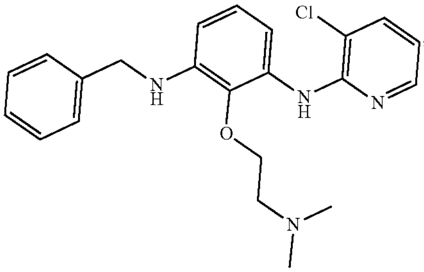
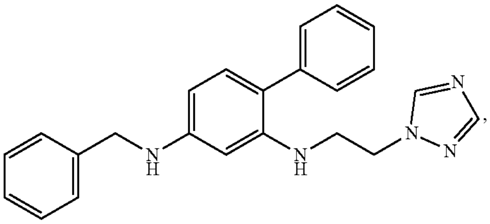
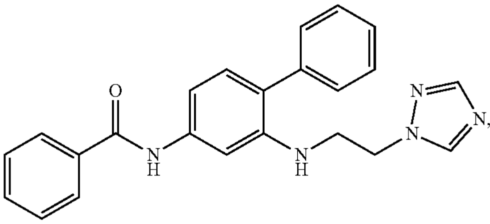
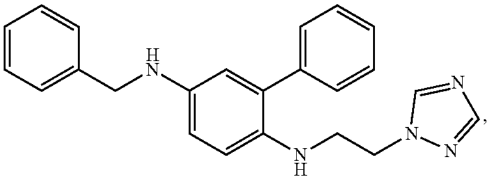
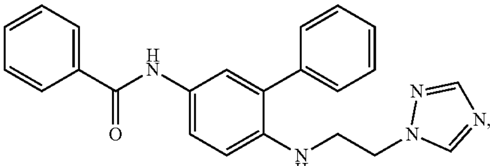

-continued
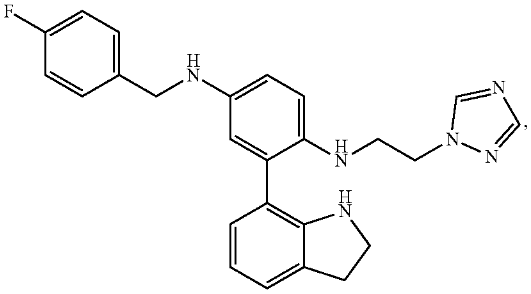
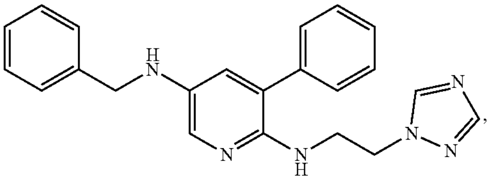
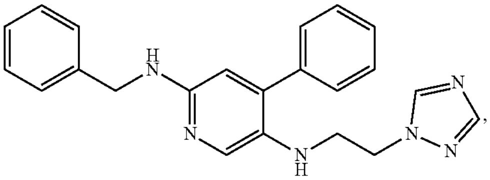
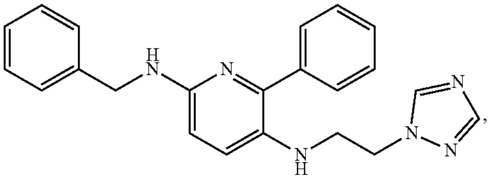
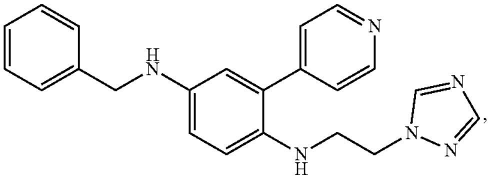
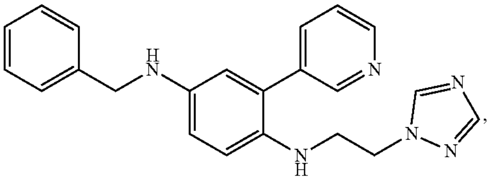
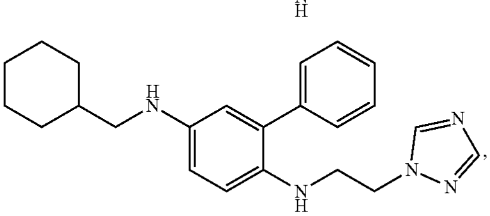
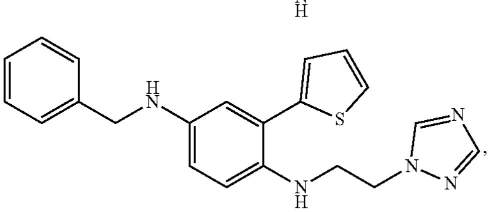
-continued
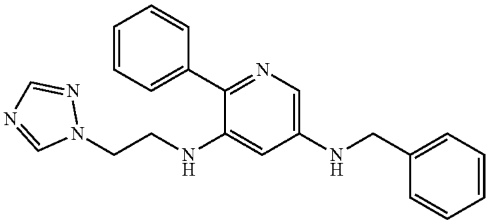
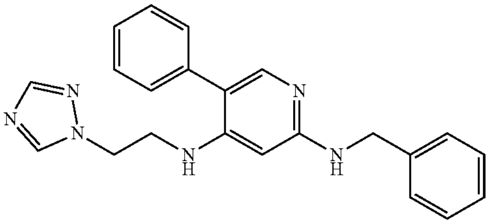
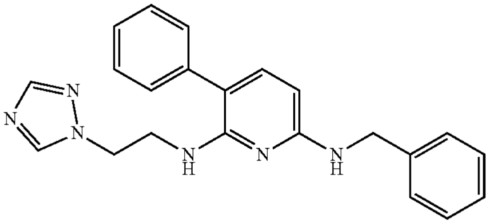
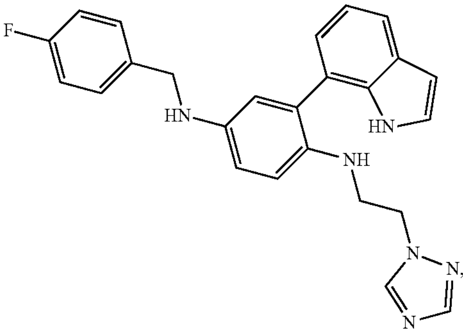
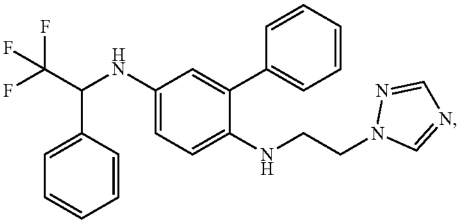
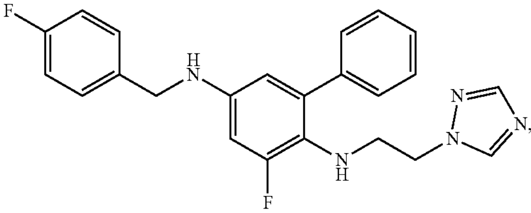
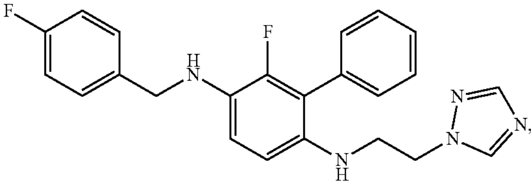

-continued
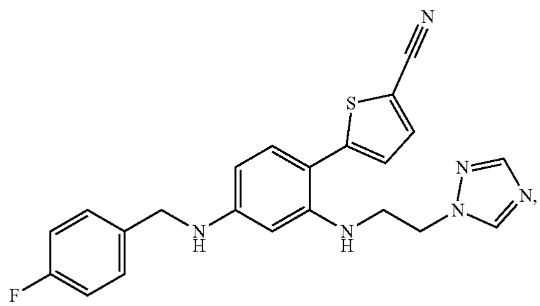
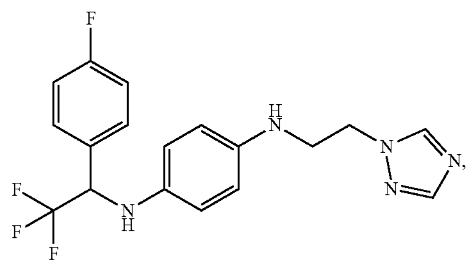
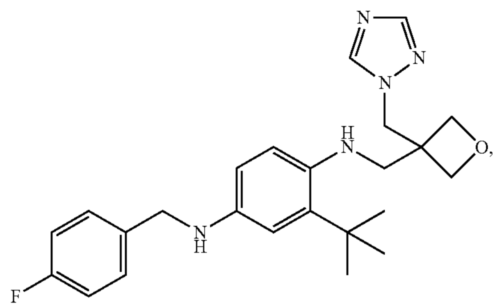
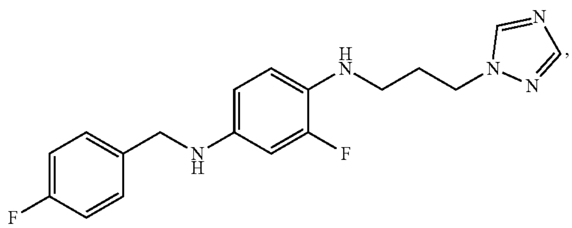
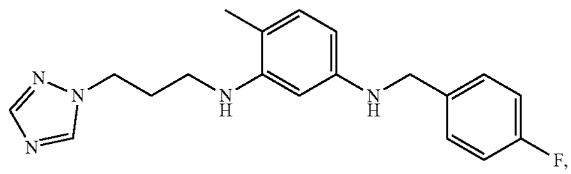
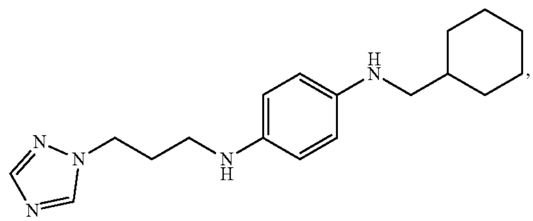
-continued
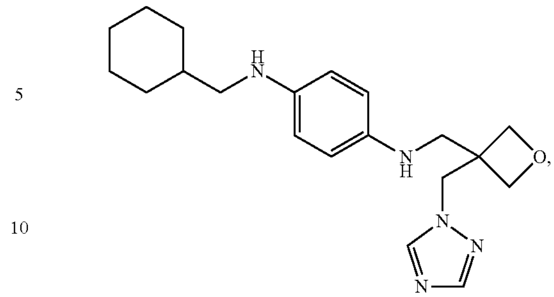
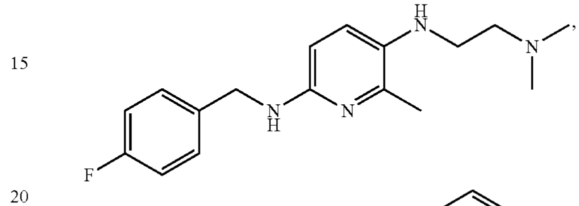
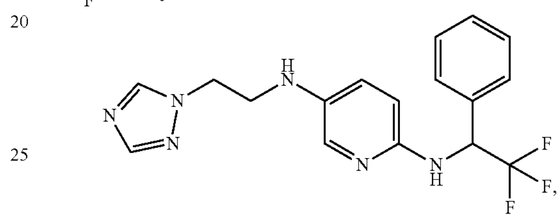
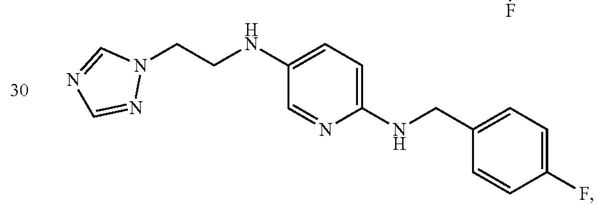
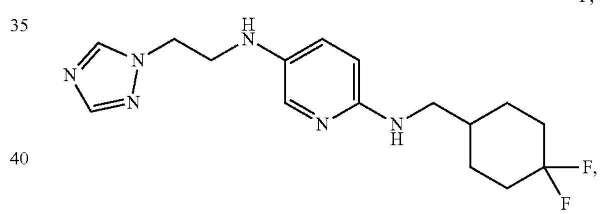
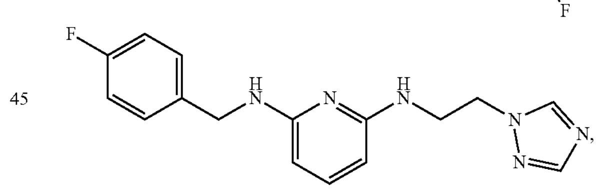
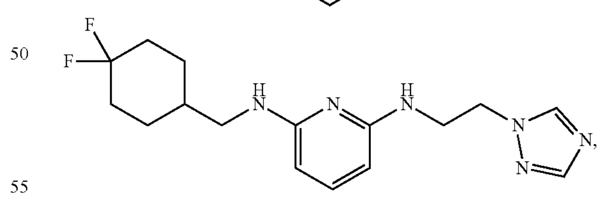
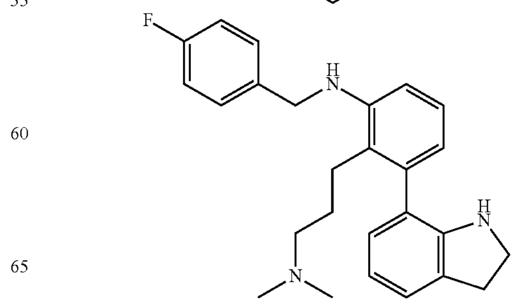

-continued
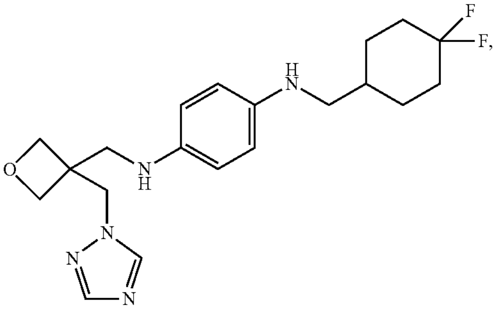
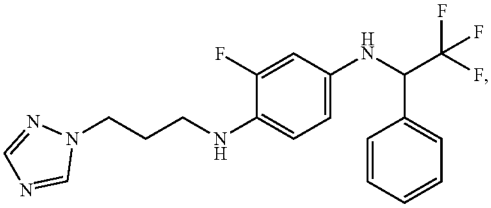
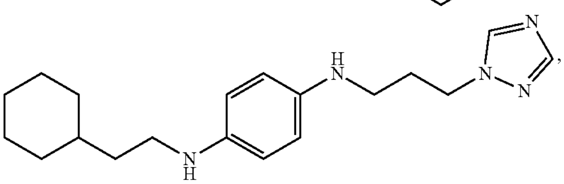
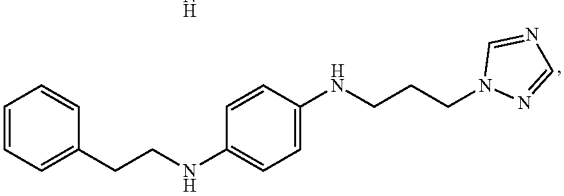
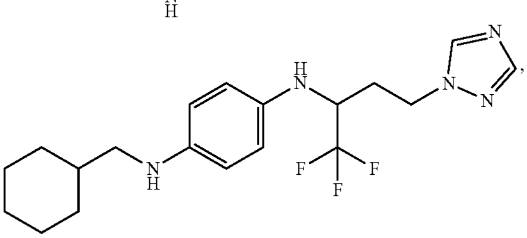
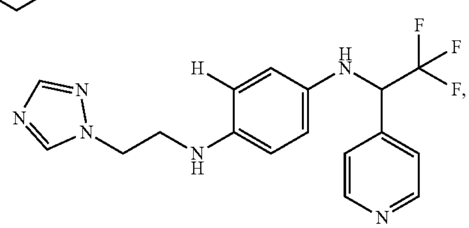
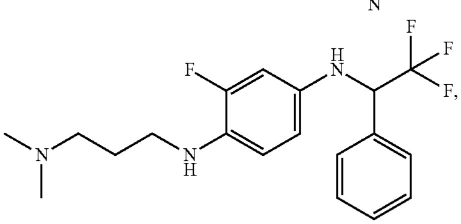
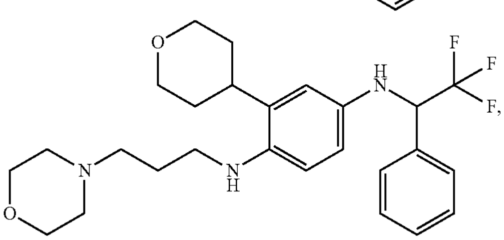
-continued
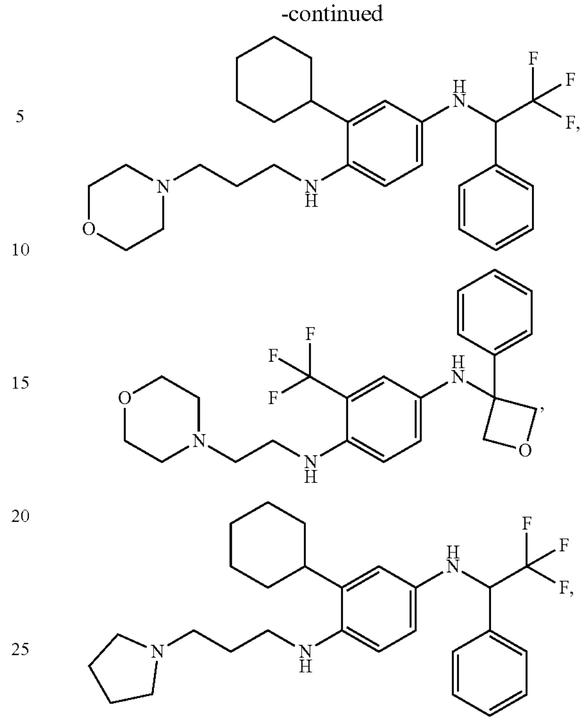
and pharmaceutically acceptable salts thereof.
8. The compound of claim 7, wherein the compound is selected from:
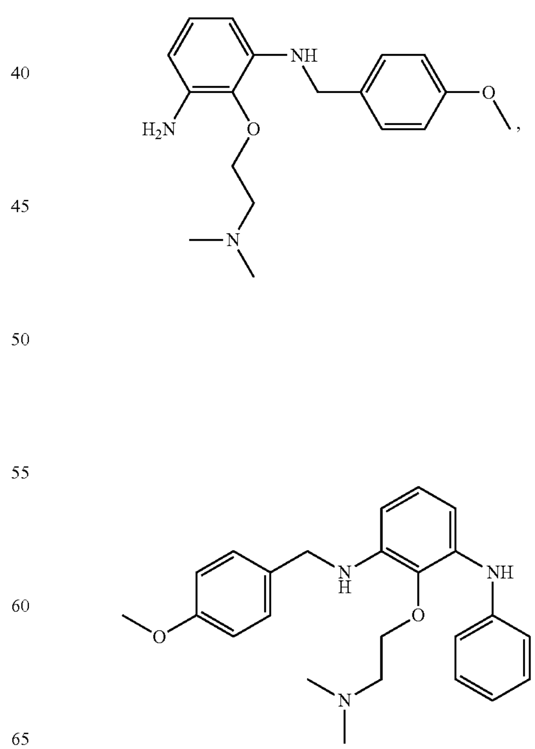

-continued
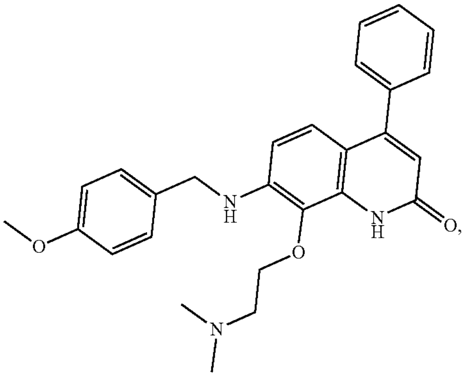
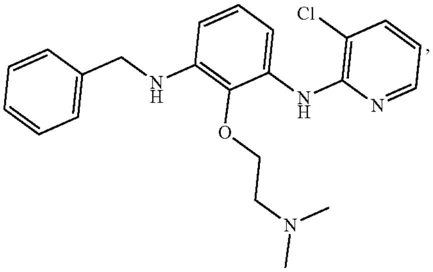
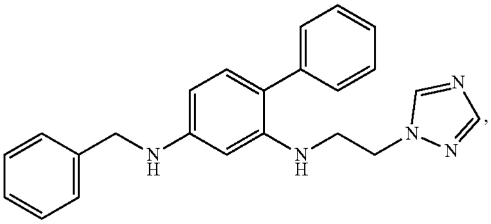
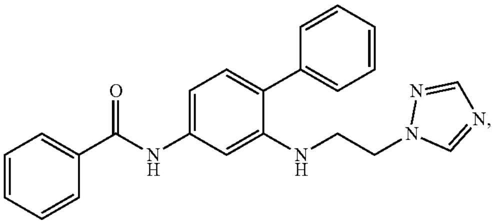
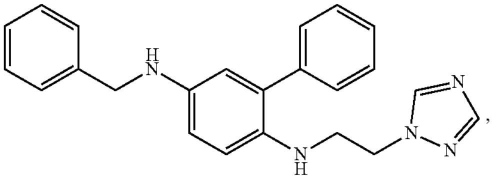
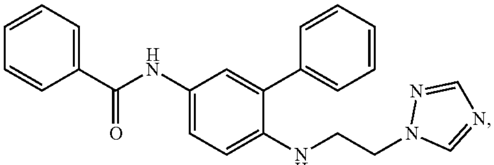
-continued
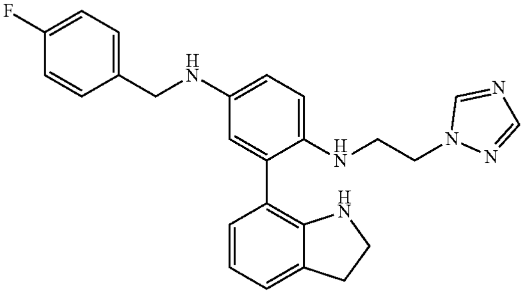
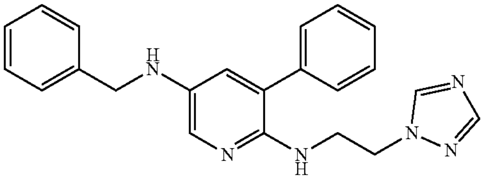
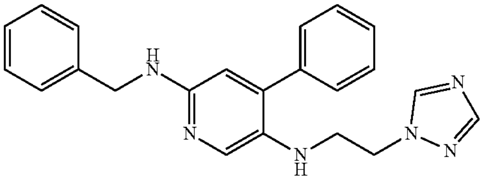
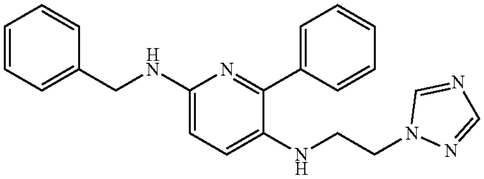
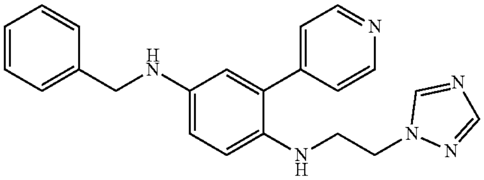
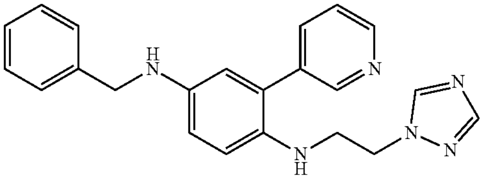
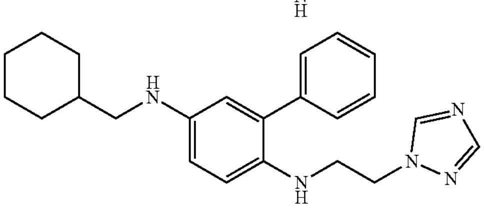
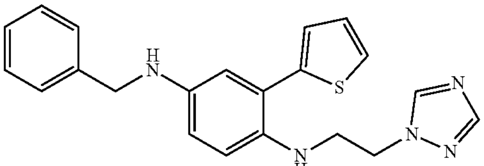

-continued
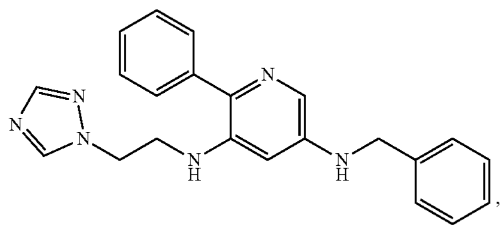
,
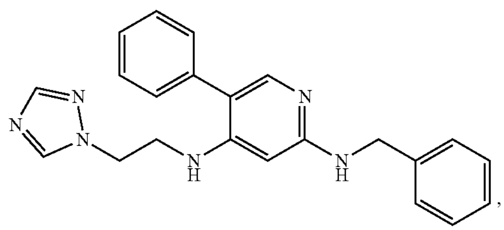
,
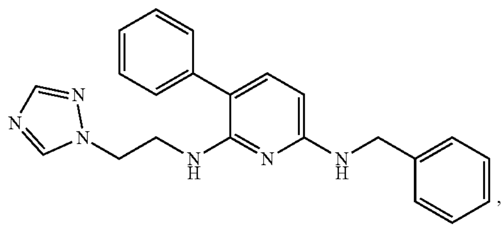
,
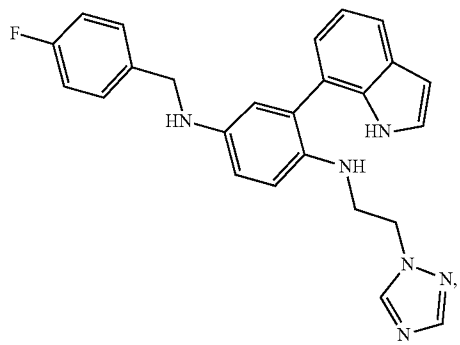
,
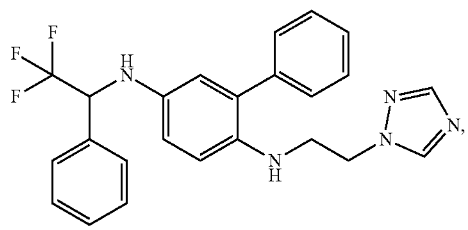
,
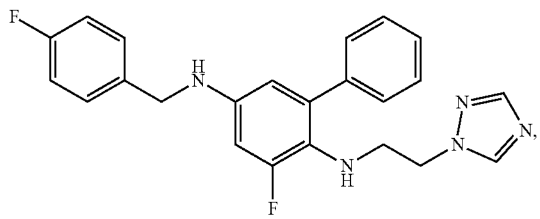
,
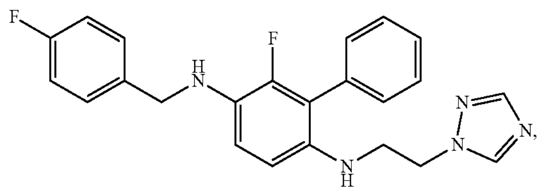
,
-continued
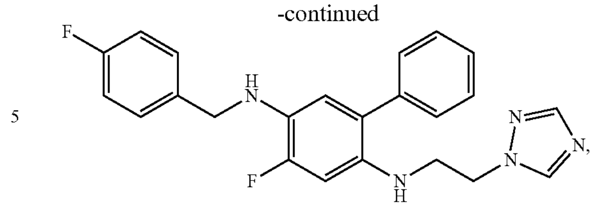
,
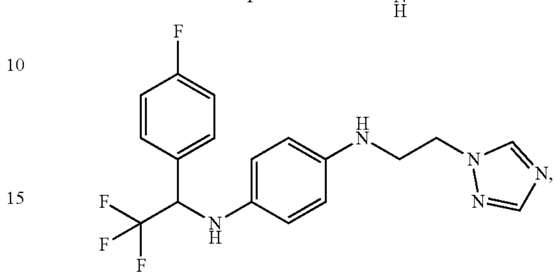
,
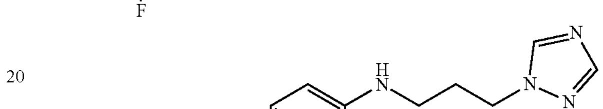
,
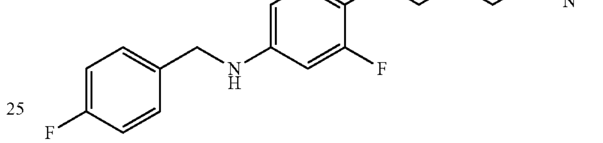
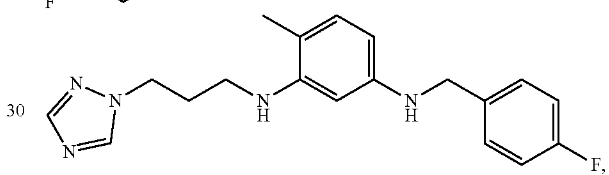
,
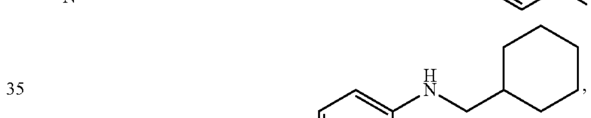
,
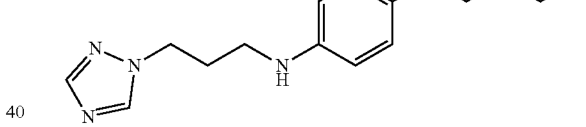
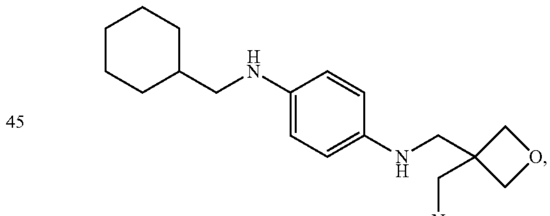
,
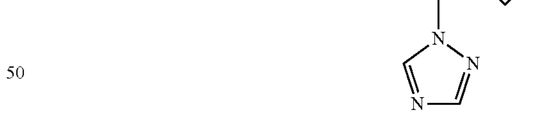
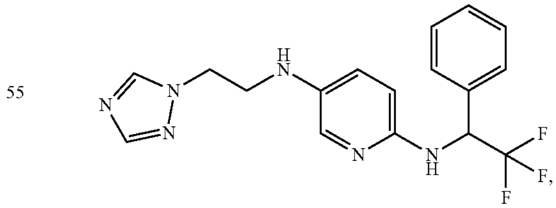
,
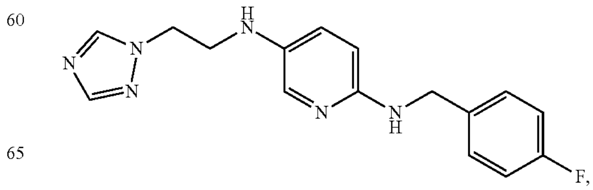
, -continued
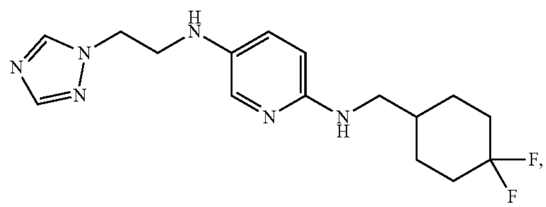
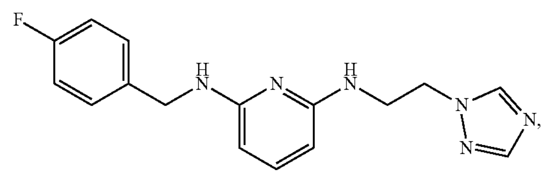
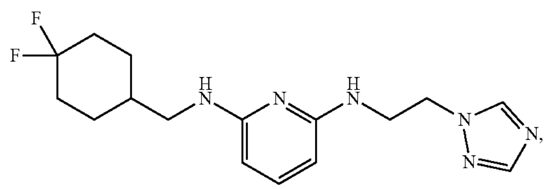
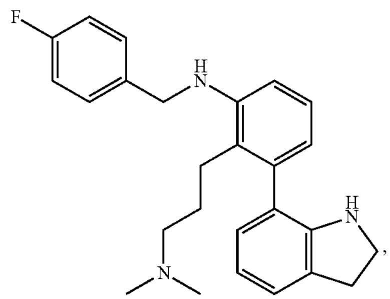
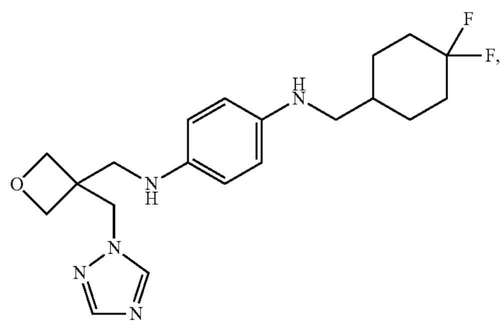
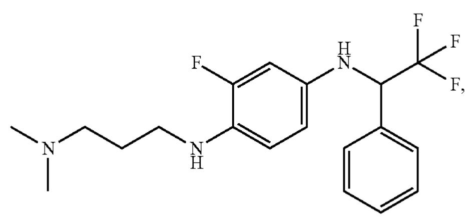
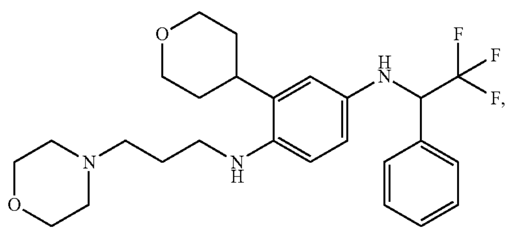
-continued
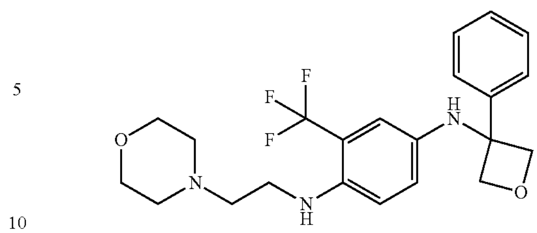
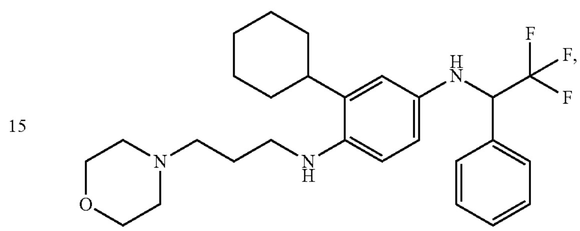
and pharmaceutically acceptable salts thereof.
9. The compound of claim 7, wherein the compound is selected from:
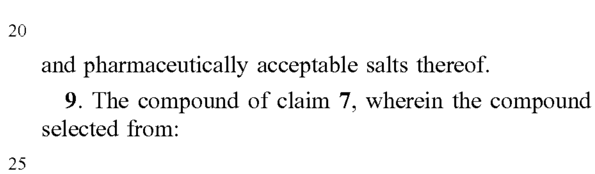
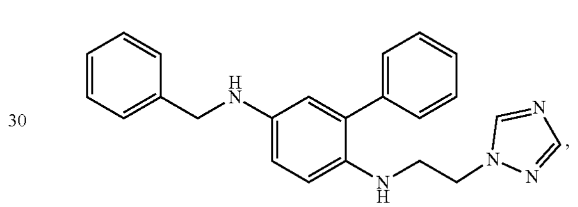
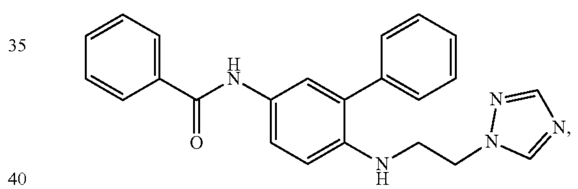
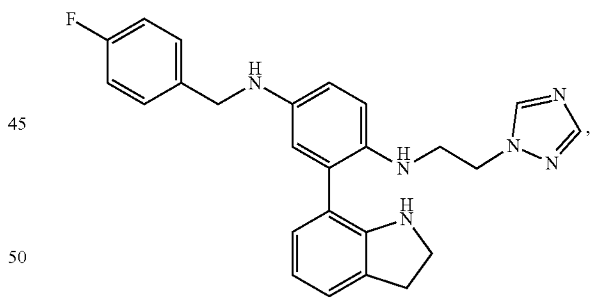
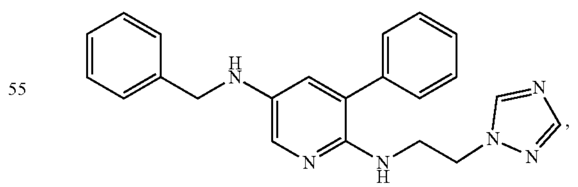
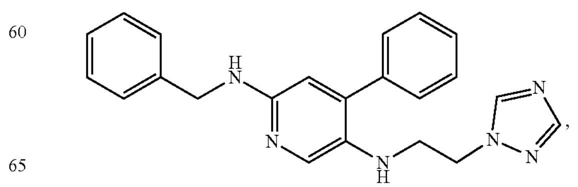

-continued
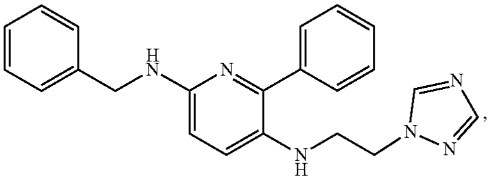
,
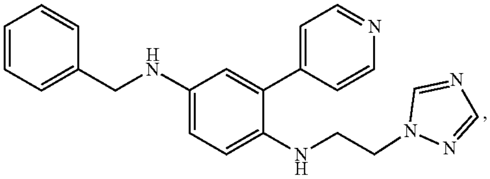
,
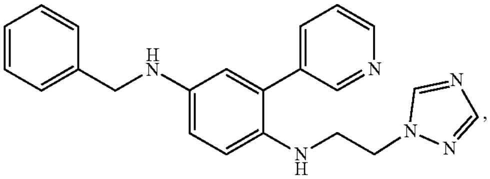
,
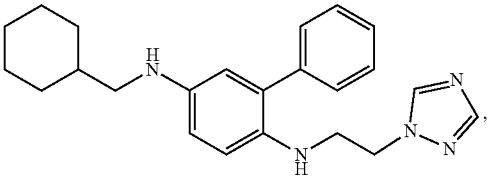
,
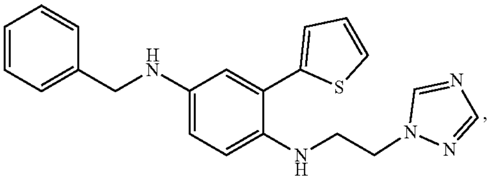
,
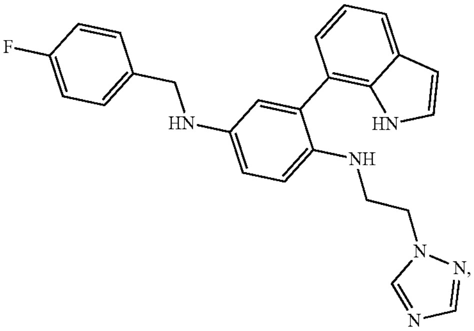
,
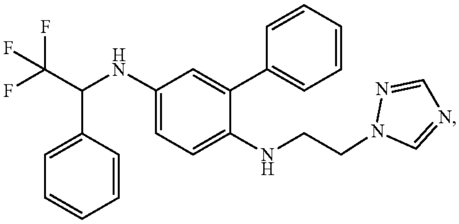
,
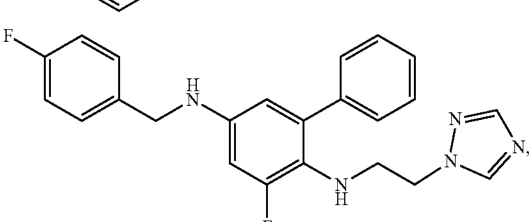
,
-continued
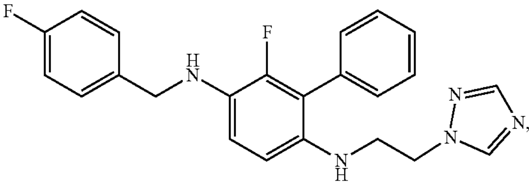
,
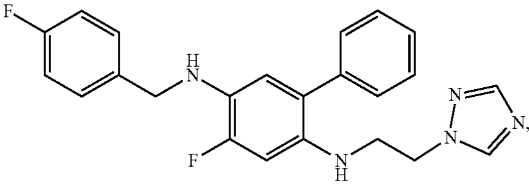
,
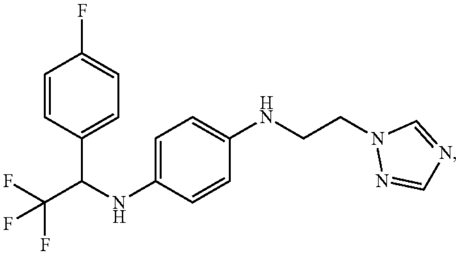
,
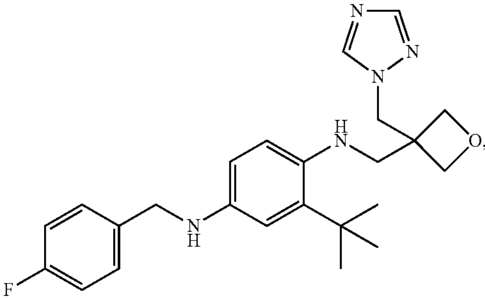
,
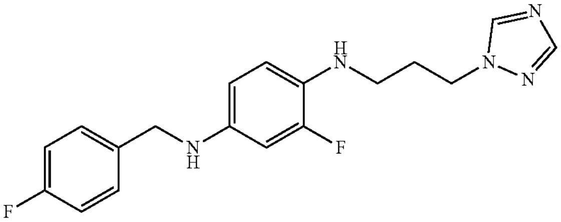
,
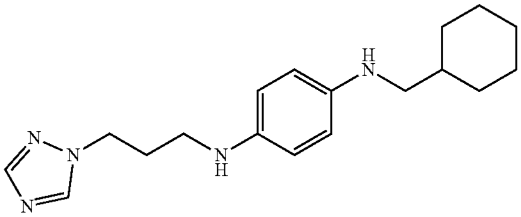
,
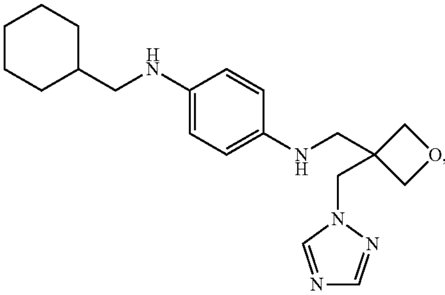
, -continued
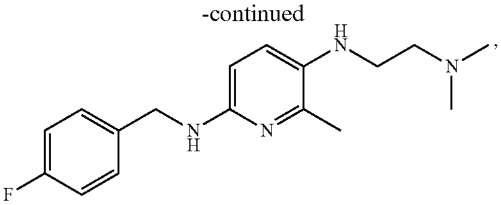,
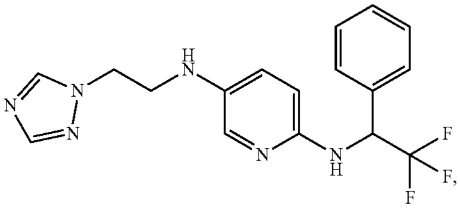,
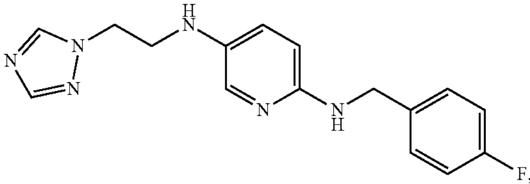,
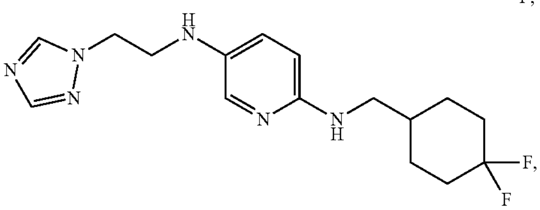,
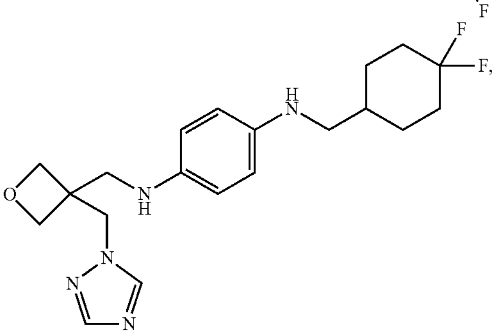,
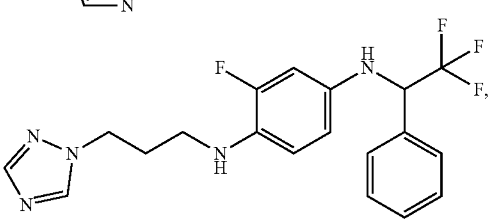
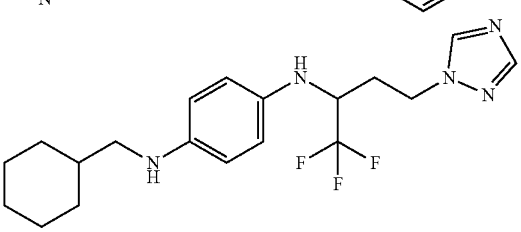,
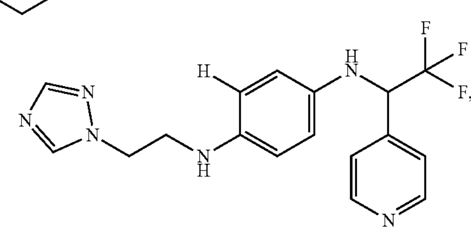
-continued
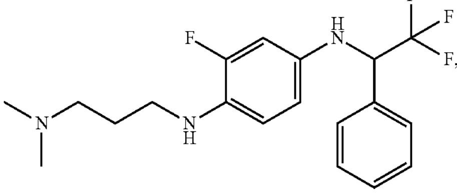,
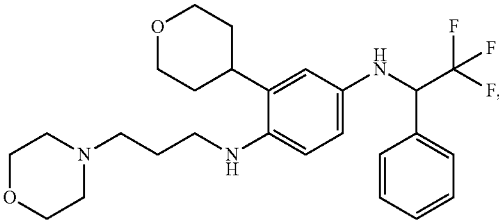,
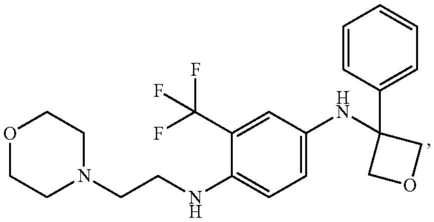,
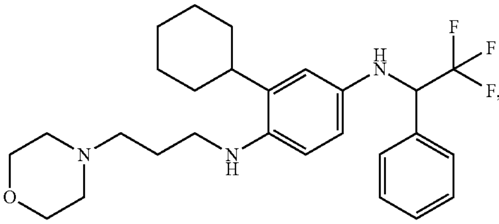,
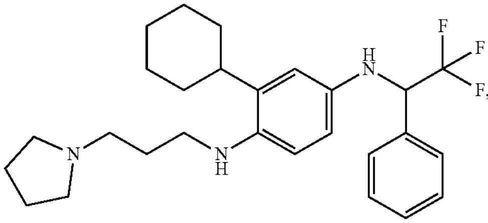,
and pharmaceutically acceptable salts thereof.
10. The compound of claim 7, wherein the compound is selected from:
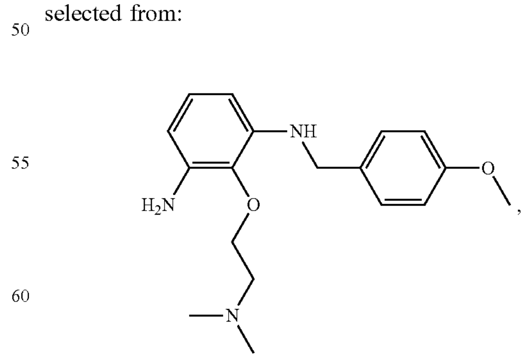, -continued
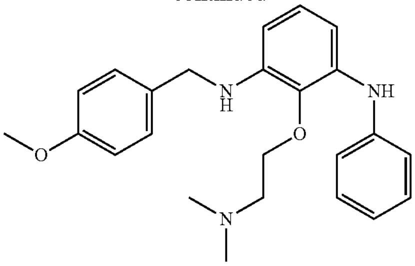
,
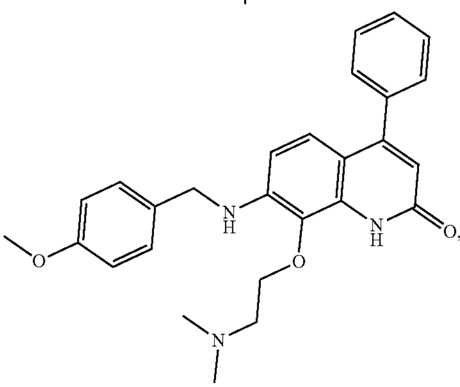
,
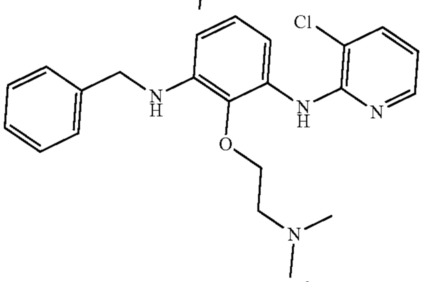
,
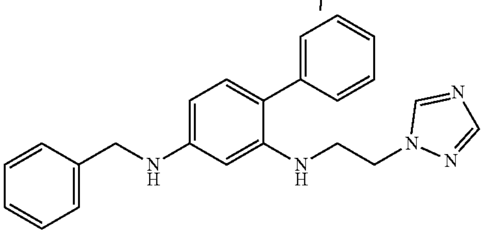
,
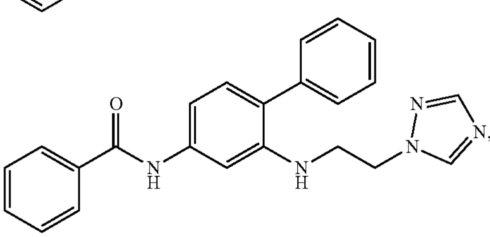
,
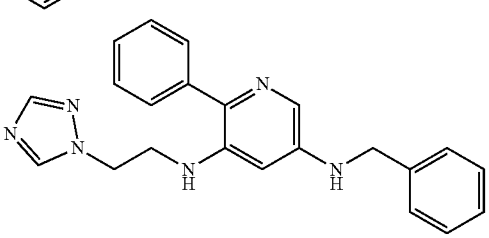
,
-continued
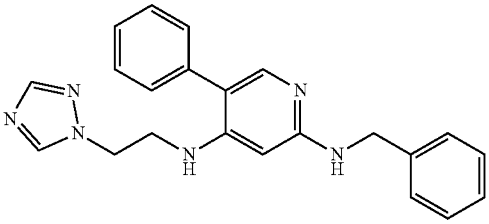
,
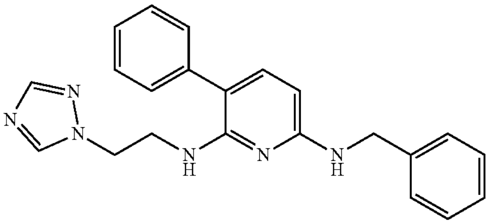
,
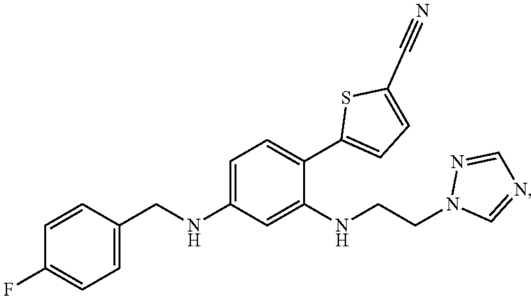
,
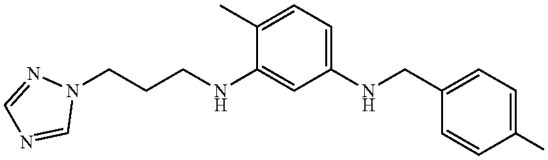
,
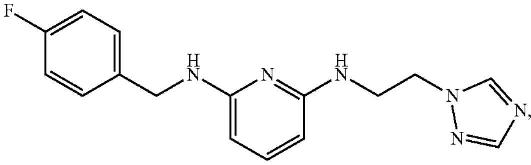
,
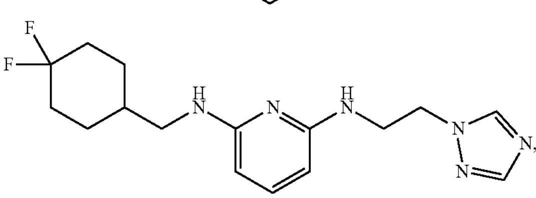
,
and pharmaceutically acceptable salts and/or hydrates thereof.
* * * * *